US009457027B2

(12) United States Patent
Scott et al.

(10) Patent No.: US 9,457,027 B2
(45) Date of Patent: Oct. 4, 2016

(54) COMPOUNDS FOR USE IN TREATMENT OF MUCOSTIS

(71) Applicant: Cellceutix Corporation, Beverly, MA (US)

(72) Inventors: Richard W. Scott, Radnor, PA (US); Bozena Korczak, Wayne, PA (US)

(73) Assignee: Cellceutix Corporation, Beverly, MA (US)

( * ) Notice: Subject to any disclaimer, the term of this patent is extended or adjusted under 35 U.S.C. 154(b) by 0 days.

(21) Appl. No.: 14/836,177

(22) Filed: Aug. 26, 2015

(65) Prior Publication Data

US 2016/0213668 A1 Jul. 28, 2016

Related U.S. Application Data

(63) Continuation of application No. 14/456,202, filed on Aug. 11, 2014, now Pat. No. 9,155,738, which is a continuation of application No. 13/471,689, filed on May 15, 2012, now Pat. No. 8,802,683.

(60) Provisional application No. 61/486,455, filed on May 16, 2011.

(51) Int. Cl.

*A61K 31/505* (2006.01)
*A61K 38/18* (2006.01)
*A61K 9/00* (2006.01)
*C07D 239/26* (2006.01)

(52) U.S. Cl.

CPC ............. *A61K 31/505* (2013.01); *A61K 9/006* (2013.01); *A61K 38/1825* (2013.01); *C07D 239/26* (2013.01)

(58) Field of Classification Search

CPC ........................... C07D 239/26; A61K 31/505
See application file for complete search history.

(56) References Cited

U.S. PATENT DOCUMENTS 3,496,179 A 2/1970 Hess
5,656,591 A 8/1997 Tomita et al.
6,025,326 A 2/2000 Steinberg et al.
6,172,104 B1 1/2001 Tidwell et al.
6,482,799 B1 11/2002 Tuse et al.
6,835,808 B2 12/2004 Quentin et al.
7,173,102 B2 2/2007 DeGrado et al.
7,590,517 B2 9/2009 Doerksen et al.
7,951,829 B2 * 5/2011 Player .................. C07D 235/08 514/394
8,236,800 B2 * 8/2012 DeGrado ............... A61K 31/16 514/247
8,278,309 B2 * 10/2012 DeGrado et al. ..... C07D 403/14 514/256
8,455,490 B2 * 6/2013 DeGrado ............... A61K 31/16 514/247
8,796,275 B2 * 8/2014 Scott ........................ 514/252.13
8,802,683 B2 * 8/2014 Scott .................... A61K 31/167 514/256
8,975,262 B2 * 3/2015 DeGrado ............. C07D 403/14 514/256
9,155,738 B2 * 10/2015 Scott .................... A61K 31/167
9,192,623 B2 * 11/2015 Scott .................... A61K 9/0046
9,296,800 B2 * 3/2016 Willett .................. C07K 14/47
2003/0109570 A1 6/2003 Tsunoda et al.
2004/0102941 A1 5/2004 Lopez et al.
2004/0107056 A1 6/2004 Doerksen et al.
2004/0185257 A1 9/2004 DeGrado et al.
2004/0202639 A1 10/2004 DeGrado et al.
2004/0202687 A1 10/2004 Babu et al.
2005/0065091 A1 3/2005 Peyman
2005/0287108 A1 12/2005 DeGrado et al.
2006/0024264 A1 2/2006 Kuroda et al.
2006/0041023 A1 2/2006 DeGrado et al.
2006/0041024 A1 2/2006 Shaker
2006/0078626 A1 4/2006 Smith
2007/0259936 A1 * 11/2007 Player .................. C07D 235/08 514/394
2008/0131731 A1 6/2008 Igawa et al.
2008/0176807 A1 * 7/2008 DeGrado ............... A61K 31/16 514/616
2009/0092574 A1 * 4/2009 Scott .................... A61K 9/0046 424/78.04
2010/0081665 A1 * 4/2010 Scott ..................... C07C 217/90 514/252.11
2010/0105703 A1 * 4/2010 DeGrado ............ C07D 403/14 514/256
2010/0144761 A1 * 6/2010 Scott ...................... A01N 47/44 514/256
2010/0317596 A1 * 12/2010 Willett ................... C07K 14/47 514/20.9
2011/0178104 A1 * 7/2011 Scott .................... A61K 31/167 514/256
2011/0190344 A1 * 8/2011 Player .................. C07D 235/08 514/314
2011/0190364 A1 * 8/2011 Player .................. C07D 235/08 514/394
2012/0295922 A1 * 11/2012 Scott .................... A61K 31/167 514/256
2013/0023561 A1 * 1/2013 DeGrado ............... A61K 31/16 514/316
2013/0065818 A1 * 3/2013 Scott .................... A61K 9/0046 514/2.3
2013/0090345 A1 * 4/2013 DeGrado ............ C07D 403/14 514/256
2013/0137706 A1 * 5/2013 Scott ...................... A01N 47/44 514/256
2014/0171438 A1 * 6/2014 Pan .................... C07D 295/135 514/252.11
2014/0308317 A1 * 10/2014 Fan ...................... C07D 417/12 424/278.1
2014/0364364 A1 * 12/2014 Scott .................... A61K 31/167 514/9.2
2015/0072997 A1 * 3/2015 Scott ..................... C07C 217/90 514/256

FOREIGN PATENT DOCUMENTS

EP 1704860 A1 9/2006
JP 2010514798 A 5/2010

(Continued)

OTHER PUBLICATIONS

D.M. Keefe et al., 109 Cancer 820-831, 821 (2007).*

(Continued)

*Primary Examiner* — Alexander R Pagano
(74) *Attorney, Agent, or Firm* — Pepper Hamilton LLP

(57) ABSTRACT

The present invention provides methods for treating and/or preventing mucostitis with one or more compounds, or pharmaceutically acceptable salts thereof, disclosed herein, or compositions comprising the same.

15 Claims, No Drawings

(56) References Cited

FOREIGN PATENT DOCUMENTS

| | | | | |
|---|---|---|---|---|
| WO | 9718827 | A1 | 5/1997 | |
| WO | 02080939 | A2 | 10/2002 | |
| WO | 02100295 | A2 | 12/2002 | |
| WO | 03024391 | A2 | 3/2003 | |
| WO | 2004046109 | A2 | 6/2004 | |
| WO | 2004082634 | A2 | 9/2004 | |
| WO | 2004082643 | A2 | 9/2004 | |
| WO | 2005072246 | A2 | 8/2005 | |
| WO | 2005123660 | A2 | 12/2005 | |
| WO | 2006093813 | A2 | 9/2006 | |
| WO | 2006122162 | A2 | 11/2006 | |
| WO | 2006132647 | A2 | 12/2006 | |
| WO | 2008/083256 | A2 | 7/2008 | |
| WO | WO 2008083256 | A2 * | 7/2008 | ........... A61K 9/0046 |
| WO | 2009061697 | A1 | 5/2009 | |
| WO | 2010062573 | A1 | 6/2010 | |

OTHER PUBLICATIONS

J.P. Donnelly et al., 3 The Lancet Infectious Diseases, 405-412, 405 (2003).*

D.J. Loury et al., 87 Oral Surgery, Oral Medicine, Oral Pathology 544-551 (1999).*

S. Choi et al., 106 Proceedings of the National Academy of Sciences of the United States of America, 6968-6973 (2009).*

T. Sonis et al., 69 Oral Surgery, Oral Medicine, Oral Pathology 437-443 (1990).*

C. Avery et al., 81 Analytical Chemistry, 8365-8372 (2009).*

Spielberger et al., Palifermin for Oral Muscositis after Intensive Therapy for Hematologic Cancers, The New England Journal of Medicine, 2004, vol. 351, No. 25, 2598-2598.

DM. Keefe et al., 109 Cancer 820-831 (2007).

J.P. Donnelly et al., 3 The Lancet Infectious Diseases, 405-412 (2003).

C.W. Avery et al., 81 Analytical Chemistry, 8365-8372 (2009).

A. Papas et al., 31 Bone Marrow Transplantation, 705-712 (2003).

Trotti et al., A multinational randomized phase III trial of iseganan hcl oral solution for reducing the severity of oral mucositis in patients receiving radiotherapy for head-and-neck malignancy, Int. J. Radiation Oncology Bilo. Phys. 200458(3):674-681.

"PolyMedix PMX-30063 Defensin-Mimetic Antibiotic Compound Shows Promising Activity for Oral Mucositis", Business Wire May 19, 2011.

T Le et al., 20 Journal of Clinical Onocology, 2808-2811 (2011).

Tew et al., "De novo design of biomimetic antimicrobial polymers," Proc Natl Acad Sci USA (2002) 99(8):5110-5114.

Thu Le et al., Palifermin Reduces Severe Mucositis in Definitive Chemoradiotherapy of Locally Advanced Head and Neck Cancer: A Randomized, Placebo-Controlled Study, Journal of Clinical Oncology, Jul. 10, 2011, vol. 29, No. 20, pp. 2808-2811.

Tew et al., "De nove design of biomimetic antimicrobial polymers", Proc Natl Acad Sci USA (2002) 99(8):5110-5114.

Loury et al., Effect of local application of the antimicrobial peptide IB-367 on the incidence and severity of oral mucositis in hamsters, Oral Surgery, Oral Medicine, Oral Pathology, 1999, pp. 544-551, vol. 87, No. 5.

Sonis et al., An animal model for mucositis induced by cencer chemotherapy, Oral Surgery, Oral Medicine, Oral Pathology, 1990, vol. 69, pp. 437-443.

Keefe et al., Updated Clinical Practice Guidelines for the Prevention and Treatment of Mucositis, Cancer, 2007, vol. 109, No. 5, pp. 820-831.

Donnelly et al., Antimicrobial therapy to prevent or treat oral mucositis, The Lancet Infectious Diseases, 2003, vol. 3, pp. 405-412.

Antman EM, et al., "Enoxaparin prevents death and cardiac ischemic events in unstable angina/non-Q-wave myocardial infarction. Results of the thrombolysis in myocardial infarction (TIMI) 11B trial," Circulation. Oct. 12, 1999;100(15)1593-601.

Arnt, L., et al., Rapid Communication: Nonhemolytic Abiogenic Polymers as Antimicrobial Peptide Mimics, Journal of Polymer Science, Part A: Polymer Chemistry, 2004; 42:3860-3864.

Barany G., et al. "Solid-phase peptide synthesis: a silver anniversary report," Int J Pept Protein Res. Dec. 1987;30(6):705-39.

Becker RC., "New thrombolytics, anticoagulants, and platelet antagonists: the future of clinical practice," J Thromb Thrombolysis. Apr. 1999; 7(2): 1995-220.

Bendetowicz AV, et al., "Pharmacokinetics and pharmacodynamics of a low molecular weight heparin (enoxaparin) after subcutaneous injection, comparison with unfractionated heparin—a three way cross over study in human volunteers," Thromb Haemost. Mar. 1994;71(3)305-13.

Brooks, B. R., et al., Charmm: A Program for Macromolecular Energy, Minimization, and Dynamics Calculations, J. Comp. Chem. 4, 187-217, 1983.

Car R., et al., "Unified approach for molecular dynamics and density-functional theory," Phys Rev Lett. Nov. 25, 1985;55(22):2471-2474.

Cohen M., et al., "A comparison of low-molecular-weight heparin with unfractionated heparin for unstable coronary artery disease. Efficacy and Safety of Subcutaceous Enoxaparin in Non-Q-Wave Coronary Events Study Groups," N Engl J. Med. Aug. 14, 1997;337(7):447-52.

Doutremepuich C., et al., "In vivo neutralization of low-molecular weight heparin fraction CY 216 by protamine," Semin Thromb Hemost. Jul. 1985;11(3):318-22.

Guillemot, D. et al., Low Dosage and Long Treatment Duration of Beta-Lactam, JAMA, Feb. 4, 1998; 279(5)365-370.

Hirsh J., et al., "Heparin and low-molecular-weight heparin: mechanisms of action, phrmacokinetics, dosing, monitoring, efficacy, and safety," Chest. Jan. 2001; 119 (1 Suppl): 64S-94S.

Hirsh J., et al., "Heparin and low-molecular-weight heparin: the Seventh ACCP Conference on Antithrombotic and Thrombolytic Therapy." Chest. Sep. 2004; 126 (3Suppl): 188S-203S.

Hirsh J., et al., "Low Molecular Weight Heparin," Blood. Jan. 1, 1992; 79(1): 1-17.

Horrow JC., "Protamine: a review of its toxicity," Anesth Analg. Mar. 1985;64(3):348-61.

Hubbard AR, et al., "Neurtralisation of heparan sulphate and low molecular weight heparin by protamine," Thromb Haemost. Feb. 18, 1985;53(1):86-9.

Lathers, C.M., Clinical pharmacology of antimicrobial use in humans and animals, The Journal of Clinical Pharmacology, 2002; 42:587-600.

Lee AT, et al., "Randomized comparision of low molecular weight heparin and coumarin derivatives on the survival of patients with cancer and venous thromboembolism," J Clin Oncol. Apr. 1, 2005; 23(10):2123-9.

Lee, M. K. and Lander, A. D., "Analysis of affinity and structural selectivity in the binding of proteins to glycosaminoglycans: development of a sensitive electrophoretic approach" Proc Natl Acad Sci U S A. Apr. 1, 1991;88(7):2768-72.

Liu, et al., Angew Chem Int Ed Engl, 2004;43:1158-1162.

Lubenow N., et al., "Heparin-induced thrombocytopenia: temporal pattern of thrombocytopenia in relation to initial use or reexposure to heparin," Chest. Jul. 2002; 122(1): 37-42.

Martin, M. G., et al., Novel Configurational-Bias Monte Carlo Method for Branched Molecules. Transferable Potentials for Phase Equilibria. 2. United-Atom Description of Branched Alkanes, J. Phys. Chem. B 103, 4508-4517, 1999.

Massonnet-Castel S., et al., "Partial reversal of low molecular weight heparin (PK 10169) anti-Xa activity by protamine sulfate: in vitro and in vivo study during cardiac surgery with extracorporeal circulation," Haemostasis. 1986;16(2):139-46.

Mehta SR, et al., "Efficacy and safety of fondaparinux versus enoxaparin in patients with acute coronary syndromes undergoing percutaneous coronary internevtion: results from the OASIS-5 trial," J Am Coll Cardiol. Oct. 30, 2007;50(18):1742-51. Epub Oct. 15, 2007.

Monroe, S., et al., Antimicrobial use and bacterial resistance, Curr Opin Microbiol, Oct. 2000; 3(5):496-501.

(56) References Cited

OTHER PUBLICATIONS

Montecolvo, M. A., et al., Outbreak of Vancomycin-, Ampicillin-, and Aminoglycosid-Resistant Enterococcus faecium Bacteremia in an Adult Oncology Unit, Antimicrobial Agents and Chemotherapy, Jun. 1994; 38(6):1363-1367.
Morabia A., "Heparin doses and major bleeding," Lancet. May 31, 1986;1(8492):1278-9.
Mureebe L., et al., "Heparin-induced thrombovytopenia: pathophysiology and management," Vasc Endovascular Surg. May-Jun. 2002;36(3:163-70.
Ofosu FA., et al., "Mechanisms of Action of Low Molecular Weight Haparins and Heparinoids," Baillieres Clin Haematol. Jul. 1990; 3(3): 505-29.
Poon MC, et al., "Platelet factor four and protamine sulfate neutralization of heparin fractionated according to anionic charge density," Thromb Haemost. Apr. 30, 1982;47(2):162-5.
Porsche R., et al., "Allergy to protamine sulfate," Heart Lung. Nov.-Dec. 1999; 28(6):418-28.
Rothlisberger, U., et al., The torsional potential of perfluoro n-alkanes: A density functional study, J. Chem. Phys., 1996, 3692-3700.
Siepmann, J. I., et al., Configurational bias Monte Carlo: a new sampling scheme for flexible chains, Mol. Phys., 1992;75(1):59-70.
Tang et al., Biomimetic facially amphilphilic antibacterial oligomers with conformationally stiff backbones, Chemistry & Biology 2006, 13:427-435.
Vippagunta et al., "Crystalline solids," Advanced Drug Delivery Reviews (2001) 48:3-26.
Vlugt, T. J. H., et al., Improving the efficiency of the configurational-bias Monte Carlo algorithm, Mol. Phys., 1998, 94 727-733.
Walenga et al., "Factor Xa inhibition in mediating anthrombotic actions: application of a synthetic haprin pentasaccharide," doctoral thesis. In. Paris: Universite Pierre et Marie Curie, Pariv VI, Paris, France, Jun. 1987.
Walenga JM, et al., "Short- and long-acting synthetic pentasaccharides as antithrombotic agents," Expert Opin Investig Drugs. Jul. 2005; 14(7):847-58.
Weiler JM, et al., "Serious adverse reactions to protamine sulfate: are alternatives needed?" J Allergy Clin Immunol. Feb. 1985;75(2):297-303.
West "Solid State Chemistry and its Application," Wiley, New York, 1988, pp. 358 and 365.

* cited by examiner

COMPOUNDS FOR USE IN TREATMENT OF MUCOSTIS

CROSS-REFERENCE TO RELATED APPLICATIONS

This application is a continuation of U.S. Ser. No. 14/456,202 filed Aug. 11, 2014, which is a continuation of U.S. Ser. No. 13/471,689 filed May 15, 2012, which claims priority to U.S. Ser. No. 61/486,455 filed May 16, 2011, each of which is incorporated herein by reference in its entirety.

FIELD OF THE INVENTION

The present invention is directed, in part, to methods of treating and/or preventing mucostitis with one or more compounds, or pharmaceutically acceptable salts thereof, disclosed herein, or compositions comprising the same.

BACKGROUND OF THE INVENTION

Oral ulcerative mucositis is a common, painful, dose-limiting toxicity of chemotherapy and radiation therapy for cancer (Sonis, Nat. Rev. Cancer, 2004, 4, 277-284; Keefe et al., Cancer, 2007, 109, 820-831; Belim et al., Support Care Cancer, 2000, 8, 33-39; and Parulekar et al., Oral Oncol., 1998, 34, 63-71). The disorder is characterized by breakdown of the oral mucosa and results in the formation of ulcerative lesions. It can significantly affect nutritional intake, mouth care, and quality of life (Lalla et al., Dent. Clin. North Am., 2005, 49, 167-184; and Duncan et al., Head Neck, 2005, 27, 421-428). The ulcerations that accompany mucositis are frequent portals of entry for oral bacteria often leading to sepsis or bacteremia. For patients receiving high-dose chemotherapy prior to hematopoietic cell transplantation, oral mucositis has been reported to be the single most debilitating complication of transplantation (Belim et al., Support Care Cancer, 2000, 8, 33-39). Infections associated with the oral mucositis lesions can cause life-threatening systemic sepsis during periods of immunosuppression (Rapoport et al., J. Clin. Oncol., 1999, 17, 2446-2453). Mucositis results in increased hospital stays and re-admission rates, and can result in interruptions or early cessation of treatment regimens (Pico et al., The Oncologist, 1998, 3, 446-451; and Elting et al., Cancer, 2003, 98, 1531-1539). The prevalence of mucositis is variable and dependent on the disease and type of treatment being used. Moderate to severe mucositis occurs in virtually all patients who receive radiation therapy for tumors of the head and neck. Among patients who are treated with induction therapy for leukemia or with many of the conditioning regimens for bone marrow transplant, is not unusual for more than three-quarters of patients to develop moderate to severe mucositis. (Belim et al., Support Care Cancer, 2000, 8, 33-39). Annually, nearly 60,000 patients receive a diagnosis of head and neck cancer (Jemal et al., CA Cancer J Clin., 2002, 52, 23-47) and severe mucositis occurs in up to 92% of these treated patients (Parulekar et al., Oral Oncol., 1998, 34, 63-71; Sonis et al., Cancer, 85, 2103-2113). Even in regimens considered to be low risk for development of mucosal toxicity, where incidence rates may range between 10-15%, the large numbers of patients receiving chemotherapy translates to a significant number of patients who experience mucositis (Rubenstein et al., Cancer, 2004, 100, 2026-2046). In addition to quality of life issues, there is a substantial impact of oral mucositis on medical care resources and costs, estimated to be $17,000 per patient, which are related to increased hospitalization stays, medical treatments and medications (Nonzee et al., Cancer, 2008, 113, 1446-1452).

Originally, it was believed that mucositis associated with chemotherapy or radiation treatment was a result of direct cytotoxicity on the basal epithelial cells of the alimentary tract believed to be particularly vulnerable because of their high turnover rate. It has become clear that the pathobiology of mucositis is more complex and involves interactions between the epithelial and the underlying layers and components of the mucosa including fibroblasts, endothelium and extracellular matrix1. Five inter-related stages have been described for the pathobiology associated with oral mucositis and appear to be similar between chemotherapy and radiation-induced lesions. An initiation phase is characterized by DNA damage, reactive oxygen species generation and basal epithelial cell death. These events lead to primary activation of various transcription factors and signal transduction pathways, including NF-κB and p53. NF-kB activation results in the production of inflammatory cytokines including tumor necrosis factor (TNF), interleukin-1β (IL-1β), interleukin-6 (IL-6) and other genes that affect mucosal integrity (Sonis, Nat. Rev. Cancer, 2004, 4, 277-284; and Sonis, Crit. Rev. Oral Biol. Med., 2002, 13, 380-390). These factors and cytokines have been identified in the mucosa and blood of patients experiencing mucositis during cancer treatments (Hall et al., Exp. Hematol., 1995, 23, 1256-1260; and Ferra et al., Haematologica, 1998, 83, 1082-1087). The primary response is amplified through positive feedback loops activating additional pro-inflammatory mediators and transduction pathways such as cyclooxygenase-2 (COX-2) and mitogen-activated protein kinase signaling (e.g., p38). Together, these pro-inflammatory responses initiate an inflammatory cascade leading to activation of matrix metalloproteinases, including MMP-1 and MMP-3, that cause further tissue damage (Tadashi, Modern Rheumatol., 2006, 16, 197-205). Ulceration then develops which damages the mucosal epithelium and creates portals for bacterial entry and colonization. This is the clinically-important stage where patients experience significant pain and debilitation. It is likely that the bacterial membrane and cell wall components, lipopolysaccharides (LPS) and lipoteichoic acid (LTA), interact with invading macrophages further stimulating the release of pro-inflammatory cytokines and tissue damage (Sonis, Oral Oncol., 1998, 34, 39-43). In severe cases, there is a risk that the bacteria can spread systemically through the underlying vasculature causing bacteremia and sepsis. Finally, healing occurs via signaling from the extracellular matrix resulting in re-epithelialization and restoration of normal mucosal integrity.

Based upon the robust population of bacteria, fungi and viruses in the oral cavity, numerous studies have concluded that the oral microflora, although not a significant factor in the primary etiology of mucositis may influence the course of the disease (Sonis, Oral Oncol., 2009, 45, 1015-1020). There is a high degree of similarity between the oral microflora of hamsters and humans, and in a hamster model of mucositis the increase in bacterial load in the ulcer lagged behind the development of the mucositis (Sonis, Oral Oncol., 2009, 45, 1015-1020). These findings do not support a primary role for bacterial numbers in driving mucositis but rather are consistent with the ulcer being a favorable environment for bacterial colonization that exacerbates the initial pathology and increases the risk of subsequent bacteremia, fever and serious infection and sepsis. Although anti-bacterial and anti-fungal strategies have proven to be ineffective in treating oral mucositis (Donnelly et al., Lancet Infect. Dis., 2003, 3, 405-412; and El-Sayed et al., J. Clin. Oncol., 2002, 20, 3956-3963), they will likely be of value in controlling fever and infection aspects of the disease at its later stages.

Despite its frequency, severity and impact on patients' ability to tolerate cancer treatment, there is currently only one approved pharmaceutical for the prevention or treatment for oral mucositis. Palifermin (Kepivance®, recombinant human keratinocyte growth factor-1) was approved for a mucositis indication in patients with hematologic malignancies receiving stem cell transplants. Its efficacy may be related to mitogenic effects on mucosal epithelium and/or alteration of cytokine profiles, including down-regulation of TNF (Logan et al., Cancer Treatment Rev., 2007, 33, 448-460). Palifermin is not widely used due in part to concerns on the potential impact of a growth factor on antineoplastic treatment. Therefore, the care for mucositis is largely palliative. Available agents include topical analgesics (lidocaine), barrier devices (GelClair), or rinses (Caphosol). Systemic analgesics are used for symptom control and antibiotics are used to control secondary infections, and mucositis-related bacteremias and sepsis. Another agent proposed to be used for treatment of mucositis is NX002, which is a peptide derived from AMP-18 (see, U.S. Pat. Nos. 7,910,543 and 7,629,317).

Antimicrobial peptides (AMPs) isolated from organisms across the phylogenetic spectrum form part of the innate immune system, and serve as the first line of defense against microbial infection in many species (Brogden, Nat. Rev. Microbiol., 2005, 3, 238-250; and Zasloff Nature, 2002, 415, 389-395). They are typically small (12-80 amino acids) cationic amphiphiles that provide protection against a wide variety of pathogenic organisms. Despite the large diversity observed in AMPs, they generally adopt highly amphiphilic topologies in which the hydrophilic and hydrophobic side chains segregate into distinctly opposing regions or faces of the molecule. It is generally believed that this amphiphilic topology is essential for insertion into and disruption of the membrane leading to microbe death (Zasloff, Nature, 2002, 415, 389-395). AMPs have remained an effective weapon against bacterial infection over evolutionary time indicating that their mechanism of action thwarts bacterial responses that lead to resistance against toxic substances. This premise is supported by direct experimental data showing that no appreciable resistance to the action of the AMPs occurs after multiple serial passages of bacteria in the presence of sub-lethal concentrations of the peptides (Gazit et al., Biochemistry, 1995, 34, 11479-11488; and Pouny et al., Biochemistry, 1992, 31, 12416-12423).

The cytotoxic activity of the cationic and amphiphilic peptides specifically targets bacteria over mammalian cells. This specificity is most likely related to fundamental differences between the two membrane types; bacteria have a large proportion of negatively charged phospholipid headgroups on their surface while the outer leaflet of mammalian cells is composed mainly of neutral lipids (Zasloff, Nature, 2002, 415, 389-395). Also, the presence of cholesterol in the animal cell membrane and other differences in lipid compositions with bacterial membranes contribute to the selectivity of the AMPs (Yang et al., J. Am. Chem. Soc., 2007, 129, 12141-12147).

Given their very broad specificity, amphiphilic AMPs appear to be ideal therapeutic agents. However, significant pharmaceutical issues, including poor tissue distribution, systemic toxicity, and difficulty and expense of manufacturing, have severely hampered their clinical progress. A series of non-peptidic mimics of the AMPs that have distinct advantages over peptides for pharmaceutical uses have been developed. The goal of the synthetic approach was to capture the structural and biological properties of AMPs within the framework of inexpensive oligomers (Scott et al., Curr. Opin. Biotechnol., 2008, 19, 620-627; and Tew et al., ACC, 2009, 43, 30-39). It was reasoned that small synthetic oligomers that adopt amphiphilic secondary structures while exhibiting potent and selective antimicrobial activity would be less expensive to produce, have better tissue distribution, and be much easier to fine-tune structurally to improve activity and minimize toxicity.

Clearly, there is a high medical need for the development of safe and effective therapies that can prevent or significantly lessen the clinical course of ulcerative mucositis without negatively influencing the cancer therapy. The apparent multifactorial pathogenesis of oral mucositis suggests that a therapeutic agent that possesses dual anti-inflammatory and antimicrobial activities may be highly effective in treating the disease.

SUMMARY OF THE INVENTION

The present invention provides methods of treating and/or preventing mucositis in a mammal comprising administering to the mammal in need thereof a therapeutically effective amount of a compound of Formula I:

I

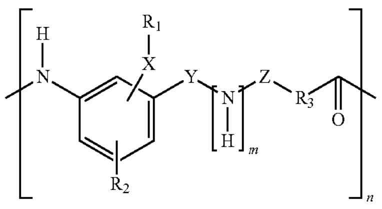

or a pharmaceutically acceptable salt thereof, wherein: X is O or S; $R_1$ is $C_1$-$C_9$ straight or branched chain alkyl, optionally substituted with one or more —$NH_2$ or —NH—C(═NH)$NH_2$; Y is a bond or a carbonyl; Z is a bond or a carbonyl; $R_2$ is hydrogen or $C_1$-$C_9$ straight or branched chain alkyl optionally substituted with one or more —$NH_2$ or —NH—C(═NH)$NH_2$; or $R_2$ is —X—$R_1$; $R_3$ is methylene or

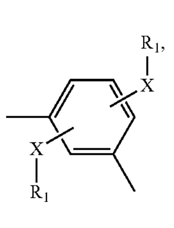

wherein the methylene is substituted with $C_1$-$C_9$ straight or branched chain alkyl, wherein the $C_1$-$C_9$ straight or branched chain alkyl is optionally substituted with one or more —$NH_2$ or —NH—C(═NH)$NH_2$; n is 2-10; and m is 1 or 2.

The present invention also provides methods of treating and/or preventing mucositis in a mammal comprising administering to the mammal in need thereof a therapeutically effective amount of a compound of Formula II:

II

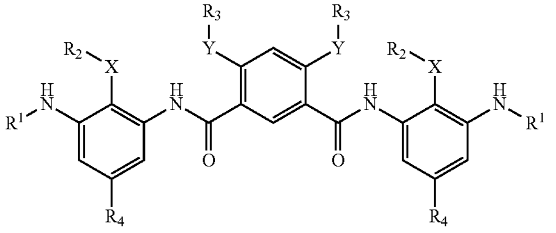

or a pharmaceutically acceptable salt thereof, wherein: X is O or S; Y is O or S; $R_1$ is H or —C(═O)-A, where A is $C_1$-$C_9$ straight or branched alkyl optionally substituted with one or more —$NH_2$, —$N(CH_3)_2$ or —NH—C(═NH)$NH_2$; $R_2$ is $C_1$-$C_9$ straight or branched alkyl optionally substituted with one or more —$NH_2$, —$N(CH_3)_2$ or —NH—C(═NH)$NH_2$; $R_3$ is $C_1$-$C_9$ straight or branched alkyl optionally substituted with one or more —$NH_2$, —$N(CH_3)_2$ or —NH—C(═NH)$NH_2$; and $R_4$ is H, —B, or —C(═O)—O—B, where B is $C_1$-$C_9$ straight or branched alkyl.

The present invention also provides methods of treating and/or preventing mucositis in a mammal comprising administering to the mammal in need thereof a therapeutically effective amount of a compound of Formula III:

III

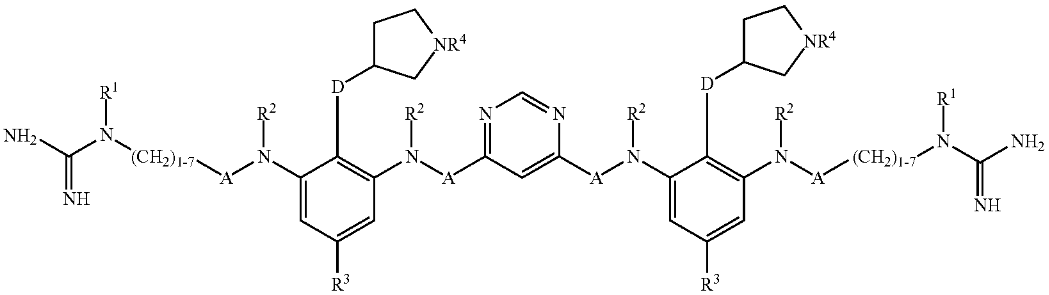

or a pharmaceutically acceptable salt thereof, wherein: each A is, independently, —C═O, —C═S, or $CH_2$; each D is, independently, O or S; each $R^1$ is, independently, hydrogen, $C_{1-3}$alkyl, $C_{1-3}$alkoxy, halo, or halo$C_{1-3}$alkyl; each $R^2$ is, independently, hydrogen, $C_{1-3}$alkyl, $C_{1-3}$alkoxy, halo, or halo$C_{1-3}$alkyl; each $R^3$ is, independently, hydrogen, $C_{1-4}$alkyl, $C_{1-4}$alkoxy, halo, or halo$C_{1-4}$alkyl; and each $R^4$ is, independently, hydrogen, $C_{1-3}$alkyl, $C_{1-3}$alkoxy, halo, or halo$C_{1-3}$alkyl.

The present invention also provides methods of treating and/or preventing mucositis in a mammal comprising administering to the mammal in need thereof a therapeutically effective amount of a compound of Formula IV:

IV

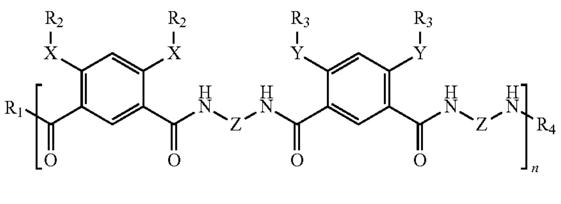

or a pharmaceutically acceptable salt thereof, wherein: n=1 to 10; X is O or S; Y is O or S; Z is a bond, $C_1$-$C_9$ straight or branched alkyl, or a 1,4-cyclohexyl; $R_1$ is $NH_2$ or NH-A, where A is $C_1$-$C_9$ straight or branched alkyl, where A is optionally substituted with —$NH_2$, —$N(CH_3)_2$ or —NH—C(═NH)$NH_2$; $R_2$ is $C_1$-$C_9$ straight or branched alkyl, where $R_2$ is optionally substituted with one or more —$NH_2$, —$N(CH_3)_2$ or —NH—C(═NH)$NH_2$; $R_3$ is $C_1$-$C_9$ straight or branched alkyl, where $R_3$ is optionally substituted with one or more —$NH_2$, —$N(CH_3)_2$ or —NH—C(═NH)$NH_2$; $R_4$ is H or

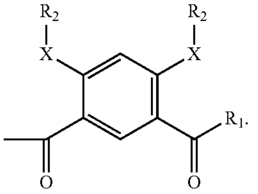

The present invention also provides methods of treating and/or preventing mucositis in a mammal comprising administering to the mammal in need thereof a therapeutically effective amount of a compound of Formula V:

V

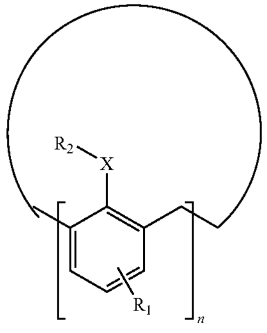

or a pharmaceutically acceptable salt thereof, wherein: n is 2-8; X is a bond, O or —O—$CH_2$—C(═O)—O—; $R_1$ is -A or —O-A, where A is $C_1$-$C_9$ straight or branched alkyl; and $R_2$ is $C_1$-$C_9$ straight or branched alkyl, where $R_2$ is optionally substituted with one or more —$NH_2$, —$N(CH_3)_2$, or —NH—C(═NH)$NH_2$.

The present invention also provides methods of treating and/or preventing mucositis in a mammal comprising administering to the mammal in need thereof a therapeutically effective amount of a compound of Formula VI:

VI

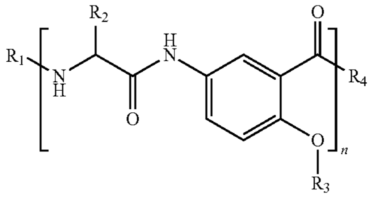

or a pharmaceutically acceptable salt thereof, wherein: n is 2 to 10; $R_1$ is H or

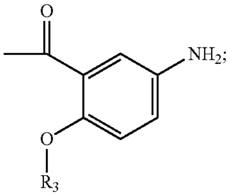

$R_2$ is $C_1$-$C_9$ straight or branched alkyl, where $R_2$ is optionally substituted with one or more —$NH_2$, —$N(CH_3)_2$ or —NH—C(═NH)$NH_2$; $R_3$ is $C_1$-$C_9$ straight or branched alkyl, where $R_2$ is optionally substituted with one or more —$NH_2$, —$N(CH_3)_2$ or —NH—C(═NH)$NH_2$; $R_4$ is OH, $NH_2$ or

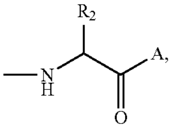

where A is OH or $NH_2$.

The present invention also provides methods of treating and/or preventing mucositis in a mammal comprising administering to the mammal in need thereof a therapeutically effective amount of a compound of Formula VII:

VII

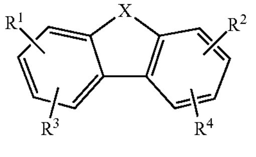

or a pharmaceutically acceptable salt thereof, wherein: X is $C(R^7)C(R^8)$, C(═O), $N(R^9)$, O, S, S(═O), or S(═O)$_2$; $R^7$, $R^8$, and $R^9$ are, independently, H, $C_1$-$C_8$alkyl, $C_1$-$C_8$alkoxy, halo, OH, $CF_3$, or aromatic group; $R^1$ and $R^2$ are, independently, H, $C_1$-$C_8$alkyl, $C_1$-$C_8$alkoxy, halo, OH, halo$C_1$-$C_8$alkyl, or CN; $R^3$ and $R^4$ are, independently, carbocycle $(R^5)(R^6)$; each $R^5$ and each $R^6$ are, independently, H, $C_1$-$C_8$alkyl, $C_1$-$C_8$alkoxy, halo, OH, $CF_3$, aromatic group, heterocycle, or the free base or salt form of —$(CH_2)_n$—$NH_2$, or —$(CH_2)_n$—NH—$(CH_2)_n$—$NH_2$, or —$(CH_2)_n$—NH—C(═NH)$NH_2$, where each n is, independently, 1 to 8.

The present invention also provides methods of treating and/or preventing mucositis in a mammal comprising administering to the mammal in need thereof a therapeutically effective amount of a compound of Formula VIII:

VIII

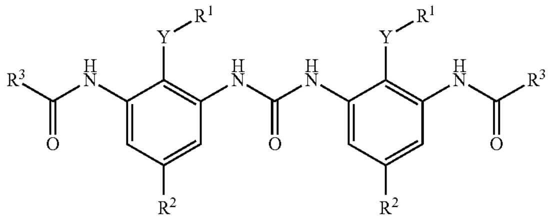

or a pharmaceutically acceptable salt thereof, wherein: X is O or S; each Y is, independently, O, S, or N; each $R^1$ is, independently, H, 5- or 6-membered heterocycle, or the free base or salt form of —$(CH_2)_n$—$NH_2$ or —$(CH_2)_n$—NH—C(═NH)$NH_2$, where each n is, independently, 1 to 4; or each $R^1$ is, independently, together with Y a 5- or 6-membered heterocycle; each $R^2$ is, independently, H, $CF_3$, $C(CH_3)_3$, halo, or OH; and each $R^3$ is, independently, —$(CH_2)_n$—$NH_2$ or —$(CH_2)_n$—NH—C(═NH)$NH_2$, where each n is, independently, 1 to 4.

The present invention also provides methods of treating and/or preventing mucositis in a mammal comprising administering to the mammal in need thereof a therapeutically effective amount of a compound of Formula IX:

$$Q—X—Z—X—Q \qquad IX$$

or a pharmaceutically acceptable salt thereof, wherein: Z is

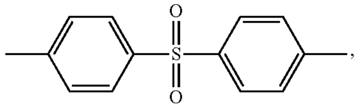

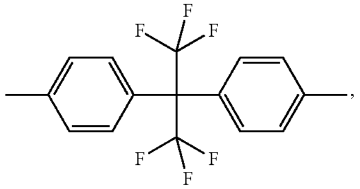

or phenyl; each Q is, independently,

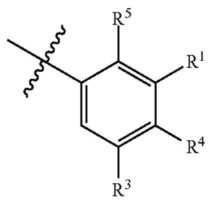

or —C(═O)—$(CH_2)_b$—NH—C(═NH)—$NH_2$, where each b is, independently, 1 to 4; each X is, independently, O, S, or N; each $R^1$ is, independently, H, $CF_3$, $C(CH_3)_3$, halo, or OH; each $R^3$ is, independently, H, —NH—$R^2$, —$(CH_2)_r$—$NH_2$, —$NH_2$, —NH—$(CH_2)_w$—$NH_2$, or

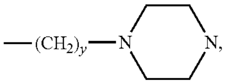

where each r is, independently, 1 or 2, each w is, independently, 1 to 3, and each y is, independently, 1 or 2; each $R^2$ is, independently, H, or the free base or salt form of —$(CH_2)_n$—$NH_2$ or —$(CH_2)_n$—NH—C(═NH)$NH_2$, where each n is, independently, 1 to 4; each $R^4$ is, independently, H, —NH—C(═O)—$(CH_2)_p$—NH—C(═NH)—$NH_2$ or

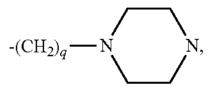

where each p is, independently, 1 to 6, and each q is, independently, 1 or 2; and each $R^5$ is, independently, H or $CF_3$.

The present invention also provides methods of treating and/or preventing mucositis in a mammal comprising administering to the mammal in need thereof a therapeutically effective amount of a compound of Formula X:

X

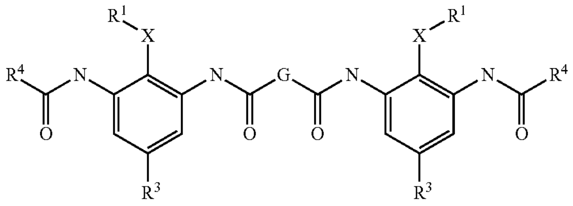

or a pharmaceutically acceptable salt thereof, wherein: G is

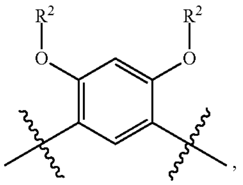

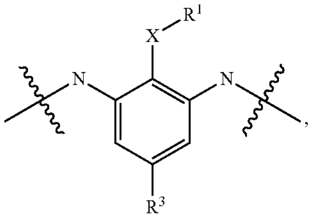

or

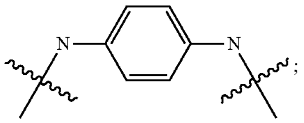 [SMILES: *Nc1ccc(N*)cc1]

each X is, independently, O or S; each $R^1$ is, independently,

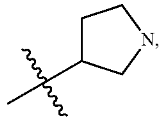

or the free base or salt form of —$(CH_2)_n$—$NH_2$ or —$(CH_2)_n$—NH—C(═NH)$NH_2$, where each n is, independently, 1 to 4; each $R^2$ is, independently, H, $C_1$-$C_8$alkyl, or the free base or salt form of —$(CH_2)_n$—$NH_2$ or —$(CH_2)_n$—NH—C(═NH)$NH_2$, where each n is, independently, 1 to 4; each $R^3$ is, independently, H, $CF_3$, $C(CH_3)_3$, halo, or OH; and each $R^4$ is, independently, —$(CH_2)_n$—$NH_2$ or —$(CH_2)_n$—NH—C(═NH)$NH_2$, where each n is, independently, 1 to 4.

The present invention also provides methods of treating and/or preventing mucositis in a mammal comprising administering to the mammal in need thereof a therapeutically effective amount of a compound of Formula XI:

XI

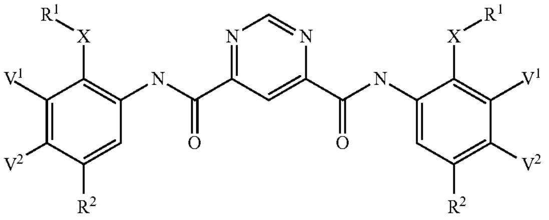

or a pharmaceutically acceptable salt thereof, wherein: each X is, independently, O, S, or S(═O)$_2$; each $R^1$ is, independently, —$(CH_2)_n$—$NH_2$, —$(CH_2)_n$—NH—C(═NH)$NH_2$, or —$(CH_2)_n$—NH—C(═O)—$R^4$, where each n is, independently, 1 to 4, and each $R^4$ is, independently, H, $C_1$-$C_3$alkyl, or —$(CH_2)_p$—$NH_2$, where each p is, independently, 1 or 2; each $R^2$ is, independently, H, halo, $CF_3$, or $C(CH_3)_3$; and each $V^2$ is H, and each $V^1$ is, independently, —N—C(═O)—$R^3$, where each $R^3$ is, independently, —$(CH_2)_n$—$NH_2$ or —$(CH_2)_n$—NH—C(═NH)$NH_2$, where each n is, independently, 1 to 4; or each $V^1$ is H and each $V^2$ is, independently, —S—$R^5$, where each $R^5$ is, independently, —$(CH_2)_n$—$NH_2$ or —$(CH_2)_n$—NH—C(═NH)$NH_2$, where each n is, independently, 1 to 4.

The present invention also provides methods of treating and/or preventing mucositis in a mammal comprising administering to the mammal in need thereof a therapeutically effective amount of a compound of Formula XII:

XII

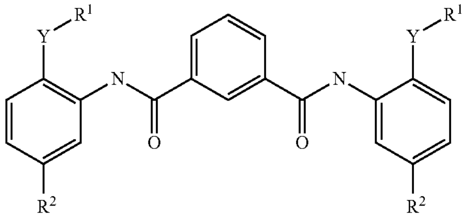

or a pharmaceutically acceptable salt thereof, wherein: each Y is, independently, O, S, or NH; each $R^1$ is, independently, —$(CH_2)_n$—$NH_2$ or —$(CH_2)_n$—NH—C(═NH)$NH_2$, where each n is, independently, 1 to 4; and each $R^2$ is, independently, H, halo, $CF_3$, or $C(CH_3)_3$.

The present invention also provides methods of treating and/or preventing mucositis in a mammal comprising administering to the mammal in need thereof a therapeutically effective amount of a compound of Formula XIII:

XIII

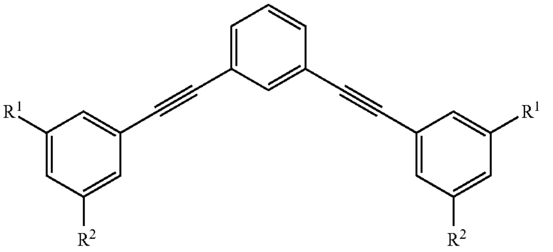

or a pharmaceutically acceptable salt thereof, wherein: each $R^1$ is, independently, H, $C_1$-$C_8$alkyl, $C_1$-$C_8$alkoxy, halo, OH, $CF_3$, or CN; each $R^2$ is, independently, —$(CH_2)_n$—$NH_2$ or —$(CH_2)_n$—NH—C(═NH)$NH_2$, where each n is, independently, 1 to 4.

The present invention also provides methods of treating and/or preventing mucositis in a mammal comprising administering to the mammal in need thereof a therapeutically effective amount of a compound of Formula XIV:

XIV

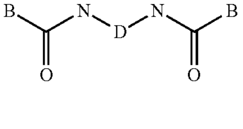

or a pharmaceutically acceptable salt thereof, wherein: D is

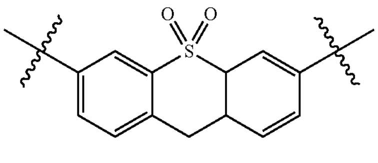 [SMILES: *C1=CC2C(C=C1)Cc1ccc(*)cc1S2(=O)=O]

or

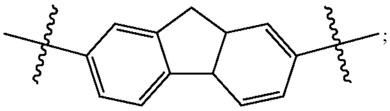 [SMILES: *C1=CC2Cc3cc(*)ccc3C2C=C1]

;

each B is, independently, —$(CH_2)_n$—NH—C(═NH)$NH_2$, where each n is, independently, 1 to 4

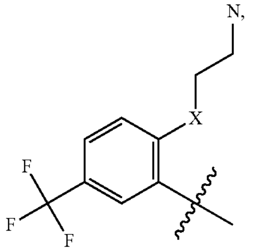

or

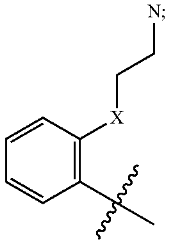

and each X is, independently, O or S.

The present invention also provides methods of treating and/or preventing mucositis in a mammal comprising administering to the mammal in need thereof a therapeutically effective amount of a compound of Formula XV:

XV

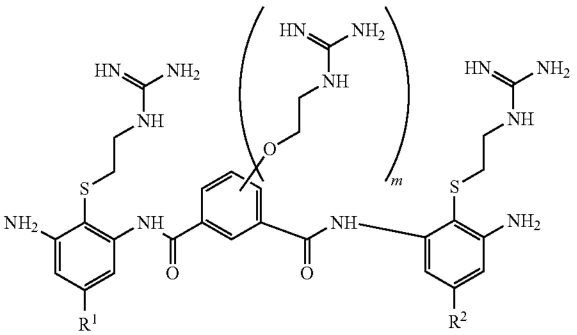

or a pharmaceutically acceptable salt thereof, wherein: $R^1$ is H or $C_{1-10}$ alkyl; $R^2$ is H or $C_{1-10}$ alkyl; and m is 1 or 2.

The present invention also provides methods of treating and/or preventing mucositis in a mammal comprising administering to the mammal in need thereof a therapeutically effective amount of a compound of Formula XVI:

XVI

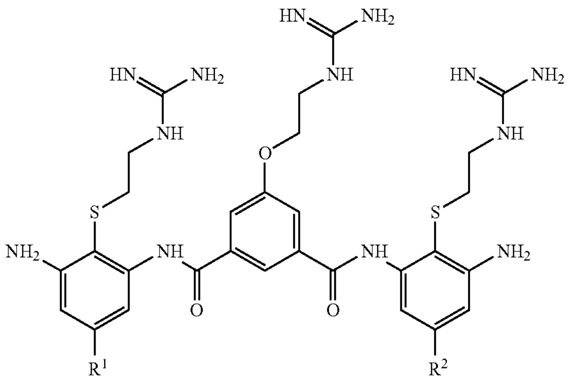

or a pharmaceutically acceptable salt thereof, wherein: $R^1$ is H or $C_{1-8}$ alkyl; and $R^2$ is H or $C_{1-8}$ alkyl.

The present invention also provides methods of treating and/or preventing mucositis in a mammal comprising administering to the mammal in need thereof a therapeutically effective amount of a compound of Formula XVII:

XVII

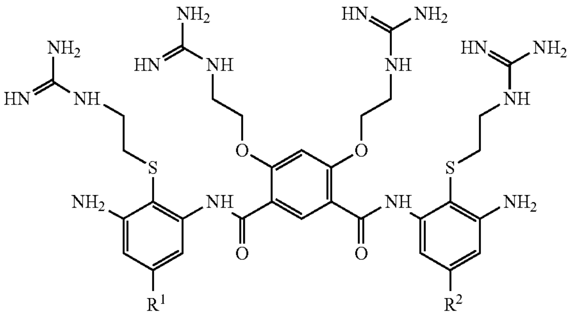

or a pharmaceutically acceptable salt thereof, wherein: $R^1$ is H or $C_{1-8}$ alkyl; and $R^2$ is H or $C_{1-8}$ alkyl.

The present invention also provides methods of treating and/or preventing mucositis in a mammal comprising administering to the mammal in need thereof a therapeutically effective amount of a compound of Formula XVIII:

$$R^1—[—X\text{-}A_1\text{-}Y—X\text{-}A_2\text{-}Y—]_m—R^2 \quad \text{XVIII}$$

or a pharmaceutically acceptable salt thereof, wherein: each X is, independently, $NR^8$, —$N(R^8)N(R^8)$—, O, or S; each Y is, independently, C═O, C═S, O═S═O, —C(═O)C(═O)—, or —$CR^aR^b$—; $R^a$ and $R^b$ are each, independently, hydrogen, a PL group, or an NPL group; each $R^8$ is, independently, hydrogen or alkyl; $A_1$ and $A_2$ are each, independently, optionally substituted arylene or optionally substituted heteroarylene, wherein $A_1$ and $A_2$ are, independently, optionally substituted with one or more PL group(s), one or more NPL group(s), or a combination of one or more PL group(s) and one or more NPL group(s); or each $A_1$ is, independently, optionally substituted arylene or optionally substituted heteroarylene, and each $A_2$ is a $C_3$ to $C_8$ cycloalkyl or —$(CH_2)_q$—, wherein q is 1 to 7, wherein $A_1$ and $A_2$ are, independently, optionally substituted with one or more PL group(s), one or more NPL group(s), or a combination of one or more PL group(s) and one or more NPL group(s); or each $A_2$ is optionally substituted arylene or optionally substituted heteroarylene, and each $A_1$ is a $C_3$ to $C_8$ cycloalkyl or —$(CH_2)_q$—, wherein q is 1 to 7, wherein $A_1$ and $A_2$ are each, independently, optionally substituted with one or more PL group(s), one or more NPL group(s), or a combination of one or more PL group(s) and one or more NPL group(s); $R^1$ is hydrogen, a PL group, or an NPL group, and $R^2$ is —X-$A_1$—Y—$R^{11}$, wherein $R^{11}$ is hydrogen, a PL group, or an NPL group; or $R^1$ and $R^2$ are each, independently, hydrogen, a PL group, or an NPL group; or $R^1$ and $R^2$ together are a single bond; or $R^1$ is —Y-$A_2$-X—$R^{12}$, wherein $R^{12}$ is hydrogen, a PL group, or an NPL group, and $R^2$ is hydrogen, a PL group, or an NPL group; each NPL group is, independently, —$B(OR^4)_2$ or —$(NR^{3'})_{q1NPL}$—$U^{NPL}$-$LK^{NPL}$-$(NR^{3''})_{q2NPL}$—$R^{4'}$, wherein: $R^3$, $R^{3'}$, and $R^{3''}$ are each, independently, hydrogen, alkyl, or alkoxy; $R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substitutents, wherein each substituent is, independently, alkyl, halo, or haloalkyl; each $U^{NPL}$ is, independently, absent or O, S, S(═O), S(═O)$_2$, $NR^3$, —C(═O)—, —C(═O)—$NR^3$—, —C(═O)—N═N—$NR^3$—, —C(═O)—$NR^3$—N═N—, —N═N—$NR^3$—, —C(═N—$N(R^3)_2$)—, —C(═$NR^3$)—, —C(═O)O—, —C(═O)S—, —C(═S)—, —O—P(═O)$_2$O—, —S—C═N—, or —C(═O)—$NR^3$—O—, wherein groups with two chemically nonequivalent termini can adopt both possible orientations; each $LK^{NPL}$ is, independently, —$(CH_2)_{pNPL}$— or $C_{2-8}$ alkenylenyl, wherein each of the —$(CH_2)_{pNPL}$ and $C_{2-8}$ alkenylenyl is optionally substituted with one or more substituents, wherein each substituent is, independently, amino, hydroxyl, aminoalkyl, hydroxylalkyl, or alkyl; each pNPL is, independently, an integer from 0 to 8; q1 NPL and q2NPL are each, independently, 0, 1, or 2; each PL group is, independently, halo, hydroxyethoxymethyl, methoxyethoxymethyl, polyoxyethylene, or —$(NR^{5'})_{q1PL}$—$U^{PL}$-$LK^{PL}$-$(NR^{5''})_{q2PL}$—V, wherein: $R^5$, $R^{5'}$, and $R^{5''}$ are each, independently, hydrogen, alkyl, or alkoxy; each $U^{PL}$ is, independently, absent or O, S, S(═O), S(═O)$_2$, $NR^5$, —C(═O)—, —C(═O)—$NR^5$—, —C(═O)—N═N—$NR^5$—, —C(═O)—$NR^5$—N═N—, —N═N—$NR^5$—, —C(═N—$N(R^5)_2$)—, —C(═$NR^5$)—, —C(═O)O—, —C(═O)S—, —C(═S)—, —O—P(═O)$_2$O—, —S—C═N—, or —C(═O)—$NR^5$—O—, wherein groups with two chemically nonequivalent termini can adopt either of the two possible orientations; each V is, independently, nitro, cyano, amino, halo, hydroxy, alkoxy, alkylthio, alkylamino, dialkylamino, —$NH(CH_2)_pNH_2$ wherein p is 1 to 5, —C(═O)$NH(CH_2)_pNH_2$ wherein p is 1 to 5, —C(═O)$NH(CH_2)_p$NHC(═NH)$NH_2$ wherein p is 1 to 5, —C(═O)$NH(CH_2)_p$NHC(═O)$NH_2$ wherein p is 1 to 5, —NHC(═O)-alkyl, —$N(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, semicarbazone, aryl, cycloalkyl, heterocycloalkyl, or heteroaryl, wherein each of the aryl and cycloalkyl is substituted with one or more substitutents, wherein each of the heterocycloalkyl and heteroaryl is optionally substituted with one or more substituents, and wherein each of the subsituents for the aryl, cycloalkyl, heterocycloalkyl, and heteroaryl is, independently, nitro, cyano, amino, halo, hydroxy, alkoxy, alkylthio, alkylamino, dialkylamino, —$NH(CH_2)_pNH_2$ wherein p is 1 to 5, —$N(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, semicarbazone, aminosulfonyl, aminoalkoxy, aminoalkythio, lower acylamino, or benzyloxycarbonyl; each $R^c$ is, independently, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, $C_{1-6}$ alkyl, $C_{1-6}$ haloalkyl, aryl, arylalkyl, heteroaryl, heteroarylalkyl, cycloalkyl, or heterocycloalkyl; $R^d$ and $R^e$ are, independently, H, $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, or heterocycloalkyl; or $R^d$ and $R^e$ together with the N atom to which they are attached form a 4-, 5-, 6-, 7-, or 8-membered heterocycloalkyl; each $LK^{PL}$ is, independently, $—(CH_2)_{pPL}—$ or $C_{2-8}$ alkenylenyl, wherein each of the $—(CH_2)_{pNPL}—$ and $C_{2-8}$ alkenylenyl is optionally substituted with one or more substituents, wherein each substituent is, independently, amino, hydroxyl, aminoalkyl, hydroxylalkyl, or alkyl; each pPL is, independently, an integer from 0-8; q1PL and q2PL are each, independently, 0, 1, or 2; and m is an integer from 1 to about 20.

The present invention also provides methods of treating and/or preventing mucositis in a mammal comprising administering to the mammal in need thereof a therapeutically effective amount of a compound of Formula XIX:

$$R^1—[—X\text{-}A_1\text{-}X—Y\text{-}A_2\text{-}Y—]_m—R^2 \qquad \text{XIX}$$

or a pharmaceutically acceptable salt thereof, wherein: each X is, independently, $NR^8$, O, S, $—N(R^8)N(R^8)—$, $—N(R^8)—(N{=}N)—$, $—(N{=}N)—N(R^8)—$, $—C(R^7R^{7'})NR^8—$, $—C(R^7R^{7'})O—$, or $—C(R^7R^{7'})S—$; each Y is, independently, $C{=}O$, $C{=}S$, $O{=}S{=}O$, $—C({=}O)C({=}O)—$, $C(R^6R^{6'})C{=}O$, or $C(R^6R^{6'})C{=}S$; each $R^8$ is, independently, hydrogen or alkyl; each $R^7$ and each $R^{7'}$ are, independently, hydrogen or alkyl; or $R^7$ and $R^{7'}$ together form $—(CH_2)_p—$, wherein p is 4 to 8; each $R^6$ and each $R^{6'}$ are, independently, hydrogen or alkyl; or $R^6$ and $R^{6'}$ together form $—(CH_2)_2NR^{12}(CH_2)_2—$, wherein $R^{12}$ is hydrogen, $—C({=}N)CH_3$, or $—C({=}NH)—NH_2$; $A_1$ and $A_2$ are each, independently, optionally substituted arylene or optionally substituted heteroarylene, wherein $A_1$ and $A_2$ are each, independently, optionally substituted with one or more PL group(s), one or more NPL group(s), or a combination of one or more PL group(s) and one or more NPL group(s); or each $A_2$ is, independently, optionally substituted arylene or optionally substituted heteroarylene, and each $A_1$ is, independently, optionally substituted $C_3$ to $C_8$ cycloalkyl, wherein $A_1$ and $A_2$ are each, independently, optionally substituted with one or more PL group(s), one or more NPL group(s), or a combination of one or more PL group(s) and one or more NPL group(s); $R^1$ is hydrogen, a PL group, or an NPL group, and $R^2$ is $—X\text{-}A_1\text{-}X—R^1$, wherein $A_1$ is as defined above and is optionally substituted with one or more PL group(s), one or more NPL group(s), or a combination of one or more PL group(s) and one or more NPL group(s); or $R^1$ is hydrogen, a PL group, or an NPL group, and $R^2$ is $—X\text{-}A'\text{-}X—R^1$, wherein A' is $C_3$ to $C_8$ cycloalkyl, aryl, or heteroaryl and is optionally substituted with one or more PL group(s), one or more NPL group(s), or a combination of one or more PL group(s) and one or more NPL group(s); or $R^1$ is $—Y\text{-}A_2\text{-}Y—R^2$, and each $R^2$ is, independently, hydrogen, a PL group, or an NPL group; or $R^1$ is —Y-A' and $R^2$ is —X-A', wherein each A' is, independently, $C_3$ to $C_8$ cycloalkyl, aryl, or heteroaryl and is optionally substituted with one or more PL group(s), one or more NPL group(s), or a combination of one or more PL group(s) and one or more NPL group(s); or $R^1$ and $R^2$ are, independently, a PL group or an NPL group; or $R^1$ and $R^2$ together form a single bond; each NPL is, independently, $—B(OR^4)_2$ or $—(NR^{3'})_{q1NPL}—U^{NPL}\text{-}LK^{NPL}\text{-}(NR^{3'})_{q2NPL}—R^{4'}$, wherein: $R^3$, $R^{3'}$, and $R^{3''}$ are each, independently, hydrogen, alkyl, or alkoxy; $R^4$ and $R^{4'}$ are each, independently, hydrogen, alkyl, alkenyl, alkynyl, cycloalkyl, aryl, and heteroaryl, wherein each of the alkyl, alkenyl, alkynyl, cycloalkyl, aryl, and heteroaryl is optionally substituted with one or more alkyl or halo groups; each $U^{NPL}$ is, independently, absent or O, S, $S({=}O)$, $S({=}O)_2$, $NR^3$, $—C({=}O)—$, $—C({=}O)—NR^3—$, $—C({=}O)—N{=}N—NR^3—$, $—C({=}O)—NR^3—N{=}N—$, $—N{=}N—NR^3—$, $—C({=}N—N(R^3)_2)—$, $—C({=}NR^3)—$, $—C({=}O)O—$, $—C({=}O)S—$, $—C({=}S)—$, $—O—P({=}O)_2O—$, $—S—C{=}N—$, or $—C({=}O)—NR^3—O—$, wherein groups with two chemically nonequivalent termini can adopt both possible orientations; each $LK^{NPL}$ is, independently, $—(CH_2)_{pNPL}—$ or $C_{2-8}$ alkenylenyl, wherein each of the $—(CH_2)_{pNPL}—$ and $C_{2-8}$ alkenylenyl is optionally substituted with one or more substituents, wherein each substituent is, independently, amino, hydroxyl, aminoalkyl, hydroxylalkyl, or alkyl; each pNPL is, independently, an integer from 0 to 8; q1NPL and q2NPL are each, independently, 0, 1, or 2; each PL is, independently, halo, hydroxyethoxymethyl, methoxyethoxymethyl, polyoxyethylene, or $—(NR^{5'})_{q1PL}—U^{PL}\text{-}LK^{PL}\text{-}(NR^{5'})_{q2PL}—V$, wherein: $R^5$, $R^{5'}$, and $R^{5''}$ are each, independently, hydrogen, alkyl, and alkoxy; each $U^{PL}$ is, independently, absent or O, S, $S({=}O)$, $S({=}O)_2$, $NR^5$, $—C({=}O)—$, $—C({=}O)—NR^5—$, $—C({=}O)—N{=}N—NR^5—$, $—C({=}O)—NR^5—N{=}N—$, $—N{=}N—NR^5—$, $—C({=}N—N(R^5)_2)—$, $—C({=}NR^5)—$, $—C({=}O)O—$, $—C({=}O)S—$, $—C({=}S)—$, $—O—P({=}O)_2O—$, $—S—C{=}N—$, or $—C({=}O)—NR^5—O—$, wherein groups with two chemically nonequivalent termini can adopt either of the two possible orientations; each V is, independently, nitro, cyano, amino, halo, hydroxy, alkoxy, alkylthio, alkylamino, dialkylamino, $—NH(CH_2)_pNH_2$ wherein p is 1 to 5, $—C({=}O)NH(CH_2)_pNH_2$ wherein p is 1 to 5, $—C({=}O)NH(CH_2)_pNHC({=}NH)NH_2$ wherein p is 1 to 5, $—C({=}O)NH(CH_2)_pNHC({=}O)NH_2$ wherein p is 1 to 5, $—NHC({=}O)$-alkyl, $—N(CH_2CH_2NH_2)_2$, diazamino, amidino, guanidino, ureido, carbamoyl, $—C({=}O)OH$, $—C({=}O)OR^c$, $—C({=}O)NH—OH$, $—O—NH—C({=}NH)NH_2$, $—NH—S({=}O)_2OH$, $S({=}O)_2OH$, $NR^dR^e$, semicarbazone, aryl, cycloalkyl, heterocycloalkyl, or heteroaryl, wherein each of the aryl and cycloalkyl is substituted with one or more substitutents, wherein each of the heterocycloalkyl, and heteroaryl is optionally substituted with one or more substituents, and wherein each of the subsituents for the aryl, cycloalkyl, heterocycloalkyl, and heteroaryl is, independently, nitro, cyano, amino, halo, hydroxy, alkoxy, alkylthio, alkylamino, dialkylamino, $—NH(CH_2)_pNH_2$ wherein p is 1 to 5, $—N(CH_2CH_2NH_2)_2$, diazamino, amidino, guanidino, ureido, carbamoyl, $—C({=}O)OH$, $—C({=}O)OR^c$, $—C({=}O)NH—OH$, $—O—NH—C({=}NH)NH_2$, $—NH—S({=}O)_2OH$, $S({=}O)_2OH$, $NR^dR^e$, semicarbazone, aminosulfonyl, aminoalkoxy, aminoalkythio, lower acylamino, or benzyloxycarbonyl; each $LK^{PL}$ is, independently, $—(CH_2)_{pPL}—$ or $C_{2-8}$ alkenylenyl, wherein each of the $—(CH_2)_{pNPL}—$ and $C_{2-8}$ alkenylenyl is optionally substituted with one or more substituents, wherein each substituent is, independently, amino, hydroxyl, aminoalkyl, hydroxylalkyl, or alkyl; each pPL is, independently, an integer from 0 to 8; q1PL and q2PL are each, independently, 0, 1, or 2; and m is an integer from 1 to about 20.

The present invention also provides methods of treating and/or preventing mucositis in a mammal comprising administering to the mammal in need thereof a therapeutically effective amount of a compound of Formula XX:

$$\begin{array}{l} \quad Y\text{-}[\text{-}X\text{-}A_1\text{-}Y\text{-}X\text{-}A_2\text{-}Y\text{-}]_{m11}\text{-}R^{2a} \\ / \\ L^1 \\ \backslash \\ \quad Y\text{-}[\text{-}X\text{-}A_1\text{-}Y\text{-}X\text{-}A_2\text{-}Y\text{-}]_{m12}\text{-}R^{2b} \end{array}$$

or a pharmaceutically acceptable salt thereof, wherein: each X is, independently, $NR^8$; each Y is C═O; each $R^8$ is, independently, hydrogen or alkyl; each $A_2$ is optionally substituted arylene or optionally substituted heteroarylene, and each $A_1$ is —$(CH_2)_q$—, wherein q is 1 to 7, wherein $A_1$ and $A_2$ are each, independently, optionally substituted with one or more PL group(s), one or more NPL group(s), or a combination of one or more PL group(s) and one or more NPL group(s); $R^2$ and $R^{2a}$ are each, independently, hydrogen, a PL group, an NPL group or —X-$A_1$-Y—$R^{11}$, wherein $R^{11}$ is hydrogen, a PL group, or an NPL group; $L^1$ is $C_{1-10}$alkylene optionally substituted with one or more substitutents, wherein each substituent is, independently, alkyl, halo, haloalkyl, aminoalkyl, hydroxylalkyl, V, or —$(CH_2)_{pPL}$—V, wherein pPL is an integer from 1 to 5; each NPL group is, independently, —$B(OR^4)_2$ or —$(NR^{3'})_{q1NPL}$—$U^{NPL}$-$LK^{NPL}$-$(NR^{3''})_{q2NPL}$—$R^{4'}$, wherein: $R^3$, $R^{3'}$, and $R^{3''}$ are each, independently, hydrogen, alkyl, or alkoxy; $R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substituents, wherein each substituent is, independently, alkyl, halo, or haloalkyl; each $U^{NPL}$ is, independently, absent or O, S, S(═O), $S(═O)_2$, $NR^3$, —C(═O)—, —C(═O)—$NR^3$—, —C(═O)—N═N—$NR^3$—, —C(═O)—$NR^3$—N═N—, —N═N—$NR^3$—, —C(═N—$N(R^3)_2$)—, —C(═$NR^3$)—, —C(═O)O—, —C(═O)S—, —C(═S)—, —O—P$(═O)_2$O—, —S—C═N—, or —C(═O)—$NR^3$—O—, wherein groups with two chemically nonequivalent termini can adopt both possible orientations; each $LK^{NPL}$ is, independently, —$(CH_2)_{pNPL}$— and $C_{2-8}$ alkenylenyl, wherein each of the —$(CH_2)_{pNPL}$ and $C_{2-8}$ alkenylenyl is optionally substituted with one or more substituents, wherein each substituent is, independently, amino, hydroxyl, aminoalkyl, hydroxylalkyl, or alkyl; each pNPL is, independently, an integer from 0 to 8; q1NPL and q2NPL are each, independently, 0, 1, or 2; each PL group is, independently, halo, hydroxyethoxymethyl, methoxyethoxymethyl, polyoxyethylene, or —$(NR^{5'})_{q1PL}$—$U^{PL}$-$LK^{PL}$-$(NR^{5''})_{q2PL}$—V, wherein: $R^5$, $R^{5'}$, and $R^{5''}$ are each, independently, hydrogen, alkyl, or alkoxy; each $U^{PL}$ is, independently, absent or O, S, S(═O), $S(═O)_2$, $NR^5$, —C(═O)—, —C(═O)—$NR^5$—, —C(═O)—N═N—$NR^5$—, —C(═O)—$NR^5$—N═N—, —N═N—$NR^5$—, —C(═N—$N(R^5)_2$)—, —C(═$NR^5$)—, —C(═O)O—, —C(═O)S—, —C(═S)—, —O—P$(═O)_2$O—, —S—C═N—, or —C(═O)—$NR^5$—O—, wherein groups with two chemically nonequivalent termini can adopt either of the two possible orientations; each V is, independently, nitro, cyano, amino, halo, hydroxy, alkoxy, alkylthio, alkylamino, dialkylamino, —$NH(CH_2)_pNH_2$ wherein p is 1 to 5, —C(═O)$NH(CH_2)_pNH_2$ wherein p is 1 to 5, —C(═O)$NH(CH_2)_p$NHC(═NH)$NH_2$ wherein p is 1 to 5, —C(═O)$NH(CH_2)_p$NHC(═O)$NH_2$ wherein p is 1 to 5, —NHC(═O)-alkyl, —$N(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—$S(═O)_2$OH, $S(═O)_2$OH, $NR^dR^e$, semicarbazone, aryl, cycloalkyl, heterocycloalkyl, or heteroaryl, wherein each of the aryl and cycloalkyl is substituted with one or more substitutents, wherein each of the heterocycloalkyl and heteroaryl is optionally substituted with one or more substituents, and wherein each of the subsituents for the aryl, cycloalkyl, heterocycloalkyl, and heteroaryl is, independently, nitro, cyano, amino, halo, hydroxy, alkoxy, alkylthio, alkylamino, dialkylamino, —$NH(CH_2)_pNH_2$ wherein p is 1 to 5, —$N(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—$S(═O)_2$OH, $S(═O)_2$OH, $NR^dR^e$, semicarbazone, aminosulfonyl, aminoalkoxy, aminoalkythio, lower acylamino, or benzyloxycarbonyl; each $R^c$ is, independently, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, $C_{1-6}$ alkyl, $C_{1-6}$haloalkyl, aryl, arylalkyl, heteroaryl, heteroarylalkyl, cycloalkyl, or heterocycloalkyl; $R^d$ and $R^e$ are, independently, H, $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted by OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, or heterocycloalkyl; or $R^d$ and $R^e$ together with the N atom to which they are attached form a 4-, 5-, 6-, 7-, or 8-membered heterocycloalkyl; each $LK^{PL}$ is, independently, —$(CH_2)_{pPL}$— or $C_{2-8}$ alkenylenyl, wherein each of the —$(CH_2)_{pNPL}$— and $C_{2-8}$ alkenylenyl is optionally substituted with one or more substituents, wherein each substituent is, independently, amino, hydroxyl, aminoalkyl, hydroxylalkyl, or alkyl; each pPL is, independently, an integer from 0 to 8; q1PL and q2PL are each, independently, 0, 1, or 2; m11 is an integer from 1 to about 20; and m12 is an integer from 1 to about 20.

The present invention also provides methods of treating and/or preventing mucositis in a mammal comprising administering to the mammal in need thereof a therapeutically effective amount of a compound of Formula XXI:

$$R^1—[—X\text{-}A_1\text{-}Y—X\text{-}A_2\text{-}Y—]_{m13}—X\text{-}L^1\text{-}Y—[—X\text{-}A_1\text{-}Y—X\text{-}A_2\text{-}Y—]_{m14}—R^2 \qquad \text{XXI}$$

or a pharmaceutically acceptable salt thereof, wherein: each X is, independently, $NR^8$; each Y is C═O; each $R^8$ is, independently, hydrogen or alkyl; each $A_2$ is optionally substituted arylene or optionally substituted heteroarylene, and each $A_1$ is —$(CH_2)_q$—, wherein q is 1 to 7, wherein $A_1$ and $A_2$ are each, independently, optionally substituted with one or more PL group(s), one or more NPL group(s), or a combination of one or more PL group(s) and one or more NPL group(s); $R^1$ is hydrogen, a PL group, or an NPL group, and $R^2$ is —X-$A_1$-Y—$R^{11}$, wherein $R^{11}$ is hydrogen, a PL group, or an NPL group; or $R^1$ and $R^2$ are each, independently, hydrogen, a PL group, or an NPL group; or $R^1$ and $R^2$ together are a single bond; or $R^1$ is —Y-$A_2$-X—$R^{12}$, wherein $R^{12}$ is hydrogen, a PL group, or an NPL group, and $R^2$ is hydrogen, a PL group, or an NPL group; $L^1$ is $C_{1-10}$alkylene optionally substituted with one or more substitutents, wherein each substituent is, independently, alkyl, halo, haloalkyl, aminoalkyl, hydroxylalkyl, V, or —$(CH_2)_{pPL}$—V wherein pPL is an integer from 1 to 5; each V is, independently, hydroxy, amino, alkylamino, dialkylamino, —$NH(CH_2)_pNH_2$ wherein p is 1 to 5, —C(═O)NH$(CH_2)_pNH_2$ wherein p is 1 to 5, —C(═O)NH$(CH_2)_p$NHC(═NH)$NH_2$ wherein p is 1 to 5, —C(═O)NH$(CH_2)_p$NHC(═O)$NH_2$ wherein p is 1 to 5, —NHC(═O)-alkyl, —$N(CH_2CH_2NH_2)_2$, guanidino, amidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, a substituted aryl group, heterocycloalkyl, or heteroaryl, wherein each of the heterocycloalkyl and heteroaryl is optionally substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl; each NPL group is, independently, —$B(OR^4)_2$ or —$(NR^{3'})_{q1NPL}$—$U^{NPL}$-$LK^{NPL}$-$(NR^{3''})_{q2NPL}$—$R^{4'}$, wherein: $R^3$, $R^{3'}$, and $R^{3''}$ are each, independently, hydrogen, alkyl, or alkoxy; $R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substitutents, wherein each substituent is, independently, alkyl, halo, or haloalkyl; each $U^{NPL}$ is, independently, absent or O, S, S(═O), S(═O)$_2$, $NR^3$, —C(═O)—, —C(═O)—$NR^3$—, —C(═O)—N═N—$NR^3$—, —C(═O)—$NR^3$—N═N—, —N═N—$NR^3$—, —C(═N—N$(R^3)_2$)—, —C(═$NR^3$)—, —C(═O)O—, —C(═O)S—, —C(═S)—, —O—P(═O)$_2$O—, —S—C═N—, or —C(═O)—$NR^3$—O—, wherein groups with two chemically nonequivalent termini can adopt both possible orientations; each $LK^{NPL}$ is, independently, —$(CH_2)_{pNPL}$— or $C_{2-8}$ alkenylenyl, wherein each of the —$(CH_2)_{pNPL}$ and $C_{2-8}$ alkenylenyl is optionally substituted with one or more substituents, wherein each substituent is, independently, amino, hydroxyl, aminoalkyl, hydroxylalkyl, or alkyl; each pNPL is, independently, an integer from 0 to 8; q1NPL and q2NPL are each, independently, 0, 1, or 2; each PL group is, independently, halo, hydroxyethoxymethyl, methoxyethoxymethyl, polyoxyethylene, or —$(NR^{5'})_{q1PL}$—$U^{PL}$-$LK^{PL}$-$(NR^{5''})_{q2PL}$—V, wherein: $R^5$, $R^{5'}$, and $R^{5''}$ are each, independently, hydrogen, alkyl, or alkoxy; each $U^{PL}$ is, independently, absent or O, S, S(═O), S(═O)$_2$, $NR^5$, —C(═O)—, —C(═O)—$NR^5$—, —C(═O)—N═N—$NR^5$—, —C(═O)—$NR^5$—N═N—, —N═N—$NR^5$—, —C(═N—N$(R^5)_2$)—, —C(═$NR^5$)—, —C(═O)O—, —C(═O)S—, —C(═S)—, —O—P(═O)$_2$O—, —S—C═N—, or —C(═O)—$NR^5$—O—, wherein groups with two chemically nonequivalent termini can adopt either of the two possible orientations; each $R^c$ is, independently, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, $C_{1-6}$ alkyl, $C_{1-6}$ haloalkyl, aryl, arylalkyl, heteroaryl, heteroarylalkyl, cycloalkyl, or heterocycloalkyl; $R^d$ and $R^e$ are, independently, H, $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl is optionally substituted by OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl; or $R^d$ and $R^e$ together with the N atom to which they are attached form a 4-, 5-, 6-, 7-, or 8-membered heterocycloalkyl; each $LK^{PL}$ is, independently, —$(CH_2)_{pPL}$— or $C_{2-8}$ alkenylenyl, wherein each of the —$(CH_2)_{pNPL}$— and $C_{2-8}$ alkenylenyl is optionally substituted with one or more substituents, wherein each substituent is, independently, amino, hydroxyl, aminoalkyl, hydroxylalkyl, or alkyl; each pPL is, independently, an integer from 0 to 8; q1PL and q2PL are each, independently, 0, 1, or 2; m13 is an integer from 1 to about 10; and m14 is an integer from 1 to about 10.

The present invention also provides methods of treating and/or preventing mucositis in a mammal comprising administering to the mammal in need thereof a therapeutically effective amount of a compound of Formula XXII:

$$R^1—[—X-A_1-X—Z—Y-A_2-Y—Z]_m—R^2 \qquad XXII$$

or a pharmaceutically acceptable salt thereof, wherein: X is $NR^8$, —$NR^8NR^8$—, C═O, or O; Y is $NR^8$, —$NR^8NR^8$—, C═O, S, or O; $R^8$ is hydrogen or alkyl; Z is C═O, C═S, O═S═O, —$NR^8NR^8$—, or —C(═O)C(═O)—; $A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s); $R^1$ is (i) hydrogen, a polar group (PL), or a non-polar group (NPL), and $R^2$ is —X-$A_1$-X—$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and $R^2$ is —X-$A_1$-X—Z—Y-$A_2$-Y—$R^1$, wherein $A_1$ and $A_2$ are as defined above, and each of which is optionally substituted with one or more polar (PL) group(s), one or more non-polar (NPL) group(s), or a combination of one or more polar (PL) group(s) and one or more non-polar (NPL) group(s); or (iii) hydrogen, a polar group (PL), or a non-polar group (NPL), and $R^2$ is —X-A'-X—$R^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or (iv) hydrogen, a polar group (PL), or a non-polar group (NPL), and $R^2$ is —X-$A_1$-X—Z—Y-A'-Y—$R^1$, wherein $A_1$ is as defined above, A' is aryl or heteroaryl, and each of $A_1$ and A' is optionally substituted with one or more polar (PL) group(s), one or more non-polar (NPL) group(s), or a combination of one or more polar (PL) group(s) and one or more non-polar (NPL) group(s); or (v) —Z—Y-A' and $R^2$ is hydrogen, a polar group (PL), or a non-polar group (NPL), wherein A' is aryl or heteroaryl and is optionally substituted with one or more polar (PL) group(s), one or more non-polar (NPL) group(s), or a combination of one or more polar (PL)

group(s) and one or more non-polar (NPL) group(s); or (vi) —Z—Y-A', and $R^2$ is —X-A", wherein A' and A" are, independently, aryl or heteroaryl, and each of A and A" is optionally substituted with one or more polar (PL) group(s), one or more non-polar (NPL) group(s), or a combination of one or more polar (PL) group(s) and one or more non-polar (NPL) group(s); or (vii) $R^1$ and $R^2$ are, independently, a polar group (PL) or a non-polar group (NPL); or (viii) $R^1$ and $R^2$ together form a single bond; NPL is a nonpolar group independently selected from —$B(OR^4)_2$ and —$(NR^3)_{q1NPL}$—$U^{NPL}$—$(CH_2)_{pNPL}$—$(NR^{3''})_{q2NPL}$—$R^{4'}$, wherein: $R^3$, $R^{3'}$, and $R^{3''}$ are, independently, selected from hydrogen, alkyl, and alkoxy; $R^4$ and $R^{4'}$ are, independently, selected from hydrogen, alkyl, alkenyl, alkynyl, cycloalkyl, aryl, and heteroaryl, any of which is optionally substituted with one or more alkyl or halo groups; $U^{NPL}$ is absent or selected from O, S, S(═O), S(═O)$_2$, $NR^3$, —C(═O)—, —C(═O)—N═N—$NR^3$—, —C(═O)—$NR^3$—N═N—, —N═N—$NR^3$—, —C(═N—N($R^3$)$_2$)—, —C(═$NR^3$)—, —C(═O)O—, —C(═O)S—, —C(═S)—, —O—P(═O)$_2$O—, —$R^3$O—, —$R^3$S—, —S—C═N—, and —C(═O)—$NR^3$—O—, wherein groups with two chemically non-equivalent termini can adopt both possible orientations; the —$(CH_2)_{pNPL}$— alkylene chain is optionally substituted with one or more amino or hydroxy groups, or is unsaturated; pNPL is 0 to 8; q1NPL and q2NPL are, independently, 0, 1, or 2; PL is a polar group selected from halo, hydroxyethoxymethyl, methoxyethoxymethyl, polyoxyethylene, and —$(NR^{5'})_{q1PL}$—$U^{PL}$—$(CH_2)_{pPL}$—$(NR^{5'})_{q2PL}$—V, wherein: $R^5$, $R^{5'}$, and $R^{5''}$ are, independently, selected from hydrogen, alkyl, and alkoxy; $U^{PL}$ is absent or selected from O, S, S(═O), S(═O)$_2$, $NR^5$, —C(═O)—, —C(═O)—N═N—$NR^5$—, —C(═O)—$NR^5$—N═N—, —N═N—$NR^5$—, —C(═N—N($R^5$)$_2$)—, —C(═$NR^5$)—, —C(═O)O—, —C(═O)S—, —C(═S)—, —O—P(═O)$_2$O—, —$R^5$O—, —$R^5$S—, —S—C═N—, and —C(═O)—$NR^5$—O—, wherein groups with two chemically nonequivalent termini can adopt both possible orientations; V is selected from nitro, cyano, amino, hydroxy, alkoxy, alkylthio, alkylamino, dialkylamino, —$NH(CH_2)_pNH_2$ wherein p is 1 to 4, —$N(CH_2CH_2NH_2)_2$, diazamino, amidino, guanidino, guanyl, semicarbazone, aryl, heterocycle, and heteroaryl, any of which is optionally substituted with one or more of amino, halo, cyano, nitro, hydroxy, —$NH(CH_2)_pNH_2$ wherein p is 1 to 4, —$N(CH_2CH_2NH_2)_2$, amidino, guanidino, guanyl, aminosulfonyl, aminoalkoxy, aminoalkythio, lower acylamino, or benzyloxycarbonyl; the —$(CH_2)_{pPL}$— alkylene chain is optionally substituted with one or more amino or hydroxy groups, or is unsaturated; pPL is 0 to 8; q1PL and q2PL are, independently, 0, 1, or 2; and m is 1 to about 20.

The present invention also provides methods of treating and/or preventing mucositis in a mammal comprising administering to the mammal in need thereof a therapeutically effective amount of a compound of Formula XXIII:

$$R^1—[-A_1-W-A_2-W—]_m—R^2 \qquad XXIII$$

or a pharmaceutically acceptable salt thereof, wherein: $A_1$ and $A_2$ are, independently, optionally substituted arylene or optionally substituted heteroarylene, wherein: (i) $A_1$ and $A_2$ are, independently, optionally substituted with one or more polar (PL) group(s), one or more non-polar (NPL) group(s), or a combination of one or more polar (PL) group(s) and one or more non-polar (NPL) group(s); or (ii) one of $A_1$ or $A_2$ is as defined above and is optionally substituted with one or more polar (PL) group(s), one or more non-polar (NPL) group(s), or a combination of one or more polar (PL) group(s) and one or more non-polar (NPL) group(s); and the other of $A_1$ or $A_2$ is the group —C≡C$(CH_2)_p$C≡C—, wherein p is 0 to 8, and the —$(CH_2)_p$— alkylene chain is optionally substituted with one or more amino or hydroxyl groups; W is absent, or represents —$CH_2$—, —$CH_2$—$CH_2$—, —CH═CH—, or —C≡C—; $R^1$ is (i) hydrogen, a polar group (PL), or a non-polar group (NPL), and $R^2$ is -$A_1$-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and $R^2$ is -$A_1$-W-$A_2$-$R^1$, wherein each of $A_1$ and $A_2$ is as defined above and is optionally substituted with one or more polar (PL) group(s), one or more non-polar (NPL) group(s), or a combination of one or more polar (PL) group(s) and one or more non-polar (NPL) group(s); or (iii) A'-W— and $R^2$ is -$A_1$-W-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s); or (iv) A'-W— and $R^2$ is -A', wherein A' is aryl or heteroaryl, either of which is optionally substituted with one or more polar (PL) group(s), one or more non-polar (NPL) groups(s), or a combination of one or more polar (PL) group(s) and one or more non-polar (NPL) group(s); or (iv) $R^1$ and $R^2$ together form a single bond; NPL is a nonpolar group independently selected from —$B(OR^4)_2$ or —$(NR^{3'})_{q1NPL}$—$U^{NPL}$— $(CH_2)_{pNPL}$—$(NR^{3''})_{q2NPL}$—$R^4$, wherein: $R^3$, $R^{3'}$, and $R^{3''}$ are, independently, selected from hydrogen, alkyl, and alkoxy; $R^4$ is selected from hydrogen, alkyl, alkenyl, alkynyl, cycloalkyl, aryl, and heteroaryl, any of which is optionally substituted with one or more alkyl or halo groups; $U^{NPL}$ is absent or selected from O, S, S(═O), S(═O)$_2$, $NR^3$, —(C═O)—, —(C═O)—N═N—$NR^3$—, —(C═O)—$NR^3$—N═N—, —N═N—$NR^3$—, —C(═N—N($R^3$)$_2$)—, —C(═$NR^3$)—, —C(═O)O—, —C(═O)S—, —C(═S)—, —O—P(═O)$_2$O—, —$R^3$O—, —$R^3$S—, —S—C═N— and —(C═O)—$NR^3$—O—, wherein groups with two chemically nonequivalent termini can adopt both possible orientations; the —$(CH_2)_{pNPL}$— alkylene chain is optionally substituted with one or more alkyl, amino or hydroxyl groups, or the alkylene chain is unsaturated; pNPL is 0 to 8; q1NPL and q2NPL are, independently, 0 to 2; PL is a polar group selected from halo, hydroxyethoxymethyl, methoxyethoxymethyl, polyoxyethylene, and —$(NR^{5'})_{q1PL}$—$U^{PL}$—$(CH_2)_{pPL}$—$(NR^{5'})_{q2PL}$—V, wherein: $R^5$, $R^{5'}$, and $R^{5''}$ are, independently, selected from hydrogen, alkyl, and alkoxy; $U^{PL}$ is absent or selected from O, S, S(═O), S(═O)$_2$, $NR^5$, —(C═O)—, —(C═O)—N═N—$NR^5$—, —(C═O)—$NR^5$—N═N—, —N═N—$NR^5$—, —C(═N—N($R^5$)$_2$)—, —C(═$NR^5$)—, —C(═O)O—, —C(═O)S—, —C(═S)—, —O—P(═O)$_2$O—, —$R^5$O—, —$R^5$S—, —S—C═N—, and —(C═O)—$NR^5$—O—, wherein groups with two chemically nonequivalent termini can adopt both possible orientations; V is selected from nitro, cyano, amino, hydroxyl, alkoxy, alkylthio, alkylamino, dialkylamino, —$NH(CH_2)_pNH_2$, —$N(CH_2CH_2NH_2)_2$, diazamino, amidino, guanidino, guanyl, semicarbazone, aryl, heterocycle, and heteroaryl, any of which is optionally substituted with one or more of amino, halo, cyano, nitro, hydroxyl, —$NH(CH_2)_pNH_2$, —$N(CH_2CH_2NH_2)_2$, amidino, guanidino, guanyl, aminosulfonyl, aminoalkoxy, aminoalkythio, lower acylamino, or benzyloxycarbonyl; the —$(CH_2)_{pPL}$-alkylene chain is optionally substituted with one or more amino or hydroxyl groups, or the alkylene chain is unsaturated; pPL is 0 to 8; q1PL and q2PL are, independently, 0 to 2; and m is 1 to about 25.

The present invention also provides methods of treating and/or preventing mucositis in a mammal comprising administering to the mammal in need thereof a therapeutically effective amount of a compound of Formula XXIV:

$$R^1—X\text{-}A_1\text{-}X—Y\text{-}A_2\text{-}Y—X\text{-}A_1\text{-}X—R^2 \qquad \text{XXIV}$$

or a pharmaceutically acceptable salt thereof, wherein: X is $NR^8$, O, S, or —$N(R^8)N(R^8)$—; Y is C═O, C═S, or O═S═O; $R^8$ is hydrogen or alkyl; $A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s); $R^1$ is a polar group (PL) or a non-polar group (NPL); $R^2$ is $R^1$; NPL is a nonpolar group independently selected from —$B(OR^4)_2$ and —$(NR^{3'})_{q1NPL}$—$U^{NPL}$—$(CH_2)_{pNPL}$—$(NR^{3''})_{q2NPL}$—$R^{4'}$, wherein: $R^3$, $R^{3'}$, and $R^{3''}$ are, independently, selected from hydrogen, alkyl, and alkoxy; $R^4$ and $R^{4'}$ are, independently, selected from the group consisting of hydrogen, alkyl, alkenyl, alkynyl, cycloalkyl, aryl, and heteroaryl, any of which is optionally substituted with one or more alkyl or halo groups; $U^{NPL}$ is absent or selected from O, S, S(═O), $S(═O)_2$, $NR^3$, —C(═O)—, —C(═O)—N═N—$NR^3$—, —C(═O)—$NR^3$—N═N—, —N═N—$NR^3$—, —C(═N—$N(R^3)_2$)—, —C(═$NR^3$)—, —C(═O)O—, —C(═O)S—, —C(═S)—, —O—P(═O)$_2$O—, —$R^3$O—, —$R^3$S—, —S—C═N—, and —C(═O)—$NR^3$—O—, wherein groups with two chemically nonequivalent termini can adopt both possible orientations; the —$(CH_2)_{pNPL}$— alkylene chain is optionally substituted with one or more amino or hydroxy groups, or is unsaturated; pNPL is 0 to 8; q1NPL and q2NPL are, independently, 0, 1, or 2; PL is a polar group selected from halo, hydroxyethoxymethyl, methoxyethoxymethyl, polyoxyethylene, and —$(NR^{5'})_{q1PL}$—$U^{PL}$—$(CH_2)_{pPL}$—$(NR^{5'})_{q2PL}$—V, wherein: $R^5$, $R^{5'}$, and $R^{5''}$ are, independently, selected from hydrogen, alkyl, and alkoxy; $U^{PL}$ is absent or selected from O, S, S(═O), $S(═O)_2$, $NR^5$, —C(═O)—, —C(═O)—N═N—$NR^5$—, —C(═O)—$NR^5$—N═N—, —N═N—$NR^5$—, —C(═N—$N(R^5)_2$)—, —C(═$NR^5$)—, —C(═O)O—, —C(═O)S—, —C(═S)—, —O—P(═O)$_2$O—, —$R^5$O—, —$R^5$S—, —S—C═N—, and —C(═O)—$NR^5$—O—, wherein groups with two chemically nonequivalent termini can adopt both possible orientations; V is selected from nitro, cyano, amino, hydroxy, alkoxy, alkylthio, alkylamino, dialkylamino, —NH$(CH_2)_pNH_2$ wherein p is 1 to 4, —$N(CH_2CH_2NH_2)_2$, diazamino, amidino, guanidino, guanyl, semicarbazone, aryl, heterocycle and heteroaryl, any of which is optionally substituted with one or more of amino, halo, cyano, nitro, hydroxy, —$NH(CH_2)_pNH_2$ wherein p is 1 to 4, —$N(CH_2CH_2NH_2)_2$, amidino, guanidino, guanyl, aminosulfonyl, aminoalkoxy, aminoalkythio, lower acylamino, or benzyloxycarbonyl; the —$(CH_2)_{pPL}$— alkylene chain is optionally substituted with one or more amino or hydroxy groups, or is unsaturated; pPL is 0 to 8; and q1PL and q2PL are, independently, 0, 1, or 2.

The present invention also provides methods of treating and/or preventing mucositis in a mammal comprising administering to the mammal in need thereof a therapeutically effective amount of a compound of Formula XXV:

$$A\text{-}(B)_{n1}\text{-}(D)_{m1}\text{-}H \qquad \text{XXV}$$

or a pharmaceutically acceptable salt thereof, wherein: A is the residue of a chain transfer agent; B is —[$CH_2$—C($R^{11}$)($B_{11}$)]—, wherein $B_{11}$ is —$X_{11}$—$Y_{11}$—$Z_{11}$, wherein $X_{11}$ is carbonyl (—C(═O)—) or optionally substituted $C_{1-6}$ alkylene; or $X_{11}$ is absent; $Y_{11}$ is O, NH, or optionally substituted $C_{1-6}$ alkylene; or $Y_{11}$ is absent; $Z_{11}$ is —$Z_{11A}$—$Z_{11B}$, wherein $Z_{11A}$ is alkylene, arylene, or heteroarylene, any of which is optionally substituted; or $Z_{11A}$ is absent; and $Z_{11B}$ is -guanidino, -amidino, —$N(R^3)(R^4)$, or —$N^+(R^3)(R^4)(R^5)$, wherein $R^3$, $R^4$, and $R^5$ are, independently, hydrogen, alkyl, aminoalkyl, aryl, heteroaryl, heterocyclic, or aralkyl; or $Z_{11}$ is pyridinium

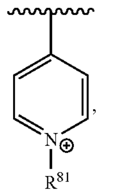

or phosphonium

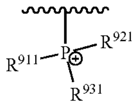

wherein $R^{81}$, $R^{911}$, $R^{921}$, and $R^{931}$ are, independently, hydrogen or alkyl; $R^{11}$ is hydrogen or $C_{1-4}$ alkyl; D is —[$CH_2$—C($R^{21}$)($D_{21}$)]-, wherein $D_{21}$ is —$X_{21}$—$Y_{21}$—$Z_{21}$, wherein $X_{21}$ is carbonyl (—C(═O)—) or optionally substituted $C_{1-6}$ alkylene; or $X_{21}$ is absent; $Y_2$, is O, NH, or optionally substituted $C_{1-6}$ alkylene, or $Y_2$, is absent; $Z_{21}$ is alkyl, cycloalkyl, alkoxy, aryl, or aralkyl, any of which is optionally substituted; $R^{21}$ is hydrogen or $C_{1-4}$ alkyl; $m_1$, the mole fraction of D, is about 0.1 to about 0.9; and $n_1$, the mole fraction of B, is 1-$m_1$; wherein the compound is a random copolymer of B and D, and wherein the copolymer has a degree of polymerization of about 5 to about 50.

The present invention also provides methods of treating and/or preventing mucositis in a mammal comprising administering to the mammal in need thereof a therapeutically effective amount of

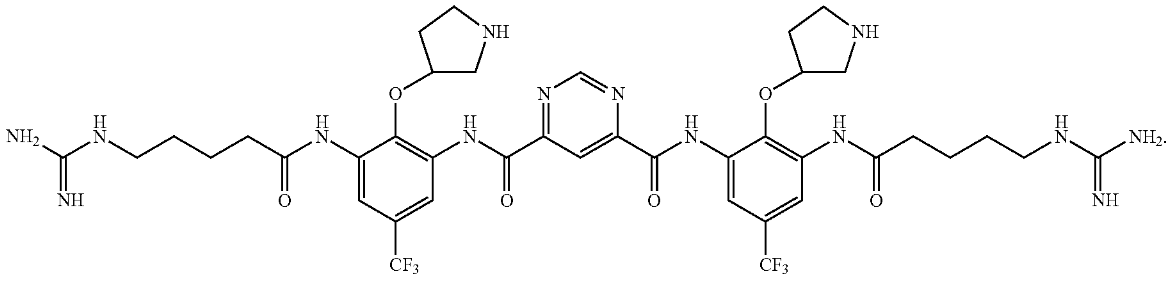 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3OC3CCNC3)ncn2)c1OC1CCNC1]

In some embodiments, the compounds described herein, or compositions comprising the same, can be combined with other therapeutic agents, such as palifermin, or compositions comprising the same for treatment and/or prevention of mucositis.

In some embodiments, the present methods for treating and/or preventing mucositis can be used in a patient who receives chemotherapy and/or radiation therapy for cancer. In some embodiments, the patient is receiving or will be receiving high-dose chemotherapy prior to hematopoietic cell transplantation. In some embodiments, the patient is receiving or will be receiving radiation therapy for tumors of the head and neck. In some embodiments, the patient is receiving or will be receiving induction therapy for leukemia. In some embodiments, the patient is receiving or will be receiving conditioning regimens for bone marrow transplant. In some embodiments, the patient is experiencing or will be experiencing basal epithelial cell death.

The present invention is also directed to use of the compounds and compositions of the invention in the preparation of medicaments for treating and/or preventing mucositis.

The present invention is also directed to use of the compounds and compositions of the invention for treating and/or preventing mucositis.

DESCRIPTION OF EMBODIMENTS

Unless defined otherwise, all technical and scientific terms have the same meaning as is commonly understood by one of ordinary skill in the art to which the embodiments disclosed belongs.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, un-recited elements or method steps.

As used herein, the terms "a" or "an" means "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the term "alkyl" refers to a saturated hydrocarbon group which is straight-chained or branched. An alkyl group can contain from 1 to 20, from 2 to 20, from 1 to 10, from 1 to 8, from 1 to 6, from 1 to 4, or from 1 to 3 carbon atoms. Examples of alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

As used herein, the term "alkylene" or "alkylenyl" refers to a divalent alkyl linking group. An example of an alkylene (or alkylenyl) is methylene or methylenyl ($-CH_2-$).

As used herein, the term "alkenyl" refers to an alkyl group having one or more double carbon-carbon bonds. Examples of alkenyl groups include, but are not limited to, ethenyl, propenyl, cyclohexenyl, and the like.

As used herein, the term "alkenylenyl" refers to a divalent linking alkenyl group.

As used herein, the term "alkynyl" refers to an alkyl group having one or more triple carbon-carbon bonds. Examples of alkynyl groups include, but are not limited to, ethynyl, propynyl, and the like.

As used herein, the term "alkynylenyl" refers to a divalent linking alkynyl group.

As used herein, the term "haloalkyl" refers to an alkyl group having one or more halogen substituents. Examples of haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, the term "aryl" refers to monocyclic or polycyclic (e.g., having 2, 3 or 4 fused rings) aromatic hydrocarbons. In some embodiments, aryl groups have from 6 to about 20 carbon atoms. In some embodiments, aryl groups have from 6 to 10 carbon atoms. Examples of aryl groups include, but are not limited to, phenyl, naphthyl, anthracenyl, phenanthrenyl, indanyl, indenyl, and the like.

As used herein, the term "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to about 15, from 3 to 10, from 3 to 8, from 3 to 6, from 4 to 6, from 3 to 5, or from 5 to 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "heteroaryl" refers to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 1 to about 20 carbon atoms, from 1 to 5, from 1 to 4, from 1 to 3, or from 1 to 2, carbon atoms as ring-forming atoms. In some embodiments, the heteroaryl group contains 3 to 14, 3 to 7, or 5 to 6 ring-forming atoms. In some embodiments, the heteroaryl group has 1 to 4, 1 to 3, or 1 to 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, the term "heterocycloalkyl" refers to non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Heterocycloalkyl groups can be mono or polycyclic (e.g., fused, bridged, or spiro systems). In some embodiments, the heterocycloalkyl group has from 1 to about 20 carbon atoms, or 3 to about 20 carbon atoms. In some embodiments, the heterocycloalkyl group contains 3 to 14, 3 to 7, or 5 to 6 ring-forming atoms. In some embodiments, the heterocycloalkyl group has 1 to 4, 1 to 3, or 1 to 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or $S(O)_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "halo" refers to halogen groups including, but not limited to fluoro, chloro, bromo, and iodo.

As used herein, the term "alkoxy" refers to an —O-alkyl group. Examples of alkoxy groups include, but are not limited to, methoxy, ethoxy, propoxy (e.g., n-propoxy and isopropoxy), t-butoxy, and the like.

As used herein, the term "haloalkoxy" refers to an —O-haloalkyl group. An example of an haloalkoxy group is $OCF_3$.

As used herein, the term "alkylthio" refers to an —S-alkyl group. An example of an alkylthio group is $—SCH_2CH_3$.

As used herein, the term "arylalkyl" refers to a $C_{1-6}$ alkyl substituted by aryl and "cycloalkylalkyl" refers to $C_{1-6}$ alkyl substituted by cycloalkyl.

As used herein, the term "heteroarylalkyl" refers to a $C_{1-6}$ alkyl group substituted by a heteroaryl group, and "heterocycloalkylalkyl" refers to a $C_{1-6}$ alkyl substituted by heterocycloalkyl.

As used herein, the term "amino" refers to $NH_2$.

As used herein, the term "alkylamino" refers to an amino group substituted by an alkyl group. An example of an alkylamino is $—NHCH_2CH_3$.

As used herein, the term "arylamino" refers to an amino group substituted by an aryl group. An example of an alkylamino is —NH(phenyl).

As used herein, the term "aminoalkyl" refers to an alkyl group substituted by an amino group. An example of an aminoalkyl is $—CH_2CH_2NH_2$.

As used herein, the term "aminosulfonyl" refers to $—S(=O)_2NH_2$.

As used herein, the term "aminoalkoxy" refers to an alkoxy group substituted by an amino group. An example of an aminoalkoxy is $—OCH_2CH_2NH_2$.

As used herein, the term "aminoalkylthio" refers to an alkylthio group substituted by an amino group. An example of an aminoalkylthio is $—SCH_2CH_2NH_2$.

As used herein, the term "amidino" refers to $—C(=NH)NH_2$.

As used herein, the term "acylamino" refers to an amino group substituted by an acyl group (e.g., —O—C(=O)—H or —O—C(=O)-alkyl). An example of an acylamino is —NHC(=O)H or $—NHC(=O)CH_3$. The term "lower acylamino" refers to an amino group substituted by a lower acyl group (e.g., —O—C(=O)—H or —O—C(=O)—$C_{1-6}$alkyl). An example of a lower acylamino is —NHC(=O)H or $—NHC(=O)CH_3$.

As used herein, the term "carbamoyl" refers to $—C(=O)—NH_2$.

As used herein, the term "cyano" refers to —CN.

As used herein, the term "dialkylamino" refers to an amino group substituted by two alkyl groups.

As used herein, the term "diazamino" refers to $—N(NH_2)_2$.

As used herein, the term "guanidino" refers to $—NH(=NH)NH_2$.

As used herein, the term "heteroarylamino" refers to an amino group substituted by a heteroaryl group. An example of an alkylamino is —NH-(2-pyridyl).

As used herein, the term "hydroxyalkyl" or "hydroxylalkyl" refers to an alkyl group substituted by a hydroxyl group. Examples of a hydroxylalkyl include, but are not limited to, $—CH_2OH$ and $—CH_2CH_2OH$.

As used herein, the term "nitro" refers to $—NO_2$.

As used herein, the term "semicarbazone" refers to $=NNHC(=O)NH_2$.

As used herein, the term "ureido" refers to $—NHC(=O)—NH_2$.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the term, "compound" refers to all stereoisomers, tautomers, and isotopes of the compounds described in the present invention.

As used herein, the phrase "substantially isolated" refers to a compound that is at least partially or substantially separated from the environment in which it is formed or detected.

As used herein, the phrase "pharmaceutically acceptable" refers to those compounds, materials, compositions, and/or dosage forms which are, within the scope of sound medical judgment, suitable for use in contact with tissues of humans and animals.

As used herein, the term "animal" includes, but is not limited to, humans and non-human vertebrates such as wild, domestic and farm animals.

As used herein, the term "contacting" refers to the bringing together of an indicated moiety in an in vitro system or an in vivo system.

As used herein, the term "individual" or "patient," used interchangeably, refers to any animal, including mammals, such as mice, rats, other rodents, rabbits, dogs, cats, swine, cattle, sheep, horses, or primates, such as humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form:

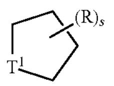

then it is understood that substituent R can occur s number of times on the ring, and R can be a different moiety at each occurrence. Further, in the above example, where the variable $T^1$ is defined to include hydrogens, such as when $T^1$ is $CH_2$, NH, etc., any floating substituent such as R in the above example, can replace a hydrogen of the $T^1$ variable as well as a hydrogen in any other non-variable component of the ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The compounds described herein can be asymmetric (e.g., having one or more stereocenters). All stereoisomers, such as enantiomers and diastereomers, are intended to be included within the scope of the invention unless otherwise indicated. Compounds of the present invention that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds of the invention may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include hydrates and solvates, as well as anhydrous and non-solvated forms.

All compounds and pharmaceutically acceptable salts thereof can be prepared or be present together with other substances such as water and solvents (e.g., hydrates and solvates) or can be isolated.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, or salts thereof, are substantially isolated. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Compounds of the invention are intended to include compounds with stable structures. As used herein, the phrases "stable compound" and "stable structure" refer to a compound that is sufficiently robust to survive isolation to a useful degree of purity from a reaction mixture, and formulation into an efficacious therapeutic agent.

The present invention also includes quaternary ammonium salts of the compounds described herein, where the compounds have one or more tertiary amine moiety. As used herein, the phrase "quaternary ammonium salts" refers to derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

The present invention provides methods of treating and/or preventing mucositis in a mammal comprising administering to the mammal in need thereof a therapeutically effective amount of a compound of Formula I:

I

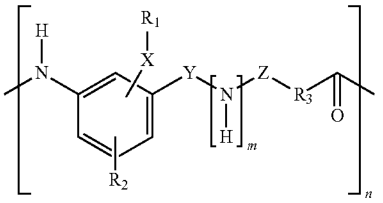

or a pharmaceutically acceptable salt thereof,
wherein:

X is O or S;

$R_1$ is $C_1$-$C_9$ straight or branched chain alkyl, optionally substituted with one or more —$NH_2$ or —NH—C(=NH)$NH_2$;

Y is a bond or a carbonyl;

Z is a bond or a carbonyl;

$R_2$ is hydrogen or $C_1$-$C_9$ straight or branched chain alkyl optionally substituted with one or more —$NH_2$ or —NH—C(=NH)$NH_2$;

or $R_2$ is —X—$R_1$;

$R_3$ is methylene or

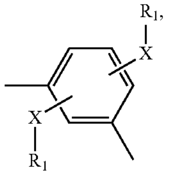

wherein the methylene is substituted with $C_1$-$C_9$ straight or branched chain alkyl, wherein the $C_1$-$C_9$ straight or branched chain alkyl is optionally substituted with one or more —$NH_2$ or —NH—C(=NH)$NH_2$;

n is 2-10; and m is 1 or 2.

The present invention also provides methods of treating and/or preventing mucositis in a mammal comprising administering to the mammal in need thereof a therapeutically effective amount of a compound of Formula II:

II

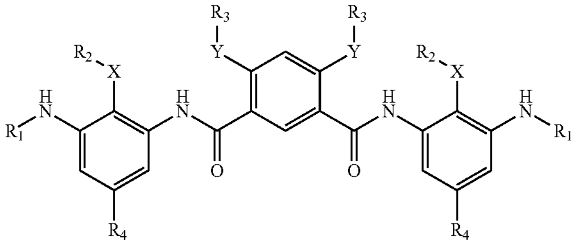

or a pharmaceutically acceptable salt thereof, wherein:

X is O or S;

Y is O or S;

$R_1$ is H or —C(=O)-A, where A is $C_1$-$C_9$ straight or branched alkyl optionally substituted with one or more —$NH_2$, —$N(CH_3)_2$ or —NH—C(=NH)$NH_2$;

$R_2$ is $C_1$-$C_9$ straight or branched alkyl optionally substituted with one or more —$NH_2$, —$N(CH_3)_2$ or —NH—C(=NH)$NH_2$;

$R_3$ is $C_1$-$C_9$ straight or branched alkyl optionally substituted with one or more —$NH_2$, —$N(CH_3)_2$ or —NH—C(=NH)$NH_2$; and $R_4$ is H, —B, or —C(=O)—O—B, where B is $C_1$-$C_9$ straight or branched alkyl.

The present invention also provides methods of treating and/or preventing mucositis in a mammal comprising administering to the mammal in need thereof a therapeutically effective amount of a compound chosen from:

Compound X

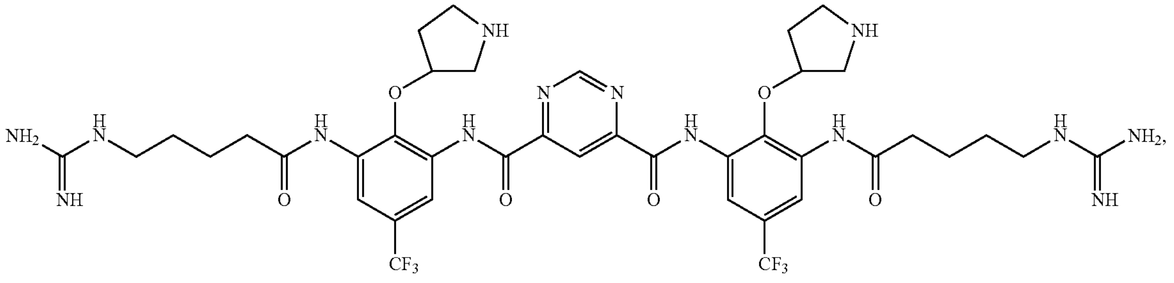 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3OC3CCNC3)ncn2)c1OC1CCNC1]

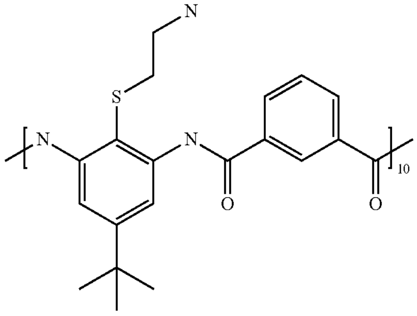
,
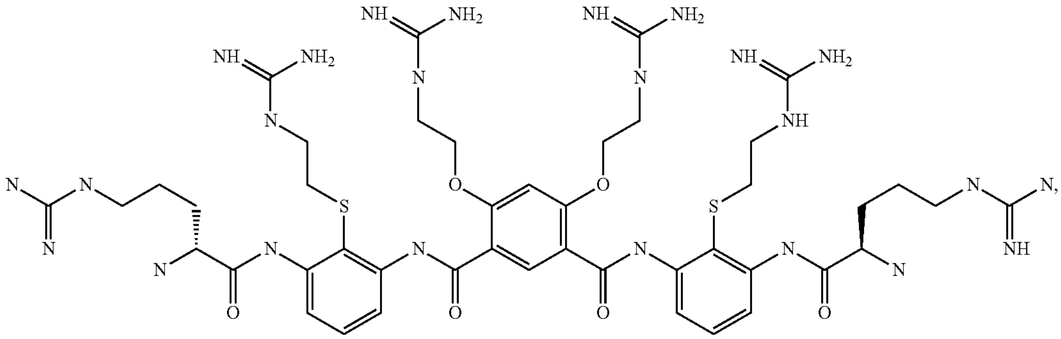
,
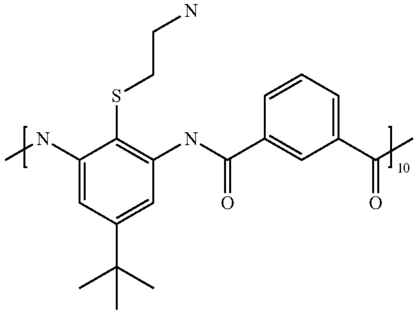
,
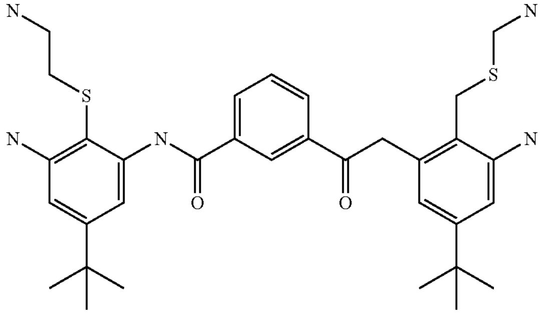
,
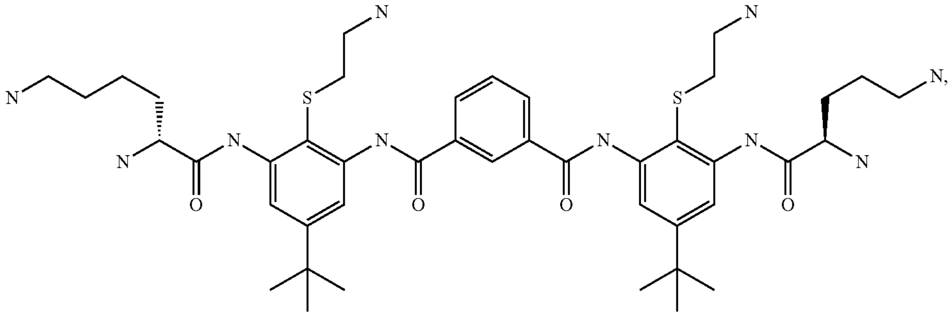
,
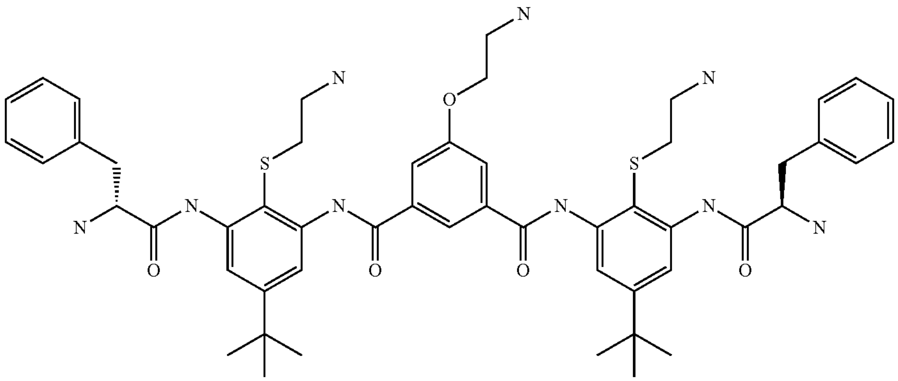
,

-continued
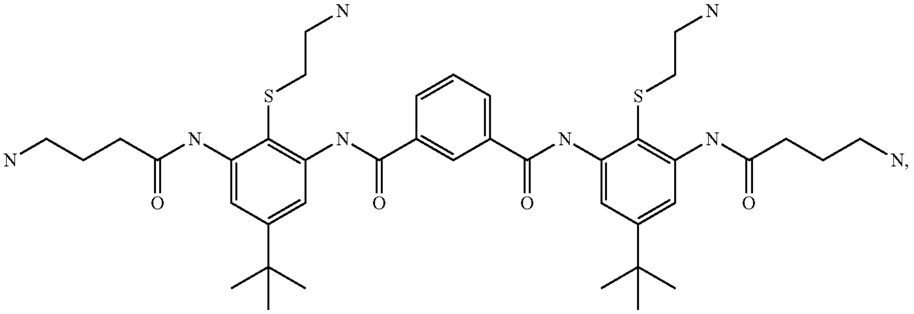
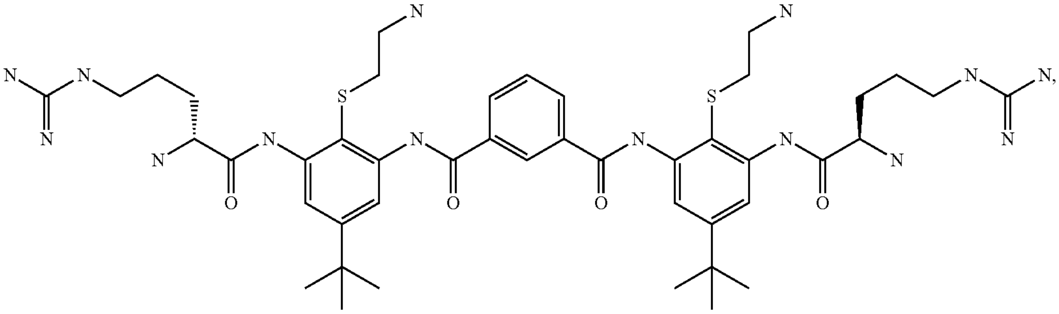
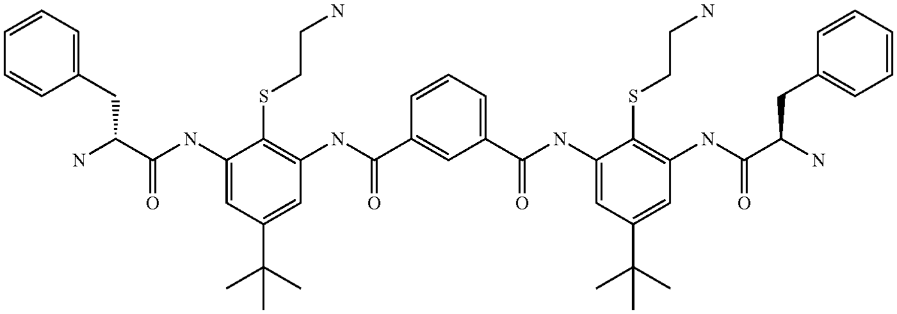
,
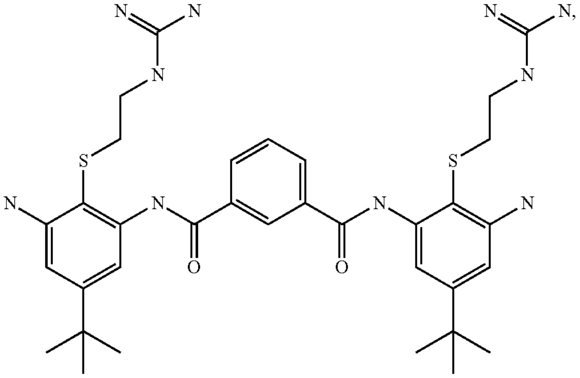
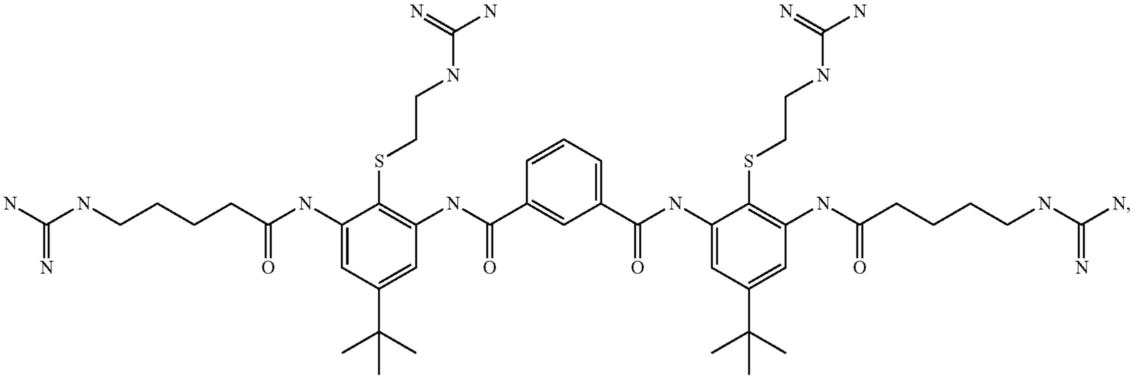

-continued
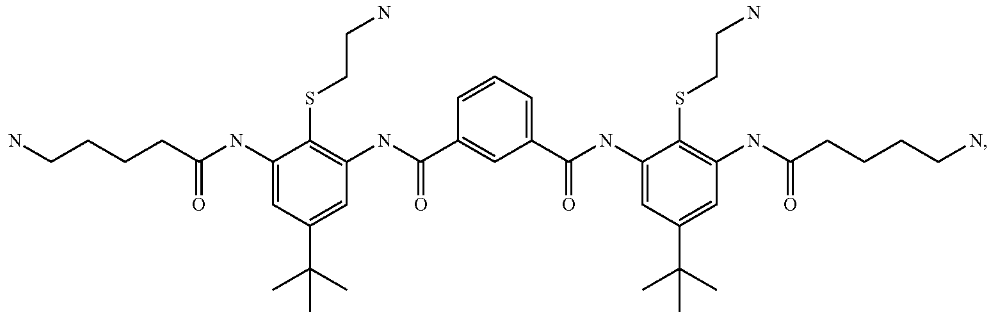
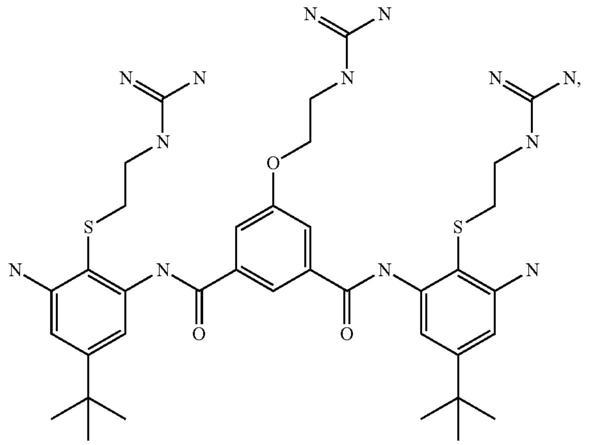
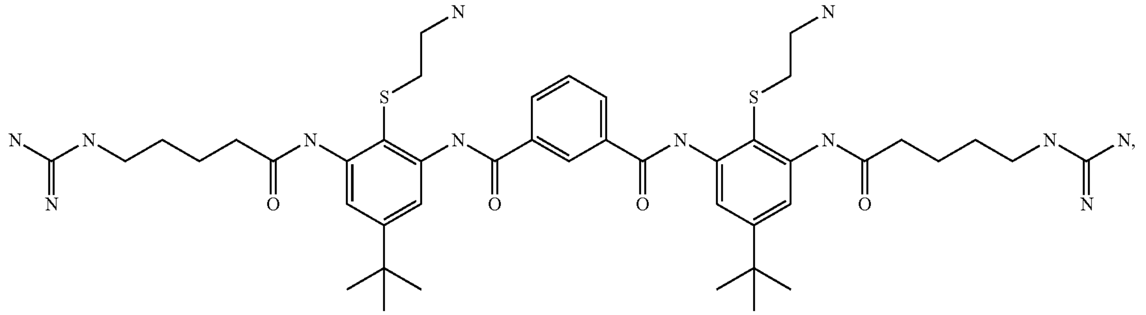
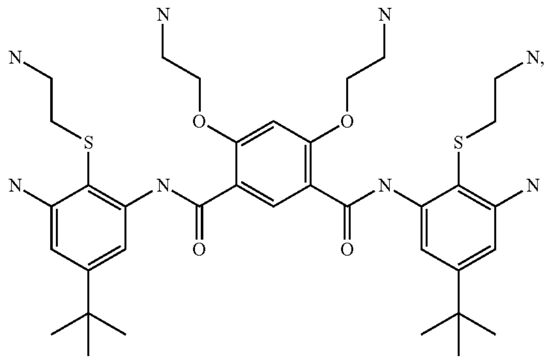

-continued
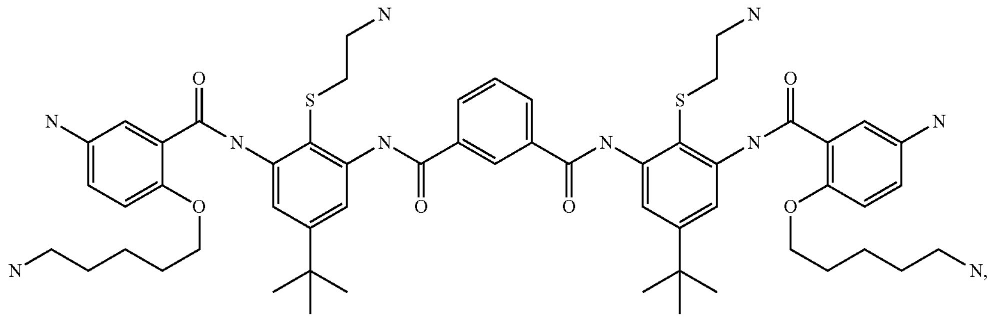
,
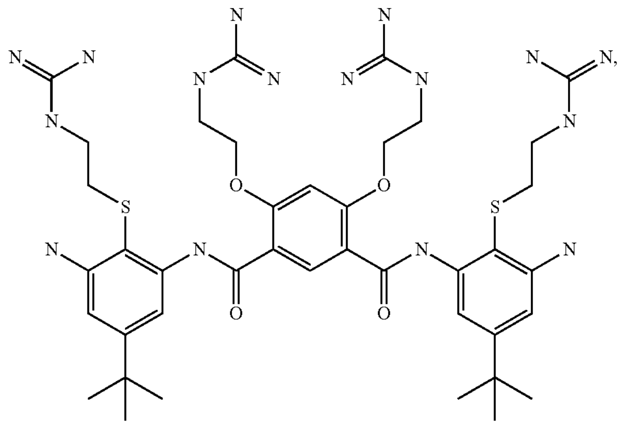
,
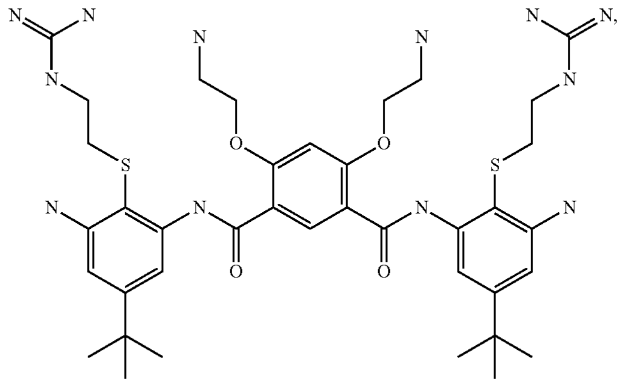
,
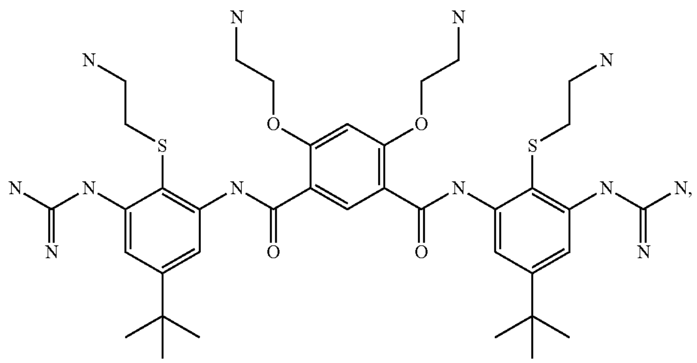
,

-continued
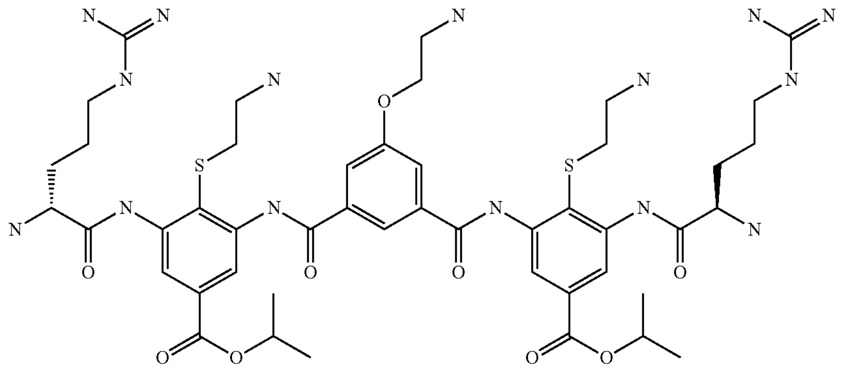
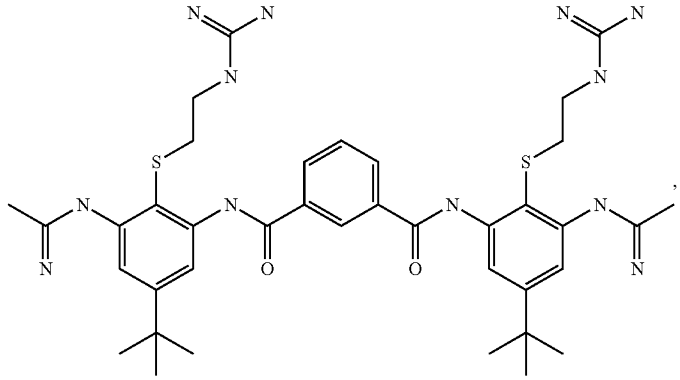
,
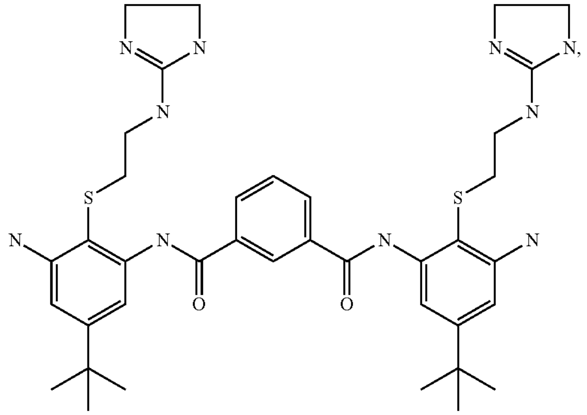
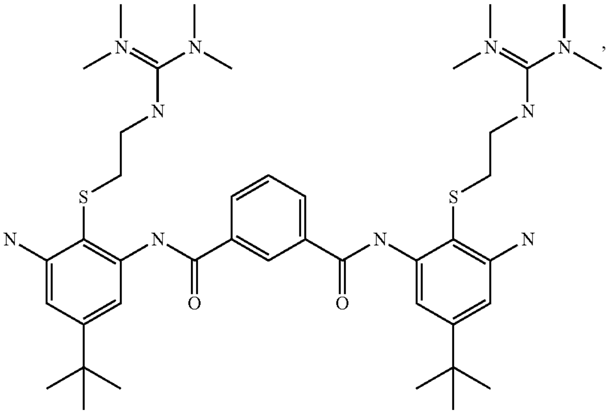
,
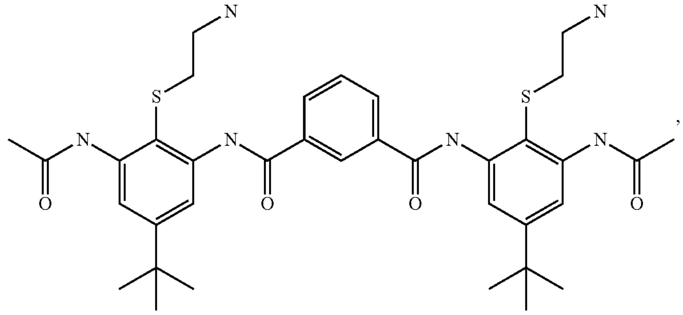
,

-continued
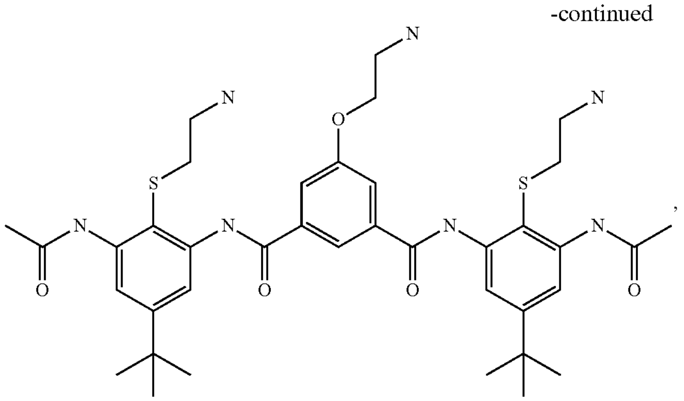
,
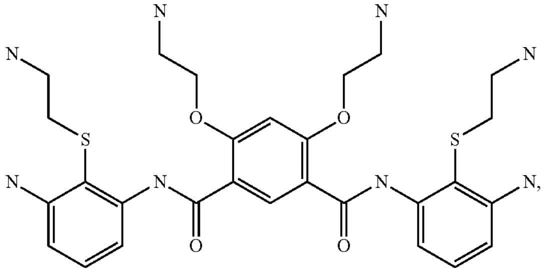
,
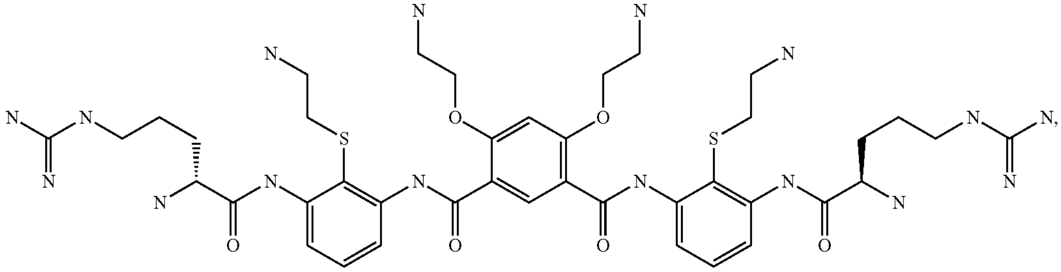
,
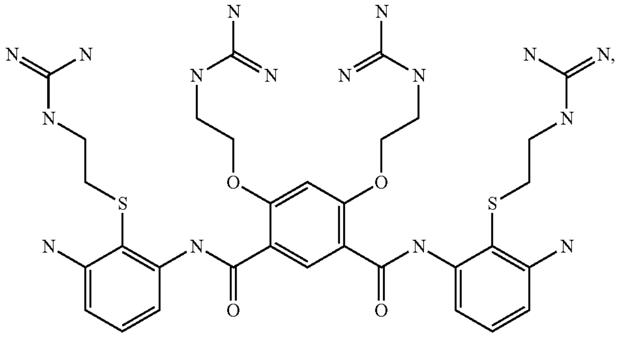
, and
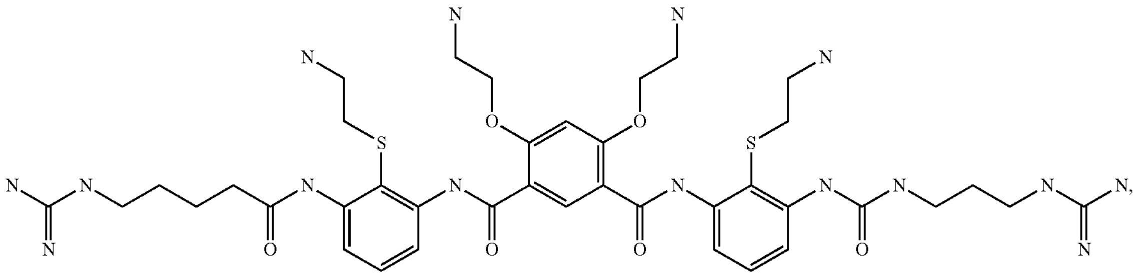
,
or a pharmaceutically acceptable salt thereof.
The present invention also provides methods of treating and/or preventing mucositis in a mammal comprising administering to the mammal in need thereof a therapeutically effective amount of a compound of Formula III:

III

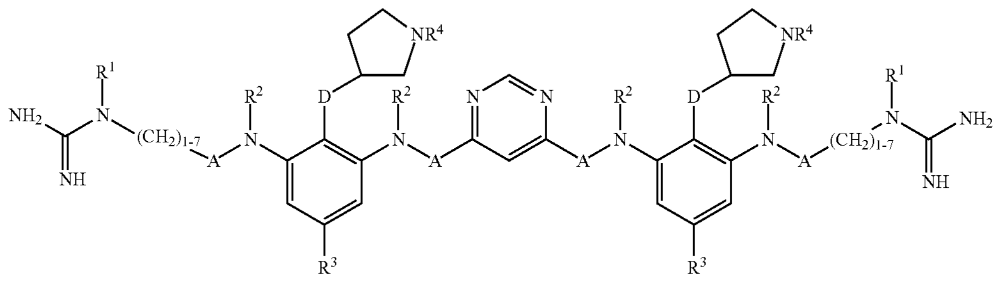

or a pharmaceutically acceptable salt thereof, wherein:

each A is, independently, —C═O, —C═S, or $CH_2$;

each D is, independently, O or S;

each $R^1$ is, independently, hydrogen, $C_{1-3}$alkyl, $C_{1-3}$alkoxy, halo, or halo$C_{1-3}$alkyl;

each $R^2$ is, independently, hydrogen, $C_{1-3}$alkyl, $C_{1-3}$alkoxy, halo, or halo$C_{1-3}$alkyl;

each $R^3$ is, independently, hydrogen, $C_{1-4}$alkyl, $C_{1-4}$alkoxy, halo, or halo$C_{1-4}$alkyl; and each $R^4$ is, independently, hydrogen, $C_{1-3}$alkyl, $C_{1-3}$alkoxy, halo, or halo$C_{1-3}$alkyl.

In some embodiments, at least one A is —C═O. In some embodiments, each A is —C═O.

In some embodiments, at least one D is O. In some embodiments, each D is O.

In some embodiments, each $R^1$ is, independently, hydrogen, methyl, ethyl, methoxy, ethoxy, halo, or halo$C_{1-3}$alkyl. In some embodiments, each $R^1$ is, independently, hydrogen, methyl, methoxy, halo, or halo$C_{1-3}$alkyl. In some embodiments, each $R^1$ is, independently, hydrogen, methyl, or methoxy. In some embodiments, at least one $R^1$ is hydrogen. In some embodiments, each $R^1$ is hydrogen.

In some embodiments, each $R^2$ is, independently, hydrogen, methyl, ethyl, methoxy, ethoxy, halo, or halo$C_{1-3}$alkyl. In some embodiments, each $R^2$ is, independently, hydrogen, methyl, methoxy, or halo. In some embodiments, at least one $R^2$ is hydrogen. In some embodiments, each $R^2$ is hydrogen.

In some embodiments, each $R^3$ is, independently, hydrogen, methyl, ethyl, methoxy, ethoxy, halo, or halo$C_{1-3}$alkyl. In some embodiments, each $R^3$ is, independently, methyl, methoxy, halo, or halo$C_{1-3}$alkyl. In some embodiments, each $R^3$ is, independently, halo or halo$C_{1-3}$alkyl. In some embodiments, each $R^3$ is, independently, halo$C_{1-3}$alkyl. In some embodiments, at least one $R^3$ is trifluoromethyl. In some embodiments, each $R^3$ is trifluoromethyl.

In some embodiments, each $R^4$ is, independently, hydrogen, methyl, ethyl, methoxy, ethoxy, or halo$C_{1-3}$alkyl. In some embodiments, each $R^4$ is, independently, hydrogen, methyl, methoxy, halo, or halo$C_{1-3}$alkyl. In some embodiments, each $R^4$ is, independently, hydrogen, methyl, methoxy, or halo. In some embodiments, at least one $R^4$ is hydrogen. In some embodiments, each $R^4$ is hydrogen.

In some embodiments, each A is, independently, —C═O or —C═S; each D is, independently, O or S; each $R^1$ is, independently, hydrogen, methyl, ethyl, methoxy, ethoxy, halo, halomethyl, or haloethyl; each $R^2$ is, independently, hydrogen, methyl, methoxy, halo, or halomethyl; each $R^3$ is, independently, $C_{1-3}$alkyl, $C_{1-3}$alkoxy, halo, or haloalkyl; and each $R^4$ is, independently, hydrogen, methyl, ethyl, methoxy, ethoxy, halo, halomethyl, or haloethyl.

In some embodiments, each A is, independently, —C═O or —C═S; each D is, independently, O or S; each $R^1$ is, independently, hydrogen, methyl, methoxy, halo, or halomethyl; each $R^2$ is, independently, hydrogen, halo, or halomethyl; each $R^3$ is, independently, methyl, ethyl, methoxy, ethoxy, halo, halomethyl, or haloethyl; and each $R^4$ is, independently, hydrogen, methyl, ethyl, methoxy, ethoxy, halo, halomethyl, or haloethyl.

In some embodiments, each A is —C═O; each D is O; each $R^1$ is, independently, hydrogen, halo, or halomethyl; each $R^2$ is, independently, hydrogen or halo; each $R^3$ is, independently, methyl, methoxy, halo, or halomethyl; and each $R^4$ is, independently, hydrogen, methyl, methoxy, halo, or halomethyl.

In some embodiments, each A is —C═O; each D is O; each $R^1$ is, independently, hydrogen or halo; each $R^2$ is, independently, hydrogen or halo; each $R^3$ is, independently, methyl, halo, or halomethyl; and each $R^4$ is, independently, hydrogen, methyl, halo, or halomethyl.

In some embodiments, each A is —C═O; each D is O; each $R^1$ is, independently, hydrogen or halo; each $R^2$ is, independently, hydrogen or halo; each $R^3$ is, independently, halo or halomethyl; and each $R^4$ is, independently, hydrogen or halo.

In some embodiments, each A is —C═O; each D is O; each $R^1$ is, independently, hydrogen or halo; each $R^2$ is, independently, hydrogen or halo; each $R^3$ is, independently, methyl, halo, or halomethyl; and each $R^4$ is, independently, hydrogen, methyl, halo, or halomethyl.

In some embodiments, each A is —C═O; each D is O; each $R^1$ is, independently, hydrogen or halo; each $R^2$ is, independently, hydrogen or halo; each $R^3$ is, independently, halo or halomethyl; and each $R^4$ is, independently, hydrogen, halo, or halomethyl.

The present invention also provides methods of treating and/or preventing mucositis in a mammal comprising administering to the mammal in need thereof a therapeutically effective amount of

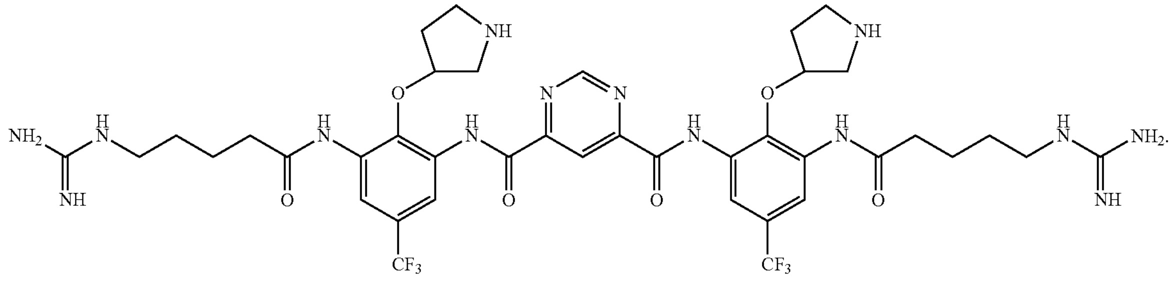

The present invention also provides methods of treating and/or preventing mucositis in a mammal comprising administering to the mammal in need thereof a therapeutically effective amount of a compound of Formula IV:

IV

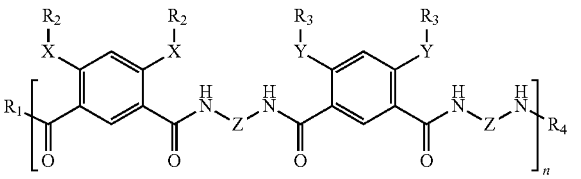

or a pharmaceutically acceptable salt thereof, wherein:

n=1 to 10;

X is O or S;

Y is O or S;

Z is a bond, $C_1$-$C_9$ straight or branched alkyl, or a 1,4-cyclohexyl;

$R_1$ is $NH_2$ or NH-A, where A is $C_1$-$C_9$ straight or branched alkyl, where A is optionally substituted with —$NH_2$, —$N(CH_3)_2$ or —NH—C(=NH)$NH_2$;

$R_2$ is $C_1$-$C_9$ straight or branched alkyl, where $R_2$ is optionally substituted with one or more —$NH_2$, —$N(CH_3)_2$ or —NH—C(=NH)$NH_2$;

$R_3$ is $C_1$-$C_9$ straight or branched alkyl, where $R_3$ is optionally substituted with one or more —$NH_2$, —$N(CH_3)_2$ or —NH—C(=NH)$NH_2$;

$R_4$ is H or

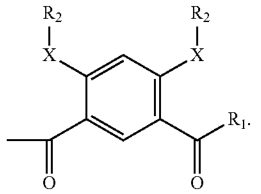

The present invention also provides methods of treating and/or preventing mucositis in a mammal comprising administering to the mammal in need thereof a therapeutically effective amount of a compound chosen from:

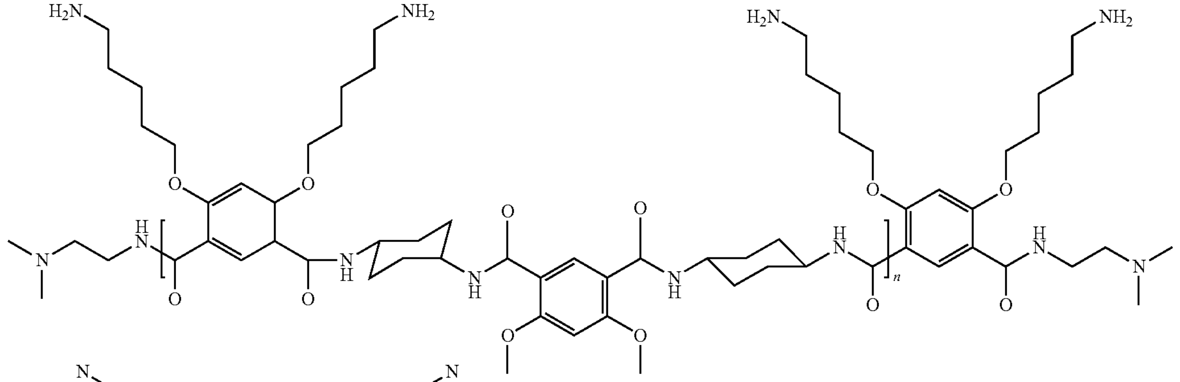

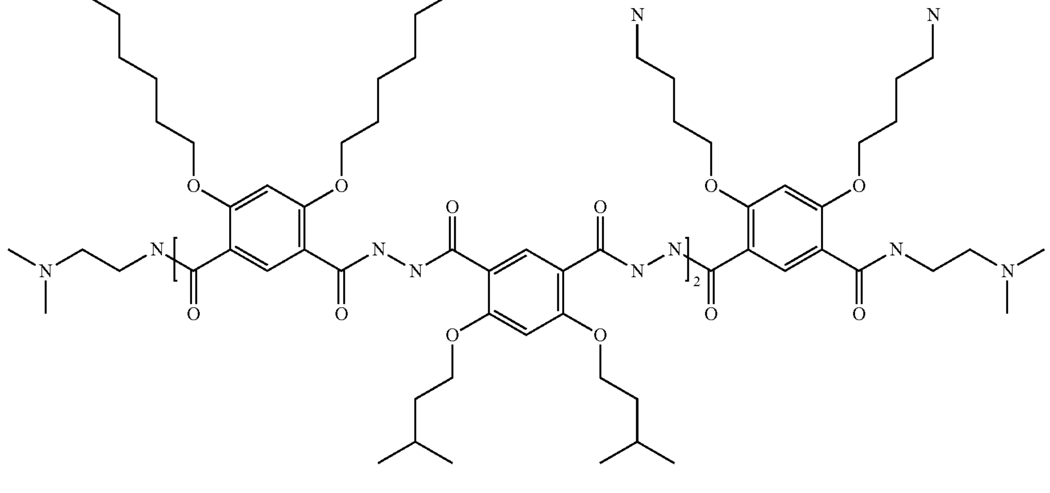

-continued

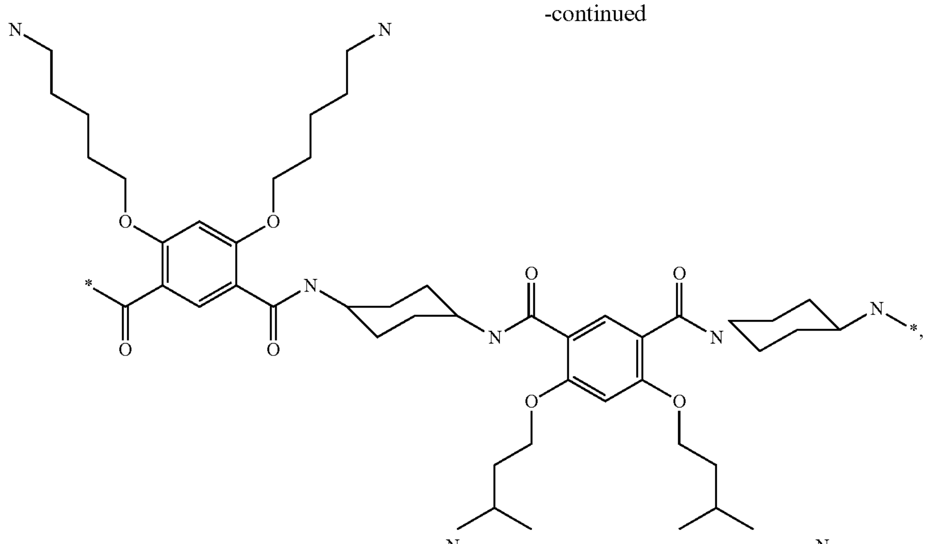

and

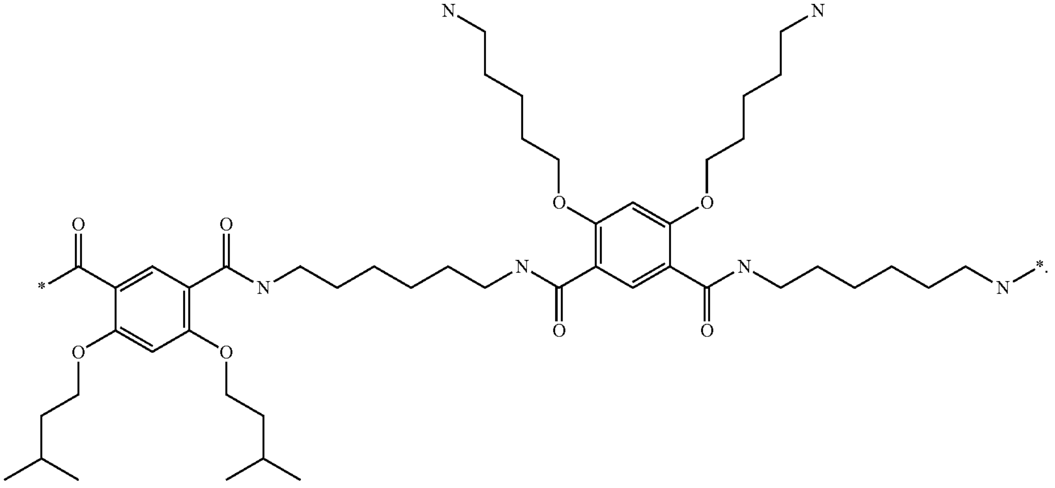

The present invention also provides methods of treating and/or preventing mucositis in a mammal comprising administering to the mammal in need thereof a therapeutically effective amount of a compound of Formula V:

V

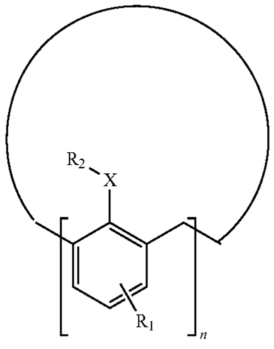

or a pharmaceutically acceptable salt thereof, wherein:

n is 2-8;

X is a bond, O or —O—$CH_2$—C(═O)—O—, $R_1$ is -A or —O-A, where A is $C_1$-$C_9$ straight or branched alkyl; and $R_2$ is $C_1$-$C_9$ straight or branched alkyl, where $R_2$ is optionally substituted with one or more —$NH_2$, —$N(CH_3)_2$, or —NH—C(═NH)$NH_2$.

In some embodiments, n is 4-8.

The present invention also provides methods of treating and/or preventing mucositis in a mammal comprising administering to the mammal in need thereof a therapeutically effective amount of a compound chosen from:

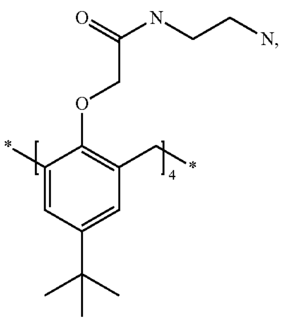

-continued

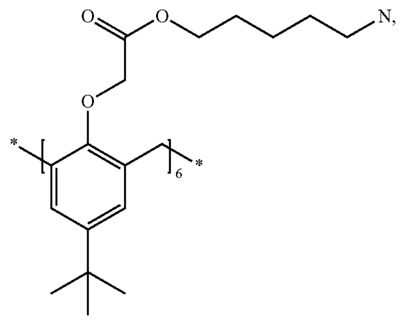

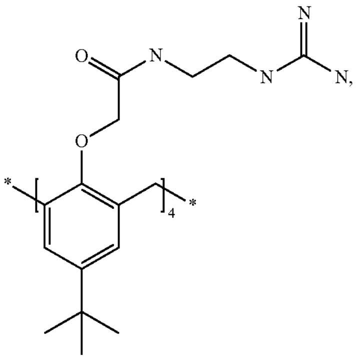

and

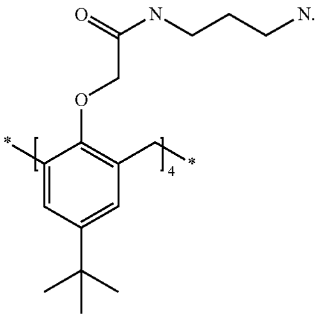

The present invention also provides methods of treating and/or preventing mucositis in a mammal comprising administering to the mammal in need thereof a therapeutically effective amount of a compound of Formula VI:

VI

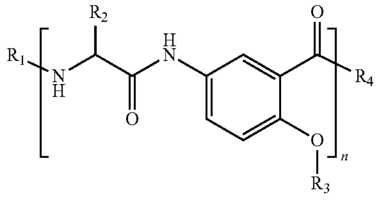

or a pharmaceutically acceptable salt thereof, wherein:

n is 2 to 10;

$R_1$ is H or

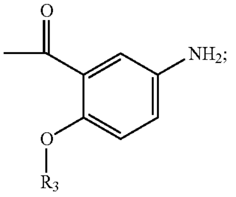

$R_2$ is $C_1$-$C_9$ straight or branched alkyl, where $R_2$ is optionally substituted with one or more —$NH_2$, —$N(CH_3)_2$ or —NH—C(=NH)$NH_2$;

$R_3$ is $C_1$-$C_9$ straight or branched alkyl, where $R_2$ is optionally substituted with one or more —$NH_2$, —$N(CH_3)_2$ or —NH—C(=NH)$NH_2$;

$R_4$ is OH, $NH_2$ or

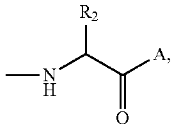

where A is OH or $NH_2$.

The present invention also provides methods of treating and/or preventing mucositis in a mammal comprising administering to the mammal in need thereof a therapeutically effective amount of a compound chosen from:

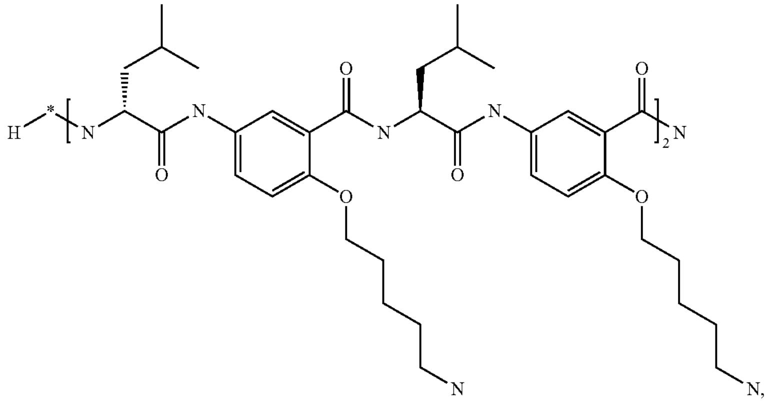

-continued
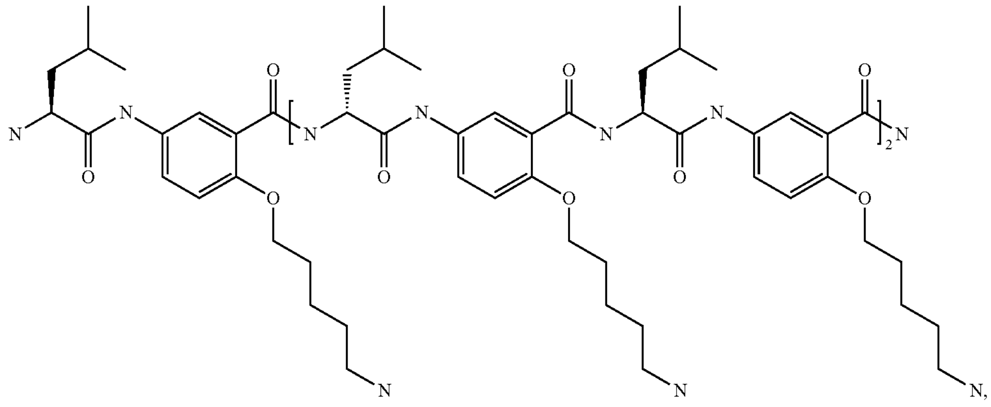
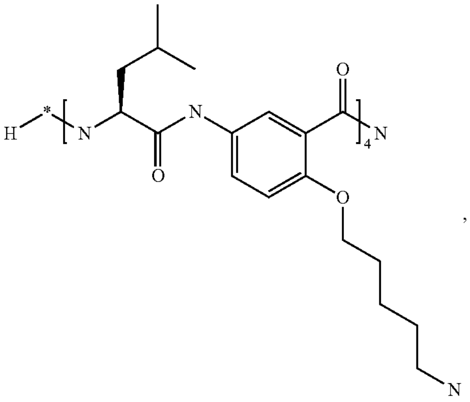
,
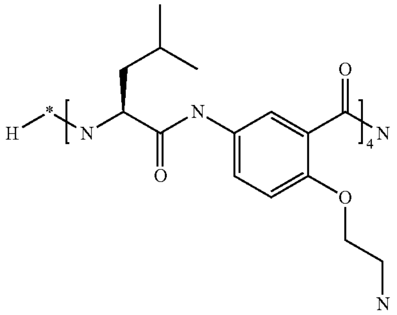
,
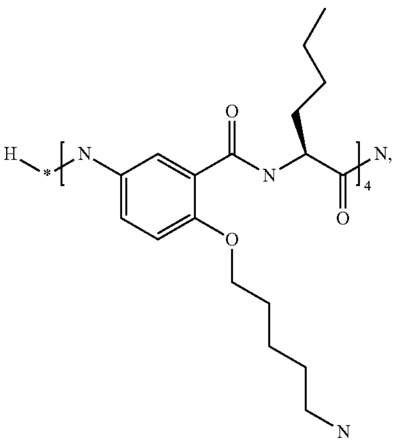
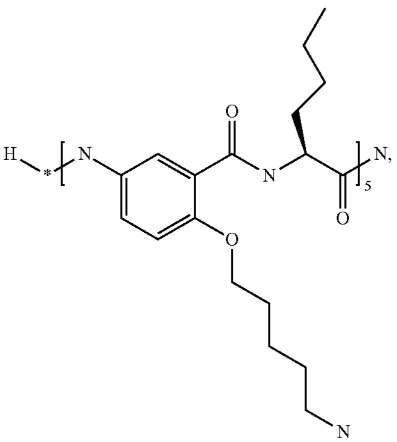
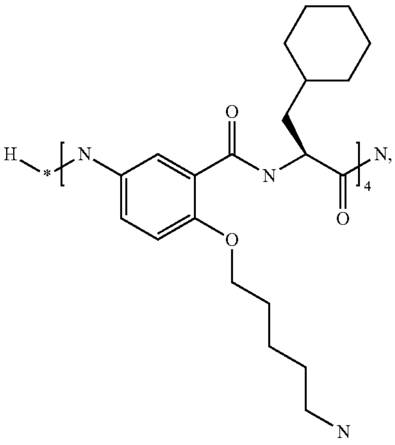
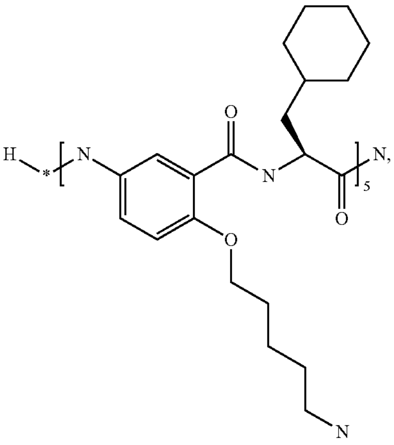

-continued

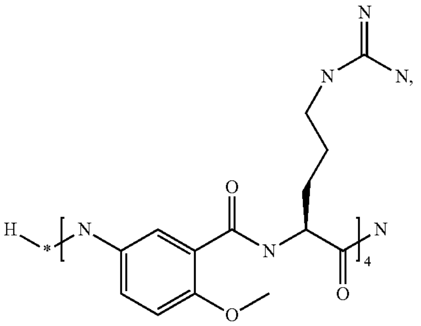

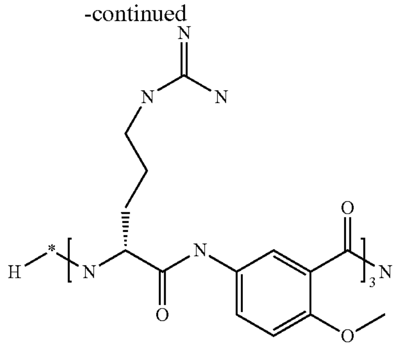

,

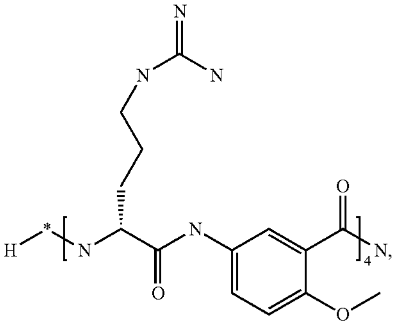

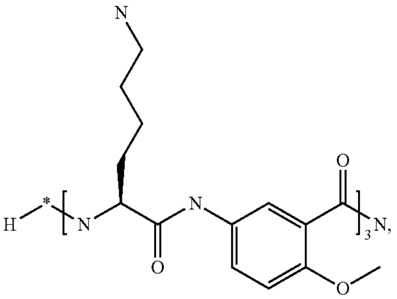

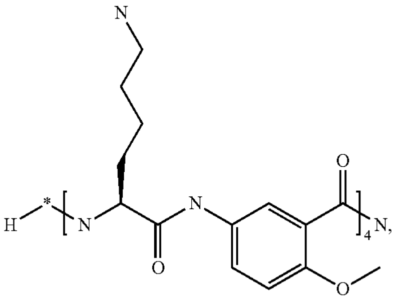

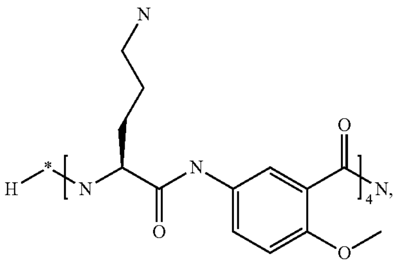

and

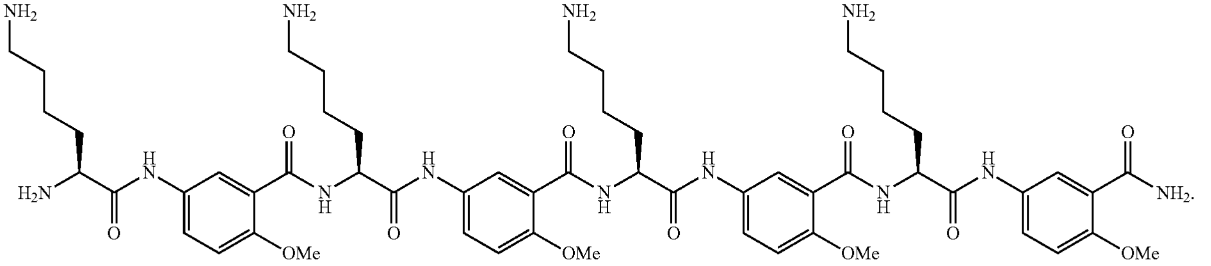 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O]

The present invention also provides methods of treating and/or preventing mucositis in a mammal comprising administering to the mammal in need thereof a therapeutically effective amount of a compound of Formula VII:

VII

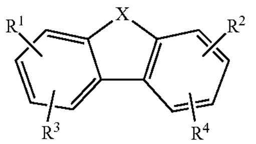

or a pharmaceutically acceptable salt thereof, wherein:

X is $C(R^7)C(R^8)$, C(═O), $N(R^9)$, O, S, S(═O), or $S(═O)_2$;

$R^7$, $R^8$, and $R^9$ are, independently, H, $C_1$-$C_8$alkyl, $C_1$-$C_8$alkoxy, halo, OH, $CF_3$, or aromatic group;

$R^1$ and $R^2$ are, independently, H, $C_1$-$C_8$alkyl, $C_1$-$C_8$alkoxy, halo, OH, halo$C_1$-$C_8$alkyl, or CN;

$R^3$ and $R^4$ are, independently, carbocycle$(R^5)(R^6)$;

each $R^5$ and each $R^6$ are, independently, H, $C_1$-$C_8$alkyl, $C_1$-$C_8$alkoxy, halo, OH, $CF_3$, aromatic group, heterocycle, or the free base or salt form of $—(CH_2)_n—NH_2$, or $—(CH_2)_n—NH—(CH_2)_n—NH_2$, or $—(CH_2)_n—NH—C(═NH)NH_2$, where each n is, independently, 1 to 8;

or a pharmaceutically acceptable salt thereof.

In some embodiments, X is $N(R^9)$, O, S, or $S(═O)_2$. In some embodiments, X is NH, O, or S. In some embodiments, X is NH or S.

In some embodiments, $R^1$ and $R^2$ are, independently, H, $C_1$-$C_3$alkyl, $C_1$-$C_3$alkoxy, halo, OH, halo$C_1$-$C_3$alkyl, or CN. In some embodiments, $R^1$ and $R^2$ are, independently, H, $C_1$-$C_3$alkyl, $C_1$-$C_3$alkoxy, halo, or OH. In some embodiments, $R^1$ and $R^2$ are, independently, H, $C_1$-$C_3$alkyl, or halo. In some embodiments, $R^1$ and $R^2$ are H.

In some embodiments, $R^3$ and $R^4$ are, independently,

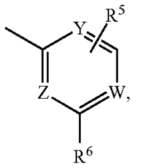

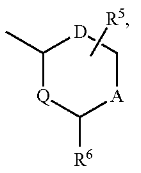

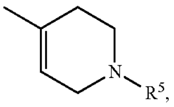

or

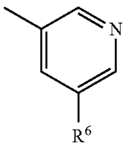

wherein:

each W, Y, and Z are, independently, C or N;

each A, D, and Q are, independently, $C(R^{10})C(R^{11})$, C(=O), $N(R^{12})$, O, or S; and each $R^{10}$, $R^{11}$, and $R^{12}$ are, independently, H, $C_1$-$C_8$alkyl, $C_1$-$C_8$alkoxy, halo, OH, $CF_3$, or aromatic group. In some embodiments, $R^3$ and $R^4$ are, independently

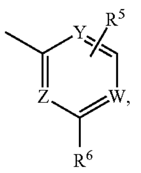

wherein each W, Y, and Z are, independently, C or N. In some embodiments, $R^3$ and $R^4$ are, independently

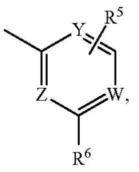

wherein each W, Y, and Z are C; or each Y and Z are C and each W is N.

In some embodiments, each $R^5$ is, independently, H, $C_1$-$C_8$alkyl, $C_1$-$C_8$alkoxy, halo, OH, $CF_3$, or the free base or salt form of $-(CH_2)_n-NH_2$, $-(CH_2)_n-NH-(CH_2)_n-NH_2$, or $-(CH_2)_n-NH-C(=NH)NH_2$, where each n is, independently, 1 to 8; and each $R^6$ is, independently, heterocycle or the free base or salt form of $-(CH_2)_n-NH_2$, $-(CH_2)_n-NH-(CH_2)_n-NH_2$, or $-(CH_2)_n-NH-C(=NH)NH_2$, where each n is, independently, 1 to 8.

In some embodiments, each $R^5$ is, independently, H, $C_1$-$C_3$alkyl, $C_1$-$C_3$alkoxy, halo, OH, or $CF_3$; and each $R^6$ is, independently, heterocycle or the free base or salt form of $-(CH_2)_n-NH_2$, where each n is, independently, 1 to 8.

In some embodiments, each $R^5$ is, independently, H, $C_1$-$C_3$alkyl, halo, or OH; and each $R^6$ is, independently, heterocycle or the free base or salt form of $-(CH_2)_n-NH_2$, where each n is, independently, 1 to 4.

In some embodiments, each $R^5$ is, independently, H, $C_1$-$C_3$alkyl, halo, or OH; and each $R^6$ is, independently, 6-membered heterocycle or the free base or salt form of $-(CH_2)_n-NH_2$, where each n is, independently, 1 to 3.

In some embodiments, each $R^5$ is, independently, H or halo; and each $R^6$ is piperazinyl or the free base or salt form of $-(CH_2)_n-NH_2$ where each n is, independently, 1 to 3.

In some embodiments, each $R^5$ is piperazinyl; and each $R^6$ is, independently, H, $C_1$-$C_3$alkyl, $C_1$-$C_3$alkoxy, halo, OH, or $CF_3$.

In some embodiments, each $R^5$ is piperazinyl; and each $R^6$ is H, $C_1$-$C_3$alkyl, halo, OH, or $CF_3$.

In some embodiments, X is NH, O, S, or $S(=O)_2$; $R^1$ and $R^2$ are H; $R^3$ and $R^4$ are, independently

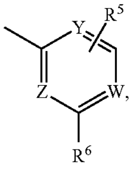 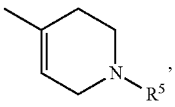 , or 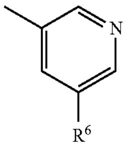

wherein: each W, Y, and Z are, independently, C or N; and each $R^5$ and each $R^6$ are, independently, H, heterocycle, or the free base or salt form of $-(CH_2)_n-NH_2$, where each n is, independently, 1 to 3.

In some embodiments, X is NH, O, or S; $R^1$ and $R^2$ are H; $R^3$ and $R^4$ are

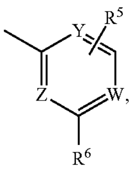

where each Z and Y are C, and each W is N; or each W, Y, and Z are C; and each $R^5$ is, independently, H or halo, and each $R^6$ is piperazinyl or the free base or salt form of $-(CH_2)_n-NH_2$, where each n is, independently, 1 to 3; or each $R^5$ is piperazinyl, and each $R^6$ is, independently, H, $C_1$-$C_3$alkyl, $C_1$-$C_3$alkoxy, halo, OH, or $CF_3$.

In some embodiments, X is NH, O, or S; $R^1$ and $R^2$ are H; $R^3$ and $R^4$ are

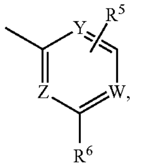

where each Z and Y are C, and each W is N; or each W, Y, and Z are C; and each $R^5$ is H, and each $R^6$ is piperazinyl or the free base or salt form of $-(CH_2)_n-NH_2$, where each n is, independently, 1 to 3; or each $R^5$ is piperazinyl; and each $R^6$ is H.

The present invention also provides methods of treating and/or preventing mucositis in a mammal comprising administering to the mammal in need thereof a therapeutically effective amount of a compound chosen from:

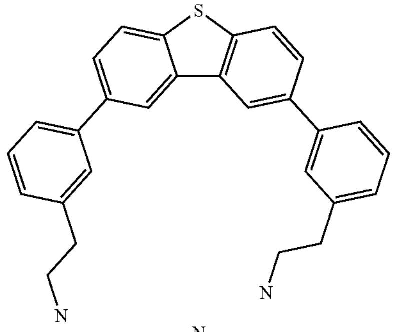

,

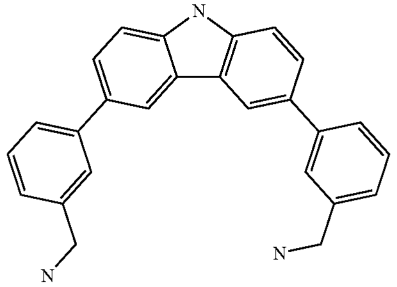

,

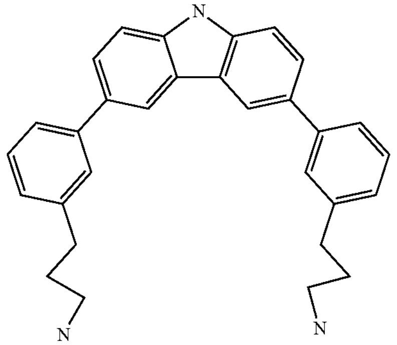

,

-continued

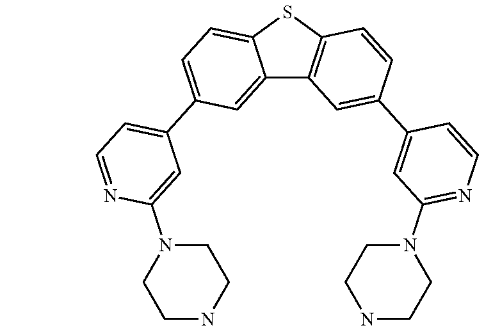

,

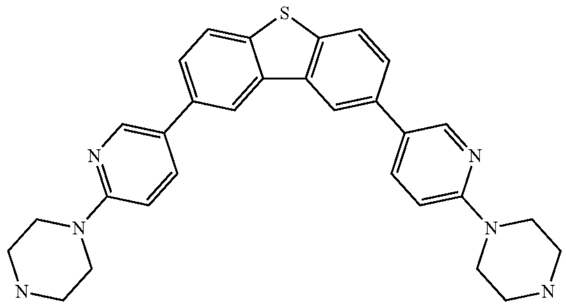

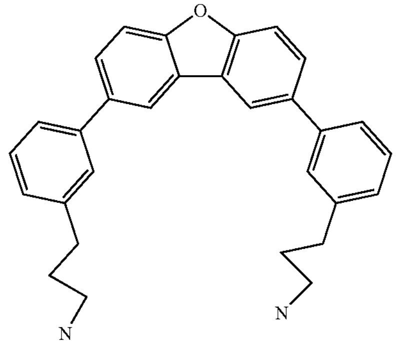

,

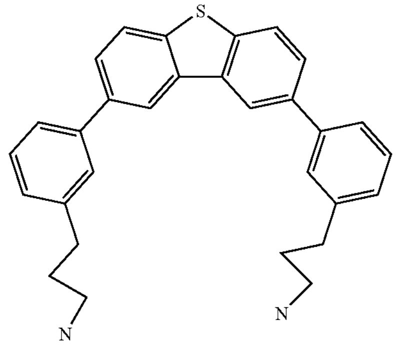

,

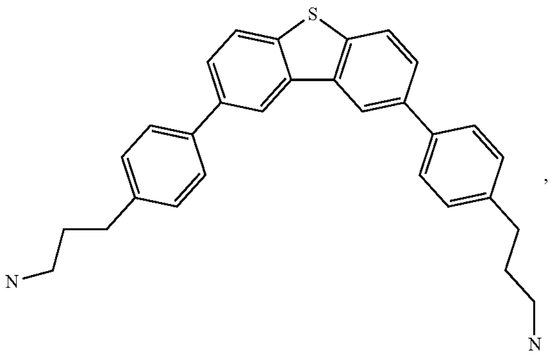

,

-continued
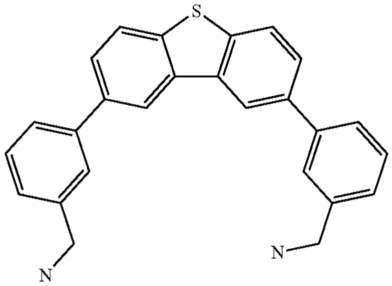
,
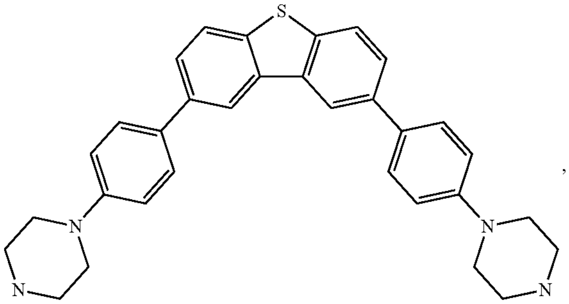
,
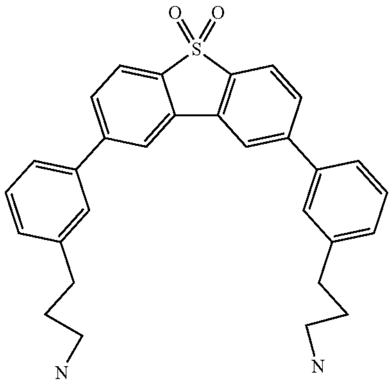
,
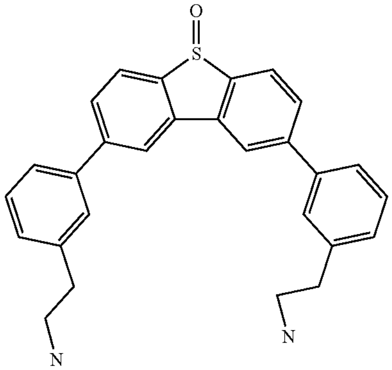
,
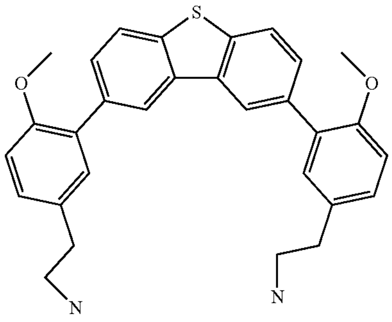
,
-continued
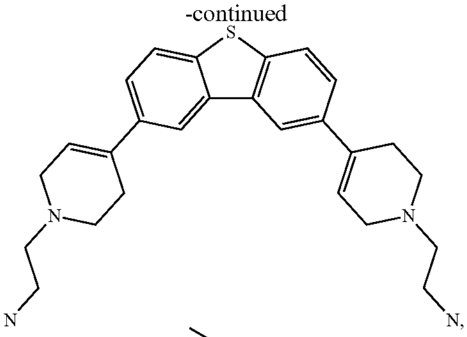
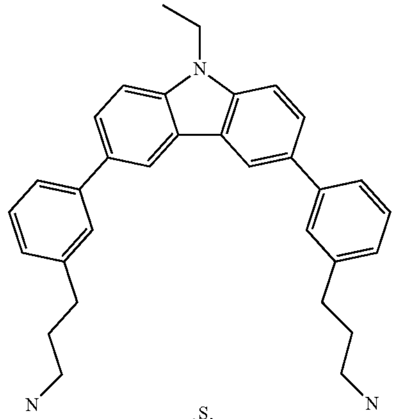
,
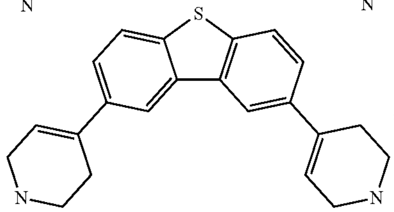
,
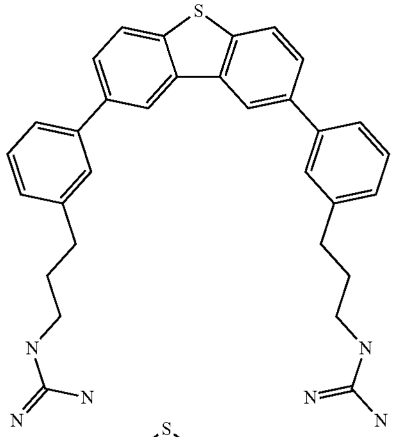
,
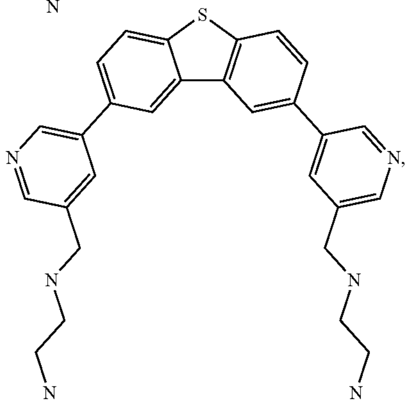
and -continued

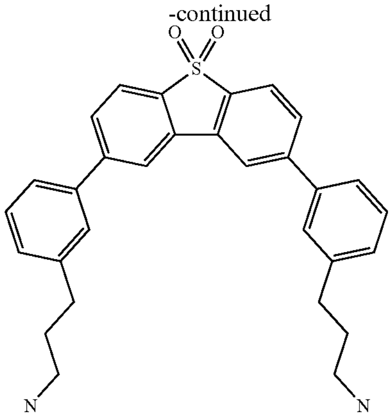

or pharmaceutically acceptable salt thereof.

The present invention also provides methods of treating and/or preventing mucositis in a mammal comprising administering to the mammal in need thereof a therapeutically effective amount of a compound of Formula VIII:

VIII

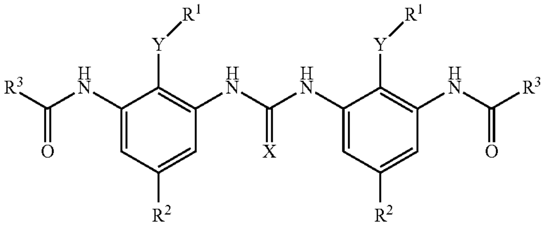

or a pharmaceutically acceptable salt thereof, wherein:

X is O or S;

each Y is, independently, O, S, or N;

each $R^1$ is, independently, H, 5- or 6-membered heterocycle, or the free base or salt form of $-(CH_2)_n-NH_2$ or $-(CH_2)_n-NH-C(=NH)NH_2$, where each n is, independently, 1 to 4; or each $R^1$ is, independently, together with Y a 5- or 6-membered heterocycle;

each $R^2$ is, independently, H, $CF_3$, $C(CH_3)_3$, halo, or OH; and each $R^3$ is, independently, $-(CH_2)_n-NH_2$ or $-(CH_2)_n-NH-C(=NH)NH_2$, where each n is, independently, 1 to 4;

or a pharmaceutically acceptable salt thereof.

In some embodiments, X is O.

In some embodiments, Y is O or S.

In some embodiments, each $R^1$ is, independently, 5-membered heterocycle or the free base or salt form of $-(CH_2)_n-NH_2$, where each n is, independently, 1 to 4. In some embodiments, each $R^1$ is, independently, 3-pyrrolyl or the free base or salt form of $-(CH_2)_n-NH_2$, where each n is, independently, 1 or 2.

In some embodiments, each $R^2$ is, independently, $CF_3$, $C(CH_3)_3$, or halo.

In some embodiments, each $R^3$ is, independently, $-(CH_2)_n-NH-C(=NH)NH_2$, where each n is, independently, 1 to 4. In some embodiments, each $R^3$ is $-(CH_2)_n-NH-C(=NH)NH_2$, where each n is 4.

In some embodiments, X is O or S; each Y is, independently, O or S; each $R^1$ is, independently, 5-membered heterocycle, or the free base or salt form of $-(CH_2)_n-NH_2$, where each n is, independently, 1 to 4; each $R^2$ is, independently, $CF_3$ or $C(CH_3)_3$; and each $R^3$ is, independently, $-(CH_2)_n-NH-C(=NH)NH_2$, where each n is, independently, 1 to 4.

In some embodiments, X is O or S; each Y is O or S; each $R^1$ is 5-membered heterocycle, or the free base or salt form of $-(CH_2)_n-NH_2$, where each n is 1 to 4; each $R^2$ is $CF_3$ or $C(CH_3)_3$; and each $R^3$ is $-(CH_2)_n-NH-C(=NH)NH_2$, where each n is 1 to 4.

In some embodiments, X is O or S; each Y is O or S; each $R^1$ is 3-pyrrolyl, or the free base or salt form of $-(CH_2)_n-NH_2$, where each n is 2; each $R^2$ is $CF_3$ or $C(CH_3)_3$; and each $R^3$ is $-(CH_2)_n-NH-C(=NH)NH_2$, where each n is 4.

The present invention also provides methods of treating and/or preventing mucositis in a mammal comprising administering to the mammal in need thereof a therapeutically effective amount of a compound chosen from:

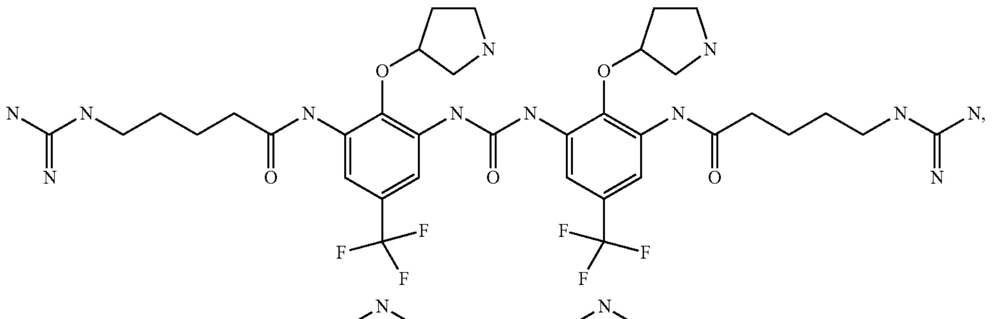

,

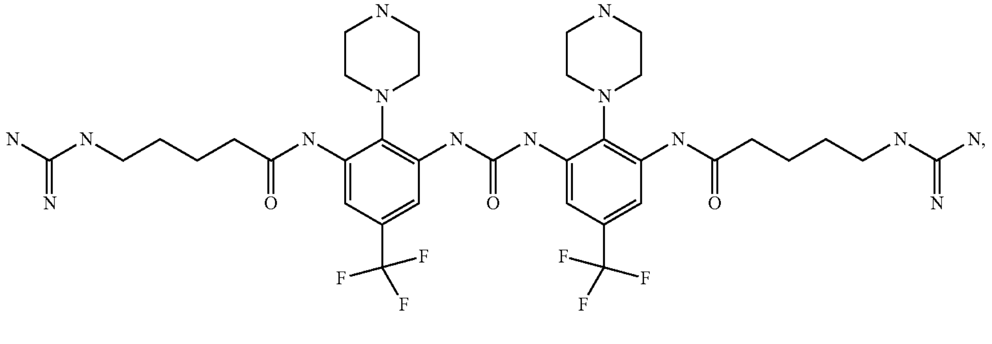

,

-continued

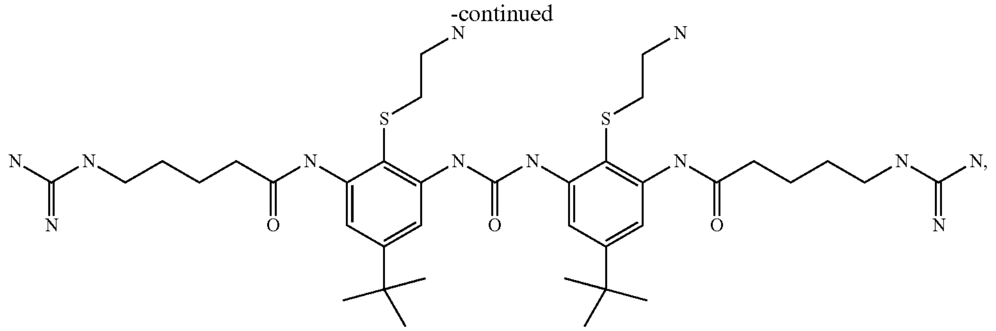

or pharmaceutically acceptable salt thereof.

The present invention also provides methods of treating and/or preventing mucositis in a mammal comprising administering to the mammal in need thereof a therapeutically effective amount of a compound of Formula IX:

$$Q—X—Z—X—Q \quad \text{IX}$$

or a pharmaceutically acceptable salt thereof, wherein:

Z is

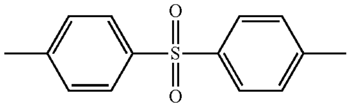

,

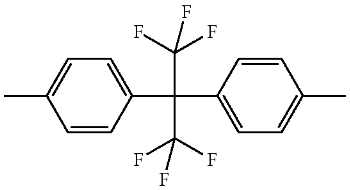

or phenyl;

each Q is, independently

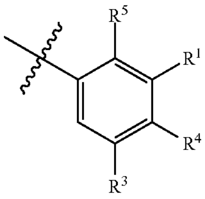

or —C(=O)—$(CH_2)_b$—NH—C(=NH)—$NH_2$, where each b is, independently, 1 to 4;

each X is, independently, O, S, or N;

each $R^1$ is, independently, H, $CF_3$, $C(CH_3)_3$, halo, or OH;

each $R^3$ is, independently, H, —NH—$R^2$, —$(CH_2)_r$—$NH_2$, —$NH_2$, —NH—$(CH_2)_w$—$NH_2$, or

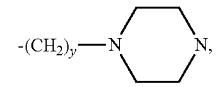

where each r is, independently, 1 or 2, each w is, independently, 1 to 3, and each y is, independently, 1 or 2;

each $R^2$ is, independently, H, or the free base or salt form of —$(CH_2)_n$—$NH_2$ or —$(CH_2)_n$—NH—C(=NH)$NH_2$, where each n is, independently, 1 to 4;

each $R^4$ is, independently, H, —NH—C(=O)—$(CH_2)_p$—NH—C(=NH)—$NH_2$ or

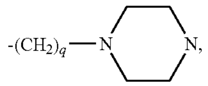

where each p is, independently, 1 to 6, and each q is, independently, 1 or 2; and each $R^5$ is, independently, H or $CF_3$;

or a pharmaceutically acceptable salt thereof.

In some embodiments, Z is

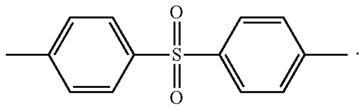

.

In some embodiments, each Q is, independently

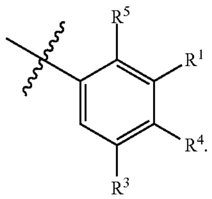

In some embodiments, each X is O.

In some embodiments, each $R^1$ is, independently, H, $CF_3$, or halo. In some embodiments, each $R^1$ is $CF_3$.

In some embodiments, each $R^3$ is, independently, —NH—$R^2$.

In some embodiments, each $R^2$ is, independently, H, or the free base or salt form of —$(CH_2)_n$—$NH_2$, where each n is, independently, 1 to 4. In some embodiments, each $R^2$ is, independently, the free base or salt form of $—(CH_2)_n—NH_2$, where each n is, independently, 1 or 2. In some embodiments, each $R^2$ is the free base or salt form of $—(CH_2)_n—NH_2$, where each n is 2.

In some embodiments, each $R^4$ and each $R^5$ is H.

In some embodiments, Z is

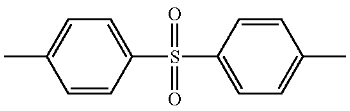
;

each Q is, independently,

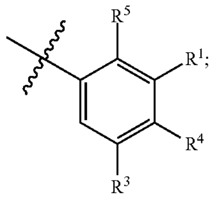

each X is O or S; each $R^1$ is, independently, $CF_3$, $C(CH_3)_3$, or halo; each $R^3$ is, independently, $—NH—R^2$; each $R^2$ is, independently, H, or the free base or salt form of $—(CH_2)_n—NH_2$, where each n is, independently, 1 to 4; and each $R^4$ and each $R^5$ is H.

In some embodiments, Z is

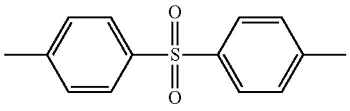
;

each Q is, independently,

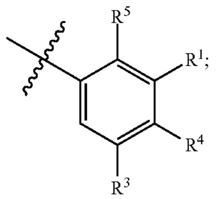

each X is O; each $R^1$ is $CF_3$, $C(CH_3)_3$, or halo; each $R^3$ is, independently, $—NH—R^2$; each $R^2$ is, independently, the free base or salt form of $—(CH_2)_n—NH_2$, where each n is 1 or 2; and each $R^4$ and each $R^5$ is H.

In some embodiments, Z is

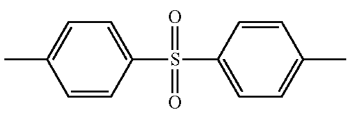
;

each Q is, independently,

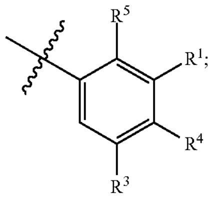

each X is O; each $R^1$ is $CF_3$ or halo; each $R^3$ is, independently, $—NH—R^2$; each $R^2$ is the free base or salt form of $—(CH_2)_n—NH_2$, where each n is 2; and each $R^4$ and each $R^5$ is H.

In some embodiments, Z is

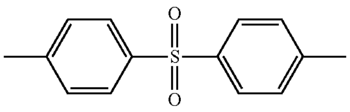
;

each Q is, independently,

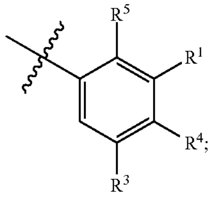

each X is, independently, O, or S; each $R^1$ is, independently, H, or $CF_3$; each $R^3$ is H; each $R^4$ is, independently, H or $—NH—C(=O)—(CH_2)_p—NH—C(=NH)—NH_2$, where each p is, independently, 3 or 4; and each $R^5$ is, independently, H or $CF_3$.

In some embodiments, Z is

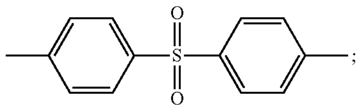
;

each Q is, independently, $—C(=O)—(CH_2)_b—NH—C(=NH)—NH_2$, where each b is, independently, 3 or 4; and each X is N.

In some embodiments, Z is

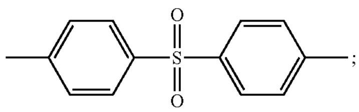
;

each Q is, independently,

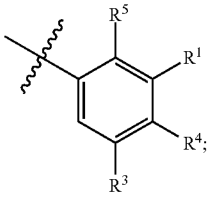

each X is O or S; each $R^1$ is, independently, H or $CF_3$; each $R^3$ is, independently, $-(CH_2)_r-NH_2$, $-NH_2$, $-NH-(CH_2)_w-NH_2$, or

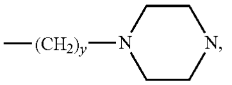

where each r is, independently, 1 or 2, each w is, independently, 1 to 3, and each y is, independently, 1 or 2; each $R^4$ is H; and each $R^5$ is, independently, H or $CF_3$.

In some embodiments, Z is

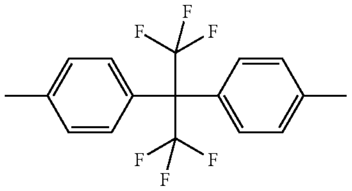

or phenyl; each Q is, independently,

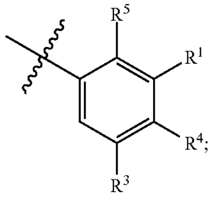

each X is, independently, O or S; each $R^1$ is, independently, H or $CF_3$; each $R^3$ is H; each $R^4$ is, independently,

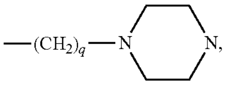

where each q is, independently, 1 or 2; and each $R^5$ is, independently, H or $CF_3$.

The present invention also provides methods of treating and/or preventing mucositis in a mammal comprising administering to the mammal in need thereof a therapeutically effective amount of a compound chosen from:

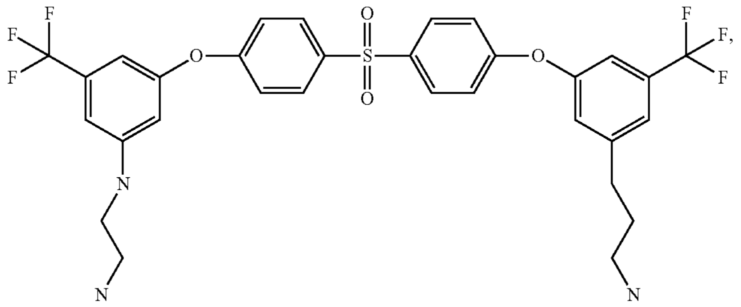

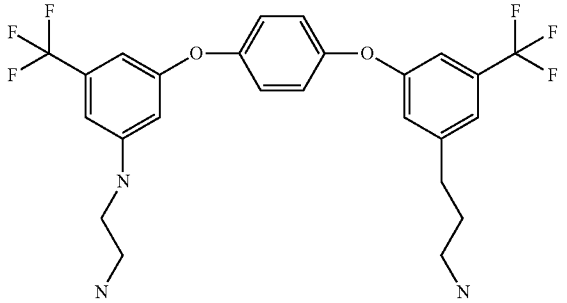

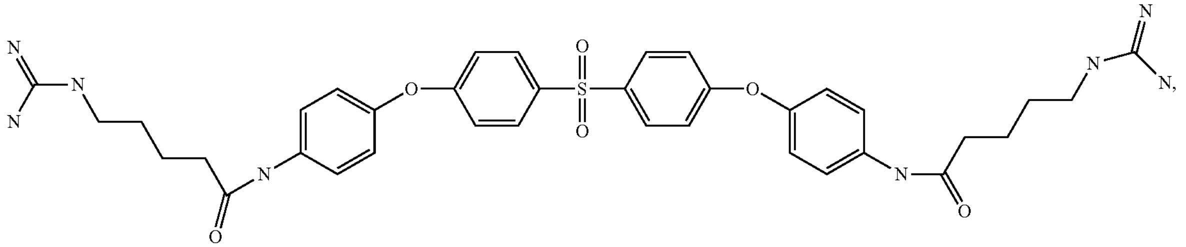

-continued
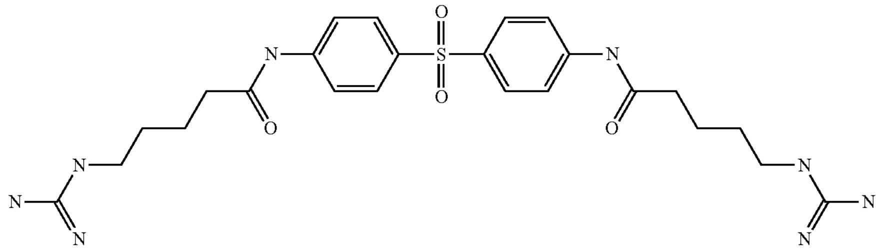
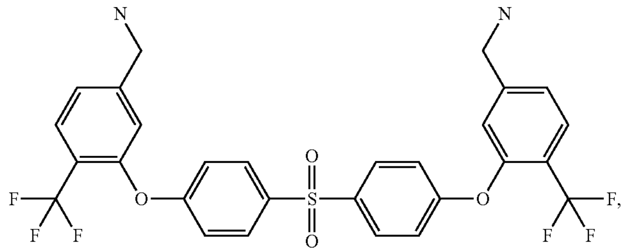
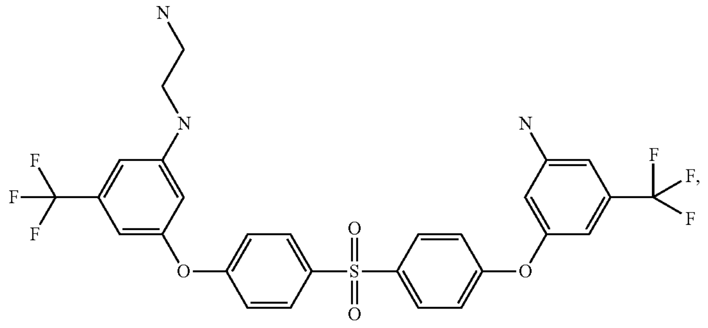
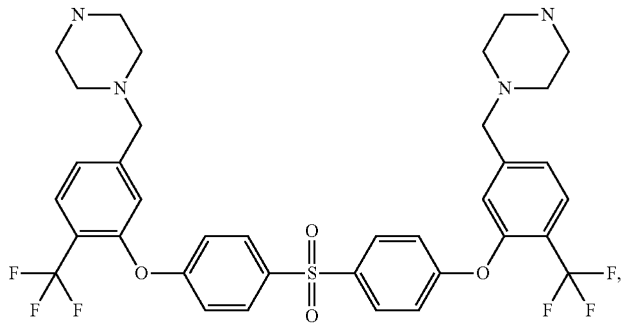
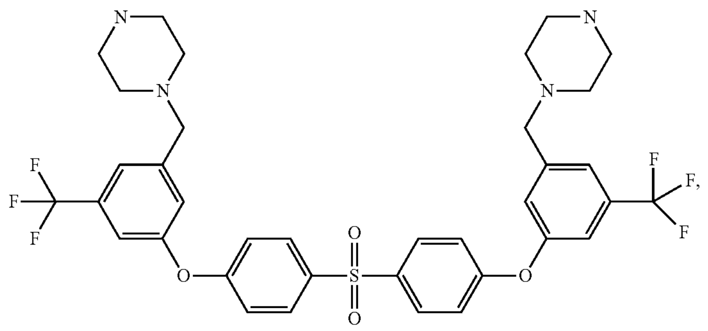

-continued

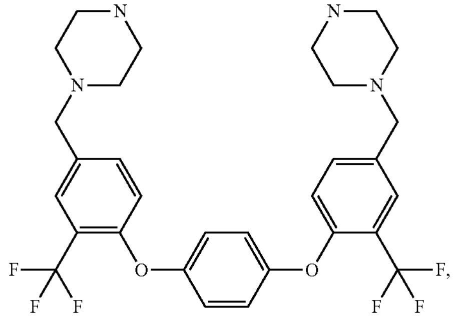

and

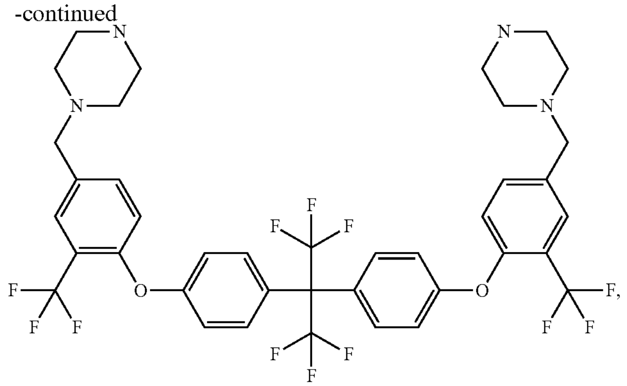

or a pharmaceutically acceptable salt thereof.

The present invention also provides methods of treating and/or preventing mucositis in a mammal comprising administering to the mammal in need thereof a therapeutically effective amount of a compound of Formula X:

X

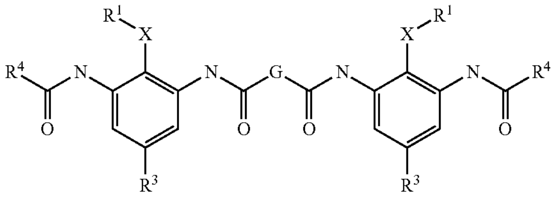

or a pharmaceutically acceptable salt thereof, wherein:

G is

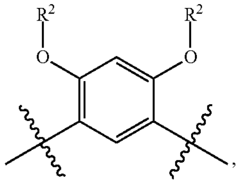

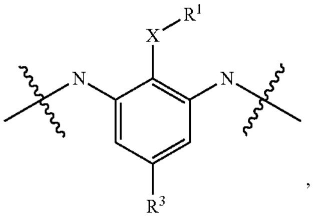

, or

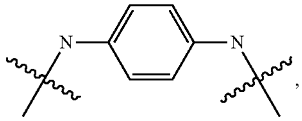

each X is, independently, O or S;

each $R^1$ is, independently,

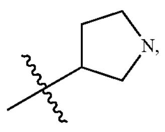

or the free base or salt form of $-(CH_2)_n-NH_2$ or $-(CH_2)_n-NH-C(=NH)NH_2$, where each n is, independently, 1 to 4;

each $R^2$ is, independently, H, $C_1$-$C_8$alkyl, or the free base or salt form of $-(CH_2)_n-NH_2$ or $-(CH_2)_n-NH-C(=NH)NH_2$, where each n is, independently, 1 to 4;

each $R^3$ is, independently, H, $CF_3$, $C(CH_3)_3$, halo, or OH; and each $R^4$ is, independently, $-(CH_2)_n-NH_2$ or $-(CH_2)_n-NH-C(=NH)NH_2$, where each n is, independently, 1 to 4.

In some embodiments, G is

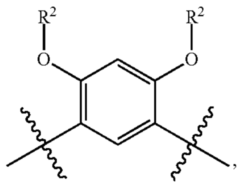

and each X is S.

In some embodiments, each $R^1$ is, independently, the free base or salt form of $-(CH_2)_n-NH_2$, where each n is, independently, 1 to 4. In some embodiments, each $R^1$ is, independently, the free base or salt form of $-(CH_2)_n-NH_2$, where each n is, independently, 1 or 2. In some embodiments, each $R^1$ is the free base or salt form of $-(CH_2)_n-NH_2$, where each n is 2.

In some embodiments, each $R^2$ is, independently, $C_1$-$C_3$alkyl or the free base or salt form of $-(CH_2)_n-NH_2$ where n is 1 to 4. In some embodiments, each $R^2$ is, independently, $C_1$-$C_3$alkyl or the free base or salt form of $-(CH_2)_n-NH_2$, where each n is, independently, 1 or 2. In some embodiments, each $R^2$ is, independently, methyl or the free base or salt form of $-(CH_2)_n-NH_2$, where each n is, independently, 2. In some embodiments, each $R^2$ is methyl or the free base or salt form of $-(CH_2)_n-NH_2$, where each n is 2.

In some embodiments, each $R^3$ is, independently, $CF_3$, $C(CH_3)_3$, or halo. In some embodiments, each $R^3$ is $CF_3$.

In some embodiments, each $R^4$ is, independently, $—(CH_2)_n—NH—C(=NH)NH_2$, where each n is, independently, 1 to 4. In some embodiments, each $R^4$ is $—(CH_2)_n—NH—C(=NH)NH_2$, where each n is 4.

In some embodiments, G is

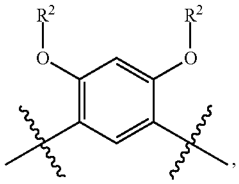

, each X is S; each $R^1$ is, independently, the free base or salt form of $—(CH_2)_n—NH_2$, where each n is, independently, 1 or 2; each $R^2$ is, independently, $C_1$-$C_8$alkyl or the free base or salt form of $—(CH_2)_n—NH_2$, where each n is, independently, 1 or 2; each $R^3$ is, independently, $CF_3$, $C(CH_3)_3$, or halo; and each $R^4$ is, independently, $—(CH_2)_n—NH—C(=NH)NH_2$, where each n is, independently, 3 or 4.

In some embodiments, G is

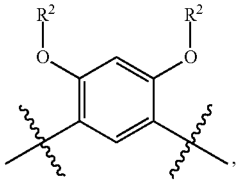

, each X is S; each $R^1$ is the free base or salt form of $—(CH_2)_n—NH_2$, where each n is 1 or 2; each $R^2$ is, independently, $C_1$-$C_3$alkyl or the free base or salt form of $—(CH_2)_n—NH_2$, where each n is 2; each $R^3$ is, independently, $CF_3$ or $C(CH_3)_3$; and each $R^4$ is $—(CH_2)_n—NH—C(=NH)NH_2$, where each n is 3 or 4.

In some embodiments, G is

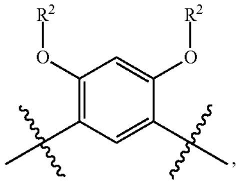

, each X is S; each $R^1$ is the free base or salt form of $—(CH_2)_n—NH_2$, where each n is 2; each $R^2$ is, independently, methyl or the free base or salt form of $—(CH_2)_n—NH_2$, where each n is 2; each $R^3$ is, independently, $CF_3$ or $C(CH_3)_3$; and each $R^4$ is $—(CH_2)_n—NH—C(=NH)NH_2$, where each n is 4.

In some embodiments, G is

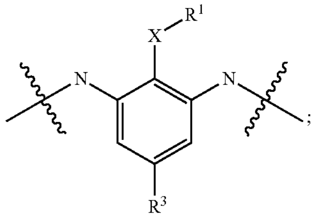

;

each X is, independently, O or S; each $R^1$ is, independently, the free base or salt form of $—(CH_2)_n—NH_2$ or $—(CH_2)_n—NH—C(=NH)NH_2$, where each n is, independently, 1 to 4; each $R^3$ is, independently, H or $CF_3$; and each $R^4$ is, independently, $—(CH_2)_n—NH_2$ or $—(CH_2)_n—NH—C(=NH)NH_2$, where each n is, independently, 1 to 4.

In some embodiments, G is

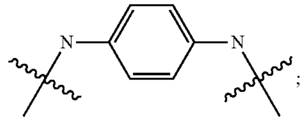 [SMILES: *Nc1ccc(N*)cc1]

;

each X is, independently, O or S; each $R^1$ is

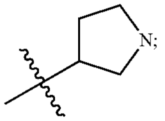

each $R^3$ is, independently, H or $CF_3$; and each $R^4$ is, independently, $—(CH_2)_n—NH_2$ or $—(CH_2)_n—NH—C(=NH)NH_2$, where each n is, independently, 1 to 4.

The present invention also provides methods of treating and/or preventing mucositis in a mammal comprising administering to the mammal in need thereof a therapeutically effective amount of a compound chosen from:

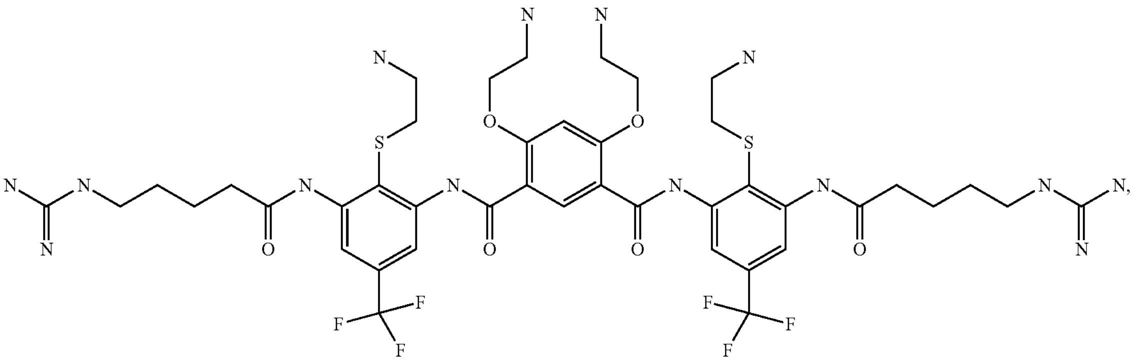

-continued

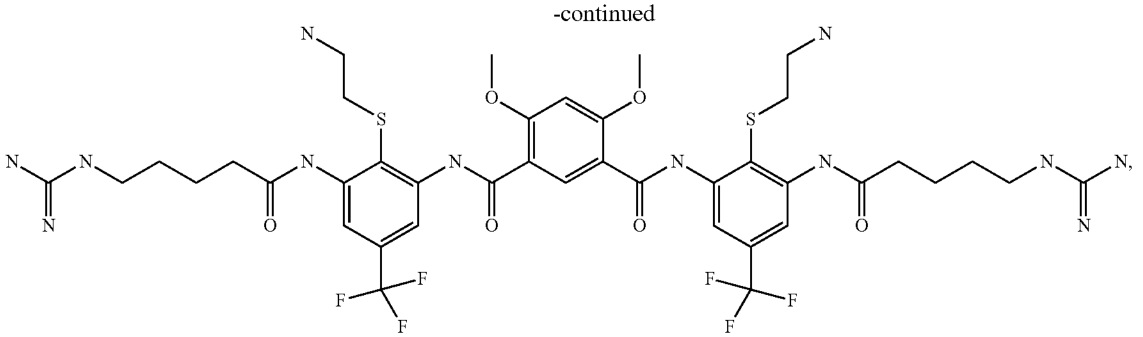

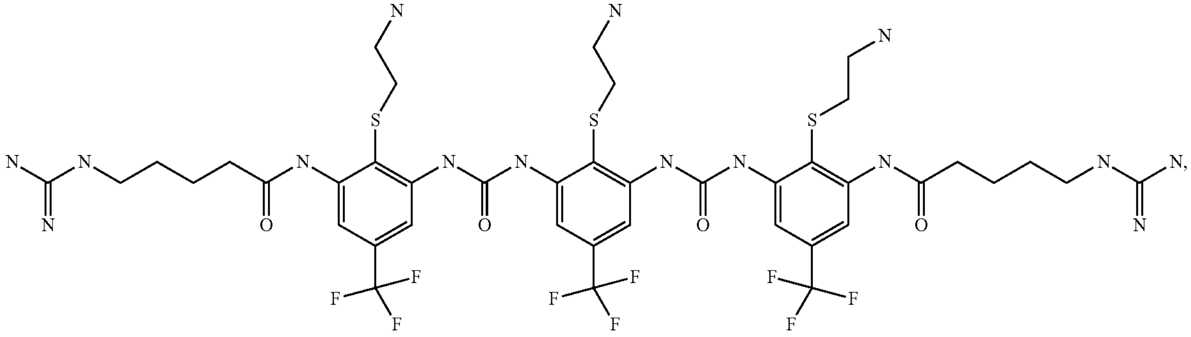

and

Compound Y

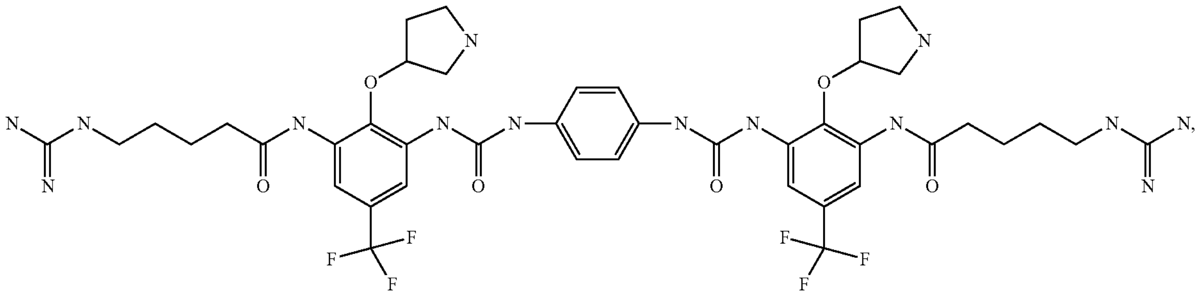

or a pharmaceutically acceptable salt thereof.

In some embodiments of the invention, the compound used for treating and/or preventing mucositis is not Compound Y.

The present invention also provides methods of treating and/or preventing mucositis in a mammal comprising administering to the mammal in need thereof a therapeutically effective amount of a compound of Formula XI:

XI

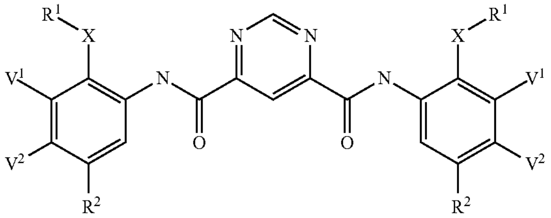

or a pharmaceutically acceptable salt thereof, wherein:

each X is, independently, O, S, or $S(=O)_2$;

each $R^1$ is, independently, $-(CH_2)_n-NH_2$, $-(CH_2)_n-NH-C(=NH)NH_2$, or $-(CH_2)_n-NH-C(=O)-R^4$, where each n is, independently, 1 to 4, and each $R^4$ is, independently, H, $C_1$-$C_3$alkyl, or $-(CH_2)_p-NH_2$, where each p is, independently, 1 or 2;

each $R^2$ is, independently, H, halo, $CF_3$, or $C(CH_3)_3$; and each $V^2$ is H, and each $V^1$ is, independently, $-N-C(=O)-R^3$, where each $R^3$ is, independently, $-(CH_2)_n-NH_2$ or $-(CH_2)_n-NH-C(=NH)NH_2$, where each n is, independently, 1 to 4; or each $V^1$ is H and each $V^2$ is, independently, $-S-R^5$, where each $R^5$ is, independently, $-(CH_2)_n-NH_2$ or $-(CH_2)_n-NH-C(=NH)NH_2$, where each n is, independently, 1 to 4;

or a pharmaceutically acceptable salt thereof.

In some embodiments, each X is S.

In some embodiments, each $R^1$ is, independently, $-(CH_2)_n-NH_2$, $-(CH_2)_n-NH-C(=NH)NH_2$, or $-(CH_2)_n-NH-C(=O)-R^4$, where each n is, independently, 1 or 2, and each $R^4$ is, independently, H or methyl. In some embodiments, each $R^1$ is, independently, $-(CH_2)_n-NH_2$, $-(CH_2)_n-NH-C(=NH)NH_2$, or $-(CH_2)_n-NH-C(=O)-R^4$, where each n is 2 and each $R^4$ is H. In some embodiments, each $R^1$ is, independently, $-(CH_2)_n-NH_2$ or $-(CH_2)_n-NH-C(=NH)NH_2$, where each n is 2. In some embodiments, each $R^1$ is $-(CH_2)_n-NH_2$ or $-(CH_2)_n-NH-C(=NH)NH_2$, where each n is 2.

In some embodiments, each $R^2$ is, independently, H, Br, F, Cl, $CF_3$, or $C(CH_3)_3$. In some embodiments, each $R^2$ is Br, F, Cl, $CF_3$, or $C(CH_3)_3$.

In some embodiments, each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4. In some embodiments, each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 or 2. In some embodiments, each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is 2. In some embodiments, each $V^2$ is H and each $V^1$ is —N—C(=O)—$R^3$, where each $R^3$ is —$(CH_2)_n$—$NH_2$ or —$(CH_2)_n$—NH—C(=NH)$NH_2$, where n is 2.

In some embodiments, each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is, independently, 1 to 4. In some embodiments, each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is 1 or 2. In some embodiments, each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is 2. In some embodiments, each $V^1$ is H and each $V^2$ is —S—$R^5$, where each $R^5$ is —$(CH_2)_n$—$NH_2$ or —$(CH_2)_n$—NH—C(=NH)$NH_2$, where each n is 2.

In some embodiments, each X is S; each $R^1$ is, independently, —$(CH_2)_n$—$NH_2$ or —$(CH_2)_n$—NH—C(=NH)$NH_2$, where each n is, independently, 1 to 4; each $R^2$ is, independently, halo, $CF_3$, or $C(CH_3)_3$; and each $V^1$ is H and each $V^2$ is, independently, —S—$R^5$, where each $R^5$ is, independently, —$(CH_2)_n$—$NH_2$, where each n is, independently, 1 to 4.

In some embodiments, each X is S; each $R^1$ is, independently, —$(CH_2)_n$—$NH_2$, where each n is, independently, 1 or 2; each $R^2$ is, independently, $CF_3$ or $C(CH_3)_3$; and each $V^1$ is H and each $V^2$ is, independently, —S—$R^5$, where each $R^5$ is, independently, —$(CH_2)_n$—$NH_2$, where each n is, independently, 1 or 2.

In some embodiments, each X is S; each $R^1$ is —$(CH_2)_n$—$NH_2$, where each n is 1 or 2; each $R^2$ is, independently, $CF_3$ or $C(CH_3)_3$; and each $V^1$ is H and each $V^2$ is —S—$R^5$, where each $R^5$ is —$(CH_2)_n$—$NH_2$, where each n is 1 or 2.

In some embodiments, each X is O or S; each $R^1$ is, independently, —$(CH_2)_n$—$NH_2$, —$(CH_2)_n$—NH—C(=NH)$NH_2$, or —$(CH_2)_n$—NH—C(=O)—$R^4$, where each n is, independently, 1 to 4, and each $R^4$ is, independently, H or methyl; each $R^2$ is, independently, halo, $CF_3$, or $C(CH_3)_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4.

In some embodiments, each X is S; each $R^1$ is, independently, —$(CH_2)_n$—NH—C(=O)—$R^4$, where each n is, independently, 1 or 2, and each $R^4$ is, independently, H or methyl; each $R^2$ is, independently, halo; and each $V^2$ is H, and each $V^1$ is —N—C(=O)—$R^3$, where each $R^3$ is —$(CH_2)_n$—$NH_2$ or —$(CH_2)_n$—NH—C(=NH)$NH_2$, where each n is 4.

In some embodiments, each X is O or S; each $R^1$ is, independently, —$(CH_2)_n$—$NH_2$ or —$(CH_2)_n$—NH—C(=NH)$NH_2$, where each n is, independently, 1 to 4; each $R^2$ is, independently, halo, $CF_3$, or $C(CH_3)_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4.

In some embodiments, each X is O or S; each $R^1$ is —$(CH_2)_n$—$NH_2$ or —$(CH_2)_n$—NH—C(=NH)$NH_2$, where each n is 1 or 2; each $R^2$ is halo, $CF_3$, or $C(CH_3)_3$; and each $V^2$ is H, and each $V^1$ is —N—C(=O)—$R^3$, where each $R^3$ is —$(CH_2)_n$—$NH_2$ or —$(CH_2)_n$—NH—C(=NH)$NH_2$, where each n is 3 or 4.

In some embodiments, each X is, independently, S or $S(=O)_2$; each $R^1$ is, independently, —$(CH_2)_n$—$NH_2$ or —$(CH_2)_n$—NH—C(=O)—$R^4$, where each n is, independently, 1 or 2, and each $R^4$ is, independently, —$(CH_2)_p$—$NH_2$, where each p is, independently, 1 or 2; each $R^2$ is, independently, halo or $CF_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 3 or 4.

The present invention also provides methods of treating and/or preventing mucositis in a mammal comprising administering to the mammal in need thereof a therapeutically effective amount of a compound chosen from:

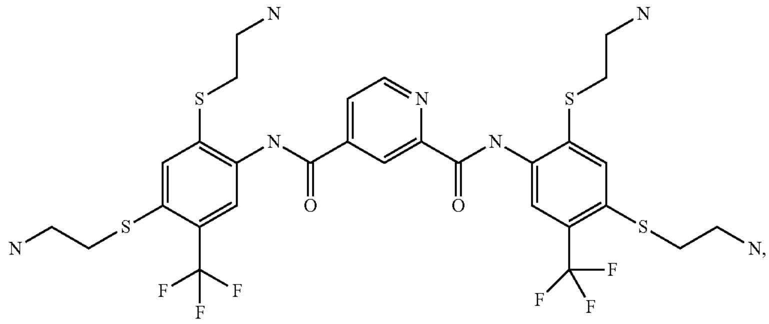

,

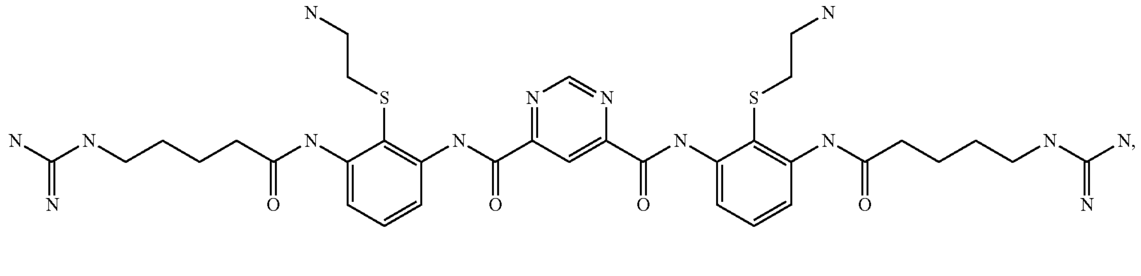

,

-continued
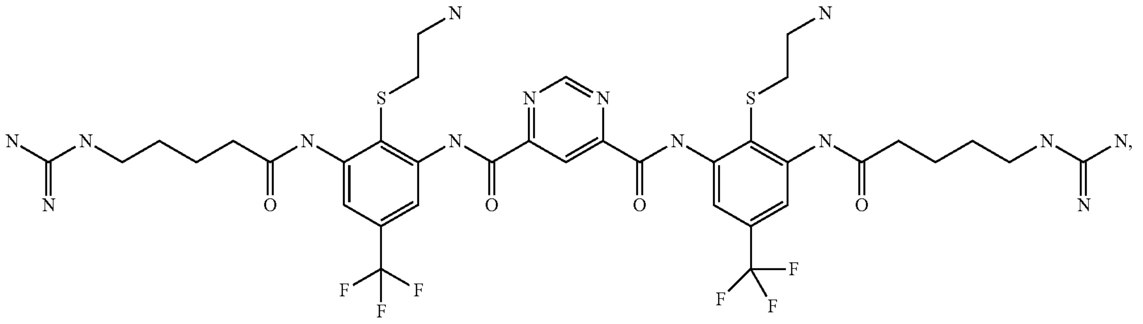
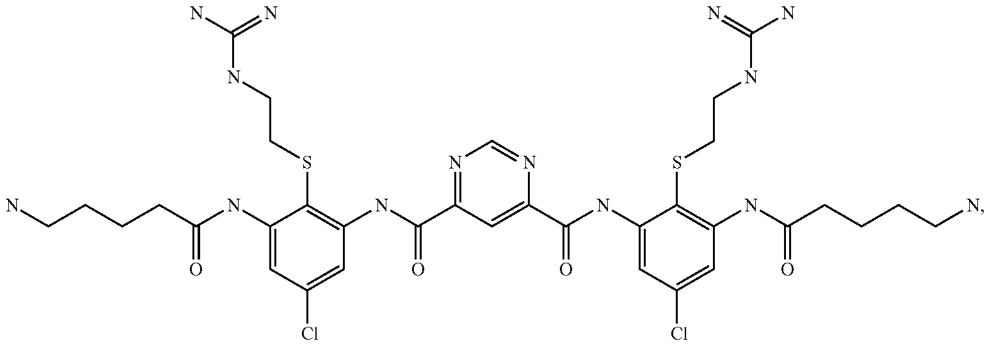
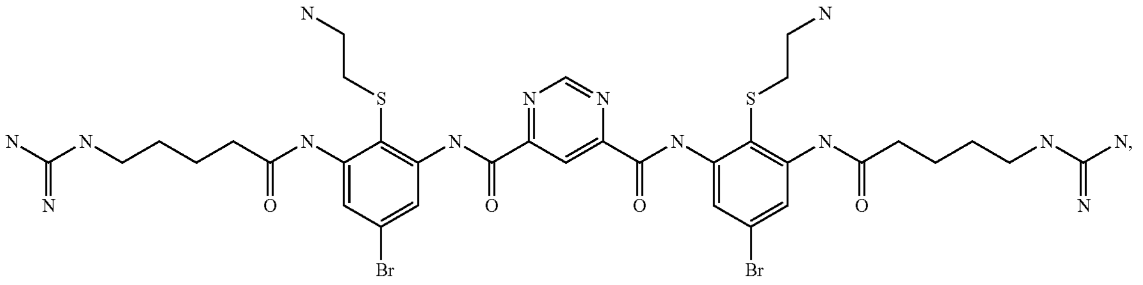
Compound Z (Compound 6)
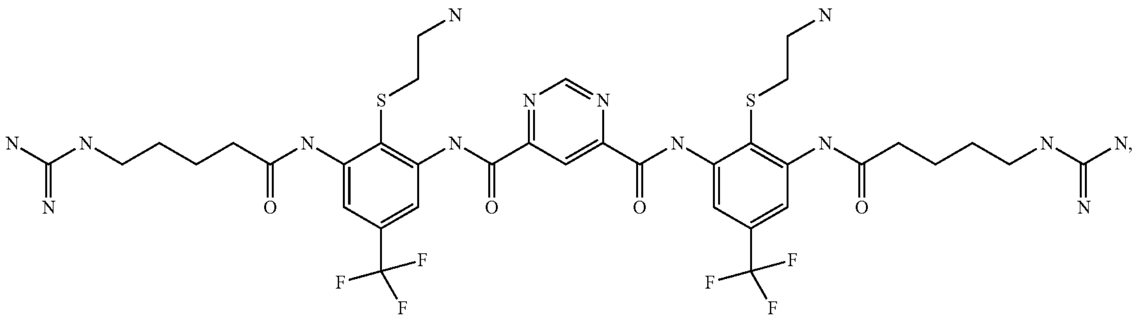
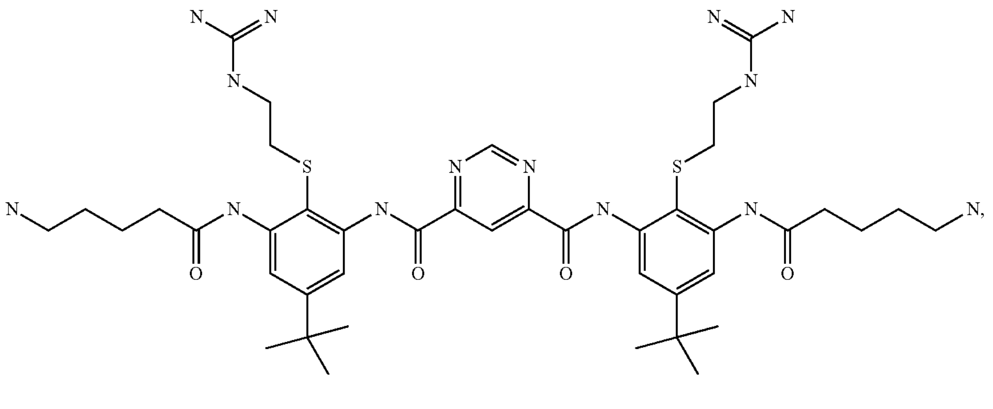

-continued
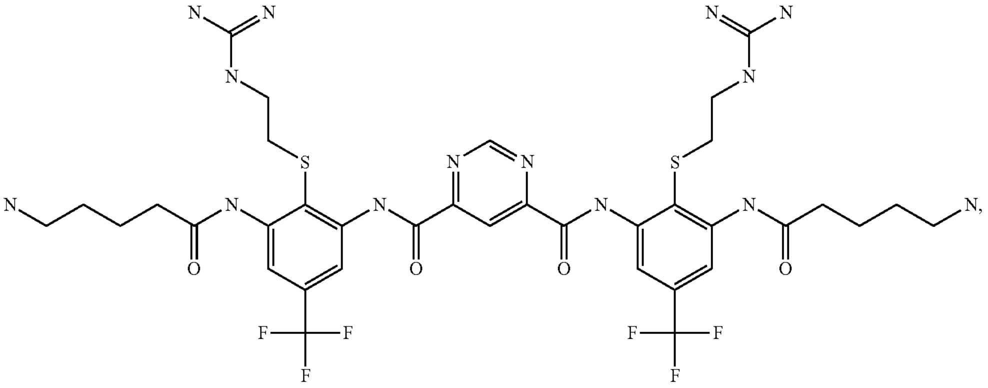
,
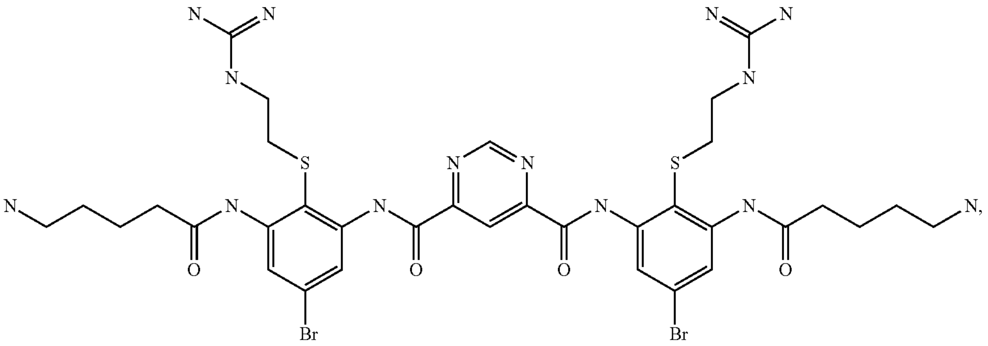
,
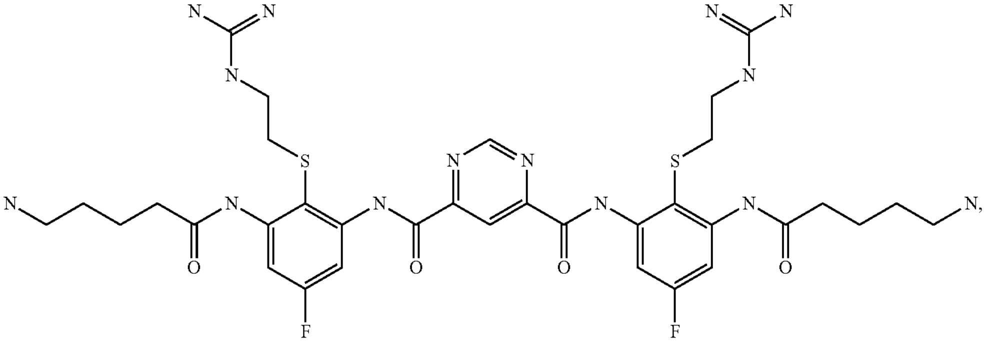
,
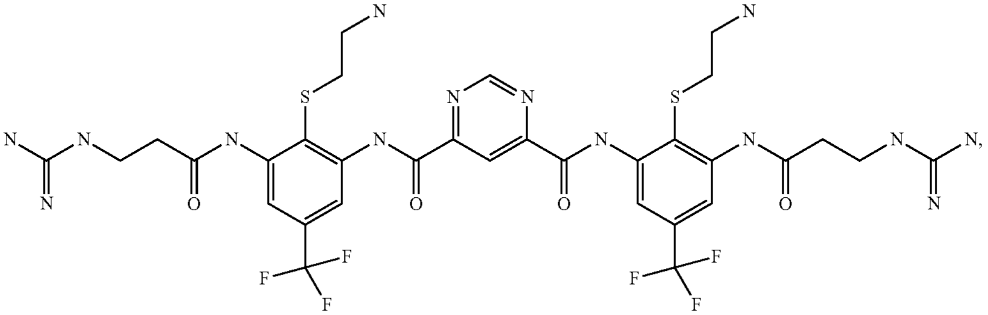
,
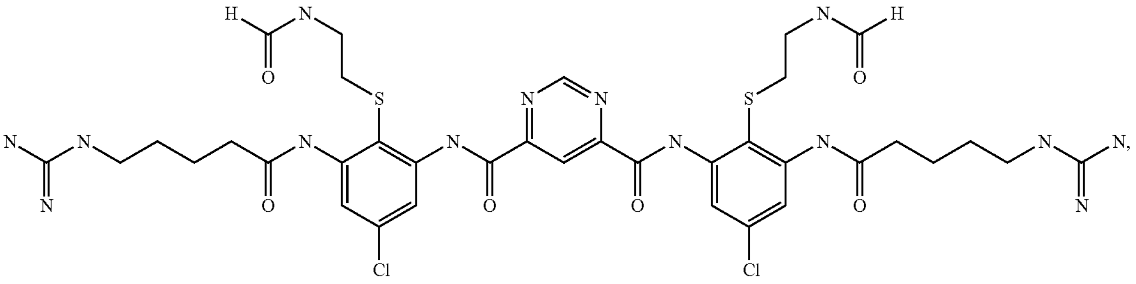
, -continued

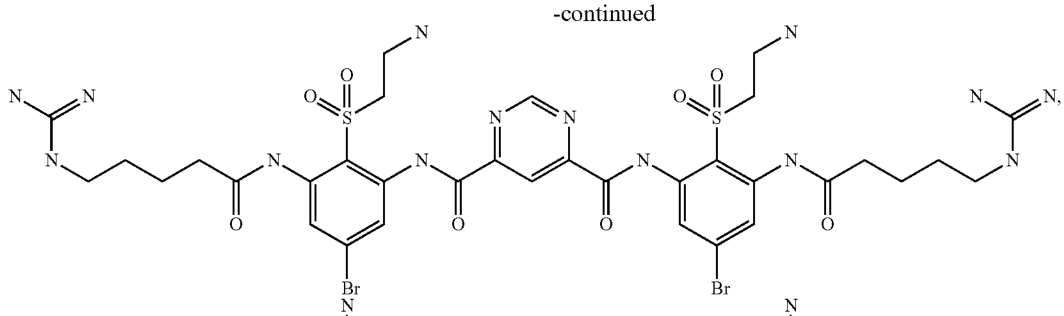

and

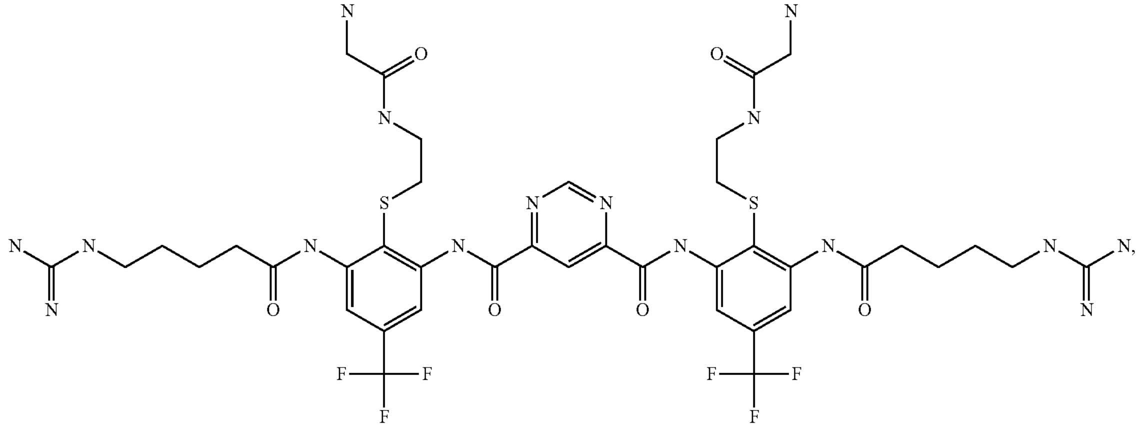

or a pharmaceutically acceptable salt thereof.

In some embodiments of the invention, the compound used for treating and/or preventing mucositis is not Compound Z.

The present invention also provides methods of treating and/or preventing mucositis in a mammal comprising administering to the mammal in need thereof a therapeutically effective amount of a compound of Formula XII:

XII

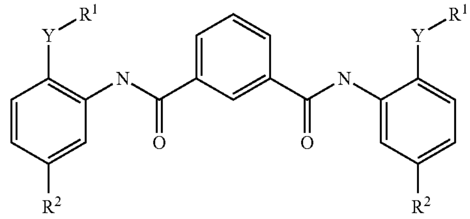

or a pharmaceutically acceptable salt thereof, wherein:

each Y is, independently, O, S, or NH;

each $R^1$ is, independently, $—(CH_2)_n—NH_2$ or $—(CH_2)_n—NH—C(═NH)NH_2$, where each n is, independently, 1 to 4; and each $R^2$ is, independently, H, halo, $CF_3$, or $C(CH_3)_3$;

or a pharmaceutically acceptable salt thereof.

In some embodiments, each Y is, independently, O, or S. In some embodiments, each Y is O or S.

In some embodiments, each $R^1$ is, independently, $—(CH_2)_n—NH_2$, where each n is, independently, 2 to 4. In some embodiments, each $R^1$ is $—(CH_2)_n—NH_2$, where each n is 2 to 4.

In some embodiments, each $R^2$ is, independently, halo, $CF_3$, or $C(CH_3)_3$. In some embodiments, each $R^2$ is halo, $CF_3$, or $C(CH_3)_3$.

The present invention also provides methods of treating and/or preventing mucositis in a mammal comprising administering to the mammal in need thereof a therapeutically effective amount of a compound which is:

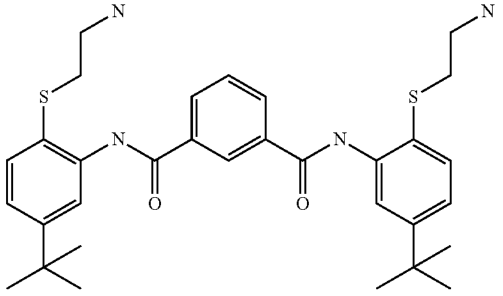 [SMILES: CC(C)(C)c1ccc(SCCN)c(NC(=O)c2cccc(C(=O)Nc3cc(C(C)(C)C)ccc3SCCN)c2)c1]

or a pharmaceutically acceptable salt thereof.

The present invention also provides methods of treating and/or preventing mucositis in a mammal comprising administering to the mammal in need thereof a therapeutically effective amount of a compound of Formula XIII:

XIII

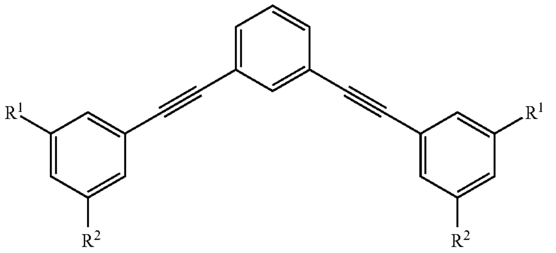

or a pharmaceutically acceptable salt thereof, wherein:

each $R^1$ is, independently, H, $C_1$-$C_8$alkyl, $C_1$-$C_8$alkoxy, halo, OH, $CF_3$, or CN;

each $R^2$ is, independently, $—(CH_2)_n—NH_2$ or $—(CH_2)_n—NH—C(=NH)NH_2$, where each n is, independently, 1 to 4;

or a pharmaceutically acceptable salt thereof.

In some embodiments, each $R^1$ is, independently, $C_1$-$C_8$alkyl, halo, OH, $CF_3$, or CN. In some embodiments, each $R^1$ is, independently, $C_1$-$C_3$alkyl, halo, $CF_3$, or CN. In some embodiments, each $R^1$ is methyl or halo. In some embodiments, each $R^1$ is Br, F, or Cl.

In some embodiments, each $R^2$ is, independently, $—(CH_2)_n—NH—C(=NH)NH_2$, where each n is, independently, 1 to 4. In some embodiments, each $R^2$ is $—(CH_2)_n—NH—C(=NH)NH_2$, where each n is 1 to 4. In some embodiments, each $R^2$ is $—(CH_2)_n—NH—C(=NH)NH_2$, where each n is 1 or 2.

In some embodiments, each $R^1$ is, independently, $C_1$-$C_8$alkyl, halo, OH, $CF_3$, or CN; and each $R^2$ is, independently, $—(CH_2)_n—NH—C(=NH)NH_2$, where each n is, independently, 1 to 4.

In some embodiments, each $R^1$ is, independently, $C_1$-$C_3$alkyl, halo, $CF_3$, or CN; and each $R^2$ is $—(CH_2)_n—NH—C(=NH)NH_2$, where each n is 1 to 4.

In some embodiments, each $R^1$ is methyl or halo; and each $R^2$ is $—(CH_2)_n—NH—C(=NH)NH_2$, where each n is 1 or 2.

The present invention also provides methods of treating and/or preventing mucositis in a mammal comprising administering to the mammal in need thereof a therapeutically effective amount of a compound which is:

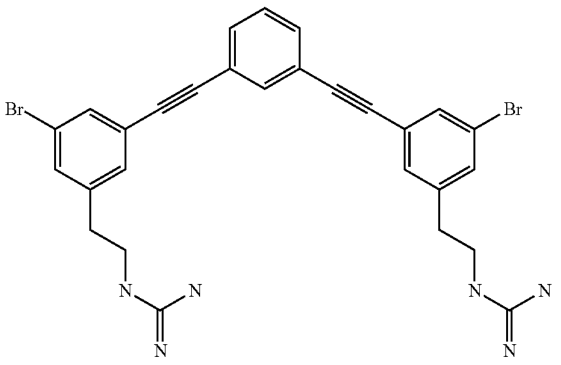 [SMILES: N=C(N)NCCc1cc(Br)cc(C#Cc2cccc(C#Cc3cc(Br)cc(CCNC(=N)N)c3)c2)c1]

or

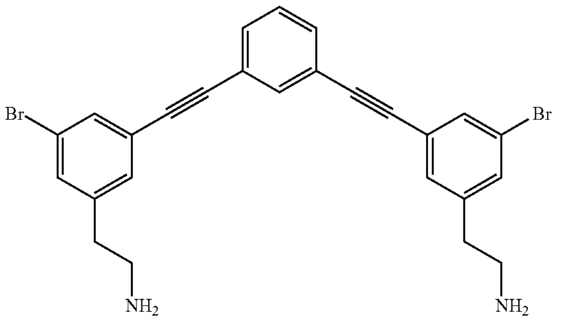

mPE or a pharmaceutically acceptable salt thereof.

The present invention also provides methods of treating and/or preventing mucositis in a mammal comprising administering to the mammal in need thereof a therapeutically effective amount of a compound of Formula XIV:

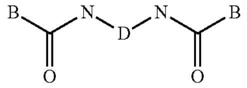

XIV or a pharmaceutically acceptable salt thereof, wherein:

D is

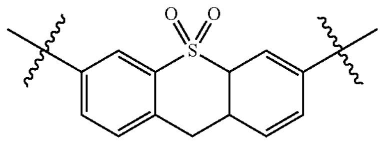 [SMILES: *C1=CC2C(C=C1)Cc1ccc(*)cc1S2(=O)=O]

or

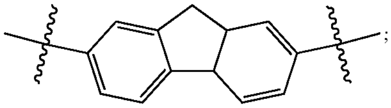 [SMILES: *C1=CC2Cc3cc(*)ccc3C2C=C1]

;

each B is, independently, $—(CH_2)_n—NH—C(=NH)NH_2$, where each n is, independently, 1 to 4,

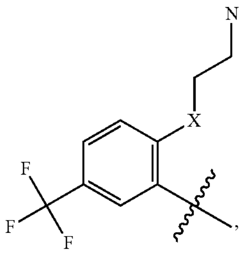

, or

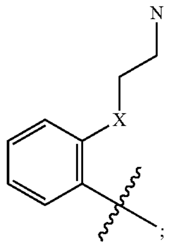

;

and each X is, independently, O or S;

or a pharmaceutically acceptable salt thereof.

In some embodiments, D is

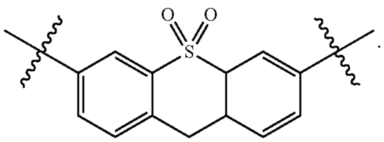 [SMILES: *C1=CC2C(C=C1)Cc1ccc(*)cc1S2(=O)=O]

.

In some embodiments, each B is, independently, $-(CH_2)_n-NH-C(=NH)NH_2$, where each n is, independently, 1 to 4.

In some embodiments, each X is S.

In some embodiments, D is

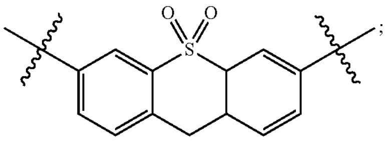 [SMILES: *C1=CC2C(C=C1)Cc1ccc(*)cc1S2(=O)=O]

each B is, independently, $-(CH_2)_n-NH-C(=NH)NH_2$, where each n is, independently, 3 or 4, or

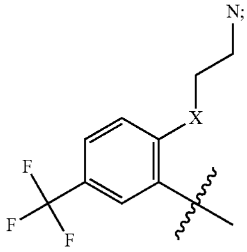

and each X is S.

In some embodiments, D is

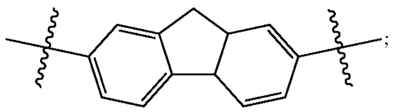 [SMILES: *C1=CC2Cc3cc(*)ccc3C2C=C1]

each B is, independently,

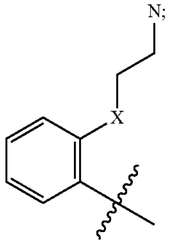

and each X is, independently, O or S.

The present invention also provides methods of treating and/or preventing mucositis in a mammal comprising administering to the mammal in need thereof a therapeutically effective amount of a compound which is:

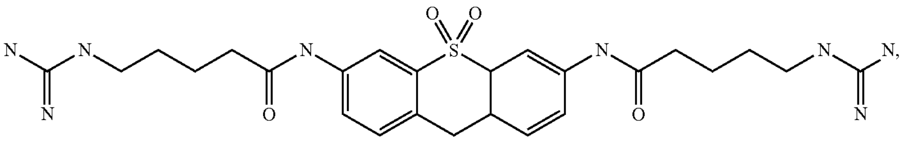

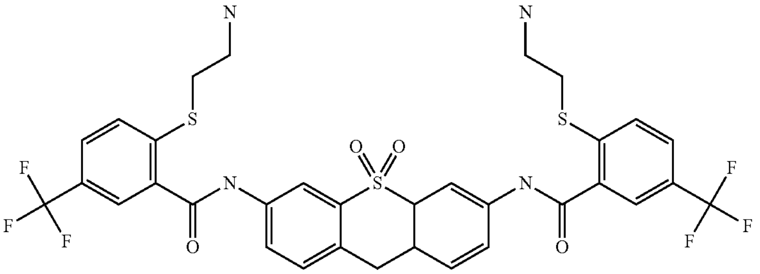

and

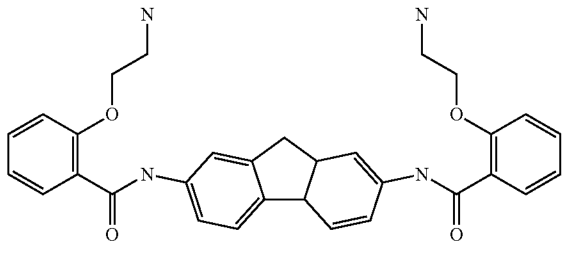 [SMILES: NCCOc1ccccc1C(=O)NC1=CC2Cc3cc(NC(=O)c4ccccc4OCCN)ccc3C2C=C1]

or a pharmaceutically acceptable salt thereof.

The present invention also provides methods of treating and/or preventing mucositis in a mammal comprising administering to the mammal in need thereof a therapeutically effective amount of a compound of Formula XV:

XV

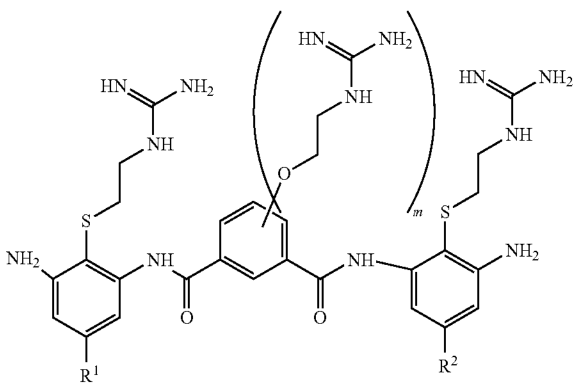

or a pharmaceutically acceptable salt thereof,
wherein:

$R^1$ is H or $C_{1-10}$ alkyl;

$R^2$ is H or $C_{1-10}$ alkyl; and m is 1 or 2.

The present invention also provides methods of treating and/or preventing mucositis in a mammal comprising administering to the mammal in need thereof a therapeutically effective amount of a compound of Formula XVI:

XVI

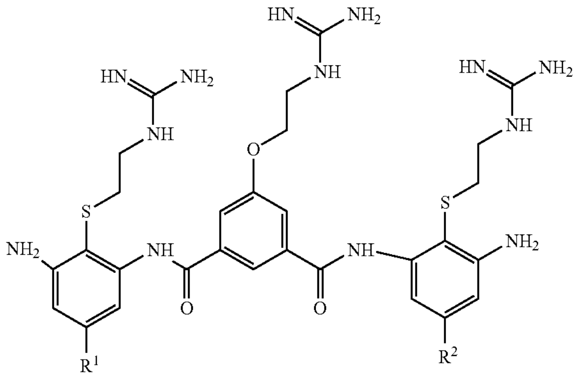

or a pharmaceutically acceptable salt thereof,
wherein:

$R^1$ is H or $C_{1-8}$ alkyl; and $R^2$ is H or $C_{1-8}$ alkyl.

In some embodiments, $R^1$ and $R^2$ are each, independently, H or $C_{1-8}$ alkyl. In some embodiments, $R^1$ and $R^2$ are each, independently, $C_{1-8}$ alkyl, $C_{2-7}$ alkyl, $C_{3-7}$ alkyl, or $C_{3-6}$ alkyl. In some embodiments, $R^1$ and $R^2$ are each, independently, 2-methylpropan-2-yl, propan-2-yl, 2-methylbutan-2-yl, 2,3-dimethylbutan-2-yl, or 2,3,3-trimethylbutan-2-yl. In some embodiments, $R^1$ and $R^2$ are each, independently, branched $C_{3-7}$ alkyl or branched $C_{3-6}$ alkyl. In some embodiments, $R^1$ and $R^2$ are each, independently, H or $C_{1-4}$ alkyl. In some embodiments, $R^1$ and $R^2$ are each independently, H, methyl, ethyl, propan-1 yl, propan-2-yl, butan-1-yl, butan-2-yl, or 2-methylpropan-2-yl. In some embodiments, $R^1$ and $R^2$ are each independently, H, methyl, or ethyl. In some embodiments, $R^1$ and $R^2$ are the same. In some embodiments, $R^1$ and $R^2$ are different. In some embodiments, $R^1$ and $R^2$ are each 2-methylpropan-2-yl.

The present invention also provides methods of treating and/or preventing mucositis in a mammal comprising administering to the mammal in need thereof a therapeutically effective amount of a compound of Formula XVII:

XVII

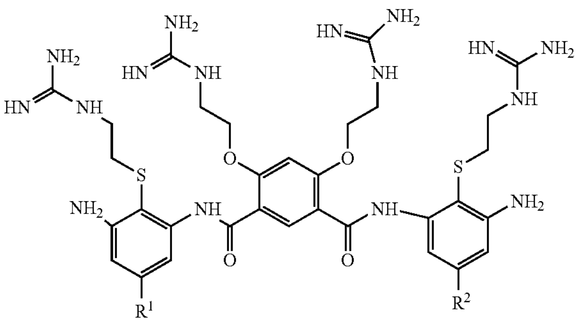

or a pharmaceutically acceptable salt thereof,
wherein:

$R^1$ is H or $C_{1-8}$ alkyl; and $R^2$ is H or $C_1$-8 alkyl.

In some embodiments, $R^1$ and $R^2$ are each, independently, H or $C_{1-8}$ alkyl. In some embodiments, $R^1$ and $R^2$ are each, independently, $C_{1-8}$ alkyl, $C_{2-7}$ alkyl, $C_{3-7}$ alkyl, or $C_{3-6}$ alkyl. In some embodiments, $R^1$ and $R^2$ are each, independently, propan-2-yl, 2-methylpropan-2-yl, 2-methylbutan-2-yl, 2,3-dimethylbutan-2-yl, or 2,3,3-trimethylbutan-2-yl. In some embodiments, $R^1$ and $R^2$ are each, independently, branched $C_{3-7}$ alkyl or branched $C_{3-6}$ alkyl. In some embodiments, $R^1$ and $R^2$ are each, independently, H or $C_{1-4}$ alkyl. In some embodiments, $R^1$ and $R^2$ are each independently, H, methyl, ethyl, propan-1 yl, propan-2-yl, butan-1-yl, butan-2-yl, or 2-methylpropan-2-yl. In some embodiments, $R^1$ and $R^2$ are each independently, H, methyl, or ethyl. In some embodiments, $R^1$ and $R^2$ are the same. In some embodiments, $R^1$ and $R^2$ are different. In some embodiments, $R^1$ and $R^2$ are each 2-methylpropan-2-yl.

The present invention also provides methods of treating and/or preventing mucositis in a mammal comprising administering to the mammal in need thereof a therapeutically effective amount of a compound which is:

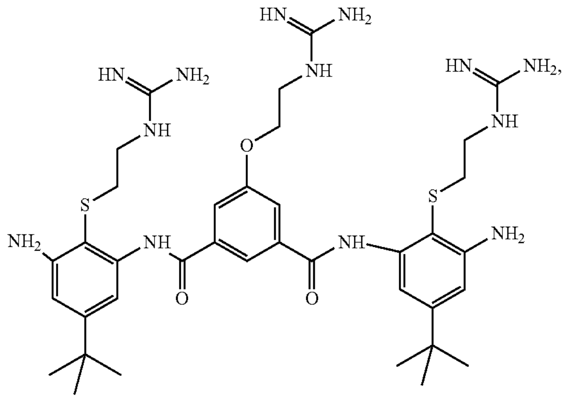 [SMILES: CC(C)(C)c1cc(N)c(SCCNC(=N)N)c(NC(=O)c2cc(OCCNC(=N)N)cc(C(=O)Nc3cc(C(C)(C)C)cc(N)c3SCCNC(=N)N)c2)c1]

and

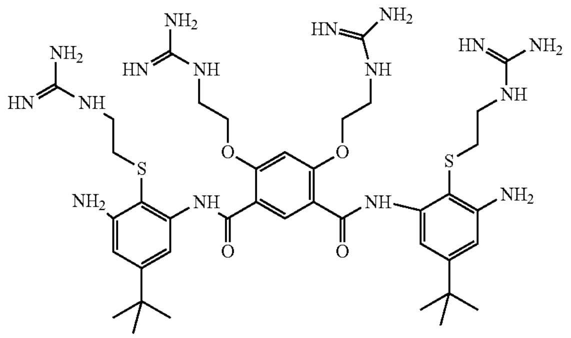 [SMILES: CC(C)(C)c1cc(N)c(SCCNC(=N)N)c(NC(=O)c2cc(C(=O)Nc3cc(C(C)(C)C)cc(N)c3SCCNC(=N)N)c(OCCNC(=N)N)cc2OCCNC(=N)N)c1]

or a pharmaceutically acceptable salt thereof.

The present invention also provides methods of treating and/or preventing mucositis in a mammal comprising administering to the mammal in need thereof a therapeutically effective amount of a compound of Formula XVIII:

$$R^1—[—X-A_1-Y—X-A_2-Y—]_m—R^2 \quad \text{XVIII}$$

or a pharmaceutically acceptable salt thereof, wherein:

each X is, independently, $NR^8$, $—N(R^8)N(R^8)—$, O, or S;

each Y is, independently, C═O, C═S, O═S═O, —C(═O)C(═O)—, or $—CR^aR^b—$;

$R^a$ and $R^b$ are each, independently, hydrogen, a PL group, or an NPL group;

each $R^8$ is, independently, hydrogen or alkyl;

$A_1$ and $A_2$ are each, independently, optionally substituted arylene or optionally substituted heteroarylene, wherein $A_1$ and $A_2$ are, independently, optionally substituted with one or more PL group(s), one or more NPL group(s), or a combination of one or more PL group(s) and one or more NPL group(s); or each $A_1$ is, independently, optionally substituted arylene or optionally substituted heteroarylene, and each $A_2$ is a $C_3$ to $C_8$ cycloalkyl or $—(CH_2)_q—$, wherein q is 1 to 7, wherein $A_1$ and $A_2$ are, independently, optionally substituted with one or more PL group(s), one or more NPL group(s), or a combination of one or more PL group(s) and one or more NPL group(s); or each $A_2$ is optionally substituted arylene or optionally substituted heteroarylene, and each $A_1$ is a $C_3$ to $C_8$ cycloalkyl or $—(CH_2)_q—$, wherein q is 1 to 7, wherein $A_1$ and $A_2$ are each, independently, optionally substituted with one or more PL group(s), one or more NPL group(s), or a combination of one or more PL group(s) and one or more NPL group(s);

$R^1$ is hydrogen, a PL group, or an NPL group, and $R^2$ is $—X-A_1-Y—R^{11}$, wherein $R^{11}$ is hydrogen, a PL group, or an NPL group; or $R^1$ and $R^2$ are each, independently, hydrogen, a PL group, or an NPL group; or $R^1$ and $R^2$ together are a single bond; or $R^1$ is $—Y-A_2-X—R^{12}$, wherein $R^{12}$ is hydrogen, a PL group, or an NPL group, and $R^2$ is hydrogen, a PL group, or an NPL group;

each NPL group is, independently, $—B(OR^4)_2$ or $—(NR^{3'})_{q1NPL}—U^{NPL}-LK^{NPL}(NR^{3''})_{q2NPL}—R^{4'}$, wherein:

$R^3$, $R^{3'}$, and $R^{3''}$ are each, independently, hydrogen, alkyl, or alkoxy;

$R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substitutents, wherein each substituent is, independently, alkyl, halo, or haloalkyl;

each $U^{NPL}$ is, independently, absent or O, S, S(═O), $S(═O)_2$, $NR^3$, —C(═O)—, $—C(═O)—NR^3—$, $—C(═O)—N═N—NR^3—$, $—C(═O)—NR^3—N═N—$, $—N═N—NR^3—$, $—C(═N—N(R^3)_2)—$, $—C(═NR^3)—$, —C(═O)O—, —C(═O)S—, —C(═S)—, $—O—P(═O)_2O—$, —S—C═N—, or $—C(═O)—NR^3—O—$, wherein groups with two chemically nonequivalent termini can adopt both possible orientations;

each $LK^{NPL}$ is, independently, $—(CH_2)_{pNPL}—$ or $C_{2-8}$ alkenylenyl, wherein each of the $—(CH_2)_{pNPL}$ and $C_{2-8}$ alkenylenyl is optionally substituted with one or more substituents, wherein each substituent is, independently, amino, hydroxyl, aminoalkyl, hydroxylalkyl, or alkyl;

each pNPL is, independently, an integer from 0 to 8;

q1NPL and q2NPL are each, independently, 0, 1, or 2;

each PL group is, independently, halo, hydroxyethoxymethyl, methoxyethoxymethyl, polyoxyethylene, or $—(NR^{5'})_{q1PL}—U^{PL}-LK^{PL}-(NR^{5''})_{q2PL}—V$, wherein:

$R^5$, $R^{5'}$, and $R^{5''}$ are each, independently, hydrogen, alkyl, or alkoxy;

each $U^{PL}$ is, independently, absent or O, S, S(═O), $S(═O)_2$, $NR^5$, —C(═O)—, $—C(═O)—NR^5—$, $—C(═O)—N═N—NR^5—$, $—C(═O)—NR^5—N═N—$, $—N═N—NR^5—$, $—C(═N—N(R^5)_2)—$, $—C(═NR^5)—$, —C(═O)O—, —C(═O)S—, —C(═S)—, $—O—P(═O)_2O—$, —S—C═N—, or $—C(═O)—NR^5—O—$, wherein groups with two chemically nonequivalent termini can adopt either of the two possible orientations;

each V is, independently, nitro, cyano, amino, halo, hydroxy, alkoxy, alkylthio, alkylamino, dialkylamino, $—NH(CH_2)_pNH_2$ wherein p is 1 to 5, $—C(═O)NH(CH_2)_pNH_2$ wherein p is 1 to 5, $—C(═O)NH(CH_2)_pNHC(═NH)NH_2$ wherein p is 1 to 5, $—C(═O)NH(CH_2)_pNHC(═O)NH_2$ wherein p is 1 to 5, —NHC(═O)-alkyl, $—N(CH_2CH_2NH_2)_2$, diazamino, amidino, guanidino, ureido, carbamoyl, —C(═O)OH, $—C(═O)OR^c$, —C(═O)NH—OH, $—O—NH—C(═NH)NH_2$, $—NH—S(═O)_2OH$, $S(═O)_2OH$, $NR^dR^e$, semicarbazone, aryl, cycloalkyl, heterocycloalkyl, or heteroaryl, wherein each of the aryl and cycloalkyl is substituted with one or more substitutents, wherein each of the heterocycloalkyl and heteroaryl is optionally substituted with one or more substituents, and wherein each of the subsituents for the aryl, cycloalkyl, heterocycloalkyl, and heteroaryl is, independently, nitro, cyano, amino, halo, hydroxy, alkoxy, alkylthio, alkylamino, dialkylamino, $—NH(CH_2)_pNH_2$ wherein p is 1 to 5, $—N(CH_2CH_2NH_2)_2$, diazamino, amidino, guanidino, ureido, carbamoyl, —C(═O)OH, $—C(═O)OR^c$, —C(═O)NH—OH, $—O—NH—C(═NH)NH_2$, $—NH—S(═O)_2OH$, $S(═O)_2OH$, $NR^dR^e$, semicarbazone, aminosulfonyl, aminoalkoxy, aminoalkythio, lower acylamino, or benzyloxycarbonyl;

each $R^c$ is, independently, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, $C_{1-6}$ alkyl, $C_{1-6}$ haloalkyl, aryl, arylalkyl, heteroaryl, heteroarylalkyl, cycloalkyl, or heterocycloalkyl;

$R^d$ and $R^e$ are, independently, H, $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, or heterocycloalkyl;

or $R^d$ and $R^e$ together with the N atom to which they are attached form a 4-, 5-, 6-, 7-, or 8-membered heterocycloalkyl;

each $LK^{PL}$ is, independently, $—(CH_2)_{pPL}—$ or $C_{2-8}$ alkenylenyl, wherein each of the $—(CH_2)_{pNPL}—$ and $C_{2-8}$ alkenylenyl is optionally substituted with one or more substituents, wherein each substituent is, independently, amino, hydroxyl, aminoalkyl, hydroxylalkyl, or alkyl;

each pPL is, independently, an integer from 0-8;

q1PL and q2PL are each, independently, 0, 1, or 2; and m is an integer from 1 to about 20.

In some embodiments, each X is, independently, $NR^8$; each Y is C═O; and each $A_2$ is optionally substituted arylene or optionally substituted heteroarylene, and each $A_1$ is a $C_3$ to $C_8$ cycloalkyl or $—(CH_2)_q—$, wherein q is 1 to 7, wherein $A_1$ and $A_2$ are each, independently, optionally substituted with one or more PL group(s), one or more NPL group(s), or a combination of one or more PL group(s) and one or more NPL group(s).

In some embodiments, each $A_2$ is optionally substituted phenyl, and each $A_1$ is a $—(CH_2)—$, wherein $A_1$ and $A_2$ are each, independently, optionally substituted with one or more PL group(s), one or more NPL group(s), or a combination of one or more PL group(s) and one or more NPL group(s).

In some embodiments, each NPL group is, independently, $—(NR^{3'})_{q1NPL}—U^{NPL}\text{-}LK^{NPL}(NR^{3''})_{q2NPL}—R^{4'}$, wherein: $R^3$, $R^{3'}$, and $R^{3''}$ are each, independently, hydrogen, alkyl, or alkoxy; and $R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substitutents, wherein each substituent is, independently, alkyl, halo, or haloalkyl.

In some embodiments, each NPL group is, independently, $—B(OR^4)_2$, $R^{4'}$, or $OR^{4'}$, and $R^4$ and $R^{4'}$ are each, independently, alkyl, alkenyl, alkynyl, cycloalkyl, or aryl, each is optionally substituted with one or more substitutents, wherein each substituent is, independently, alkyl, halo, or haloalkyl.

In some embodiments, each NPL group is, independently, $R^{4'}$ or $OR^{4'}$, and each $R^{4'}$ is, independently, alkyl, alkenyl, alkynyl, cycloalkyl, or aryl, each is optionally substituted with one or more substitutents, wherein each substituent is, independently, alkyl, halo, or haloalkyl.

In some embodiments, each NPL group is, independently, alkyl, alkenyl, alkynyl, cycloalkyl, aryl, or alkoxy, each is optionally substituted with one or more substitutents, wherein each substituent is, independently, alkyl, halo, or haloalkyl. In some embodiments, each NPL group is, independently, alkyl, haloalkyl, alkoxy, or haloalkoxy.

In some embodiments, each V is, independently, nitro, cyano, amino, hydroxy, alkoxy, alkylthio, alkylamino, dialkylamino, $—NH(CH_2)_pNH_2$ wherein p is 1 to 5, $—N(CH_2CH_2NH_2)_2$, diazamino, amidino, guanidino, ureido, carbamoyl, —C(═O)OH, $—C(═O)OR^c$, —C(═O)NH—OH, —O—NH—C(═NH)$NH_2$, —NH—S(═O)$_2$OH, S(═O)$_2$OH, $NR^dR^e$, semicarbazone, aryl, heterocycloalkyl, or heteroaryl, wherein the aryl is substituted with one or more substitutents, wherein each of the heterocycloalkyl and heteroaryl is optionally substituted with one or more substituents, and wherein each of the subsituents for the aryl, heterocycloalkyl, and heteroaryl is, independently, nitro, cyano, amino, hydroxy, alkoxy, alkylthio, alkylamino, dialkylamino, $—NH(CH_2)_pNH_2$ wherein p is 1 to 5, $—N(CH_2CH_2NH_2)_2$, diazamino, amidino, guanidino, ureido, carbamoyl, —C(═O)OH, $—C(═O)OR^c$, —C(═O)NH—OH, —O—NH—C(═NH)$NH_2$, —NH—S(═O)$_2$OH, S(═O)$_2$OH, $NR^dR^e$, semicarbazone, aminosulfonyl, aminoalkoxy, aminoalkythio, lower acylamino, or benzyloxycarbonyl.

In some embodiments, each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(═O)OH, $—C(═O)OR^c$, —C(═O)NH—OH, —O—NH—C(═NH)$NH_2$, —NH—S(═O)$_2$OH, S(═O)$_2$OH, $NR^dR^e$, a substituted aryl group, heterocycloalkyl, or heteroaryl, wherein each of the heterocycloalkyl and heteroaryl is optionally substituted with one more substituents, wherein each substituent is, independently, alkyl, haloalkyl, alkoxy, haloalkoxy, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(═O)OH, $—C(═O)OR^c$, —C(═O)NH—OH, —O—NH—C(═NH)$NH_2$, —NH—S(═O)$_2$OH, S(═O)$_2$OH, $NR^dR^e$, a substituted aryl group, heterocycloalkyl, or heteroaryl, wherein each of the heterocycloalkyl and heteroaryl is optionally substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(═O)NH—OH, —O—NH—C(═NH)$NH_2$, —NH—S(═O)$_2$OH, $NR^dR^e$, heterocycloalkyl, or heteroaryl, wherein each of the heterocycloalkyl and heteroaryl is optionally substituted with one more substituents, wherein each substituent is, independently, alkyl, haloalkyl, alkoxy, haloalkoxy, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(═O)NH—OH, —O—NH—C(═NH)$NH_2$, —NH—S(═O)$_2$OH, $NR^dR^e$, heterocycloalkyl, or heteroaryl, wherein each of the heterocycloalkyl and heteroaryl is optionally substituted with one more substituents, wherein each substituent is, independently, amino, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, arylamino, heteroarylamino, ureido, guanidino, carbamoyl, —C(═O)OH, —C(═O)$OR^c$, —C(═O)NH—OH, —O—NH—C(═NH)$NH_2$, —NH—S(═O)$_2$OH, S(═O)$_2$OH, a 3-8 membered heterocycloalkyl, a 5- to 10-membered heteroaryl, or a 6- to 10-membered substituted aryl, wherein the substituted aryl is substituted with one or more substituents, wherein each substituent is, independently, OH, amino, hydroxylalkyl, or aminoalkyl, and wherein each of the 3-8 membered heterocycloalkyl and the 5- to 10-membered heteroaryl is optionally substituted with one or more substituents, wherein each substituent is, independently, alkyl, haloalkyl, alkoxy, haloalkoxy, amino, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, arylamino, heteroarylamino, ureido, guanidino, carbamoyl, —C(═O)OH, —C(═O)$OR^c$, —C(═O)NH—OH, —O—NH—C(═NH)$NH_2$, —NH—S(═O)$_2$OH, S(═O)$_2$OH, a 3-8 membered heterocycloalkyl, a 5- to 10-membered heteroaryl, or a 6- to 10-membered substituted aryl, wherein the substituted aryl is substituted with one or more substituents, wherein each substituent is, independently, OH, amino, hydroxylalkyl, or aminoalkyl.

In some embodiments, each V is, independently, amino, heteroarylamino, ureido, guanidino, carbamoyl, C(═O)OH, —C(═O)$OR^c$, —C(═O)NH—OH, —O—NH—C(═NH)$NH_2$, —NH—S(═O)$_2$OH, S(═O)$_2$OH, aziridinyl, azetidinyl, pyrrolidinyl, piperidinyl, piperazinyl, morpholino, azepanyl, azocanyl, tetrazolyl, 1,2,4-oxadiazolyl, 1,3,4-oxadiazolyl, imidazolyl, pyridinyl, indolyl, or a substituted phenyl, wherein the substituted phenyl is substituted with one or more substituents, wherein each substituent is, independently, OH or amino.

In some embodiments, each V is, independently, amino, alkylamino, dialkylamino, —$NH(CH_2)_pNH_2$ wherein p is 1 to 5, —$N(CH_2CH_2NH_2)_2$, guanidino, amidino, ureido, heterocycloalkyl, or heteroaryl, wherein each of the heterocycloalkyl and heteroaryl is optionally substituted with one more substituents, wherein each substituent is, independently, amino, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl.

In some embodiments, each V is, independently, amino, alkylamino, dialkylamino, —$NH(CH_2)_pNH_2$ wherein p is 1 to 5, —$N(CH_2CH_2NH_2)_2$, guanidino, amidino, ureido, pyrrodinyl, piperidinyl, piperazinyl, 4-methylpiperazinyl, pyridinyl, pyrimidinyl, pyrazinyl, or indolyl. In some embodiments, each V is, independently, amino, alkylamino, dialkylamino, —$NH(CH_2)_pNH_2$ wherein p is 1 to 5, —$N(CH_2CH_2NH_2)_2$, guanidino, amidino, ureido, or indolyl.

In some embodiments, each PL group is, independently, halo, hydroxyethoxymethyl, methoxyethoxymethyl, polyoxyethylene, or —$(NR^{5'})_{q1PL}$—$U^{PL}$—$(CH_2)_{pPL}$—$(NR^{5''})_{q2PL}$—V.

In some embodiments, each PL group is, independently, halo, —$(CH_2)_{pPL}$—V, O—$(CH_2)_{pPL}$—V, and S—$(CH_2)_{pPL}$—V; each pPL is an integer from 0 to 5; and each V is, independently, hydroxy, amino, halo, alkylamino, dialkylamino, —$NH(CH_2)_pNH_2$ wherein p is 1 to 5, —$N(CH_2CH_2NH_2)_2$, guanidino, amidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, a substituted aryl group, heterocycloalkyl, or heteroaryl, wherein each of the heterocycloalkyl and heteroaryl is optionally substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl.

In some embodiments, each PL group is, independently, halo, —$(CH_2)_{pPL}$—V, O—$(CH_2)_{pPL}$—V, and S—$(CH_2)_{pPL}$—V; each pPL is an integer from 0 to 5; and each V is, independently, hydroxy, amino, alkylamino, dialkylamino, —$NH(CH_2)_pNH_2$ wherein p is 1 to 5, —$N(CH_2CH_2NH_2)_2$, guanidino, amidino, ureido, carbamoyl, —C(═O)NH—OH, —O—NH—C(═NH)$NH_2$, —NH—S(═O)$_2$OH, $NR^dR^e$, heterocycloalkyl, or heteroaryl, wherein each of the heterocycloalkyl and heteroaryl is optionally substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl.

In some embodiments, each NPL group is, independently, —$B(OR^4)_2$, $R^{4'}$, or $OR^{4'}$, $R^4$ and $R^{4'}$ are each, independently, alkyl, alkenyl, alkynyl, cycloalkyl, or aryl, each is optionally substituted with one or more substitutents, wherein each substituent is, independently, alkyl, halo, or haloalkyl; each PL group is, independently, halo, —$(CH_2)_{pPL}$—V, O—$(CH_2)_{pPL}$—V, or S—$(CH_2)_{pPL}$—V; each pPL is an integer from 0 to 5; and each V is, independently, hydroxy, amino, halo, alkylamino, dialkylamino, —$NH(CH_2)_pNH_2$ wherein p is 1 to 5, —$N(CH_2CH_2NH_2)_2$, guanidino, amidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, a substituted aryl group, heterocycloalkyl, or heteroaryl, wherein each of the heterocycloalkyl and heteroaryl is optionally substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl.

In some embodiments, each NPL group is, independently, $R^{4'}$ or $OR^{4'}$, $R^4$ and $R^{4'}$ are each, independently, alkyl, alkenyl, alkynyl, cycloalkyl, or aryl, each is optionally substituted with one or more substitutents, wherein each substituent is, independently, alkyl, halo, or haloalkyl; each PL group is, independently, halo, —$(CH_2)_{pPL}$—V, O—$(CH_2)_{pPL}$—V, or S—$(CH_2)_{pPL}$—V; each pPL is an integer from 0 to 5; and each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(═O)NH—OH, —O—NH—C(═NH)$NH_2$, —NH—S(═O)$_2$OH, $NR^dR^e$, heterocycloalkyl, or heteroaryl, wherein each of the heterocycloalkyl and heteroaryl is optionally substituted with one more substituents, wherein each substituent is, independently, amino, halo, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each $A_2$ is phenyl optionally substituted with one or more substituents, wherein each substituent is, independently, $OR^{4'}$, halo, O—$(CH_2)_{pPL}$—V, or S—$(CH_2)_{pPL}$—V; and each $A_1$ is a —$(CH_2)$— group optionally substituted with one or more substituents, wherein each substituent is, independently, alkyl or —$(CH_2)_{pPL}$—V.

In some embodiments, each $A_2$ is phenyl optionally substituted with one or more substituents, wherein each substituent is, independently, O-alkyl, halo, or O—$(CH_2)_{pPL}$—V, wherein pPL is an integer from 1 to 5; each $A_1$ is a —$(CH_2)$— group optionally substituted with one or more substituents, wherein each substituent is, independently, $CH_3$ or —$(CH_2)_{pPL}$—V, wherein pPL is an integer from 1 to 5; and each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, a substituted aryl group, a substituted cycloalkyl group, heterocycloalkyl, or heteroaryl, wherein each of the heterocycloalkyl and heteroaryl is optionally substituted with one more substituents, wherein each substituent is, independently, amino, halo, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl; and wherein each of the substituted aryl group and the substituted cycloalkyl group is substituted with one more substituents, wherein each substituent is, independently, amino, halo, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each $A_2$ is phenyl optionally substituted with one or more substituents, wherein each substituent is, independently, O-alkyl, halo, or O—$(CH_2)_{pPL}$—V, wherein pPL is an integer from 1 to 5; each $A_1$ is a —$(CH_2)$— group optionally substituted with one or more substituents, wherein each substituent is, independently, $CH_3$ or —$(CH_2)_{pPL}$—V, wherein pPL is an integer from 1 to 5; and each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, a substituted aryl group, a substituted cycloalkyl group, heterocycloalkyl, or heteroaryl, wherein each of the heterocycloalkyl and heteroaryl is optionally substituted with one more substituents, wherein each substituent is, independently, amino, halo, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl; and wherein each of the substituted aryl group and the substituted cycloalkyl group is substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each $A_2$ is phenyl optionally substituted with one or more substituents, wherein each substituent is, independently, O-alkyl, halo, or O—$(CH_2)_{pPL}$—V, wherein pPL is an integer from 1 to 5; each $A_1$ is a —$(CH_2)$— group optionally substituted with one or more substituents, wherein each substituent is, independently, $CH_3$ or —$(CH_2)_{pPL}$—V, wherein pPL is an integer from 1 to 5; and each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, a substituted aryl group, heterocycloalkyl, or heteroaryl, wherein each of the heterocycloalkyl and heteroaryl is optionally substituted with one more substituents, wherein each substituent is, independently, amino, halo, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each $A_2$ is phenyl optionally substituted with one or more substituents, wherein each substituent is, independently, O—$(CH_3)$; halo, or O—$(CH_2)_2$—V; each $A_1$ is a —$(CH_2)$— group optionally substituted with one substituent, wherein each substituent is, independently, $CH_3$, $(CH_2)$—V, $(CH_2)_2$—V, $(CH_2)_3$—V, —$(CH_2)_4$—V, or —$(CH_2)_5$—V; and each V is, independently, hydroxy, amino, alkylamino, arylamino, heteroarylamino, ureido, guanidino, carbamoyl, —C(═O)OH, —C(═O)$OR^c$, —C(═O)NH—OH, —O—NH—C(═NH)$NH_2$, —NH—S(═O)$_2$OH, S(═O)$_2$OH, a 3-8 membered heterocycloalkyl, a 5- to 10-membered heteroaryl, or a 6- to 10-membered substituted aryl, wherein the substituted aryl is substituted with one or more substituents, wherein each substituent is, independently, OH, amino, hydroxylalkyl, or aminoalkyl.

In some embodiments, each $A_2$ is phenyl optionally substituted with one or more substituents, wherein each substituent is, independently, O—$(CH_3)$, halo, or O—$(CH_2)_2$—V; each $A_1$ is a —$(CH_2)$— group optionally substituted with one substituent, wherein each substituent is, independently, $CH_3$, $(CH_2)$—V, $(CH_2)_3$—V, —$(CH_2)_4$—V, and —$(CH_2)_5$—V; and each V is, independently, hydroxyl, amino, heteroarylamino, ureido, guanidino, carbamoyl, C(═O)OH, —C(═O)$OR^c$, —C(═O)NH—OH, —O—NH—C(═NH)$NH_2$, —NH—S(═O)$_2$OH, S(═O)$_2$OH, aziridinyl, azetidinyl, pyrrolidinyl, piperidinyl, piperazinyl, morpholino, azepanyl, azocanyl, tetrazolyl, 1,2,4-oxadiazolyl, 1,3,4-oxadiazolyl, imidazolyl, pyridinyl, indolyl, or a substituted phenyl, wherein the substituted phenyl is substituted with one or more substituents, wherein each substituent is, independently, OH or amino.

In some embodiments, each $A_2$ is phenyl optionally substituted with one or more substituents, wherein each substituent is, independently, O—$(CH_3)$, halo, or O—$(CH_2)_2$—V; each $A_1$ is a —$(CH_2)$— group optionally substituted with one substituent, wherein each substituent is, independently, $(CH_2)$—V, $(CH_2)_3$—V, —$(CH_2)_4$—V, and —$(CH_2)_5$—V;

and each V, is independently, hydroxyl, amino, ureido, guanidino, carbamoyl, or indolyl.

In some embodiments, each $A_2$ is phenyl optionally substituted with one or more substituents, wherein each substituent is, independently, O—($CH_3$), halo, or O—$(CH_2)_2$—V; each $A_1$ is a —($CH_2$)— group optionally substituted with one substituent, wherein each substituent is, independently, ($CH_2$)—V, $(CH_2)_3$—V, —$(CH_2)_4$—V, and —$(CH_2)_5$—V; and each V, is independently, amino, ureido, guanidino, carbamoyl, or indolyl.

In some embodiments, each $A_2$ is phenyl optionally substituted with one or more substituents, wherein each substituent is, independently, O—($CH_3$), halo, or O—$(CH_2)_2$—V; each $A_1$ is a —($CH_2$)— group optionally substituted with one substituent, wherein each substituent is, independently, $CH_3$, —($CH_2$)—V, $(CH_2)_2$—V, —$(CH_2)_3$—V, —$(CH_2)_4$—V, or —$(CH_2)_5$—V; each V is, independently, hydroxyl, amino, heteroarylamino, ureido, guanidino, carbamoyl, C(═O)OH, —C(═O)OR$^c$, —C(═O)NH—OH, —O—NH—C(═NH)$NH_2$, —NH—S(═O)$_2$OH, S(═O)$_2$OH, aziridinyl, azetidinyl, pyrrolidinyl, piperidinyl, piperazinyl, morpholino, azepanyl, azocanyl, tetrazolyl, 1,2,4-oxadiazolyl, 1,3,4-oxadiazolyl, imidazolyl, pyridinyl, indolyl, or a substituted phenyl, wherein the substituted phenyl is substituted with one or more substituents, wherein each substituent is, independently, OH or amino; and at least one of $A_1$ is a —($CH_2$)— group substituted with one substituent, wherein each substituent is, independently, ($CH_2$)—$V^1$, $(CH_2)_2$—$V^1$, —$(CH_2)_3$—$V^1$, —$(CH_2)_4$—$V^1$, or —$(CH_2)_5$—$V^1$, wherein $V^1$ is indolyl.

In some embodiments, $R^1$ is hydrogen, —C(═$NR^3$)—$NR^{3''}R^{4'}$, —C(═O)—$(CH_2)_{pNPL}$—$R^{4'}$, —C(═O)—$(CH_2)_{pPL}$—V, —C(═O)-$A_2$-NH—C(═O)—$(CH_2)_{pPL}$—V; or —C(═O)-$A_2$-NH—C(═O)—$(CH_2)_{pNPL}$—$R^{4'}$; and $R^2$ is $NH_2$, —NH—$(CH_2)_{pPL}$—V, or —NH-$A_1$-C(═O)—$NH_2$.

In some embodiments, $R^1$ is hydrogen, —C(═$NR^3$)—$NR^{3'}R^{4'}$, —C(═O)—$(CH_2)_{pNPL}$—$R^{4'}$, —C(═O)—$(CH_2)_{pPL}$—V, —C(═O)-$A_2$-NH—C(═O)—$(CH_2)_{pPL}$—V, or —C(═O)-$A_2$-NH—C(═O)—$(CH_2)_{pNPL}$—$R^{4'}$, wherein each V is, independently, hydroxy, amino, alkylamino, dialkylamino, —NH$(CH_2)_p$$NH_2$ wherein p is 1 to 5, —N$(CH_2CH_2NH_2)_2$, guanidino, amidino, ureido, carbamoyl, heterocycloalkyl, or heteroaryl, and where $R^3$, $R^{3''}$, and $R^{4'}$ are each, independently, H or alkyl; and $R^2$ is $NH_2$, —NH$(CH_2)_p$$NH_2$ wherein p is 1 to 5, —NH—$(CH_2)_{pPL}$—V, or NH-$A_1$-C(═O)—$NH_2$, wherein V is hydroxy, amino, alkylamino, dialkylamino, —NH$(CH_2)_p$$NH_2$ wherein p is 1 to 5, —N$(CH_2CH_2NH_2)_2$, guanidino, amidino, ureido, carbamoyl, heterocycloalkyl, or heteroaryl.

In some embodiments, $R^1$ is hydrogen, —C(═NH)—$NH_2$, —C(═O)—$R^{4'}$, —C(═O)—$(CH_2)_{pPL}$—V, —C(═O)-$A_2$-NH—C(═O)—$(CH_2)_{pPL}$—V, or —C(═O)-$A_2$-NH—C(═O)—$R^4$, wherein each V is, independently, amino, alkylamino, dialkylamino, —NH$(CH_2)_p$$NH_2$ wherein p is 1 to 5, —N$(CH_2CH_2NH_2)_2$, guanidino, amidino, ureido, carbamoyl, heterocycloalkyl, or heteroaryl, and where $R^{4'}$ is alkyl; and $R^2$ is $NH_2$, —NH$(CH_2)_p$$NH_2$ wherein p is 1 to 5, —NH—$(CH_2)_{pPL}$—V, or NH-$A_1$-C(═O)—$NH_2$, wherein V is amino, alkylamino, dialkylamino, —NH$(CH_2)_p$$NH_2$ wherein p is 1 to 5, —N$(CH_2CH_2NH_2)_2$, guanidino, amidino, ureido, or carbamoyl.

In some embodiments, m is 3 or 4. In some embodiments, m is 4.

In some embodiments, at least one of $A_2$ group is different from other $A_2$ groups. In some embodiments, all $A_2$ groups are the same.

In some embodiments, at least one of $A_1$ group is different from other $A_1$ groups. In some embodiments, all $A_1$ groups are the same.

In some embodiments, the compound is a compound of Formula XVIIIa:

XVIIIa

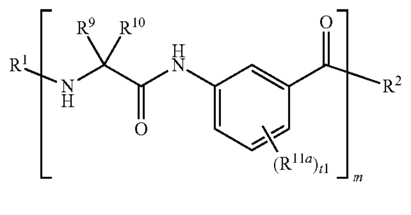

or pharmaceutically acceptable salt thereof, wherein:

each $R^9$ is, independently, H, a PL group, or an NPL group;

each $R^{10}$ is, independently, H, a PL group, or an NPL group;

each $R^{11a}$ is, independently, a PL group or an NPL group; and each t1 is, independently, 0, 1, or 2.

In some embodiments, each $R^9$ is, independently, a PL group or an NPL group. In some embodiments, each $R^9$ is, independently, alkyl or $(CH_2)_{pPL}$—V wherein pPL is an integer from 1 to 5. In some embodiments, each $R^9$ is, independently, $(CH_2)_{pPL}$—V wherein pPL is an integer from 1 to 5.

In some embodiments, each $R^{10}$ is H.

In some embodiments, each $R^{11a}$ is, independently, halo, alkyl, alkoxy, haloalkyl, haloalkoxy, —$(CH_2)_{pPL}$—V, —O$(CH_2)_{pPL}$—V, or —S$(CH_2)_{pPL}$—V, wherein pPL is an integer from 1 to 5. In some embodiments, each $R^{11a}$ is, independently, halo, alkyl, alkoxy, haloalkyl, or haloalkoxy. In some embodiments, each $R^{11a}$ is, independently, alkoxy. In some embodiments, each $R^{11a}$ is methoxy.

In some embodiments, the compound is a compound of Formula XVIIIa-1, XVIIIa-2, or XVIIIa-3:

XVIIIa-1

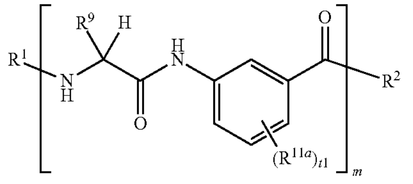

XVIIIa-2

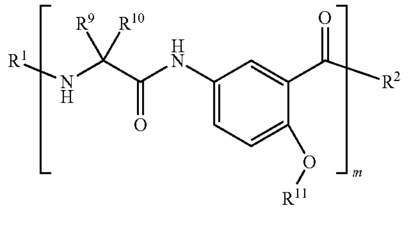

XVIIIa-3

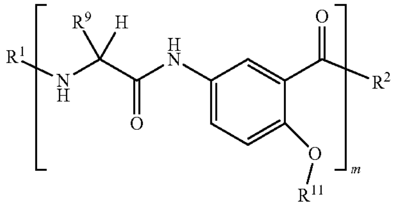

or pharmaceutically acceptable salt thereof, wherein each $R^{11}$ is, independently, H, alkyl, haloalkyl, or $—(CH_2)_{pPL}—V$, wherein pPL is an integer from 1 to 5.

In some embodiments, in Formula XVIIIa-2 or XVIIIa-3, or pharmaceutically acceptable salt thereof, each $R^{11}$ is, independently, alkyl.

In some embodiments, each $R^{11}$ is methyl.

The compounds of Formula XVIII, XVIIIa, XVIIIa-1, XVIIIa-2, or XVIIIa-3 (such as the polymers and oligomers), or salts thereof, useful in the present invention can be made, for example, by methods described in U.S. Patent Application Publication No. 2006-0041023, U.S. Pat. No. 7,173,102, and International Application No. WO 2005/123660. In some embodiments, the compounds of Formula XVIII, XVIIIa, XVIIIa-1, XVIIIa-2, or XVIIIa-3 (such as the polymers and oligomers), or salts thereof, useful in the present invention can be selected from those described in U.S. Patent Application Publication No. 2006-0041023, U.S. Pat. No. 7,173,102, and International Application No. WO 2005/123660. In some embodiments, the compound of Formula XVIII, XVIIIa, XVIIIa-1, XVIIIa-2, or XVIIIa-3 (such as the polymers and oligomers), or salts thereof, useful in the present invention is a compound or salt thereof selected from those described in U.S. Patent Application Publication No. 2006-0041023, U.S. Pat. No. 7,173,102, and International Application No. WO 2005/123660.

The present invention also provides methods of treating and/or preventing mucositis in a mammal comprising administering to the mammal in need thereof a therapeutically effective amount of a compound of Formula XIX:

$$R^1—[—X\text{-}A_1\text{-}X—Y\text{-}A_2\text{-}Y—]_m—R^2 \qquad \text{XIX}$$

or a pharmaceutically acceptable salt thereof, wherein:

each X is, independently, $NR^8$, O, S, $—N(R^8)N(R^8)—$, $—N(R^8)—(N{=}N)—$, $—(N{=}N)—N(R^8)—$, $—C(R^7R^{7'})NR^8—$, $—C(R^7R^{7'})O—$, or $—C(R^7R^{7'})S—$;

each Y is, independently, C═O, C═S, O═S═O, $—C({=}O)C({=}O)—$, $C(R^6R^{6'})C{=}O$, or $C(R^6R^{6'})C{=}S$;

each $R^8$ is, independently, hydrogen or alkyl;

each $R^7$ and each $R^{7'}$ are, independently, hydrogen or alkyl; or $R^7$ and $R^{7'}$ together form $—(CH_2)_p—$, wherein p is 4 to 8;

each $R^6$ and each $R^{6'}$ are, independently, hydrogen or alkyl; or $R^6$ and $R^{6'}$ together form $—(CH_2)_2NR^{12}(CH_2)_2—$, wherein $R^{12}$ is hydrogen, $—C({=}N)CH_3$, or $—C({=}NH)—NH_2$;

$A_1$ and $A_2$ are each, independently, optionally substituted arylene or optionally substituted heteroarylene, wherein $A_1$ and $A_2$ are each, independently, optionally substituted with one or more PL group(s), one or more NPL group(s), or a combination of one or more PL group(s) and one or more NPL group(s);

or each $A_2$ is, independently, optionally substituted arylene or optionally substituted heteroarylene, and each $A_1$ is, independently, optionally substituted $C_3$ to $C_8$ cycloalkyl, wherein $A_1$ and $A_2$ are each, independently, optionally substituted with one or more PL group(s), one or more NPL group(s), or a combination of one or more PL group(s) and one or more NPL group(s);

$R^1$ is hydrogen, a PL group, or an NPL group, and $R^2$ is $—X\text{-}A_1\text{-}X—R^1$, wherein $A_1$ is as defined above and is optionally substituted with one or more PL group(s), one or more NPL group(s), or a combination of one or more PL group(s) and one or more NPL group(s); or $R^1$ is hydrogen, a PL group, or an NPL group, and $R^2$ is $—X\text{-}A'\text{-}X—R^1$, wherein A' is $C_3$ to $C_8$ cycloalkyl, aryl, or heteroaryl and is optionally substituted with one or more PL group(s), one or more NPL group(s), or a combination of one or more PL group(s) and one or more NPL group(s); or $R^1$ is $—Y\text{-}A_2\text{-}Y—R^2$, and each $R^2$ is, independently, hydrogen, a PL group, or an NPL group; or $R^1$ is $—Y\text{-}A'$ and $R^2$ is $—X\text{-}A'$, wherein each A' is, independently, $C_3$ to $C_8$ cycloalkyl, aryl, or heteroaryl and is optionally substituted with one or more PL group(s), one or more NPL group(s), or a combination of one or more PL group(s) and one or more NPL group(s); or $R^1$ and $R^2$ are, independently, a PL group or an NPL group; or $R^1$ and $R^2$ together form a single bond;

each NPL is, independently, $—B(OR^4)_2$ or $—(NR^{3'})_{q1NPL}—U^{NPL}\text{-}LK^{NPL}(NR^{3''})_{q2NPL}—R^{4'}$, wherein:

$R^3$, $R^{3'}$, and $R^{3''}$ are each, independently, hydrogen, alkyl, or alkoxy;

$R^4$ and $R^{4'}$ are each, independently, hydrogen, alkyl, alkenyl, alkynyl, cycloalkyl, aryl, and heteroaryl, wherein each of the alkyl, alkenyl, alkynyl, cycloalkyl, aryl, and heteroaryl is optionally substituted with one or more alkyl or halo groups;

each $U^{NPL}$ is, independently, absent or O, S, S(═O), $S({=}O)_2$, $NR^3$, —C(═O)—, $—C({=}O)—NR^3—$, $—C({=}O)—N{=}N—NR^3—$, $—C({=}O)—NR^3—N{=}N—$, $—N{=}N—NR^3—$, $—C({=}N—N(R^3)_2)—$, $—C({=}NR^3)—$, —C(═O)O—, —C(═O)S—, —C(═S)—, $—O—P({=}O)_2O—$, —S—C═N—, or $—C({=}O)—NR^3—O—$, wherein groups with two chemically nonequivalent termini can adopt both possible orientations;

each $LK^{NPL}$ is, independently, $—(CH_2)_{pNPL}—$ or $C_{2\text{-}8}$ alkenylenyl, wherein each of the $—(CH_2)_{pNPL}—$ and $C_{2\text{-}8}$ alkenylenyl is optionally substituted with one or more substituents, wherein each substituent is, independently, amino, hydroxyl, aminoalkyl, hydroxylalkyl, or alkyl;

each pNPL is, independently, an integer from 0 to 8;

q1NPL and q2NPL are each, independently, 0, 1, or 2;

each PL is, independently, halo, hydroxyethoxymethyl, methoxyethoxymethyl, polyoxyethylene, or $—(NR^{5'})_{q1PL}—U^{PL}\text{-}LK^{PL}\text{-}(NR^{5'})_{q2PL}—V$, wherein:

$R^5$, $R^{5'}$, and $R^{5''}$ are each, independently, hydrogen, alkyl, and alkoxy;

each $U^{PL}$ is, independently, absent or O, S, S(═O), $S({=}O)_2$, $NR^5$, —C(═O)—, $—C({=}O)—NR^5—$, $—C({=}O)—N{=}N—NR^5—$, $—C({=}O)—NR^5—N{=}N—$, $—N{=}N—NR^5—$, $—C({=}N—N(R^5)_2)—$, $—C({=}NR^5)—$, —C(═O)O—, —C(═O)S—, —C(═S)—, $—O—P({=}O)_2O—$, —S—C═N—, or $—C({=}O)—NR^5—O—$, wherein groups with two chemically nonequivalent termini can adopt either of the two possible orientations;

each V is, independently, nitro, cyano, amino, halo, hydroxy, alkoxy, alkylthio, alkylamino, dialkylamino, $—NH(CH_2)_pNH_2$ wherein p is 1 to 5, $—C({=}O)NH(CH_2)_pNH_2$ wherein p is 1 to 5, $—C({=}O)NH(CH_2)_pNHC({=}NH)NH_2$ wherein p is 1 to 5, $—C({=}O)NH(CH_2)_pNHC({=}O)NH_2$ wherein p is 1 to 5, —NHC(=O)-alkyl, —$N(CH_2CH_2NH_2)_2$, diazamino, amidino, guanidino, ureido, carbamoyl, —C(=O)OH, —C(=O)$OR^c$, —C(=O)NH—OH, —O—NH—C(=NH)$NH_2$, —NH—S(=O)$_2$OH, S(=O)$_2$OH, $NR^dR^e$, semicarbazone, aryl, cycloalkyl, heterocycloalkyl, or heteroaryl, wherein each of the aryl and cycloalkyl is substituted with one or more substitutents, wherein each of the heterocycloalkyl, and heteroaryl is optionally substituted with one or more substituents, and wherein each of the subsituents for the aryl, cycloalkyl, heterocycloalkyl, and heteroaryl is, independently, nitro, cyano, amino, halo, hydroxy, alkoxy, alkylthio, alkylamino, dialkylamino, —$NH(CH_2)_pNH_2$ wherein p is 1 to 5, —$N(CH_2CH_2NH_2)_2$, diazamino, amidino, guanidino, ureido, carbamoyl, —C(=O)OH, —C(=O)$OR^c$, —C(=O)NH—OH, —O—NH—C(=NH)$NH_2$, —NH—S(=O)$_2$OH, S(=O)$_2$OH, $NR^dR^e$, semicarbazone, aminosulfonyl, aminoalkoxy, aminoalkythio, lower acylamino, or benzyloxycarbonyl;

each $LK^{PL}$ is, independently, —$(CH_2)_{pPL}$— or $C_{2-8}$ alkenylenyl, wherein each of the —$(CH_2)_{pNPL}$— and $C_{2-8}$ alkenylenyl is optionally substituted with one or more substituents, wherein each substituent is, independently, amino, hydroxyl, aminoalkyl, hydroxylalkyl, or alkyl;

each pPL is, independently, an integer from 0 to 8;

q1PL and q2PL are each, independently, 0, 1, or 2; and m is an integer from 1 to about 20.

In some embodiments, each of the moiety of —Y-$A_2$-Y— is, independently, a moiety of Formula XIX-1, XIX-2, or XIX-3:

XIX-1

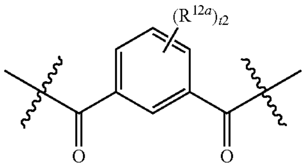

XIX-2

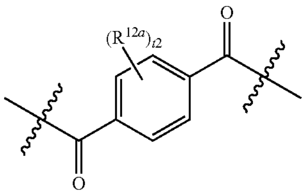

XIX-3

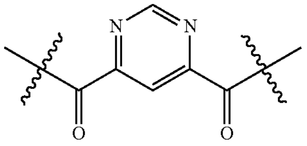

wherein each $R^{12a}$ is, independently, a PL group or an NPL group; and t2 is 0, 1, or 2.

In some embodiments, each of the moiety of —Y-$A_2$-Y— is, independently, a moiety of Formula XIX-1 or XIX-2; and each $R^{12a}$ is, independently, halo, alkyl, alkoxy, haloalkyl, haloalkoxy, —$(CH_2)_{pPL}$—V, —$O(CH_2)_{pPL}$—V, or —$S(CH_2)_{pPL}$—V, wherein pPL is an integer from 1 to 5.

In some embodiments, each $R^{12a}$ is, independently, halo, alkyl, alkoxy, haloalkyl, or haloalkoxy. In some embodiments, each $R^{12a}$ is, independently, alkoxy. In some embodiments, each $R^{12a}$ is methoxy.

In some embodiments, each of the moiety of —Y-$A_2$-Y— is, independently, a moiety of Formula XIX-1 or XIX-2; and t2 is 2.

In some embodiments, each $R^{12a}$ is, independently, alkoxy. In some embodiments, each $R^{12a}$ is methoxy.

In some embodiments, each of the moiety of —Y-$A_2$-Y— is, independently, a moiety of Formula XIX-1, and the moiety of Formula XIX-1 is a moiety of Formula XIX-1a:

XIX-1a

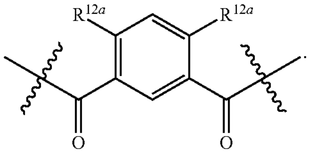

In some embodiments, each of the moiety of —X-$A_1$-X— is, independently, a moiety of Formula XIX-B:

XIX-B

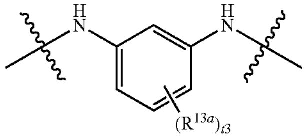

wherein each $R^{13a}$ is, independently, a PL group or an NPL group; and t3 is 0, 1, or 2.

In some embodiments, each of the moiety of —X-$A_1$-X— is, independently, a moiety of Formula XIX-C:

XIX-C

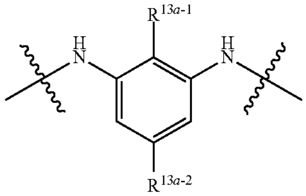

wherein each of $R^{13a-1}$ and $R^{13a-2}$ is, independently, H, a PL group, or an NPL group.

In some embodiments, each of $R^{13a-1}$ and $R^{13a-2}$ is, independently, a PL group or an NPL group. In some embodiments, each of $R^{13a-1}$ and $R^{13a-2}$ is, independently, halo, alkyl, haloalkyl, —$O(CH_2)_{pPL}$—V, or —$S(CH_2)_{pPL}$—V, wherein pPL is an integer from 1 to 5. In some embodiments, each of $R^{13a-1}$ and $R^{13a-2}$ is, independently, haloalkyl or —$S(CH_2)_{pPL}$—V, wherein pPL is an integer from 1 to 5.

In some embodiments, each of the moiety of —X-$A_1$-X— is, independently, a moiety of Formula XIX-D:

XIX-D

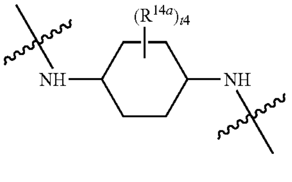

wherein each $R^{14a}$ is, independently, a PL group or an NPL group; and t4 is 0, 1, or 2.

In some embodiments, t4 is 0.

In some embodiments, each moiety of —Y-$A_2$-Y— is, independently, a moiety of Formula XIX-1, XIX-1a, XIX-2, or XIX-3; and each of the moiety of —X-$A_1$-X— is, independently, a moiety of Formula XIX-B, XIX-C, or XIX-D. In some embodiments, each moiety of —Y-$A_2$-Y— is, independently, a moiety of Formula XIX-1 or XIX-1a; and each of the moiety of —X-$A_1$-X— is, independently, a moiety of Formula XIX-B or XIX-C. In some embodiments, each moiety of —Y-$A_2$-Y— is, independently, a moiety of Formula XIX-1a; and each of the moiety of —X-$A_1$-X— is, independently, a moiety of Formula XIX-C. In some embodiments, each moiety of —Y-$A_2$-Y— is, independently, a moiety of Formula XIX-1, XIX-1a, XIX-2, or XIX-3; and each of the moiety of —X-$A_1$-X— is, independently, a moiety of Formula XIX-D. In some embodiments, each moiety of —Y-$A_2$-Y— is, independently, a moiety of Formula XIX-1a.

In some embodiments, the compound is of Formula XIXa:

$$R^1\text{—X-}A_1\text{-X—Y-}A_2\text{-Y—X-}A_1\text{-X—}R^2 \qquad \text{XIXa}$$

or pharmaceutically acceptable salt thereof, wherein:

each X is, independently, $NR^8$, O, S, or —N($R^8$)N($R^8$)—;

each Y is, independently, C═O, C═S, or O═S═O;

each $R^8$ is, independently, hydrogen or alkyl;

$A_1$ and $A_2$ are each, independently, optionally substituted arylene or optionally substituted heteroarylene, wherein $A_1$ and $A_2$ are each, independently, optionally substituted with one or more PL group(s), one or more NPL group(s), or a combination of one or more PL group(s) and one or more NPL group(s);

$R^1$ is a PL group or an NPL group;

$R^2$ is $R^1$;

each NPL is, independently, —$(NR^{3'})_{q1NPL}$—$U^{NPL}$-$LK^{NPL}$$(NR^{3''})_{q2NPL}$—$R^{4'}$, wherein:

$R^3$, $R^{3'}$, and $R^{3''}$ are each, independently, hydrogen, alkyl, or alkoxy;

$R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more alkyl or halo groups;

$U^{NPL}$ is, independently, absent or O, S, S(═O), S(═O)$_2$, $NR^3$, —C(═O)—, —C(═O)—N═N—$NR^3$—, —C(═O)—$NR^3$—N═N—, —N═N—$NR^3$—, —C(═N—N($R^3$)$_2$)—, —C(═$NR^3$)—, —C(═O)O—, —C(═O)S—, —C(═S)—, —O—P(═O)$_2$O—, —S—C═N—, or —C(═O)—$NR^3$—O—, wherein groups with two chemically nonequivalent termini can adopt either of the two possible orientations;

each $LK^{NPL}$ is, independently, —$(CH_2)_{pNPL}$— or $C_{2-8}$ alkenylenyl, wherein the —$(CH_2)_{pNPL}$— is optionally substituted with one or more substituents, wherein each substituent is, independently, amino, hydroxyl, or alkyl;

each pNPL is, independently, an integer from 0 to 8;

q1NPL and q2NPL are each, independently, 0, 1, or 2;

each PL is, independently, halo, hydroxyethoxymethyl, methoxyethoxymethyl, polyoxyethylene, or —$(NR^{5'})_{q1PL}$—$U^{PL}$-$LK^{PL}$-$(NR^{5'})_{q2PL}$—V, wherein:

$R^5$, $R^{5'}$, and $R^{5''}$ are each, independently, hydrogen, alkyl, or alkoxy;

each $U^{PL}$ is, independently, absent or O, S, S(═O), S(═O)$_2$, $NR^5$, —C(═O)—, —C(═O)—N═N—$NR^5$—, —C(═O)—$NR^5$—N═N—, —N═N—$NR^5$—, —C(═N—N($R^5$)$_2$)—, —C(═$NR^5$)—, —C(═O)O—, —C(═O)S—, —C(═S)—, —O—P(═O)$_2$O—, —$R^5$O—, —$R^5$S—, —S—C═N—, or —C(═O)—$NR^5$—O—, wherein groups with two chemically nonequivalent termini can adopt both possible orientations;

each V is, independently, nitro, cyano, amino, halo, hydroxy, alkoxy, alkylthio, alkylamino, dialkylamino, —NH$(CH_2)_pNH_2$ wherein p is 1 to 5, —N$(CH_2CH_2NH_2)_2$, diazamino, amidino, guanidino, ureido, carbamoyl, —C(═O)OH, —C(═O)OR', —C(═O)NH—OH, —O—NH—C(═NH)$NH_2$, —NH—S(═O)$_2$OH, S(═O)$_2$OH, $NR^dR^e$, semicarbazone, aryl, heterocycloalkyl, or heteroaryl, wherein the aryl is substituted with one or more substitutents, wherein each of the heterocycloalkyl and heteroaryl is optionally substituted with one or more substituents, and wherein each of each of the subsituents for the aryl, heterocycloalkyl, and heteroaryl is, independently, nitro, cyano, amino, halo, hydroxy, alkoxy, alkylthio, alkylamino, dialkylamino, —NH$(CH_2)_pNH_2$ wherein p is 1 to 5, —N$(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, semicarbazone, aminosulfonyl, aminoalkoxy, aminoalkythio, lower acylamino, or benzyloxycarbonyl;

each $LK^{PL}$ is, independently, —$(CH_2)_{pPL}$— or $C_{2-8}$ alkenylenyl, wherein the —$(CH_2)_{pNPL}$— is optionally substituted with one or more substituents, wherein each substituent is, independently, amino, hydroxyl, or alkyl;

each pPL is, independently, an integer from 0 to 8; and q1PL and q2PL are each, independently, 0, 1, or 2.

In some embodiments, each NPL group is, independently, —B$(OR^4)_2$, $R^{4'}$, or $OR^{4'}$, and $R^4$ and $R^{4'}$ are each, independently, alkyl, alkenyl, alkynyl, cycloalkyl, or aryl, each is optionally substituted with one or more substitutents, wherein each substituent is, independently, alkyl, halo, or haloalkyl.

In some embodiments, each NPL group is, independently, $R^{4'}$ or $OR^{4'}$, and each $R^{4'}$ is, independently, alkyl, alkenyl, alkynyl, cycloalkyl, or aryl, each is optionally substituted with one or more substitutents, wherein each substituent is, independently, alkyl, halo, or haloalkyl.

In some embodiments, each NPL group is, independently, alkyl, alkenyl, alkynyl, cycloalkyl, aryl, or alkoxy, each is optionally substituted with one or more substitutents, wherein each substituent is, independently, alkyl, halo, or haloalkyl. In some embodiments, each NPL group is, independently, alkyl, haloalkyl, alkoxy, or haloalkoxy.

In some embodiments, each V is, independently, nitro, cyano, amino, hydroxy, alkoxy, alkylthio, alkylamino, dialkylamino, —NH$(CH_2)_pNH_2$ wherein p is 1 to 5, —N$(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, semicarbazone, aryl, heterocycloalkyl, or heteroaryl, wherein the aryl is substituted with one or more substitutents, wherein each of the heterocycloalkyl and heteroaryl is optionally substituted with one or more substituents, and wherein each of each of the subsituents for the aryl, heterocycloalkyl, and heteroaryl is, independently, nitro, cyano, amino, hydroxy, alkoxy, alkylthio, alkylamino, dialkylamino, —NH$(CH_2)_pNH_2$ wherein p is 1 to 5, —N$(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—S(═O)$_2$ OH, $S(=O)_2OH$, $NR^dR^e$, semicarbazone, aminosulfonyl, aminoalkoxy, aminoalkythio, lower acylamino, or benzyloxycarbonyl.

In some embodiments, each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(=O)OH, $—C(=O)OR^c$, —C(=O)NH—OH, $—O—NH—C(=NH)NH_2$, $—NH—S(=O)_2OH$, $S(=O)_2OH$, $NR^dR^e$, a substituted aryl group, heterocycloalkyl, or heteroaryl, wherein each of the heterocycloalkyl and heteroaryl is optionally substituted with one more substituents, wherein each substituent is, independently, alkyl, haloalkyl, alkoxy, haloalkoxy, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(=O)OH, $—C(=O)OR^c$, —C(=O)NH—OH, $—O—NH—C(=NH)NH_2$, $—NH—S(=O)_2OH$, $S(=O)_2OH$, $NR^dR^e$, a substituted aryl group, heterocycloalkyl, or heteroaryl, wherein each of the heterocycloalkyl and heteroaryl is optionally substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(=O)NH—OH, $—O—NH—C(=NH)NH_2$, $—NH—S(=O)_2OH$, $NR^dR^e$, heterocycloalkyl, or heteroaryl, wherein each of the heterocycloalkyl and heteroaryl is optionally substituted with one more substituents, wherein each substituent is, independently, alkyl, haloalkyl, alkoxy, haloalkoxy, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, dialkylamino, $—NH(CH_2)_pNH_2$ wherein p is 1 to 5, $—N(CH_2CH_2NH_2)_2$, guanidino, amidino, ureido, carbamoyl, —C(=O)NH—OH, $—O—NH—C(=NH)NH_2$, $—NH—S(=O)_2OH$, $NR^dR^e$, heterocycloalkyl, or heteroaryl, wherein each of the heterocycloalkyl and heteroaryl is optionally substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, arylamino, heteroarylamino, ureido, carbamoyl, —C(=O)OH, $—C(=O)OR^c$, —C(=O)NH—OH, $—O—NH—C(=NH)NH_2$, $—NH—S(=O)_2OH$, $S(=O)_2OH$, a 3-8 membered heterocycloalkyl, a 5- to 10-membered heteroaryl, or a 6- to 10-membered substituted aryl, wherein the substituted aryl is substituted with one or more substituents, wherein each substituent is, independently, OH, amino, hydroxylalkyl, or aminoalkyl, and wherein each of the 3-8 membered heterocycloalkyl and the 5- to 10-membered heteroaryl is optionally substituted with one or more substituents, wherein each substituent is, independently, alkyl, haloalkyl, alkoxy, haloalkoxy, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, hydroxy, amino, alkylamino, arylamino, heteroarylamino, ureido, carbamoyl, —C(=O)OH, $—C(=O)OR^c$, —C(=O)NH—OH, $—O—NH—C(=NH)NH_2$, $—NH—S(=O)_2OH$, $S(=O)_2OH$, a 3-8 membered heterocycloalkyl, a 5- to 10-membered heteroaryl, or a 6- to 10-membered substituted aryl, wherein the substituted aryl is substituted with one or more substituents, wherein each substituent is, independently, OH, amino, hydroxylalkyl, or aminoalkyl.

In some embodiments, each V is, independently, amino, heteroarylamino, ureido, carbamoyl, C(=O)OH, $—C(=O)OR^c$, —C(=O)NH—OH, $—O—NH—C(=NH)NH_2$, $—NH—S(=O)_2OH$, $S(=O)_2OH$, aziridinyl, azetidinyl, pyrrolidinyl, piperidinyl, piperazinyl, morpholino, azepanyl, azocanyl, tetrazolyl, 1,2,4-oxadiazolyl, 1,3,4-oxadiazolyl, imidazolyl, pyridinyl, indolyl, or a substituted phenyl, wherein the substituted phenyl is substituted with one or more substituents, wherein each substituent is, independently, OH or amino.

In some embodiments, each V is, independently, amino, alkylamino, dialkylamino, $—NH(CH_2)_pNH_2$ wherein p is 1 to 5, $—N(CH_2CH_2NH_2)_2$, guanidino, amidino, ureido, heterocycloalkyl, or heteroaryl, wherein each of the heterocycloalkyl and heteroaryl is optionally substituted with one more substituents, wherein each substituent is, independently, amino, cyano, nitro, hydroxy, $—NH(CH_2)_pNH_2$ wherein p is 1 to 5, $—N(CH_2CH_2NH_2)_2$, amidino, guanidino, aminosulfonyl, aminoalkoxy, aminoalkythio, lower acylamino, or benzyloxycarbonyl.

In some embodiments, each V is, independently, amino, alkylamino, dialkylamino, $—NH(CH_2)_pNH_2$ wherein p is 1 to 5, $—N(CH_2CH_2NH_2)_2$, guanidino, amidino, ureido, pyrrodinyl, piperidinyl, piperazinyl, 4-methylpiperazinyl, pyridinyl, pyrimidinyl, pyrazinyl, or indolyl. In some embodiments, each V is, independently, amino, alkylamino, dialkylamino, $—NH(CH_2)_pNH_2$ wherein p is 1 to 5, $—N(CH_2CH_2NH_2)_2$, guanidino, amidino, ureido, or indolyl.

In some embodiments, each PL is, independently, halo, hydroxyethoxymethyl, methoxyethoxymethyl, polyoxyethylene, and $—(NR^{5'})_{q1PL}—U^{PL}—(CH_2)_{pPL}—(NR^{5'})_{q2PL}—V$.

In some embodiments, each PL group is, independently, halo, $—(CH_2)_{pPL}—V$, $O—(CH_2)_{pPL}—V$, or $S—(CH_2)_{pPL}—V$; each pPL is an integer from 0 to 5; and each V is, independently, hydroxy, amino, halo, alkylamino, dialkylamino, $—NH(CH_2)_pNH_2$ wherein p is 1 to 5, $—N(CH_2CH_2NH_2)_2$, guanidino, amidino, ureido, carbamoyl, —C(=O)OH, $—C(=O)OR^c$, —C(=O)NH—OH, $—O—NH—C(=NH)NH_2$, $—NH—S(=O)_2OH$, $S(=O)_2OH$, $NR^dR^e$, a substituted aryl group, heterocycloalkyl, or heteroaryl, wherein each of the heterocycloalkyl and heteroaryl is optionally substituted with one more substituents, wherein each substituent is, independently, amino, halo, cyano, nitro, hydroxy, $-NH(CH_2)_pNH_2$ wherein p is 1 to 5, $-N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, halo, cyano, nitro, hydroxy, $-NH(CH_2)_pNH_2$ wherein p is 1 to 5, $-N(CH_2CH_2NH_2)_2$, amidino, guanidino, aminosulfonyl, aminoalkoxy, aminoalkythio, lower acylamino, or benzyloxycarbonyl.

In some embodiments, each PL group is, independently, halo, $-(CH_2)_{pPL}-V$, $O-(CH_2)_{pPL}-V$, or $S-(CH_2)_{pPL}-V$; each pPL is an integer from 0 to 5; and each V is, independently, hydroxy, amino, alkylamino, dialkylamino, $-NH(CH_2)_pNH_2$ wherein p is 1 to 5, $-N(CH_2CH_2NH_2)_2$, guanidino, amidino, ureido, carbamoyl, $-C(=O)NH-OH$, $-O-NH-C(=NH)NH_2$, $-NH-S(=O)_2OH$, $NR^dR^e$, heterocycloalkyl, or heteroaryl, wherein each of the heterocycloalkyl and heteroaryl is optionally substituted with one more substituents, wherein each substituent is, independently, amino, halo, cyano, nitro, hydroxy, $-NH(CH_2)_pNH_2$ wherein p is 1 to 5, $-N(CH_2CH_2NH_2)_2$, amidino, guanidino, aminosulfonyl, aminoalkoxy, aminoalkythio, lower acylamino, or benzyloxycarbonyl.

In some embodiments, each NPL group is, independently, $-B(OR^4)_2$, $R^{4'}$, or $OR^{4'}$, $R^4$ and $R^{4'}$ are each, independently, alkyl, alkenyl, alkynyl, cycloalkyl, or aryl, each is optionally substituted with one or more substitutents, wherein each substituent is, independently, alkyl, halo, or haloalkyl; each PL group is, independently, halo, $-(CH_2)_{pPL}-V$, $O-(CH_2)_{pPL}-V$, or $S-(CH_2)_{pPL}-V$; each pPL is an integer from 0 to 5; and each V is, independently, hydroxy, amino, alkylamino, dialkylamino, $-NH(CH_2)_pNH_2$ wherein p is 1 to 5, $-N(CH_2CH_2NH_2)_2$, guanidino, amidino, ureido, carbamoyl, $-C(=O)OH$, $-C(=O)OR^c$, $-C(=O)NH-OH$, $-O-NH-C(=NH)NH_2$, $-NH-S(=O)_2OH$, $S(=O)_2OH$, $NR^dR^e$, a substituted aryl group, heterocycloalkyl, or heteroaryl, wherein each of the heterocycloalkyl and heteroaryl is optionally substituted with one more substituents, wherein each substituent is, independently, amino, halo, cyano, nitro, hydroxy, $-NH(CH_2)_pNH_2$ wherein p is 1 to 5, $-N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, halo, cyano, nitro, hydroxy, $-NH(CH_2)_pNH_2$ wherein p is 1 to 5, $-N(CH_2CH_2NH_2)_2$, amidino, guanidino, aminosulfonyl, aminoalkoxy, aminoalkythio, lower acylamino, or benzyloxycarbonyl.

In some embodiments, each X is, independently, $NR^8$; each Y is C═O; $A_1$ and $A_2$ are each, independently, phenyl or a 6-membered heteroaryl, each optionally substituted with one or more substituents, wherein each substituent is, independently, alkyl, haloalkyl, halo, —O-alkyl, $O-(CH_2)_{pPL}-V$, or $S-(CH_2)_{pPL}-V$; $R^1$ is $-C(=O)-(CH_2)_{pPL}-V$ or $-C(=O)-(CH_2)_{pNPL}-R^{4'}$; $R^2$ is $R^1$; $R^{4'}$ is H or alkyl; and each V is, independently, hydroxy, amino, alkylamino, dialkylamino, $-NH(CH_2)_pNH_2$ wherein p is 1 to 4, $-N(CH_2CH_2NH_2)_2$, guanidino, amidino, ureido, carbamoyl, heterocycloalkyl, or heteroaryl.

In some embodiments, each X is NH; each Y is C═O; each $A_1$ is, independently, phenyl optionally substituted with one or two substituents, wherein each substituent is, independently, haloalkyl, halo, —O-alkyl, $O-(CH_2)_{pPL}-V$, or $S-(CH_2)_{pPL}-V$; $A_2$ is phenyl or a 6-membered heteroaryl, each optionally substituted with one or two substituents, wherein each substituent is, independently, —O-alkyl; $R^1$ is $-C(=O)-(CH_2)_{pPL}-V$; $R^2$ is $R^1$; and each V is, independently, hydroxy, amino, alkylamino, dialkylamino, $-NH(CH_2)_pNH_2$ wherein p is 1 to 5, $-N(CH_2CH_2NH_2)_2$, guanidino, amidino, ureido, carbamoyl, heterocycloalkyl, or heteroaryl.

In some embodiments, each X is NH; each Y is C═O; each $A_1$ is, independently, phenyl optionally substituted with one or two substituents, wherein each substituent is, independently, haloalkyl, $O-(CH_2)_{pPL}-V$, or $S-(CH_2)_{pPL}-V$; $A_2$ is phenyl or pyrimidinyl, each optionally substituted with one or two substituents, wherein each substituent is, independently, —O-alkyl; $R^1$ is $-C(=O)-(CH_2)_{pPL}-V$; $R^2$ is $R^1$; and each V is, independently, amino, alkylamino, dialkylamino, $-NH(CH_2)_pNH_2$ wherein p is 1 to 4, $-N(CH_2CH_2NH_2)_2$, guanidino, amidino, ureido, carbamoyl, or indolyl.

In some embodiments, the moiety of $-Y-A_2-Y-$ is a moiety of Formula XIX-1, XIX-2, or XIX-3:

SI-1

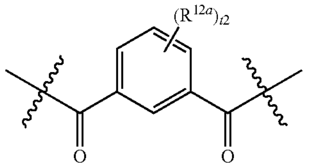

SI-2

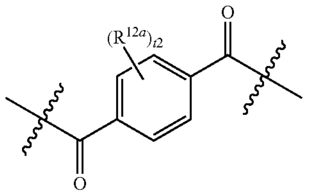

SI-3

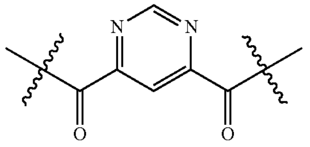

wherein each $R^{12a}$ is, independently, a PL group or an NPL group; and t2 is 0, 1, or 2.

In some embodiments, the moiety of $-Y-A_2-Y-$ is a moiety of Formula XIX-1 or XIX-2; and each $R^{12a}$ is, independently, halo, alkyl, alkoxy, haloalkyl, haloalkoxy, $-(CH_2)_{pPL}-V$, $-O(CH_2)_{pPL}-V$, or $-S(CH_2)_{pPL}-V$, wherein pPL is an integer from 1 to 5.

In some embodiments, each $R^{12a}$ is, independently, halo, alkyl, alkoxy, haloalkyl, or haloalkoxy. In some embodiments, each $R^{12a}$ is, independently, alkoxy. In some embodiments, each $R^{12a}$ is methoxy.

In some embodiments, the moiety of $-Y-A_2-Y-$ is a moiety of Formula XIX-1 or XIX-2; and t2 is 2.

In some embodiments, each $R^{12a}$ is, independently, alkoxy. In some embodiments, each $R^{12a}$ is methoxy.

In some embodiments, the moiety of $-Y-A_2-Y-$ is a moiety of Formula XIX-1, and the moiety of Formula XIX-1 is a moiety of Formula XIX-1a:

XIX-1a

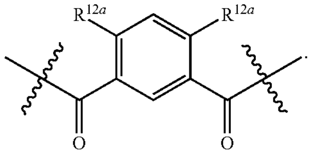

In some embodiments, each of the moiety of —X-$A_1$-X— is, independently, a moiety of Formula XIX-B:

XIX-B

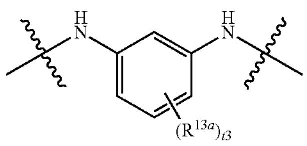

wherein each $R^{13a}$ is, independently, a PL group or an NPL group; and t3 is 0, 1, or 2.

In some embodiments, wherein each of the moiety of —X-$A_1$-X— is, independently, a moiety of Formula XIX-C:

XIX-C

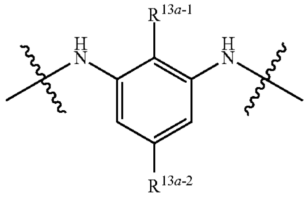

wherein each of $R^{13a-1}$ and $R^{13a-2}$ is, independently, H, a PL group, or an NPL group.

In some embodiments, each of $R^{13a-1}$ and $R^{13a-2}$ are, independently, a PL group or an NPL group. In some embodiments, each of $R^{13a-1}$ and $R^{13a-2}$ are, independently, halo, alkyl, haloalkyl, —O$(CH_2)_{pPL}$—V, or —S$(CH_2)_{pPL}$—V, wherein pPL is an integer from 1 to 5. In some embodiments, each of $R^{13a-1}$ and $R^{13a-2}$ are, independently, haloalkyl or —S$(CH_2)_{pPL}$—V, wherein pPL is an integer from 1 to 5.

In some embodiments, each $A_2$ is, independently, optionally substituted arylene or optionally substituted heteroarylene, and each $A_1$ is, independently, optionally substituted $C_3$ to $C_8$ cycloalkyl, wherein $A_1$ and $A_2$ are each, independently, optionally substituted with one or more PL group(s), one or more NPL group(s), or a combination of one or more PL group(s) and one or more NPL group(s); $R^1$ is —Y-$A_2$-Y—$R^2$; and each $R^2$ is, independently, hydrogen, a PL group, or an NPL group. In some embodiments, each X is NH; and each Y is C═O. In some embodiments, m is 1 or 2.

In some embodiments, each $A_2$ is, independently, optionally substituted phenyl, and each $A_1$ is, independently, optionally substituted $C_3$-$C_8$ cycloalkyl, wherein $A_1$ and $A_2$ are each, independently, optionally substituted with one or more PL group(s), one or more NPL group(s), or a combination of one or more PL group(s) and one or more NPL group(s); $R^1$ is —Y-$A_2$-Y—$R^2$; and each $R^2$ is, independently, hydrogen, a PL group, or an NPL group. In some embodiments, each X is NH; and each Y is C═O. In some embodiments, m is 1 or 2.

In some embodiments, each $A_1$ is, independently, $C_5$-$C_6$ cycloalkyl; each $A_2$ is, independently, phenyl optionally substituted with one or more PL group(s), one or more NPL group(s), or a combination of one or more PL group(s) and one or more NPL group(s); $R^1$ is —Y-$A_2$-Y—$R^2$; and each $R^2$ is, independently, hydrogen, a PL group, or an NPL group. In some embodiments, each X is NH; and each Y is C═O. In some embodiments, m is 1 or 2.

In some embodiments, each NPL group is, independently, —B$(OR^4)_2$, $R^{4'}$, or $OR^{4'}$; $R^4$ and $R^{4'}$ are each, independently, alkyl, alkenyl, alkynyl, cycloalkyl, or aryl, each is optionally substituted with one or more substitutents, wherein each substituent is, independently, alkyl, halo, or haloalkyl; each PL group is, independently, halo, —$(CH_2)_{pPL}$—V, O—$(CH_2)_{pPL}$—V, or S—$(CH_2)_{pPL}$—V; each pPL is an integer from 0 to 5; and each V is, independently, hydroxy, amino, alkylamino, dialkylamino, —NH$(CH_2)_pNH_2$ wherein p is 1 to 5, —N$(CH_2CH_2NH_2)_2$, guanidino, amidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, a substituted aryl group, heterocycloalkyl, and heteroaryl, wherein each of the heterocycloalkyl and heteroaryl is optionally substituted with one more substituents, wherein each substituent is, independently, amino, halo, cyano, nitro, hydroxy, —NH$(CH_2)_pNH_2$ wherein p is 1 to 5, —N$(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, halo, cyano, nitro, hydroxy, —NH$(CH_2)_pNH_2$ wherein p is 1 to 5, —N$(CH_2CH_2NH_2)_2$, amidino, guanidino, aminosulfonyl, aminoalkoxy, aminoalkythio, lower acylamino, or benzyloxycarbonyl. In some embodiments, each X is NH; and each Y is C═O. In some embodiments, m is 1 or 2.

In some embodiments, each $A_1$ is $C_6$ cycloalkyl; each $A_2$ is, independently, phenyl optionally substituted with one or more substituents, wherein each substituent is, independently, haloalkyl, halo, —O-alkyl, O—$(CH_2)_{pPL}$—V, or S—$(CH_2)_{pPL}$—V; $R^1$ is —Y-$A_2$-Y—$R^2$; each $R^2$ is, independently, NH—$(CH_2)_{pPL}$—V; and each V is, independently, hydroxy, amino, alkylamino, dialkylamino, —NH$(CH_2)_pNH_2$ wherein p is 1 to 5, —N$(CH_2CH_2NH_2)_2$, guanidino, amidino, ureido, carbamoyl, heterocycloalkyl, or heteroaryl. In some embodiments, each X is NH; and each Y is C═O. In some embodiments, m is 1 or 2.

In some embodiments, each $A_1$ is $C_6$ cycloalkyl; each $A_2$ is, independently, phenyl optionally substituted with one or more substituents, wherein each substituent is, independently, haloalkyl, —O-alkyl, O—$(CH_2)_{pPL}$—V, or S—$(CH_2)_{pPL}$—V; $R^1$ is —Y-$A_2$-Y—$R^2$; each $R^2$ is, independently, NH—$(CH_2)_{pPL}$—V; and each V is, independently, amino, alkylamino, dialkylamino, —NH$(CH_2)_pNH_2$ wherein p is 1 to 5, —N$(CH_2CH_2NH_2)_2$, guanidino, amidino, ureido, carbamoyl, or indolyl. In some embodiments, each X is NH; and each Y is C═O. In some embodiments, m is 1 or 2.

In some embodiments, each of the moiety of —Y-$A_2$-Y— is a moiety of Formula XIX-1 or XIX-1a:

SI-1

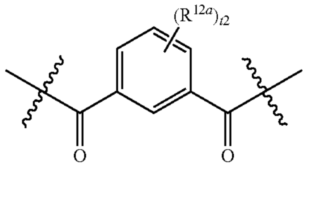

-continued

SI-1a

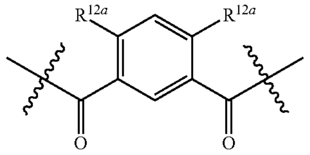

wherein each $R^{12a}$ is, independently, a PL group or an NPL group; and t2 is 0, 1, or 2; and each of the moiety of —X-$A_1$-X— is, independently, a moiety of Formula XIX-D:

XIX-D

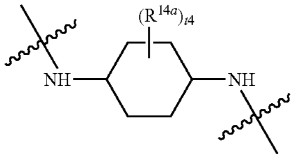

wherein each $R^{14a}$ is, independently, a PL group or an NPL group. In some embodiments, each of the moiety of —Y-$A_2$-Y— is a moiety of Formula XIX-1a, and each of the moiety of —X-$A_1$-X— is a moiety of Formula XIX-D wherein t4 is 0. In some embodiments, each $R^{12a}$ is, independently, halo, alkyl, alkoxy, haloalkyl, haloalkoxy, —$(CH_2)_{pPL}$—V, —$O(CH_2)_{pPL}$—V, or —$S(CH_2)_{pPL}$—V, wherein pPL is an integer from 1 to 5. In some embodiments, each $R^{12a}$ is, independently, alkoxy or —$O(CH_2)_{pPL}$—V, wherein pPL is an integer from 1 to 5. In some embodiments, $R^1$ is —Y-$A_2$-Y—$R^2$; and each $R^2$ is, independently, hydrogen, a PL group, or an NPL group. In some embodiments, m is 1, 2, or 3. In some embodiments, m is 1 or 2.

The present invention also provides methods of treating and/or preventing mucositis in a mammal comprising administering to the mammal in need thereof a therapeutically effective amount of a compound chosen from:

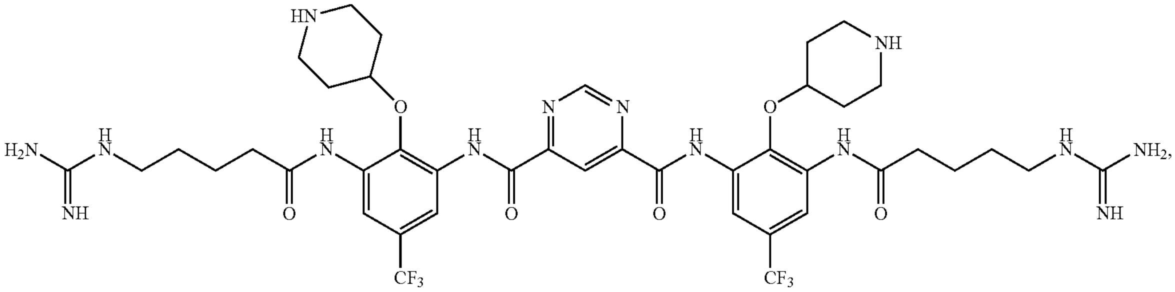

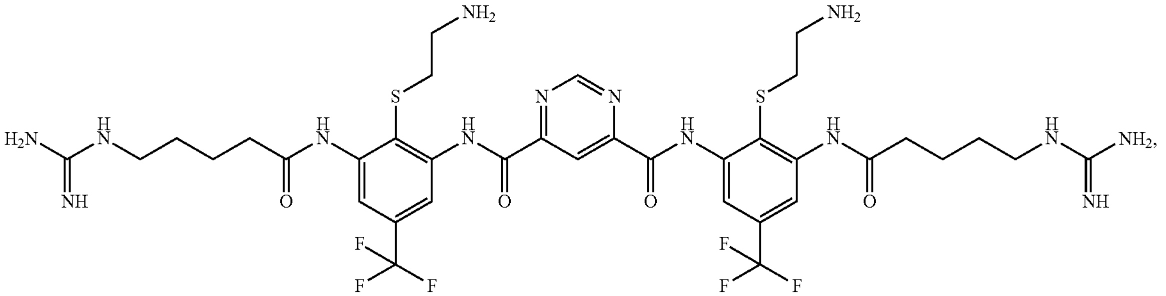

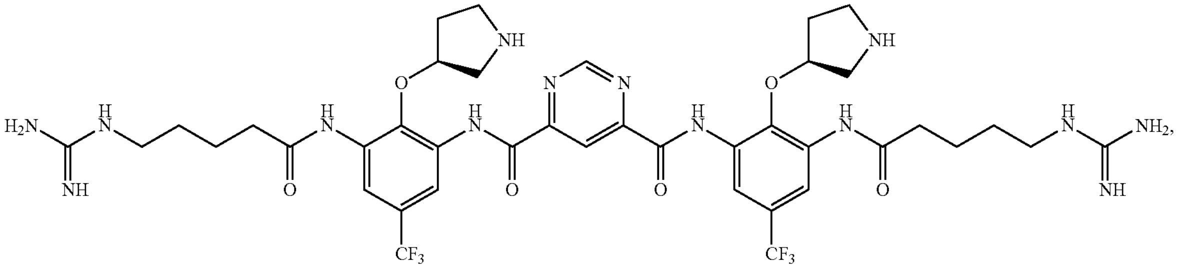

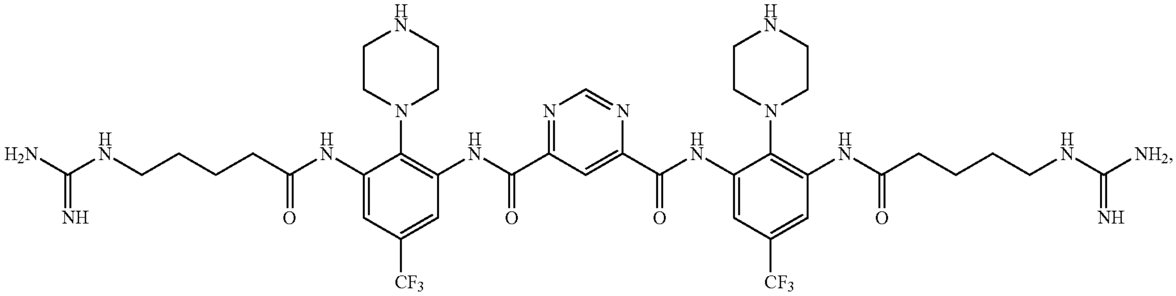

-continued

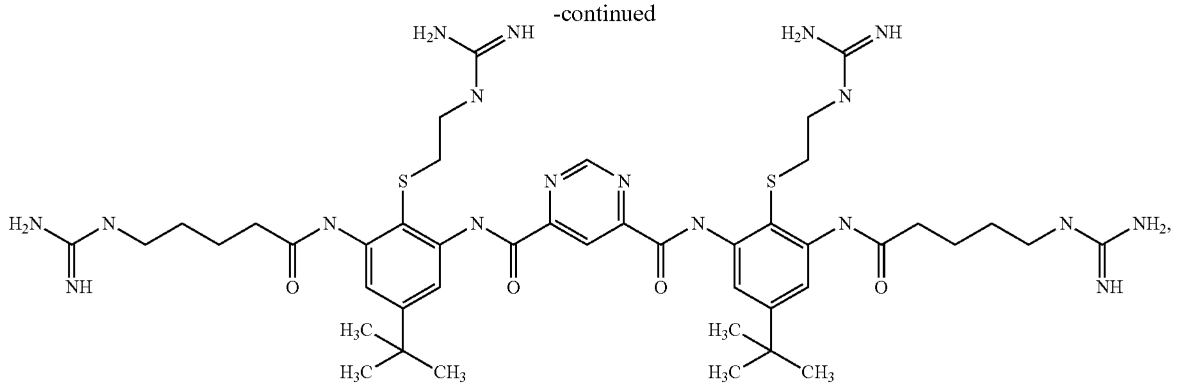

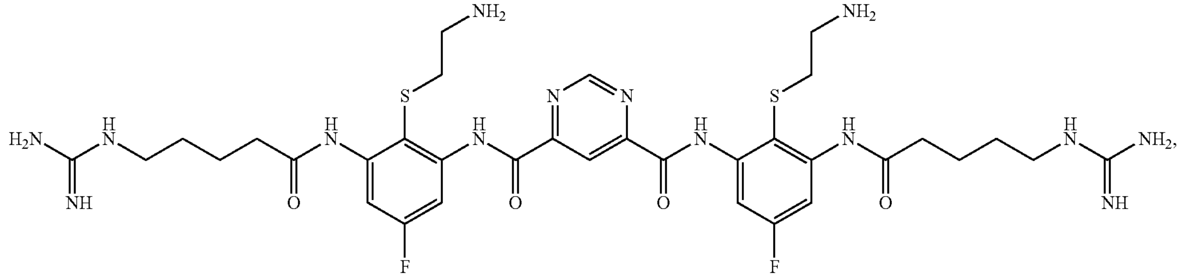

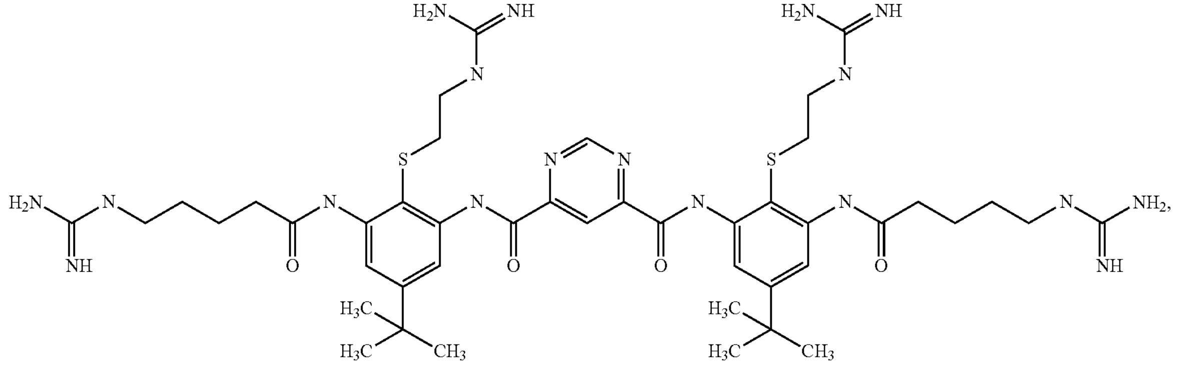 [SMILES: CC(C)(C)c1cc(NC(=O)CCCCNC(=N)N)c(SCCNC(=N)N)c(NC(=O)c2cc(C(=O)Nc3cc(C(C)(C)C)cc(NC(=O)CCCCNC(=N)N)c3SCCNC(=N)N)ncn2)c1]

or

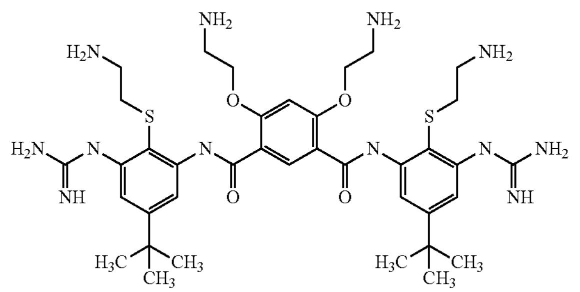 [SMILES: CC(C)(C)c1cc(NC(=N)N)c(SCCN)c(NC(=O)c2cc(C(=O)Nc3cc(C(C)(C)C)cc(NC(=N)N)c3SCCN)c(OCCN)cc2OCCN)c1]

or a pharmaceutically acceptable salt thereof.

The compounds of Formula XIX or XIXa (such as the polymers and oligomers) or pharmaceutically acceptable salts thereof useful in the present invention can be made, for example, by methods described in U.S. Patent Application Publication No. 2006-0041023, U.S. Pat. No. 7,173,102, International Publication No. WO 2004/082643, International Publication No. WO2006093813, and U.S. Patent Application Publication 2010-0081665. In some embodiments, the compounds of Formula XIX or XIXa (such as the polymers and oligomers) or pharmaceutically acceptable salts thereof useful in the present invention can be selected from those described in U.S. Patent Application Publication No. 2006-0041023, U.S. Pat. No. 7,173,102, International Publication No. WO 2004/082643, International Publication No. WO2006093813, and U.S. Patent Application Publication 2010-0081665.

In some embodiments, the compound(s) useful in the method of present invention can be chosen from one or more of the compounds (i.e., genuses, sub-genuses, and species) disclosed in U.S. Patent Application Publication No. 2006-0041023, U.S. Pat. No. 7,173,102, International Publication No. WO 2005/123660, International Publication No. WO 2004/082643, International Publication No. WO 2006/093813, and U.S. Patent Application Publication 2010-0081665, each of which is hereby incorporated by reference in its entirety.

The present invention also provides methods of treating and/or preventing mucositis in a mammal comprising administering to the mammal in need thereof a therapeutically effective amount of a compound of Formula XX:

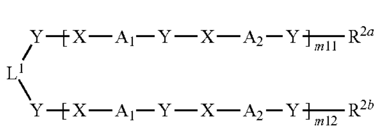

XX or a pharmaceutically acceptable salt thereof,
wherein:

each X is, independently, $NR^8$;

each Y is C═O;

each $R^8$ is, independently, hydrogen or alkyl;

each $A_2$ is optionally substituted arylene or optionally substituted heteroarylene, and each $A_1$ is —$(CH_2)_q$—, wherein q is 1 to 7, wherein $A_1$ and $A_2$ are each, independently, optionally substituted with one or more PL group(s), one or more NPL group(s), or a combination of one or more PL group(s) and one or more NPL group(s);

$R^2$ and $R^{2a}$ are each, independently, hydrogen, a PL group, an NPL group or —X-$A_1$-Y—$R^{11}$, wherein $R^{11}$ is hydrogen, a PL group, or an NPL group;

$L^1$ is $C_{1-10}$alkylene optionally substituted with one or more substitutents, wherein each substituent is, independently, alkyl, halo, haloalkyl, aminoalkyl, hydroxylalkyl, V, or —$(CH_2)_{pPL}$—V, wherein pPL is an integer from 1 to 5;

each NPL group is, independently, —$B(OR^4)_2$ or —$(NR^{3'})_{q1NPL}$—$U^{NPL}$-$LK^{NPL}$-$(NR^{3''})_{q2NPL}$—$R^{4'}$, wherein:

$R^3$, $R^{3'}$, and $R^{3''}$ are each, independently, hydrogen, alkyl, or alkoxy;

$R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substitutents, wherein each substituent is, independently, alkyl, halo, or haloalkyl;

each $U^{NPL}$ is, independently, absent or O, S, S(═O), $S(═O)_2$, $NR^3$, —C(═O)—, —C(═O)—$NR^3$—, —C(═O)—N═N—$NR^3$—, —C(═O)—$NR^3$—N═N—, —N═N—$NR^3$—, —C(═N—$N(R^3)_2$)—, —C(═$NR^3$)—, —C(═O)O—, —C(═O)S—, —C(═S)—, —O—P$(═O)_2$O—, —S—C═N—, or —C(═O)—$NR^3$—O—, wherein groups with two chemically nonequivalent termini can adopt both possible orientations;

each $LK^{NPL}$ is, independently, —$(CH_2)_{pNPL}$— and $C_{2-8}$ alkenylenyl, wherein each of the —$(CH_2)_{pNPL}$ and $C_{2-8}$ alkenylenyl is optionally substituted with one or more substituents, wherein each substituent is, independently, amino, hydroxyl, aminoalkyl, hydroxylalkyl, or alkyl;

each pNPL is, independently, an integer from 0 to 8;

q1NPL and q2NPL are each, independently, 0, 1, or 2;

each PL group is, independently, halo, hydroxyethoxymethyl, methoxyethoxymethyl, polyoxyethylene, or —$(NR^{5'})_{q1PL}$—$U^{PL}$-$LK^{PL}$-$(NR^{5''})_{q2PL}$—V, wherein:

$R^5$, $R^{5'}$, and $R^{5''}$ are each, independently, hydrogen, alkyl, or alkoxy;

each $U^{PL}$ is, independently, absent or O, S, S(═O), $S(═O)_2$, $NR^5$, —C(═O)—, —C(═O)—$NR^5$—, —C(═O)—N═N—$NR^5$—, —C(═O)—$NR^5$—N═N—, —N═N—$NR^5$—, —C(═N—$N(R^5)_2$)—, —C(═$NR^5$)—, —C(═O)O—, —C(═O)S—, —C(═S)—, —O—P$(═O)_2$O—, —S—C═N—, or —C(═O)—$NR^5$—O—, wherein groups with two chemically nonequivalent termini can adopt either of the two possible orientations;

each V is, independently, nitro, cyano, amino, halo, hydroxy, alkoxy, alkylthio, alkylamino, dialkylamino, —NH$(CH_2)_pNH_2$ wherein p is 1 to 5, —C(═O)NH$(CH_2)_pNH_2$ wherein p is 1 to 5, —C(═O)NH$(CH_2)_p$NHC(═NH)$NH_2$ wherein p is 1 to 5, —C(═O)NH$(CH_2)_p$NHC(═O)$NH_2$ wherein p is 1 to 5, —NHC(═O)-alkyl, —$N(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—$S(═O)_2$OH, $S(═O)_2$OH, $NR^dR^e$, semicarbazone, aryl, cycloalkyl, heterocycloalkyl, or heteroaryl, wherein each of the aryl and cycloalkyl is substituted with one or more substitutents, wherein each of the heterocycloalkyl and heteroaryl is optionally substituted with one or more substituents, and wherein each of the subsituents for the aryl, cycloalkyl, heterocycloalkyl, and heteroaryl is, independently, nitro, cyano, amino, halo, hydroxy, alkoxy, alkylthio, alkylamino, dialkylamino, —NH$(CH_2)_pNH_2$ wherein p is 1 to 5, —$N(CH_2CH_2NH_2)_2$, diazamino, amidino, guanidino, ureido, carbamoyl, —C(═O)OH, —C(═O)$OR^c$, —C(═O)NH—OH, —O—NH—C(═NH)$NH_2$, —NH—$S(═O)_2$OH, $S(═O)_2$OH, $NR^dR^e$, semicarbazone, aminosulfonyl, aminoalkoxy, aminoalkythio, lower acylamino, or benzyloxycarbonyl;

each $R^c$ is, independently, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, $C_{1-6}$ alkyl, $C_{1-6}$haloalkyl, aryl, arylalkyl, heteroaryl, heteroarylalkyl, cycloalkyl, or heterocycloalkyl;

$R^d$ and $R^e$ are, independently, H, $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted by OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, or heterocycloalkyl;

or $R^d$ and $R^e$ together with the N atom to which they are attached form a 4-, 5-, 6-, 7-, or 8-membered heterocycloalkyl;

each $LK^{PL}$ is, independently, —$(CH_2)_{pPL}$— or $C_{2-8}$ alkenylenyl, wherein each of the —$(CH_2)_{pNPL}$— and $C_{2-8}$ alkenylenyl is optionally substituted with one or more substituents, wherein each substituent is, independently, amino, hydroxyl, aminoalkyl, hydroxylalkyl, or alkyl;

each pPL is, independently, an integer from 0 to 8;

q1PL and q2PL are each, independently, 0, 1, or 2;

m11 is an integer from 1 to about 20; and m12 is an integer from 1 to about 20.

In some embodiments, each moiety of ┼X-$A_1$-Y—X-$A_2$-Y┼ is, independently, a moiety of:

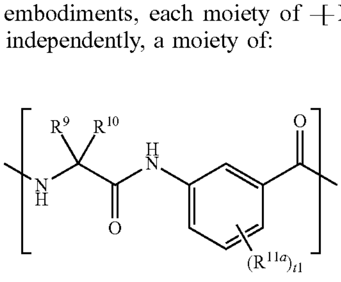

;

each $R^9$ is, independently, H, a PL group, or an NPL group; each $R^{10}$ is, independently, H, a PL group, or an NPL group; each $R^{11a}$ is, independently, a PL group or an NPL group; and each t1 is independently 0, 1, or 2.

In some embodiments, each $R^9$ is, independently, a PL group or an NPL group; and each $R^{10}$ is H. In some embodiments, each $R^9$ is, independently, alkyl or $(CH_2)_{pPL}$—V where pPL is an integer from 1 to 5; each $R^{10}$ is H; and each $R^{11a}$ is, independently, halo, alkyl, alkoxy, haloalkyl, haloalkoxy, —$(CH_2)_{pPL}$—V, —$O(CH_2)_{pPL}$—V, or —$S(CH_2)_{pPL}$—V, wherein pPL is an integer from 1 to 5.

In some embodiments, each $R^9$ is, independently, alkyl, —$(CH_2)$—V, —$(CH_2)_2$—V, —$(CH_2)_3$—V, —$(CH_2)_4$—V, or —$(CH_2)_5$—V; each $R^{10}$ is H; each V is, independently, hydroxyl, amino, heteroarylamino, ureido, guanidino, carbamoyl, C(═O)OH, —C(═O)$OR^c$, —C(═O)NH—OH, —O—NH—C(═NH)$NH_2$, —NH—S(═O)$_2$OH, S(═O)$_2$OH, aziridinyl, azetidinyl, pyrrolidinyl, piperidinyl, piperazinyl, morpholino, azepanyl, azocanyl, tetrazolyl, 1,2,4-oxadiazolyl, 1,3,4-oxadiazolyl, imidazolyl, pyridinyl, indolyl, or a substituted phenyl, wherein the substituted phenyl is substituted with one or more substituents, wherein each substituent is, independently, OH or amino; and each $R^{11a}$ is, independently, alkoxy.

In some embodiments, each $R^9$ is, independently, $CH_3$, —$(CH_2)$—V, —$(CH_2)_2$—V, —$(CH_2)_3$—V, —$(CH_2)_4$—V, and —$(CH_2)_5$—V; each $R^{10}$ is H; each V is, independently, amino, alkylamino, dialkylamino, —$NH(CH_2)_pNH_2$ wherein p is 1 to 5, —$N(CH_2CH_2NH_2)_2$, guanidino, amidino, ureido, or indolyl; and each $R^{11a}$ is, independently, alkoxy.

In some embodiments, each $R^9$ is, independently, $CH_3$, —$(CH_2)$—V, —$(CH_2)_2$—V, —$(CH_2)_3$—V, —$(CH_2)_4$—V, and —$(CH_2)_5$—V; each $R^{10}$ is H; each V is, independently, amino, alkylamino, dialkylamino, —$NH(CH_2)_pNH_2$ wherein p is 1 to 5, —$N(CH_2CH_2NH_2)_2$, guanidino, amidino, ureido, or indolyl; and each $R^{11a}$ is methoxy.

In some embodiments, each moiety of ┼X-$A_1$-Y—X-$A_2$-Y┼ is, independently, a moiety of:

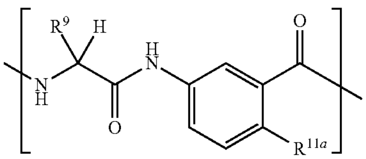
.

In some embodiments, $R^2$ and $R^{2a}$ are each, independently, $NH_2$, amidino, alkylamino, dialkylamino, —$NH(CH_2)_pNH_2$ wherein p is 1 to 5, or —NH—$(CH_2)_{pPL}$—$V^{10}$, wherein V is amino, alkylamino, dialkylamino, —$NH(CH_2)_pNH_2$ wherein p is 1 to 5, —$N(CH_2CH_2NH_2)_2$, guanidino, amidino, ureido, or carbamoyl; and $L^1$ is $C_{5-10}$alkylene optionally substituted with one or more substitutents, wherein each substituent is, independently, alkyl, halo, haloalkyl, aminoalkyl, or hydroxylalkyl.

In some embodiments, each of $R^2$ and $R^{2a}$ is $NH_2$; and $L^1$ is $C_{5-10}$alkylene, such as, for example $C_{7-10}$alkylene or $C_{7-9}$alkylene.

In some embodiments, m11 is an integer from 1 to about 10; and m12 is an integer from 1 to about 10. In some embodiments, m11 is an integer from 3 to 7; and m12 is an integer from 3 to 7. In some embodiments, m11 is an integer from 3 to 5; and m12 is an integer from 3 to 5.

The present invention also provides methods of treating and/or preventing mucositis in a mammal comprising administering to the mammal in need thereof a therapeutically effective amount of a compound of Formula XXI:

$$R^1\text{—}[\text{—}X\text{-}A_1\text{-}Y\text{—}X\text{-}A_2\text{-}Y\text{-}]_{m13}\text{-}X\text{-}L^1\text{-}Y\text{—}[\text{—}X\text{-}A_1\text{-}Y\text{—}X\text{-}A_2\text{-}Y\text{-}]_{m14}\text{—}R^2 \qquad \text{XXI}$$

or a pharmaceutically acceptable salt thereof, wherein:

each X is, independently, $NR^8$;

each Y is C═O;

each $R^8$ is, independently, hydrogen or alkyl;

each $A_2$ is optionally substituted arylene or optionally substituted heteroarylene, and each $A_1$ is —$(CH_2)_q$—, wherein q is 1 to 7, wherein $A_1$ and $A_2$ are each, independently, optionally substituted with one or more PL group(s), one or more NPL group(s), or a combination of one or more PL group(s) and one or more NPL group(s);

$R^1$ is hydrogen, a PL group, or an NPL group, and $R^2$ is —X-$A_1$-Y—$R^{11}$, wherein $R^{11}$ is hydrogen, a PL group, or an NPL group; or $R^1$ and $R^2$ are each, independently, hydrogen, a PL group, or an NPL group; or $R^1$ and $R^2$ together are a single bond; or $R^1$ is —Y-$A_2$-X—$R^{12}$, wherein $R^{12}$ is hydrogen, a PL group, or an NPL group, and $R^2$ is hydrogen, a PL group, or an NPL group;

$L^1$ is $C_{1-10}$alkylene optionally substituted with one or more substitutents, wherein each substituent is, independently, alkyl, halo, haloalkyl, aminoalkyl, hydroxylalkyl, V, or —$(CH_2)_{pPL}$—V wherein pPL is an integer from 1 to 5;

each V is, independently, hydroxy, amino, alkylamino, dialkylamino, —$NH(CH_2)_pNH_2$ wherein p is 1 to 5, —C(═O)$NH(CH_2)_pNH_2$ wherein p is 1 to 5, —C(═O)$NH(CH_2)_pNHC$(═NH)$NH_2$ wherein p is 1 to 5, —C(═O)$NH(CH_2)_pNHC$(═O)$NH_2$ wherein p is 1 to 5, —NHC(═O)-alkyl, —$N(CH_2CH_2NH_2)_2$, guanidino, amidino, ureido, carbamoyl, —C(═O)OH, —C(═O)$OR^c$, —C(═O)NH—OH, —O—NH—C(═NH)$NH_2$, —NH—S(═O)$_2$OH, S(═O)$_2$OH, $NR^dR^e$, a substituted aryl group, heterocycloalkyl, or heteroaryl, wherein each of the heterocycloalkyl and heteroaryl is optionally substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, halo, cyano, nitro, hydroxy, —$NH(CH_2)_pNH_2$ wherein p is 1 to 5, —$N(CH_2CH_2NH_2)_2$, amidino, guanidino, aminosulfonyl, aminoalkoxy, aminoalkythio, lower acylamino, or benzyloxycarbonyl;

each NPL group is, independently, —$B(OR^4)_2$ or —$(NR^{3'})_{q1NPL}$—$U^{NPL}$-$LK^{NPL}$-$(NR^{3''})_{q2NPL}$—$R^{4'}$, wherein:

$R^3$, $R^{3'}$, and $R^{3''}$ are each, independently, hydrogen, alkyl, or alkoxy;

$R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substitutents, wherein each substituent is, independently, alkyl, halo, or haloalkyl;

each $U^{NPL}$ is, independently, absent or O, S, S(═O), S(═O)$_2$, $NR^3$, —C(═O)—, —C(═O)—$NR^3$—, —C(═O)—N═N—$NR^3$—, —C(═O)—$NR^3$—N═N—, —N═N—$NR^3$—, —C(═N—$N(R^3)_2$)—, —C(═$NR^3$)—, —C(═O)O—, —C(═O)S—, —C(═S)—, —O—P(═O)$_2$O—, —S—C═N—, or —C(═O)—NR$^3$—O—, wherein groups with two chemically nonequivalent termini can adopt both possible orientations;

each $LK^{NPL}$ is, independently, —$(CH_2)_{pNPL}$— or $C_{2-8}$ alkenylenyl, wherein each of the —$(CH_2)_{pNPL}$ and $C_{2-8}$ alkenylenyl is optionally substituted with one or more substituents, wherein each substituent is, independently, amino, hydroxyl, aminoalkyl, hydroxylalkyl, or alkyl;

each pNPL is, independently, an integer from 0 to 8;

q1NPL and q2NPL are each, independently, 0, 1, or 2;

each PL group is, independently, halo, hydroxyethoxymethyl, methoxyethoxymethyl, polyoxyethylene, or —$(NR^{5'})_{q1PL}$—$U^{PL}$-$LK^{PL}$-$(NR^{5''})_{q2PL}$—V, wherein:

$R^5$, $R^{5'}$, and $R^{5''}$ are each, independently, hydrogen, alkyl, or alkoxy;

each $U^{PL}$ is, independently, absent or O, S, S(═O), S(═O)$_2$, NR$^5$, —C(═O)—, —C(═O)—NR$^5$—, —C(═O)—N═N—NR$^5$—, —C(═O)—NR$^5$—N═N—, —N═N—NR$^5$—, —C(═N—N(R$^5$)$_2$)—, —C(═NR$^5$)—, —C(═O)O—, —C(═O)S—, —C(═S)—, —O—P(═O)$_2$O—, —S—C═N—, or —C(═O)—NR$^5$—O—, wherein groups with two chemically nonequivalent termini can adopt either of the two possible orientations;

each $R^c$ is, independently, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, $C_{1-6}$ alkyl, $C_{1-6}$ haloalkyl, aryl, arylalkyl, heteroaryl, heteroarylalkyl, cycloalkyl, or heterocycloalkyl;

$R^d$ and $R^e$ are, independently, H, $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl is optionally substituted by OH, amino, halo, $C_{1-6}$ alkyl, $C_{1-6}$haloalkyl, $C_{1-6}$haloalkyl, aryl, arylalkyl, heteroaryl, heteroarylalkyl, cycloalkyl or heterocycloalkyl;

or $R^d$ and $R^e$ together with the N atom to which they are attached form a 4-, 5-, 6-, 7-, or 8-membered heterocycloalkyl;

each $LK^{PL}$ is, independently, —$(CH_2)_{pPL}$— or $C_{2-8}$ alkenylenyl, wherein each of the —$(CH_2)_{pNPL}$— and $C_{2-8}$ alkenylenyl is optionally substituted with one or more substituents, wherein each substituent is, independently, amino, hydroxyl, aminoalkyl, hydroxylalkyl, or alkyl;

each pPL is, independently, an integer from 0 to 8;

q1PL and q2PL are each, independently, 0, 1, or 2;

m13 is an integer from 1 to about 10; and m14 is an integer from 1 to about 10.

In some embodiments, each moiety of ┤X-$A_1$-Y—X-$A_2$-Y├ is, independently, a moiety of:

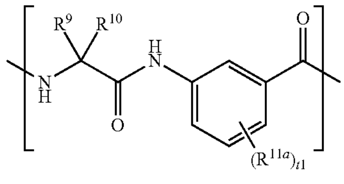

;

each $R^9$ is, independently, H, a PL group, or an NPL group; each $R^{10}$ is, independently, H, a PL group, or an NPL group; each $R^{11a}$ is, independently, a PL group or an NPL group; and each t1 is independently 0, 1, or 2.

In some embodiments, each $R^9$ is, independently, a PL group or an NPL group; and each $R^{10}$ is H. In some embodiments, each $R^9$ is, independently, alkyl or $(CH_2)_{pPL}$—V wherein pPL is an integer from 1 to 5; each $R^{10}$ is H; and each $R^{11a}$ is, independently, halo, alkyl, alkoxy, haloalkyl, haloalkoxy, —$(CH_2)_{pPL}$—V, —$O(CH_2)_{pPL}$—V, or —$S(CH_2)_{pPL}$—V, wherein pPL is an integer from 1 to 5.

In some embodiments, each $R^9$ is, independently, alkyl, —$(CH_2)$—V, —$(CH_2)_2$—V, —$(CH_2)_3$—V, —$(CH_2)_4$—V, or —$(CH_2)_5$—V; each $R^{10}$ is H; each V is, independently, hydroxyl, amino, heteroarylamino, ureido, guanidino, carbamoyl, C(═O)OH, —C(═O)OR$^c$, —C(═O)NH—OH, —O—NH—C(═NH)NH$_2$, —NH—S(═O)$_2$OH, S(═O)$_2$OH, aziridinyl, azetidinyl, pyrrolidinyl, piperidinyl, piperazinyl, morpholino, azepanyl, azocanyl, tetrazolyl, 1,2,4-oxadiazolyl, 1,3,4-oxadiazolyl, imidazolyl, pyridinyl, indolyl, or a substituted phenyl, wherein the substituted phenyl is substituted with one or more substituents, wherein each substituent is, independently, OH or amino; and each $R^{11a}$ is, independently, alkoxy.

In some embodiments, each $R^9$ is, independently, $CH_3$, —$(CH_2)$—V, —$(CH_2)_2$—V, —$(CH_2)_3$—V, —$(CH_2)_4$—V, or —$(CH_2)_5$—V; each $R^{10}$ is H; each V is, independently, amino, alkylamino, dialkylamino, —$NH(CH_2)_pNH_2$ wherein p is 1 to 5, —$N(CH_2CH_2NH_2)_2$, guanidino, amidino, ureido, or indolyl; and each $R^{11a}$ is, independently, alkoxy.

In some embodiments, each $R^9$ is, independently, $CH_3$, —$(CH_2)$—V, —$(CH_2)_2$—V, —$(CH_2)_3$—V, —$(CH_2)_4$—V, or —$(CH_2)_5$—V; each $R^{10}$ is H; each V is, independently, amino, alkylamino, dialkylamino, —$NH(CH_2)_pNH_2$ wherein p is 1 to 5, —$N(CH_2CH_2NH_2)_2$, guanidino, amidino, ureido, or indolyl; and each $R^{11a}$ is methoxy.

In some embodiments, each moiety of ┤X-$A_1$-Y—X-$A_2$-Y├ is, independently, a moiety of:

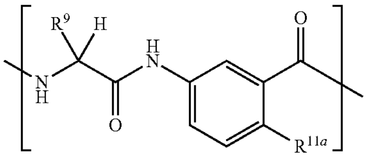

.

In some embodiments, the moiety of —X-$L^1$-Y— is a moiety of —NH-$L^1$-C(═O)—; $R^1$ is H or alkyl; $R^2$ is $NH_2$, amidino, alkylamino, dialkylamino, —$NH(CH_2)_pNH_2$ wherein p is 1 to 5, or —NH—$(CH_2)_{pPL}$—$V^{10}$, wherein $V^{10}$ is amino, alkylamino, dialkylamino, —$NH(CH_2)_pNH_2$ wherein p is 1 to 5, —$N(CH_2CH_2NH_2)_2$, guanidino, amidino, ureido, or carbamoyl; and $L^1$ is $C_{1-3}$alkylene optionally substituted with one or more substitutents, wherein each substituent is, independently, alkyl, halo, haloalkyl, aminoalkyl, hydroxylalkyl, $V^{11}$, or —$(CH_2)_{pPL}$—$V^{11}$ wherein pPL is an integer from 1 to 5, wherein each $V^{11}$ is, independently, amino, alkylamino, dialkylamino, —$NH(CH_2)_pNH_2$ wherein p is 1 to 5, —$N(CH_2CH_2NH_2)_2$, guanidino, amidino, ureido, or carbamoyl.

In some embodiments, the moiety of —X-$L^1$-Y— is a moiety of —NH-$L^1$-C(═O)—; $R^1$ is H; $R^2$ is $NH_2$; and $L^1$ is $C_1$alkylene optionally substituted with one or more substitutents, wherein each substituent is, independently, alkyl, halo, haloalkyl, aminoalkyl, hydroxylalkyl, $V^{11}$, or $-(CH_2)_{pPL}-V^{11}$ wherein pPL is an integer from 1 to 5, wherein $V^{11}$ is amino, alkylamino, dialkylamino, $-NH(CH_2)_pNH_2$ wherein p is 1 to 5, $-N(CH_2CH_2NH_2)_2$, guanidino, amidino, ureido, or carbamoyl.

In some embodiments, m13 is an integer from 1 to about 5; and m14 is an integer from 1 to about 5. In some embodiments, m13 is an integer from 1 to 3; and m12 is an integer from 1 to 3. In some embodiments, the sum of m13 and m14 is an integer from 3 to 5. In some embodiments, the sum of m13 and m14 is 4.

The present invention also provides methods of treating and/or preventing mucositis in a mammal comprising administering to the mammal in need thereof a therapeutically effective amount of a compound of Formula XXII:

$$R^1-[-X-A_1-X-Z-Y-A_2-Y-Z]_m-R^2 \quad \text{XXII}$$

or a pharmaceutically acceptable salt thereof,
wherein:

X is $NR^8$, $-NR^8NR^8-$, C=O, or O;

Y is $NR^8$, $-NR^8NR^8-$, C=O, S, or O;

$R^8$ is hydrogen or alkyl;

Z is C=O, C=S, O=S=O, $-NR^8NR^8-$, or $-C(=O)C(=O)-$;

$A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s);

$R^1$ is (i) hydrogen, a polar group (PL), or a non-polar group (NPL), and $R^2$ is $-X-A_1-X-R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and $R^2$ is $-X-A_1-X-Z-Y-A_2-Y-R^1$, wherein $A_1$ and $A_2$ are as defined above, and each of which is optionally substituted with one or more polar (PL) group(s), one or more non-polar (NPL) group(s), or a combination of one or more polar (PL) group(s) and one or more non-polar (NPL) group(s); or (iii) hydrogen, a polar group (PL), or a non-polar group (NPL), and $R^2$ is $-X-A'-X-R^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or (iv) hydrogen, a polar group (PL), or a non-polar group (NPL), and $R^2$ is $-X-A_1-X-Z-Y-A'-Y-R^1$, wherein $A_1$ is as defined above, A' is aryl or heteroaryl, and each of $A_1$ and A' is optionally substituted with one or more polar (PL) group(s), one or more non-polar (NPL) group(s), or a combination of one or more polar (PL) group(s) and one or more non-polar (NPL) group(s); or (v) $-Z-Y-A'$ and $R^2$ is hydrogen, a polar group (PL), or a non-polar group (NPL), wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or (vi) $-Z-Y-A'$, and $R^2$ is $-X-A''$, wherein A' and A'' are, independently, aryl or heteroaryl, and each of A' and A'' is optionally substituted with one or more polar (PL) group(s), one or more non-polar (NPL) group(s), or a combination of one or more polar (PL) group(s) and one or more non-polar (NPL) group(s); or (vii) $R^1$ and $R^2$ are, independently, a polar group (PL) or a non-polar group (NPL); or (viii) $R^1$ and $R^2$ together form a single bond;

NPL is a nonpolar group independently selected from $-B(OR^4)_2$ and $-(NR^{3'})_{q1NPL}-U^{NPL}-(CH_2)_{pNPL}-(NR^{3''})_{q2NPL}-R^{4'}$, wherein:

$R^3$, $R^{3'}$, and $R^{3''}$ independently, selected from hydrogen, alkyl, and alkoxy;

$R^4$ and $R^{4'}$ are, independently, selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(=O), $S(=O)_2$, $NR^3$, $-C(=O)-$, $-C(=O)-N=N-NR^3-$, $-C(=O)-NR^3-N=N-$, $-N=N-NR^3-$, $-C(=N-N(R^3)_2)-$, $-C(=NR^3)-$, $-C(=O)O-$, $-C(=O)S-$, $-C(=S)-$, $-O-P(=O)_2O-$, $-R^3O-$, $-R^3S-$, $-S-C=N-$, and $-C(=O)-NR^3-O-$, wherein groups with two chemically nonequivalent termini can adopt both possible orientations;

the $-(CH_2)_{pNPL}-$ alkylene chain is optionally substituted with one or more amino or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and $-(NR^5)_{q1PL}-U^{PL}-(CH_2)_{pPL}-(NR^{5'})_{q2PL}-V$, wherein:

$R^5$, $R^{5'}$, and $R^{5''}$ are, independently, selected from hydrogen, alkyl, and alkoxy;

$U^{PL}$ is absent or selected from O, S, S(=O), $S(=O)_2$, $NR^5$, $-C(=O)-$, $-C(=O)-N=N-NR^5-$, $-C(=O)-NR^5-N=N-$, $-N=N-NR^5-$, $-C(=N-N(R^5)_2)-$, $-C(=NR^5)-$, $-C(=O)O-$, $-C(=O)S-$, $-C(=S)-$, $-O-P(=O)_2O-$, $-R^5O-$, $-R^5S-$, $-S-C=N-$, and $-C(=O)-NR^5-O-$, wherein groups with two chemically nonequivalent termini can adopt both possible orientations;

V is selected from nitro, cyano, amino, hydroxy, alkoxy, alkylthio, alkylamino, dialkylamino, $-NH(CH_2)_pNH_2$ wherein p is 1 to 4, $-N(CH_2CH_2NH_2)_2$, diazamino, amidino, guanidino, guanyl, semicarbazone, aryl, heterocycle, and heteroaryl, any of which is optionally substituted with one or more of amino, halo, cyano, nitro, hydroxy, $-NH(CH_2)_pNH_2$ wherein p is 1 to 4, $-N(CH_2CH_2NH_2)_2$, amidino, guanidino, guanyl, aminosulfonyl, aminoalkoxy, aminoalkythio, lower acylamino, or benzyloxycarbonyl;

the $-(CH_2)_{pPL}-$ alkylene chain is optionally substituted with one or more amino or hydroxy groups, or is unsaturated;

pPL is 0 to 8;

q1PL and q2PL are, independently, 0, 1, or 2; and m is 1 to about 20.

In some embodiments, the compound is a compound of Formula XXIIa, Formula XXIIb, or Formula XXIIc:

$$R^1-X-A_1-X-Z-Y-A_2-Y-R^2 \quad \text{XXIIa}$$

$$R^1-X-A_1-X-Z-Y-A_2-Y-Z-X-A_1-X-R^2 \quad \text{XXIIb}$$

$$R^1-X-A_1-X-Z-Y-A_2-Y-Z-X-A_1-X-Z-Y-A_2-Y-R^2 \quad \text{XXIIc}$$

wherein: X is $NR^8$, $-NR^8NR^8-$, C=O, or O; Y is $NR^8$, $-NR^8NR^8-$, C=O, S, or O; $R^8$ is hydrogen or alkyl; Z is C═O, C═S, O═S═O, —$NR^8NR^8$—, or —C(═O)C(═O)—; $A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s); $R^1$ is hydrogen, a polar group (PL), or a non-polar group (NPL); $R^2$ is $R^1$; NPL is a nonpolar group —$(NR^{3'})_{q1NPL}$—$U^{NPL}$—$(CH_2)_{pNPL}$—$(NR^{3''})_{q2NPL}$—$R^{4'}$, wherein: $R^3$, $R^{3'}$, and $R^{3''}$ are, independently, selected from hydrogen, alkyl, and alkoxy; $R^4$ and $R^{4'}$ are, independently, selected from hydrogen, alkyl, alkenyl, alkynyl, cycloalkyl, aryl, and heteroaryl, any of which is optionally substituted with one or more alkyl or halo groups; $U^{NPL}$ is absent or selected from O, S, S(═O), $S(═O)_2$, $NR^3$, —C(═O)—, —C(═O)—N═N—$NR^3$—, —C(═O)—$NR^3$—N═N—, —N═N—$NR^3$—, —C(═N—$N(R^3)_2$)—, —C(═$NR^3$)—, —C(═O)O—, —C(═O)S—, —C(═S)—, —O—P(═O)$_2$O—, —$R^3$O—, —$R^3$S—, —S—C═N—, and —C(═O)—$NR^3$—O—, wherein groups with two chemically nonequivalent termini can adopt both possible orientations; the —$(CH_2)_{pNPL}$— alkylene chain is optionally substituted with one or more amino or hydroxy groups, or is unsaturated; pNPL is 0 to 8; q1NPL and q2NPL are, independently, 0, 1, or 2; PL is a polar group selected from halo, hydroxyethoxymethyl, methoxyethoxymethyl, polyoxyethylene, and —$(NR^{5'})_{q1PL}$—$U^{PL}$—$(CH_2)_{pPL}$—$(NR^{5'})_{q2PL}$—V, wherein: $R^5$, $R^{5'}$ and $R^{5''}$ are, independently, selected from hydrogen, alkyl, and alkoxy; $U^{PL}$ is absent or selected from O, S, S(═O), $S(═O)_2$, $NR^5$, —C(═O)—, —C(═O)—N═N—$NR^5$—, —C(═O)—$NR^5$—N═N—, —N═N—$NR^5$—, —C(═N—$N(R^5)_2$)—, —C(═$NR^5$)—, —C(═O)O—, —C(═O)S—, —C(═S)—, —O—P(═O)$_2$O—, —$R^5$O—, —$R^5$S—, —S—C═N—, and —C(═O)—$NR^5$—O—, wherein groups with two chemically nonequivalent termini can adopt both possible orientations; V is selected from nitro, cyano, amino, hydroxy, alkoxy, alkylthio, alkylamino, dialkylamino, —$NH(CH_2)_pNH_2$ wherein p is 1 to 4, —$N(CH_2CH_2NH_2)_2$, diazamino, amidino, guanidino, guanyl, semicarbazone, aryl, heterocycle, and heteroaryl, any of which is optionally substituted with one or more of amino, halo, cyano, nitro, hydroxy, —$NH(CH_2)_pNH_2$ wherein p is 1 to 4, —$N(CH_2CH_2NH_2)_2$, amidino, guanidino, guanyl, aminosulfonyl, aminoalkoxy, aminoalkythio, lower acylamino, or benzyloxycarbonyl; the —$(CH_2)_{pPL}$— alkylene chain is optionally substituted with one or more amino or hydroxy groups, or is unsaturated; pPL is 0 to 8; and q1PL and q2PL are, independently, 0, 1, or 2.

The present invention also provides methods of treating and/or preventing mucositis in a mammal comprising administering to the mammal in need thereof a therapeutically effective amount of a compound of Formula XXIII:

$$R^1—[-A_1\text{-}W\text{-}A_2\text{-}W—]_m—R^2 \qquad \text{XXIII}$$

or a pharmaceutically acceptable salt thereof, wherein:

$A_1$ and $A_2$ are, independently, optionally substituted arylene or optionally substituted heteroarylene, wherein:

(i) $A_1$ and $A_2$ are, independently, optionally substituted with one or more polar (PL) group(s), one or more non-polar (NPL) group(s), or a combination of one or more polar (PL) group(s) and one or more non-polar (NPL) group(s); or (ii) one of $A_1$ or $A_2$ is as defined above and is optionally substituted with one or more polar (PL) group(s), one or more non-polar (NPL) group(s), or a combination of one or more polar (PL) group(s) and one or more non-polar (NPL) group(s); and the other of $A_1$ or $A_2$ is the group —C≡C$(CH_2)_p$C≡C—, wherein p is 0 to 8, and the —$(CH_2)_p$— alkylene chain is optionally substituted with one or more amino or hydroxyl groups;

W is absent, or represents —$CH_2$—, —$CH_2$—$CH_2$—, —CH═CH—, or —C≡C—;

$R^1$ is (i) hydrogen, a polar group (PL), or a non-polar group (NPL), and $R^2$ is -$A_1$-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and $R^2$ is -$A_1$-W-$A_2$-$R^1$, wherein each of $A_1$ and $A_2$ is as defined above and is optionally substituted with one or more polar (PL) group(s), one or more non-polar (NPL) group(s), or a combination of one or more polar (PL) group(s) and one or more non-polar (NPL) group(s); or (iii) A'-W— and $R^2$ is -$A_1$-W-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s); or (iv) A'-W— and $R^2$ is -A', wherein A' is aryl or heteroaryl, either of which is optionally substituted with one or more polar (PL) group(s), one or more non-polar (NPL) groups(s), or a combination of one or more polar (PL) group(s) and one or more non-polar (NPL) group(s); or (iv) $R^1$ and $R^2$ together form a single bond;

NPL is a nonpolar group independently selected from —$B(OR^4)_2$ or —$(NR^{3'})_{q1NPL}$—$U^{NPL}$—$(CH_2)_{pNPL}$—$(NR^{3''})_{q2NPL}$—$R^4$, wherein:

$R^3$, $R^{3'}$, and $R^{3''}$ are, independently, selected from hydrogen, alkyl, and alkoxy;

$R^4$ is selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(═O), $S(═O)_2$, $NR^3$, —(C═O)—, —(C═O)—N═N—$NR^3$—, —(C═O)—$NR^3$—N═N—, —N═N—$NR^3$—, —C(═N—$N(R^3)_2$)—, —C(═$NR^3$)—, —C(═O)O—, —C(═O)S—, —C(═S)—, —O—P(═O)$_2$O—, —$R^3$O—, —$R^3$S—, —S—C═N— and —(C═O)—$NR^3$—O—, wherein groups with two chemically nonequivalent termini can adopt both possible orientations;

the —$(CH_2)_{pNPL}$— alkylene chain is optionally substituted with one or more alkyl, amino or hydroxyl groups, or the alkylene chain is unsaturated;

pNPL is 0 to 8;

q1NPL and q2NPL are, independently, 0 to 2;

PL is a polar group selected from halo, hydroxyethoxymethyl, methoxyethoxymethyl, polyoxyethylene, and —$(NR^5)_{q1PL}$—$U^{PL}$—$(CH_2)_{pPL}$—$(NR^{5'})_{q2PL}$—V, wherein:

$R^5$, $R^{5'}$, and $R^{5''}$ are, independently, selected from hydrogen, alkyl, and alkoxy;

$U^{PL}$ is absent or selected from O, S, S(═O), $S(═O)_2$, $NR^5$, —(C═O)—, —(C═O)—N═N—$NR^5$—, —(C═O)—$NR^5$—N═N—, —N═N—$NR^5$—, —C(═N—$N(R^5)_2$)—, —C(═$NR^5$)—, —C(═O)O—, —C(═O)S—, —C(═S)—, —O—P(═O)$_2$O—, —$R^5$O—, —$R^5$S—, —S—C═N—, and —(C═O)—$NR^5$—O—, wherein groups with two chemically nonequivalent termini can adopt both possible orientations;

V is selected from nitro, cyano, amino, hydroxyl, alkoxy, alkylthio, alkylamino, dialkylamino, —$NH(CH_2)_pNH_2$, —$N(CH_2CH_2NH_2)_2$, diazamino, amidino, guanidino, guanyl, semicarbazone, aryl, heterocycle, and heteroaryl, any of which is optionally substituted with one or more of amino, halo, cyano, nitro, hydroxyl, —$NH(CH_2)_pNH_2$, —$N(CH_2CH_2NH_2)_2$, amidino, guanidino, guanyl, aminosulfonyl, aminoalkoxy, aminoalkythio, lower acylamino, or benzyloxycarbonyl;

the —$(CH_2)_{pPL}$— alkylene chain is optionally substituted with one or more amino or hydroxyl groups, or the alkylene chain is unsaturated;

pPL is 0 to 8;

q1PL and q2PL are, independently, 0 to 2; and m is 1 to about 25.

In some embodiments, the compound of Formula XXIII is of Formula XXIIIa:

$R^1$-$A_1$-W-$A_2$-W-$A_1$-$R^2$ XXIIIa wherein:

$A_1$ and $A_2$ are, independently, optionally substituted arylene or optionally substituted heteroarylene, wherein:

(i) $A_1$ and $A_2$ are, independently, optionally substituted with one or more polar (PL) group(s), one or more non-polar (NPL) group(s), or a combination of one or more polar (PL) group(s) and one or more non-polar (NPL) group(s); or (ii) one of $A_1$ or $A_2$ is as defined above and is optionally substituted with one or more polar (PL) group(s), one or more non-polar (NPL) group(s), or a combination of one or more polar (PL) group(s) and one or more non-polar (NPL) group(s); and the other of $A_1$ or $A_2$ is the group —C≡C$(CH_2)_p$C≡C—, wherein p is 0 to 8, and the —$(CH_2)_p$— alkylene chain is optionally substituted with one or more amino or hydroxyl groups;

W is —C≡C—;

$R^1$ is hydrogen, a polar group (PL), a non-polar group (NPL), or —W-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s);

$R^2$ is $R^1$;

NPL is a nonpolar group —$(NR^{3'})_{q1NPL}$—$U^{NPL}$—$(CH_2)_{pNPL}$—$(NR^{3''})_{q2NPL}$—$R^4$;

$R^3$, $R^{3'}$, and $R^{3''}$ are, independently, selected from hydrogen, alkyl, and alkoxy;

$R^4$ is selected from hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(═O), S(═O)$_2$, $NR^3$, —(C═O)—, —(C═O)—N═N—$NR^3$—, —(C═O)—$NR^3$—N═N—, —N═N—$NR^3$—, —C(═N—$N(R^3)_2$)—, —C(═$NR^3$)—, —C(═O)O—, —C(═O)S—, —C(═S)—, —O—P(═O)$_2$O—, —$R^3$—O—, —$R^3$—S—, —S—C═N—, and —(C═O)—$NR^3$—O—, wherein groups with two chemically nonequivalent termini can adopt both possible orientations;

the alkylene chain —$(CH_2)_{pNPL}$— is optionally substituted with one or more alkyl, amino or hydroxyl groups, or the alkylene chain is unsaturated;

pNPL is 0 to 8;

q1NPL and q2NPL are, independently, 0 to 2;

PL is a polar group selected from halo, hydroxyethoxymethyl, methoxyethoxymethyl, polyoxyethylene, and —$(NR^{5'})_{q1PL}$—$U^{PL}$—$(CH_2)_{pPL}$—$(NR^{5'})_{q2PL}$—V, wherein:

$R^5$, $R^{5'}$, and $R^{5''}$ are, independently, selected from hydrogen, alkyl, and alkoxy;

$U^{PL}$ is absent or selected from O, S, S(═O), S(═O)$_2$, $NR^5$, —(C═O)—, —(C═O)—N═N—$NR^5$—, —(C═O)—$NR^5$—N═N—, —N═N—$NR^5$—, —C(═N—$N(R^5)_2$)—, —C(═$NR^5$)—, —C(═O)O—, —C(═O)S—, —C(═S)—, —O—P(═O)$_2$O—, —$R^5$O—, —$R^5$S—, —S—C═N—, and —(C═O)—$NR^5$—O—, wherein groups with two chemically nonequivalent termini can adopt both possible orientations;

V is selected from nitro, cyano, amino, hydroxyl, alkoxy, alkylthio, alkylamino, dialkylamino, —$NH(CH_2)_pNH_2$, —$N(CH_2CH_2NH_2)_2$, diazamino, amidino, guanidino, guanyl, semicarbazone, aryl, heterocycle, and heteroaryl, any of which is optionally substituted with one or more of amino, halo, cyano, nitro, hydroxyl, —$NH(CH_2)_pNH_2$, —$N(CH_2CH_2NH_2)_2$, amidino, guanidino, guanyl, aminosulfonyl, aminoalkoxy, aminoalkythio, lower acylamino, or benzyloxycarbonyl;

the alkylene chain —$(CH_2)_{pPL}$— is optionally substituted with one or more amino or hydroxyl groups, or the alkylene chain is unsaturated;

pPL is 0 to 8; and q1PL and q2PL are, independently, 0 to 2.

In some embodiments, $A_1$ and $A_2$ are, independently, optionally substituted m-phenylene, wherein $A_1$ is optionally substituted with two polar (PL) groups, and $A_2$ is unsubstituted; $R^1$ is a polar group; PL is independently halo or —$(NR^{5'})_{q1PL}$—$U^{PL}$—$(CH_2)_{pPL}$—$(NR^{5'})_{q2PL}$—V, wherein: $U^{PL}$ is absent or selected from O, S, $NR^5$, and —C(═O)—; V is selected from amino, amidino, and guanidino, any of which is optionally substituted with one or more of amino, halo, —$NH(CH_2)_pNH_2$ wherein p is 1 to 4, —$N(CH_2CH_2NH_2)_2$, amidino, guanidino, guanyl, aminosulfonyl, aminoalkoxy, aminoalkythio, and lower acylamino; pPL is 0 to 8; and q1PL and q2PL are 0.

In some embodiments, $R^1$ is halo; PL is or —$U^{PL}$—$(CH_2)_{pPL}$—V, wherein: $U^{PL}$ is absent; V is selected from amino, amidino, and guanidino, any of which is optionally substituted with one or more of amino and halo; and pPL is 0 to 6.

The present invention also provides methods of treating and/or preventing mucositis in a mammal comprising administering to the mammal in need thereof a therapeutically effective amount of a compound chosen from:

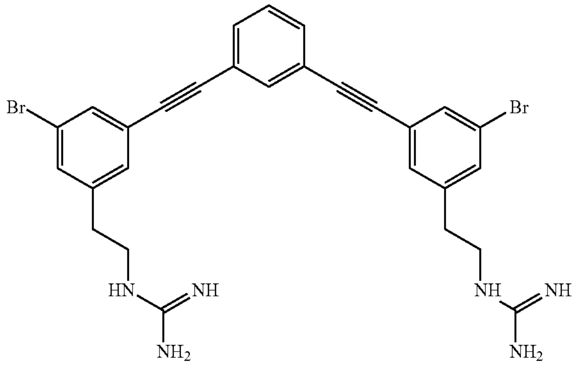

-continued

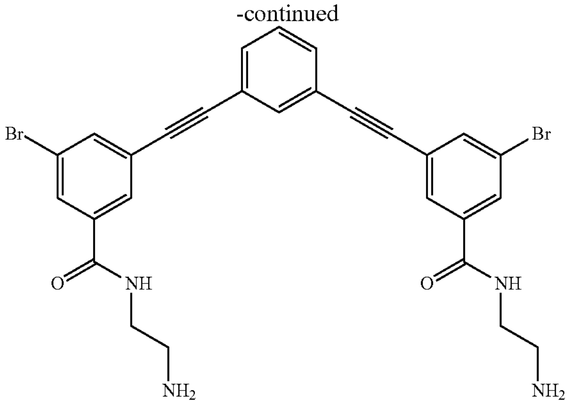

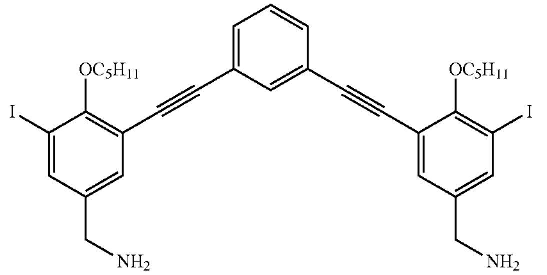

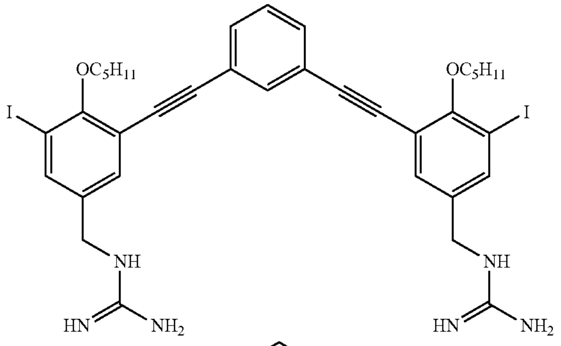

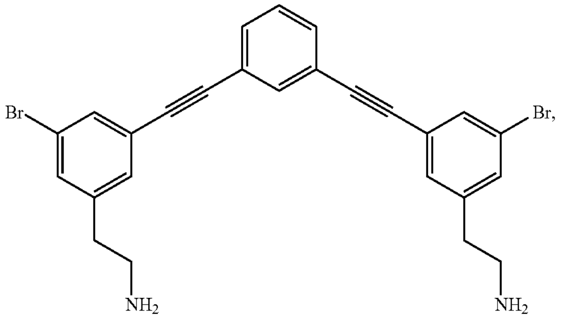

or

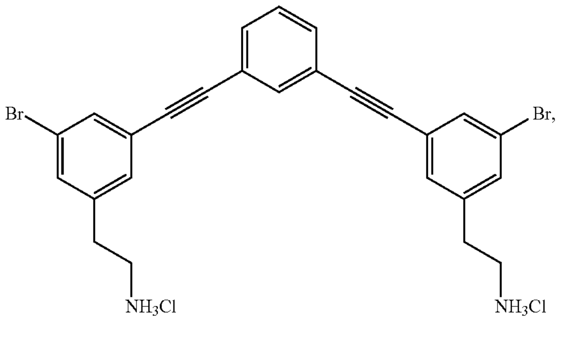

or a pharmaceutically acceptable salt thereof.

The present invention also provides methods of treating and/or preventing mucositis in a mammal comprising administering to the mammal in need thereof a therapeutically effective amount of a compound of Formula XXIV:

$$R^1—X\text{-}A_1\text{-}X—Y\text{-}A_2\text{-}Y—X\text{-}A_1\text{-}X—R^2 \qquad \text{XXIV}$$

or a pharmaceutically acceptable salt thereof, wherein:

X is $NR^8$, O, S, or $—N(R^8)N(R^8)—$;

Y is C═O, C═S, or O═S═O;

$R^8$ is hydrogen or alkyl;

$A_1$ and $A_2$ are, independently, optionally substituted arylene or optionally substituted heteroarylene, wherein $A_1$ and $A_2$ are, independently, optionally substituted with one or more polar (PL) group(s), one or more non-polar (NPL) group(s), or a combination of one or more polar (PL) group(s) and one or more non-polar (NPL) group(s);

$R^1$ is a polar group (PL) or a non-polar group (NPL);

$R^2$ is $R^1$;

NPL is a nonpolar group independently selected from $—B(OR^4)_2$ and $—(NR^{3'})_{q1NPL}—U^{NPL}—(CH_2)_{pNPL}—(NR^{3''})_{q2NPL}—R^{4'}$, wherein:

$R^3$, $R^{3'}$, and $R^{3''}$ independently, selected from hydrogen, alkyl, and alkoxy;

$R^4$ and $R^{4'}$ are, independently, selected from the group consisting of hydrogen, alkyl, alkenyl, alkynyl, cycloalkyl, aryl, and heteroaryl, any of which is optionally substituted with one or more alkyl or halo groups;

$U^{NPL}$ is absent or selected from O, S, S(═O), $S(═O)_2$, $NR^3$, —C(═O)—, $—C(═O)—N═N—NR^3—$, $—C(═O)—NR^3—N═N—$, $—N═N—NR^3—$, $—C(═N—N(R^3)_2)—$, $—C(═NR^3)—$, —C(═O)O—, —C(═O)S—, —C(═S)—, $—O—P(═O)_2O—$, $—R^3O—$, $—R^3S—$, —S—C═N—, and $—C(═O)—NR^3—O—$, wherein groups with two chemically nonequivalent termini can adopt both possible orientations;

the $—(CH_2)_{pNPL}—$ alkylene chain is optionally substituted with one or more amino or hydroxy groups, or is unsaturated;

pNPL is 0 to 8;

q1NPL and q2NPL are, independently, 0, 1, or 2;

PL is a polar group selected from halo, hydroxyethoxymethyl, methoxyethoxymethyl, polyoxyethylene, and $—(NR^{5'})_{q1PL}—U^{PL}—(CH_2)_{pPL}—(NR^{5'})_{q2PL}—V$, wherein:

$R^5$, $R^{5'}$, and $R^{5''}$ are, independently, selected from hydrogen, alkyl, and alkoxy;

$U^{PL}$ is absent or selected from O, S, S(═O), $S(═O)_2$, $NR^5$, —C(═O)—, $—C(═O)—N═N—NR^5—$, $—C(═O)—NR^5—N═N—$, $—N═N—NR^5—$, $—C(═N—N(R^5)_2)—$, $—C(═NR^5)—$, —C(═O)O—, —C(═O)S—, —C(═S)—, $—O—P(═O)_2O—$, $—R^5O—$, $—R^5S—$, —S—C═N—, and $—C(═O)—NR^5—O—$, wherein groups with two chemically nonequivalent termini can adopt both possible orientations;

V is selected from nitro, cyano, amino, hydroxy, alkoxy, alkylthio, alkylamino, dialkylamino, $—NH(CH_2)_pNH_2$ wherein p is 1 to 4, $—N(CH_2CH_2NH_2)_2$, diazamino, amidino, guanidino, guanyl, semicarbazone, aryl, heterocycle and heteroaryl, any of which is optionally substituted with one or more of amino, halo, cyano, nitro, hydroxy, $—NH(CH_2)_pNH_2$ wherein p is 1 to 4, $—N(CH_2CH_2NH_2)_2$, amidino, guanidino, guanyl, aminosulfonyl, aminoalkoxy, aminoalkythio, lower acylamino, or benzyloxycarbonyl;

the —$(CH_2)_{pPL}$— alkylene chain is optionally substituted with one or more amino or hydroxy groups, or is unsaturated;

pPL is 0 to 8; and q1PL and q2PL are, independently, 0, 1, or 2.

In some embodiments, $A_1$ is m-phenylene substituted with one (PL) group and one non-polar (NPL) group; $A_2$ is unsubstituted m-pyrimidinylene or m-pyrimidinylene substituted with one or two polar (PL) group(s); NPL is $R^{4'}$, wherein $R^{4'}$ is $(C_1\text{-}C_6)$alkyl optionally substituted with one or more halo groups; PL is —$U^{PL}$—$(CH_2)_{pPL}$—V, wherein: $U^{PL}$ is O or S; V is selected from amino, amidino, and guanidino; and pPL is 0 to 6.

In some embodiments, $A_1$ is m-phenylene substituted with one (PL) group and one non-polar (NPL) group; $A_2$ is unsubstituted m-phenylene or m-phenylene substituted with one or two polar (PL) group(s); NPL is $R^4$, wherein $R^4$ is $(C_1\text{-}C_6)$alkyl optionally substituted with one or more halo groups; PL is —$U^{PL}$—$(CH_2)_{pPL}$—V, wherein: $U^{PL}$ is O or S; V is selected from amino, amidino, and guanidino; and pPL is 0 to 6.

The present invention also provides methods of treating and/or preventing mucositis in a mammal comprising administering to the mammal in need thereof a therapeutically effective amount of a compound chosen from:

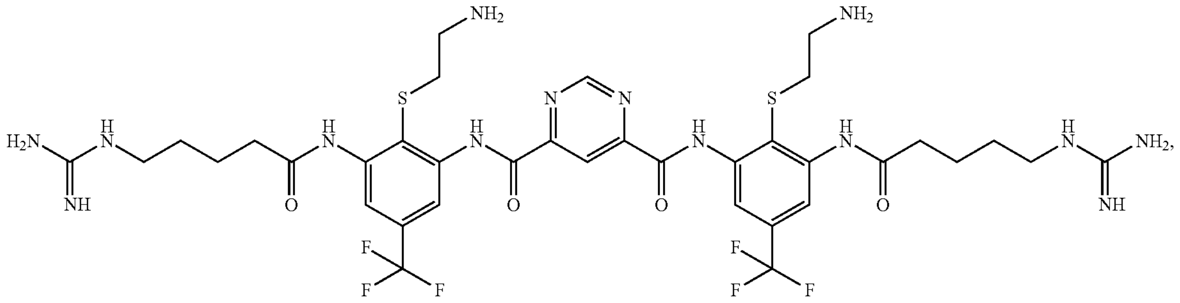

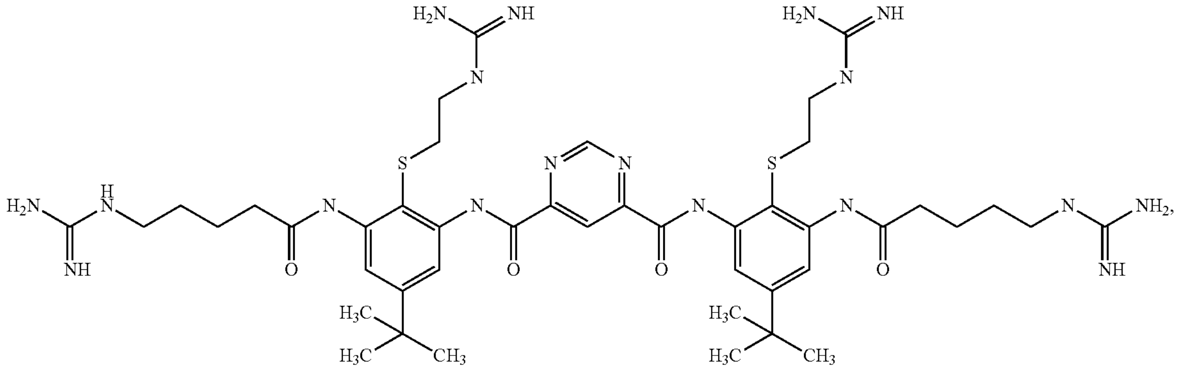

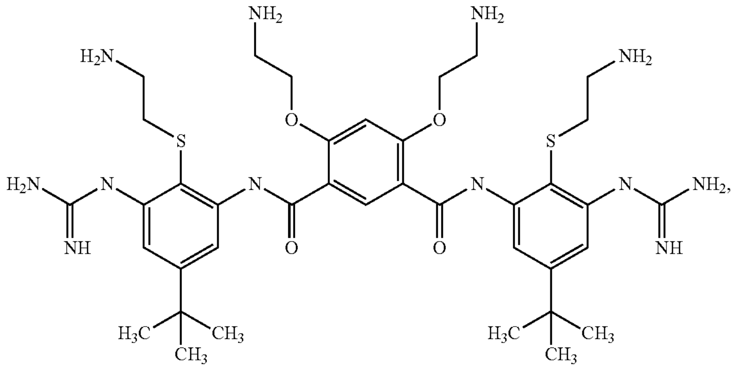

or

-continued

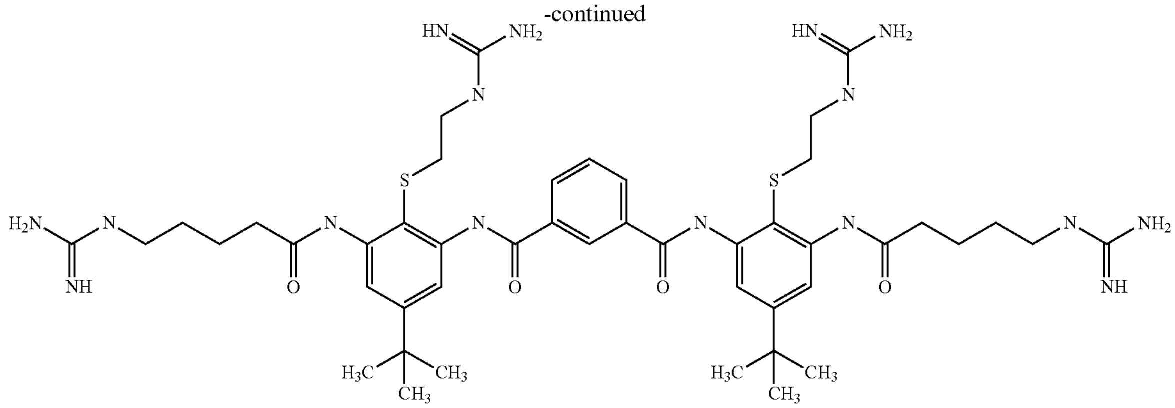

or a pharmaceutically acceptable salt thereof.

The present invention discloses compositions comprising any of the compounds described herein or any combination thereof. Polymers are generally defined as synthetic compounds assembled from monomer subunits that are polydisperse in molecular weight, and are most commonly prepared by one-pot synthetic procedures. The term "polymer" as used herein refers to a macromolecule comprising a plurality of repeating units or monomers. The term includes homopolymers, which are formed from a single type of monomer, and copolymers, which are formed from two or more different monomers. In copolymers, the monomers may be distributed randomly (random copolymer), in alternating fashion (alternating copolymers), or in blocks (block copolymer). The polymers of the present invention are either homopolymers or alternating copolymers having about 2 monomer units to about 500 monomer units, with average molecular weights that range from about 300 Daltons to about 1,000,000 Daltons, or from about 400 Daltons to about 120,000 Daltons. Preferred polymers are those having about 5 to about 100 monomer units, with average molecular weights that range from about 1,000 Daltons to about 25,000 Daltons.

The term "oligomer" as used herein refers to a homogenous polymer with a defined sequence and molecular weight. Modern methods of solid phase organic chemistry have allowed the synthesis of homodisperse, sequence-specific oligomers with molecular weights approaching 5,000 Daltons. An oligomer, in contrast to a polymer, has a defined sequence and molecular weight and is usually synthesized either by solid phase techniques or by step-wise solution chemistry and purified to homogeneity. Oligomers of the present invention are those having about 2 monomer units to about 25 monomer units, with molecular weights that range from about 300 Daltons to about 6,000 Daltons. Suitable oligomers are those having about 2 monomer units to about 10 monomer units, with molecular weights that range from about 300 Daltons to about 2,500 Daltons.

The present invention also provides methods of treating and/or preventing mucositis in a mammal comprising administering to the mammal in need thereof a therapeutically effective amount of a compound of Formula XXV:

$$A\text{-}(B)_{n1}\text{-}(D)_{m1}\text{-}H \qquad XXV$$

or a pharmaceutically acceptable salt thereof, wherein:

A is the residue of a chain transfer agent;

B is —[$CH_2$—$C(R^{11})(B_{11})$]—, wherein $B_{11}$ is —$X_{11}$—$Y_{11}$—$Z_{11}$, wherein $X_{11}$ is carbonyl (—C(═O)—) or optionally substituted $C_{1-6}$ alkylene; or $X_{11}$ is absent;

$Y_{11}$ is O, NH, or optionally substituted $C_{1-6}$ alkylene; or $Y_{11}$ is absent;

$Z_{11}$ is —$Z_{11A}$-$Z_{11B}$, wherein $Z_{11A}$ is alkylene, arylene, or heteroarylene, any of which is optionally substituted; or $Z_{11A}$ is absent; and $Z_{11B}$ is -guanidino, -amidino, —$N(R^3)(R^4)$, or —$N^+(R^3)(R^4)(R^5)$, wherein $R^3$, $R^4$, and $R^5$ are, independently, hydrogen, alkyl, aminoalkyl, aryl, heteroaryl, heterocyclic, or aralkyl; or $Z_{11}$ is pyridinium

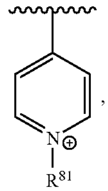

or phosphonium

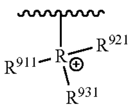

wherein $R^{81}$, $R^{911}$, $R^{921}$, and $R^{931}$ are, independently, hydrogen or alkyl;

$R^{11}$ is hydrogen or $C_{1-4}$ alkyl;

D is —[$CH_2$—$C(R^{21})(D_{21})$]-, wherein $D_{21}$ is —$X_{21}$—$Y_{21}$—$Z_{21}$, wherein $X_{21}$ is carbonyl (—C(═O)—) or optionally substituted $C_{1-6}$ alkylene; or $X_{21}$ is absent;

$Y_{21}$ is O, NH, or optionally substituted $C_{1-6}$ alkylene, or $Y_{21}$ is absent;

$Z_{21}$ is alkyl, cycloalkyl, alkoxy, aryl, or aralkyl, any of which is optionally substituted;

$R^{21}$ is hydrogen or $C_{1-4}$ alkyl;

$m_1$, the mole fraction of D, is about 0.1 to about 0.9; and $n_1$, the mole fraction of B, is 1-$m_1$;

wherein the compound is a random copolymer of B and D, and wherein the copolymer has a degree of polymerization of about 5 to about 50.

In some embodiments, A is $C_{1-4}$ alkoxycarbonyl($C_{1-4}$) alkylthio; $X_{11}$ and $X_{21}$ are carbonyl; $Y_{11}$ and $Y_{21}$ are O; $Z_{11}$ is —$Z_{11A}$—$Z_{11B}$, wherein $Z_{11A}$ is $C_{1-6}$ alkylene optionally substituted with $C_{1-4}$ alkyl or aryl; and $Z_{11B}$ is —$N(R^{31})$ ($R^{41}$) or —$N^+(R^{31})(R^{41})(R^{51})$, wherein $R^{31}$, $R^{41}$, and $R^{51}$ are independently hydrogen $C_{1-4}$ alkyl; $Z_{21}$ is $C_{1-6}$ alkyl, $C_{1-6}$ aryl, or $C_{1-6}$ ar($C_{1-4}$)alkyl; and $R^{11}$ and $R^{21}$ are, independently, hydrogen or methyl; $m_1$ is about 0.35 to about 0.60; and wherein the copolymer has a degree of polymerization of about 5 to about 10.

In some embodiments, the copolymer has a molecular weight from about 2,000 Daltons to about 15,000 Daltons. In some embodiments, the copolymer has a molecular weight from about 2,000 Daltons to about 3,000 Daltons. In some embodiments, the copolymer has a molecular weight from about 3,000 Daltons to about 4,000 Daltons. In some embodiments, the copolymer has a molecular weight from about 4000 Daltons to about 5,000 Daltons. In some embodiments, the copolymer has a molecular weight from about 5000 Daltons to about 6,000 Daltons. In some embodiments, the copolymer has a molecular weight from about 6,000 Daltons to about 7,000 Daltons. In some embodiments, the copolymer has a molecular weight from about 7,000 Daltons to about 8,000 Daltons. In some embodiments, the copolymer has a molecular weight from about 8,000 Daltons to about 9,000 Daltons. In some embodiments, the copolymer has a molecular weight from about 9,000 Daltons to about 10,000 Daltons. In some embodiments, the copolymer has a molecular weight from about 10,000 Daltons to about 11,000 Daltons. In some embodiments, the copolymer has a molecular weight from about 11,000 Daltons to about 12,000 Daltons.

In some embodiments, the copolymer is a polymethacrylate. In some embodiments, one of B and D is amino-ethyl methacrylate the other of B and D is butyl-methacrylate, ethyl-methacrylate, or methyl-methacrylate.

The present invention also provides methods of treating and/or preventing mucositis in a mammal comprising administering to the mammal in need thereof a therapeutically effective amount of a compound chosen from:

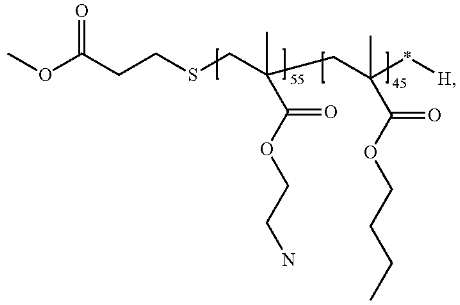

-continued

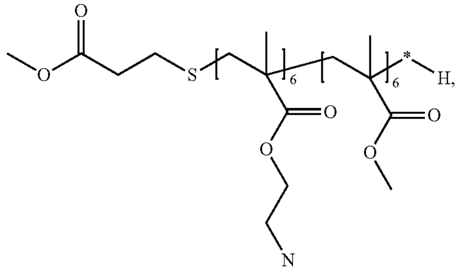

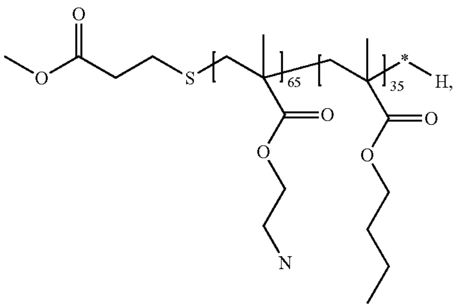

and

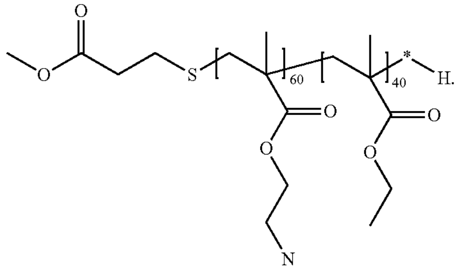

The present invention also provides methods of treating and/or preventing mucositis in a mammal comprising administering to the mammal in need thereof a therapeutically effective amount of a compound chosen from Table 1:

TABLE 1

| Compd. No. | Structure |
|---|---|
| 1 | 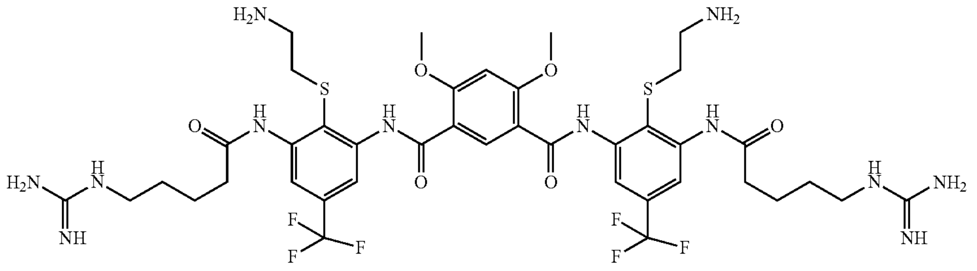 [SMILES: COc1cc(OC)c(C(=O)Nc2cc(C(F)(F)F)cc(NC(=O)CCCCNC(=N)N)c2SCCN)cc1C(=O)Nc1cc(C(F)(F)F)cc(NC(=O)CCCCNC(=N)N)c1SCCN] |

TABLE 1-continued
| Compd. No. | Structure |
|---|---|
| 2 | 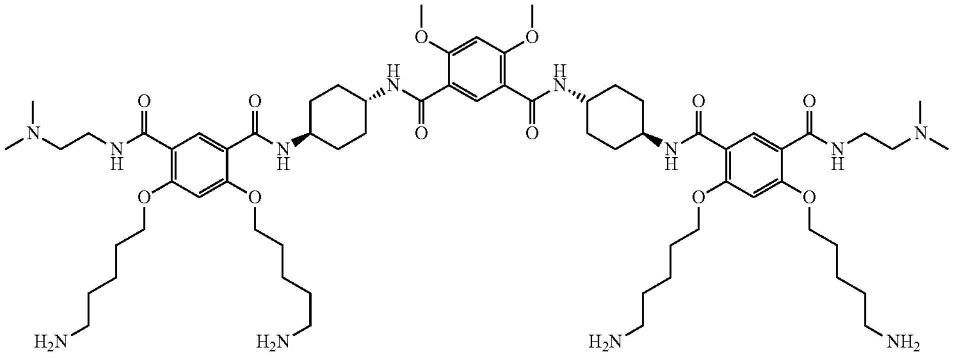 |
| 3 | 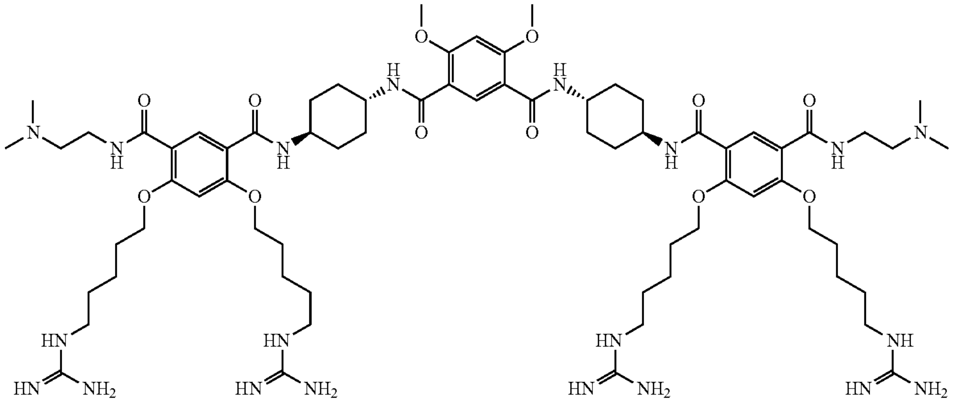 |
| 4 | 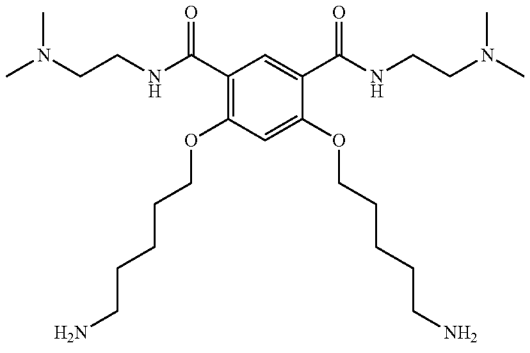 |

TABLE 1-continued
| Compd. No. | Structure |
|---|---|
| 5 | 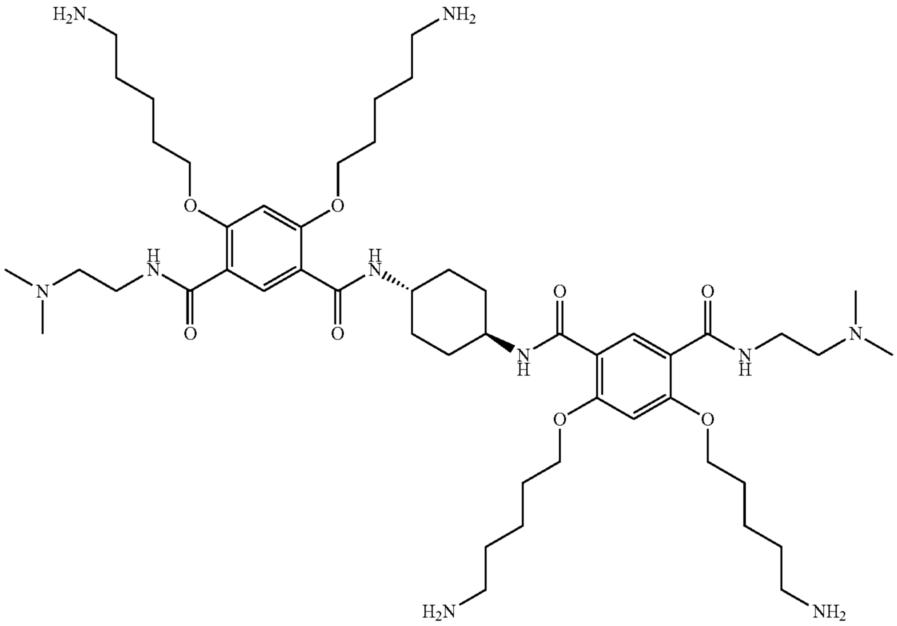 |
| 6 (Z) | 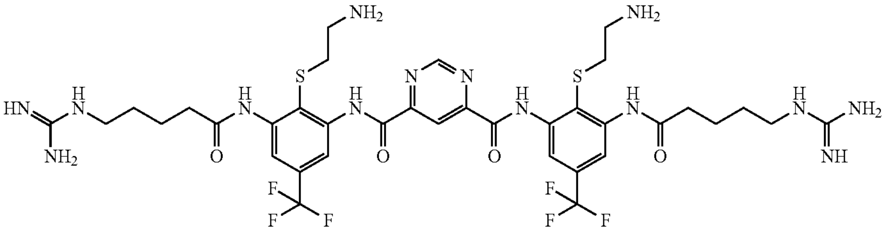 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3SCCN)ncn2)c1SCCN] |
| 7 | 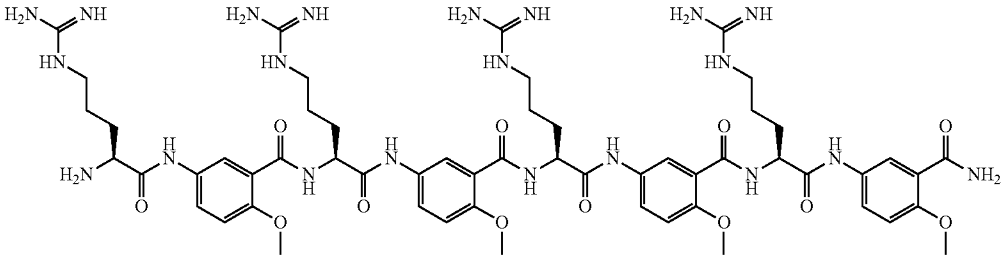 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OC)ccc2OC)cc1C(N)=O] |
| 8 | 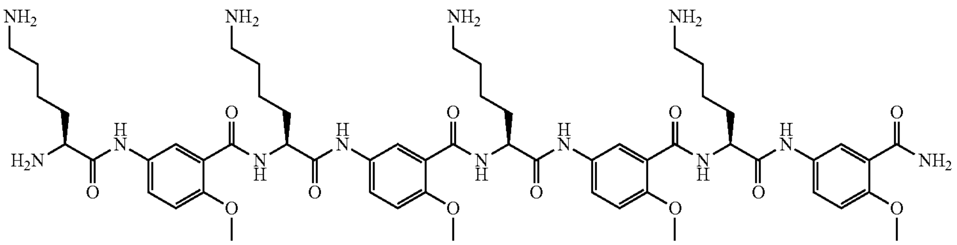 |

TABLE 1-continued
| Compd. No. | Structure |
|---|---|
| 9 | 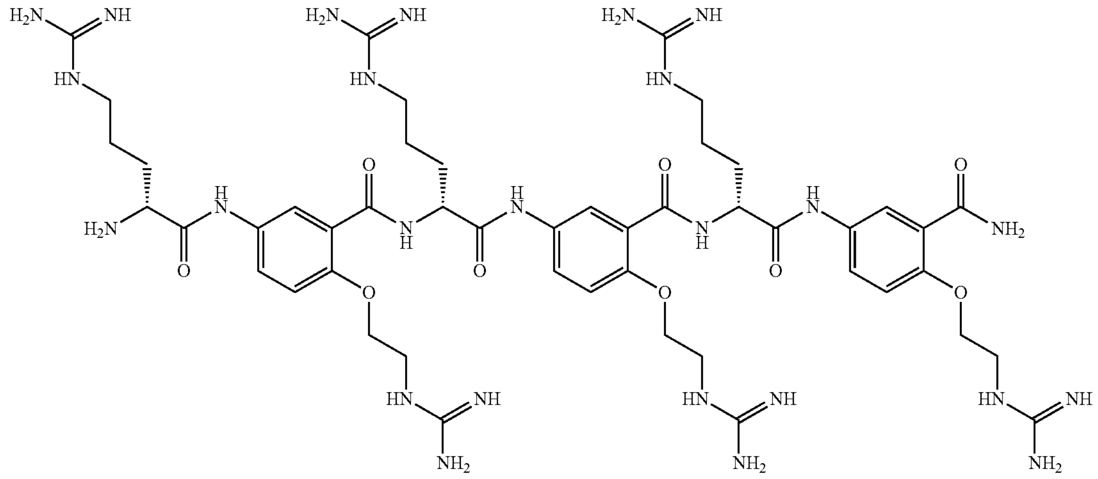 [SMILES: N=C(N)NCCC[C@@H](N)C(=O)Nc1ccc(OCCNC(=N)N)c(C(=O)N[C@H](CCCNC(=N)N)C(=O)Nc2ccc(OCCNC(=N)N)c(C(=O)N[C@H](CCCNC(=N)N)C(=O)Nc3ccc(OCCNC(=N)N)c(C(N)=O)c3)c2)c1] |
| 10 | 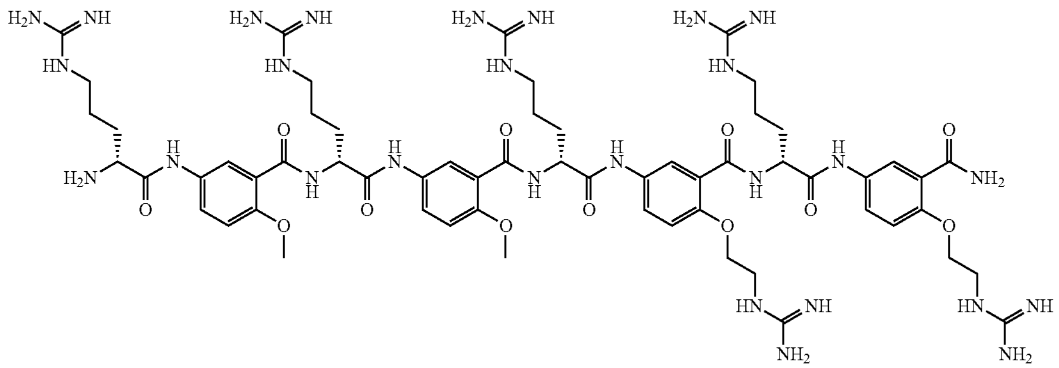 [SMILES: COc1ccc(NC(=O)[C@H](N)CCCNC(=N)N)cc1C(=O)N[C@H](CCCNC(=N)N)C(=O)Nc1ccc(OC)c(C(=O)N[C@H](CCCNC(=N)N)C(=O)Nc2ccc(OCCNC(=N)N)c(C(=O)N[C@H](CCCNC(=N)N)C(=O)Nc3ccc(OCCNC(=N)N)c(C(N)=O)c3)c2)c1] |
| 11 | 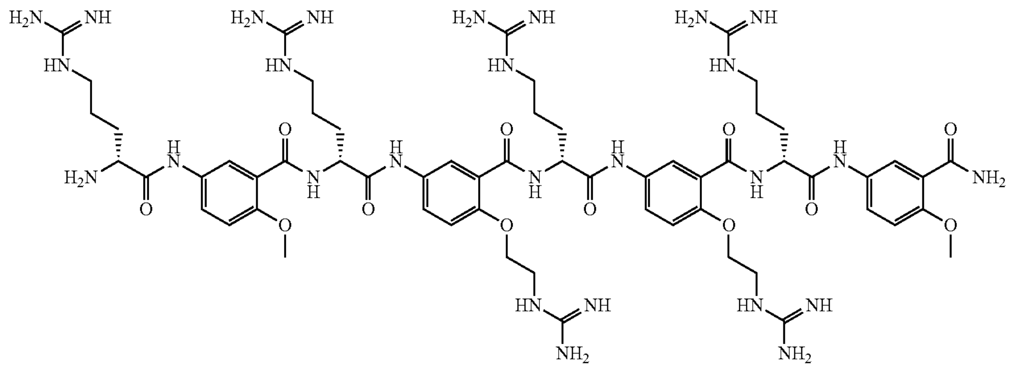 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OCCNC(=N)N)ccc2OCCNC(=N)N)cc1C(N)=O] |
| 12 | 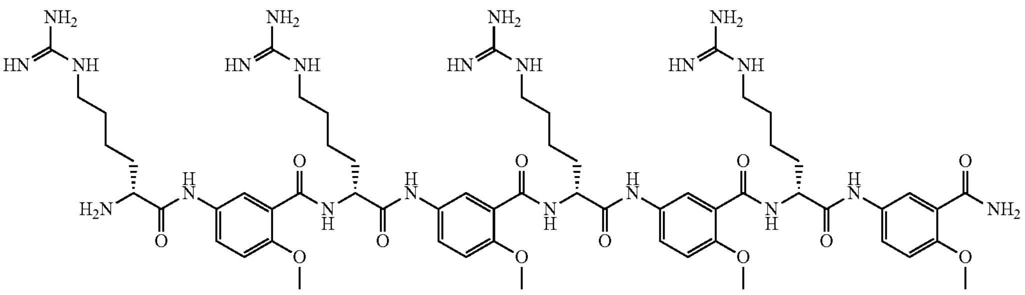 [SMILES: COc1ccc(NC(=O)[C@@H](CCCCNC(=N)N)NC(=O)c2cc(NC(=O)[C@@H](CCCCNC(=N)N)NC(=O)c3cc(NC(=O)[C@@H](CCCCNC(=N)N)NC(=O)c4cc(NC(=O)[C@H](N)CCCCNC(=N)N)ccc4OC)ccc3OC)ccc2OC)cc1C(N)=O] |

TABLE 1-continued
| Compd. No. | Structure |
|---|---|
| 13 | 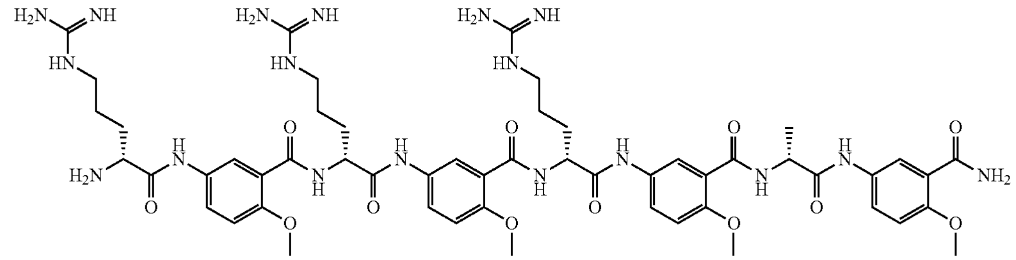 [SMILES: COc1ccc(NC(=O)[C@@H](C)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 14 | 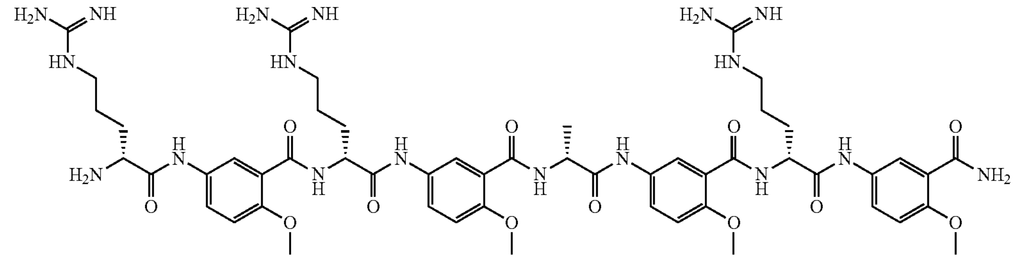 [SMILES: COc1ccc(NC(=O)[C@@H](CCCNC(=N)N)NC(=O)c2cc(NC(=O)[C@@H](C)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 15 | 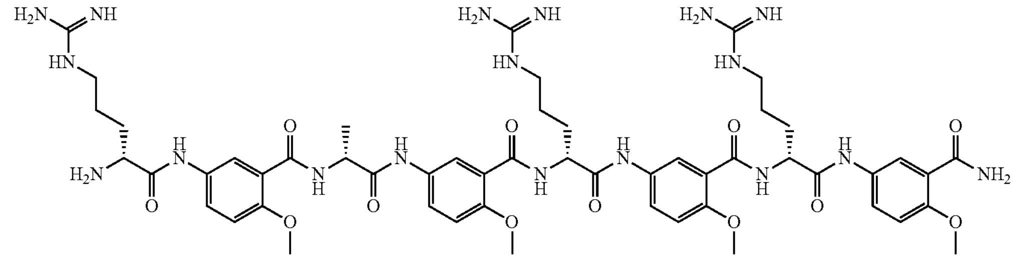 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](C)NC(=O)c4cc(NC(=O)[C@H](N)CCCNC(=N)N)ccc4OC)ccc3OC)ccc2OC)cc1C(N)=O] |
| 16 | 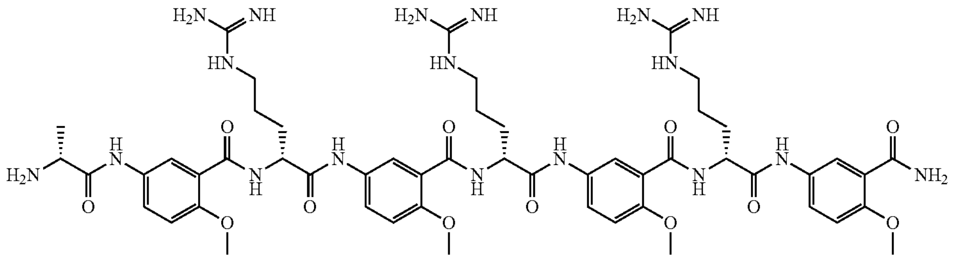 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)N)ccc4OC)ccc3OC)ccc2OC)cc1C(N)=O] |
| 17 | 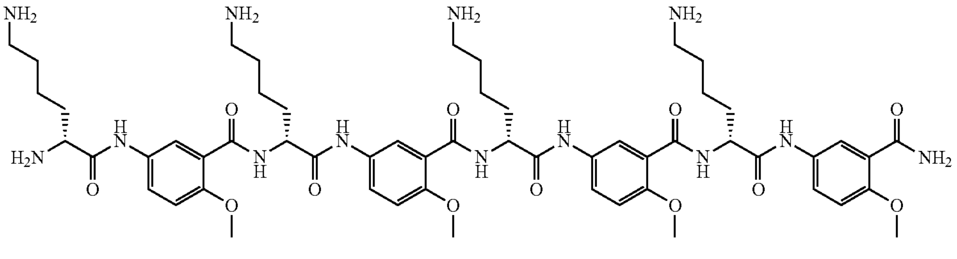 [SMILES: COc1ccc(NC(=O)[C@@H](CCCCN)NC(=O)c2cc(NC(=O)[C@@H](CCCCN)NC(=O)c3cc(NC(=O)[C@@H](CCCCN)NC(=O)c4cc(NC(=O)[C@H](N)CCCCN)ccc4OC)ccc3OC)ccc2OC)cc1C(N)=O] |

TABLE 1-continued
| Compd. No. | Structure |
|---|---|
| 18 | 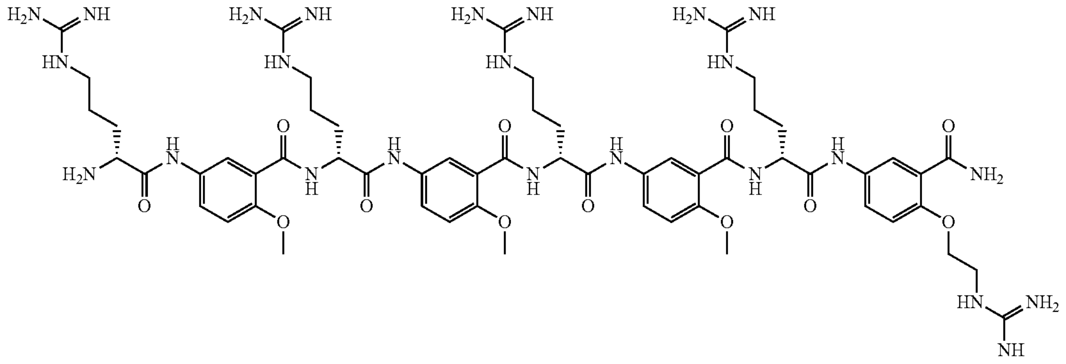 [SMILES: COc1ccc(NC(=O)[C@H](N)CCCNC(=N)N)cc1C(=O)N[C@H](CCCNC(=N)N)C(=O)Nc1ccc(OC)c(C(=O)N[C@H](CCCNC(=N)N)C(=O)Nc2ccc(OC)c(C(=O)N[C@H](CCCNC(=N)N)C(=O)Nc3ccc(OCCNC(=N)N)c(C(N)=O)c3)c2)c1] |
| 19 | 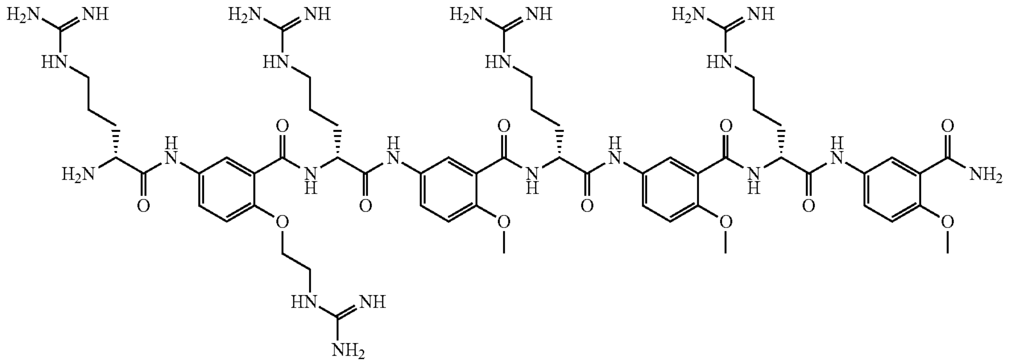 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OCCNC(=N)N)ccc3OC)ccc2OC)cc1C(N)=O] |
| 20 | 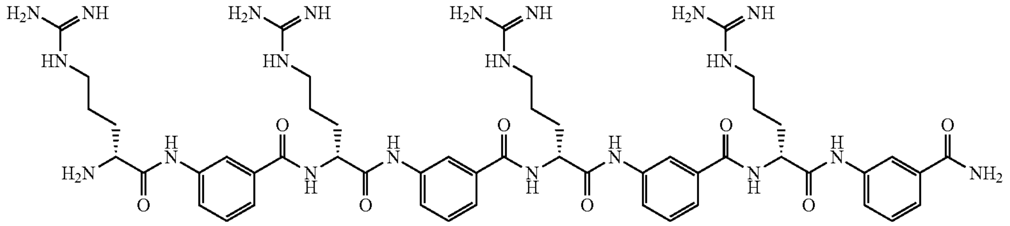 [SMILES: N=C(N)NCCC[C@@H](N)C(=O)Nc1cccc(C(=O)N[C@H](CCCNC(=N)N)C(=O)Nc2cccc(C(=O)N[C@H](CCCNC(=N)N)C(=O)Nc3cccc(C(=O)N[C@H](CCCNC(=N)N)C(=O)Nc4cccc(C(N)=O)c4)c3)c2)c1] |
| 21 | 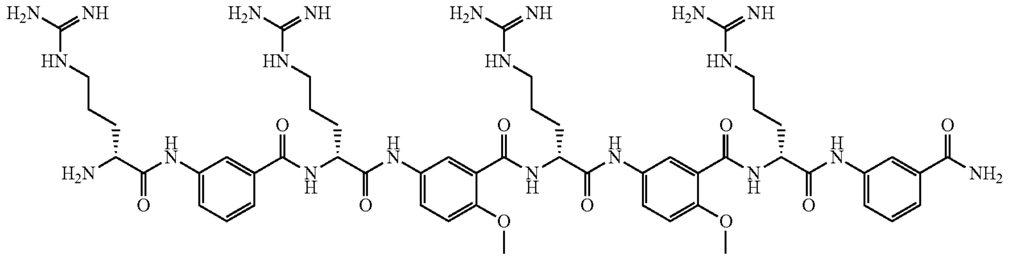 [SMILES: COc1ccc(NC(=O)[C@@H](CCCNC(=N)N)NC(=O)c2cccc(NC(=O)[C@H](N)CCCNC(=N)N)c2)cc1C(=O)N[C@H](CCCNC(=N)N)C(=O)Nc1ccc(OC)c(C(=O)N[C@H](CCCNC(=N)N)C(=O)Nc2cccc(C(N)=O)c2)c1] |
| 22 | 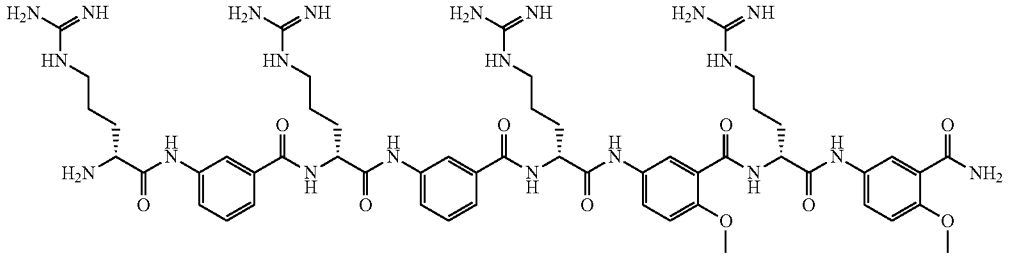 [SMILES: COc1ccc(NC(=O)[C@@H](CCCNC(=N)N)NC(=O)c2cc(NC(=O)[C@@H](CCCNC(=N)N)NC(=O)c3cccc(NC(=O)[C@@H](CCCNC(=N)N)NC(=O)c4cccc(NC(=O)[C@H](N)CCCNC(=N)N)c4)c3)ccc2OC)cc1C(N)=O] |

TABLE 1-continued
| Compd. No. | Structure |
| --- | --- |
| 23 | 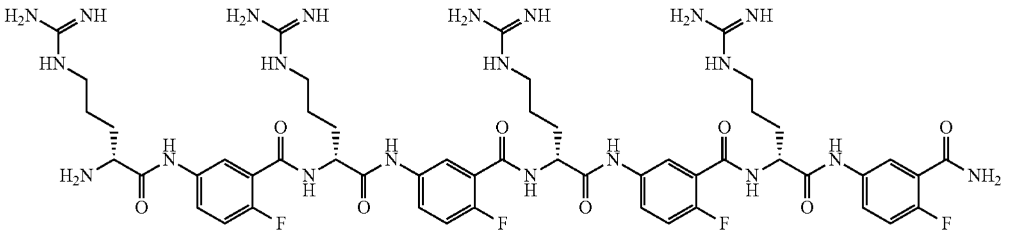 [SMILES: N=C(N)NCCC[C@@H](N)C(=O)Nc1ccc(F)c(C(=O)N[C@H](CCCNC(=N)N)C(=O)Nc2ccc(F)c(C(=O)N[C@H](CCCNC(=N)N)C(=O)Nc3ccc(F)c(C(=O)N[C@H](CCCNC(=N)N)C(=O)Nc4ccc(F)c(C(N)=O)c4)c3)c2)c1] |
| 24 | 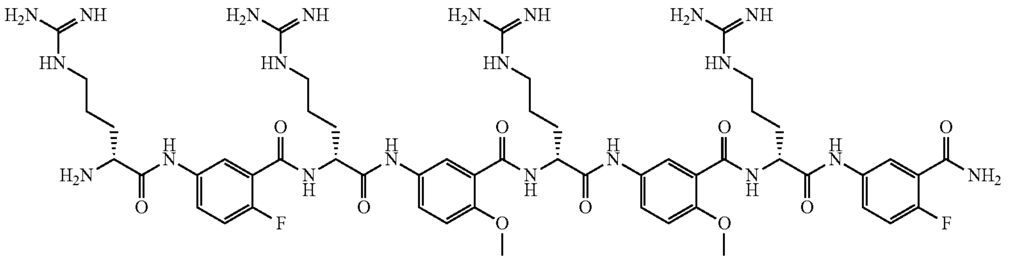 |
| 25 | 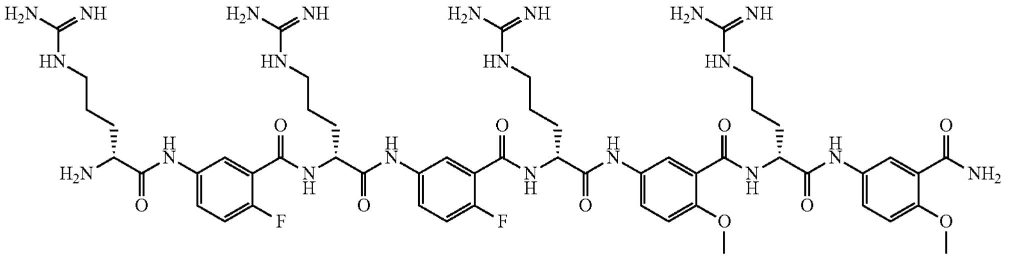 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4F)ccc3F)ccc2OC)cc1C(N)=O] |
| 26 | 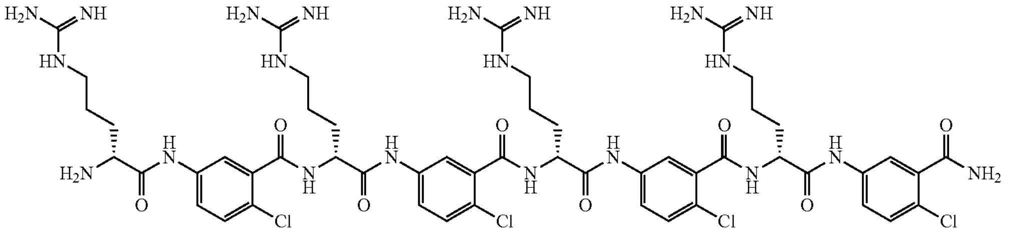 [SMILES: N=C(N)NCCC[C@@H](N)C(=O)Nc1ccc(Cl)c(C(=O)N[C@H](CCCNC(=N)N)C(=O)Nc2ccc(Cl)c(C(=O)N[C@H](CCCNC(=N)N)C(=O)Nc3ccc(Cl)c(C(=O)N[C@H](CCCNC(=N)N)C(=O)Nc4ccc(Cl)c(C(N)=O)c4)c3)c2)c1] |
| 27 | 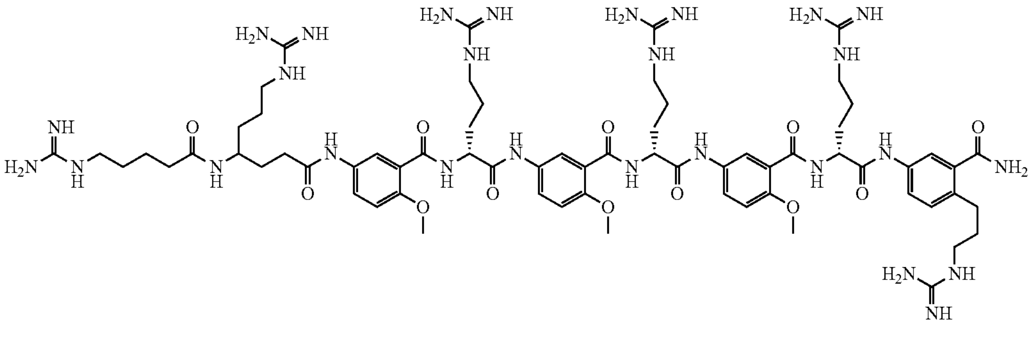 [SMILES: COc1ccc(NC(=O)CCC(CCCNC(=N)N)NC(=O)CCCCNC(=N)N)cc1C(=O)N[C@H](CCCNC(=N)N)C(=O)Nc1ccc(OC)c(C(=O)N[C@H](CCCNC(=N)N)C(=O)Nc2ccc(OC)c(C(=O)N[C@H](CCCNC(=N)N)C(=O)Nc3ccc(CCCNC(=N)N)c(C(N)=O)c3)c2)c1] |
| 28 | 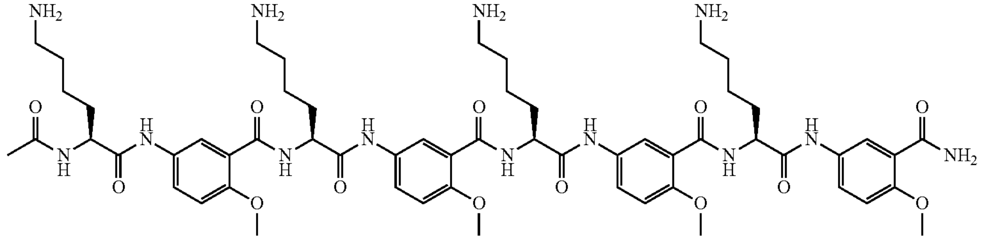 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(C)=O)ccc4OC)ccc3OC)ccc2OC)cc1C(N)=O] |

TABLE 1-continued
| Compd. No. | Structure |
|---|---|
| 29 | 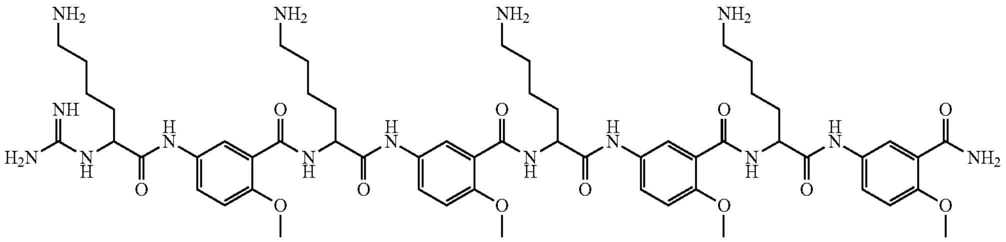 [SMILES: COc1ccc(NC(=O)C(CCCCN)NC(=O)c2cc(NC(=O)C(CCCCN)NC(=O)c3cc(NC(=O)C(CCCCN)NC(=O)c4cc(NC(=O)C(CCCCN)NC(=N)N)ccc4OC)ccc3OC)ccc2OC)cc1C(N)=O] |
| 30 | 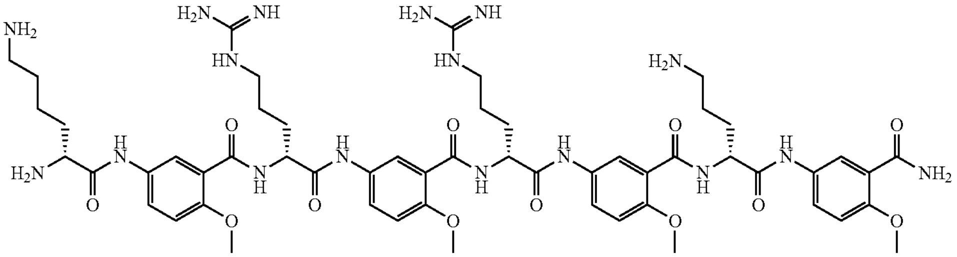 [SMILES: COc1ccc(NC(=O)[C@@H](CCCN)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCCN)ccc4OC)ccc3OC)ccc2OC)cc1C(N)=O] |
| 31 | 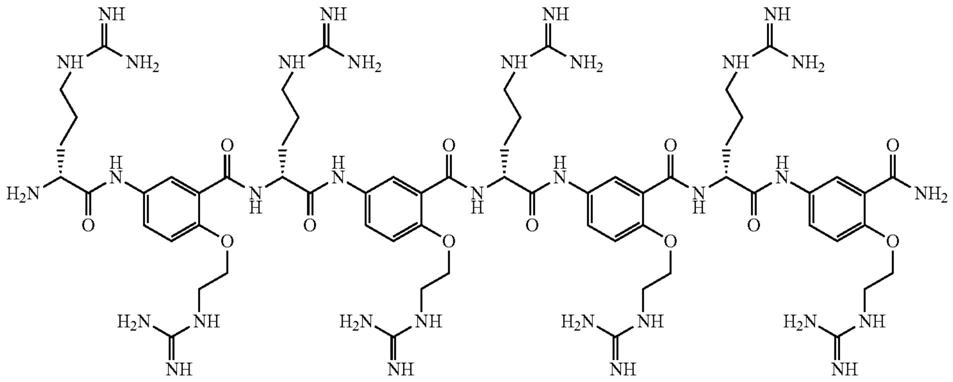 [SMILES: N=C(N)NCCC[C@@H](N)C(=O)Nc1ccc(OCCNC(=N)N)c(C(=O)N[C@H](CCCNC(=N)N)C(=O)Nc2ccc(OCCNC(=N)N)c(C(=O)N[C@H](CCCNC(=N)N)C(=O)Nc3ccc(OCCNC(=N)N)c(C(=O)N[C@H](CCCNC(=N)N)C(=O)Nc4ccc(OCCNC(=N)N)c(C(N)=O)c4)c3)c2)c1] |
| 32 | 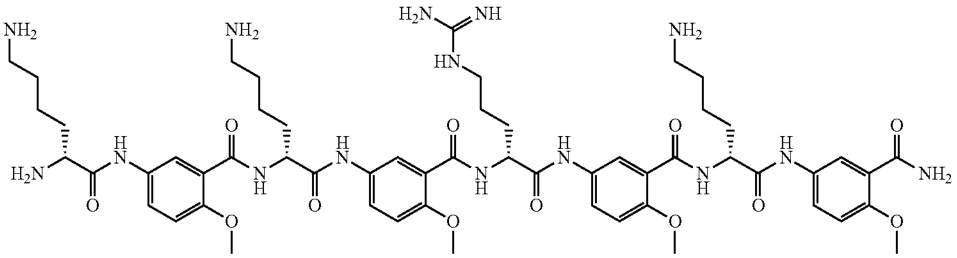 [SMILES: COc1ccc(NC(=O)[C@@H](CCCCN)NC(=O)c2cc(NC(=O)[C@@H](CCCNC(=N)N)NC(=O)c3cc(NC(=O)[C@@H](CCCCN)NC(=O)c4cc(NC(=O)[C@H](N)CCCCN)ccc4OC)ccc3OC)ccc2OC)cc1C(N)=O] |
| 33 | 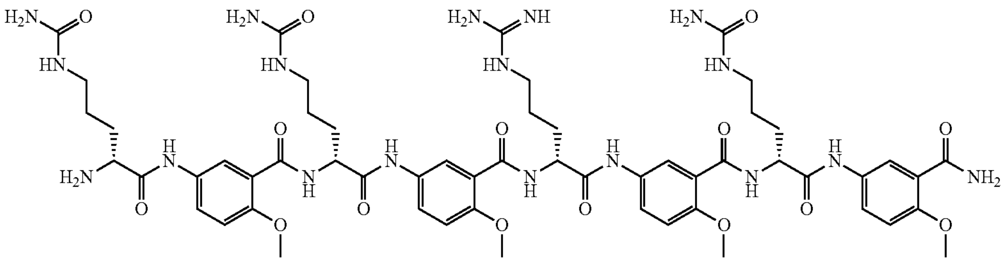 [SMILES: COc1ccc(NC(=O)[C@@H](CCCNC(N)=O)NC(=O)c2cc(NC(=O)[C@@H](CCCNC(=N)N)NC(=O)c3cc(NC(=O)[C@@H](CCCNC(N)=O)NC(=O)c4cc(NC(=O)[C@H](N)CCCNC(N)=O)ccc4OC)ccc3OC)ccc2OC)cc1C(N)=O] |

TABLE 1-continued
| Compd. No. | Structure |
|---|---|
| 34 | 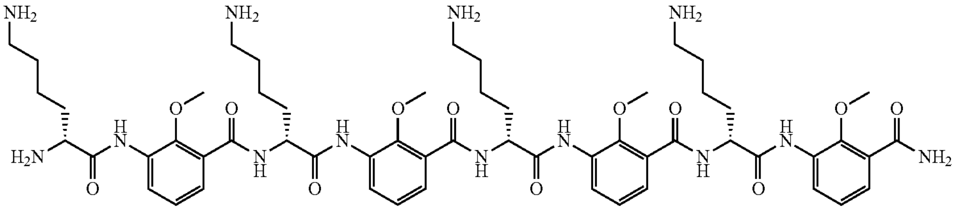 [SMILES: COc1c(NC(=O)[C@@H](CCCCN)NC(=O)c2cccc(NC(=O)[C@@H](CCCCN)NC(=O)c3cccc(NC(=O)[C@@H](CCCCN)NC(=O)c4cccc(NC(=O)[C@H](N)CCCCN)c4OC)c3OC)c2OC)cccc1C(N)=O] |
| 35 | 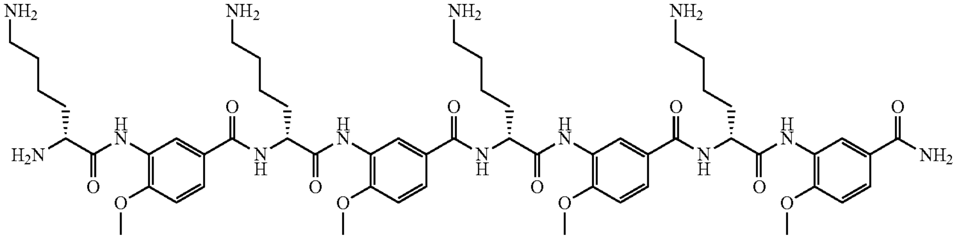 [SMILES: COc1ccc(C(=O)N[C@H](CCCCN)C(=O)Nc2cc(C(=O)N[C@H](CCCCN)C(=O)Nc3cc(C(=O)N[C@H](CCCCN)C(=O)Nc4cc(C(N)=O)ccc4OC)ccc3OC)ccc2OC)cc1NC(=O)[C@H](N)CCCCN] |
| 36 | 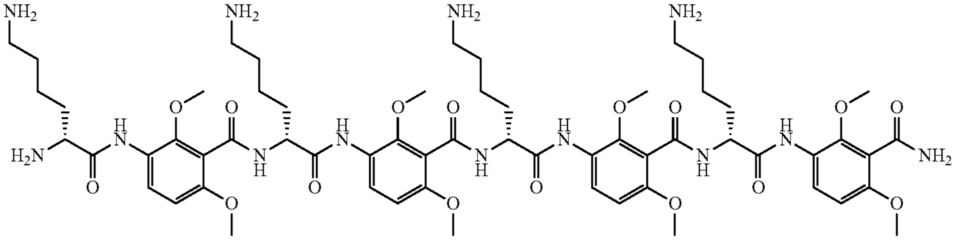 [SMILES: COc1ccc(NC(=O)[C@@H](CCCCN)NC(=O)c2c(OC)ccc(NC(=O)[C@@H](CCCCN)NC(=O)c3c(OC)ccc(NC(=O)[C@@H](CCCCN)NC(=O)c4c(OC)ccc(NC(=O)[C@H](N)CCCCN)c4OC)c3OC)c2OC)c(OC)c1C(N)=O] |
| 37 | 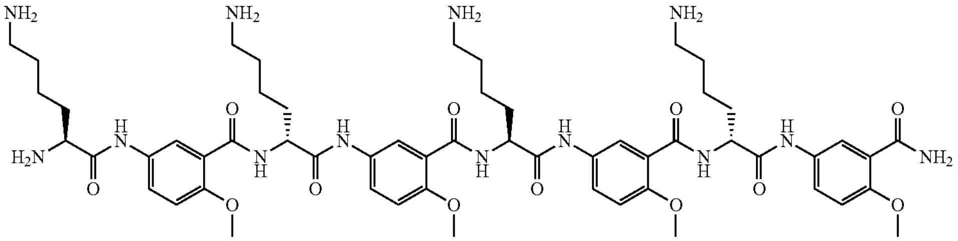 [SMILES: COc1ccc(NC(=O)[C@@H](CCCCN)NC(=O)c2cc(NC(=O)[C@H](CCCCN)NC(=O)c3cc(NC(=O)[C@@H](CCCCN)NC(=O)c4cc(NC(=O)[C@@H](N)CCCCN)ccc4OC)ccc3OC)ccc2OC)cc1C(N)=O] |
| 38 | 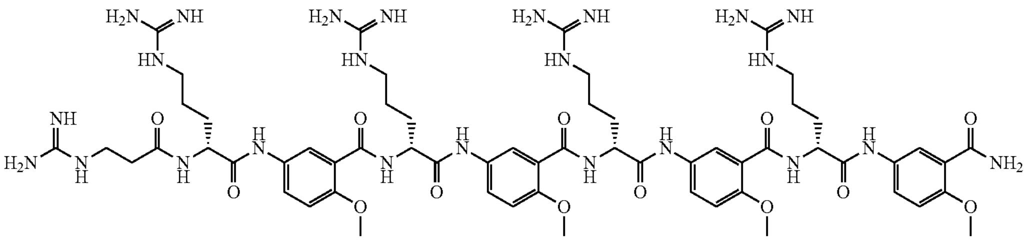 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](CCCNC(=N)N)NC(=O)CCNC(=N)N)ccc4OC)ccc3OC)ccc2OC)cc1C(N)=O] |
| 39 | 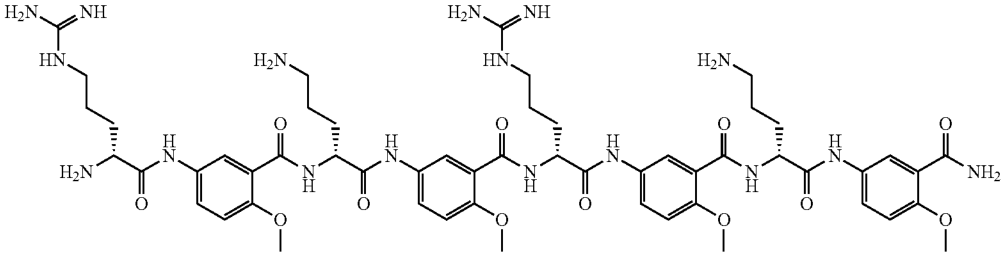 [SMILES: COc1ccc(NC(=O)[C@@H](CCCN)NC(=O)c2cc(NC(=O)[C@@H](CCCNC(=N)N)NC(=O)c3cc(NC(=O)[C@@H](CCCN)NC(=O)c4cc(NC(=O)[C@H](N)CCCNC(=N)N)ccc4OC)ccc3OC)ccc2OC)cc1C(N)=O] |

TABLE 1-continued
| Compd. No. | Structure |
| --- | --- |
| 40 | 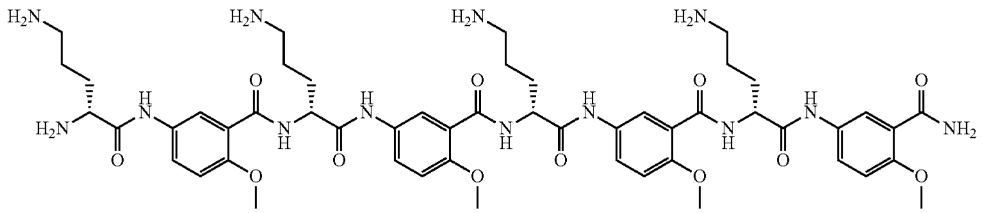 [SMILES: COc1ccc(NC(=O)[C@@H](CCCN)NC(=O)c2cc(NC(=O)[C@@H](CCCN)NC(=O)c3cc(NC(=O)[C@@H](CCCN)NC(=O)c4cc(NC(=O)[C@H](N)CCCN)ccc4OC)ccc3OC)ccc2OC)cc1C(N)=O] |
| 41 | 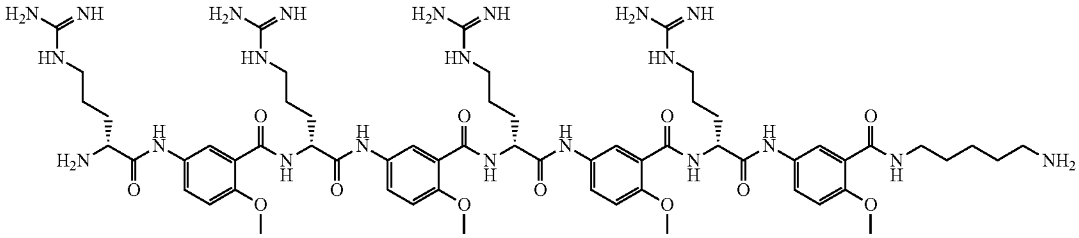 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(=O)NCCCCCN] |
| 42 | 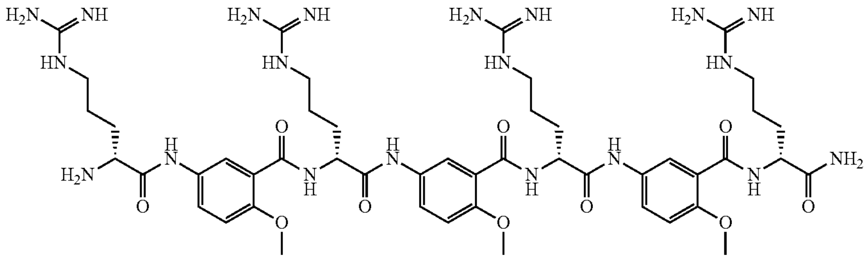 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@H](N)CCCNC(=N)N)ccc3OC)ccc2OC)cc1C(=O)N[C@H](CCCNC(=N)N)C(N)=O] |
| 43 | 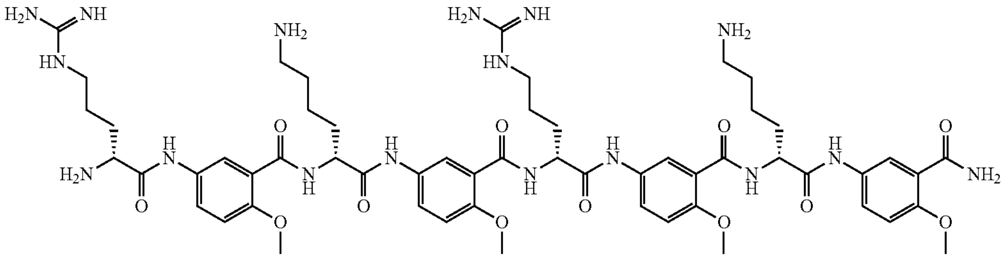 [SMILES: COc1ccc(NC(=O)[C@@H](CCCCN)NC(=O)c2cc(NC(=O)[C@@H](CCCNC(=N)N)NC(=O)c3cc(NC(=O)[C@@H](CCCCN)NC(=O)c4cc(NC(=O)[C@H](N)CCCNC(=N)N)ccc4OC)ccc3OC)ccc2OC)cc1C(N)=O] |
| 44 | 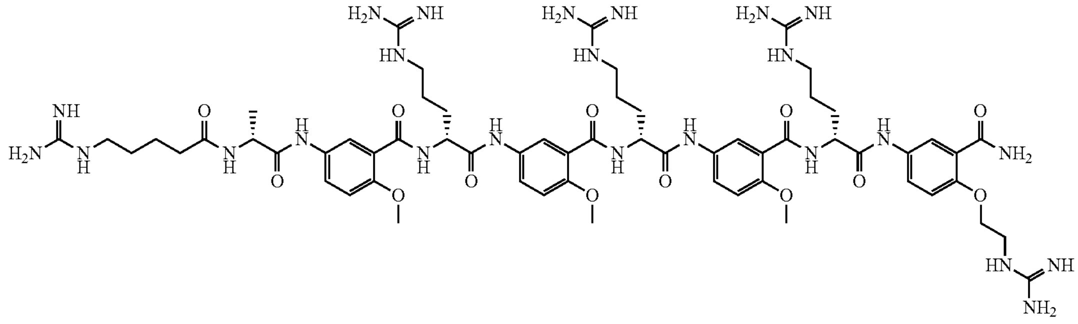 [SMILES: COc1ccc(NC(=O)[C@@H](C)NC(=O)CCCCNC(=N)N)cc1C(=O)N[C@H](CCCNC(=N)N)C(=O)Nc1ccc(OC)c(C(=O)N[C@H](CCCNC(=N)N)C(=O)Nc2ccc(OC)c(C(=O)N[C@H](CCCNC(=N)N)C(=O)Nc3ccc(OCCNC(=N)N)c(C(N)=O)c3)c2)c1] |
| 45 | 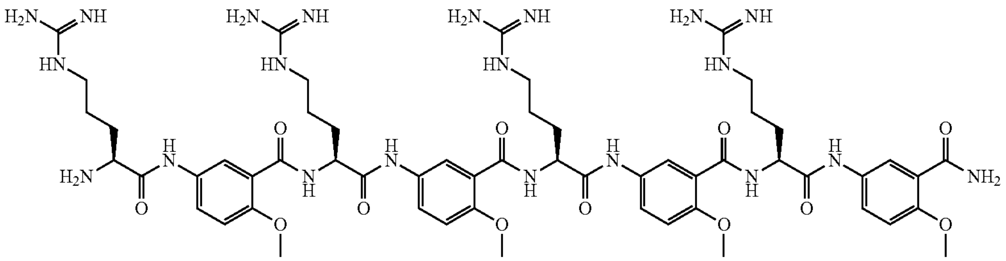 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OC)ccc2OC)cc1C(N)=O] |

TABLE 1-continued
| Compd. No. | Structure |
|---|---|
| 46 | 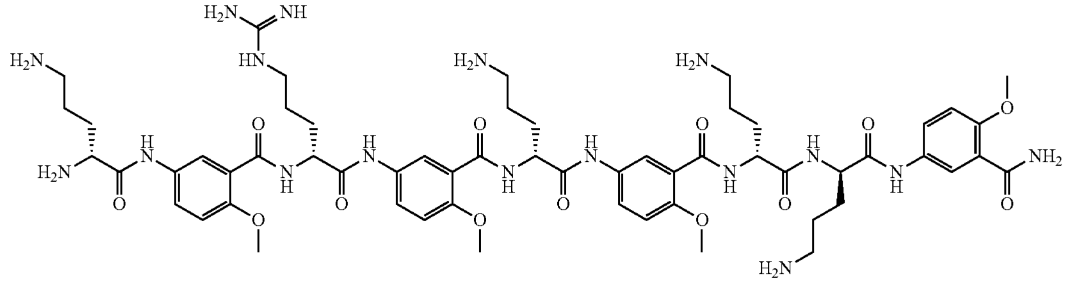 [SMILES: COc1ccc(NC(=O)[C@@H](CCCN)NC(=O)[C@@H](CCCN)NC(=O)c2cc(NC(=O)[C@@H](CCCN)NC(=O)c3cc(NC(=O)[C@@H](CCCNC(=N)N)NC(=O)c4cc(NC(=O)[C@H](N)CCCN)ccc4OC)ccc3OC)ccc2OC)cc1C(N)=O] |
| 47 | 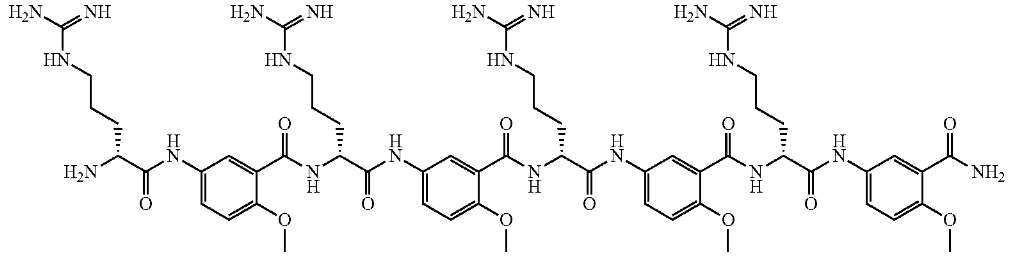 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 48 | 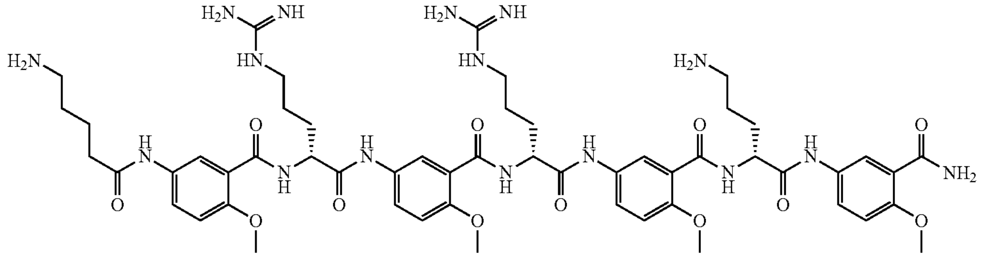 [SMILES: COc1ccc(NC(=O)[C@@H](CCCN)NC(=O)c2cc(NC(=O)[C@@H](CCCNC(=N)N)NC(=O)c3cc(NC(=O)[C@@H](CCCNC(=N)N)NC(=O)c4cc(NC(=O)CCCCN)ccc4OC)ccc3OC)ccc2OC)cc1C(N)=O] |
| 49 | 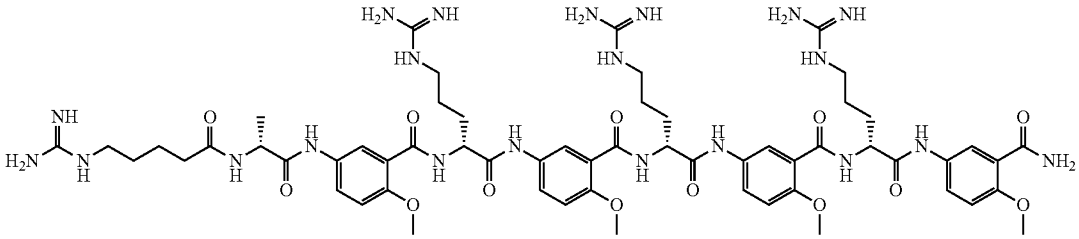 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(=O)CCCCNC(=N)N)ccc4OC)ccc3OC)ccc2OC)cc1C(N)=O] |
| 50 | 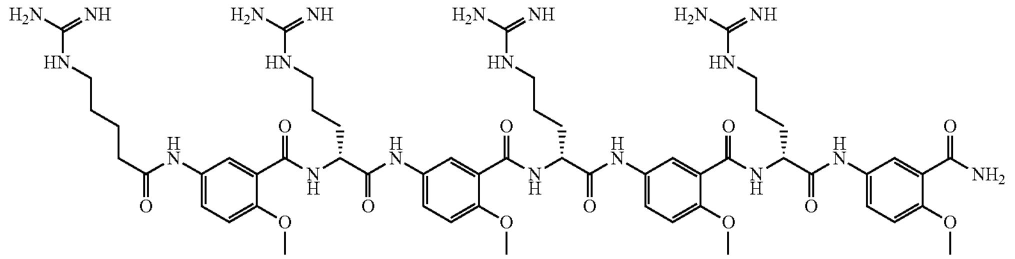 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)CCCCNC(=N)N)ccc4OC)ccc3OC)ccc2OC)cc1C(N)=O] |
| 51 | 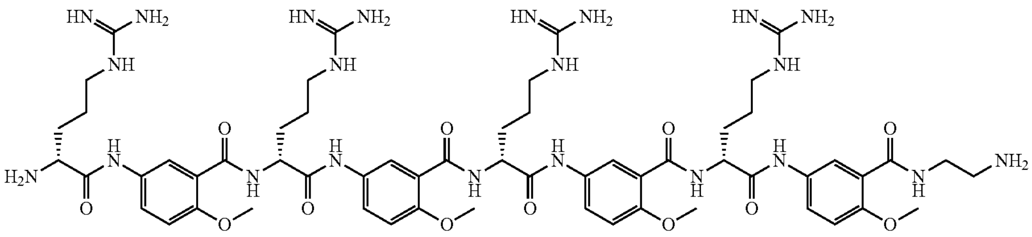 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(=O)NCCN] |

TABLE 1-continued
| Compd. No. | Structure |
| --- | --- |
| 52 | 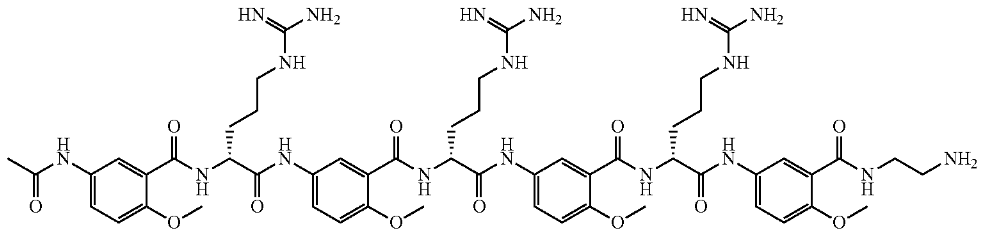 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OC)cc1C(=O)NCCN] |
| 53 | 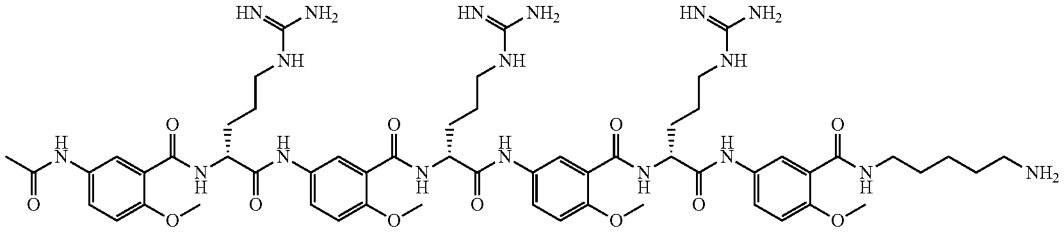 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OC)cc1C(=O)NCCCCCN] |
| 54 | 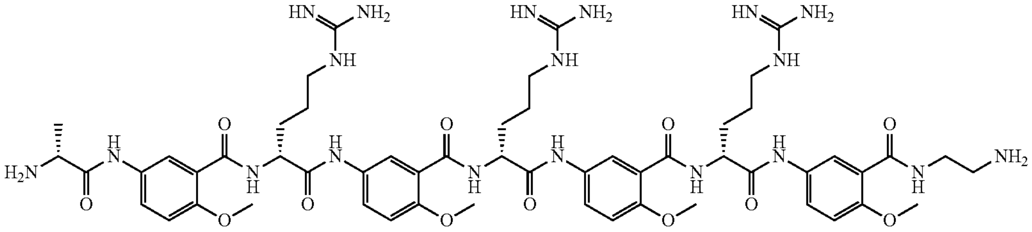 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)N)ccc4OC)ccc3OC)ccc2OC)cc1C(=O)NCCN] |
| 55 | 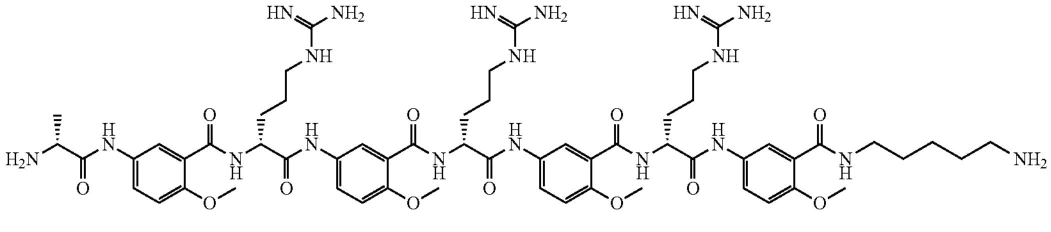 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)N)ccc4OC)ccc3OC)ccc2OC)cc1C(=O)NCCCCCN] |
| 56 | 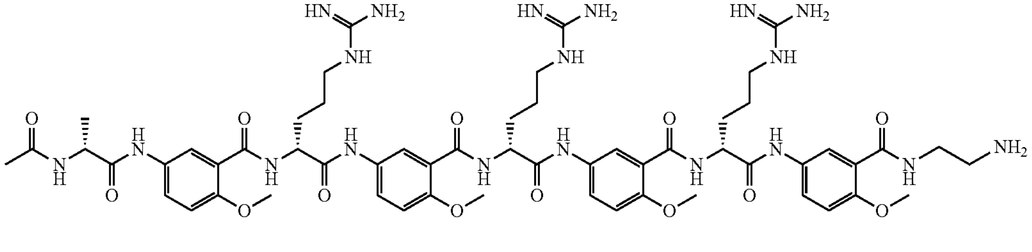 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(C)=O)ccc4OC)ccc3OC)ccc2OC)cc1C(=O)NCCN] |
| 57 | 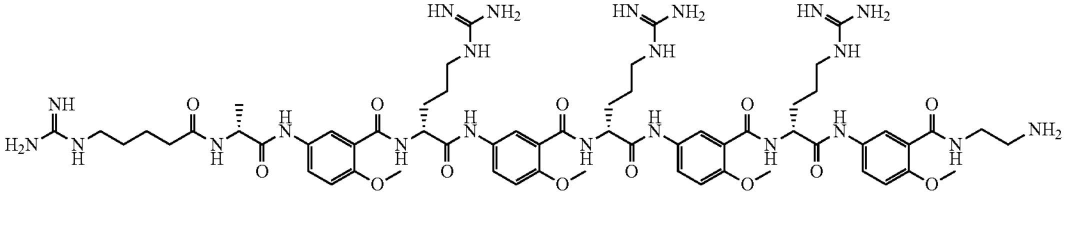 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(=O)CCCCNC(=N)N)ccc4OC)ccc3OC)ccc2OC)cc1C(=O)NCCN] |

TABLE 1-continued
| Compd. No. | Structure |
| --- | --- |
| 58 | 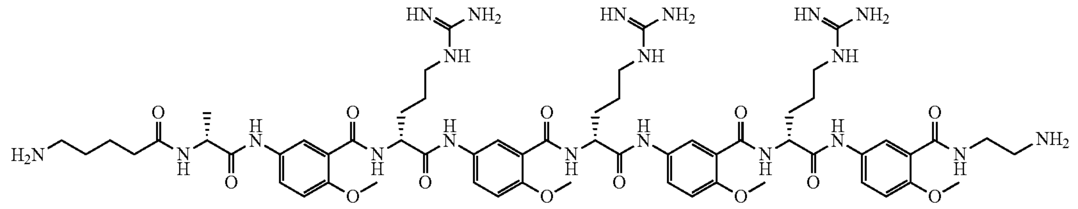 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(=O)CCCCN)ccc4OC)ccc3OC)ccc2OC)cc1C(=O)NCCN] |
| 59 | 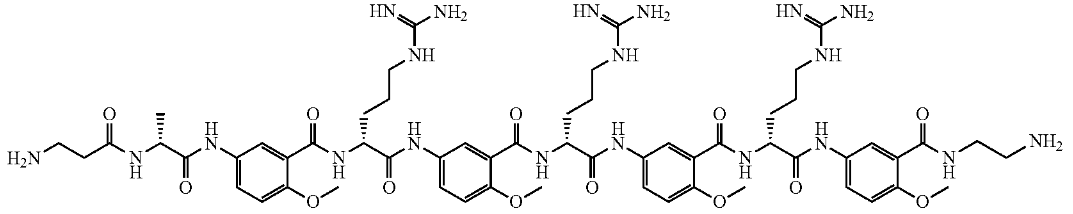 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(=O)CCN)ccc4OC)ccc3OC)ccc2OC)cc1C(=O)NCCN] |
| 60 | 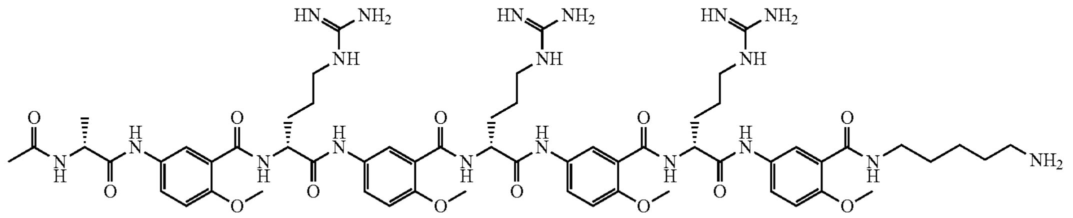 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(C)=O)ccc4OC)ccc3OC)ccc2OC)cc1C(=O)NCCCCCN] |
| 61 | 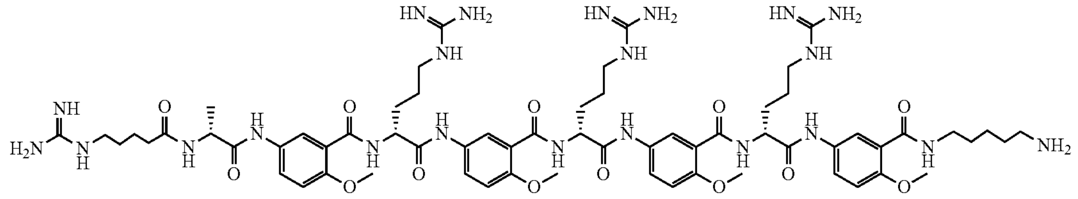 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(=O)CCCCNC(=N)N)ccc4OC)ccc3OC)ccc2OC)cc1C(=O)NCCCCCN] |
| 62 | 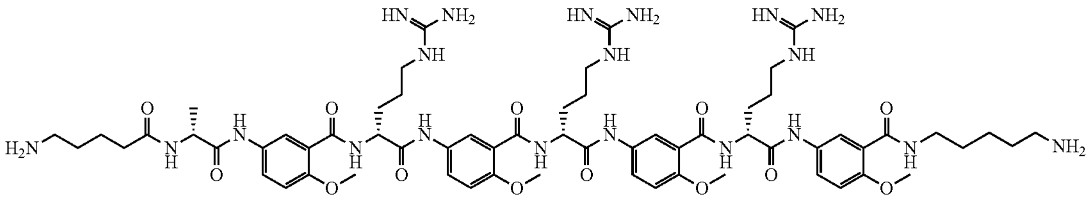 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(=O)CCCCN)ccc4OC)ccc3OC)ccc2OC)cc1C(=O)NCCCCCN] |
| 63 | 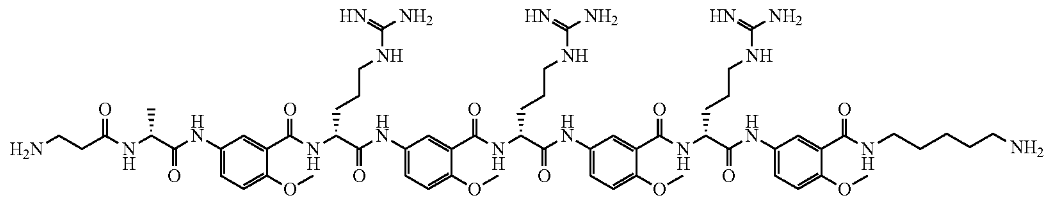 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](C)NC(=O)CCN)ccc4OC)ccc3OC)ccc2OC)cc1C(=O)NCCCCCN] |
| 64 | 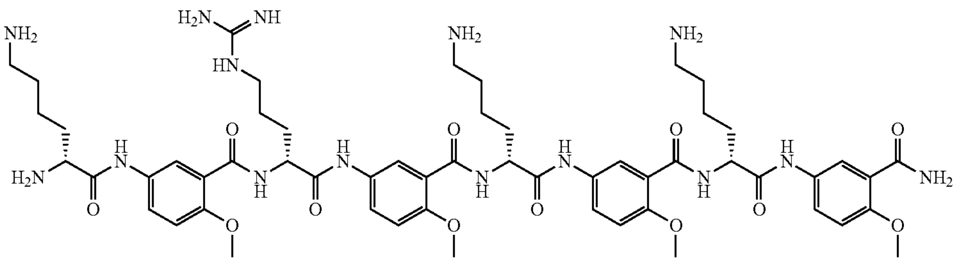 [SMILES: COc1ccc(NC(=O)[C@@H](CCCCN)NC(=O)c2cc(NC(=O)[C@@H](CCCCN)NC(=O)c3cc(NC(=O)[C@@H](CCCNC(=N)N)NC(=O)c4cc(NC(=O)[C@H](N)CCCCN)ccc4OC)ccc3OC)ccc2OC)cc1C(N)=O] |

TABLE 1-continued
| Compd. No. | Structure |
| --- | --- |
| 65 | 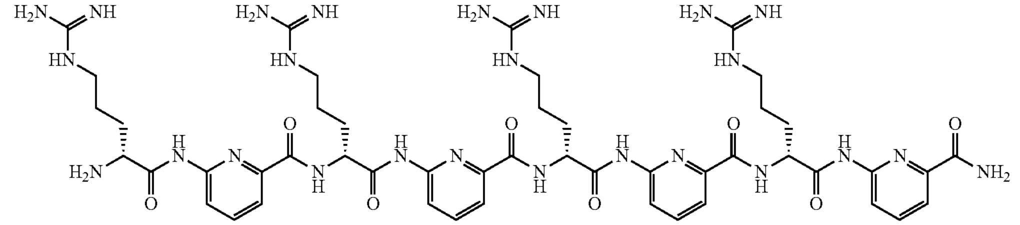 [SMILES: N=C(N)NCCC[C@@H](N)C(=O)Nc1cccc(C(=O)N[C@H](CCCNC(=N)N)C(=O)Nc2cccc(C(=O)N[C@H](CCCNC(=N)N)C(=O)Nc3cccc(C(=O)N[C@H](CCCNC(=N)N)C(=O)Nc4cccc(C(N)=O)n4)n3)n2)n1] |
| 66 | 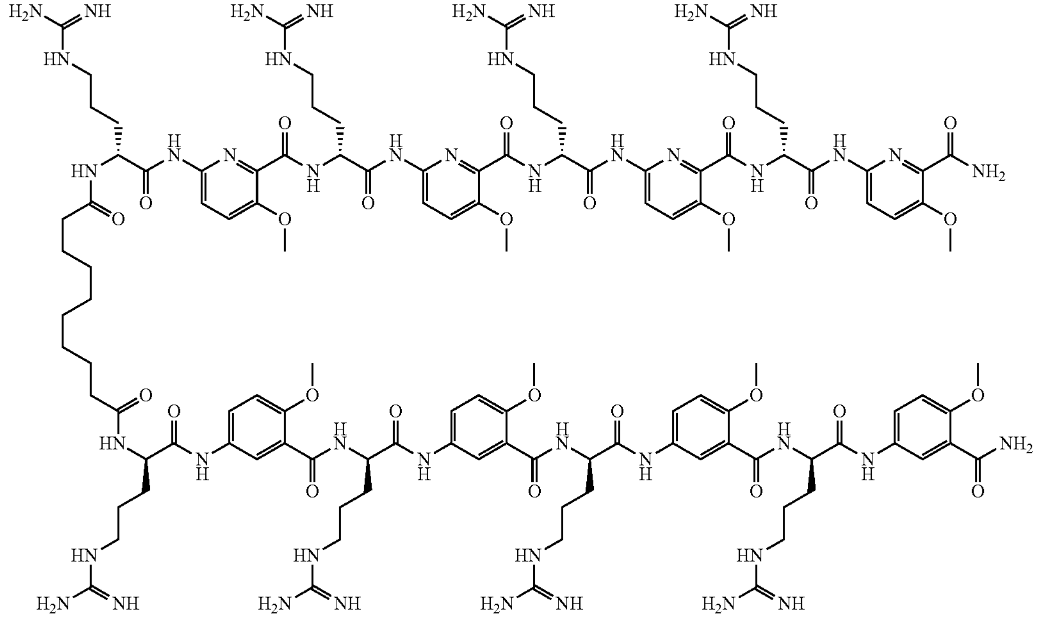 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@@H](CCCNC(=N)N)NC(=O)CCCCCCCCC(=O)N[C@H](CCCNC(=N)N)C(=O)Nc5ccc(OC)c(C(=O)N[C@H](CCCNC(=N)N)C(=O)Nc6ccc(OC)c(C(=O)N[C@H](CCCNC(=N)N)C(=O)Nc7ccc(OC)c(C(=O)N[C@H](CCCNC(=N)N)C(=O)Nc8ccc(OC)c(C(N)=O)n8)n7)n6)n5)ccc4OC)ccc3OC)ccc2OC)cc1C(N)=O] |
| 67 | 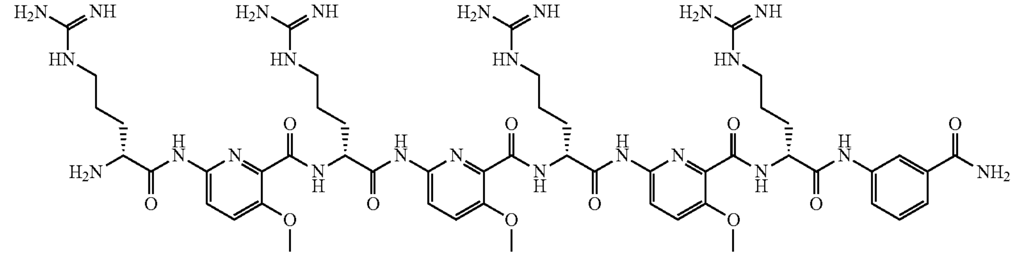 [SMILES: COc1ccc(NC(=O)[C@@H](CCCNC(=N)N)NC(=O)c2nc(NC(=O)[C@@H](CCCNC(=N)N)NC(=O)c3nc(NC(=O)[C@H](N)CCCNC(=N)N)ccc3OC)ccc2OC)nc1C(=O)N[C@H](CCCNC(=N)N)C(=O)Nc1cccc(C(N)=O)c1] |
| 68 | 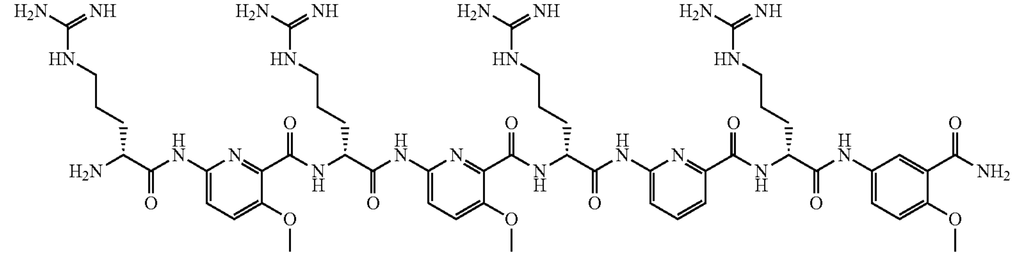 [SMILES: COc1ccc(NC(=O)[C@@H](CCCNC(=N)N)NC(=O)c2cccc(NC(=O)[C@@H](CCCNC(=N)N)NC(=O)c3nc(NC(=O)[C@@H](CCCNC(=N)N)NC(=O)c4nc(NC(=O)[C@H](N)CCCNC(=N)N)ccc4OC)ccc3OC)n2)cc1C(N)=O] |

TABLE 1-continued
| Compd. No. | Structure |
|---|---|
| 69 | 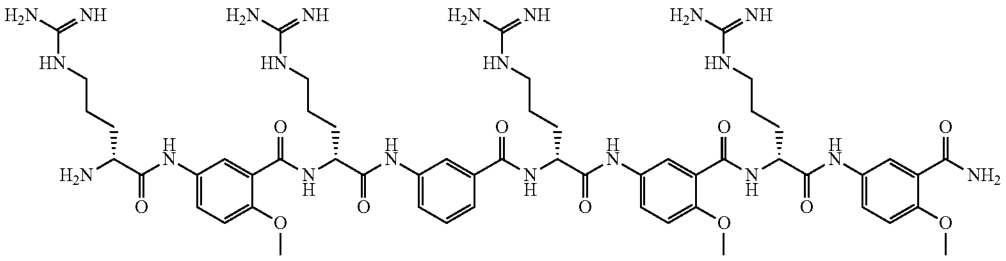 [SMILES: COc1ccc(NC(=O)[C@@H](CCCNC(=N)N)NC(=O)c2cc(NC(=O)[C@@H](CCCNC(=N)N)NC(=O)c3cccc(NC(=O)[C@@H](CCCNC(=N)N)NC(=O)c4cc(NC(=O)[C@H](N)CCCNC(=N)N)ccc4OC)c3)ccc2OC)cc1C(N)=O] |
| 70 | 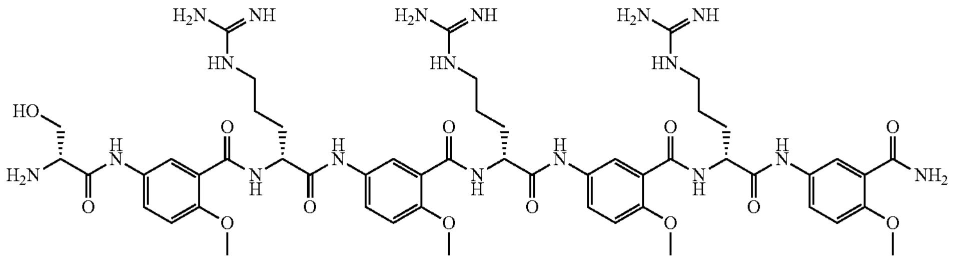 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CO)ccc4OC)ccc3OC)ccc2OC)cc1C(N)=O] |
| 71 | 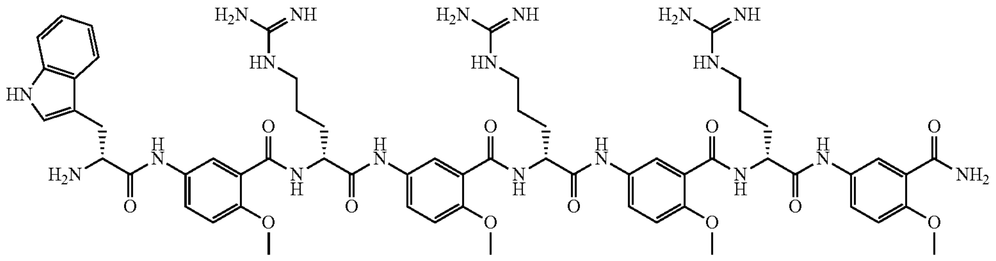 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)Cc5c[nH]c6ccccc56)ccc4OC)ccc3OC)ccc2OC)cc1C(N)=O] |
| 72 | 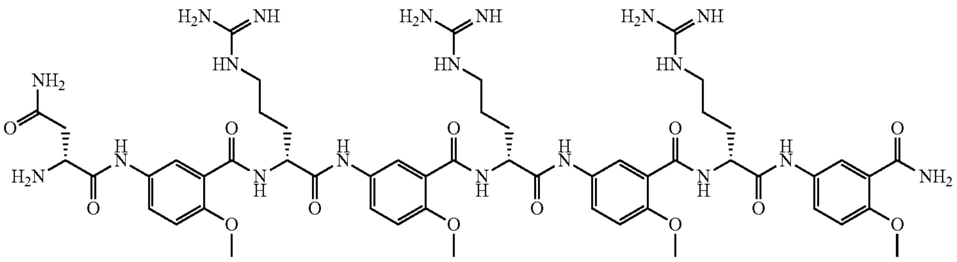 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CC(N)=O)ccc4OC)ccc3OC)ccc2OC)cc1C(N)=O] |
| 73 | 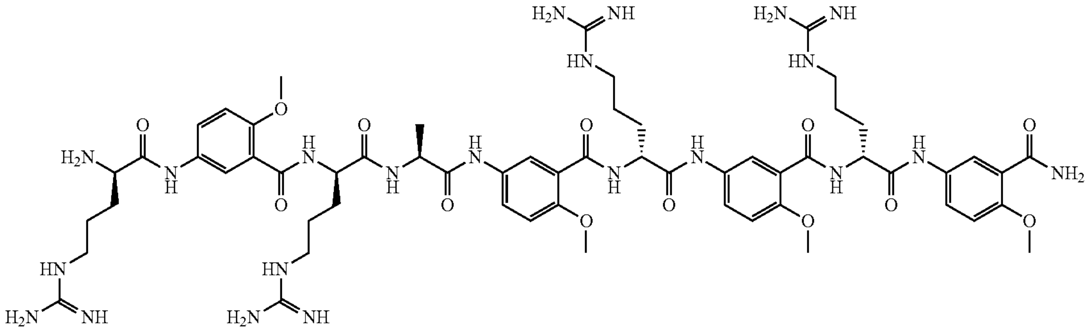 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@H](C)NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |

TABLE 1-continued
| Compd. No. | Structure |
|---|---|
| 74 | 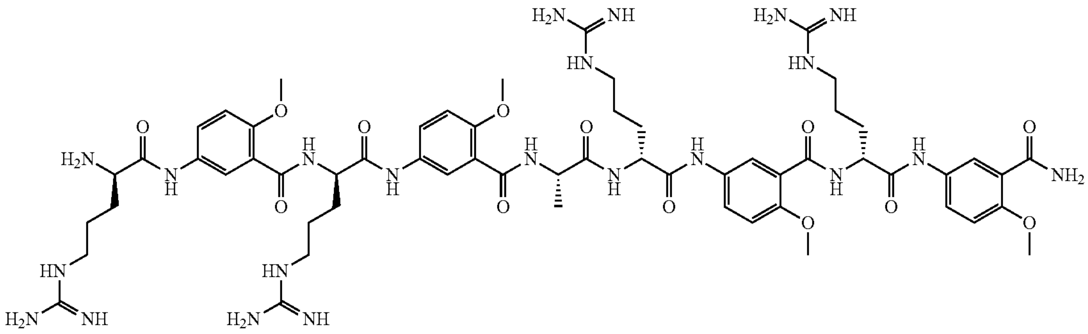 [SMILES: COc1ccc(NC(=O)[C@@H](CCCNC(=N)N)NC(=O)c2cc(NC(=O)[C@@H](CCCNC(=N)N)NC(=O)[C@H](C)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 75 | 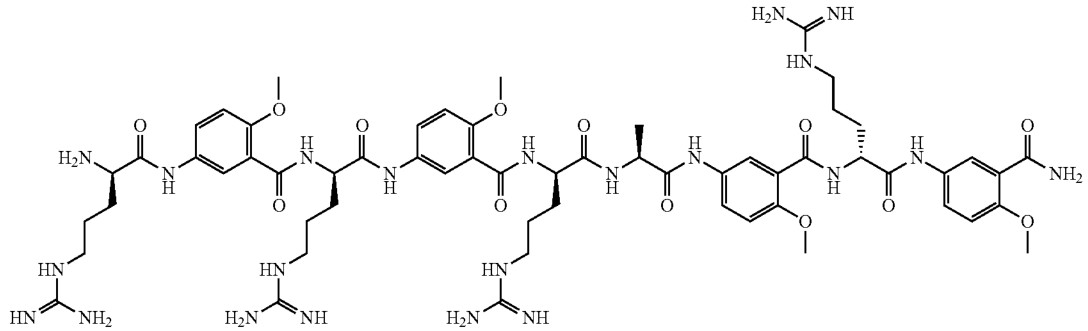 [SMILES: COc1ccc(NC(=O)[C@@H](CCCNC(=N)N)NC(=O)c2cc(NC(=O)[C@H](C)NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 76 | 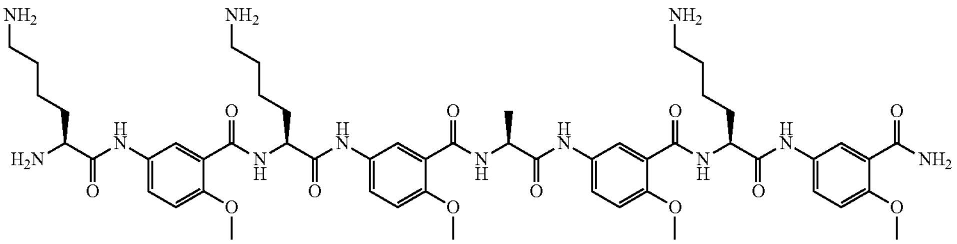 [SMILES: COc1ccc(NC(=O)[C@H](CCCCN)NC(=O)c2cc(NC(=O)[C@H](C)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 77 | 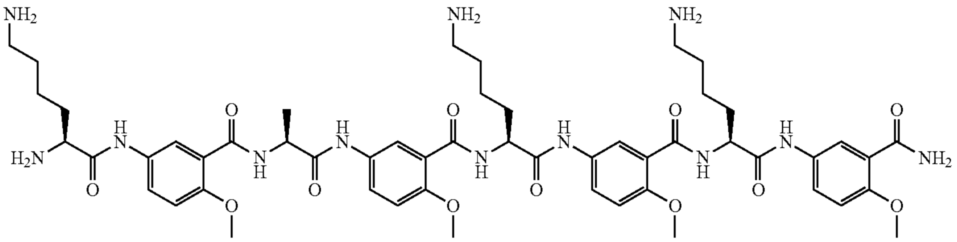 [SMILES: COc1ccc(NC(=O)[C@H](CCCCN)NC(=O)c2cc(NC(=O)[C@H](CCCCN)NC(=O)c3cc(NC(=O)[C@H](C)NC(=O)c4cc(NC(=O)[C@@H](N)CCCCN)ccc4OC)ccc3OC)ccc2OC)cc1C(N)=O] |
| 78 | 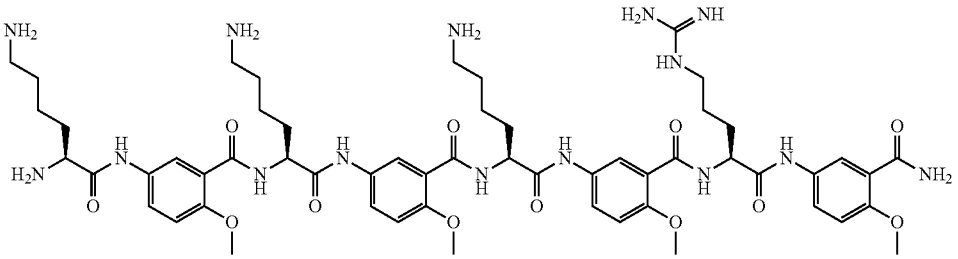 [SMILES: COc1ccc(NC(=O)[C@H](CCCNC(=N)N)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |

TABLE 1-continued
| Compd. No. | Structure |
|---|---|
| 79 | 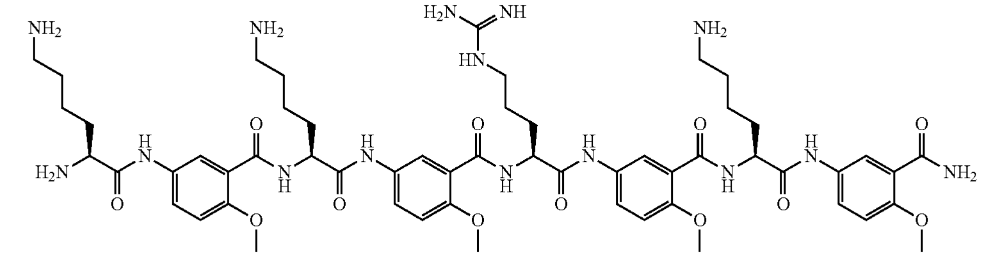 [SMILES: COc1ccc(NC(=O)[C@H](CCCCN)NC(=O)c2cc(NC(=O)[C@H](CCCNC(=N)N)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 80 | 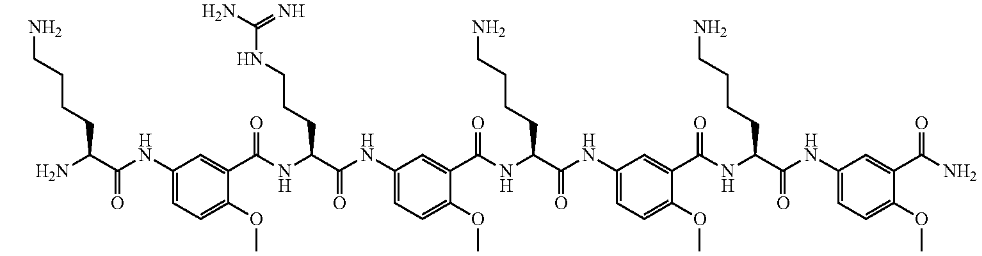 [SMILES: COc1ccc(NC(=O)[C@H](CCCCN)NC(=O)c2cc(NC(=O)[C@H](CCCCN)NC(=O)c3cc(NC(=O)[C@H](CCCNC(=N)N)NC(=O)c4cc(NC(=O)[C@@H](N)CCCCN)ccc4OC)ccc3OC)ccc2OC)cc1C(N)=O] |
| 81 | 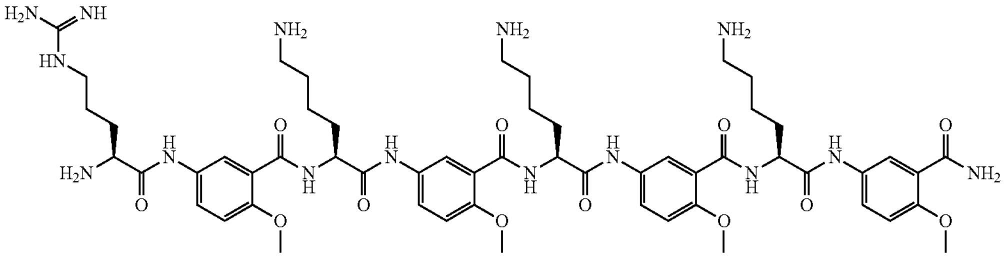 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCNC(=N)N)ccc4OC)ccc3OC)ccc2OC)cc1C(N)=O] |
| 82 | 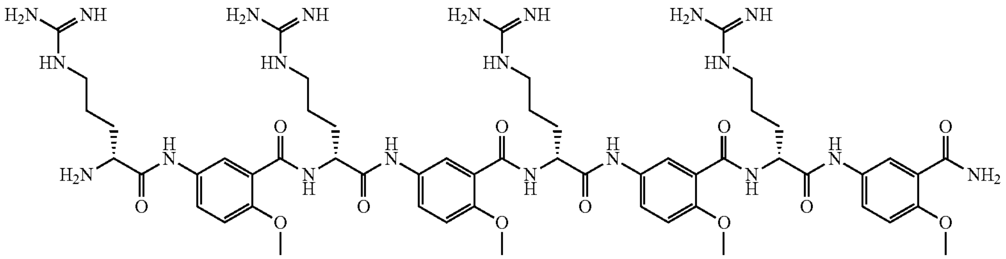 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 83 | 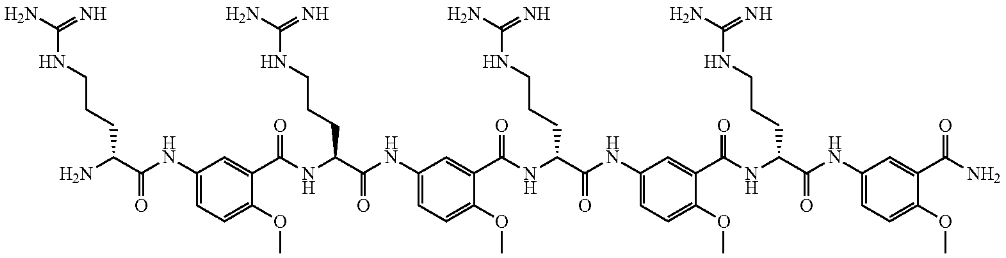 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@H](CCCNC(=N)N)NC(=O)c4cc(NC(=O)[C@H](N)CCCNC(=N)N)ccc4OC)ccc3OC)ccc2OC)cc1C(N)=O] |
| 84 | 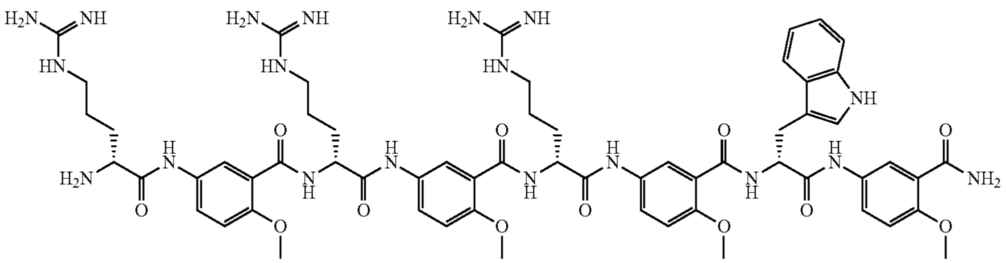 [SMILES: COc1ccc(NC(=O)[C@@H](Cc2c[nH]c3ccccc23)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |

TABLE 1-continued
| Compd. No. | Structure |
|---|---|
| 85 | 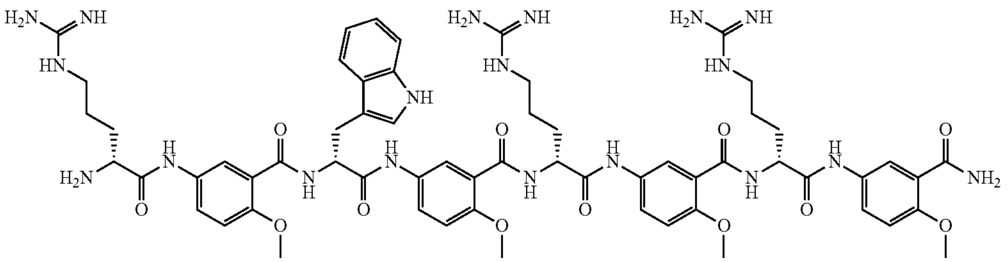 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](Cc4c[nH]c5ccccc45)NC(=O)c4cc(NC(=O)[C@H](N)CCCNC(=N)N)ccc4OC)ccc3OC)ccc2OC)cc1C(N)=O] |
| 86 | 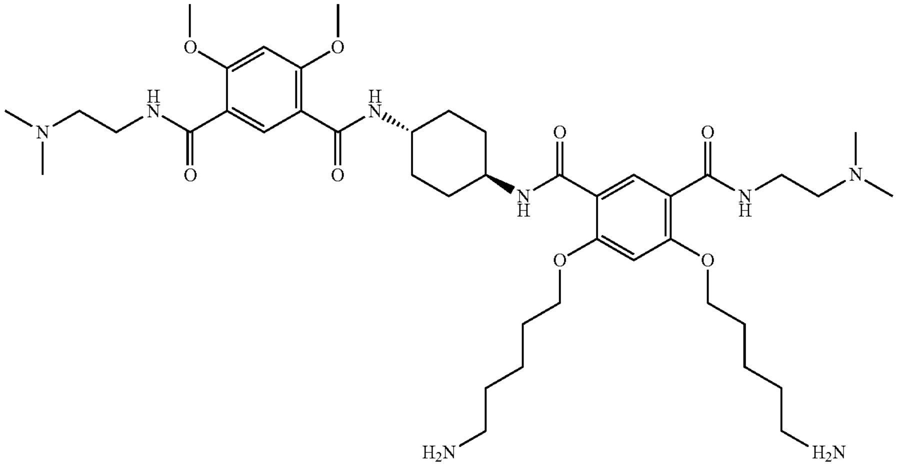 |
| 87 | 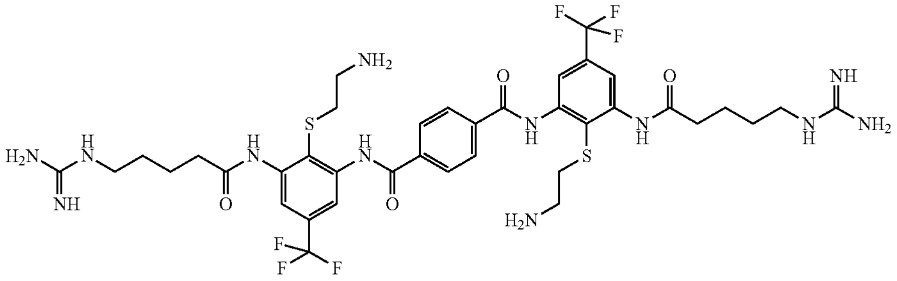 [SMILES: N=C(N)NCCCCC(=O)Nc1cc(C(F)(F)F)cc(NC(=O)c2ccc(C(=O)Nc3cc(C(F)(F)F)cc(NC(=O)CCCCNC(=N)N)c3SCCN)cc2)c1SCCN] |
| 88 | 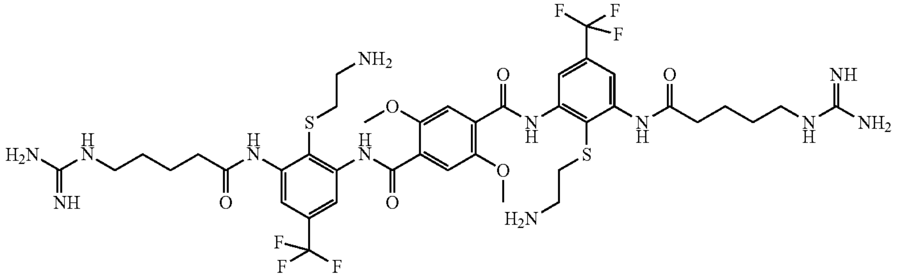 [SMILES: COc1cc(C(=O)Nc2cc(C(F)(F)F)cc(NC(=O)CCCCNC(=N)N)c2SCCN)c(OC)cc1C(=O)Nc1cc(C(F)(F)F)cc(NC(=O)CCCCNC(=N)N)c1SCCN] |
| 89 | 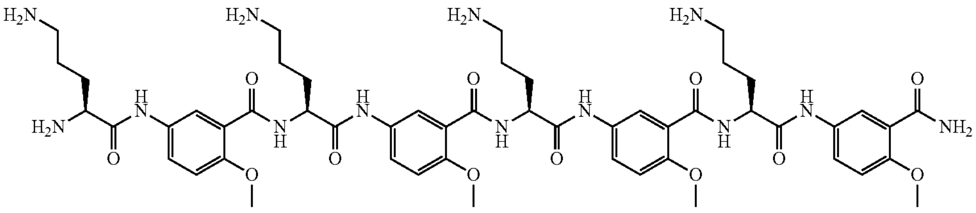 [SMILES: COc1ccc(NC(=O)[C@H](CCCN)NC(=O)c2cc(NC(=O)[C@H](CCCN)NC(=O)c3cc(NC(=O)[C@H](CCCN)NC(=O)c4cc(NC(=O)[C@@H](N)CCCN)ccc4OC)ccc3OC)ccc2OC)cc1C(N)=O] |

TABLE 1-continued
| Compd. No. | Structure |
| --- | --- |
| 90 | 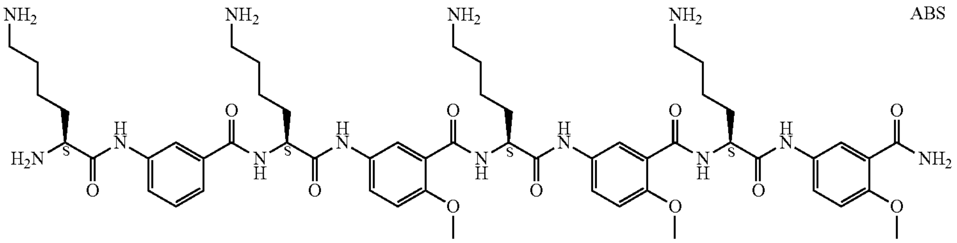 ABS |
| 91 | 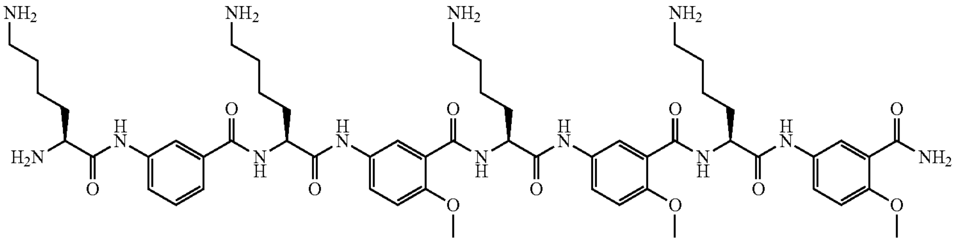 |
| 92 | 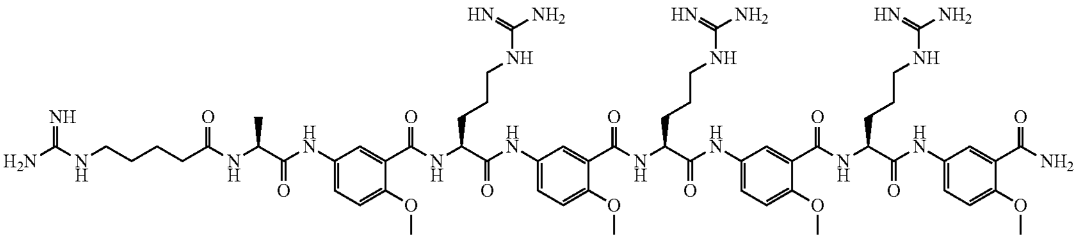 |
| 93 | 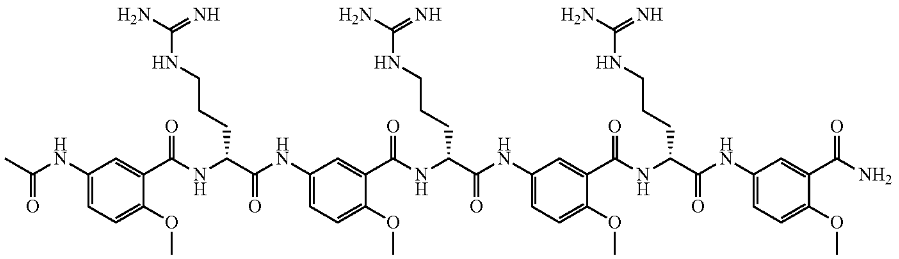 |
| 94 | 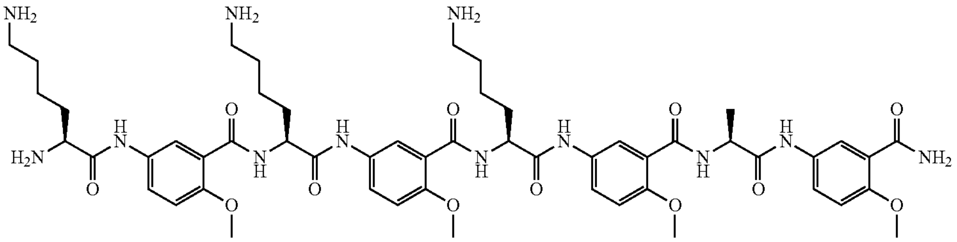 |
| 95 | 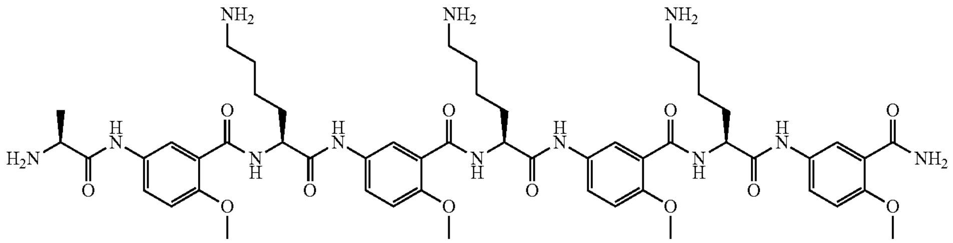 |

TABLE 1-continued
| Compd. No. | Structure |
|---|---|
| 96 | 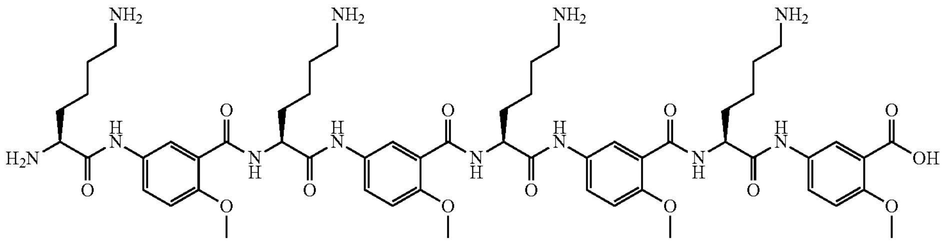 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)O] |
| 97 | 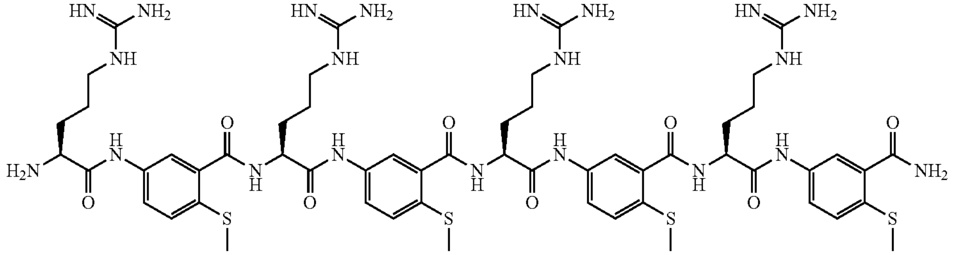 [SMILES: CSc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4SC)ccc3SC)ccc2SC)cc1C(N)=O] |
| 98 | 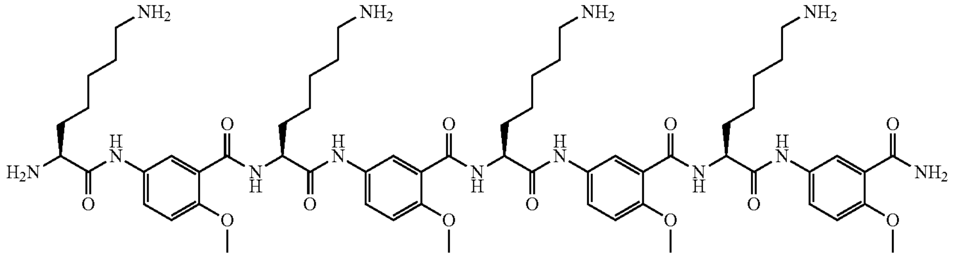 [SMILES: COc1ccc(NC(=O)[C@H](CCCCCN)NC(=O)c2cc(NC(=O)[C@H](CCCCCN)NC(=O)c3cc(NC(=O)[C@H](CCCCCN)NC(=O)c4cc(NC(=O)[C@@H](N)CCCCCN)ccc4OC)ccc3OC)ccc2OC)cc1C(N)=O] |
| 99 | 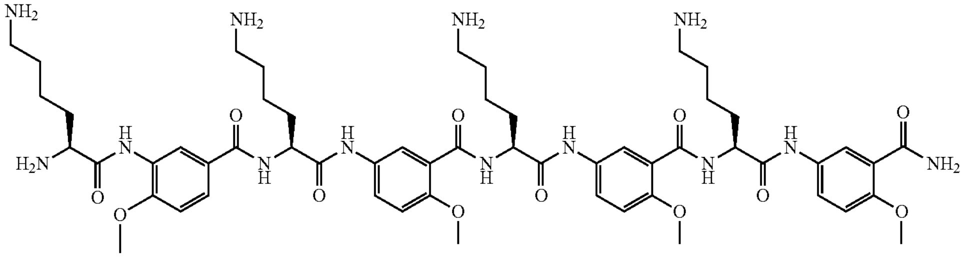 [SMILES: COc1ccc(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(N)=O)c4)c3)c2)cc1NC(=O)[C@@H](N)CCCCN] |
| 100 | 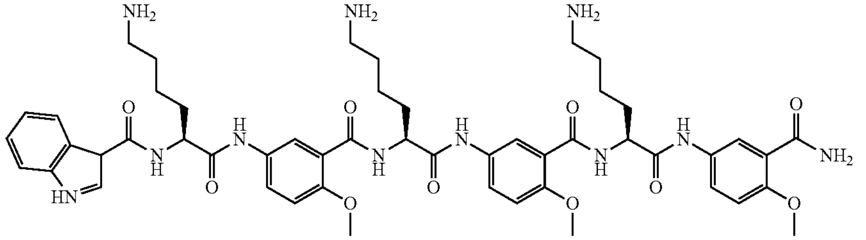 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)C4C=Nc5ccccc54)ccc3OC)ccc2OC)cc1C(N)=O] |
| 101 | 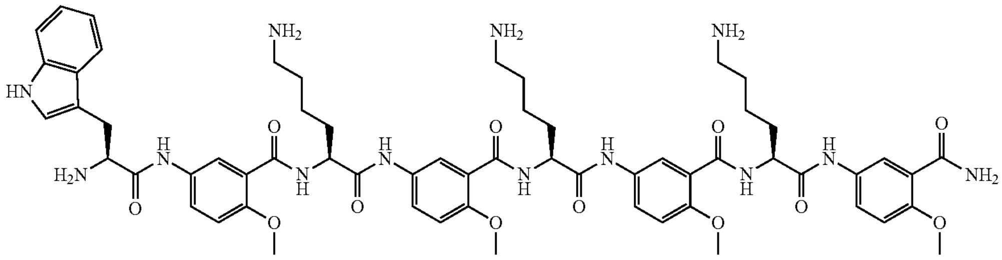 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)Cc5c[nH]c6ccccc56)ccc4OC)ccc3OC)ccc2OC)cc1C(N)=O] |

TABLE 1-continued
| Compd. No. | Structure |
|---|---|
| 102 | 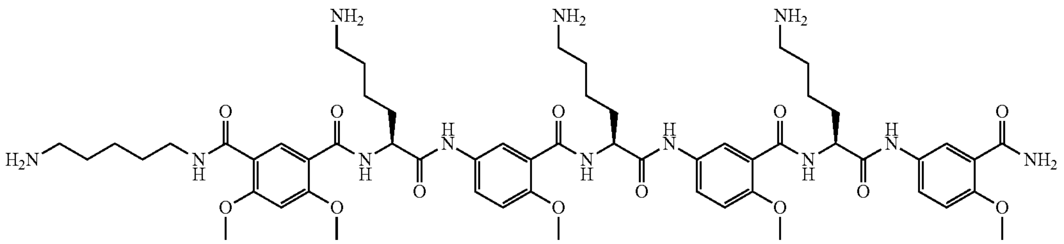 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(C(=O)NCCCCCN)c(OC)cc4OC)ccc3OC)ccc2OC)cc1C(N)=O] |
| 103 | 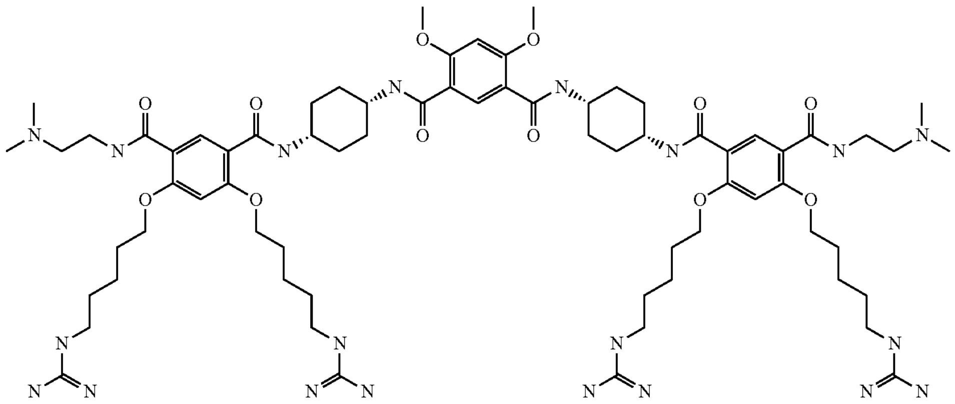 |
| 104 | 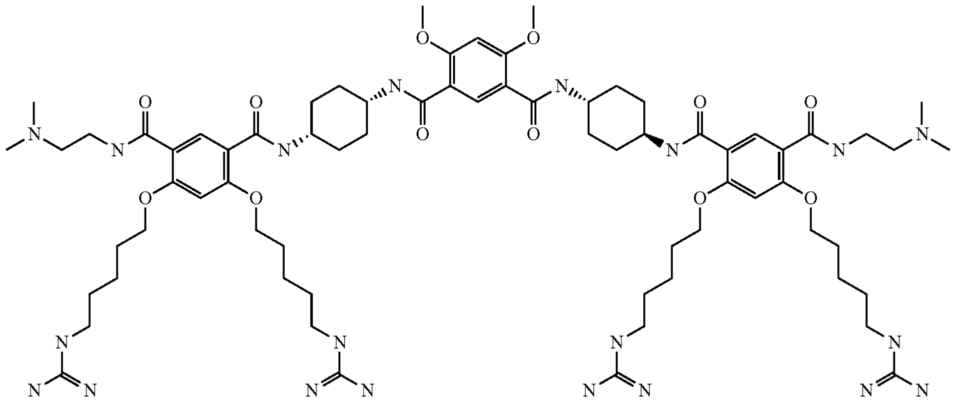 |
| 105 | 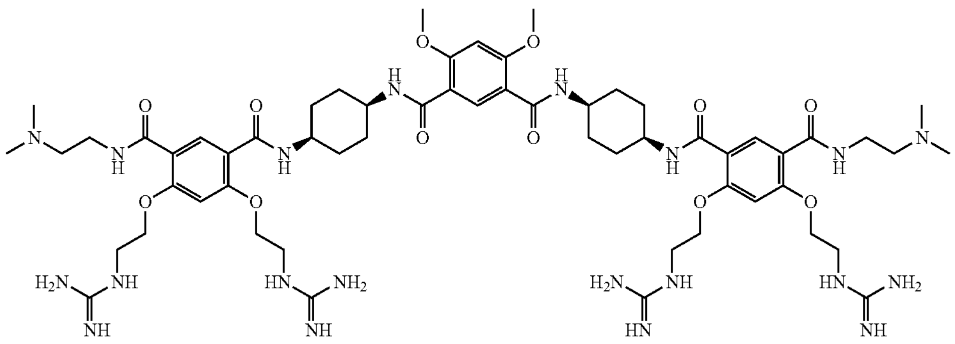 |

TABLE 1-continued
| Compd. No. | Structure |
| --- | --- |
| 106 | 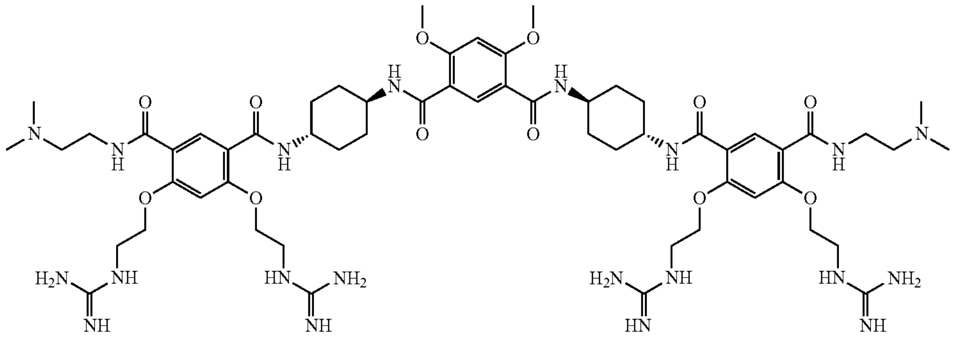 |
| 107 | 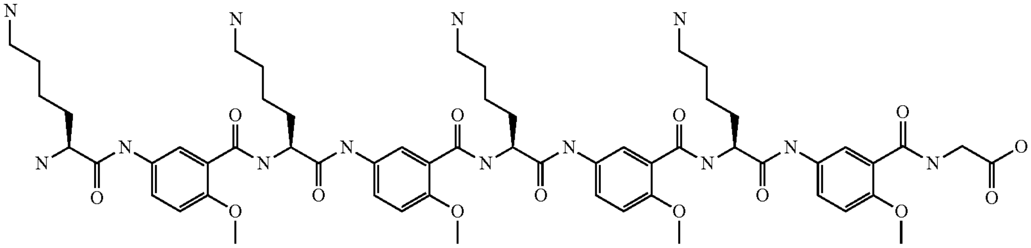 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)NCC(=O)O] |
| 108 | 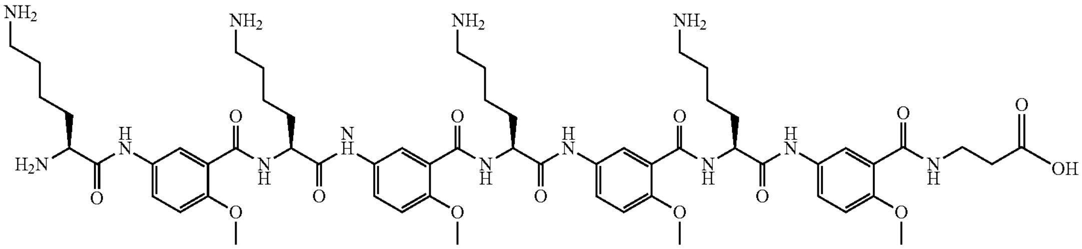 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)NCCC(=O)O] |
| 109 | 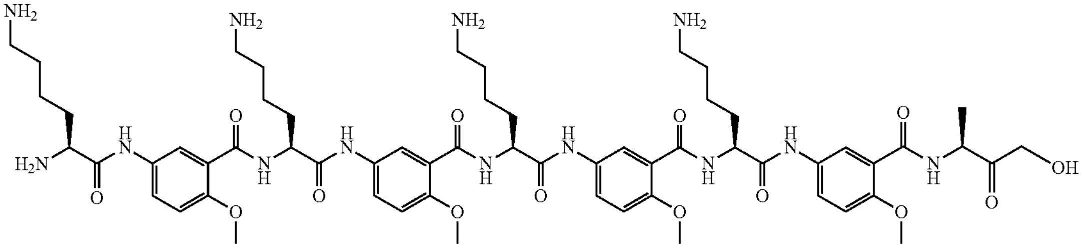 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](C)C(=O)CO] |
| 110 | 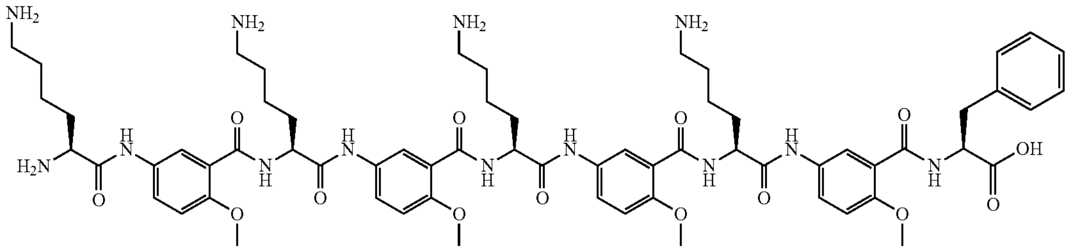 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](Cc1ccccc1)C(=O)O] |

TABLE 1-continued
| Compd. No. | Structure |
| --- | --- |
| 111 | 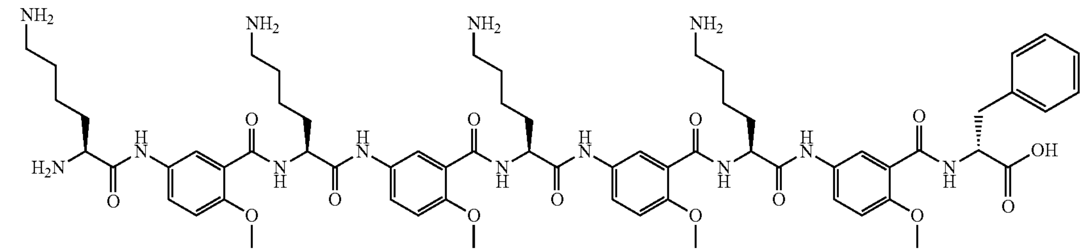 [SMILES: COc1ccc(NC(=O)[C@H](CCCCN)NC(=O)c2cc(NC(=O)[C@@H](N)CCCCN)ccc2OC)cc1C(=O)N[C@@H](CCCCN)C(=O)Nc1ccc(OC)c(C(=O)N[C@@H](CCCCN)C(=O)Nc2ccc(OC)c(C(=O)N[C@H](Cc3ccccc3)C(=O)O)c2)c1] |
| 112 | 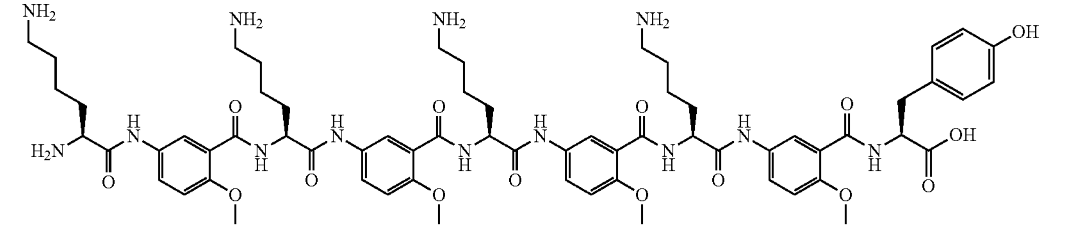 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](Cc1ccc(O)cc1)C(=O)O] |
| 113 | 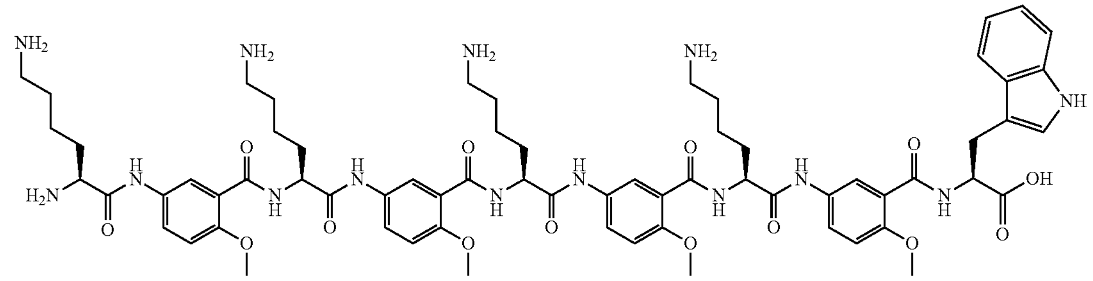 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](Cc1c[nH]c2ccccc12)C(=O)O] |
| 114 | 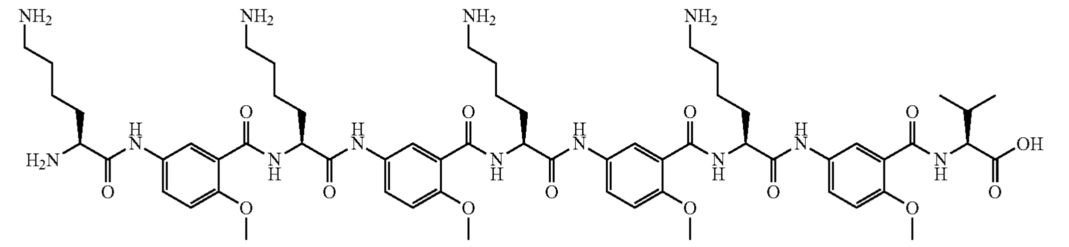 [SMILES: COc1ccc(NC(=O)[C@H](CCCCN)NC(=O)c2cc(NC(=O)[C@@H](N)CCCCN)ccc2OC)cc1C(=O)N[C@@H](CCCCN)C(=O)Nc1ccc(OC)c(C(=O)N[C@@H](CCCCN)C(=O)Nc2ccc(OC)c(C(=O)N[C@H](C(=O)O)C(C)C)c2)c1] |
| 115 | 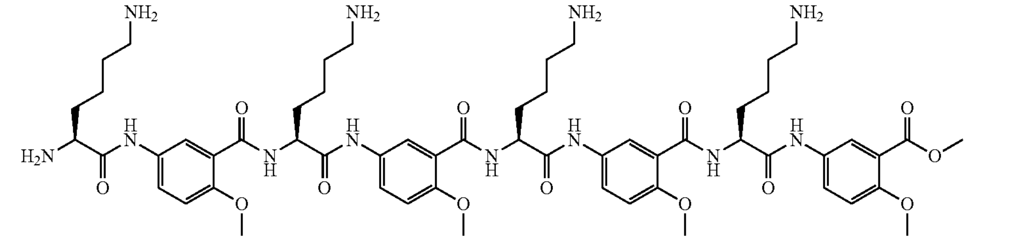 [SMILES: COC(=O)c1cc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)ccc1OC] |
| 116 | 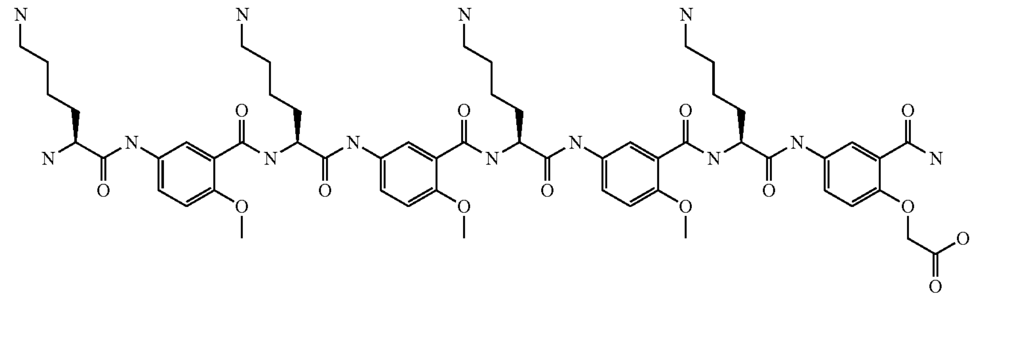 [SMILES: COc1ccc(NC(=O)[C@H](CCCCN)NC(=O)c2cc(NC(=O)[C@H](CCCCN)NC(=O)c3cc(NC(=O)[C@@H](N)CCCCN)ccc3OC)ccc2OC)cc1C(=O)N[C@@H](CCCCN)C(=O)Nc1ccc(OCC(=O)O)c(C(N)=O)c1] |

TABLE 1-continued
| Compd. No. | Structure |
|---|---|
| 117 | 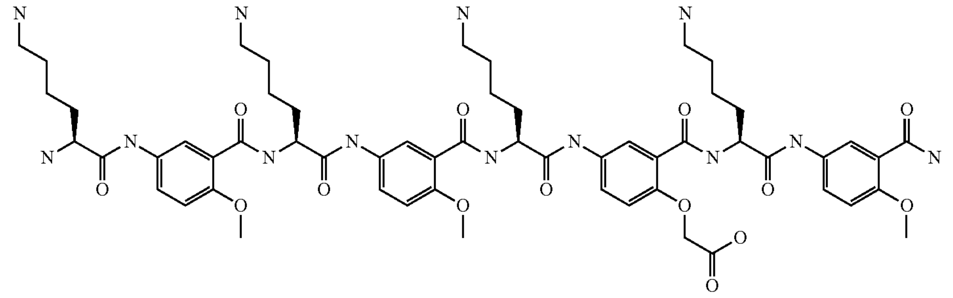 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OCC(=O)O)cc1C(N)=O] |
| 118 | 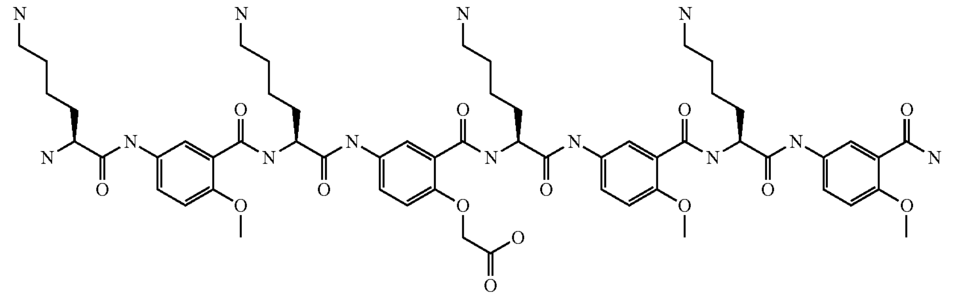 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OCC(=O)O)ccc2OC)cc1C(N)=O] |
| 119 | 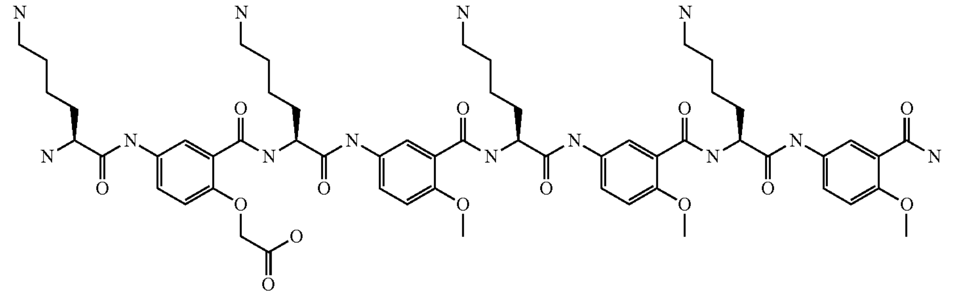 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OCC(=O)O)ccc3OC)ccc2OC)cc1C(N)=O] |
| 120 | 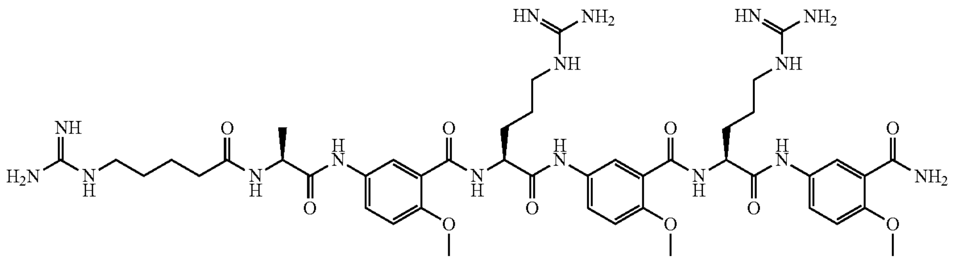 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](C)NC(=O)CCCCNC(=N)N)ccc3OC)ccc2OC)cc1C(N)=O] |
| 121 | 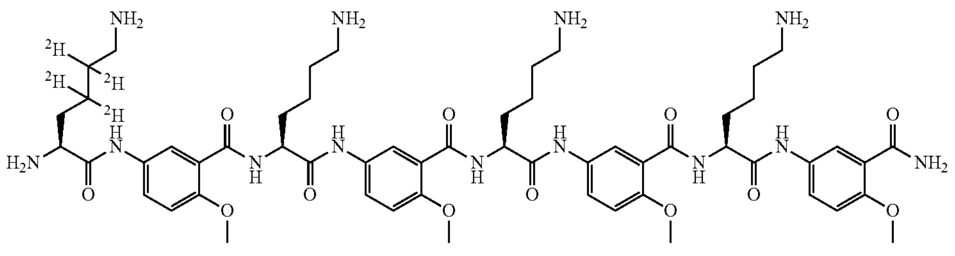 [SMILES: [2H]C([2H])(CN)C([2H])([2H])C[C@H](N)C(=O)Nc1ccc(OC)c(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(N)=O)c4)c3)c2)c1] |

TABLE 1-continued
| Compd. No. | Structure |
|---|---|
| 122 | 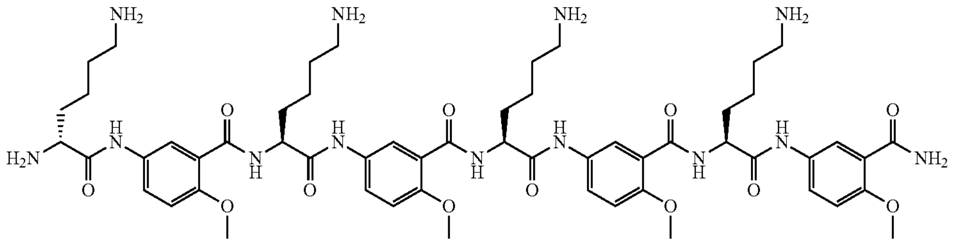 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](N)CCCCN)ccc4OC)ccc3OC)ccc2OC)cc1C(N)=O] |
| 123 | 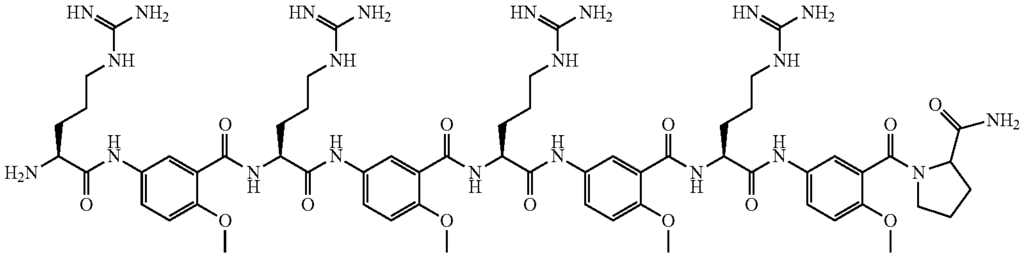 [SMILES: COc1ccc(NC(=O)[C@H](CCCNC(=N)N)NC(=O)c2cc(NC(=O)[C@@H](N)CCCNC(=N)N)ccc2OC)cc1C(=O)N[C@@H](CCCNC(=N)N)C(=O)Nc1ccc(OC)c(C(=O)N[C@@H](CCCNC(=N)N)C(=O)Nc2ccc(OC)c(C(=O)N3CCCC3C(N)=O)c2)c1] |
| 124 | 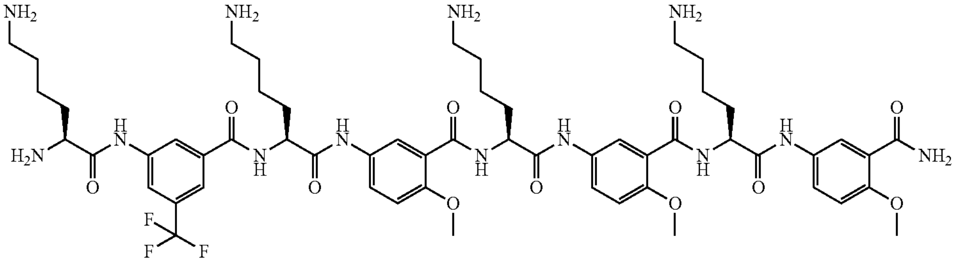 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)cc(C(F)(F)F)c4)ccc3OC)ccc2OC)cc1C(N)=O] |
| 125 | 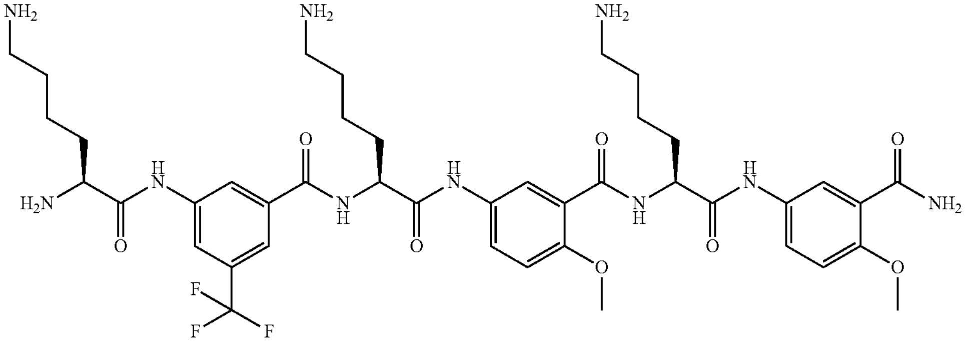 [SMILES: COc1ccc(NC(=O)[C@H](CCCCN)NC(=O)c2cc(NC(=O)[C@H](CCCCN)NC(=O)c3cc(NC(=O)[C@@H](N)CCCCN)cc(C(F)(F)F)c3)ccc2OC)cc1C(N)=O] |
| 126 | 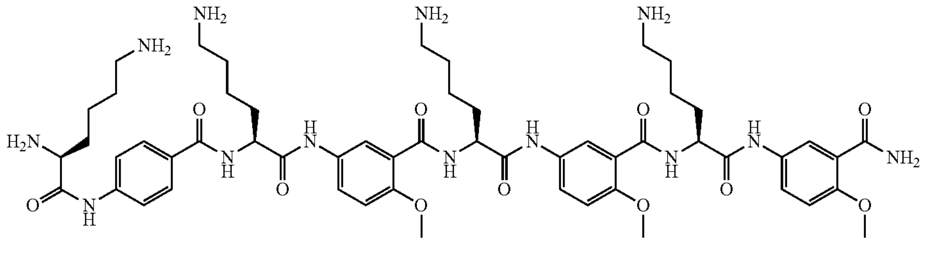 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4ccc(NC(=O)[C@@H](N)CCCCN)cc4)ccc3OC)ccc2OC)cc1C(N)=O] |

TABLE 1-continued
| Compd. No. | Structure |
|---|---|
| 127 | 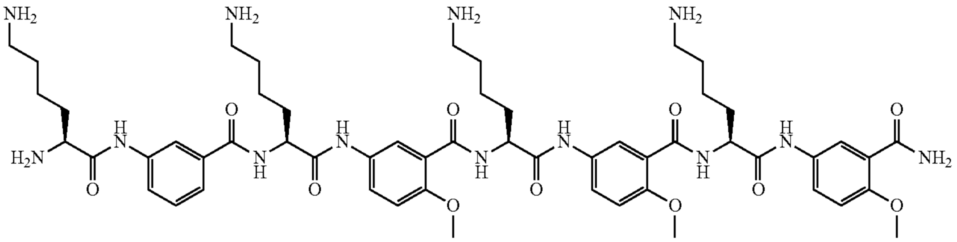 |
| 128 | 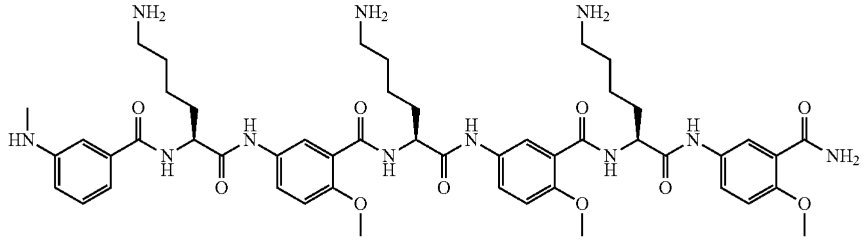 [SMILES: CNc1cccc(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(N)=O)c4)c3)c2)c1] |
| 129 | 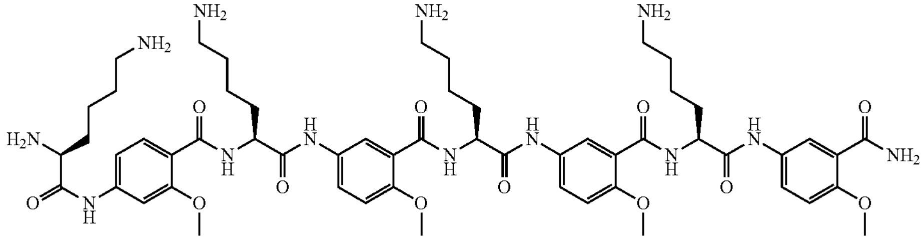 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4ccc(NC(=O)[C@@H](N)CCCCN)cc4OC)ccc3OC)ccc2OC)cc1C(N)=O] |
| 130 | 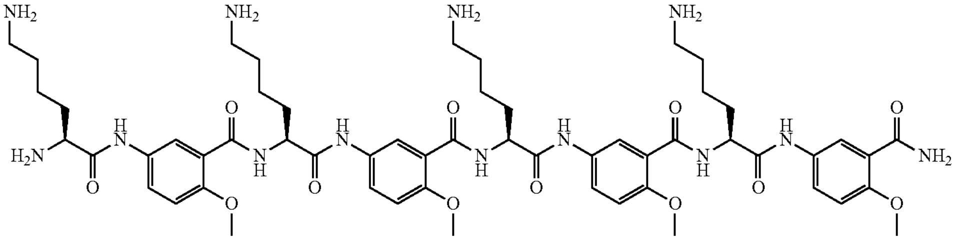 |
| 131 | 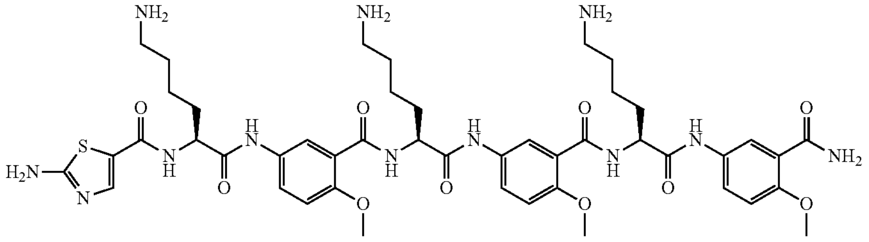 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cnc(N)s4)ccc3OC)ccc2OC)cc1C(N)=O] |
| 132 | 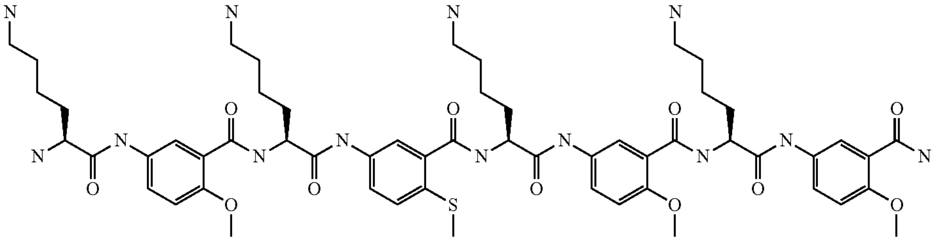 |

TABLE 1-continued
| Compd. No. | Structure |
|---|---|
| 133 | 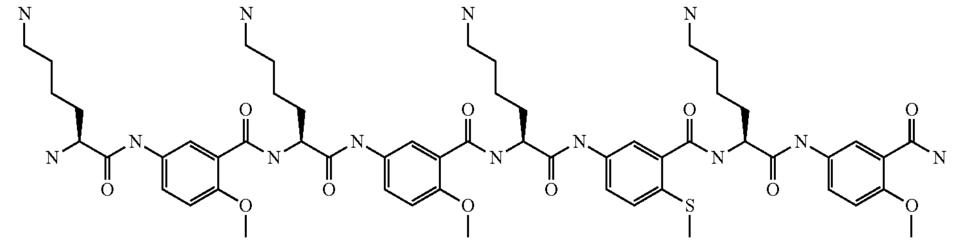 |
| 134 | 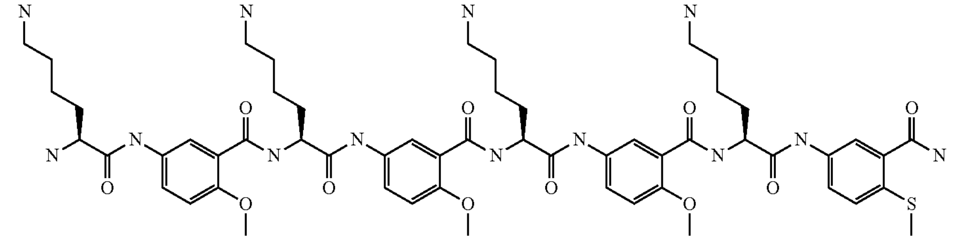 |
| 135 | 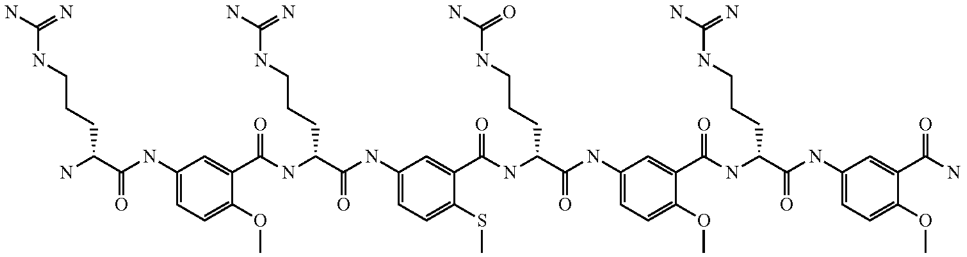 |
| 136 | 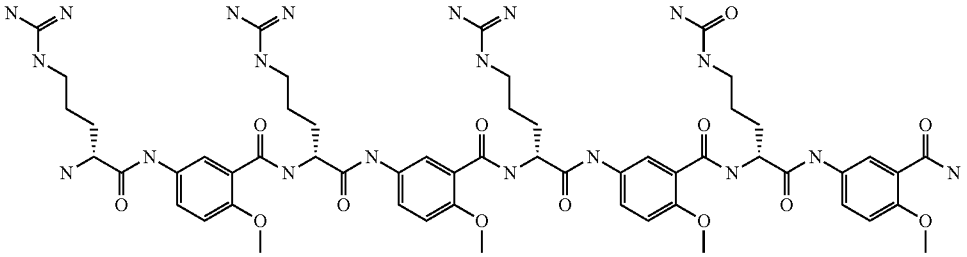 [SMILES: COc1ccc(NC(=O)[C@@H](CCCNC(N)=O)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 137 | 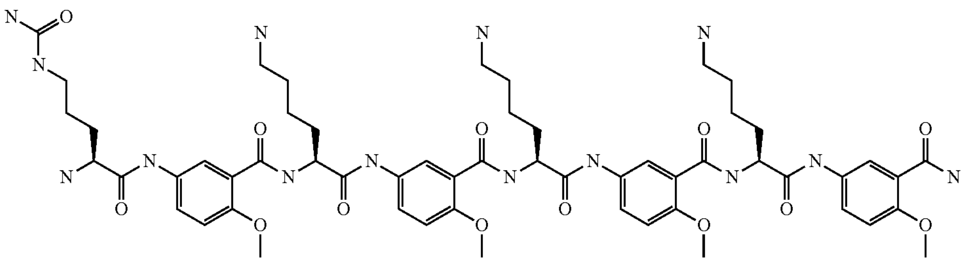 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCNC(N)=O)ccc4OC)ccc3OC)ccc2OC)cc1C(N)=O] |
| 138 | 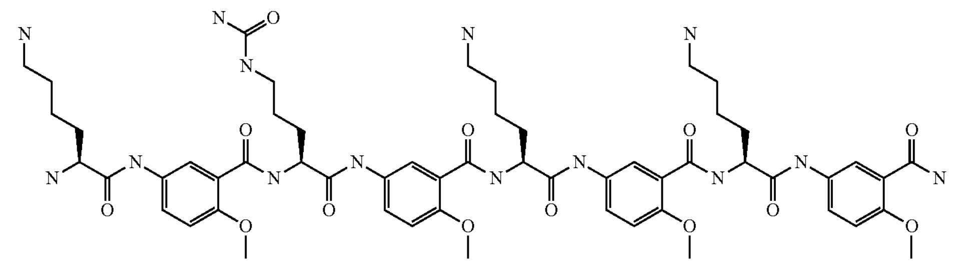 [SMILES: COc1ccc(NC(=O)[C@H](CCCCN)NC(=O)c2cc(NC(=O)[C@H](CCCCN)NC(=O)c3cc(NC(=O)[C@H](CCCNC(N)=O)NC(=O)c4cc(NC(=O)[C@@H](N)CCCCN)ccc4OC)ccc3OC)ccc2OC)cc1C(N)=O] |

TABLE 1-continued
| Compd. No. | Structure |
| --- | --- |
| 139 | 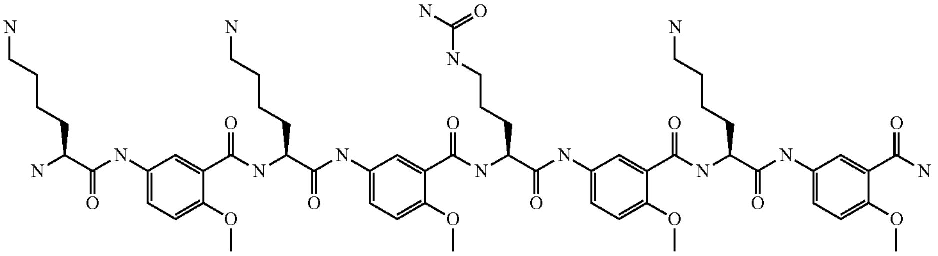 [SMILES: COc1ccc(NC(=O)[C@H](CCCCN)NC(=O)c2cc(NC(=O)[C@H](CCCNC(N)=O)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 140 | 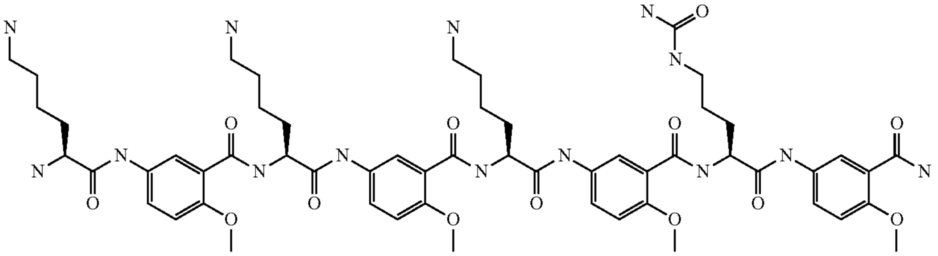 [SMILES: COc1ccc(NC(=O)[C@H](CCCNC(N)=O)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 141 | 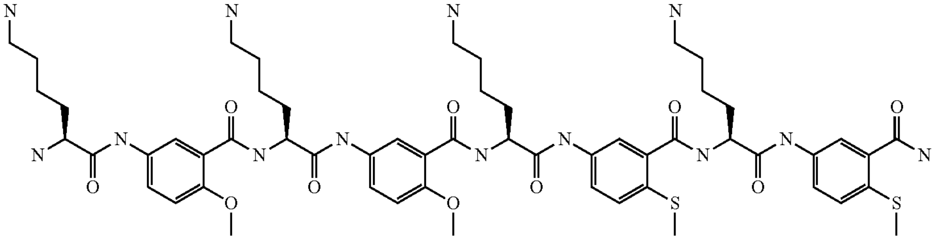 |
| 142 | 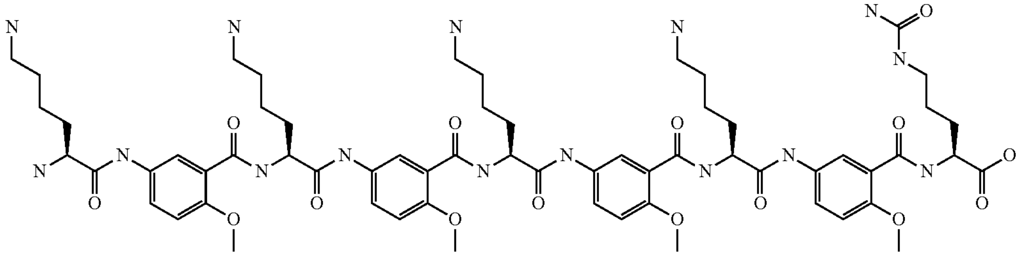 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](CCCNC(N)=O)C(=O)O] |
| 143 | 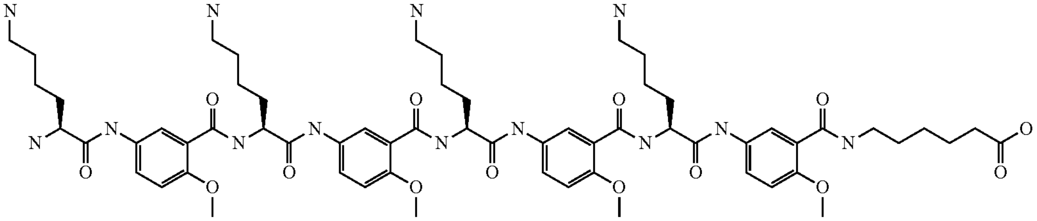 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)NCCCCCC(=O)O] |
| 144 | 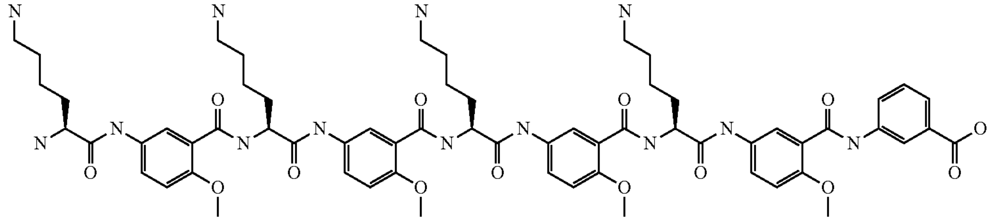 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)Nc1cccc(C(=O)O)c1] |

TABLE 1-continued

| Compd. No. | Structure |
|---|---|
| 145 | 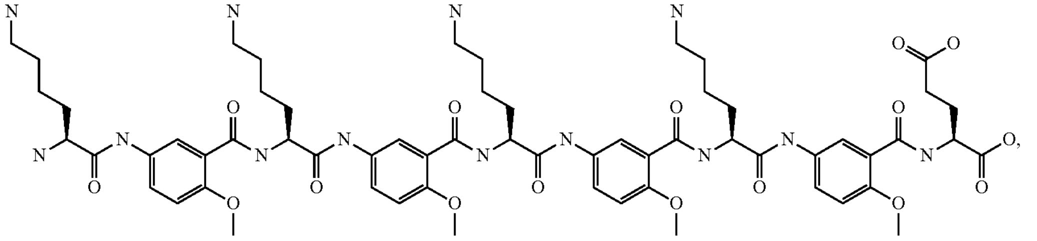 or |
| 146 | 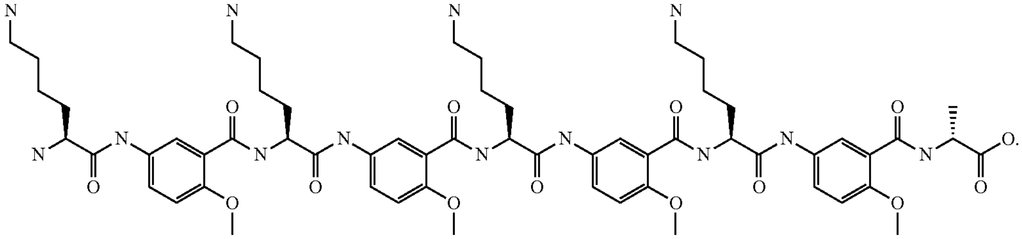 |

The exemplary compounds (and/or their salts) in Table 1 were prepared by methods such as those reported in U.S. Patent Application Publication Nos. U.S. 2005/0287108, U.S. 2006/0041023, U.S. Pat. No. 7,173,102, WO 2005/123660, WO 2004/082643, WO 2006/093813, and U.S. patent application Ser. No. 12/510,593 filed Jul. 28, 2009.

The present invention also provides methods of treating and/or preventing mucositis in a mammal comprising administering to the mammal in need thereof a therapeutically effective amount of a compound chosen from Table 2:

TABLE 2

| Compound Number | Compound Structure |
|---|---|
| 201 | 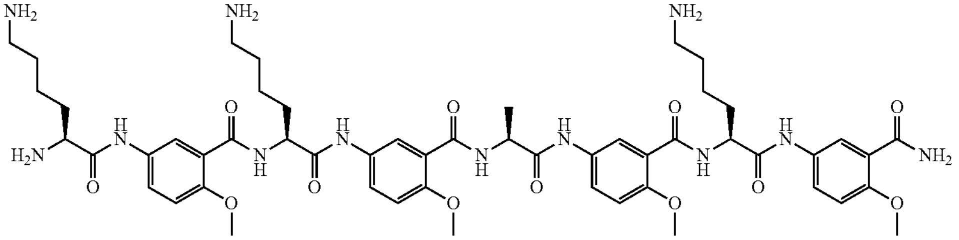 [SMILES: COc1ccc(NC(=O)[C@H](CCCCN)NC(=O)c2cc(NC(=O)[C@H](C)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 202 | 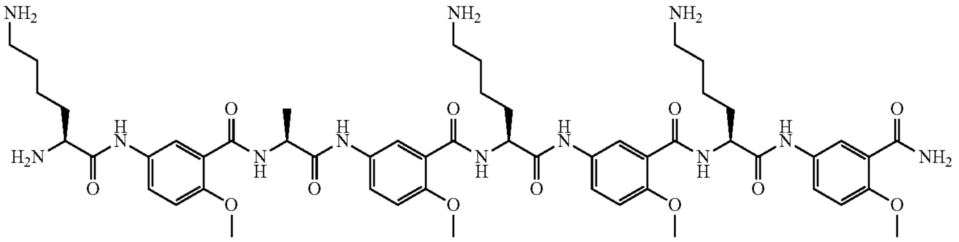 [SMILES: COc1ccc(NC(=O)[C@H](CCCCN)NC(=O)c2cc(NC(=O)[C@H](CCCCN)NC(=O)c3cc(NC(=O)[C@H](C)NC(=O)c4cc(NC(=O)[C@@H](N)CCCCN)ccc4OC)ccc3OC)ccc2OC)cc1C(N)=O] |
| 203 | 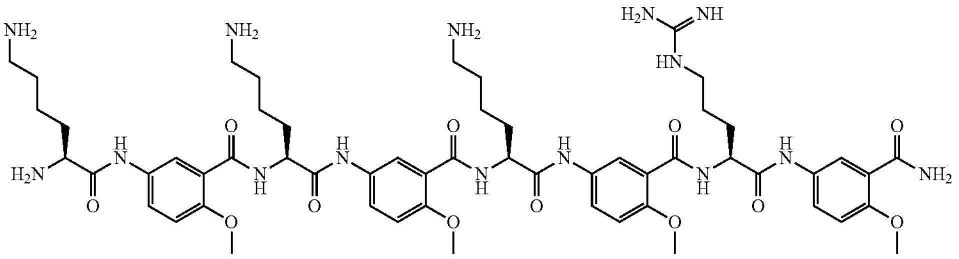 [SMILES: COc1ccc(NC(=O)[C@H](CCCNC(=N)N)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |

TABLE 2-continued
| Compound Number | Compound Structure |
| --- | --- |
| 204 | 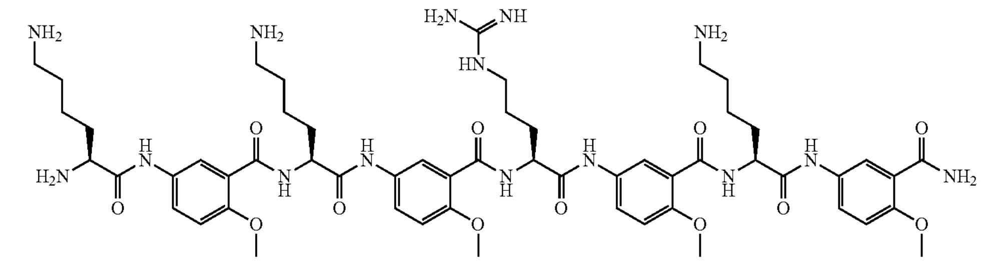 [SMILES: COc1ccc(NC(=O)[C@H](CCCCN)NC(=O)c2cc(NC(=O)[C@H](CCCNC(=N)N)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 205 | 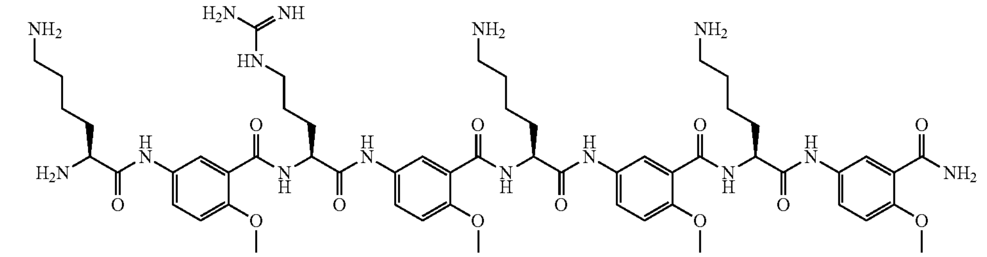 [SMILES: COc1ccc(NC(=O)[C@H](CCCCN)NC(=O)c2cc(NC(=O)[C@H](CCCCN)NC(=O)c3cc(NC(=O)[C@H](CCCNC(=N)N)NC(=O)c4cc(NC(=O)[C@@H](N)CCCCN)ccc4OC)ccc3OC)ccc2OC)cc1C(N)=O] |
| 206 | 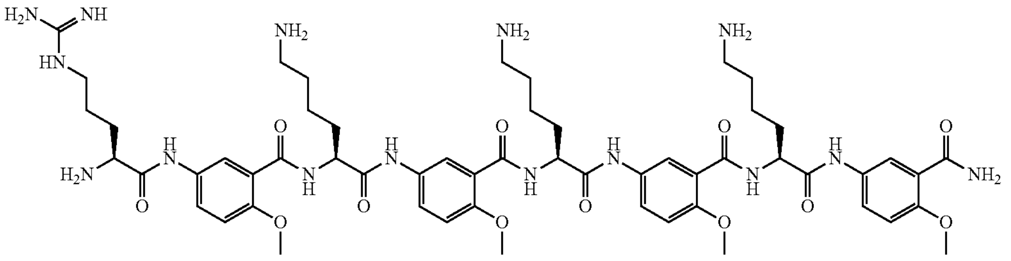 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCNC(=N)N)ccc4OC)ccc3OC)ccc2OC)cc1C(N)=O] |
| 207 | 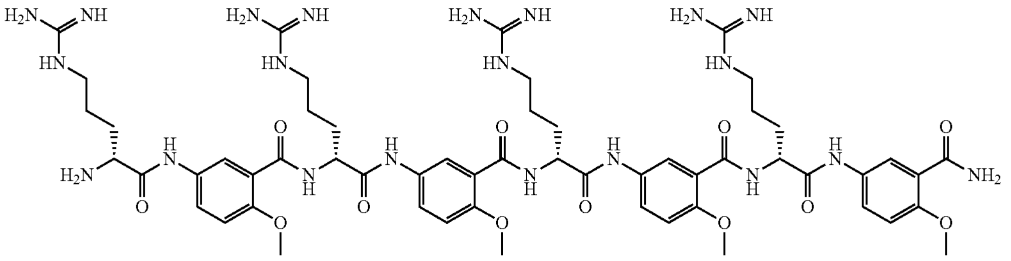 |
| 208 | 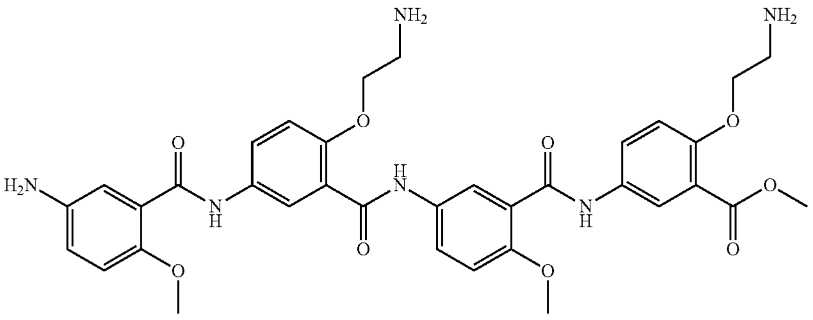 [SMILES: COC(=O)c1cc(NC(=O)c2cc(NC(=O)c3cc(NC(=O)c4cc(N)ccc4OC)ccc3OCCN)ccc2OC)ccc1OCCN] |

TABLE 2-continued
| Compound Number | Compound Structure |
|---|---|
| 209 | 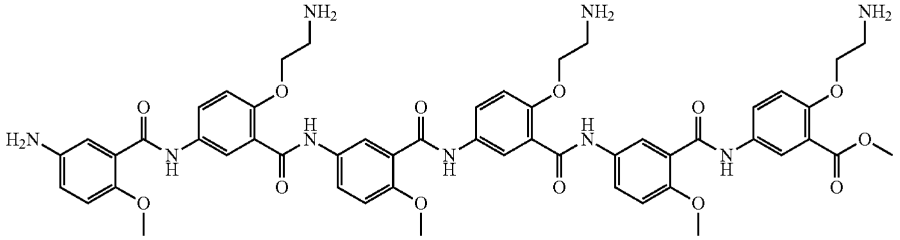 [SMILES: COC(=O)c1cc(NC(=O)c2cc(NC(=O)c3cc(NC(=O)c4cc(NC(=O)c5cc(NC(=O)c6cc(N)ccc6OC)ccc5OCCN)ccc4OC)ccc3OCCN)ccc2OC)ccc1OCCN] |
| 210 | 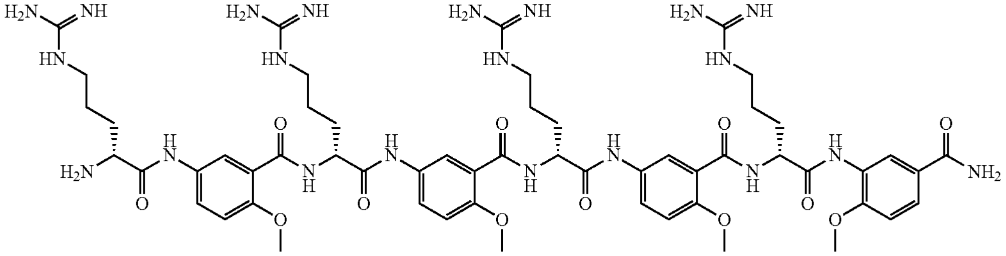 [SMILES: COc1ccc(C(N)=O)cc1NC(=O)[C@@H](CCCNC(=N)N)NC(=O)c1cc(NC(=O)[C@@H](CCCNC(=N)N)NC(=O)c2cc(NC(=O)[C@@H](CCCNC(=N)N)NC(=O)c3cc(NC(=O)[C@H](N)CCCNC(=N)N)ccc3OC)ccc2OC)ccc1OC] |
| 211 | 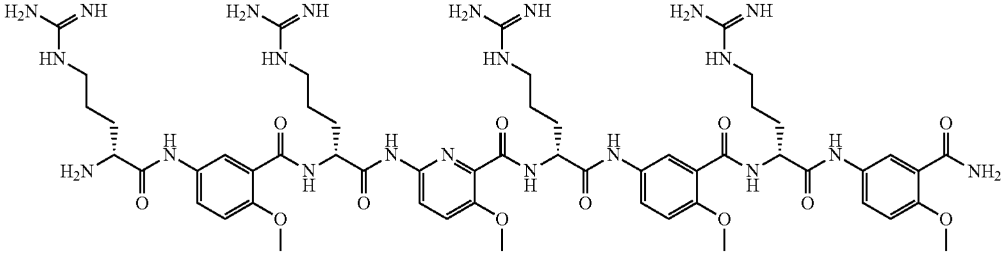 [SMILES: COc1ccc(NC(=O)[C@@H](CCCNC(=N)N)NC(=O)c2cc(NC(=O)[C@@H](CCCNC(=N)N)NC(=O)c3nc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 212 | 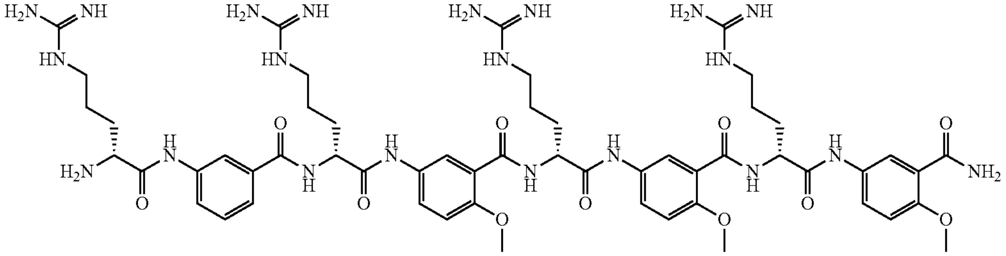 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cccc(NC(=O)[C@H](N)CCCNC(=N)N)c4)ccc3OC)ccc2OC)cc1C(N)=O] |
| 213 | 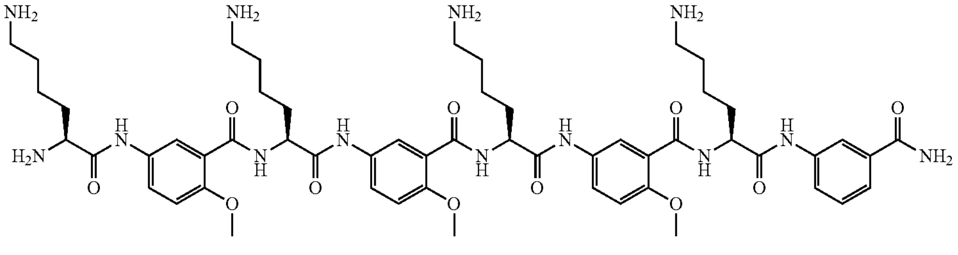 [SMILES: COc1ccc(NC(=O)[C@H](CCCCN)NC(=O)c2cc(NC(=O)[C@H](CCCCN)NC(=O)c3cc(NC(=O)[C@@H](N)CCCCN)ccc3OC)ccc2OC)cc1C(=O)N[C@@H](CCCCN)C(=O)Nc1cccc(C(N)=O)c1] |
| 214 | 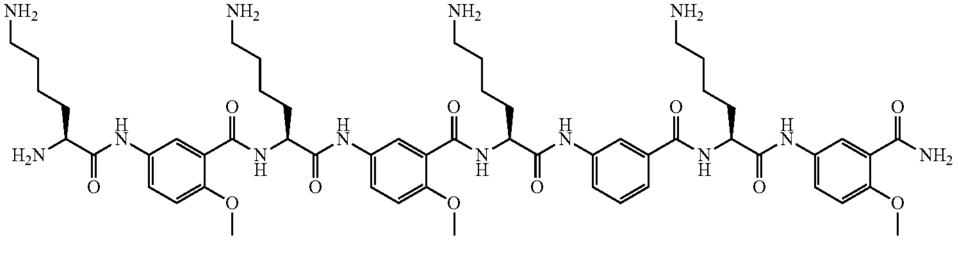 [SMILES: COc1ccc(NC(=O)[C@H](CCCCN)NC(=O)c2cccc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)c2)cc1C(N)=O] |

TABLE 2-continued
| Compound Number | Compound Structure |
| --- | --- |
| 215 | 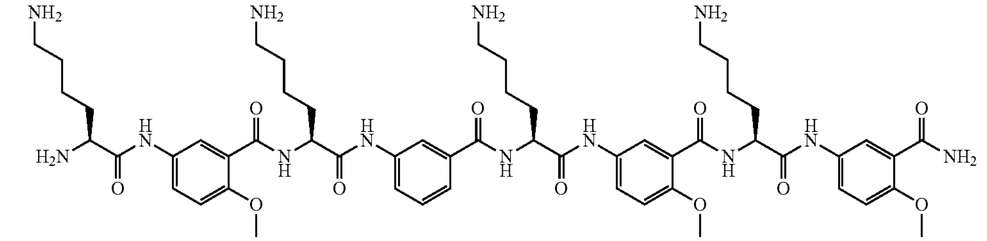 [SMILES: COc1ccc(NC(=O)[C@H](CCCCN)NC(=O)c2cc(NC(=O)[C@H](CCCCN)NC(=O)c3cccc(NC(=O)[C@H](CCCCN)NC(=O)c4cc(NC(=O)[C@@H](N)CCCCN)ccc4OC)c3)ccc2OC)cc1C(N)=O] |
| 216 | 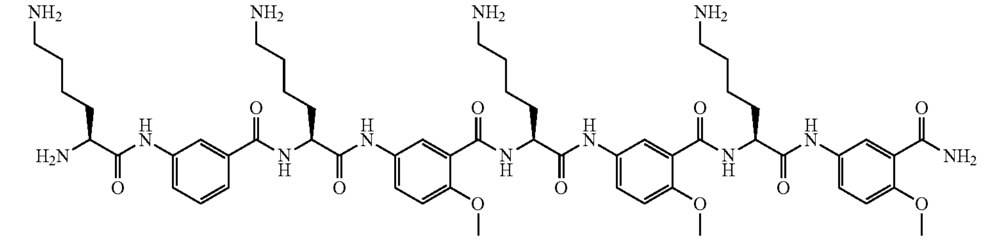 |
| 217 | 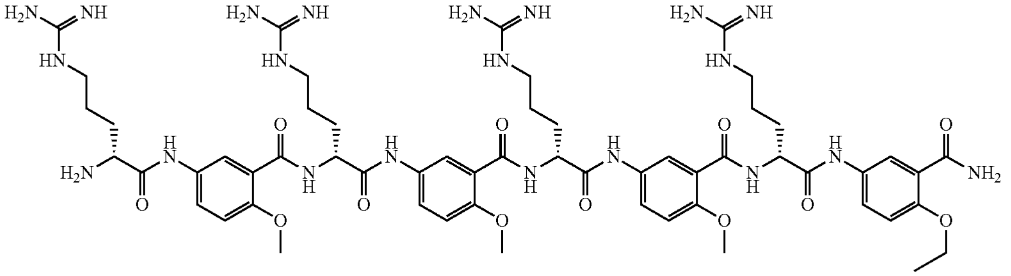 [SMILES: CCOc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 218 | 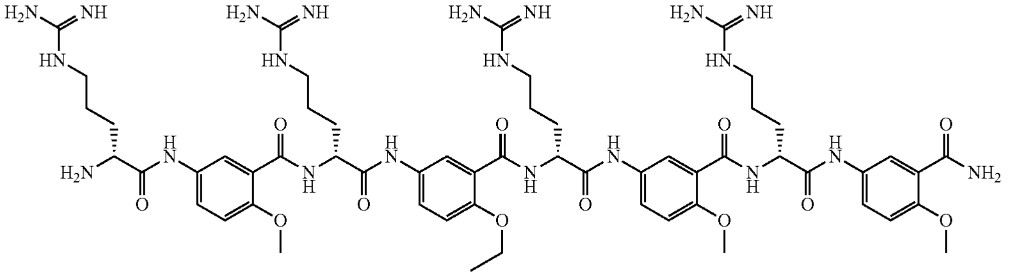 [SMILES: CCOc1ccc(NC(=O)[C@@H](CCCNC(=N)N)NC(=O)c2cc(NC(=O)[C@H](N)CCCNC(=N)N)ccc2OC)cc1C(=O)N[C@H](CCCNC(=N)N)C(=O)Nc1ccc(OC)c(C(=O)N[C@H](CCCNC(=N)N)C(=O)Nc2ccc(OC)c(C(N)=O)c2)c1] |
| 219 | 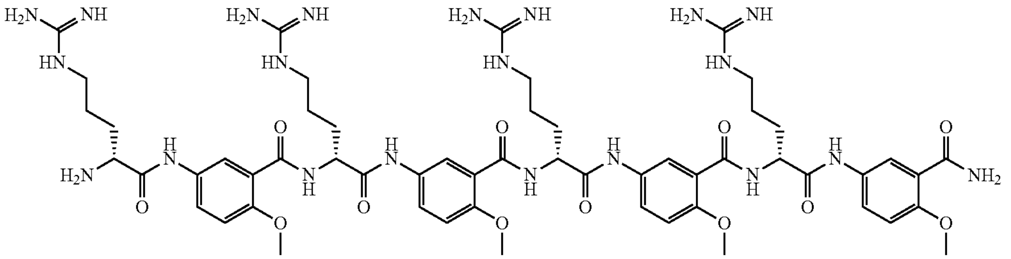 |

TABLE 2-continued
| Compound Number | Compound Structure |
|---|---|
| 220 | 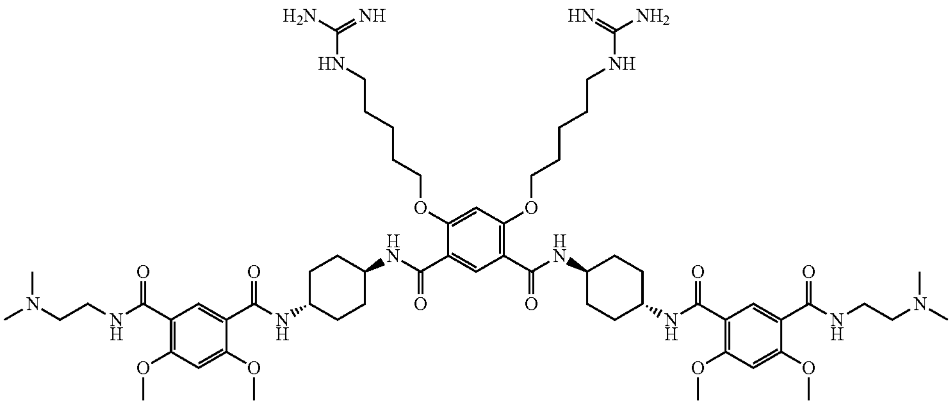 |
| 221 | 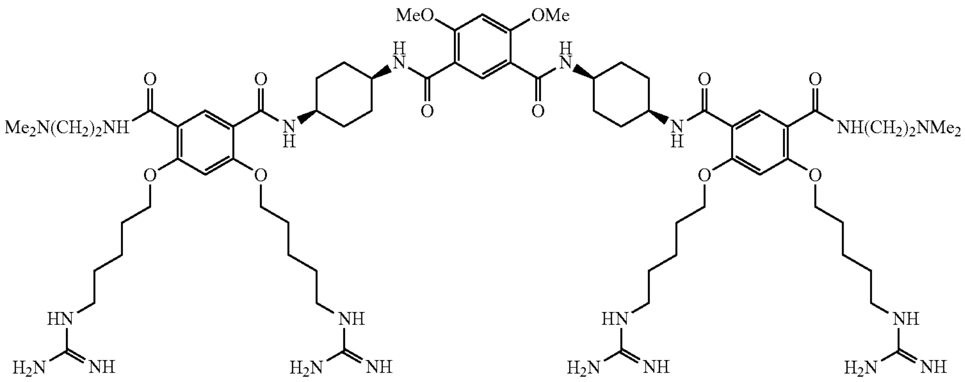 |
| 222 | 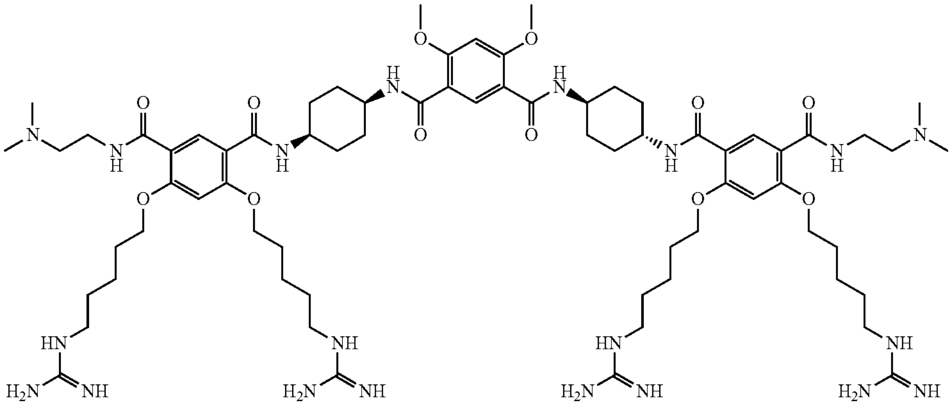 |
| 223 | 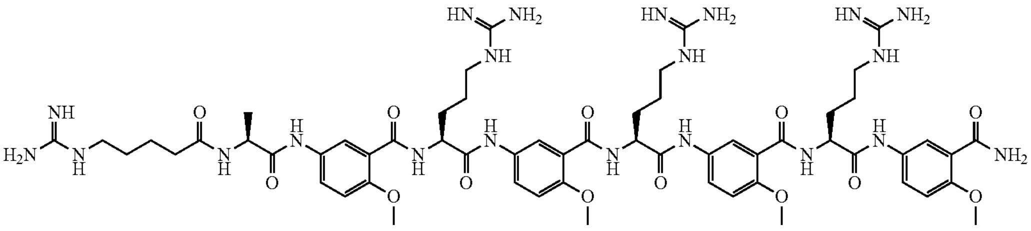 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@H](C)NC(=O)CCCCNC(=N)N)ccc4OC)ccc3OC)ccc2OC)cc1C(N)=O] |

TABLE 2-continued
| Compound Number | Compound Structure |
|---|---|
| 224 | 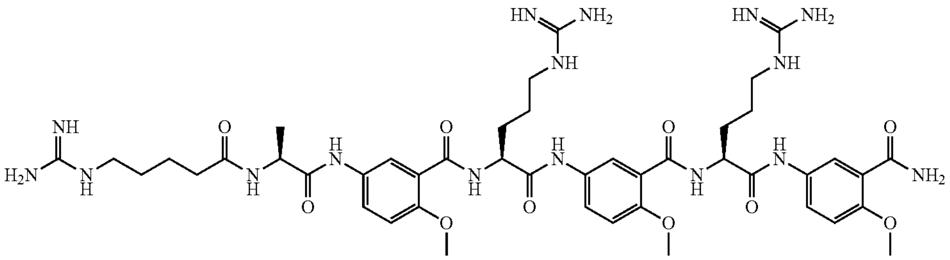 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](C)NC(=O)CCCCNC(=N)N)ccc3OC)ccc2OC)cc1C(N)=O] |
| 225 | 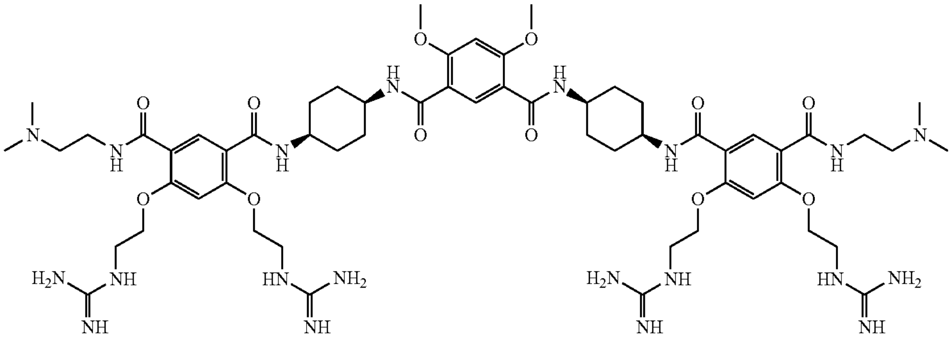 |
| 226 | 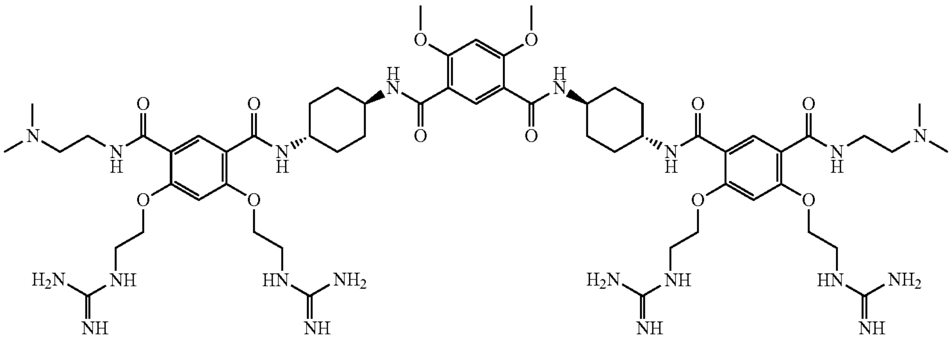 |
| 227 | 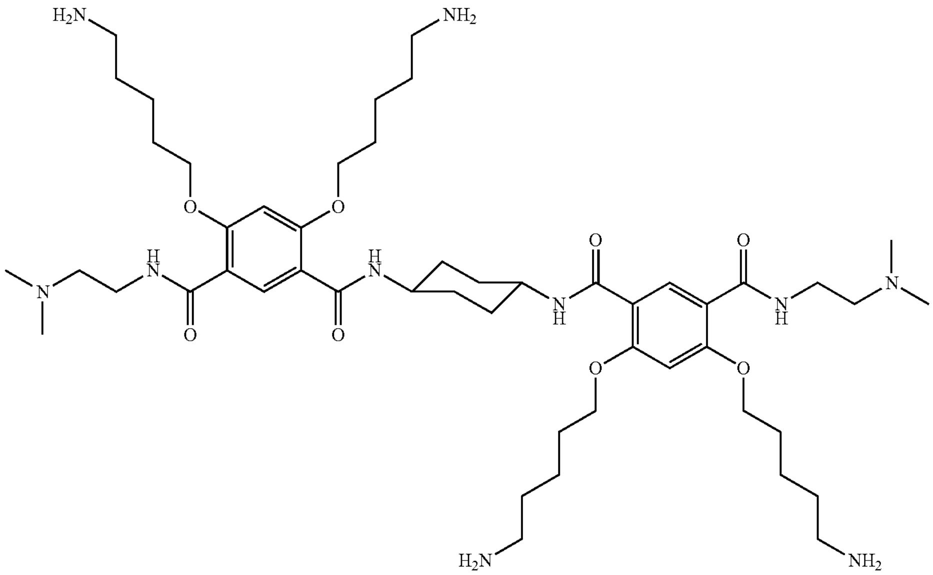 |

TABLE 2-continued
| Compound Number | Compound Structure |
|---|---|
| 228 | 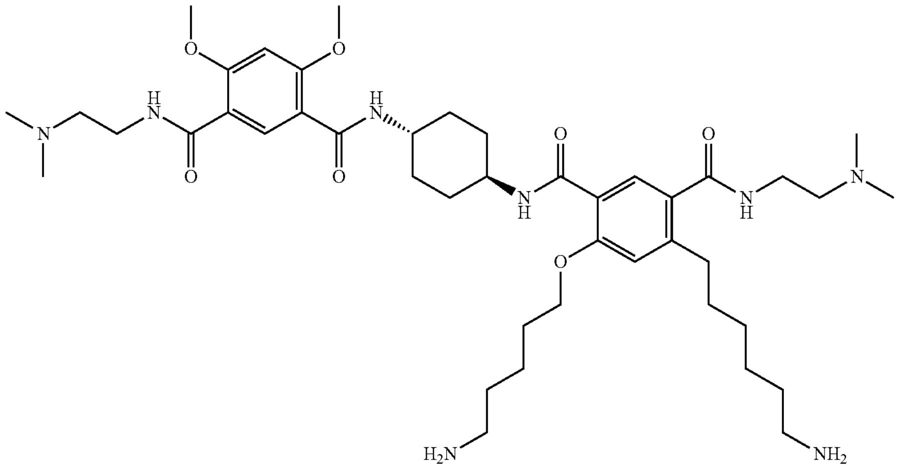 |
| 229 | 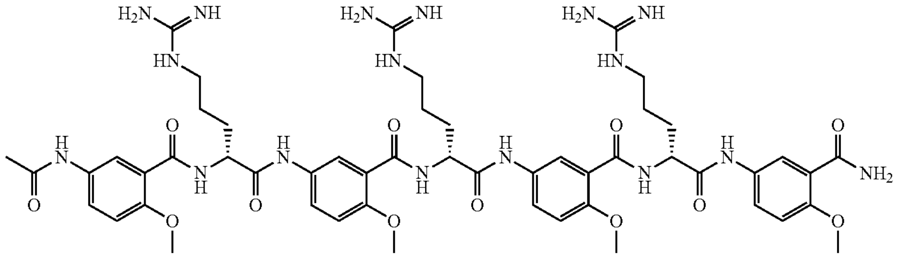 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OC)cc1C(N)=O] |
| 230 | 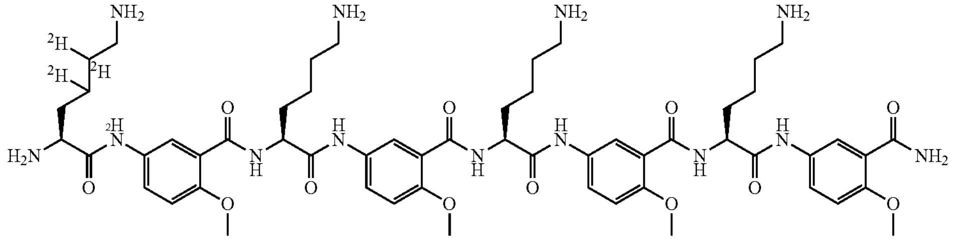 |
| 231 | 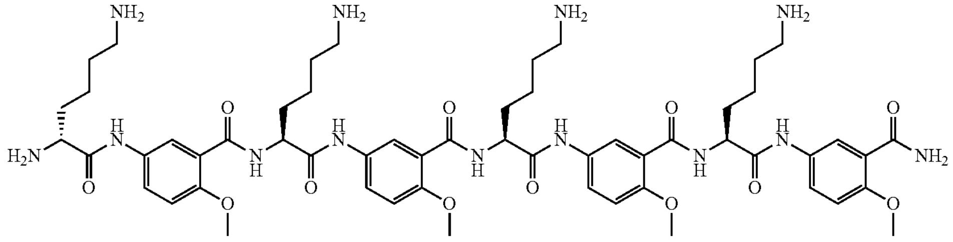 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](N)CCCCN)ccc4OC)ccc3OC)ccc2OC)cc1C(N)=O] |
| 232 | 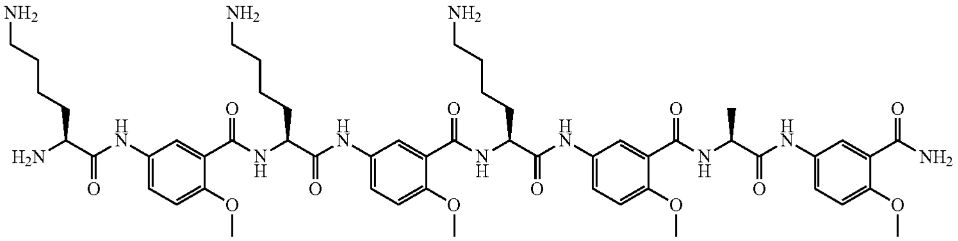 [SMILES: COc1ccc(NC(=O)[C@H](C)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |

TABLE 2-continued
| Compound Number | Compound Structure |
|---|---|
| 233 | 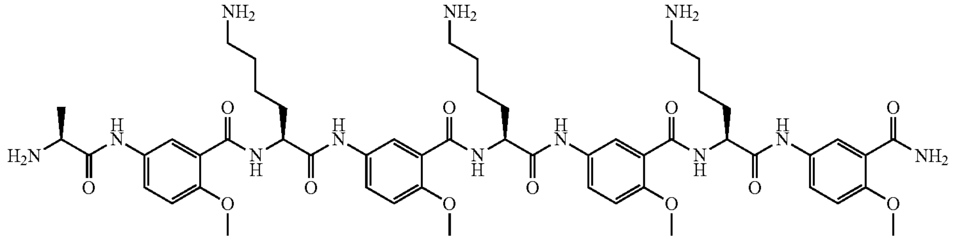 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](C)N)ccc4OC)ccc3OC)ccc2OC)cc1C(N)=O] |
| 234 | 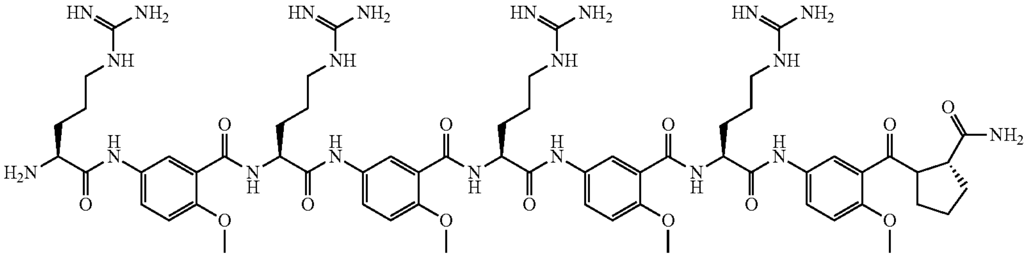 |
| 235 | 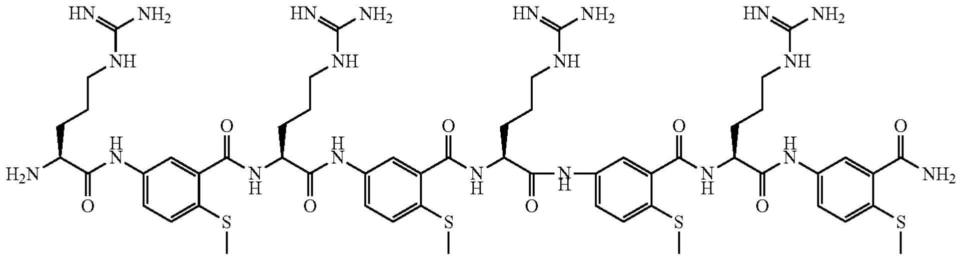 |
| 236 | 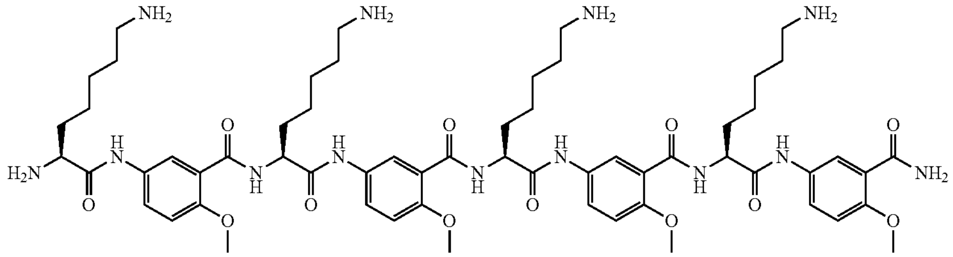 [SMILES: COc1ccc(NC(=O)[C@H](CCCCCN)NC(=O)c2cc(NC(=O)[C@H](CCCCCN)NC(=O)c3cc(NC(=O)[C@H](CCCCCN)NC(=O)c4cc(NC(=O)[C@@H](N)CCCCCN)ccc4OC)ccc3OC)ccc2OC)cc1C(N)=O] |
| 237 | 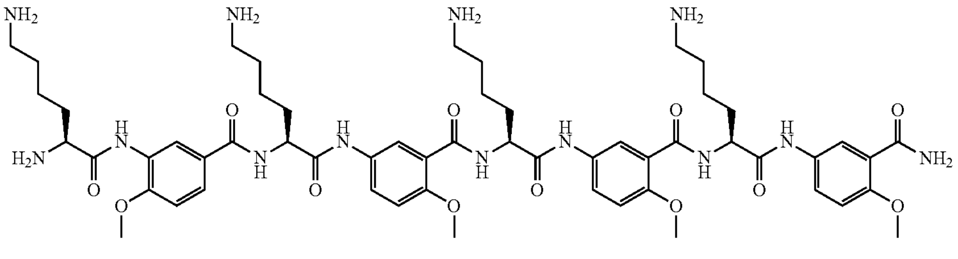 [SMILES: COc1ccc(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(N)=O)c4)c3)c2)cc1NC(=O)[C@@H](N)CCCCN] |
| 238 | 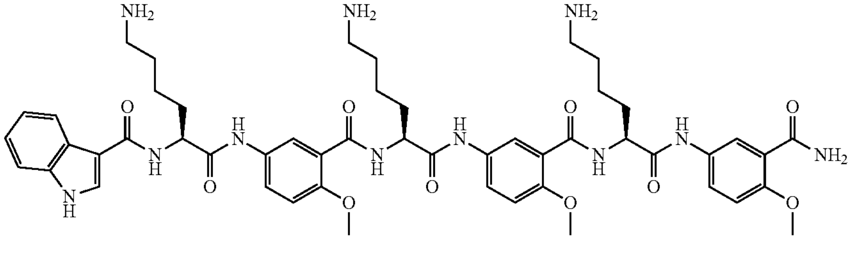 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4c[nH]c5ccccc45)ccc3OC)ccc2OC)cc1C(N)=O] |

TABLE 2-continued
| Compound Number | Compound Structure |
| --- | --- |
| 239 | 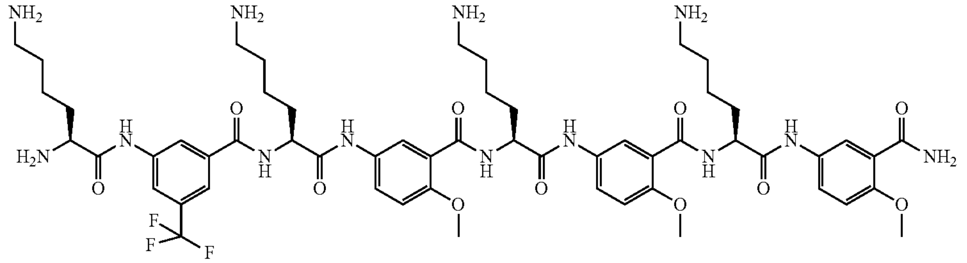 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)cc(C(F)(F)F)c4)ccc3OC)ccc2OC)cc1C(N)=O] |
| 240 | 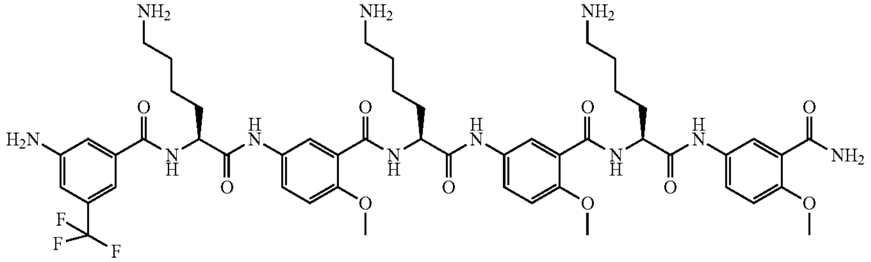 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(N)cc(C(F)(F)F)c4)ccc3OC)ccc2OC)cc1C(N)=O] |
| 241 | 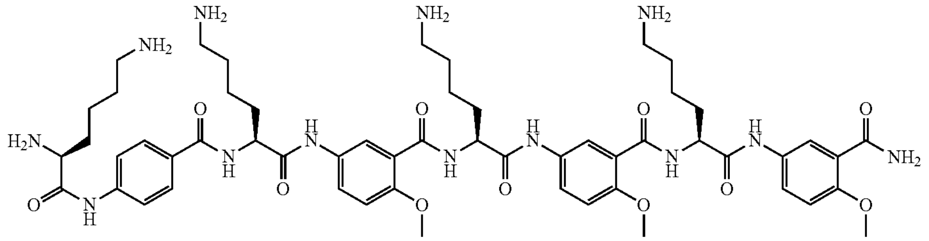 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4ccc(NC(=O)[C@@H](N)CCCCN)cc4)ccc3OC)ccc2OC)cc1C(N)=O] |
| 242 | 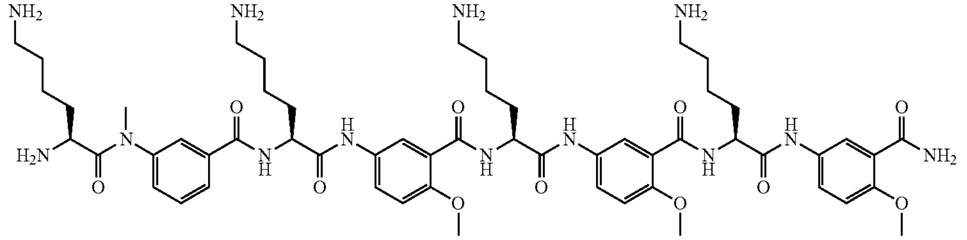 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cccc(N(C)C(=O)[C@@H](N)CCCCN)c4)ccc3OC)ccc2OC)cc1C(N)=O] |
| 243 | 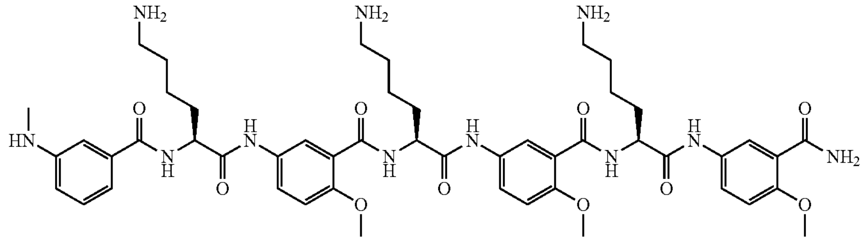 [SMILES: CNc1cccc(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(N)=O)c4)c3)c2)c1] |
| 244 | 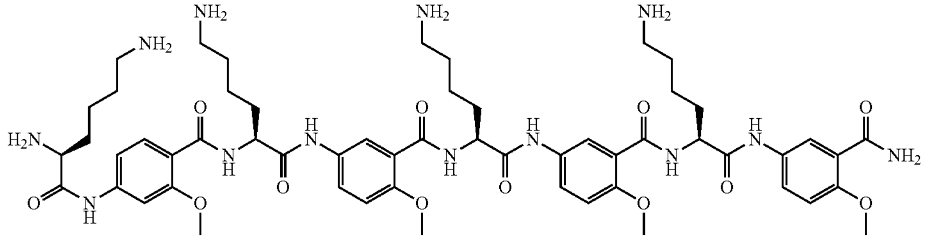 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4ccc(NC(=O)[C@@H](N)CCCCN)cc4OC)ccc3OC)ccc2OC)cc1C(N)=O] |

TABLE 2-continued
| Compound Number | Compound Structure |
|---|---|
| 245 | 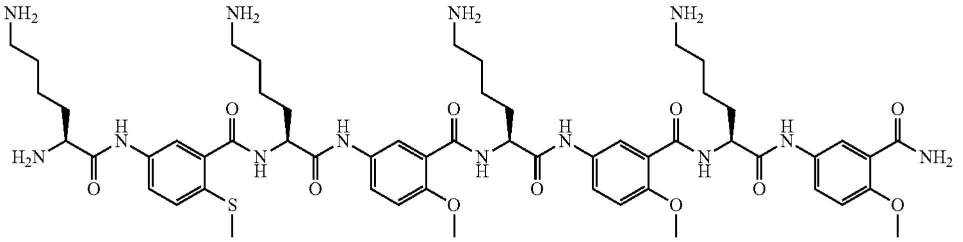 |
| 246 | 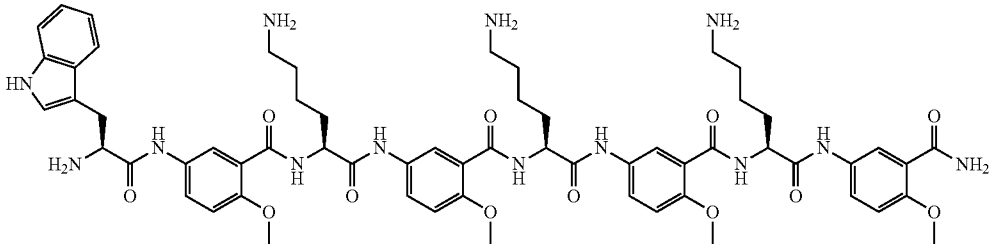 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)Cc5c[nH]c6ccccc56)ccc4OC)ccc3OC)ccc2OC)cc1C(N)=O] |
| 247 | 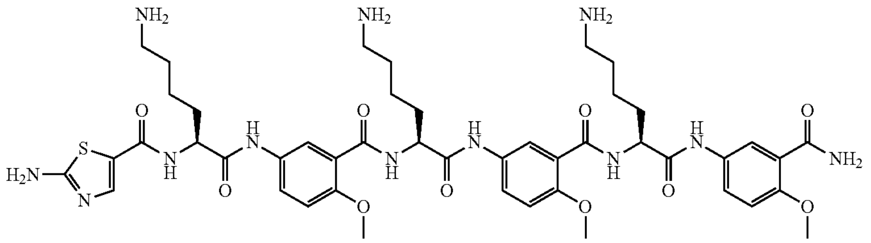 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cnc(N)s4)ccc3OC)ccc2OC)cc1C(N)=O] |
| 248 | 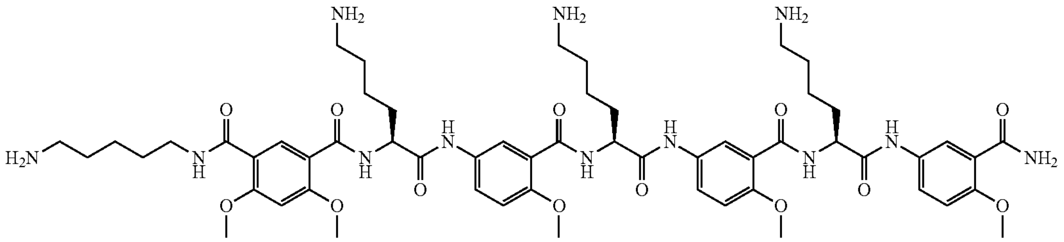 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(C(=O)NCCCCCN)c(OC)cc4OC)ccc3OC)ccc2OC)cc1C(N)=O] |
| 249 | 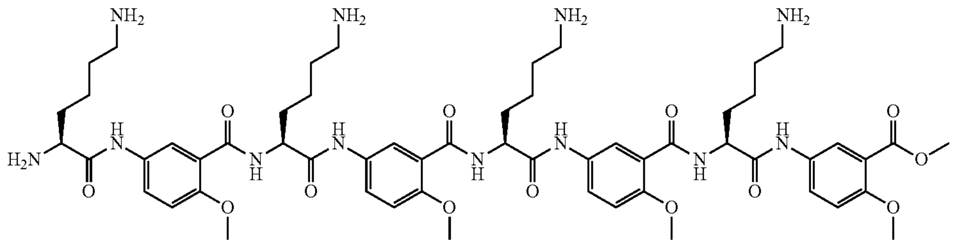 [SMILES: COC(=O)c1cc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)ccc1OC] |
| 250 | 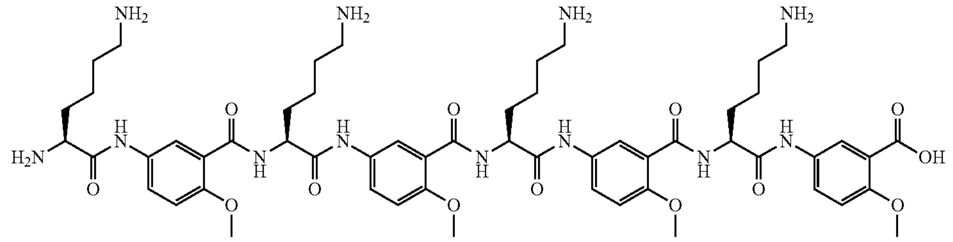 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)O] |

TABLE 2-continued
| Compound Number | Compound Structure |
|---|---|
| 251 | 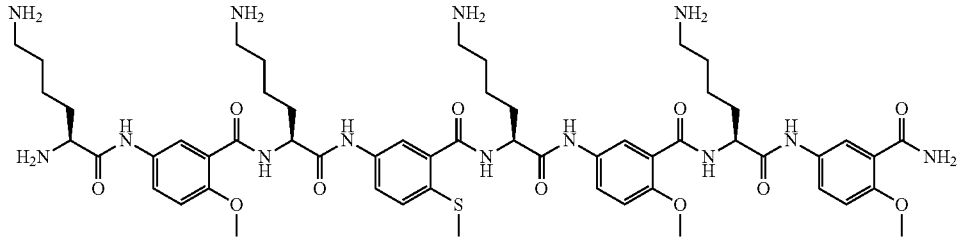 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3SC)ccc2OC)cc1C(N)=O] |
| 252 | 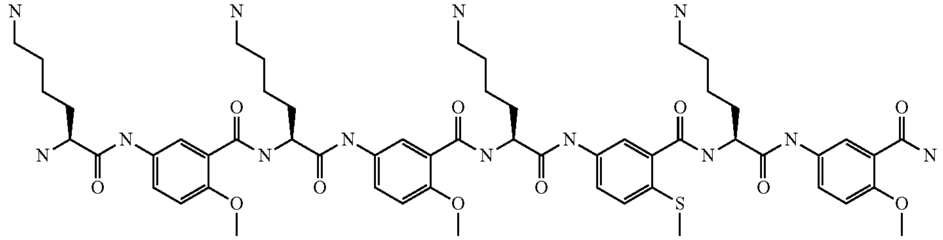 |
| 253 | 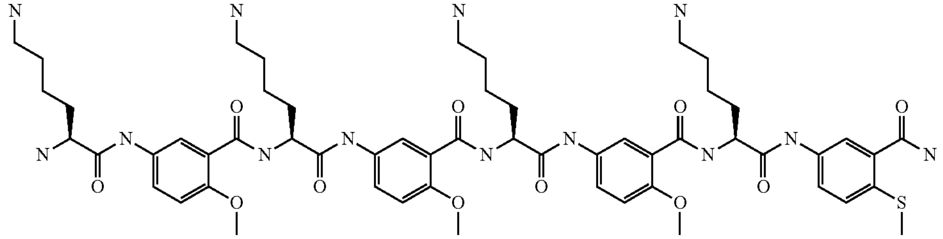 |
| 254 | 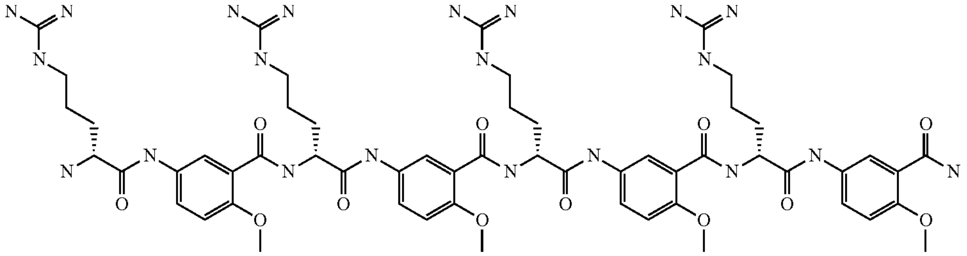 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 255 | 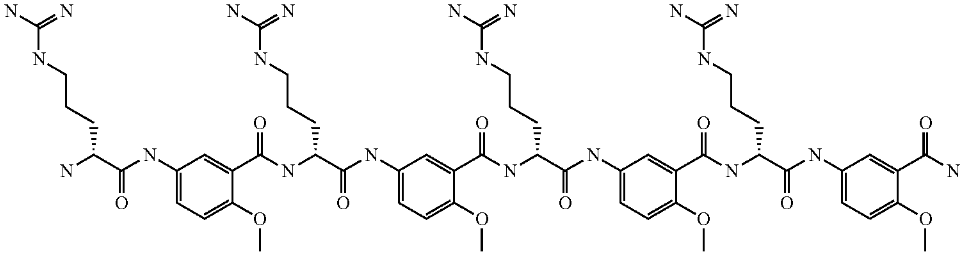 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 256 | 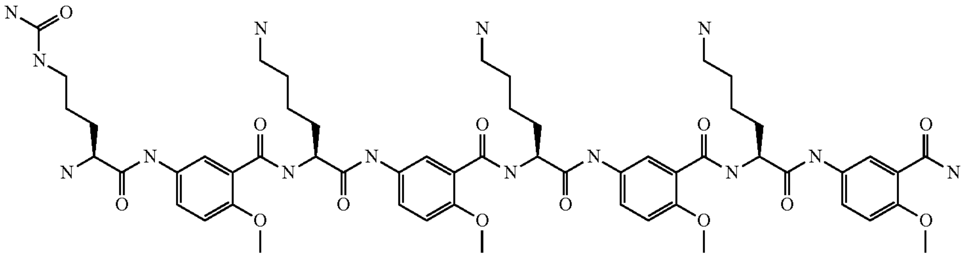 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCNC(N)=O)ccc4OC)ccc3OC)ccc2OC)cc1C(N)=O] |

TABLE 2-continued
| Compound Number | Compound Structure |
|---|---|
| 257 | 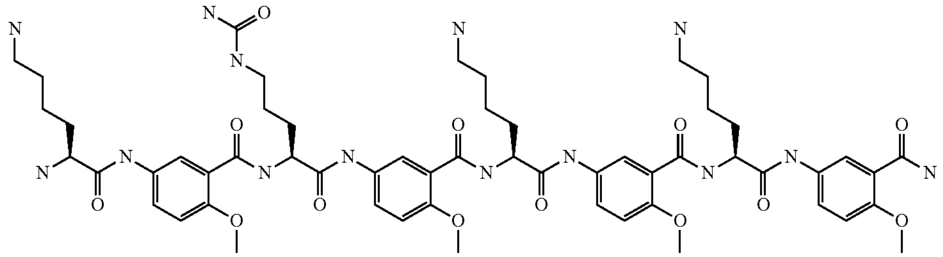 [SMILES: COc1ccc(NC(=O)[C@H](CCCCN)NC(=O)c2cc(NC(=O)[C@H](CCCCN)NC(=O)c3cc(NC(=O)[C@H](CCCNC(N)=O)NC(=O)c4cc(NC(=O)[C@@H](N)CCCCN)ccc4OC)ccc3OC)ccc2OC)cc1C(N)=O] |
| 258 | 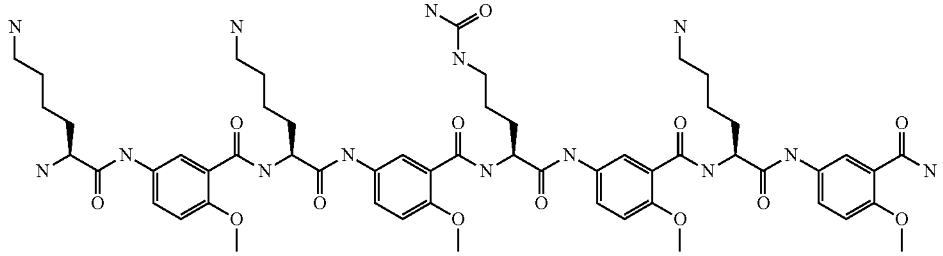 [SMILES: COc1ccc(NC(=O)[C@H](CCCCN)NC(=O)c2cc(NC(=O)[C@H](CCCNC(N)=O)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 259 | 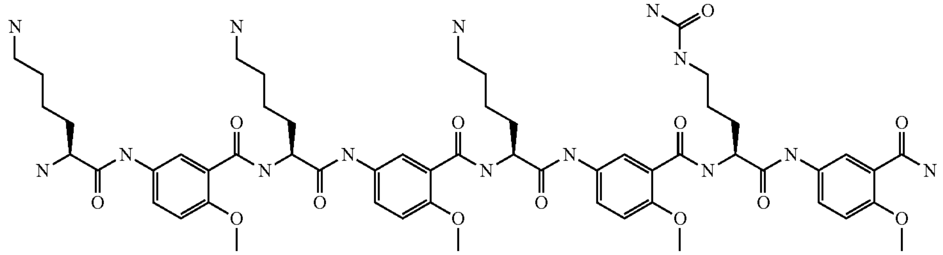 [SMILES: COc1ccc(NC(=O)[C@H](CCCNC(N)=O)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 260 | 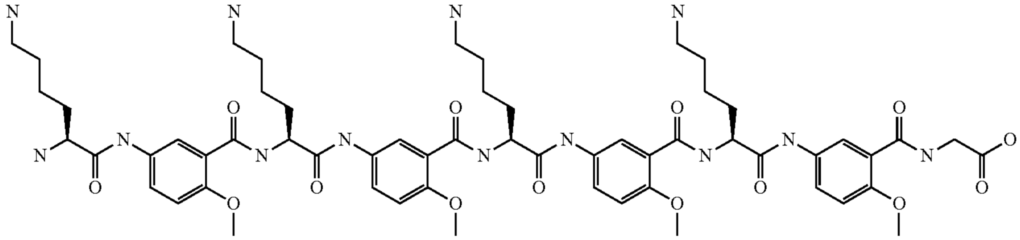 |
| 261 | 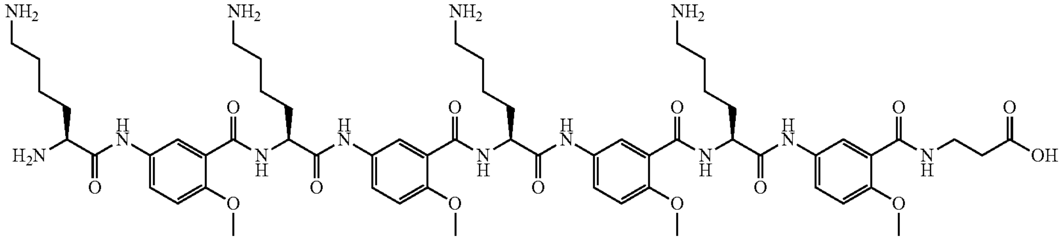 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)NCCC(=O)O] |
| 262 | 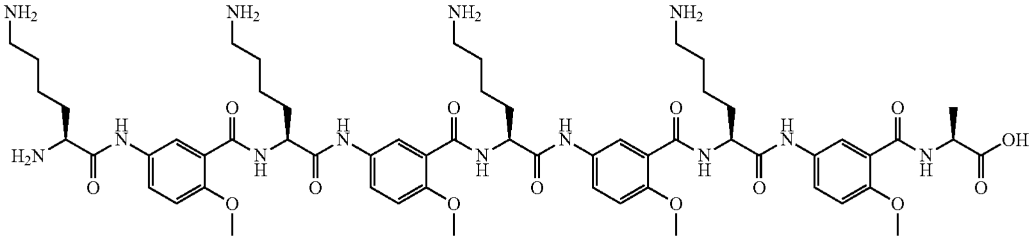 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](C)C(=O)O] |

TABLE 2-continued
| Compound Number | Compound Structure |
|---|---|
| 263 | 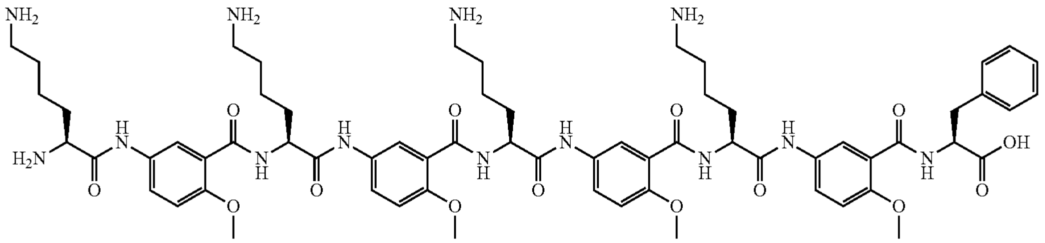 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](Cc1ccccc1)C(=O)O] |
| 264 | 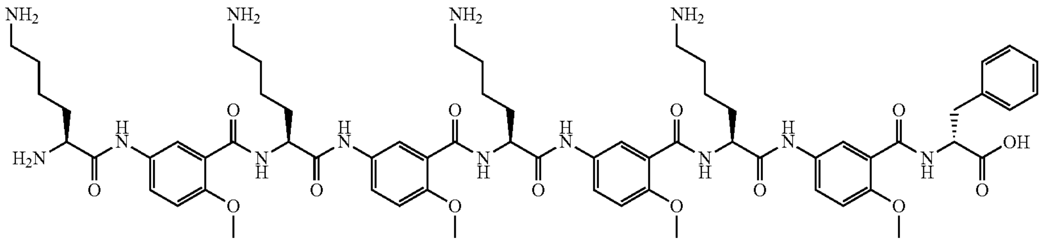 [SMILES: COc1ccc(NC(=O)[C@H](CCCCN)NC(=O)c2cc(NC(=O)[C@@H](N)CCCCN)ccc2OC)cc1C(=O)N[C@@H](CCCCN)C(=O)Nc1ccc(OC)c(C(=O)N[C@@H](CCCCN)C(=O)Nc2ccc(OC)c(C(=O)N[C@H](Cc3ccccc3)C(=O)O)c2)c1] |
| 265 | 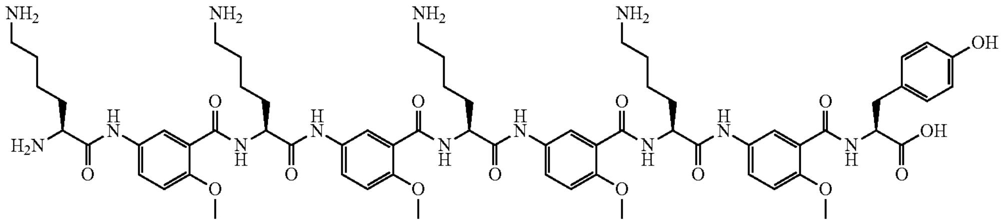 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](Cc1ccc(O)cc1)C(=O)O] |
| 266 | 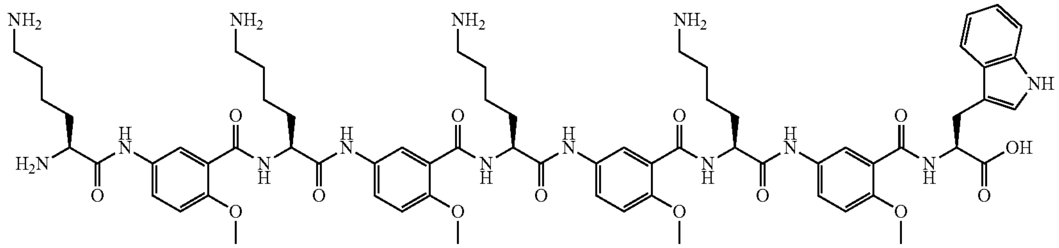 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](Cc1c[nH]c2ccccc12)C(=O)O] |
| 267 | 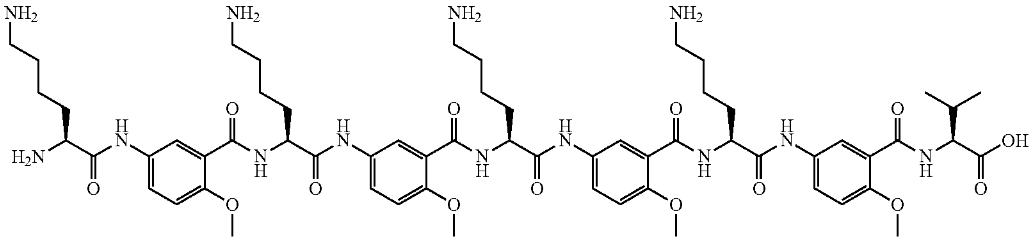 [SMILES: COc1ccc(NC(=O)[C@H](CCCCN)NC(=O)c2cc(NC(=O)[C@@H](N)CCCCN)ccc2OC)cc1C(=O)N[C@@H](CCCCN)C(=O)Nc1ccc(OC)c(C(=O)N[C@@H](CCCCN)C(=O)Nc2ccc(OC)c(C(=O)N[C@H](C(=O)O)C(C)C)c2)c1] |
| 268 | 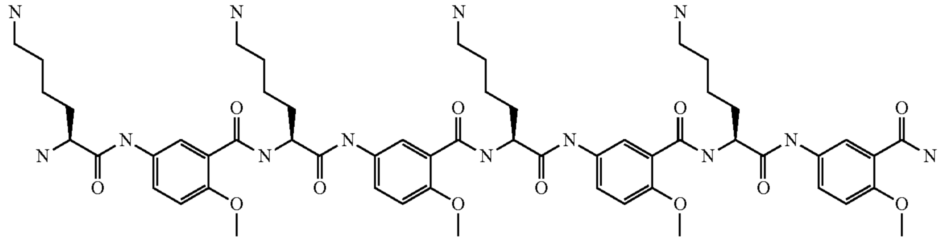 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |

TABLE 2-continued
| Compound Number | Compound Structure |
| --- | --- |
| 269 | 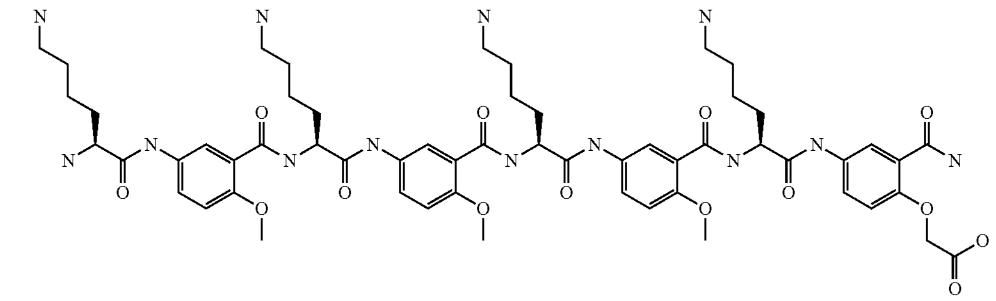 [SMILES: COc1ccc(NC(=O)[C@H](CCCCN)NC(=O)c2cc(NC(=O)[C@H](CCCCN)NC(=O)c3cc(NC(=O)[C@@H](N)CCCCN)ccc3OC)ccc2OC)cc1C(=O)N[C@@H](CCCCN)C(=O)Nc1ccc(OCC(=O)O)c(C(N)=O)c1] |
| 270 | 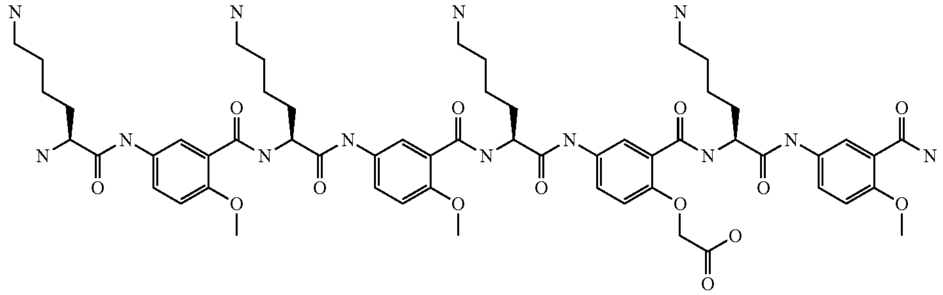 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OCC(=O)O)cc1C(N)=O] |
| 271 | 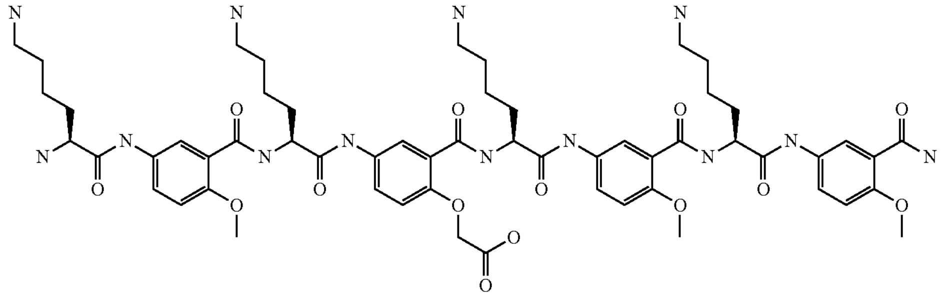 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OCC(=O)O)ccc2OC)cc1C(N)=O] |
| 272 | 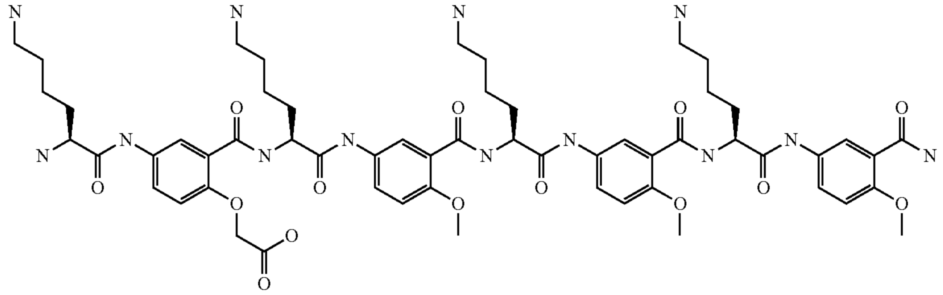 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OCC(=O)O)ccc3OC)ccc2OC)cc1C(N)=O] |
| 273 | 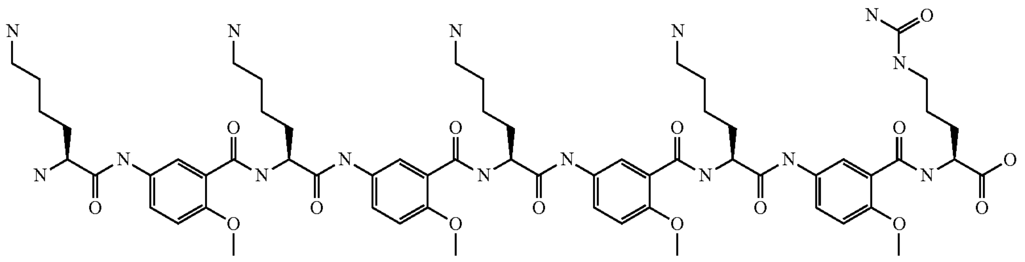 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](CCCNC(N)=O)C(=O)O] |

TABLE 2-continued
| Compound Number | Compound Structure |
|---|---|
| 274 | 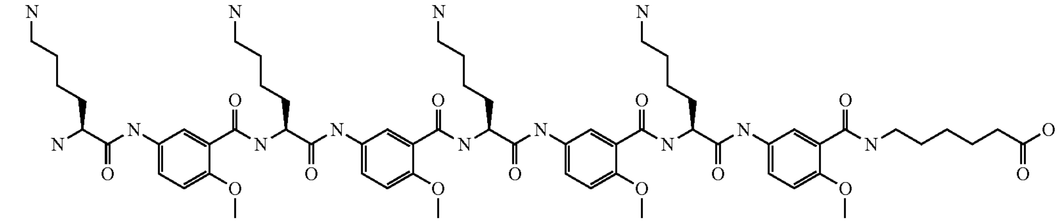 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)NCCCCCC(=O)O] |
| 275 | 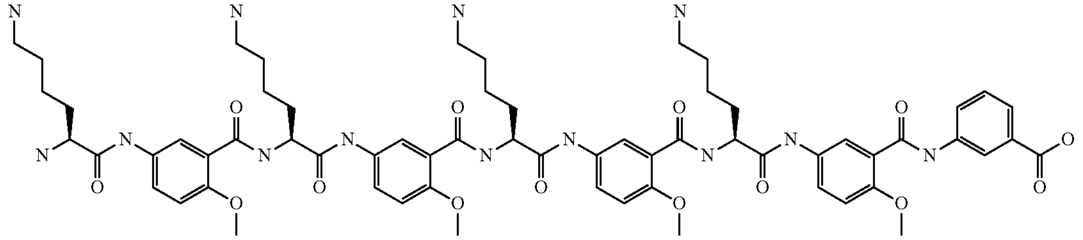 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)Nc1cccc(C(=O)O)c1] |
| 276 | 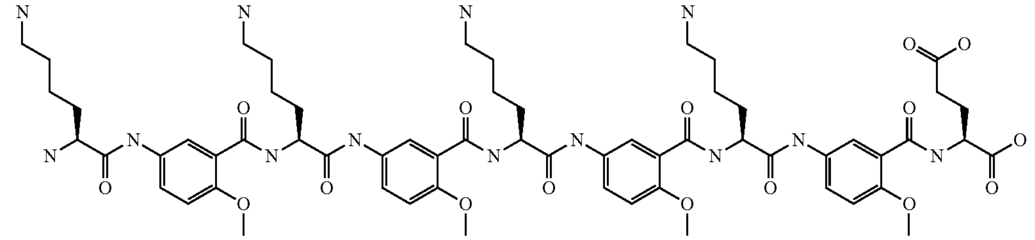 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(=O)N[C@@H](CCC(=O)O)C(=O)O] |
| 277 | 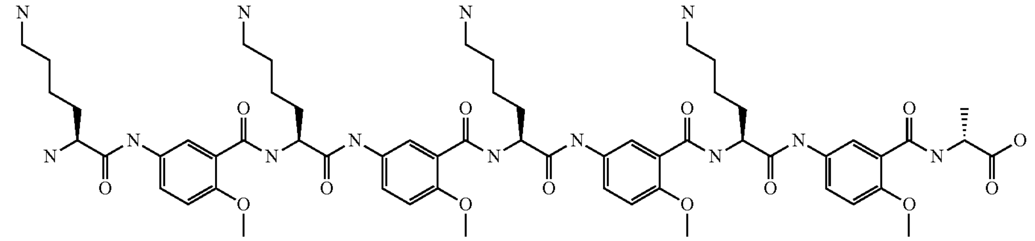 [SMILES: COc1ccc(NC(=O)[C@H](CCCCN)NC(=O)c2cc(NC(=O)[C@@H](N)CCCCN)ccc2OC)cc1C(=O)N[C@@H](CCCCN)C(=O)Nc1ccc(OC)c(C(=O)N[C@@H](CCCCN)C(=O)Nc2ccc(OC)c(C(=O)N[C@H](C)C(=O)O)c2)c1] |
| 278 | 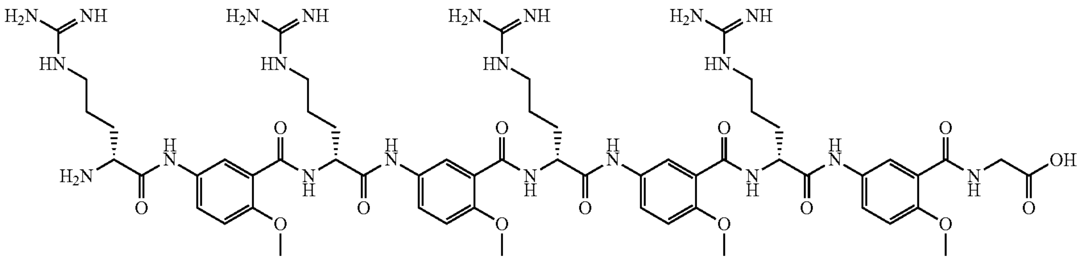 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(=O)NCC(=O)O] |
| 279 | 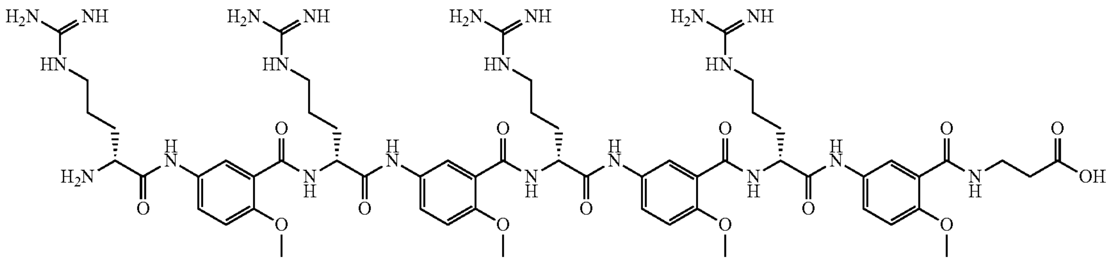 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(=O)NCCC(=O)O] |

TABLE 2-continued
| Compound Number | Compound Structure |
|---|---|
| 280 | 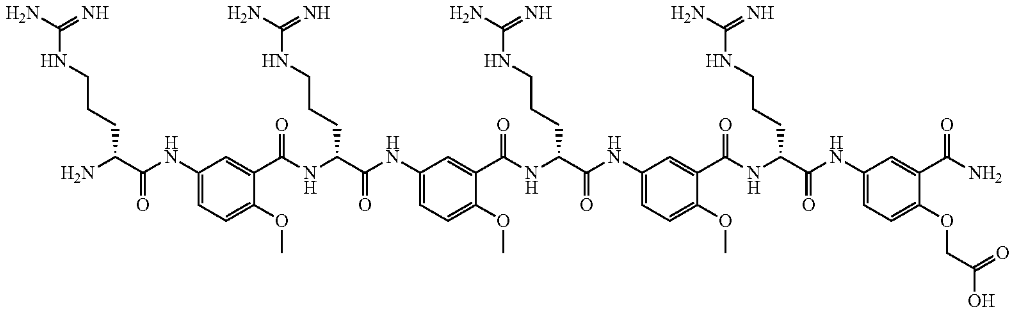 [SMILES: COc1ccc(NC(=O)[C@H](N)CCCNC(=N)N)cc1C(=O)N[C@H](CCCNC(=N)N)C(=O)Nc1ccc(OC)c(C(=O)N[C@H](CCCNC(=N)N)C(=O)Nc2ccc(OC)c(C(=O)N[C@H](CCCNC(=N)N)C(=O)Nc3ccc(OCC(=O)O)c(C(N)=O)c3)c2)c1] |
| 281 | 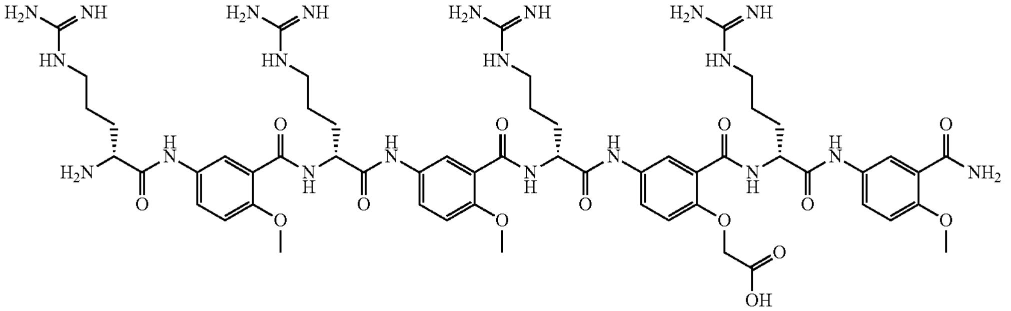 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OCC(=O)O)cc1C(N)=O] |
| 282 | 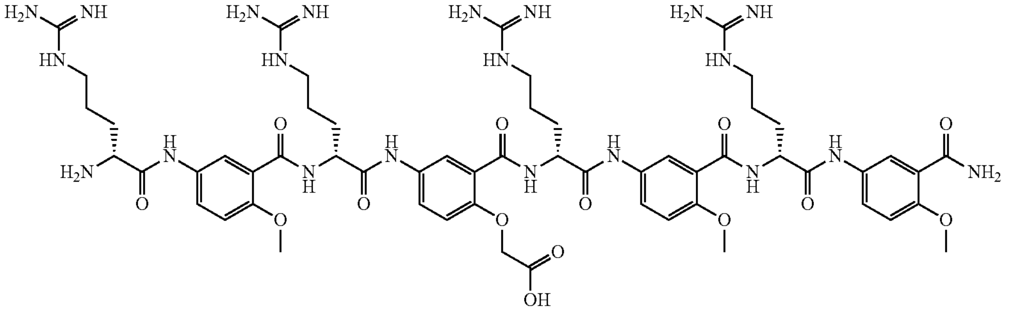 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OCC(=O)O)ccc2OC)cc1C(N)=O] |
| 283 | 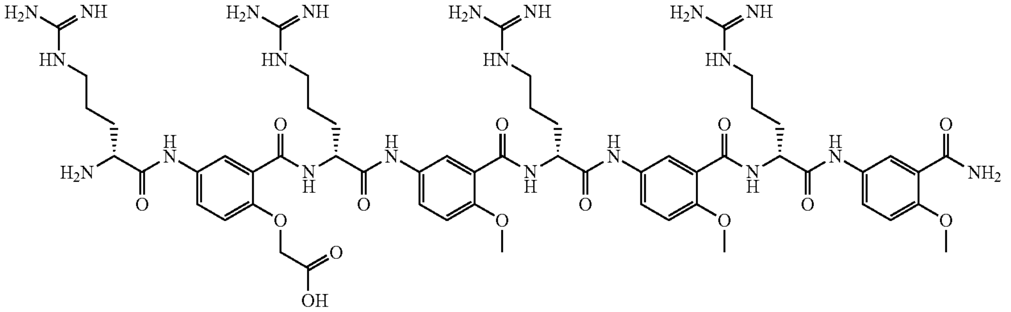 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OCC(=O)O)ccc3OC)ccc2OC)cc1C(N)=O] |
| 284 | 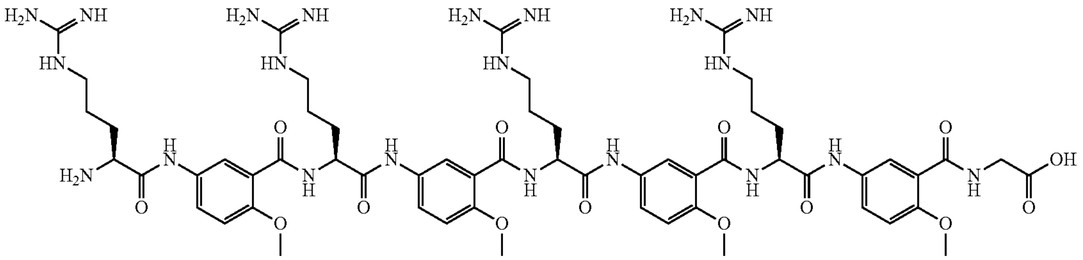 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OC)ccc2OC)cc1C(=O)NCC(=O)O] |

TABLE 2-continued
| Compound Number | Compound Structure |
| --- | --- |
| 285 | 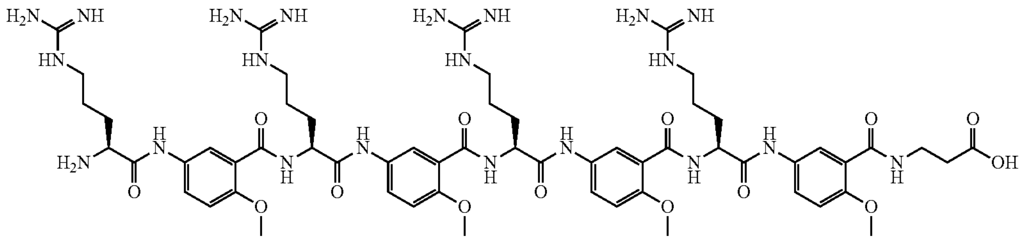 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OC)ccc2OC)cc1C(=O)NCCC(=O)O] |
| 286 | 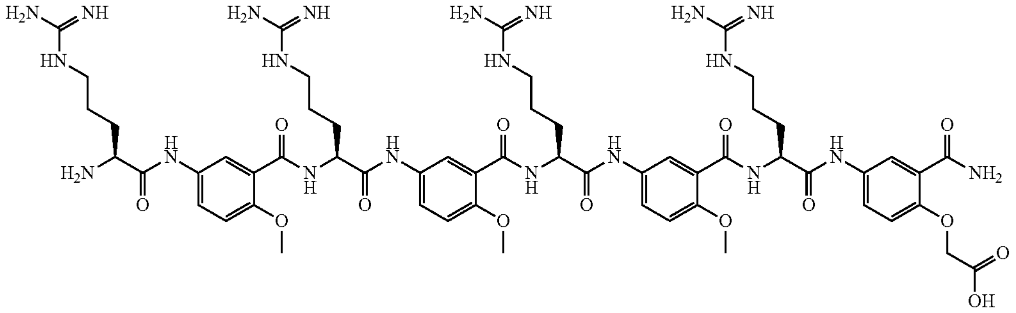 [SMILES: COc1ccc(NC(=O)[C@H](CCCNC(=N)N)NC(=O)c2cc(NC(=O)[C@H](CCCNC(=N)N)NC(=O)c3cc(NC(=O)[C@@H](N)CCCNC(=N)N)ccc3OC)ccc2OC)cc1C(=O)N[C@@H](CCCNC(=N)N)C(=O)Nc1ccc(OCC(=O)O)c(C(N)=O)c1] |
| 287 | 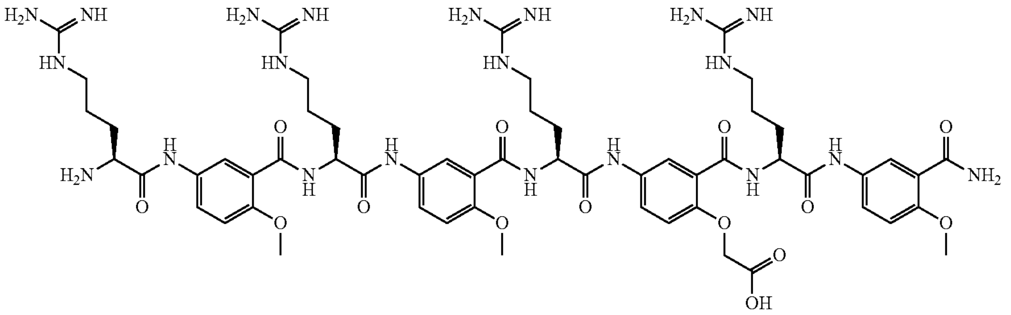 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OC)ccc2OCC(=O)O)cc1C(N)=O] |
| 288 | 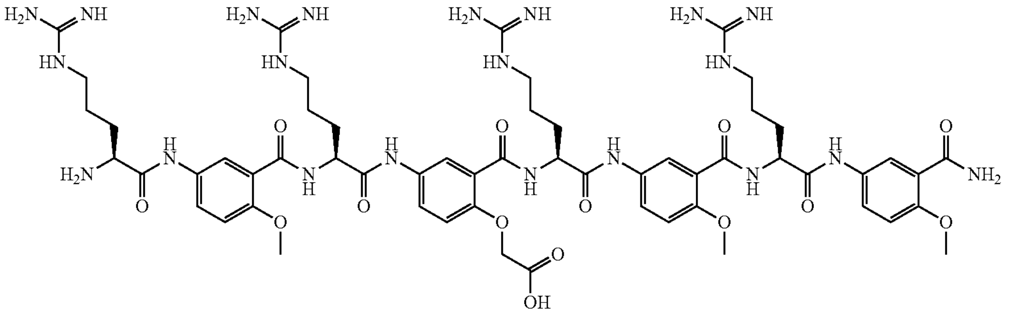 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OCC(=O)O)ccc2OC)cc1C(N)=O] |
| 289 | 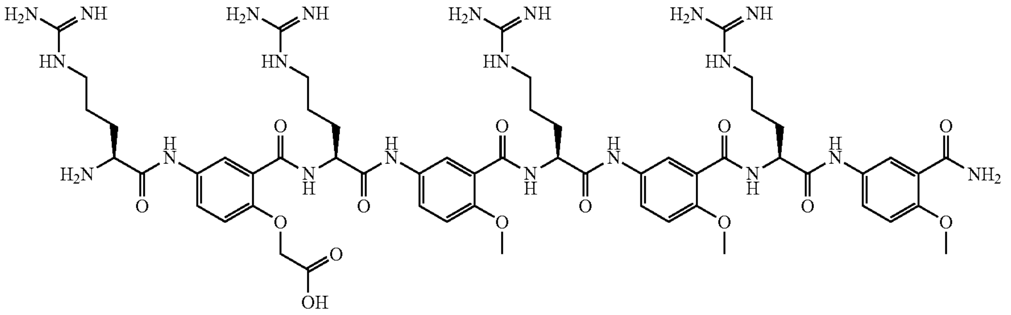 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OCC(=O)O)ccc3OC)ccc2OC)cc1C(N)=O] |

TABLE 2-continued
| Compound Number | Compound Structure |
|---|---|
| 290 | 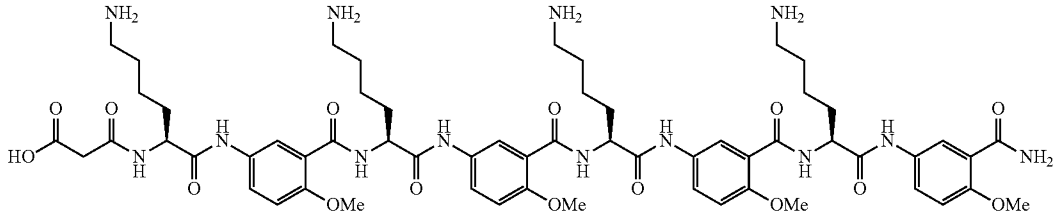 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)CC(=O)O)ccc4OC)ccc3OC)ccc2OC)cc1C(N)=O] |
| 291 | 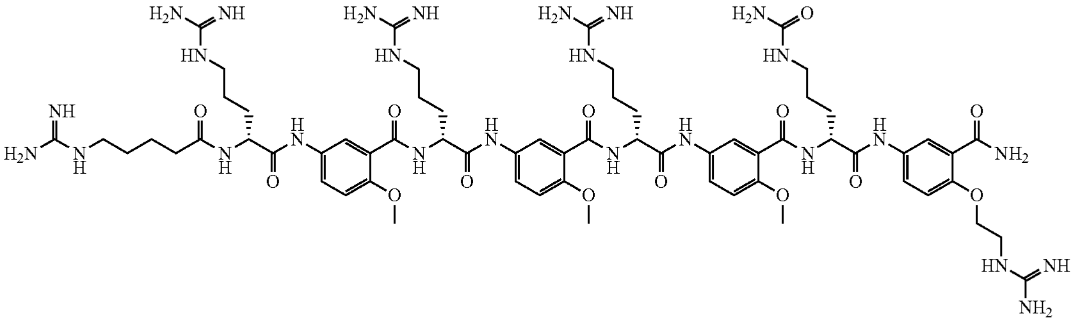 [SMILES: COc1ccc(NC(=O)[C@@H](CCCNC(=N)N)NC(=O)CCCCNC(=N)N)cc1C(=O)N[C@H](CCCNC(=N)N)C(=O)Nc1ccc(OC)c(C(=O)N[C@H](CCCNC(=N)N)C(=O)Nc2ccc(OC)c(C(=O)N[C@H](CCCNC(N)=O)C(=O)Nc3ccc(OCCNC(=N)N)c(C(N)=O)c3)c2)c1] |
| 292 | 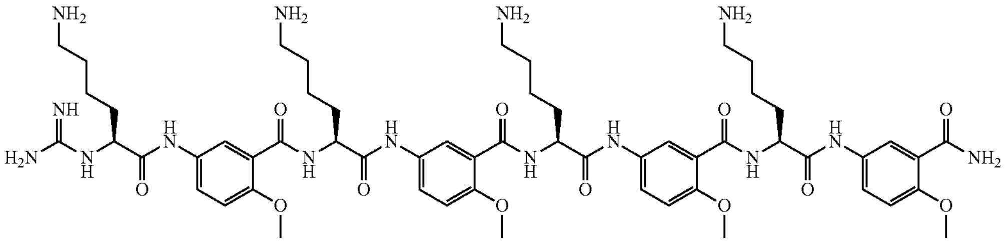 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=N)N)ccc4OC)ccc3OC)ccc2OC)cc1C(N)=O] |
| 293 | 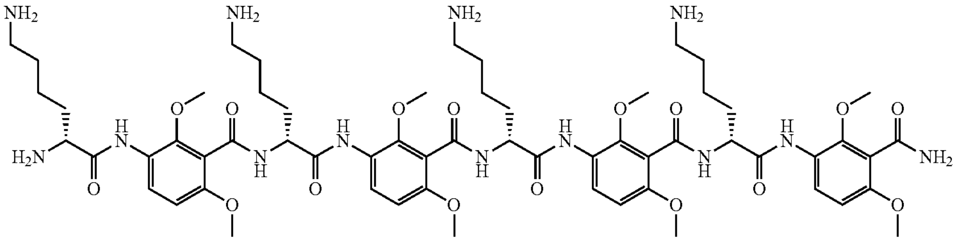 [SMILES: COc1ccc(NC(=O)[C@@H](CCCCN)NC(=O)c2c(OC)ccc(NC(=O)[C@@H](CCCCN)NC(=O)c3c(OC)ccc(NC(=O)[C@@H](CCCCN)NC(=O)c4c(OC)ccc(NC(=O)[C@H](N)CCCCN)c4OC)c3OC)c2OC)c(OC)c1C(N)=O] |
| 294 | 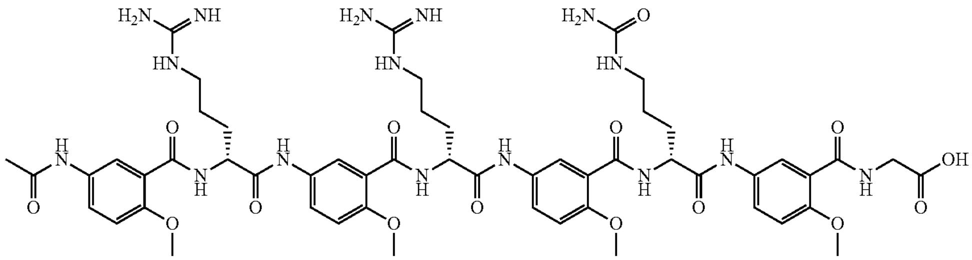 [SMILES: COc1ccc(NC(=O)[C@@H](CCCNC(N)=O)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OC)cc1C(=O)NCC(=O)O] |
| 295 | 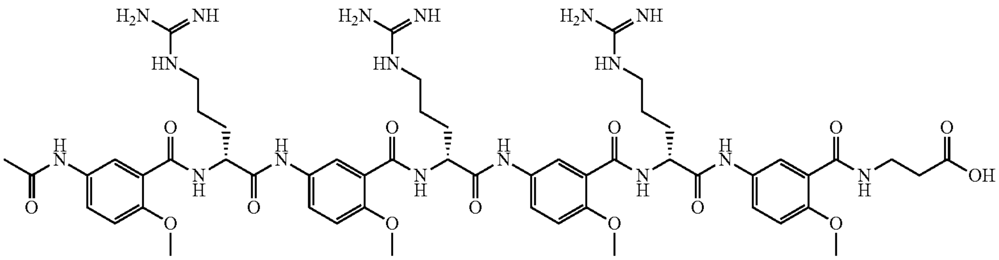 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OC)cc1C(=O)NCCC(=O)O] |

TABLE 2-continued
| Compound Number | Compound Structure |
|---|---|
| 296 | 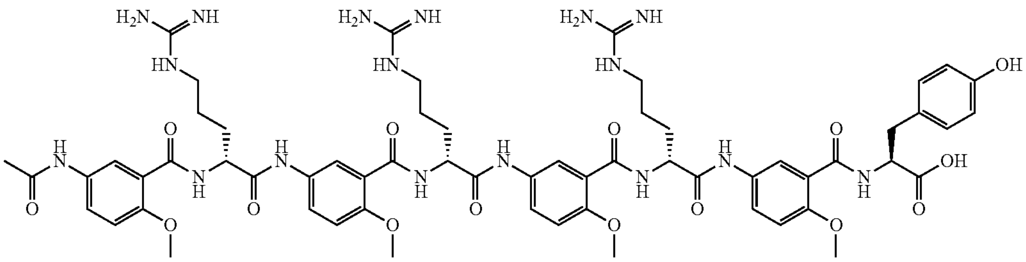 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OC)cc1C(=O)N[C@@H](Cc1ccc(O)cc1)C(=O)O] |
| 297 | 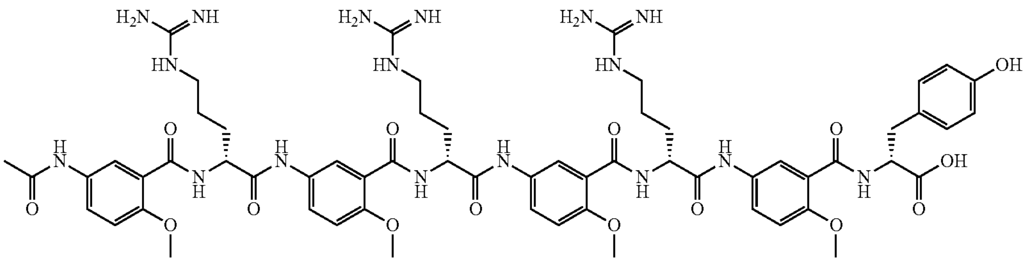 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OC)cc1C(=O)N[C@H](Cc1ccc(O)cc1)C(=O)O] |
| 298 | 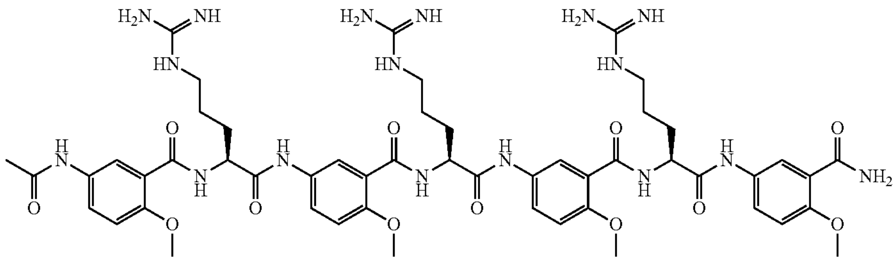 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(C)=O)ccc4OC)ccc3OC)ccc2OC)cc1C(N)=O] |
| 299 | 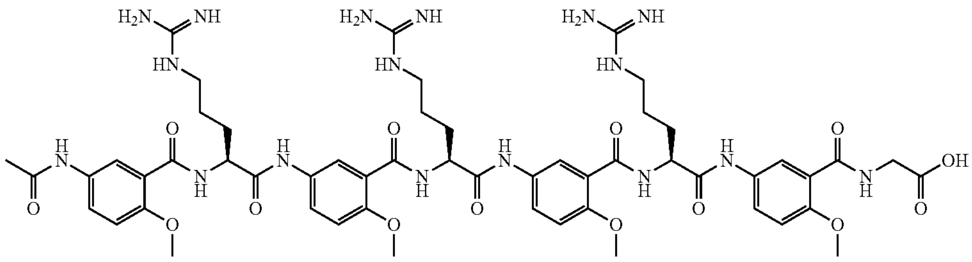 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(C)=O)ccc4OC)ccc3OC)ccc2OC)cc1C(=O)NCC(=O)O] |
| 300 | 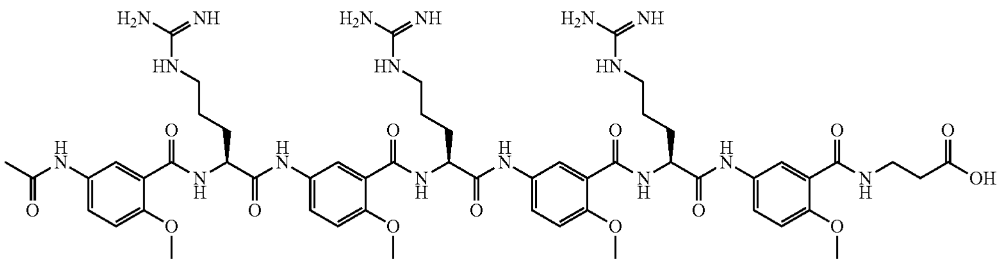 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(C)=O)ccc4OC)ccc3OC)ccc2OC)cc1C(=O)NCCC(=O)O] |

TABLE 2-continued
| Compound Number | Compound Structure |
|---|---|
| 301 | 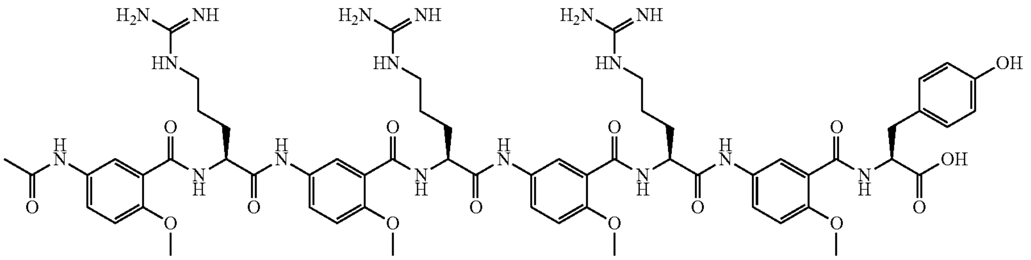 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(C)=O)ccc4OC)ccc3OC)ccc2OC)cc1C(=O)N[C@@H](Cc1ccc(O)cc1)C(=O)O] |
| 302 | 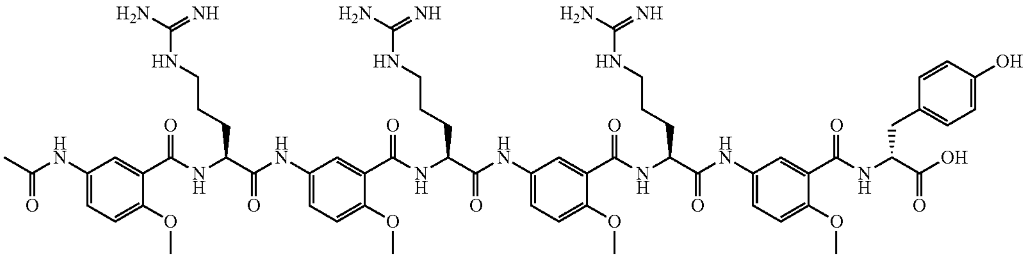 [SMILES: COc1ccc(NC(C)=O)cc1C(=O)N[C@@H](CCCNC(=N)N)C(=O)Nc1ccc(OC)c(C(=O)N[C@@H](CCCNC(=N)N)C(=O)Nc2ccc(OC)c(C(=O)N[C@@H](CCCNC(=N)N)C(=O)Nc3ccc(OC)c(C(=O)N[C@H](Cc4ccc(O)cc4)C(=O)O)c3)c2)c1] |
| 303 | 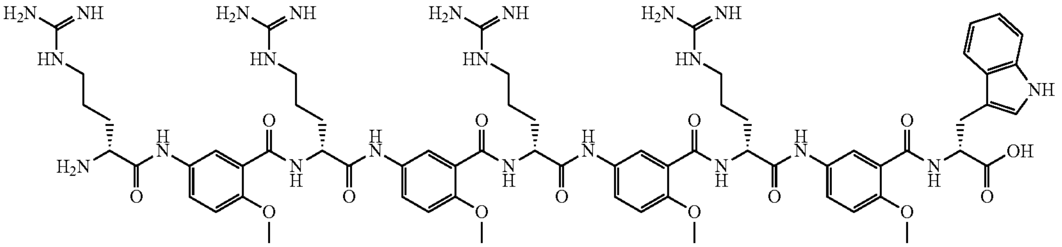 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(=O)N[C@H](Cc1c[nH]c2ccccc12)C(=O)O] |
| 304 | 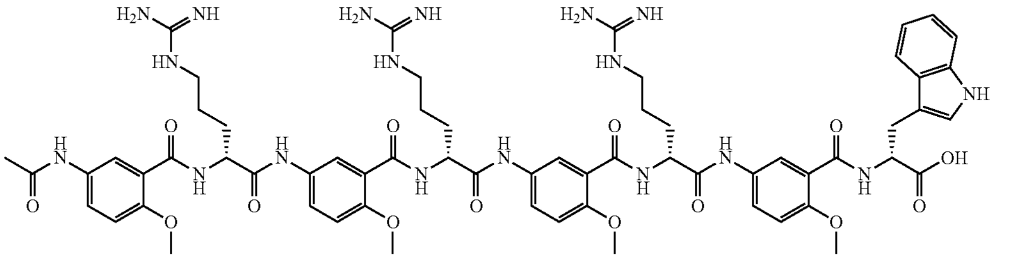 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OC)cc1C(=O)N[C@H](Cc1c[nH]c2ccccc12)C(=O)O] |
| 305 | 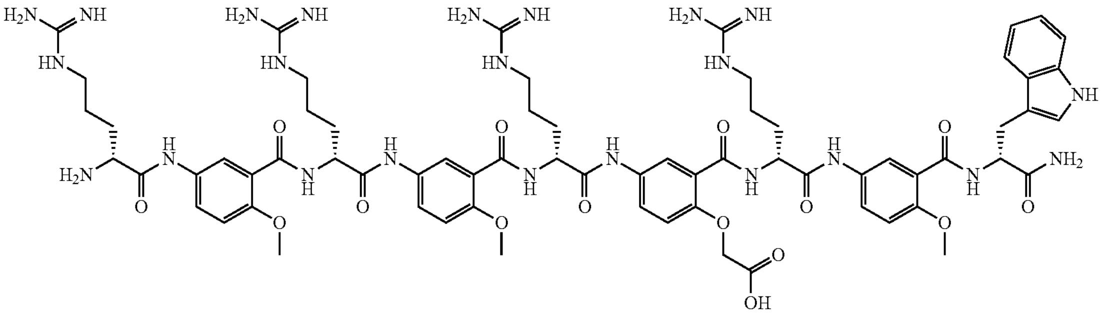 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OCC(=O)O)cc1C(=O)N[C@H](Cc1c[nH]c2ccccc12)C(N)=O] |

TABLE 2-continued
| Compound Number | Compound Structure |
|---|---|
| 306 | Chiral 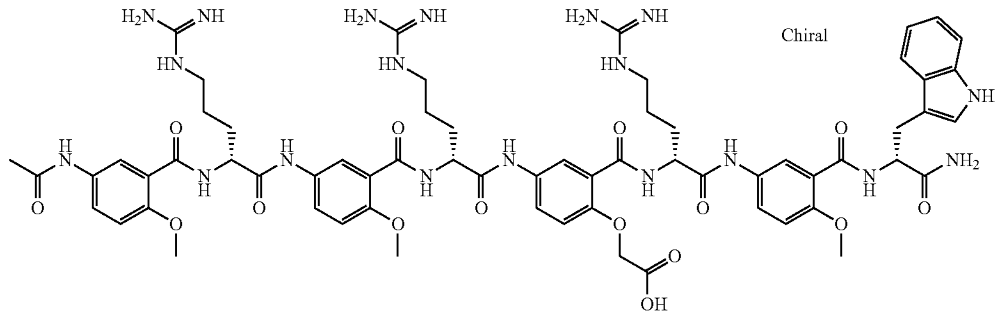 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OCC(=O)O)cc1C(=O)N[C@H](Cc1c[nH]c2ccccc12)C(N)=O] |
| 307 | 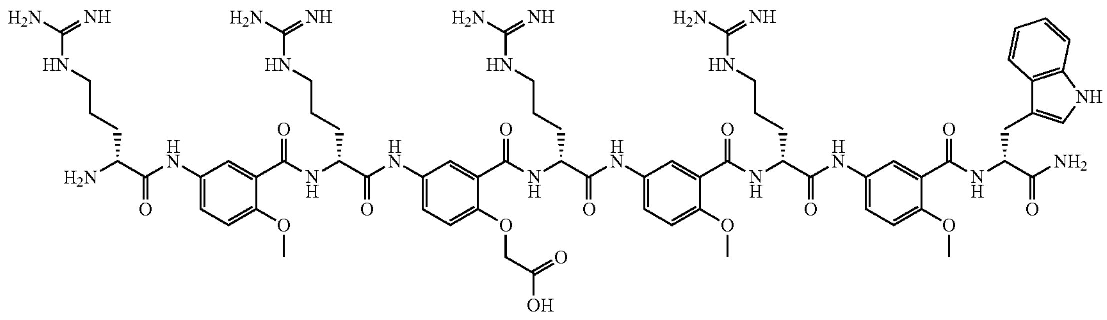 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OCC(=O)O)ccc2OC)cc1C(=O)N[C@H](Cc1c[nH]c2ccccc12)C(N)=O] |
| 308 | 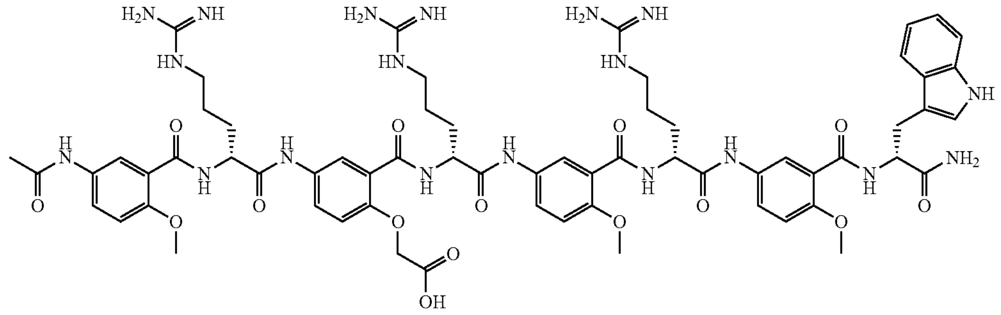 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OCC(=O)O)ccc2OC)cc1C(=O)N[C@H](Cc1c[nH]c2ccccc12)C(N)=O] |
| 309 | 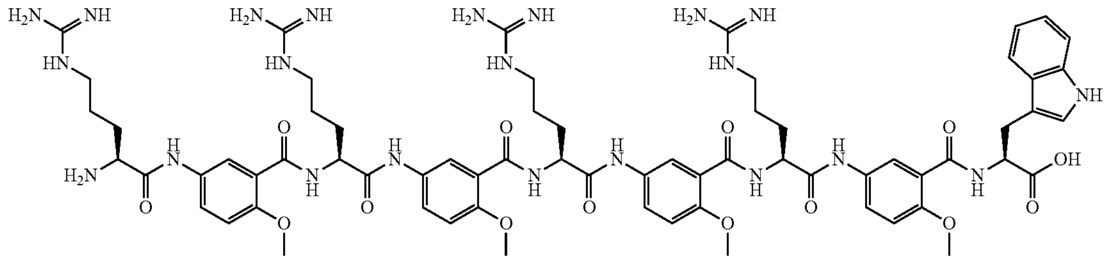 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OC)ccc2OC)cc1C(=O)N[C@@H](Cc1c[nH]c2ccccc12)C(=O)O] |
| 310 | 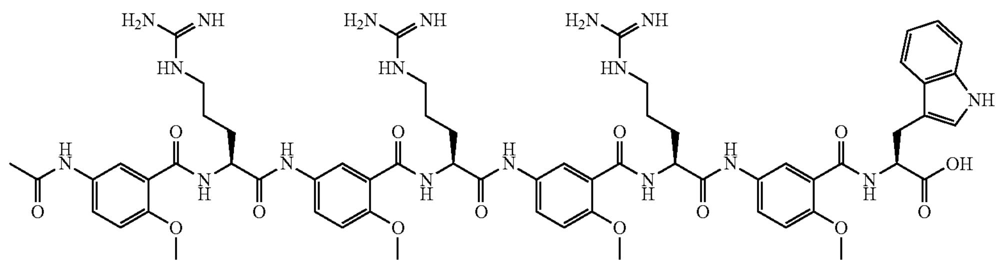 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(C)=O)ccc4OC)ccc3OC)ccc2OC)cc1C(=O)N[C@@H](Cc1c[nH]c2ccccc12)C(=O)O] |

TABLE 2-continued
| Compound Number | Compound Structure |
| --- | --- |
| 311 | 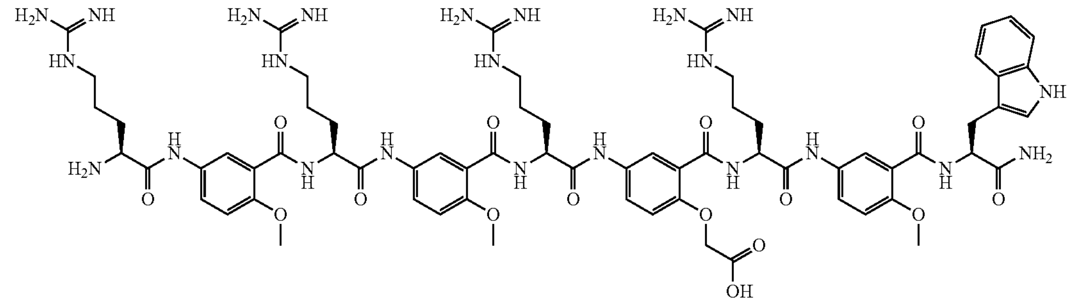 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OC)ccc2OCC(=O)O)cc1C(=O)N[C@@H](Cc1c[nH]c2ccccc12)C(N)=O] |
| 312 | 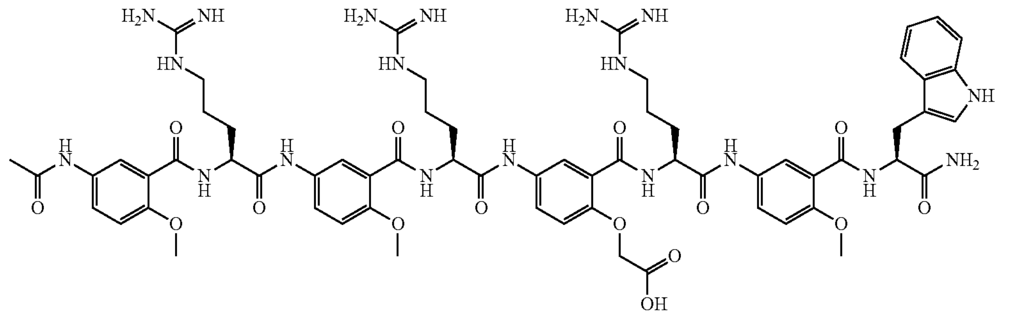 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(C)=O)ccc4OC)ccc3OC)ccc2OCC(=O)O)cc1C(=O)N[C@@H](Cc1c[nH]c2ccccc12)C(N)=O] |
| 313 | 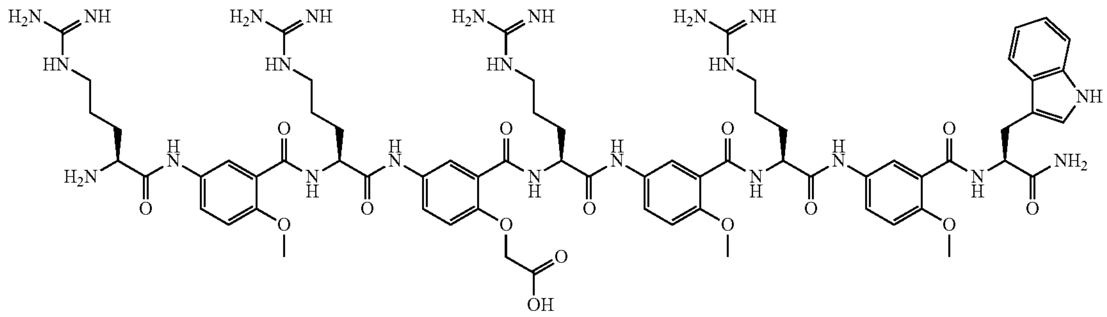 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OCC(=O)O)ccc2OC)cc1C(=O)N[C@@H](Cc1c[nH]c2ccccc12)C(N)=O] |
| 314 | 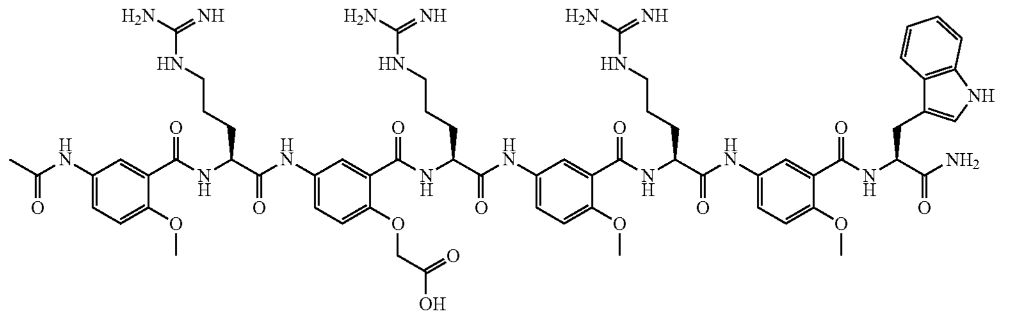 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(C)=O)ccc4OC)ccc3OCC(=O)O)ccc2OC)cc1C(=O)N[C@@H](Cc1c[nH]c2ccccc12)C(N)=O] |
| 315 | 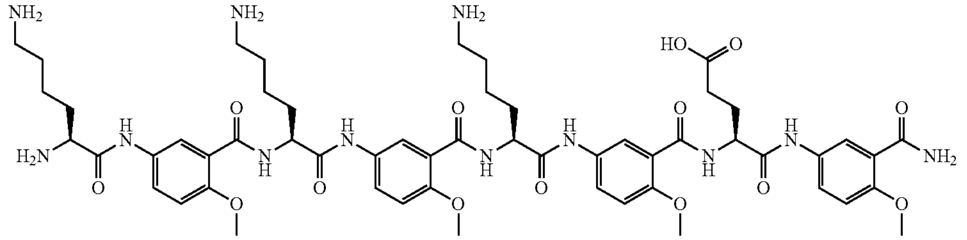 [SMILES: COc1ccc(NC(=O)[C@H](CCC(=O)O)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |

TABLE 2-continued
| Compound Number | Compound Structure |
|---|---|
| 316 | 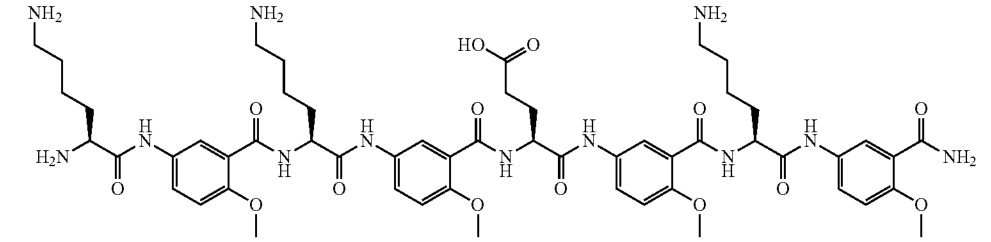 [SMILES: COc1ccc(NC(=O)[C@H](CCCCN)NC(=O)c2cc(NC(=O)[C@H](CCC(=O)O)NC(=O)c3cc(NC(=O)[C@H](CCCCN)NC(=O)c4cc(NC(=O)[C@@H](N)CCCCN)ccc4OC)ccc3OC)ccc2OC)cc1C(N)=O] |
| 317 | 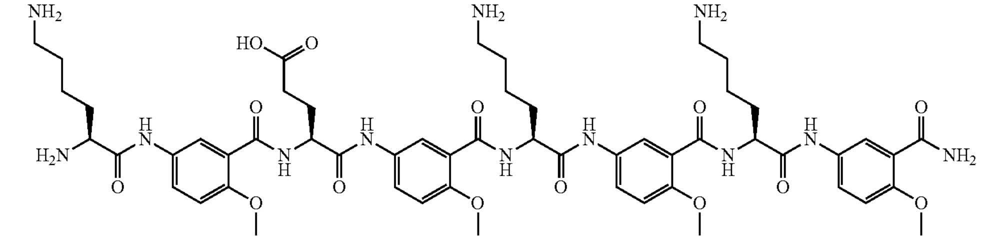 [SMILES: COc1ccc(NC(=O)[C@H](CCCCN)NC(=O)c2cc(NC(=O)[C@H](CCCCN)NC(=O)c3cc(NC(=O)[C@H](CCC(=O)O)NC(=O)c4cc(NC(=O)[C@@H](N)CCCCN)ccc4OC)ccc3OC)ccc2OC)cc1C(N)=O] |
| 318 | 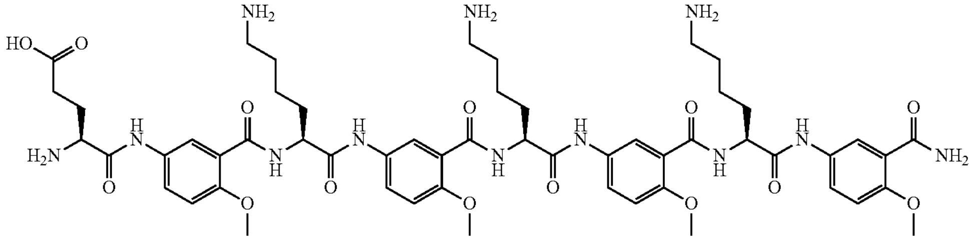 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCC(=O)O)ccc4OC)ccc3OC)ccc2OC)cc1C(N)=O] |
| 319 | 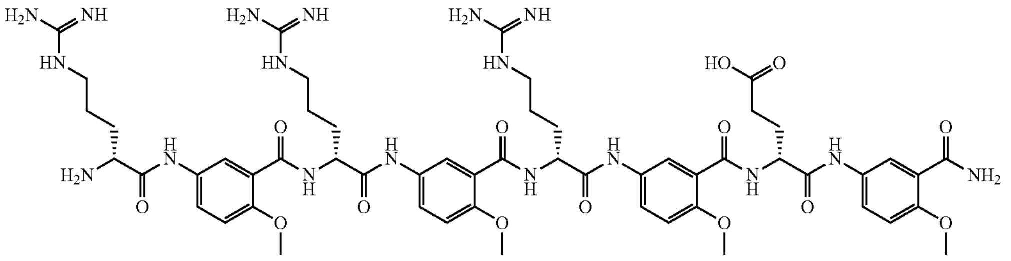 [SMILES: COc1ccc(NC(=O)[C@@H](CCC(=O)O)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 320 | 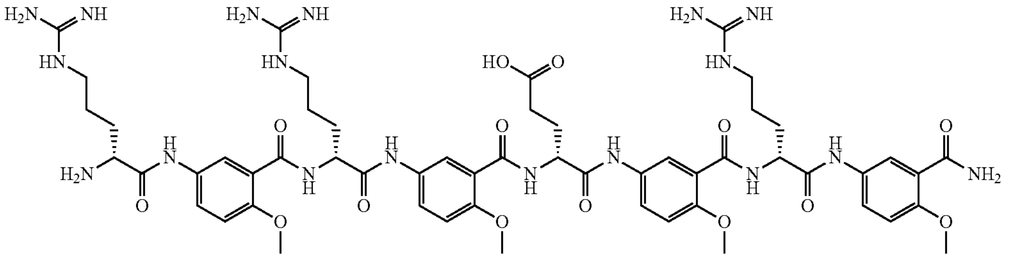 [SMILES: COc1ccc(NC(=O)[C@@H](CCCNC(=N)N)NC(=O)c2cc(NC(=O)[C@@H](CCC(=O)O)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |
| 321 | 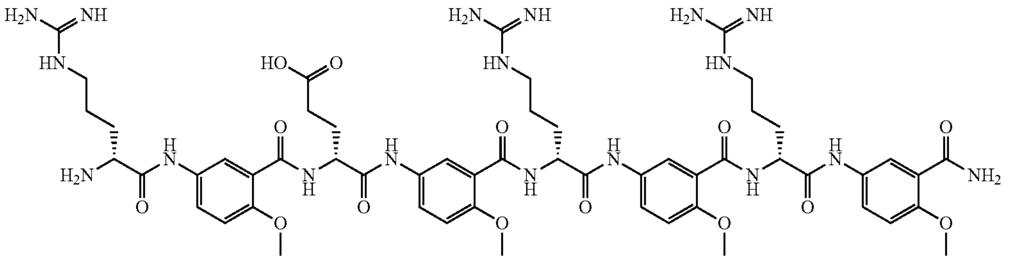 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCC(=O)O)NC(=O)c4cc(NC(=O)[C@H](N)CCCNC(=N)N)ccc4OC)ccc3OC)ccc2OC)cc1C(N)=O] |

TABLE 2-continued
| Compound Number | Compound Structure |
| --- | --- |
| 322 | 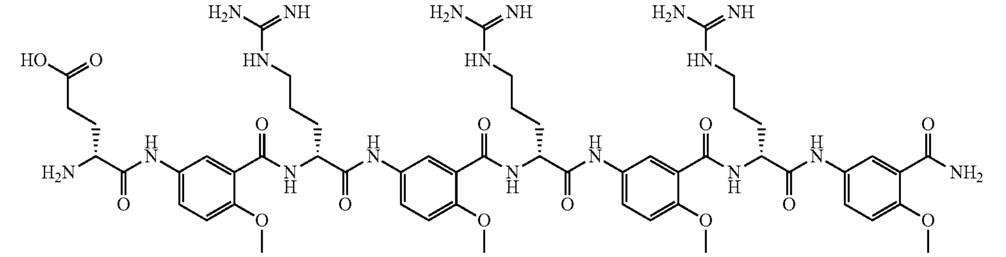 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)CCC(=O)O)ccc4OC)ccc3OC)ccc2OC)cc1C(N)=O] |
| 323 | 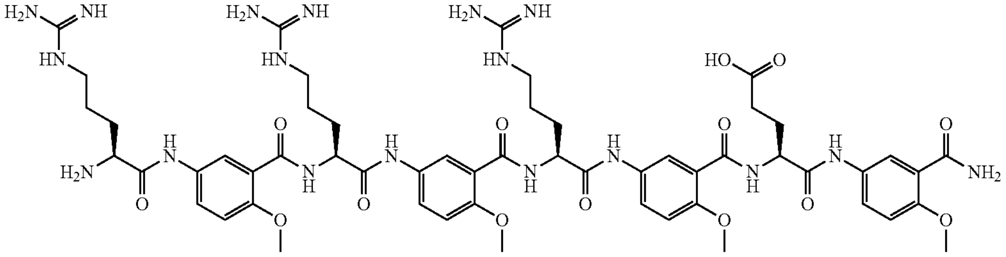 [SMILES: COc1ccc(NC(=O)[C@H](CCC(=O)O)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCCNC(=N)N)ccc4OC)ccc3OC)ccc2OC)cc1C(N)=O] |
| 324 | 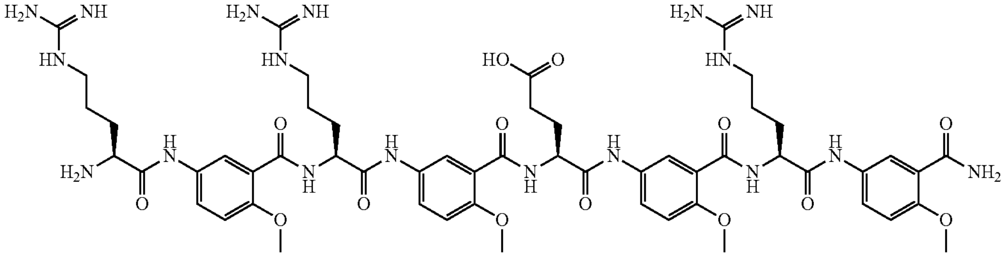 [SMILES: COc1ccc(NC(=O)[C@H](CCCNC(=N)N)NC(=O)c2cc(NC(=O)[C@H](CCC(=O)O)NC(=O)c3cc(NC(=O)[C@H](CCCNC(=N)N)NC(=O)c4cc(NC(=O)[C@@H](N)CCCNC(=N)N)ccc4OC)ccc3OC)ccc2OC)cc1C(N)=O] |
| 325 | 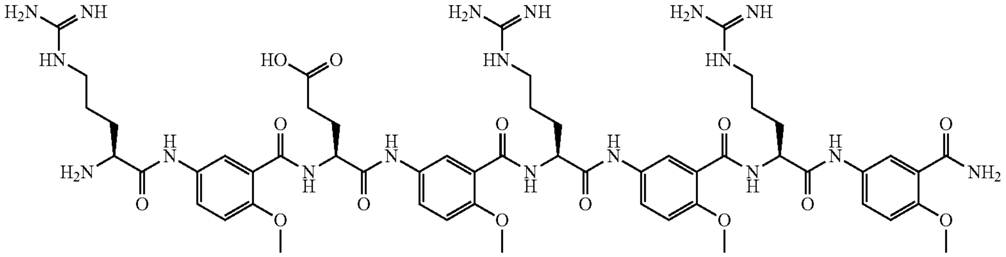 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCC(=O)O)NC(=O)c4cc(NC(=O)[C@@H](N)CCCNC(=N)N)ccc4OC)ccc3OC)ccc2OC)cc1C(N)=O] |
| 326 | 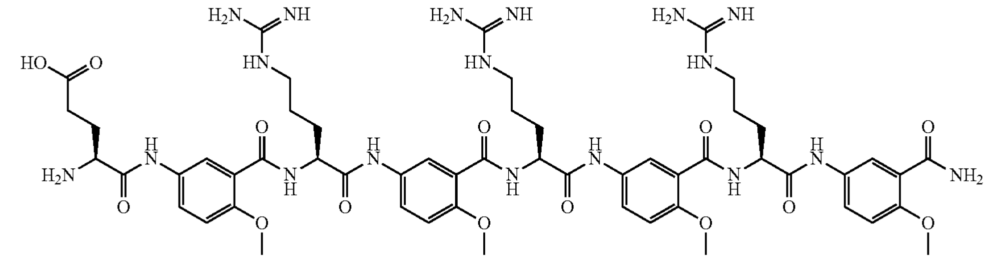 [SMILES: COc1ccc(NC(=O)[C@H](CCCNC(=N)N)NC(=O)c2cc(NC(=O)[C@H](CCCNC(=N)N)NC(=O)c3cc(NC(=O)[C@H](CCCNC(=N)N)NC(=O)c4cc(NC(=O)[C@@H](N)CCC(=O)O)ccc4OC)ccc3OC)ccc2OC)cc1C(N)=O] |
| 327 | 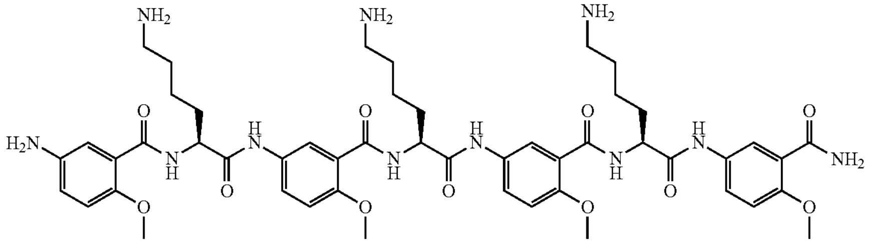 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(N)ccc4OC)ccc3OC)ccc2OC)cc1C(N)=O] |

TABLE 2-continued
| Compound Number | Compound Structure |
| --- | --- |
| 328 | 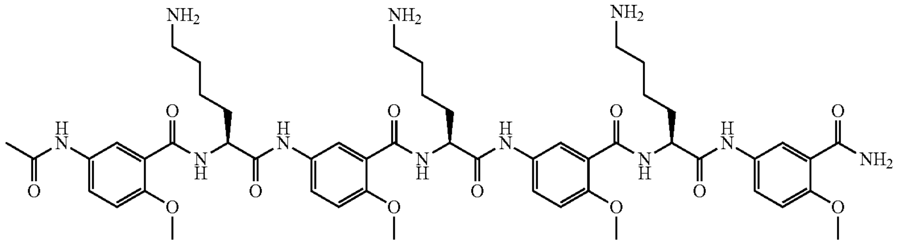 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(C)=O)ccc4OC)ccc3OC)ccc2OC)cc1C(N)=O] |
| 329 | 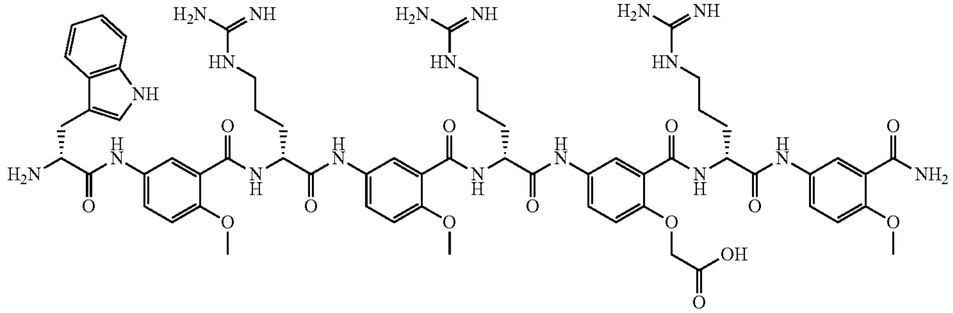 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)Cc5c[nH]c6ccccc56)ccc4OC)ccc3OC)ccc2OCC(=O)O)cc1C(N)=O] |
| 330 | 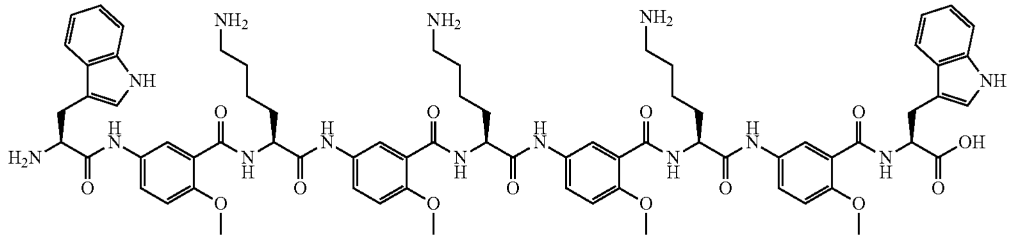 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)Cc5c[nH]c6ccccc56)ccc4OC)ccc3OC)ccc2OC)cc1C(=O)N[C@@H](Cc1c[nH]c2ccccc12)C(=O)O] |
| 331 | 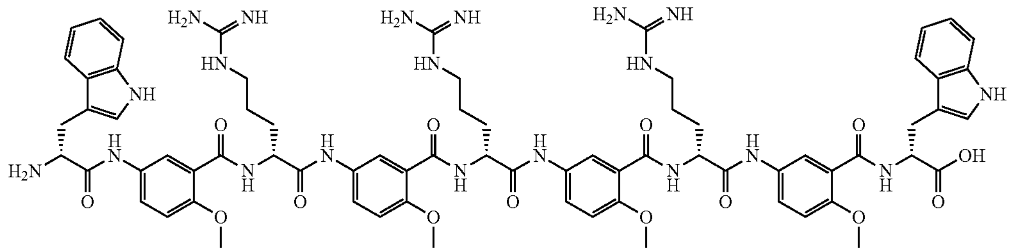 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(=N)N)NC(=O)c4cc(NC(=O)[C@H](N)Cc5c[nH]c6ccccc56)ccc4OC)ccc3OC)ccc2OC)cc1C(=O)N[C@H](Cc1c[nH]c2ccccc12)C(=O)O] |
| 332 | 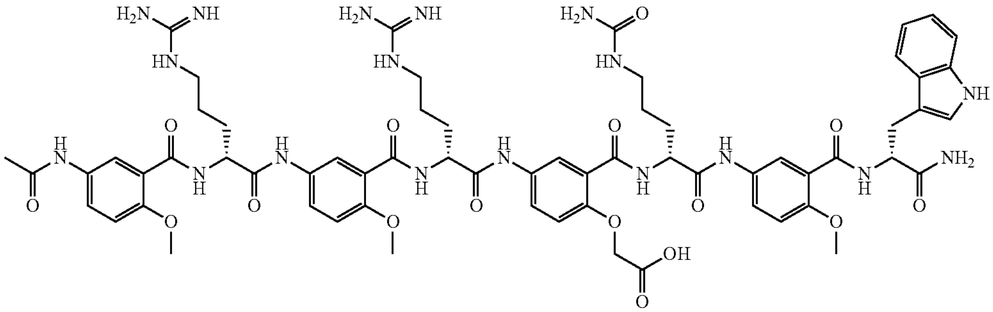 [SMILES: COc1ccc(NC(=O)[C@@H](CCCNC(N)=O)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OCC(=O)O)cc1C(=O)N[C@H](Cc1c[nH]c2ccccc12)C(N)=O] |

TABLE 2-continued
| Compound Number | Compound Structure |
| --- | --- |
| 333 | 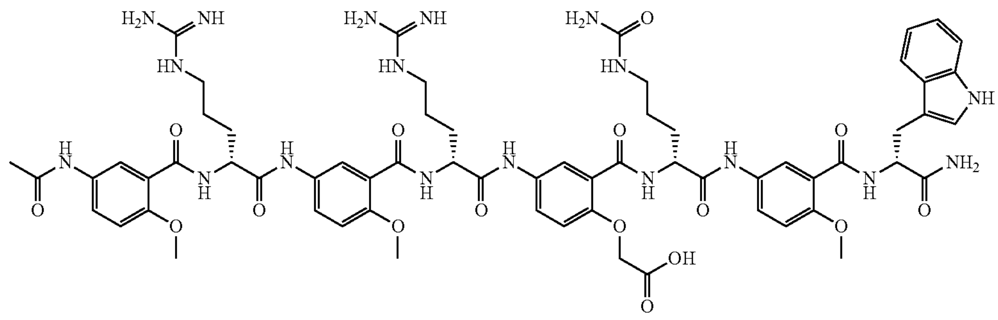 [SMILES: COc1ccc(NC(=O)[C@@H](CCCNC(N)=O)NC(=O)c2cc(NC(=O)[C@@H](CCCNC(=N)N)NC(=O)c3cc(NC(=O)[C@@H](CCCNC(=N)N)NC(=O)c4cc(NC(C)=O)ccc4OC)ccc3OC)ccc2OCC(=O)O)cc1C(=O)N[C@H](Cc1c[nH]c2ccccc12)C(N)=O] |
| 334 | 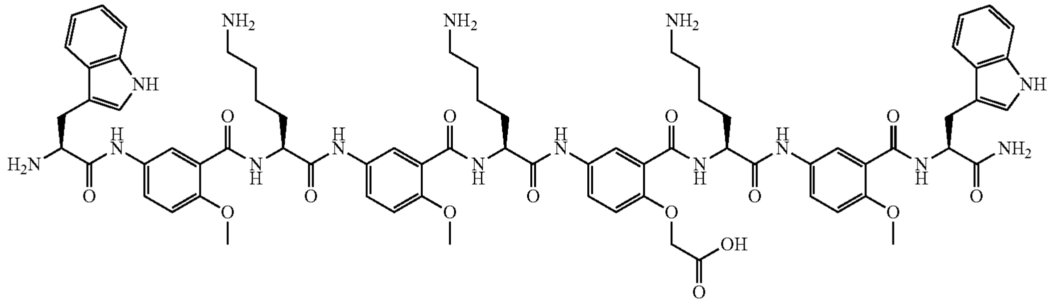 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)Cc5c[nH]c6ccccc56)ccc4OC)ccc3OC)ccc2OCC(=O)O)cc1C(=O)N[C@@H](Cc1c[nH]c2ccccc12)C(N)=O] |
| 335 | 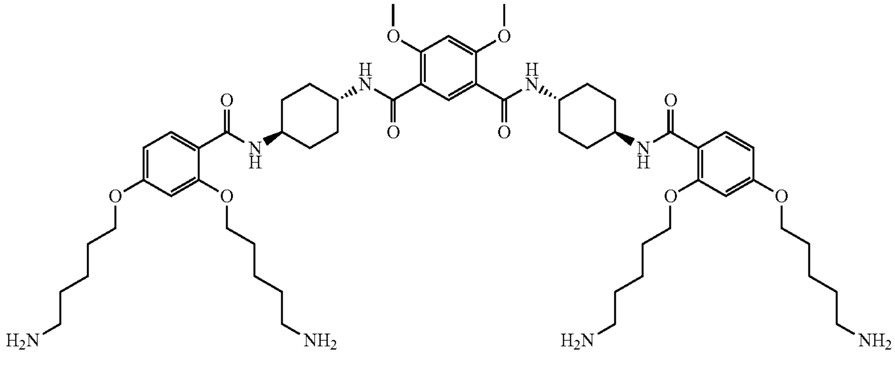 [SMILES: COc1cc(OC)c(C(=O)N[C@H]2CC[C@H](NC(=O)c3ccc(OCCCCCN)cc3OCCCCCN)CC2)cc1C(=O)N[C@H]1CC[C@H](NC(=O)c2ccc(OCCCCCN)cc2OCCCCCN)CC1] |
| 336 | 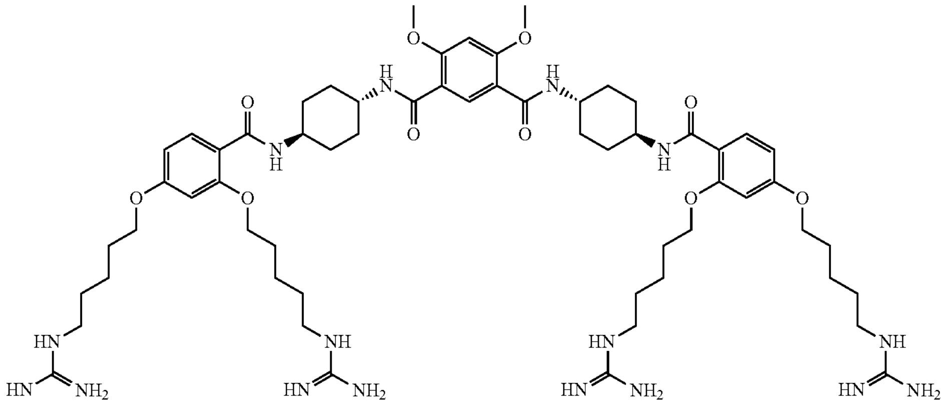 [SMILES: COc1cc(OC)c(C(=O)N[C@H]2CC[C@H](NC(=O)c3ccc(OCCCCCNC(=N)N)cc3OCCCCCNC(=N)N)CC2)cc1C(=O)N[C@H]1CC[C@H](NC(=O)c2ccc(OCCCCCNC(=N)N)cc2OCCCCCNC(=N)N)CC1] |

TABLE 2-continued
| Compound Number | Compound Structure |
|---|---|
| 337 | 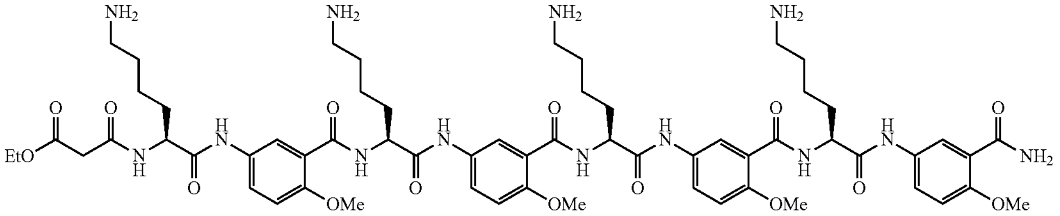 [SMILES: CCOC(=O)CC(=O)N[C@@H](CCCCN)C(=O)Nc1ccc(OC)c(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(N)=O)c4)c3)c2)c1] |
| 338 | 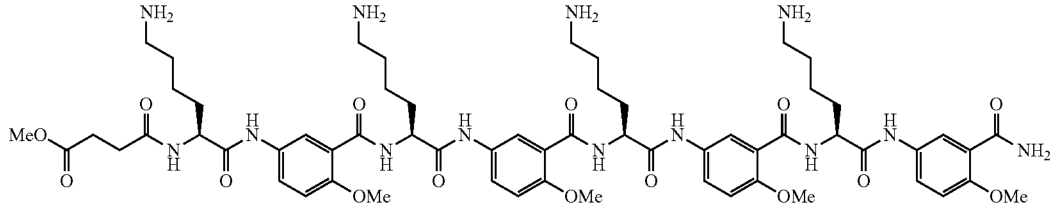 [SMILES: COC(=O)CCC(=O)N[C@@H](CCCCN)C(=O)Nc1ccc(OC)c(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(N)=O)c4)c3)c2)c1] |
| 339 | 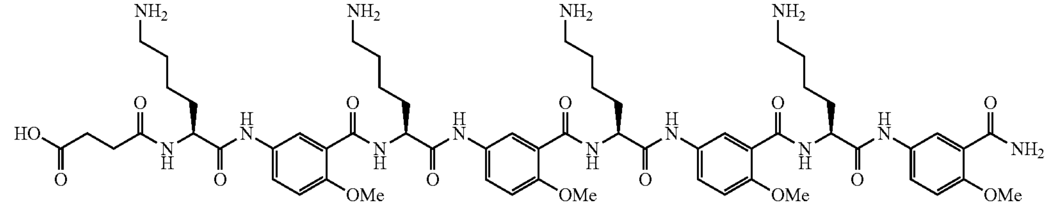 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)CCC(=O)O)ccc4OC)ccc3OC)ccc2OC)cc1C(N)=O] |
| 340 | 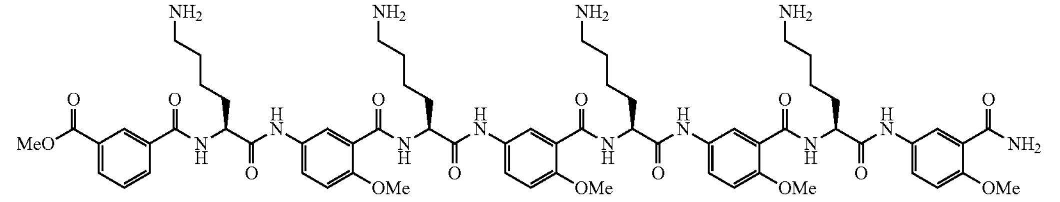 [SMILES: COC(=O)c1cccc(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(=O)N[C@@H](CCCCN)C(=O)Nc5ccc(OC)c(C(N)=O)c5)c4)c3)c2)c1] |
| 341 | 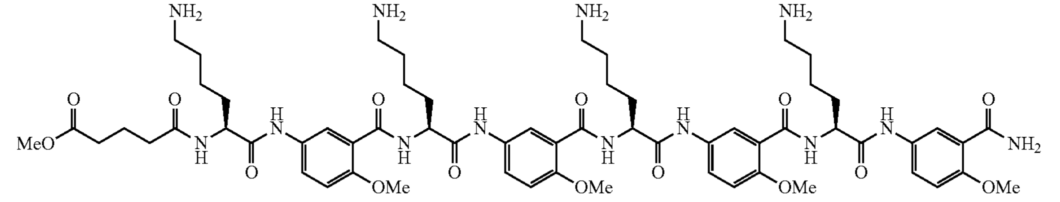 [SMILES: COC(=O)CCCC(=O)N[C@@H](CCCCN)C(=O)Nc1ccc(OC)c(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OC)c(C(N)=O)c4)c3)c2)c1] |
| 342 | 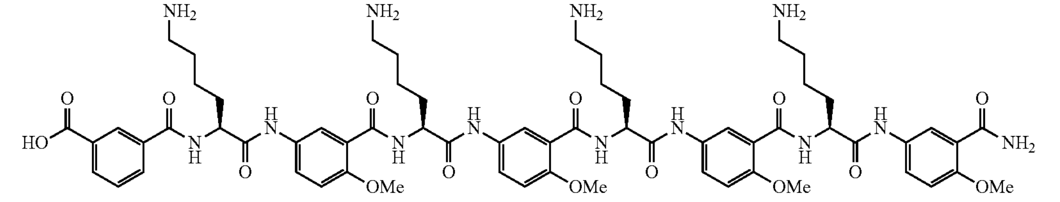 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)c5cccc(C(=O)O)c5)ccc4OC)ccc3OC)ccc2OC)cc1C(N)=O] |
| 343 | 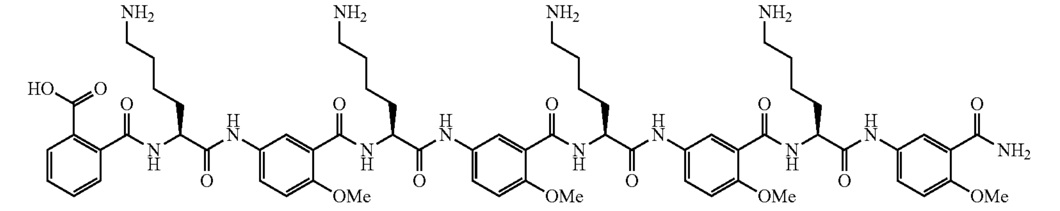 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)c5ccccc5C(=O)O)ccc4OC)ccc3OC)ccc2OC)cc1C(N)=O] |

TABLE 2-continued
| Compound Number | Compound Structure |
| --- | --- |
| 344 | 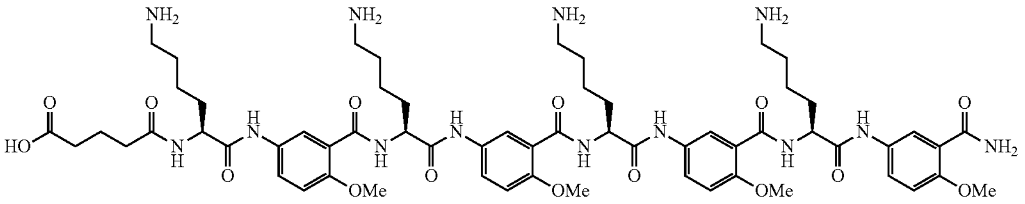 |
| 345 | 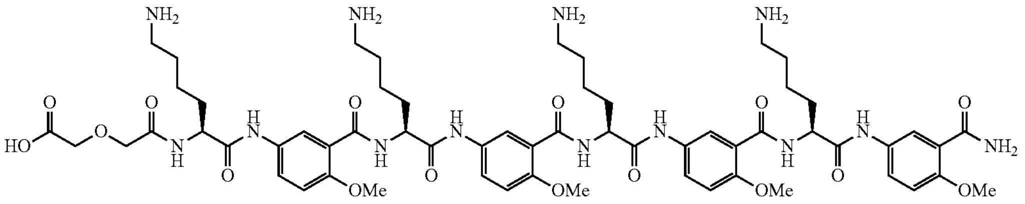 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)CCCC(=O)O)ccc4OC)ccc3OC)ccc2OC)cc1C(N)=O] |
| 346 | 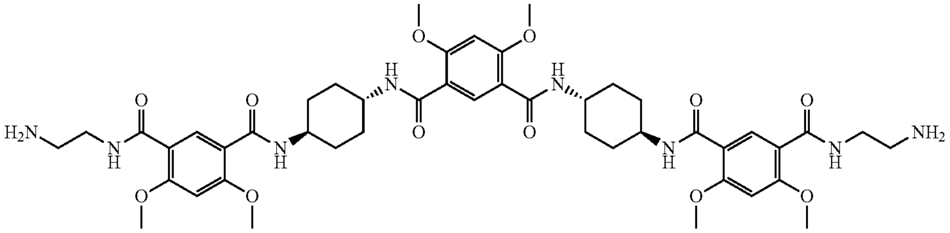 [SMILES: COc1cc(OC)c(C(=O)N[C@H]2CC[C@H](NC(=O)c3cc(C(=O)N[C@H]4CC[C@H](NC(=O)c5cc(C(=O)NCCN)c(OC)cc5OC)CC4)c(OC)cc3OC)CC2)cc1C(=O)NCCN] |
| 347 | 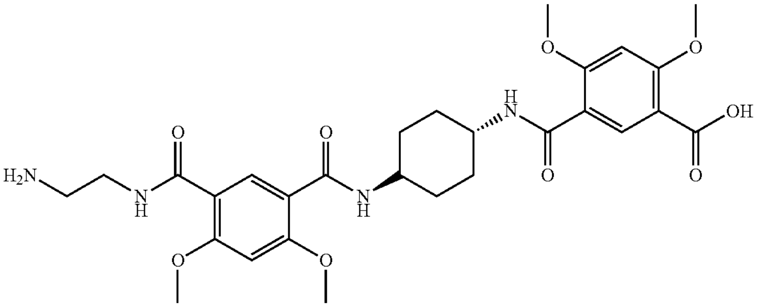 |
| 348 | 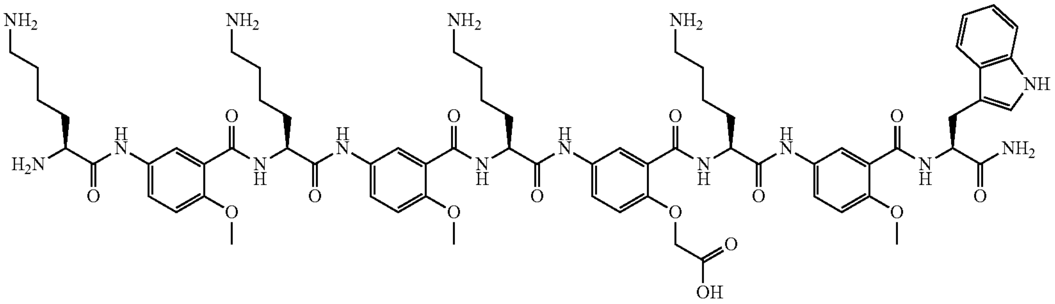 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@@H](N)CCCCN)ccc4OC)ccc3OC)ccc2OCC(=O)O)cc1C(=O)N[C@@H](Cc1c[nH]c2ccccc12)C(N)=O] |
| 349 | 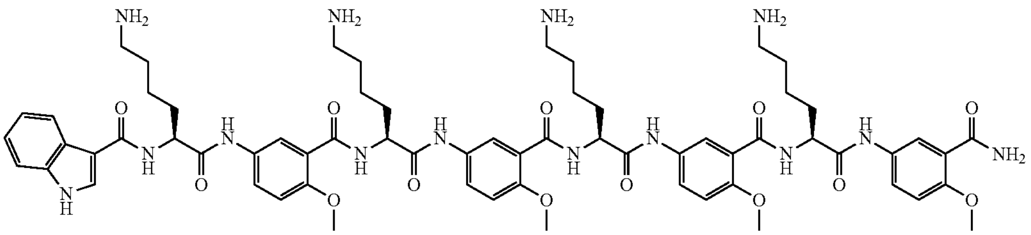 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)c5c[nH]c6ccccc56)ccc4OC)ccc3OC)ccc2OC)cc1C(N)=O] |

TABLE 2-continued
| Compound Number | Compound Structure |
|---|---|
| 350 | 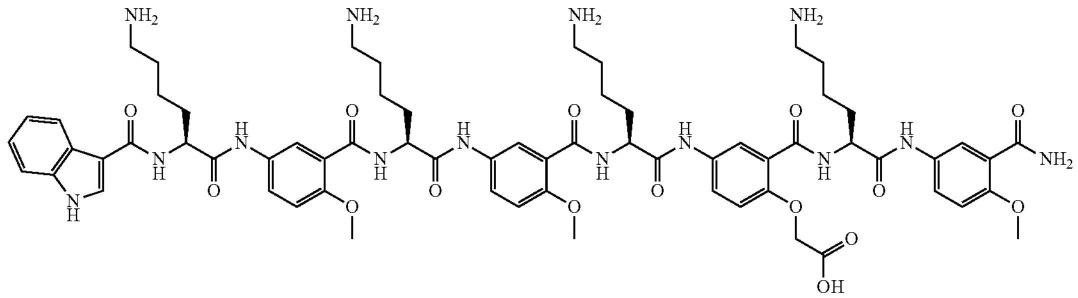 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)c5c[nH]c6ccccc56)ccc4OC)ccc3OC)ccc2OCC(=O)O)cc1C(N)=O] |
| 351 | 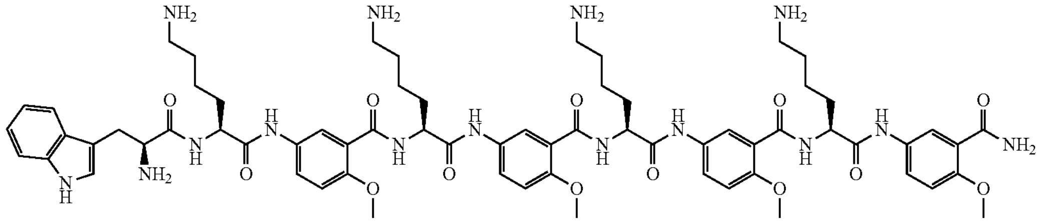 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)[C@@H](N)Cc5c[nH]c6ccccc56)ccc4OC)ccc3OC)ccc2OC)cc1C(N)=O] |
| 352 | 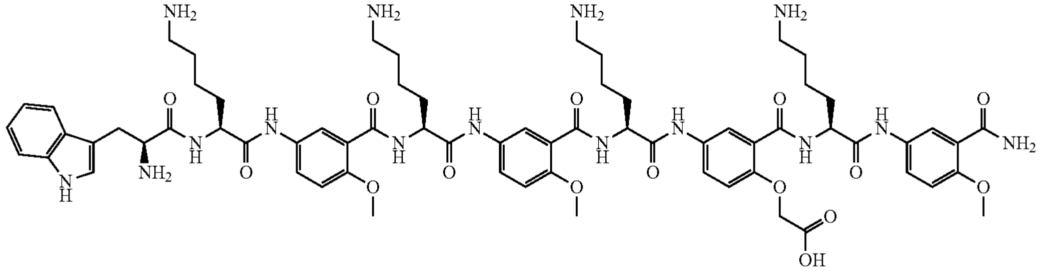 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)[C@@H](N)Cc5c[nH]c6ccccc56)ccc4OC)ccc3OC)ccc2OCC(=O)O)cc1C(N)=O] |
| 353 | 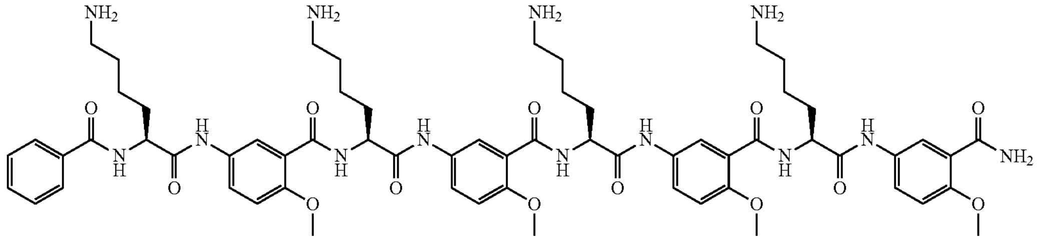 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)c5ccccc5)ccc4OC)ccc3OC)ccc2OC)cc1C(N)=O] |
| 354 | 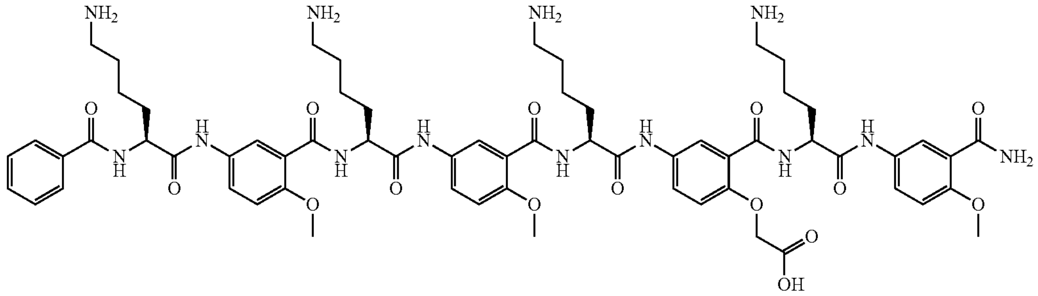 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)c5ccccc5)ccc4OC)ccc3OC)ccc2OCC(=O)O)cc1C(N)=O] |

TABLE 2-continued
| Compound Number | Compound Structure |
|---|---|
| 355 | 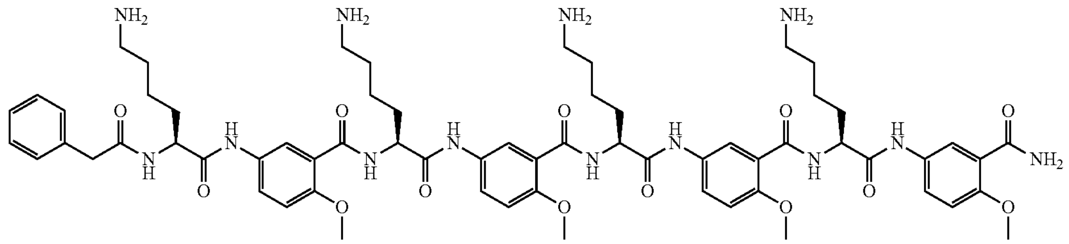 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)Cc5ccccc5)ccc4OC)ccc3OC)ccc2OC)cc1C(N)=O] |
| 356 | 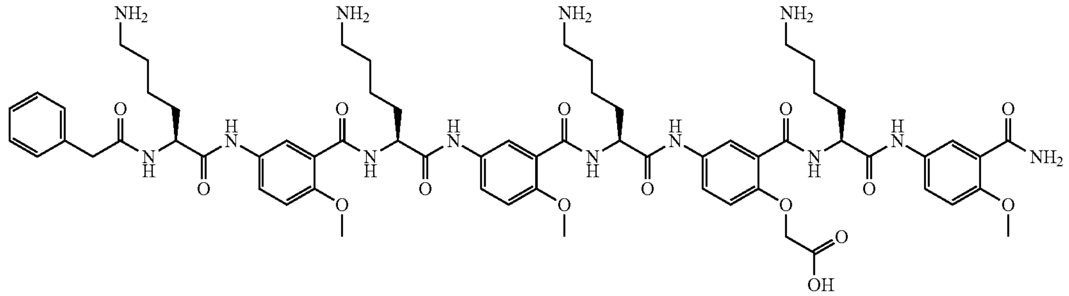 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)Cc5ccccc5)ccc4OC)ccc3OC)ccc2OCC(=O)O)cc1C(N)=O] |
| 357 | 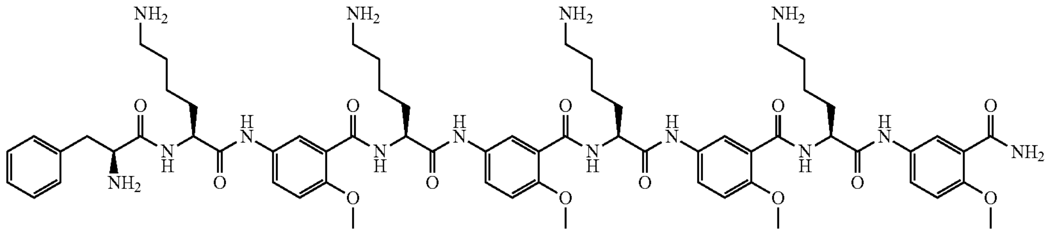 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)[C@@H](N)Cc5ccccc5)ccc4OC)ccc3OC)ccc2OC)cc1C(N)=O] |
| 358 | 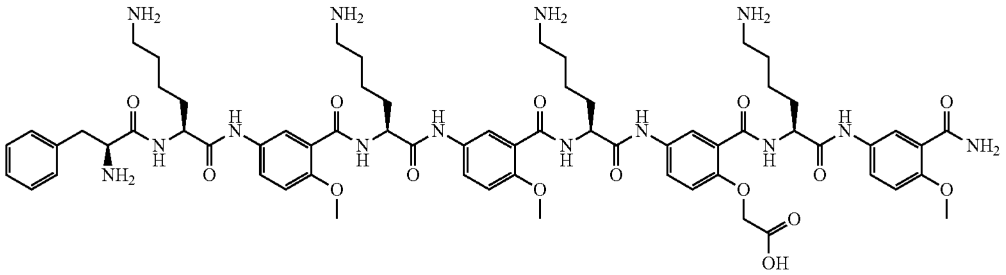 [SMILES: COc1ccc(NC(=O)[C@H](CCCCN)NC(=O)c2cc(NC(=O)[C@H](CCCCN)NC(=O)c3cc(NC(=O)[C@H](CCCCN)NC(=O)c4cc(NC(=O)[C@H](CCCCN)NC(=O)[C@@H](N)Cc5ccccc5)ccc4OC)ccc3OC)ccc2OCC(=O)O)cc1C(N)=O] |
| 359 | 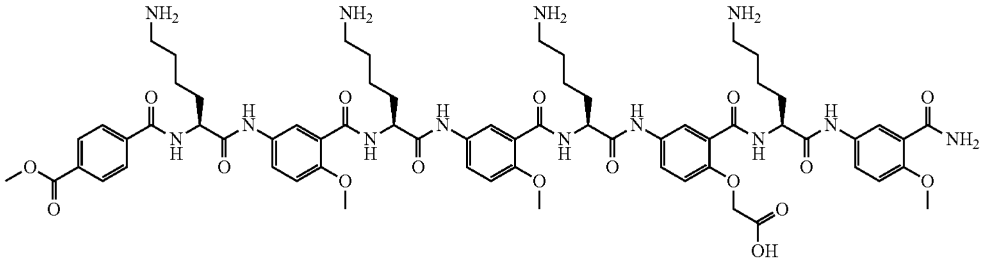 [SMILES: COC(=O)c1ccc(C(=O)N[C@@H](CCCCN)C(=O)Nc2ccc(OC)c(C(=O)N[C@@H](CCCCN)C(=O)Nc3ccc(OC)c(C(=O)N[C@@H](CCCCN)C(=O)Nc4ccc(OCC(=O)O)c(C(=O)N[C@@H](CCCCN)C(=O)Nc5ccc(OC)c(C(N)=O)c5)c4)c3)c2)cc1] |
| 360 | 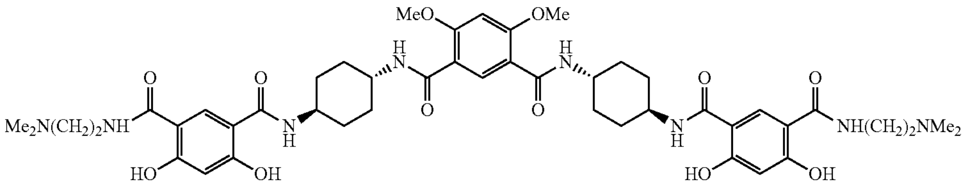 |

TABLE 2-continued
| Compound Number | Compound Structure |
|---|---|
| 361 | 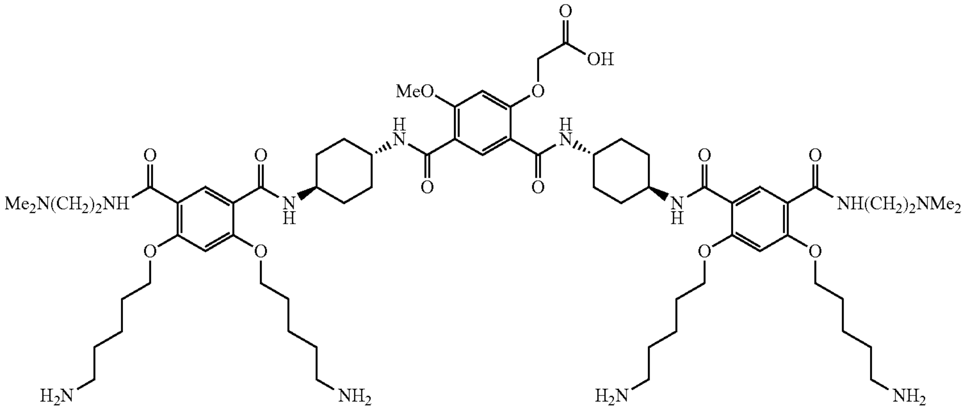 |
| 362 | 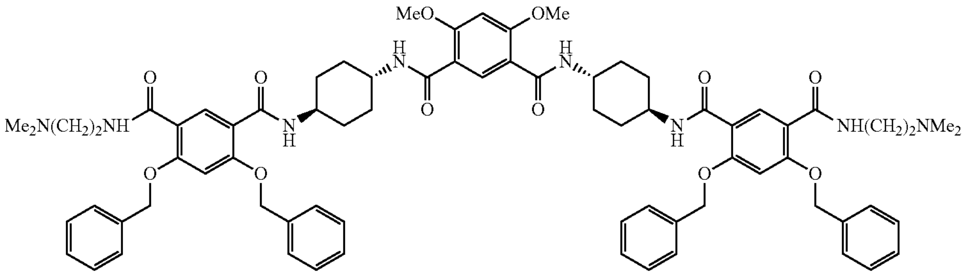 |
| 363 | 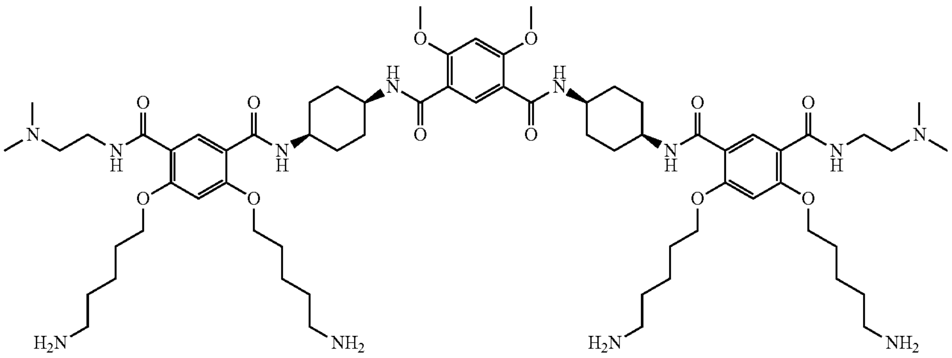 |
| 364 | 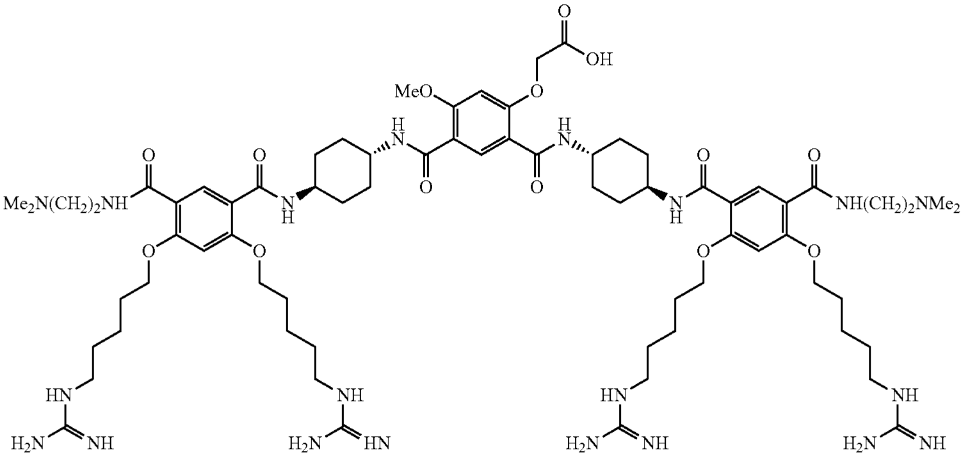 |

TABLE 2-continued
| Compound Number | Compound Structure |
|---|---|
| 365 | 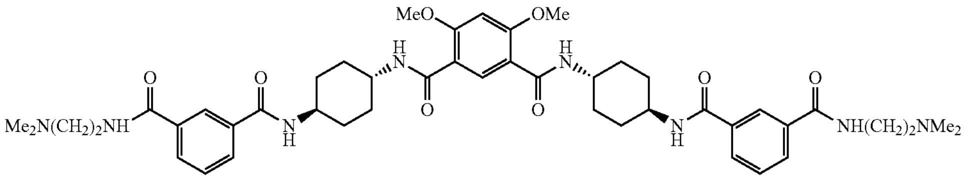 |
| 366 | 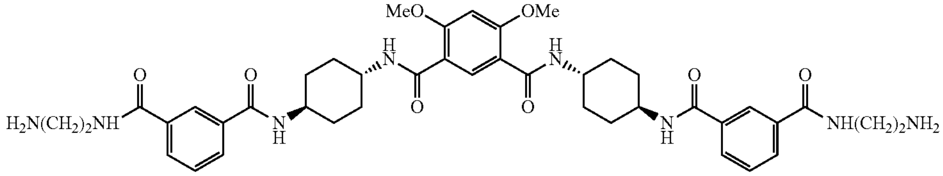 |
| 367 | 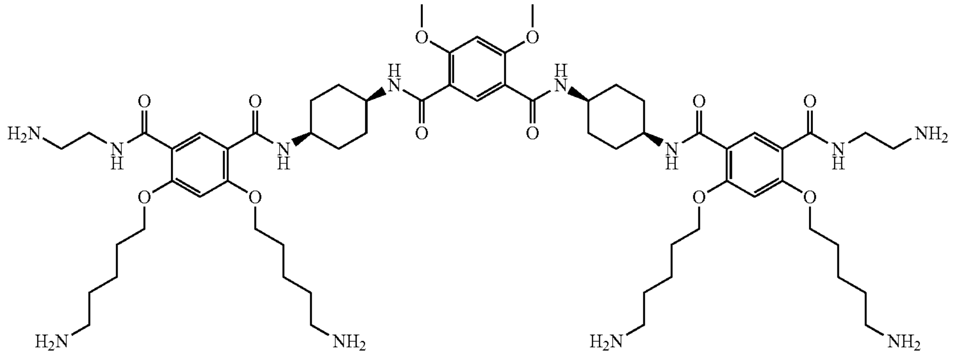 [SMILES: COc1cc(OC)c(C(=O)N[C@H]2CC[C@@H](NC(=O)c3cc(C(=O)NCCN)c(OCCCCCN)cc3OCCCCCN)CC2)cc1C(=O)N[C@H]1CC[C@@H](NC(=O)c2cc(C(=O)NCCN)c(OCCCCCN)cc2OCCCCCN)CC1] |
| 368 | 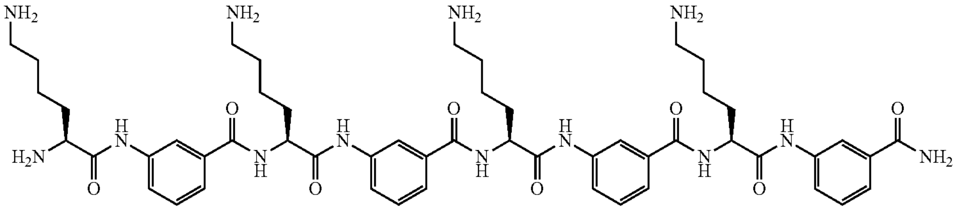 [SMILES: NCCCC[C@H](NC(=O)c1cccc(NC(=O)[C@H](CCCCN)NC(=O)c2cccc(NC(=O)[C@H](CCCCN)NC(=O)c3cccc(NC(=O)[C@@H](N)CCCCN)c3)c2)c1)C(=O)Nc1cccc(C(N)=O)c1] |
| 369 | 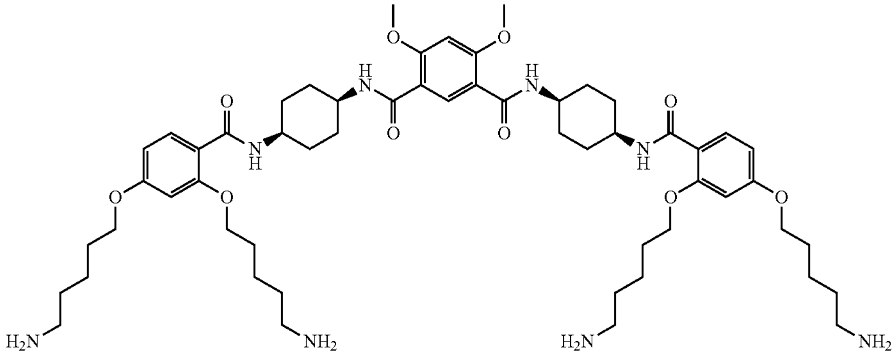 [SMILES: COc1cc(OC)c(C(=O)N[C@H]2CC[C@@H](NC(=O)c3ccc(OCCCCCN)cc3OCCCCCN)CC2)cc1C(=O)N[C@H]1CC[C@@H](NC(=O)c2ccc(OCCCCCN)cc2OCCCCCN)CC1] |
| 370 | 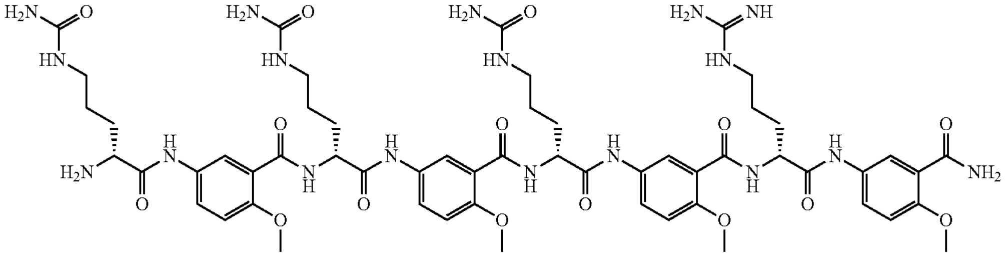 [SMILES: COc1ccc(NC(=O)[C@@H](CCCNC(=N)N)NC(=O)c2cc(NC(=O)[C@@H](CCCNC(N)=O)NC(=O)c3cc(NC(=O)[C@@H](CCCNC(N)=O)NC(=O)c4cc(NC(=O)[C@H](N)CCCNC(N)=O)ccc4OC)ccc3OC)ccc2OC)cc1C(N)=O] |

TABLE 2-continued
| Compound Number | Compound Structure |
| --- | --- |
| 371 | 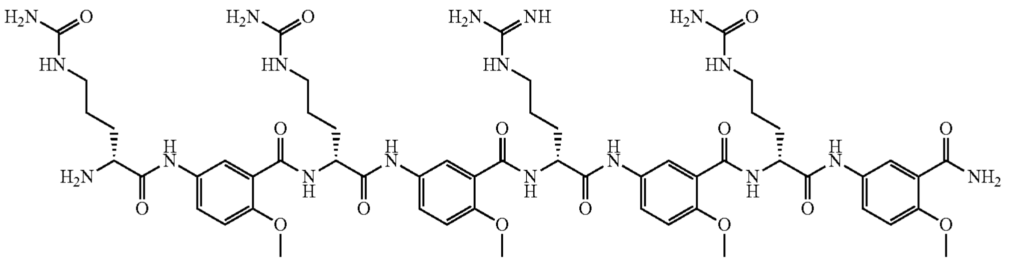 [SMILES: COc1ccc(NC(=O)[C@@H](CCCNC(N)=O)NC(=O)c2cc(NC(=O)[C@@H](CCCNC(=N)N)NC(=O)c3cc(NC(=O)[C@@H](CCCNC(N)=O)NC(=O)c4cc(NC(=O)[C@H](N)CCCNC(N)=O)ccc4OC)ccc3OC)ccc2OC)cc1C(N)=O] |
| 372 | 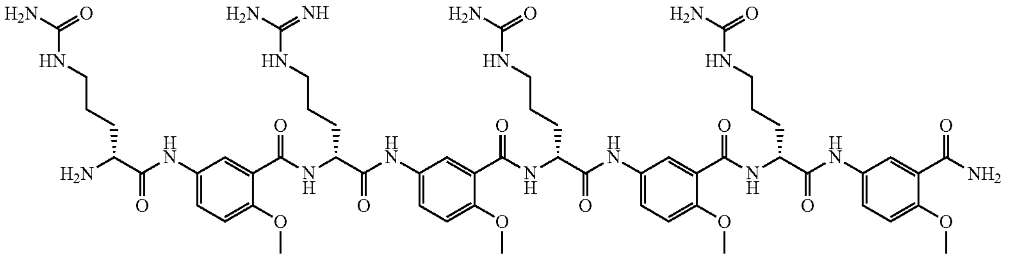 [SMILES: COc1ccc(NC(=O)[C@@H](CCCNC(N)=O)NC(=O)c2cc(NC(=O)[C@@H](CCCNC(N)=O)NC(=O)c3cc(NC(=O)[C@@H](CCCNC(=N)N)NC(=O)c4cc(NC(=O)[C@H](N)CCCNC(N)=O)ccc4OC)ccc3OC)ccc2OC)cc1C(N)=O] |
| 373 | 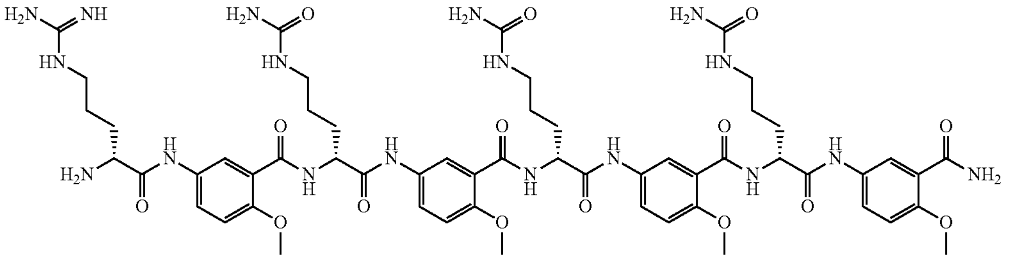 [SMILES: COc1ccc(NC(=O)[C@@H](CCCNC(N)=O)NC(=O)c2cc(NC(=O)[C@@H](CCCNC(N)=O)NC(=O)c3cc(NC(=O)[C@@H](CCCNC(N)=O)NC(=O)c4cc(NC(=O)[C@H](N)CCCNC(=N)N)ccc4OC)ccc3OC)ccc2OC)cc1C(N)=O] |
| 374 | 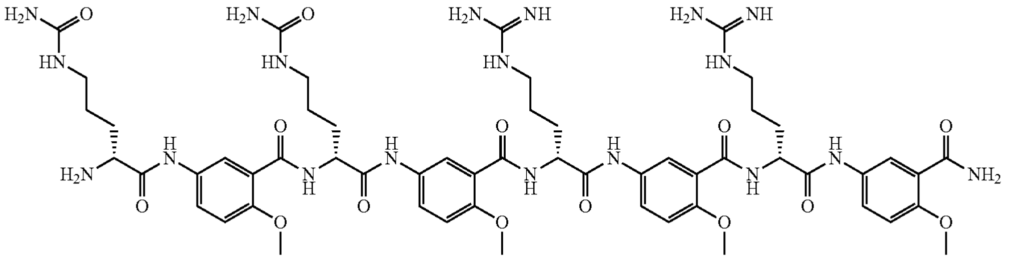 [SMILES: COc1ccc(NC(=O)[C@@H](CCCNC(=N)N)NC(=O)c2cc(NC(=O)[C@@H](CCCNC(=N)N)NC(=O)c3cc(NC(=O)[C@@H](CCCNC(N)=O)NC(=O)c4cc(NC(=O)[C@H](N)CCCNC(N)=O)ccc4OC)ccc3OC)ccc2OC)cc1C(N)=O] |
| 375 | 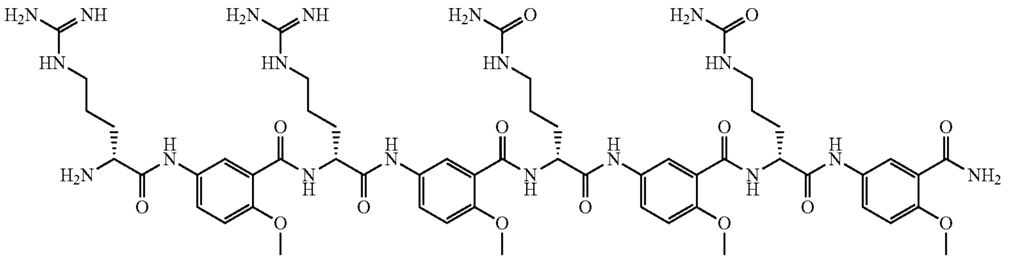 [SMILES: COc1ccc(NC(=O)[C@@H](CCCNC(N)=O)NC(=O)c2cc(NC(=O)[C@@H](CCCNC(N)=O)NC(=O)c3cc(NC(=O)[C@@H](CCCNC(=N)N)NC(=O)c4cc(NC(=O)[C@H](N)CCCNC(=N)N)ccc4OC)ccc3OC)ccc2OC)cc1C(N)=O] |

TABLE 2-continued
| Compound Number | Compound Structure |
|---|---|
| 376 | 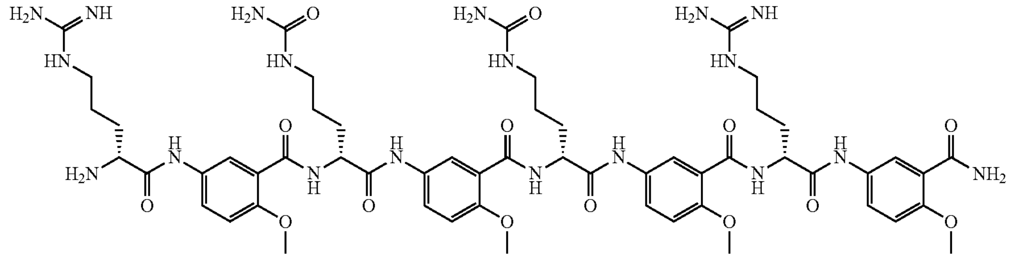 [SMILES: COc1ccc(NC(=O)[C@@H](CCCNC(=N)N)NC(=O)c2cc(NC(=O)[C@@H](CCCNC(N)=O)NC(=O)c3cc(NC(=O)[C@@H](CCCNC(N)=O)NC(=O)c4cc(NC(=O)[C@H](N)CCCNC(=N)N)ccc4OC)ccc3OC)ccc2OC)cc1C(N)=O] |
| 377 | 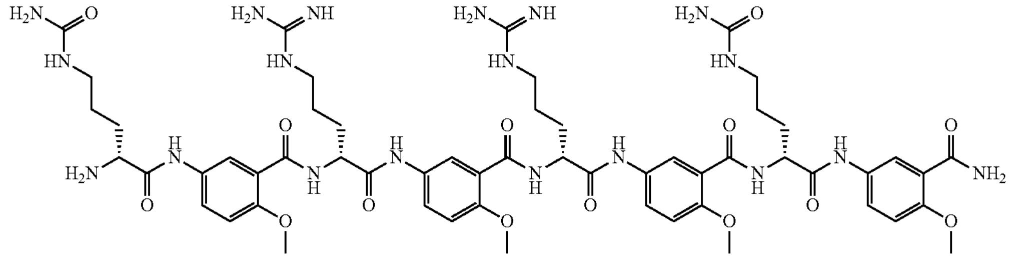 |
| 378 | 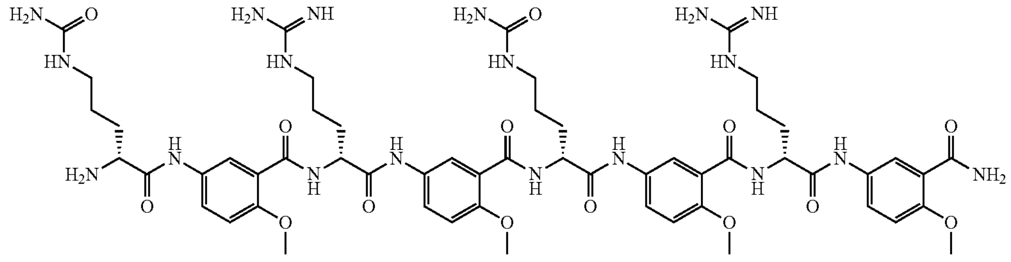 [SMILES: COc1ccc(NC(=O)[C@@H](CCCNC(=N)N)NC(=O)c2cc(NC(=O)[C@@H](CCCNC(N)=O)NC(=O)c3cc(NC(=O)[C@@H](CCCNC(=N)N)NC(=O)c4cc(NC(=O)[C@H](N)CCCNC(N)=O)ccc4OC)ccc3OC)ccc2OC)cc1C(N)=O] |
| 379 | 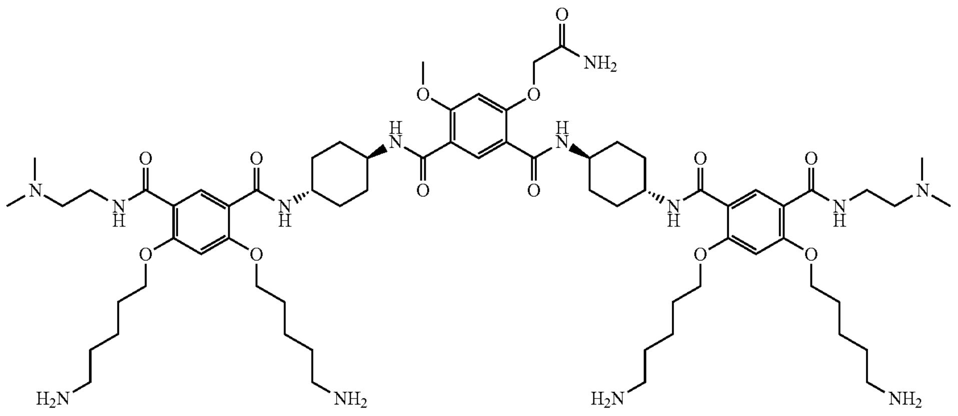 |

TABLE 2-continued
| Compound Number | Compound Structure |
| --- | --- |
| 380 | 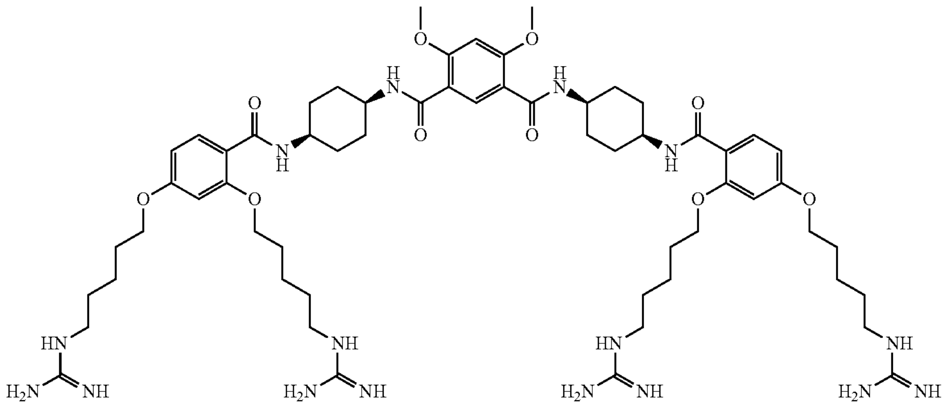 [SMILES: COc1cc(OC)c(C(=O)N[C@H]2CC[C@@H](NC(=O)c3ccc(OCCCCCNC(=N)N)cc3OCCCCCNC(=N)N)CC2)cc1C(=O)N[C@H]1CC[C@@H](NC(=O)c2ccc(OCCCCCNC(=N)N)cc2OCCCCCNC(=N)N)CC1] |
| 381 | 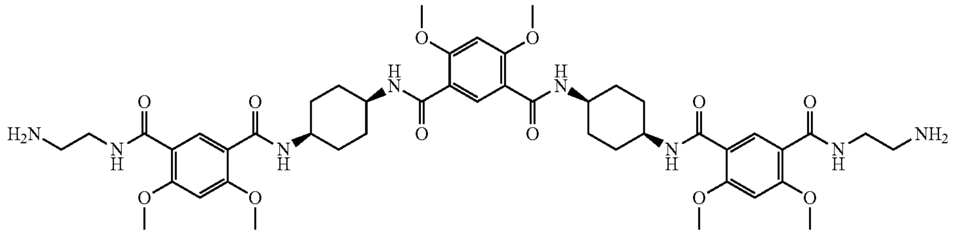 [SMILES: COc1cc(OC)c(C(=O)N[C@H]2CC[C@@H](NC(=O)c3cc(C(=O)N[C@H]4CC[C@@H](NC(=O)c5cc(C(=O)NCCN)c(OC)cc5OC)CC4)c(OC)cc3OC)CC2)cc1C(=O)NCCN] |
| 382 | 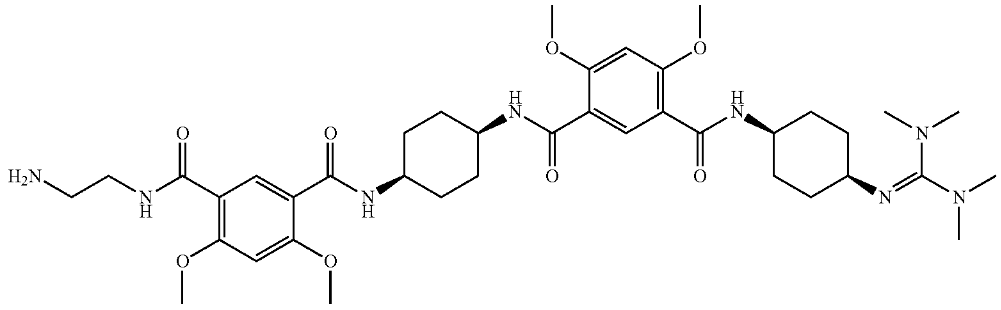 [SMILES: COc1cc(OC)c(C(=O)N[C@H]2CC[C@@H](NC(=O)c3cc(C(=O)N[C@H]4CC[C@@H](N=C(N(C)C)N(C)C)CC4)c(OC)cc3OC)CC2)cc1C(=O)NCCN] |
| 383 | 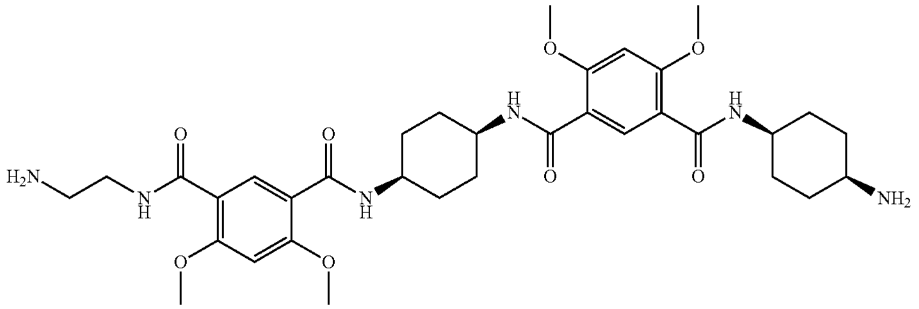 [SMILES: COc1cc(OC)c(C(=O)N[C@H]2CC[C@@H](NC(=O)c3cc(C(=O)N[C@H]4CC[C@@H](N)CC4)c(OC)cc3OC)CC2)cc1C(=O)NCCN] |
| 384 | 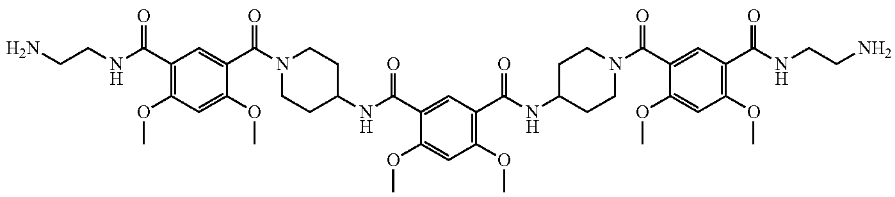 [SMILES: COc1cc(OC)c(C(=O)N2CCC(NC(=O)c3cc(C(=O)NC4CCN(C(=O)c5cc(C(=O)NCCN)c(OC)cc5OC)CC4)c(OC)cc3OC)CC2)cc1C(=O)NCCN] |

TABLE 2-continued
| Compound Number | Compound Structure |
| --- | --- |
| 385 | 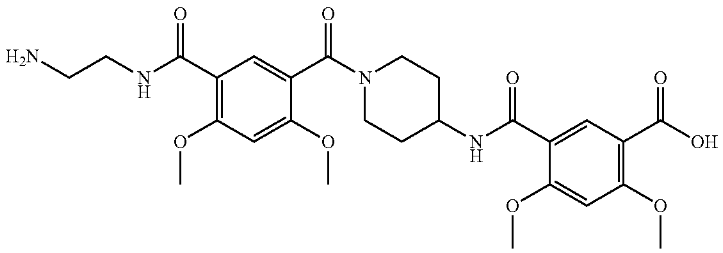 [SMILES: COc1cc(OC)c(C(=O)NC2CCN(C(=O)c3cc(C(=O)NCCN)c(OC)cc3OC)CC2)cc1C(=O)O] |
| 386 | 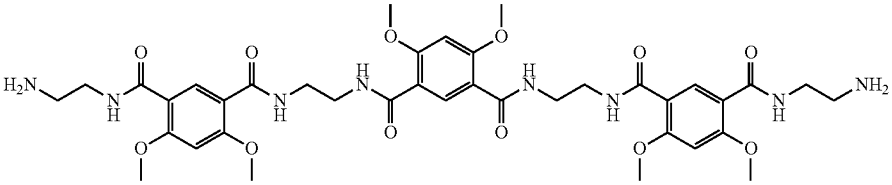 [SMILES: COc1cc(OC)c(C(=O)NCCNC(=O)c2cc(C(=O)NCCNC(=O)c3cc(C(=O)NCCN)c(OC)cc3OC)c(OC)cc2OC)cc1C(=O)NCCN] |
| 387 | 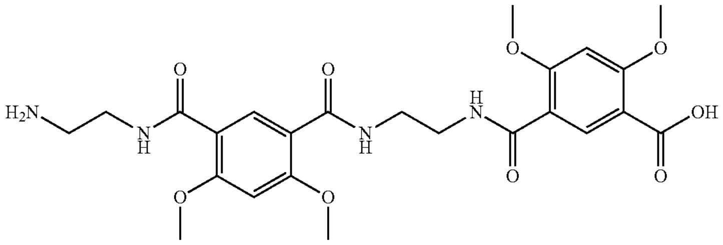 [SMILES: COc1cc(OC)c(C(=O)NCCNC(=O)c2cc(C(=O)NCCN)c(OC)cc2OC)cc1C(=O)O] |
| 388 | 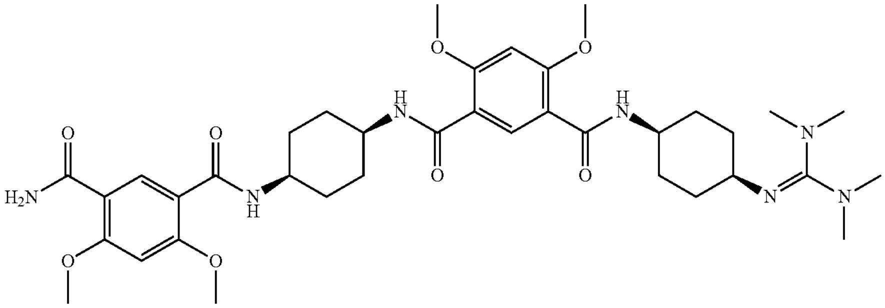 [SMILES: COc1cc(OC)c(C(=O)N[C@H]2CC[C@@H](NC(=O)c3cc(C(=O)N[C@H]4CC[C@@H](N=C(N(C)C)N(C)C)CC4)c(OC)cc3OC)CC2)cc1C(N)=O] |
| 389 | 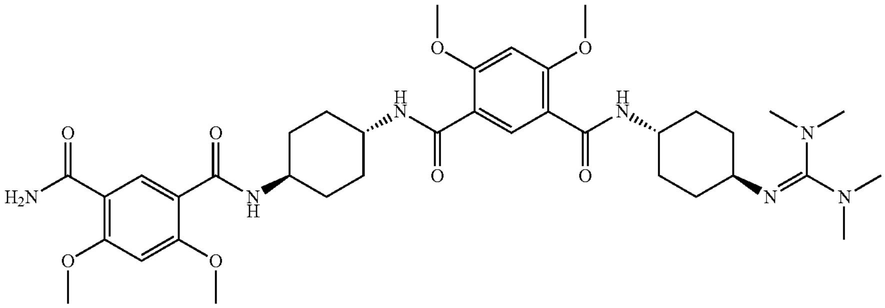 [SMILES: COc1cc(OC)c(C(=O)N[C@H]2CC[C@H](NC(=O)c3cc(C(=O)N[C@H]4CC[C@H](N=C(N(C)C)N(C)C)CC4)c(OC)cc3OC)CC2)cc1C(N)=O] |

TABLE 2-continued
| Compound Number | Compound Structure |
|---|---|
| 390 | 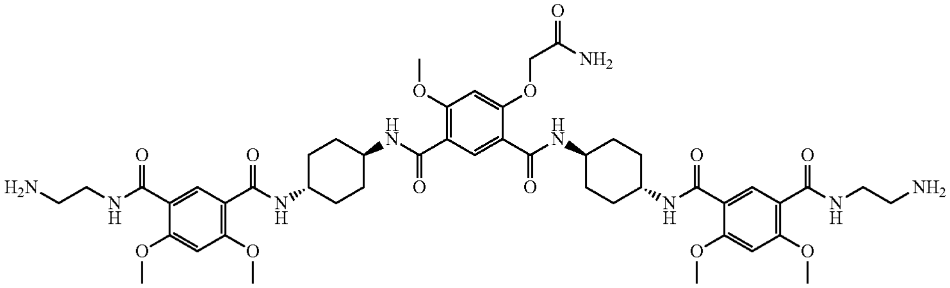 [SMILES: COc1cc(OC)c(C(=O)N[C@H]2CC[C@H](NC(=O)c3cc(C(=O)N[C@H]4CC[C@H](NC(=O)c5cc(C(=O)NCCN)c(OC)cc5OC)CC4)c(OCC(N)=O)cc3OC)CC2)cc1C(=O)NCCN] |
| 391 | 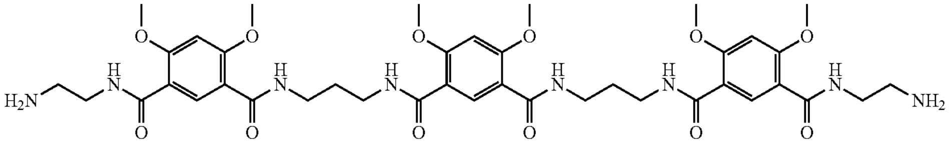 [SMILES: COc1cc(OC)c(C(=O)NCCCNC(=O)c2cc(C(=O)NCCCNC(=O)c3cc(C(=O)NCCN)c(OC)cc3OC)c(OC)cc2OC)cc1C(=O)NCCN] |
| 392 | 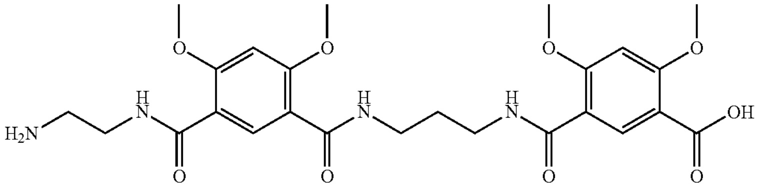 [SMILES: COc1cc(OC)c(C(=O)NCCCNC(=O)c2cc(C(=O)NCCN)c(OC)cc2OC)cc1C(=O)O] |
| 393 | 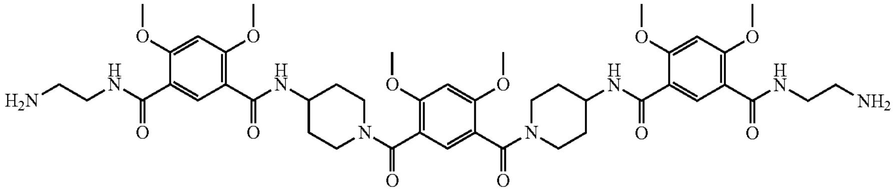 [SMILES: COc1cc(OC)c(C(=O)NC2CCN(C(=O)c3cc(C(=O)N4CCC(NC(=O)c5cc(C(=O)NCCN)c(OC)cc5OC)CC4)c(OC)cc3OC)CC2)cc1C(=O)NCCN] |
| 394 | 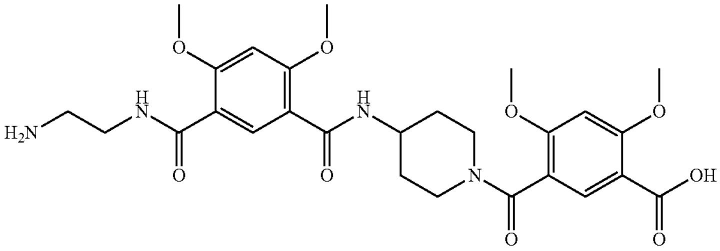 [SMILES: COc1cc(OC)c(C(=O)N2CCC(NC(=O)c3cc(C(=O)NCCN)c(OC)cc3OC)CC2)cc1C(=O)O] |
| 395 | 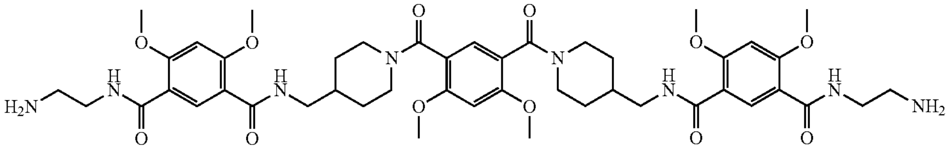 [SMILES: COc1cc(OC)c(C(=O)NCC2CCN(C(=O)c3cc(C(=O)N4CCC(CNC(=O)c5cc(C(=O)NCCN)c(OC)cc5OC)CC4)c(OC)cc3OC)CC2)cc1C(=O)NCCN] |
| 396 | 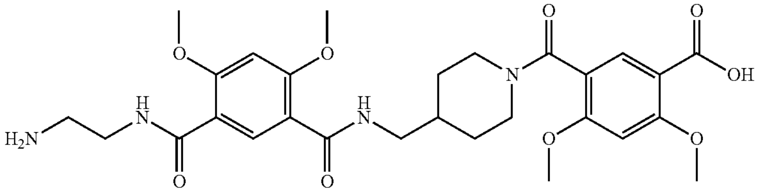 [SMILES: COc1cc(OC)c(C(=O)N2CCC(CNC(=O)c3cc(C(=O)NCCN)c(OC)cc3OC)CC2)cc1C(=O)O] |

TABLE 2-continued
| Compound Number | Compound Structure |
|---|---|
| 397 | 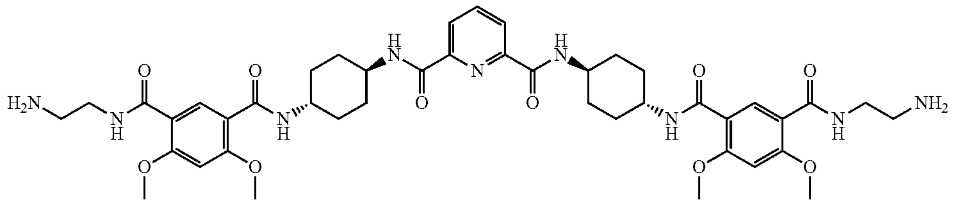 [SMILES: COc1cc(OC)c(C(=O)N[C@H]2CC[C@H](NC(=O)c3cccc(C(=O)N[C@H]4CC[C@H](NC(=O)c5cc(C(=O)NCCN)c(OC)cc5OC)CC4)n3)CC2)cc1C(=O)NCCN] |
| 398 | 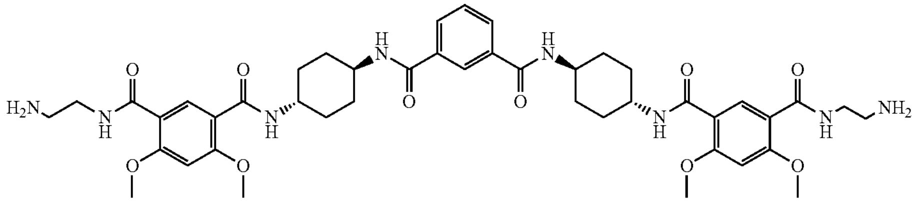 [SMILES: COc1cc(OC)c(C(=O)N[C@H]2CC[C@H](NC(=O)c3cccc(C(=O)N[C@H]4CC[C@H](NC(=O)c5cc(C(=O)NCCN)c(OC)cc5OC)CC4)c3)CC2)cc1C(=O)NCCN] |
| 399 | 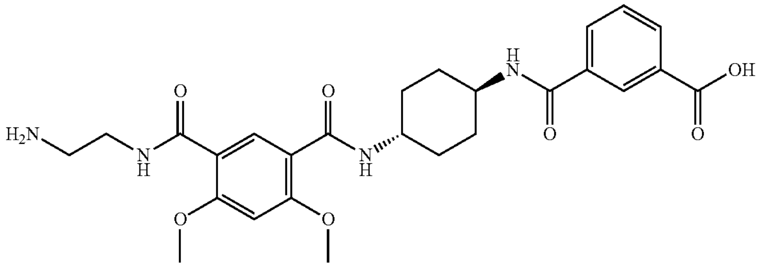 [SMILES: COc1cc(OC)c(C(=O)N[C@H]2CC[C@H](NC(=O)c3cccc(C(=O)O)c3)CC2)cc1C(=O)NCCN] |
| 400 | 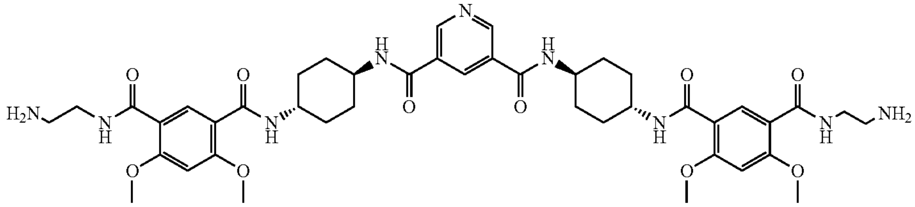 [SMILES: COc1cc(OC)c(C(=O)N[C@H]2CC[C@H](NC(=O)c3cncc(C(=O)N[C@H]4CC[C@H](NC(=O)c5cc(C(=O)NCCN)c(OC)cc5OC)CC4)c3)CC2)cc1C(=O)NCCN] |
| 401 | 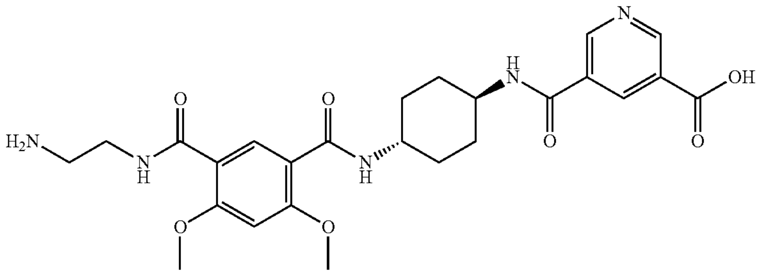 [SMILES: COc1cc(OC)c(C(=O)N[C@H]2CC[C@H](NC(=O)c3cncc(C(=O)O)c3)CC2)cc1C(=O)NCCN] |
| 402 | 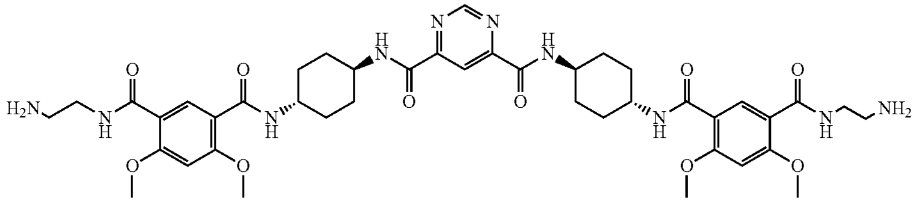 |

TABLE 2-continued
| Compound Number | Compound Structure |
|---|---|
| 403 | 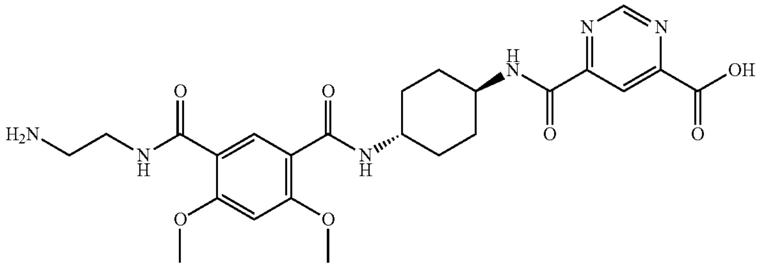 [SMILES: COc1cc(OC)c(C(=O)N[C@H]2CC[C@H](NC(=O)c3cc(C(=O)O)ncn3)CC2)cc1C(=O)NCCN] |
| 404 | 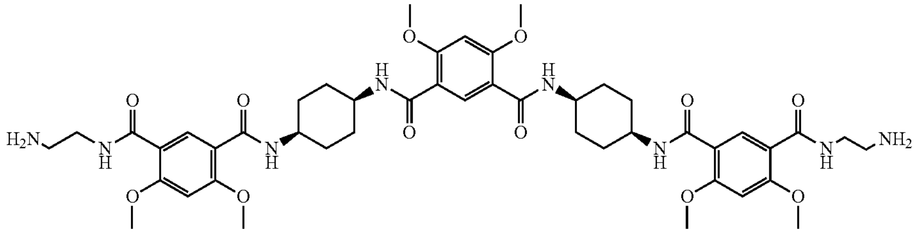 [SMILES: COc1cc(OC)c(C(=O)N[C@H]2CC[C@@H](NC(=O)c3cc(C(=O)N[C@H]4CC[C@@H](NC(=O)c5cc(C(=O)NCCN)c(OC)cc5OC)CC4)c(OC)cc3OC)CC2)cc1C(=O)NCCN] |
| 405 | 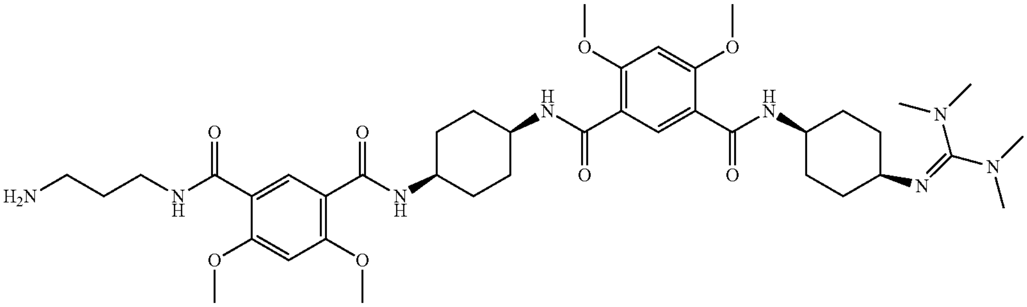 [SMILES: COc1cc(OC)c(C(=O)N[C@H]2CC[C@@H](NC(=O)c3cc(C(=O)N[C@H]4CC[C@@H](N=C(N(C)C)N(C)C)CC4)c(OC)cc3OC)CC2)cc1C(=O)NCCCN] |
| 406 | 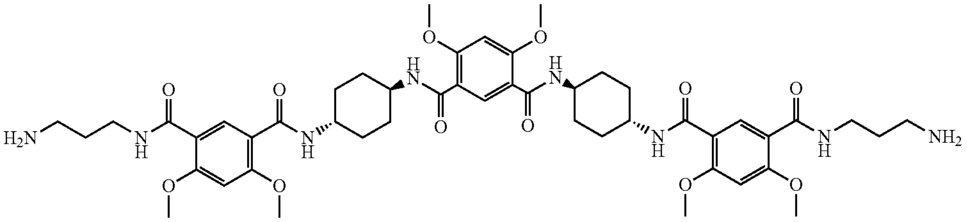 [SMILES: COc1cc(OC)c(C(=O)N[C@H]2CC[C@H](NC(=O)c3cc(C(=O)N[C@H]4CC[C@H](NC(=O)c5cc(C(=O)NCCCN)c(OC)cc5OC)CC4)c(OC)cc3OC)CC2)cc1C(=O)NCCCN] |
| 407 | 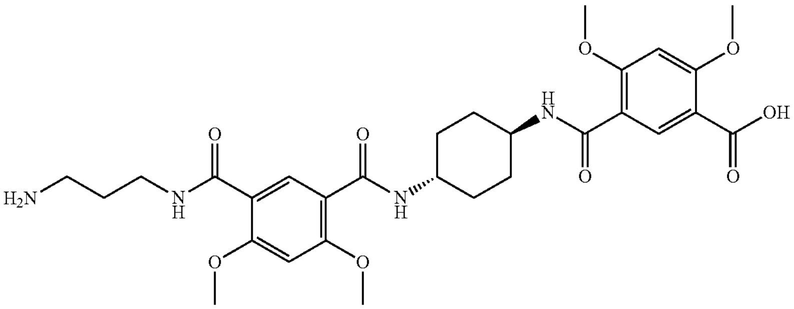 [SMILES: COc1cc(OC)c(C(=O)N[C@H]2CC[C@H](NC(=O)c3cc(C(=O)NCCCN)c(OC)cc3OC)CC2)cc1C(=O)O] |
| 408 | 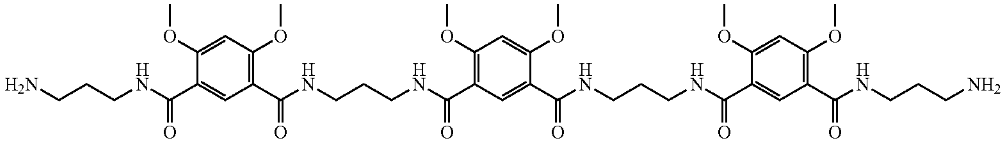 [SMILES: COc1cc(OC)c(C(=O)NCCCNC(=O)c2cc(C(=O)NCCCNC(=O)c3cc(C(=O)NCCCN)c(OC)cc3OC)c(OC)cc2OC)cc1C(=O)NCCCN] |

TABLE 2-continued
| Compound Number | Compound Structure |
|---|---|
| 409 | 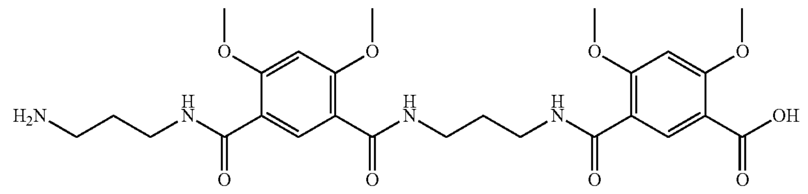 [SMILES: COc1cc(OC)c(C(=O)NCCCNC(=O)c2cc(C(=O)NCCCN)c(OC)cc2OC)cc1C(=O)O] |
| 410 | 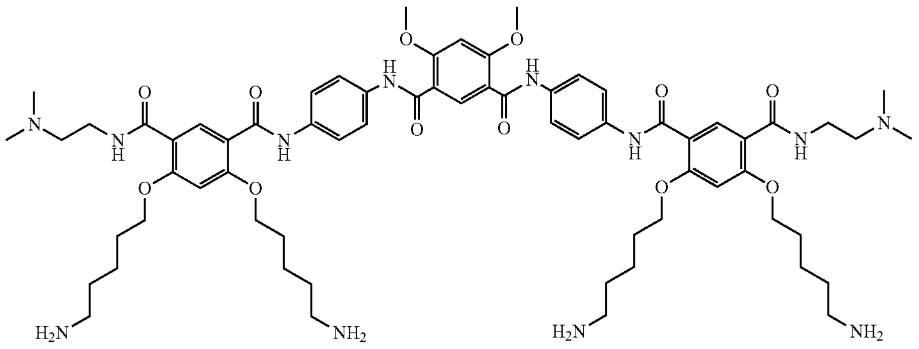 |
| 411 | 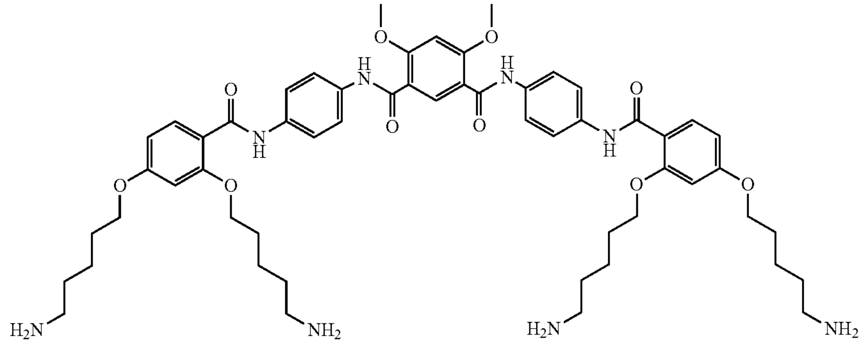 [SMILES: COc1cc(OC)c(C(=O)Nc2ccc(NC(=O)c3ccc(OCCCCCN)cc3OCCCCCN)cc2)cc1C(=O)Nc1ccc(NC(=O)c2ccc(OCCCCCN)cc2OCCCCCN)cc1] |
| 412 | 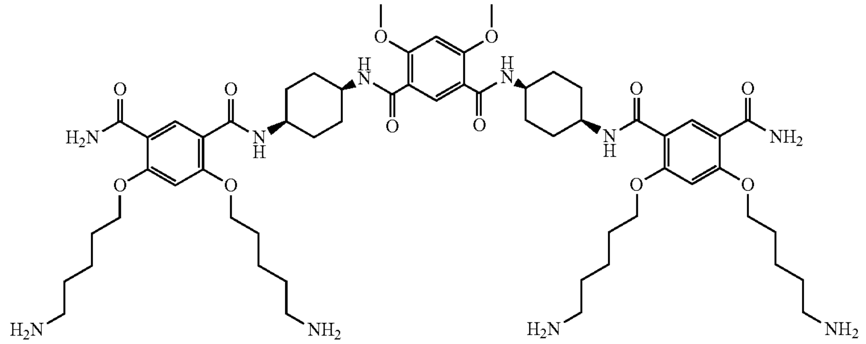 [SMILES: COc1cc(OC)c(C(=O)N[C@H]2CC[C@@H](NC(=O)c3cc(C(N)=O)c(OCCCCCN)cc3OCCCCCN)CC2)cc1C(=O)N[C@H]1CC[C@@H](NC(=O)c2cc(C(N)=O)c(OCCCCCN)cc2OCCCCCN)CC1] |

TABLE 2-continued
| Compound Number | Compound Structure |
|---|---|
| 413 | 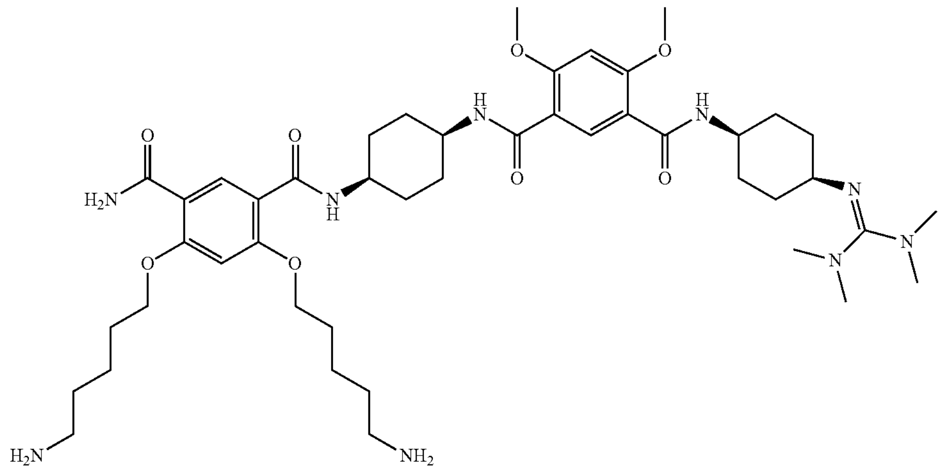 [SMILES: COc1cc(OC)c(C(=O)N[C@H]2CC[C@@H](NC(=O)c3cc(C(N)=O)c(OCCCCCN)cc3OCCCCCN)CC2)cc1C(=O)N[C@H]1CC[C@@H](N=C(N(C)C)N(C)C)CC1] |
| 414 | 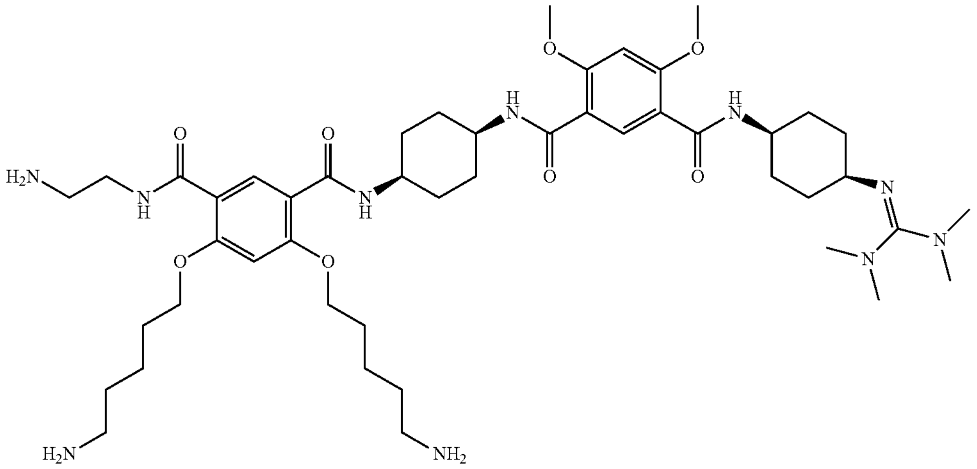 [SMILES: COc1cc(OC)c(C(=O)N[C@H]2CC[C@@H](NC(=O)c3cc(C(=O)NCCN)c(OCCCCCN)cc3OCCCCCN)CC2)cc1C(=O)N[C@H]1CC[C@@H](N=C(N(C)C)N(C)C)CC1] |
| 415 | 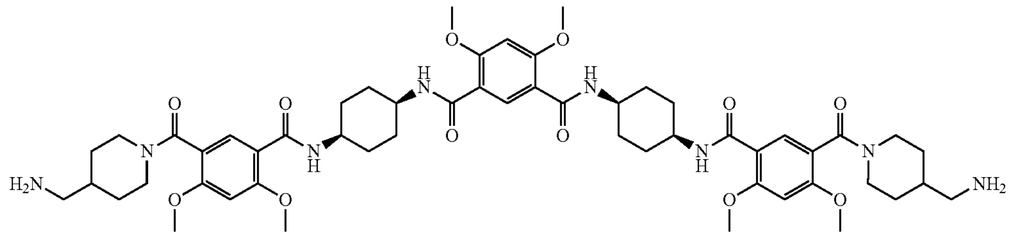 [SMILES: COc1cc(OC)c(C(=O)N[C@H]2CC[C@@H](NC(=O)c3cc(C(=O)N4CCC(CN)CC4)c(OC)cc3OC)CC2)cc1C(=O)N[C@H]1CC[C@@H](NC(=O)c2cc(C(=O)N3CCC(CN)CC3)c(OC)cc2OC)CC1] |
| 416 | 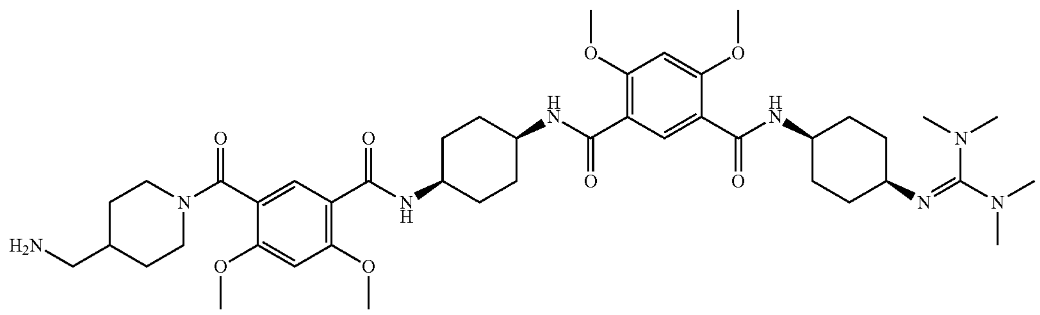 [SMILES: COc1cc(OC)c(C(=O)N[C@H]2CC[C@@H](NC(=O)c3cc(C(=O)N4CCC(CN)CC4)c(OC)cc3OC)CC2)cc1C(=O)N[C@H]1CC[C@@H](N=C(N(C)C)N(C)C)CC1] |

TABLE 2-continued
| Compound Number | Compound Structure |
|---|---|
| 417 | 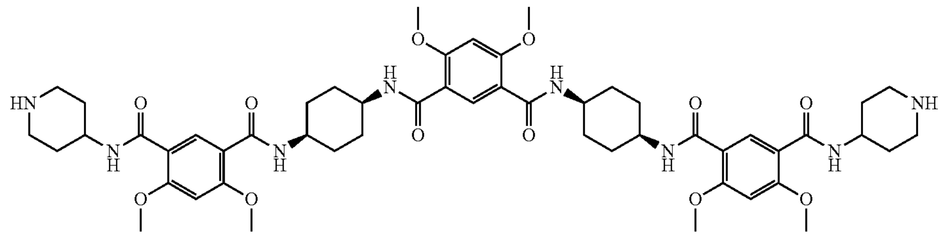 [SMILES: COc1cc(OC)c(C(=O)N[C@H]2CC[C@@H](NC(=O)c3cc(C(=O)N[C@H]4CC[C@@H](NC(=O)c5cc(C(=O)NC6CCNCC6)c(OC)cc5OC)CC4)c(OC)cc3OC)CC2)cc1C(=O)NC1CCNCC1] |
| 418 | 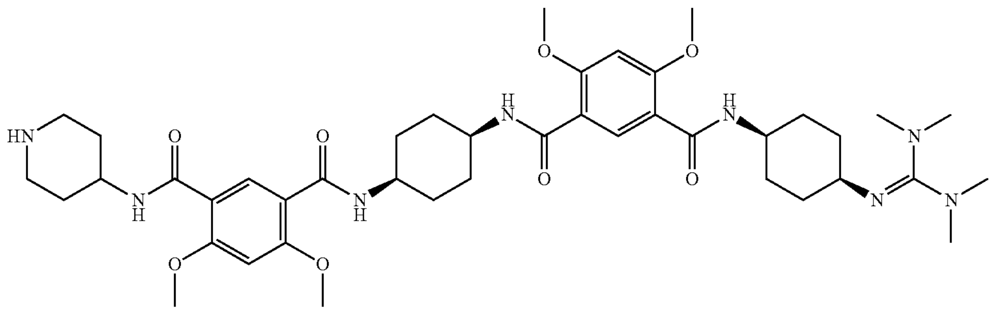 [SMILES: COc1cc(OC)c(C(=O)N[C@H]2CC[C@@H](NC(=O)c3cc(C(=O)N[C@H]4CC[C@@H](N=C(N(C)C)N(C)C)CC4)c(OC)cc3OC)CC2)cc1C(=O)NC1CCNCC1] |
| 419 | 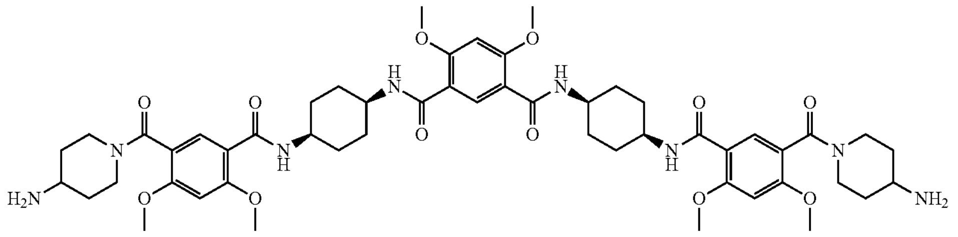 [SMILES: COc1cc(OC)c(C(=O)N[C@H]2CC[C@@H](NC(=O)c3cc(C(=O)N4CCC(N)CC4)c(OC)cc3OC)CC2)cc1C(=O)N[C@H]1CC[C@@H](NC(=O)c2cc(C(=O)N3CCC(N)CC3)c(OC)cc2OC)CC1] |
| 420 | 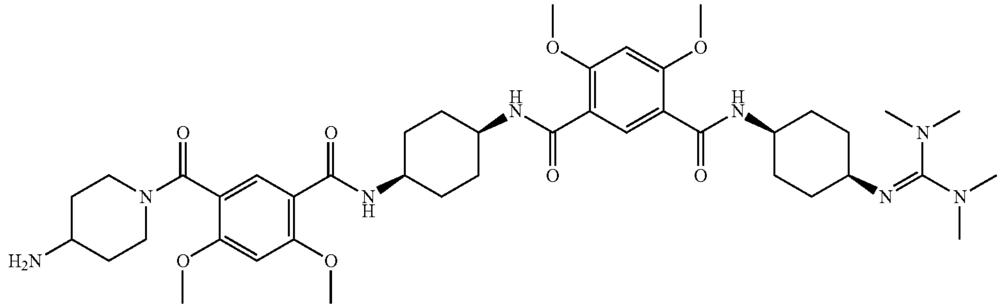 [SMILES: COc1cc(OC)c(C(=O)N[C@H]2CC[C@@H](NC(=O)c3cc(C(=O)N4CCC(N)CC4)c(OC)cc3OC)CC2)cc1C(=O)N[C@H]1CC[C@@H](N=C(N(C)C)N(C)C)CC1] |
| 421 | 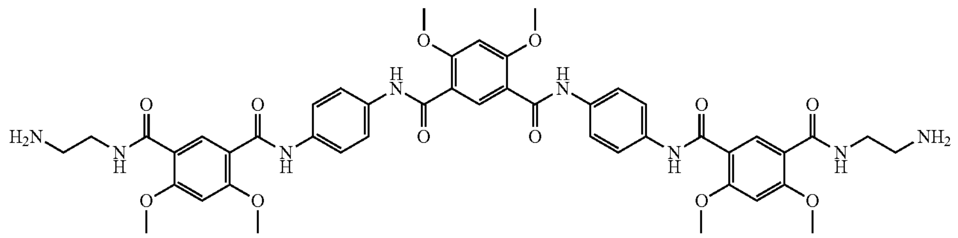 [SMILES: COc1cc(OC)c(C(=O)Nc2ccc(NC(=O)c3cc(C(=O)Nc4ccc(NC(=O)c5cc(C(=O)NCCN)c(OC)cc5OC)cc4)c(OC)cc3OC)cc2)cc1C(=O)NCCN] |

TABLE 2-continued
| Compound Number | Compound Structure |
|---|---|
| 422 | 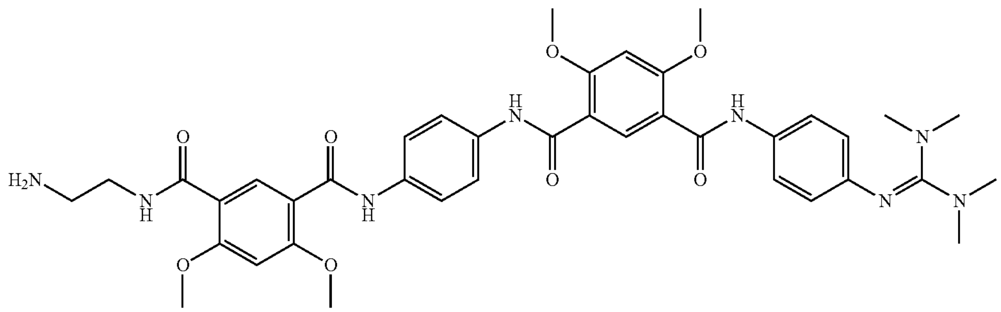 [SMILES: COc1cc(OC)c(C(=O)Nc2ccc(NC(=O)c3cc(C(=O)Nc4ccc(N=C(N(C)C)N(C)C)cc4)c(OC)cc3OC)cc2)cc1C(=O)NCCN] |
| 423 | 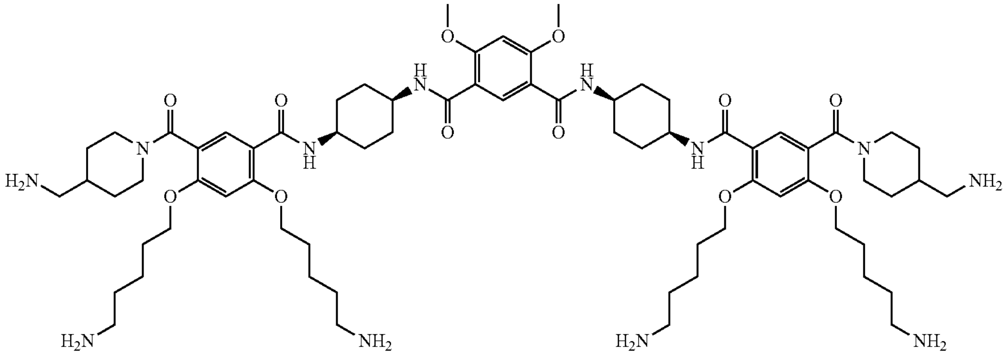 [SMILES: COc1cc(OC)c(C(=O)N[C@H]2CC[C@@H](NC(=O)c3cc(C(=O)N4CCC(CN)CC4)c(OCCCCCN)cc3OCCCCCN)CC2)cc1C(=O)N[C@H]1CC[C@@H](NC(=O)c2cc(C(=O)N3CCC(CN)CC3)c(OCCCCCN)cc2OCCCCCN)CC1] |
| 424 | 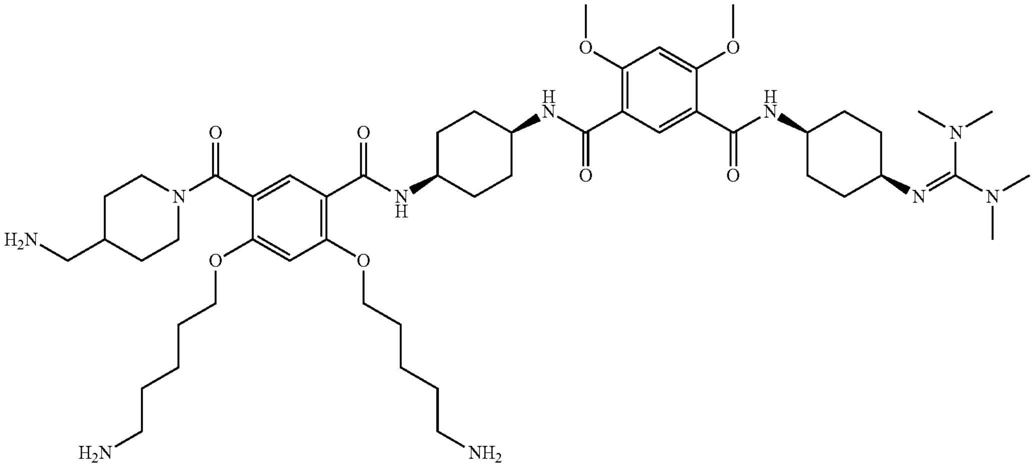 [SMILES: COc1cc(OC)c(C(=O)N[C@H]2CC[C@@H](NC(=O)c3cc(C(=O)N4CCC(CN)CC4)c(OCCCCCN)cc3OCCCCCN)CC2)cc1C(=O)N[C@H]1CC[C@@H](N=C(N(C)C)N(C)C)CC1] |
| 425 | 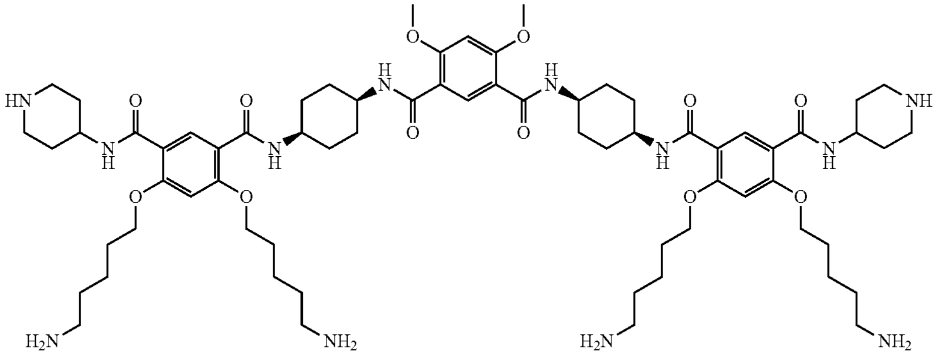 [SMILES: COc1cc(OC)c(C(=O)N[C@H]2CC[C@@H](NC(=O)c3cc(C(=O)NC4CCNCC4)c(OCCCCCN)cc3OCCCCCN)CC2)cc1C(=O)N[C@H]1CC[C@@H](NC(=O)c2cc(C(=O)NC3CCNCC3)c(OCCCCCN)cc2OCCCCCN)CC1] |

TABLE 2-continued

| Compound Number | Compound Structure |
| --- | --- |
| 426 | 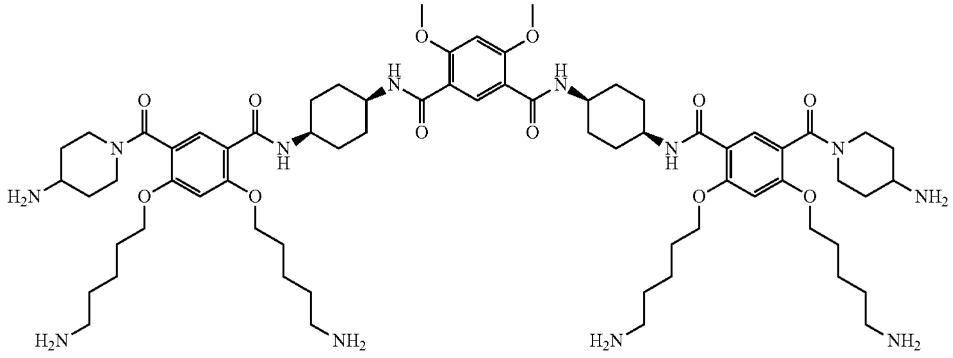 [SMILES: COc1cc(OC)c(C(=O)N[C@H]2CC[C@@H](NC(=O)c3cc(C(=O)N4CCC(N)CC4)c(OCCCCCN)cc3OCCCCCN)CC2)cc1C(=O)N[C@H]1CC[C@@H](NC(=O)c2cc(C(=O)N3CCC(N)CC3)c(OCCCCCN)cc2OCCCCCN)CC1] |
| 427 | 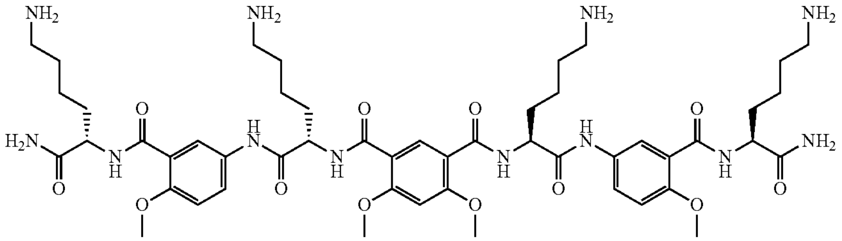 [SMILES: COc1ccc(NC(=O)[C@H](CCCCN)NC(=O)c2cc(C(=O)N[C@@H](CCCCN)C(=O)Nc3ccc(OC)c(C(=O)N[C@@H](CCCCN)C(N)=O)c3)c(OC)cc2OC)cc1C(=O)N[C@@H](CCCCN)C(N)=O] |

The exemplary compounds (and/or their salts) in Table 2 were prepared by methods such as those reported in U.S. Patent Application Publication Nos. U.S. 2005/0287108, U.S. 2006/0041023, U.S. Pat. No. 7,173,102, WO 2005/123660, WO 2004/082643, WO 2006/093813, and U.S. patent application Ser. No. 12/510,593 filed Jul. 28, 2009.

The compounds of the invention may be useful for treating and/or preventing mucositis by administering to the patient an effective amount of a compound of the invention or a salt thereof, or a pharmaceutical composition comprising a compound of the invention or a salt thereof. The compound or salt, or composition thereof, can be administered systemically or topically and can be administered to any body site or tissue.

In some embodiments, the present methods for treating and/or preventing mucositis can be used in a patient who receives chemotherapy and/or radiation therapy for cancer. In some embodiments, the patient is receiving or will be receiving high-dose chemotherapy prior to hematopoietic cell transplantation. In some embodiments, the patient is receiving or will be receiving radiation therapy for tumors of the head and neck. In some embodiments, the patient is receiving or will be receiving induction therapy for leukemia. In some embodiments, the patient is receiving or will be receiving conditioning regimens for bone marrow transplant. In some embodiments, the patient is experiencing or will be experiencing basal epithelial cell death.

In some embodiments of the invention, the compound used for treating and/or preventing mucositis is not Compound Y. In some embodiments of the invention, the compound used for treating and/or preventing mucositis is not Compound Z. In some embodiments of the invention, the compound used for treating and/or preventing mucositis is not Compound Y or Compound Z.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds of the invention also include derivatives referred to as prodrugs. As used herein, the term "prodrug" refers to a derivative of a known direct acting drug, which derivative has enhanced delivery characteristics and therapeutic value as compared to the drug, and is transformed into the active drug by an enzymatic or chemical process.

It is understood that the present invention encompasses the use, where applicable, of stereoisomers, diastereomers and optical stereoisomers of the compounds of the invention, as well as mixtures thereof. Additionally, it is understood that stereoisomers, diastereomers, and optical stereoisomers of the compounds of the invention, and mixtures thereof, are within the scope of the invention. By way of non-limiting example, the mixture may be a racemate or the mixture may comprise unequal proportions of one particular stereoisomer over the other. Additionally, the compounds of the invention can be provided as a substantially pure stereoisomers, diastereomers and optical stereoisomers (such as epimers).

The compounds of the invention can be provided in the form of an acceptable salt (i.e., a pharmaceutically acceptable salt). Salts can be provided for pharmaceutical use, or as an intermediate in preparing the pharmaceutically desired form of the compounds of the invention. One example of a salt that can be considered to be acceptable is the hydrochloride acid addition salt. Hydrochloride acid addition salts are often acceptable salts when the pharmaceutically active agent has an amine group that can be protonated. Since the compounds of the invention may be polyionic, such as a polyamine, the acceptable salt can be provided in the form of a poly(amine hydrochloride).

The compounds of the invention may be used in methods for treating and/or preventing mucositis. For example, compounds of the invention may be used therapeutically to treat and/or prevent mucositis in patients such as animals, including humans and non-human vertebrates such as wild, domestic and farm animals.

In some embodiments, suitable dosage ranges for intravenous (i.v.) administration are 0.01 mg to 500 mg per kg body weight, 0.1 mg to 100 mg per kg body weight, 1 mg to 50 mg per kg body weight, or 10 mg to 35 mg per kg body weight. Suitable dosage ranges for other modes of administration can be calculated based on the forgoing dosages as known by those skilled in the art. For example, recommended dosages for intradermal, intramuscular, intraperitoneal, subcutaneous, epidural, sublingual, intracerebral, intravaginal, transdermal administration or administration by inhalation are in the range of 0.001 mg to 200 mg per kg of body weight, 0.01 mg to 100 mg per kg of body weight, 0.1 mg to 50 mg per kg of body weight, or 1 mg to 20 mg per kg of body weight. Effective doses may be extrapolated from dose-response curves derived from in vitro or animal model test systems. Such animal models and systems are well known in the art.

Polyamides and polyesters that are useful for the present invention can be prepared by typical condensation polymerization and addition polymerization processes (see, for example, G. Odian, Principles of Polymerization, John Wiley & Sons, Third Edition (1991), and M. Steven, Polymer Chemistry, Oxford University Press (1999)). Most commonly, the polyamides are prepared by a) thermal dehydration of amine salts of carboxylic acids, b) reaction of acid chlorides with amines, and c) aminolysis of esters. Methods a) and c) are of limited use in polymerizations of aniline derivatives which are generally prepared utilizing acid chlorides. The skilled chemist, however, will recognize that there are many alternative active acylating agents, for example phosphoryl anhydrides, active esters or azides, which may replace an acid chloride and which, depending of the particular polymer being prepared, may be superior to an acid chloride. The acid chloride route is probably the most versatile and has been used extensively for the synthesis of aromatic polyamides.

Homopolymers derived from substituted aminobenzoic acid derivatives can also prepared in a stepwise fashion. A stepwise process comprises coupling an N-protected amino acid to an amine (or hydroxy group) and subsequently removing the amine-protecting group and repeating the process. These techniques have been highly refined for synthesis of specific peptides, allow for the synthesis of specific sequences, and both solid-phase and solution techniques for peptide synthesis are directly applicable to the present invention. An alternative embodiment of the present invention is the corresponding polysulfonamides that can be prepared in analogous fashion by substituting sulfonyl chlorides for carboxylic acid chlorides.

The most common method for the preparation of polyureas is the reaction of diamines with diisocyanates (see, Yamaguchi et al., Polym. Bull., 2000, 44, 247). This exothermic reaction can be carried out by solution techniques or by interfacial techniques. One skilled in organic and polymer chemistry will appreciate that the diisocyanate can be replaced with a variety of other bis-acylating agents, such as phosgene or N,N'-(diimidazolyl)carbonyl, with similar results. Polyurethanes are prepared by comparable techniques using a diisocyanate and a dialcohol or by reaction of a diamine with a bis-chloroformate.

The syntheses of compounds of the invention can be carried out by routine and/or known methods such as those disclosed in, for example, U.S. Patent Application Publication Nos. 2005-0287108, 2006-0041023, U.S. Pat. No. 7,173,102, International Publication Nos. WO 2005/123660, WO 2004/082643, and WO 2006/093813, and U.S. Application Publication No. 2010-0081665, each of which is incorporated herein by reference in its entirety. Numerous pathways are available to incorporate polar and nonpolar side chains. Phenolic groups on the monomer can be alkylated. Alkylation of the commercially available phenol will be accomplished with standard Williamson ether synthesis for the non-polar side chain with ethyl bromide as the alkylating agent. Polar sidechains can be introduced with bifunctional alkylating agents such as BOC—$NH(CH_2)_2Br$. Alternately, the phenol group can be alkylated to install the desired polar side chain function by employing the Mitsonobu reaction with BOC—$NH(CH_2)_2$—OH, triphenyl phosphine, and diethyl acetylenedicarboxylate. Standard conditions for reduction of the nitro groups and hydrolysis of the ester afford the amino acid. With the aniline and benzoic acid in hand, coupling can be effected under a variety of conditions. Alternatively, the hydroxy group of the (di)nitrophenol can be converted to a leaving group and a functionality introduced under nucleophilic aromatic substitution conditions. Other potential scaffolds that can be prepared with similar sequences are methyl 2-nitro-4-hydroxybenzoate and methyl 2-hydroxy-4-nitrobenzoate.

The compounds of the invention can also be designed using computer-aided computational techniques, such as de novo design techniques, to embody the amphiphilic properties. In general, de novo design of compounds is performed by defining a three-dimensional framework of the backbone assembled from a repeating sequence of monomers using molecular dynamics and quantum force field calculations. Next, side groups are computationally grafted onto the backbone to maximize diversity and maintain drug-like properties. The best combinations of functional groups are then computationally selected to produce a cationic, amphiphilic structures. Representative compounds can be synthesized from this selected library to verify structures and test their biological activity. Novel molecular dynamic and coarse grain modeling programs have also been developed for this approach because existing force fields developed for biological molecules, such as peptides, were unreliable in these oligomer applications (see, Car et al., Phys. Rev. Lett., 1985, 55, 2471-2474; Siepmann et al., Mol. Phys., 1992, 75, 59-70; Martin et al., J. Phys. Chem., 1999, 103, 4508-4517; and Brooks et al., J. Comp. Chem., 1983, 4, 187-217). Several chemical structural series of compounds have been prepared. See, for example, International Publication No. WO 2002/100295, which is incorporated herein by reference in its entirety. The compounds of the invention can be prepared in a similar manner. Molecular dynamic and coarse grain modeling programs can be used for a design approach. See, for example, U.S. Application Publication No. 2004-0107056, and U.S. Application Publication No. 2004-0102941, each of which is incorporated herein by reference in its entirety.

An example of the design, synthesis, and testing of arylamide polymers and oligomers, a related group of compounds of the invention, is presented in Tew et al., Proc.

Natl. Acad. Sci. USA, 2002, 99, 5110-5114, which is incorporated herein by reference in its entirety.

Compounds of the invention can be synthesized by solid-phase synthetic procedures well know to those of skill in the art (see, Tew et al., Proc. Natl. Acad. Sci. USA, 2002, 99, 5110-5114; Barany et al., Int. J. Pept. Prot. Res., 1987, 30, 705-739; Solid-phase Synthesis: A Practical Guide, Kates, S. A., and Albericio, F., eds., Marcel Dekker, New York (2000); and Dorwald, F. Z., Organic Synthesis on Solid Phase: Supports, Linkers, Reactions, 2nd Ed., Wiley-VCH, Weinheim (2002)).

The compounds of the invention can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams. The selection of the specific route of administration and the dose regimen is to be adjusted or titrated by the clinician according to methods known to the clinician to obtain the desired clinical response. The amount of compounds of the invention to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The amount of a compound described herein that will be effective in the treatment and/or prevention of mucositis will depend on the nature of the mucositis, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight. In some embodiments, the oral dose is from about 0.01 milligram to 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

The pharmaceutical compositions and/or formulations containing the compounds of the invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a compound of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

In some embodiments, the compounds described herein can be used with agents including, but not limited to, topical analgesics (e.g., lidocaine), barrier devices (e.g., GelClair), or rinses (e.g., Caphosol).

The compounds of the invention can be formulated for parenteral administration by injection, such as by bolus injection or continuous infusion. The compounds of the invention can be administered by continuous infusion subcutaneously over a period of about 15 minutes to about 24 hours. Formulations for injection can be presented in unit dosage form, such as in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds of the invention can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, such as, tablets or lozenges formulated in a conventional manner For administration by inhalation, the compounds of the invention for use according to the present invention are conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds of the invention can also be formulated in rectal compositions such as suppositories or retention enemas, such as containing conventional suppository bases such as cocoa butter or other glycerides.

In addition to the formulations described previously, the compounds of the invention can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the invention, for example, can be applied to a plaster, or can be applied by transdermal, therapeutic systems that are consequently supplied to the organism.

The pharmaceutical compositions of the compounds of the invention also can comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

The present invention also provides compounds of the invention, or compositions comprising the same, for use in treating and/or preventing mucositis in a patient. The present invention also provides compounds of the invention, or compositions comprising the same, for use in treating and/or preventing mucositis. The present invention also provides compounds of the invention, or compositions comprising the same, for use in preparation of a medicament for treating and/or preventing mucositis in a patient.

The compounds of the invention can also be administered in combination with other active ingredients such as, for example, palifermin and/or NX002, or other known compounds useful for treating and/or preventing mucositis.

The present invention also provides methods for treating and/or preventing mucositis in an animal comprising administering to the animal in need thereof an effective amount of a compound of the invention. The present invention also provides methods for treating and/or preventing mucositis in an animal comprising administering to the animal in need thereof a composition of the invention. The present invention also provides methods for treating and/or preventing mucositis comprising administering to the animal an effective amount of a compound or salt of the invention.

The present invention also provides compounds of the invention, or compositions comprising the same, for use in treating and/or preventing mucositis in a patient. The present invention also provides compounds of the invention, or compositions comprising the same, for use in preparation of a medicament for treating and/or preventing mucositis in a patient.

The structures depicted herein may omit necessary hydrogen atoms to complete the appropriate valency. Thus, in some instances a carbon atom or nitrogen atom may appear to have an open valency (i.e., a carbon atom with only two bonds showing would implicitly also be bonded to two hydrogen atoms; in addition, a nitrogen atom with a single bond depicted would implicitly also be bonded to two hydrogen atoms). For example, "—N" would be considered by one skilled in the art to be "—$NH_2$." Thus, in any structure depicted herein wherein a valency is open, one or more hydrogen atoms, as appropriate, is implicit, and is only omitted for brevity.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Synthesis

Synthesis of compound 1

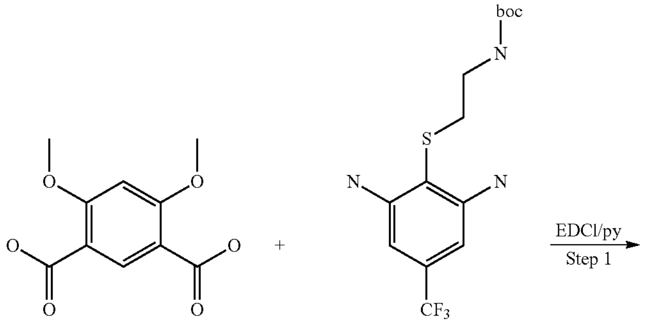

-continued

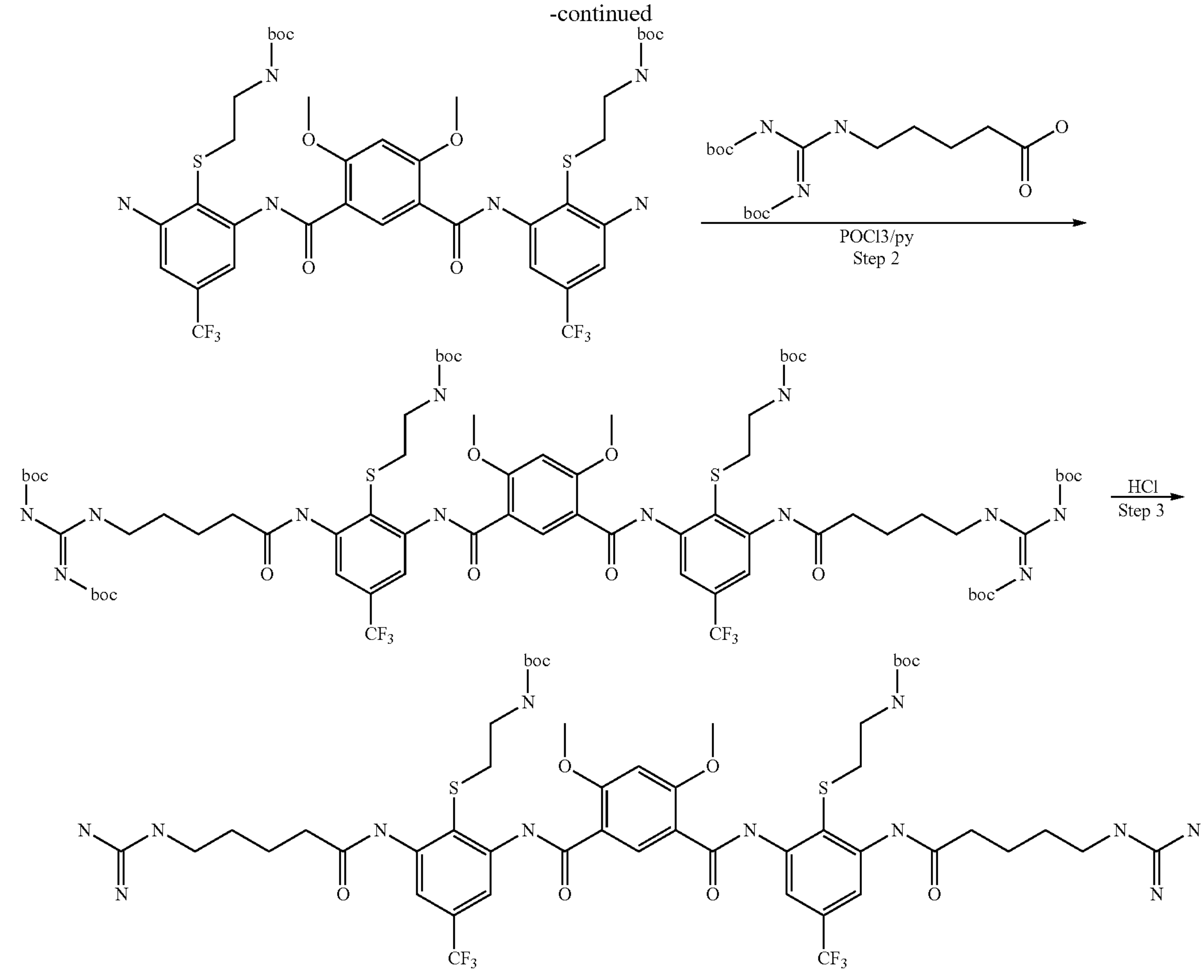

Step 1:

The diacid and dianiline (2 equiv.) were mixed in pyridine, and EDCI was added. The reaction mixture was stirred at room temperature for 24 hours before the solvent was removed. The resulting solid was washed with water and recrystalized in DCM/Hexane.

Step 2:

Product from step 1 and 5-bisBocguanidino pentoic acid were mixed and dissolved in pyridine. The solution was cooled to 0° C. before $POCl_3$ was added to the mixture. The reaction mixture was stirred at 0° C. for 2 hours before it is quenched with ice water. The product was purified by column chromatography.

Step 3:

Product from step 2 was treated with HCl in ethyl acetate for 6 hours. The product was collected by filtration. The purification was done by reverse phase column chromatography.

Compound 6, 87 and 88 are made by similar procedure using different diacid in the first step.

Diacids

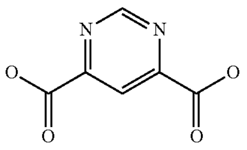

-continued

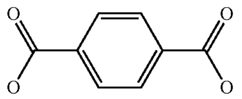

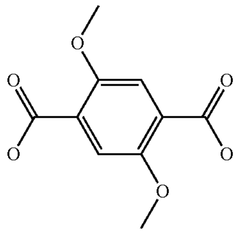

Synthesis of compound 4

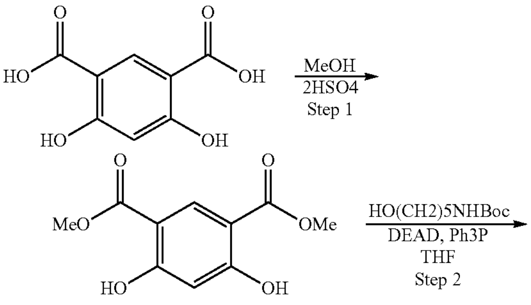

-continued

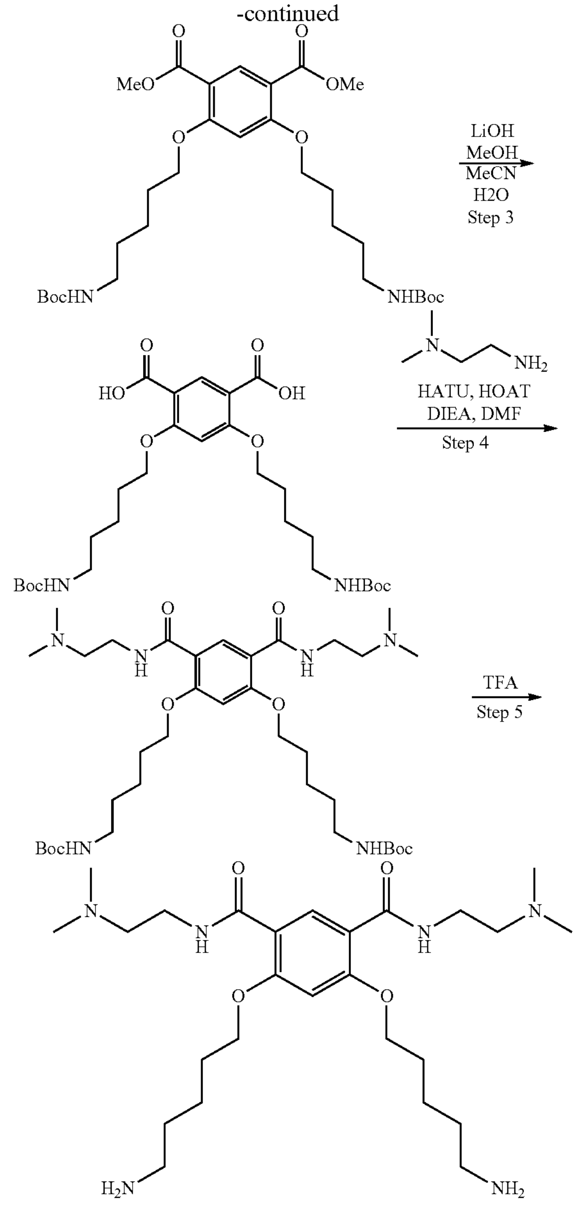

Step 1:

A solution of acid (3.18 g) and concentrated $H_2SO_4$ (~4 mL) in methanol (64 mL) was heated under reflux for 2 days. The product was obtained upon cooling and was filtered off and washed with a small amount of MeOH to give pure methyl ester.

Step 2:

A flame dried 100 mL round bottom flask was charged with diol 2 (1.32 g, 5.84 mmol), 5-N-tert-butoxycarbonylamino-1-pentanol (2.37 g, 11.7 mmol), $Ph_3P$ (3.06 g, 11.7 mmol), and THF (15 mL). The resulting solution was cooled to 0° C. under Argon, and DEAD (2.16 mL) was added to the solution dropwise to give a dard red solution. The mixture was then warmed to room temperature and stirred until no starting material remained (ca. 10 h). THF was removed and the residue was purified by column chromatography (DCM/hexane/ether=4:4:1) to give pure product.

Step 3:

To the solution of diester (3.11 mmol) in methanol (10 mL), there was added 2 N LiOH (5.1 mL) slowly. The resulting solution was stirred at room temperature overnight, the solvent was then removed in vacuo. The residue was redissolved in water (150 mL), and the aqueous solution was acidified to pH=2 using 6 N HCl. Pure product was obtained by filtration.

Step 4:

The diacid, N,N-dimethylethane-1,2-diamine (2 equiv.), HOAT (2 equiv.), HATU (2 equiv.) and DIEA (5 equiv.) were mixed in DMF and stirred at room temperature overnight. The solution was diluted with water, and the product was purified by reverse phase chromatography.

Step 5:

Product from step 4 was treated with 50% TFA in DCM for 3 hours. The solution was concentrated to an oil and triturated with cold ether. The product was collected by filtration and dried under vacuum.

Synthesis of compound 2

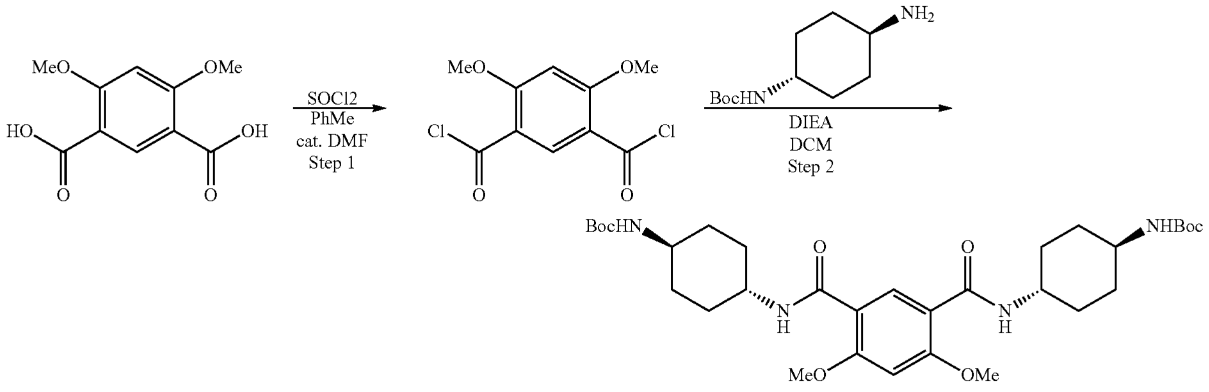

-continued

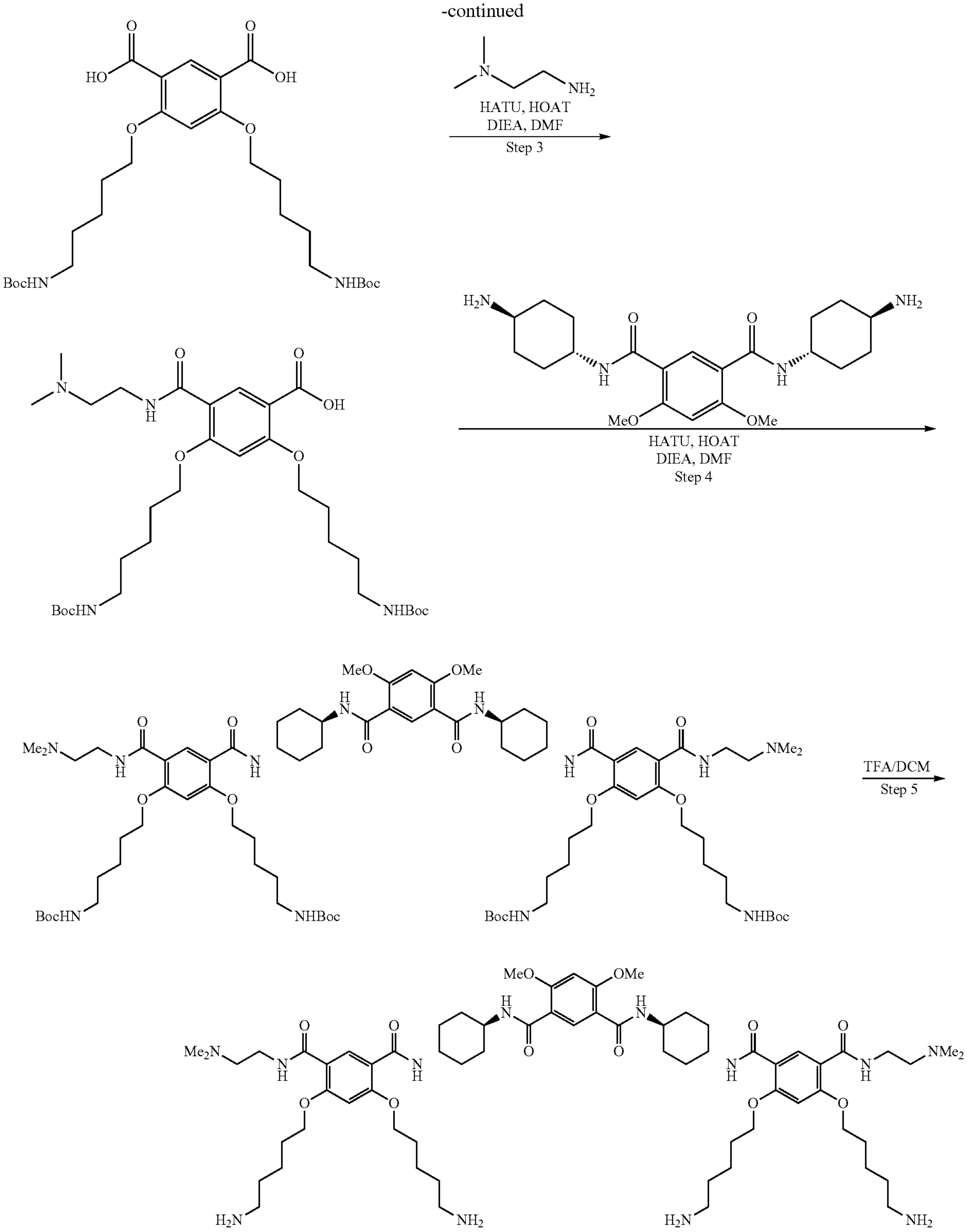

Step 1:

One 1 L round bottom flask was fitted with a magnetic stirrer condenser, drying tube and a heating mantel. Diacid (20 g) was added and slurried in toluene (256 mL). DMF (1 mL) was added, followed by $SOCl_2$ (64 mL). The resulting slurry was heated at reflux and complete solution was obtained after 10 minutes. The reaction mixture was cooled to room temperature after 90 minutes of reflux and stirred overnight. The product crystallized out from the solution.

The mixture was cooled at 5° C. for one hour. The solid was collected by filtration and washed with cold toluene. Yield: 19.71 g.

Step 2:

The mono Boc protected amine was dissolved in DCM and DIEA was added. Acid chloride was added to the solution and the reaction mixture was stirred at room temperature for 2 hours and the product precipitated out. The product was collected by filtration.

Step 3:

The diacid, N,N-dimethylethane-1,2-diamine (1 equiv.), HOAT (1 equiv.), HATU (1 equiv.) and DIEA (2 equiv.) were mixed in DMF and stirred at room temperature overnight. The solution was diluted with water, and the product was purified by reverse phase chromatography.

Step 4:

Diamine, acid (2.2 equiv.), HOAT (2.2 equiv.), HATU (2.2 equiv.) and DIEA (5 equiv.) were dissolved in DMF and stirred at room temperature overnight. The mixture was added water and extracted with DCM. The organic layer was concentrated to generate the crude solid. The product was purified by reverse phase chromatography.

Step 5:

Product from step 4 was treated with 50% TFA in DCM for 3 hours. The solution was concentrated to an oil and triturated with cold ether. The product was collected by filtration and dried under vacuum.

Synthesis of compound 3

Compound 3 was made by similar procedure as compound 2 except one extra step.

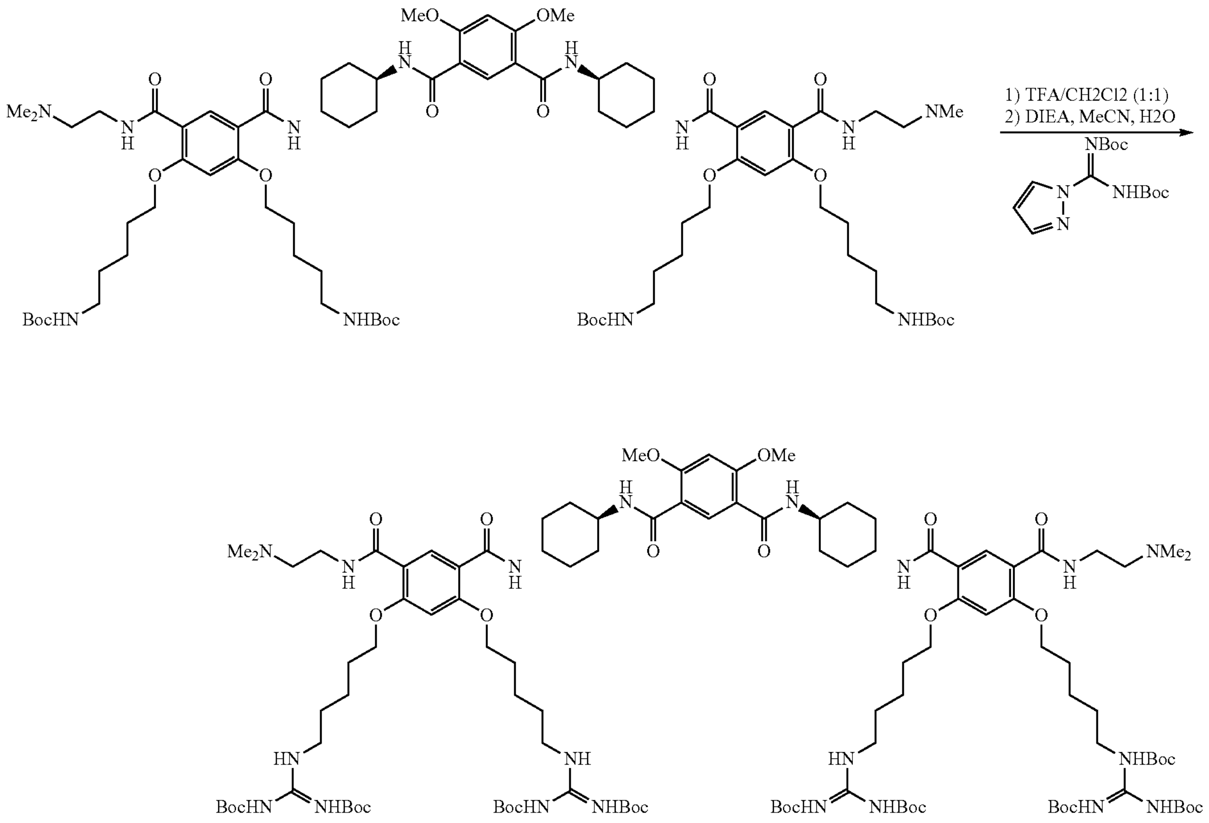

The Boc of the precursor was removed by treatment of 50% TFA/DCM. After the solid was washed and dried under vacuum, it was dissolved in acetonitrile and water, DIEA (15 equiv.) was added and followed by di-Boc pyrazole. The reaction mixture was stirred at room temperature overnight. The solvent was removed and the solid was redissolved in DCM. After trituration with hexane/diethyl ether, the product was collected by filtration and dried under vacuum.

Synthesis of compound 103, 104, 105 and 106 were synthesized using similar method as compound 3.

Synthesis of compound 5

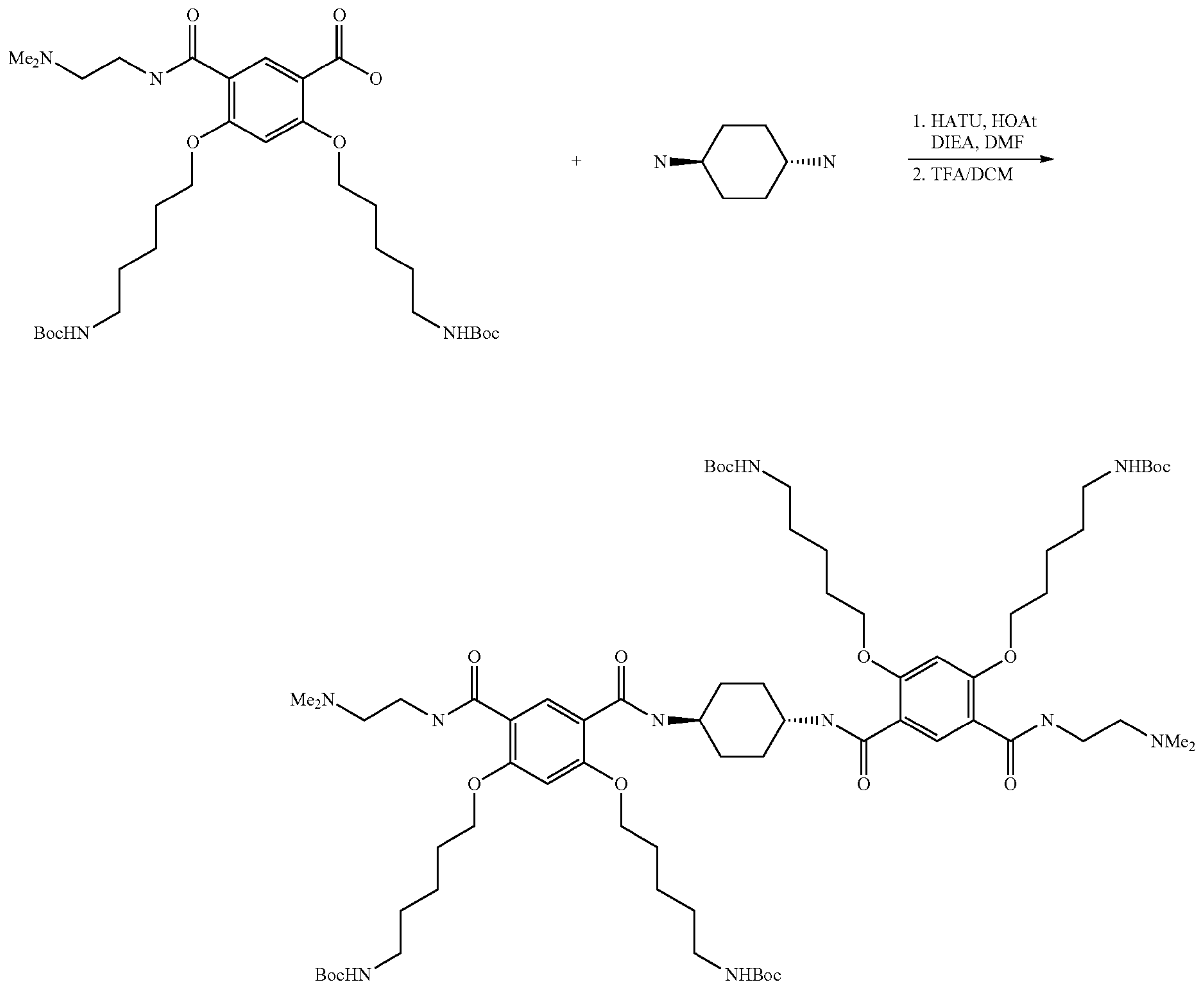

The damine, monoacid (2. equiv.), HATU (2. equiv.) and HOAT (2. equiv.) were mixed and dissolved in DMF. DIEA (4 equiv.) was added to the DMF solution and the reaction mixture was stirred at room temperature overnight. The solution was diluted with water and extracted with DCM. The organic layer was washed with water before the solvent was removed.

The solid was treated with 50% TFA in DCM for 3 hours before the solution was concentrated. The product was precipitated with diethyl ether and purified by reverse phase chromatography.

Synthesis of compound 86

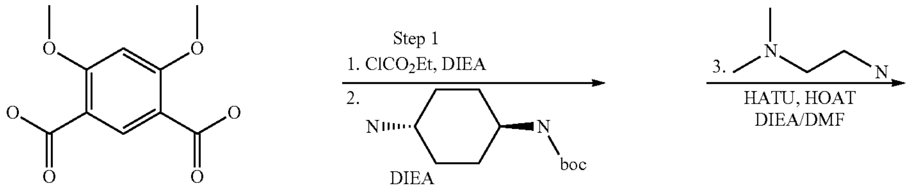

-continued

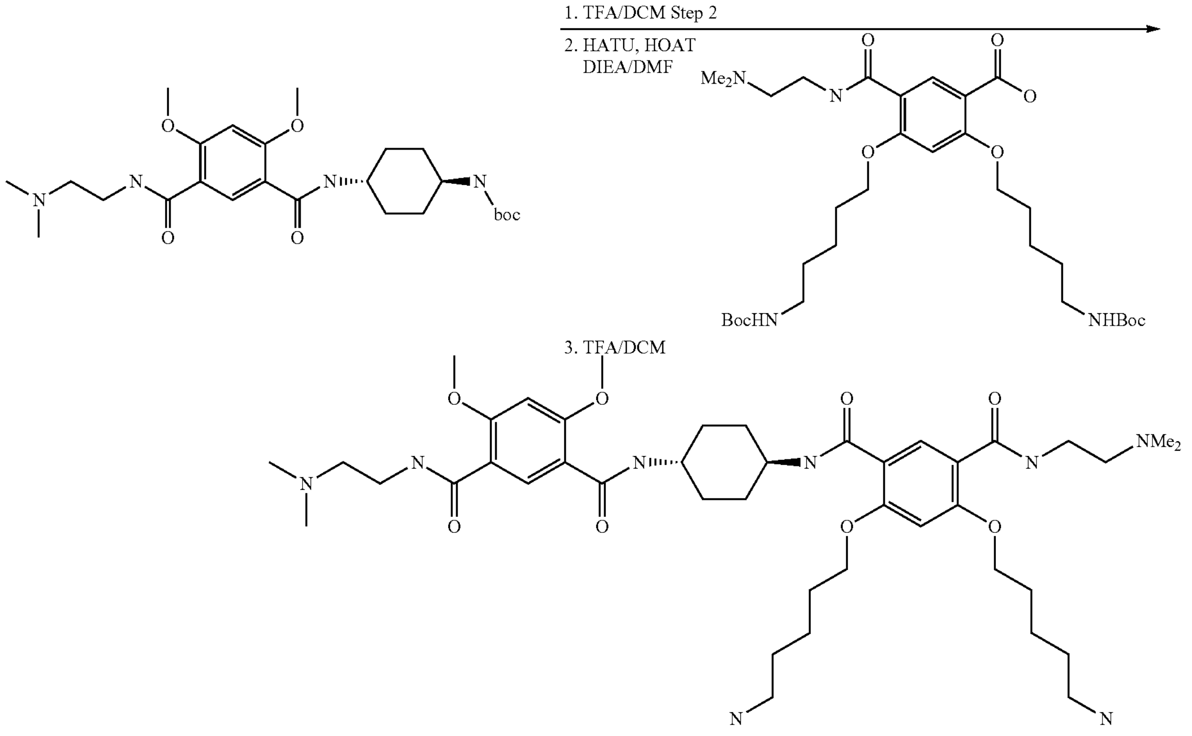

Step 1:

The diacid was suspended in chloroform and ethyl chloroformate (2.2 equiv.) was added. DIEA (2.2 equiv.) was added to the mixture and stirred for 2 hours before monoBoc hexyldiamine (2.2 equiv.) was added. The reaction mixture was stirred for 4 hours before it was added N, N-dimethyl ethylenediamine (1.5 equiv.). The reaction mixture was stirred overnight. The solution was diluted with DCM and washed with water. After the solvent was removed, the product was purified by reverse phase column chromatography.

Step 2:

Product from step 3 was treated with 50% TFA in DCM for 2 hours before the solvent was removed. The solid was dried under vacuum at 35° C. for 2 hours before it was dissolved in DMF. HATU, HOAT and monoacid was added to the solution. Then DIEA was added. The mixture was stirred overnight at room temperature. After diluted with water, the product was extracted with DCM. The organic layer was washed with water, concentrated to solid and dried under vacuum overnight. The solid was treated with 50% TFA/DCM for 2 hours. The final product was purified by reverse phase column chromatography.

Synthesis of Compound 89

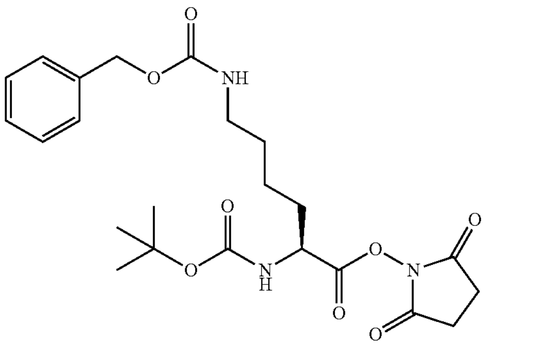

+

1

-continued

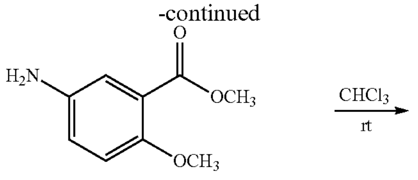

2

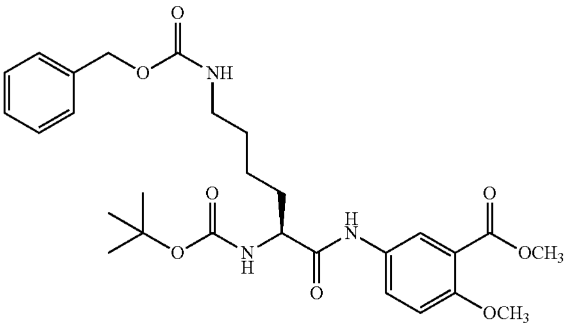

3

A mixture of 47.75 g (100.0 mmol) of 1 and 18.12 g (100.0 mmol) of 2 in 500 mL of anhydrous $CHCl_3$ was stirred at room temperature under Ar and, after 30 minutes, a clear orange solution was observed. The reaction was monitored by tlc and found to be complete after 60 hours. The reaction was concentrated in vacuo to a brown syrup that was dissolved between EtOAc and water. The layers were separated and the aqueous layer was extracted twice more with EtOAc. The EtOAc fractions were combined and washed four times with water (followed removal of byproduct HOSu by tlc). The EtOAc layer was then washed once with 10% citric acid (aqueous), twice with water, three times (carefully) with saturated $NaHCO_3$, and once with brine. The EtOAc layer was dried over $Na_2SO_4$, filtered, and concentrated to afford 53.48 g (98%) of 3.

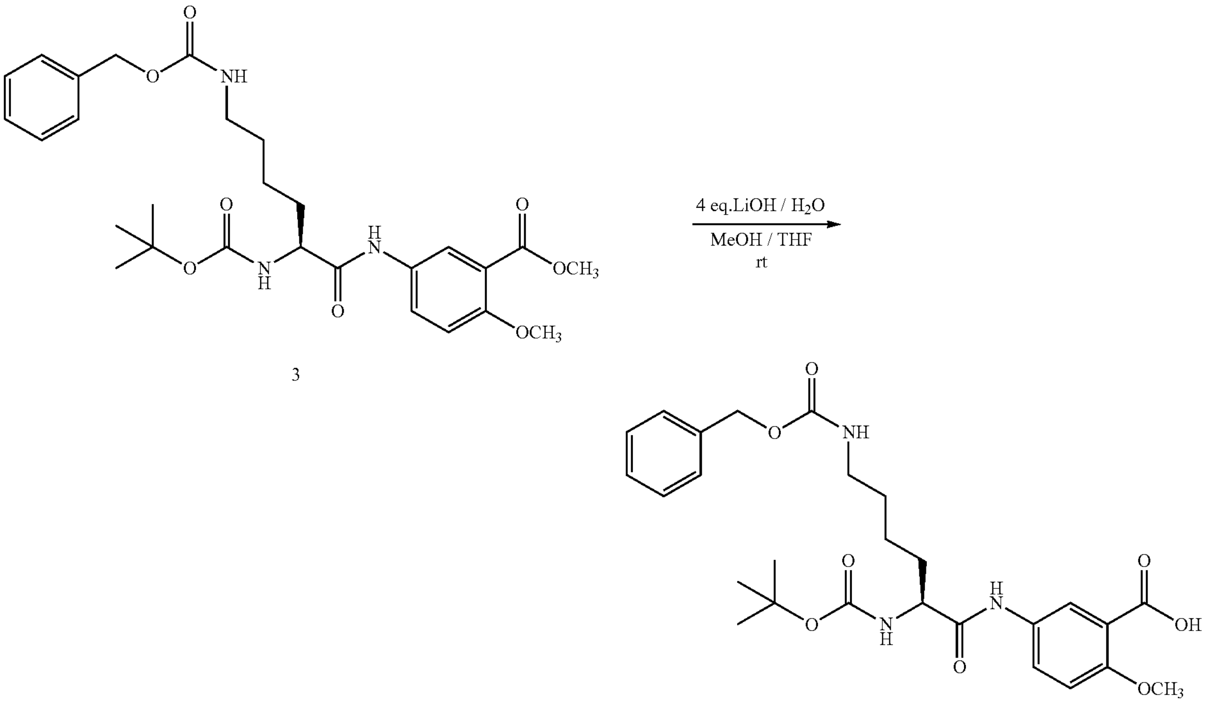

3

4

A solution of 26.74 g (49.19 mmol) of 3 in a mixture of 294 mL of THF and 196 mL of MeOH was treated with 98 mL of 2.0 M LiOH (aqueous) (196 mmol) and the resultant mixture was stirred at room temperature for 18 hours. The reaction mixture was cooled in an ice bath then treated with 196 mL of cold 1.0 M HCl (aqueous) to neutralize. The quenched reaction was partially concentrated in vacuo to an aqueous slurry that was extracted with EtOAc until tlc showed the extraction was complete. The EtOAc layer was dried over $Na_2SO_4$, filtered, and concentrated to afford 25.71 g (99%) of 4 as a beige solid.

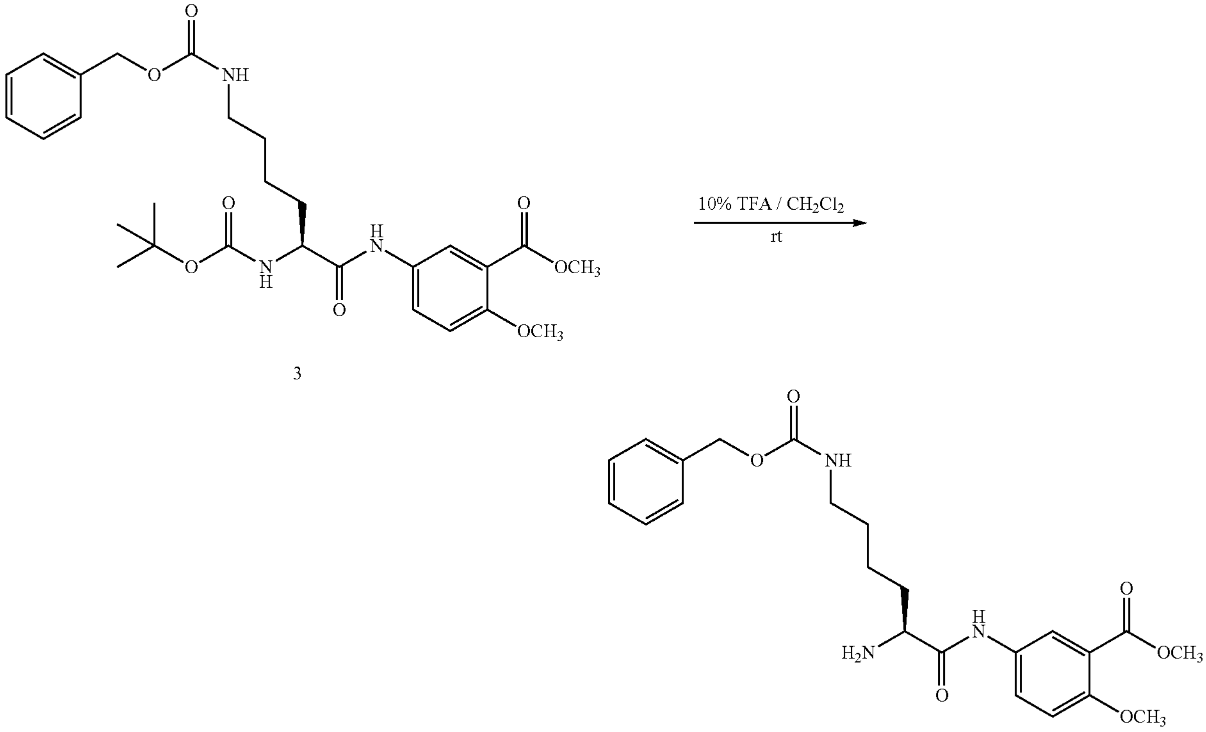

3

5

3 (26.74 g, 49.19 mmol) was introduced to a 1 L round bottom flask that was equipped with a ground glass stopper (secured by a Keck clamp) and treated with 385 mL of a cold 10% solution (v/v) of TFA in $CH_2Cl_2$ (500 mmol of TFA). The resultant brick red solution was allowed to warm to room temperature. The reaction was followed by tlc and all of 3 was consumed after 24 hours. The reaction was diluted with twice its volume of $CH_3CN$ and concentrated in vacuo without heating to a brown syrup. This residue was dissolved in EtOAc and extracted (carefully) three times with saturated $NaHCO_3$. The aqueous fractions were combined, treated with solid $NaHCO_3$ to ensure pH of 8, and back-washed twice with EtOAc. The EtOAc fractions were combined, dried over $Na_2SO_4$, filtered, concentrated, and subjected to high vacuum to afford 24.83 g of 5.

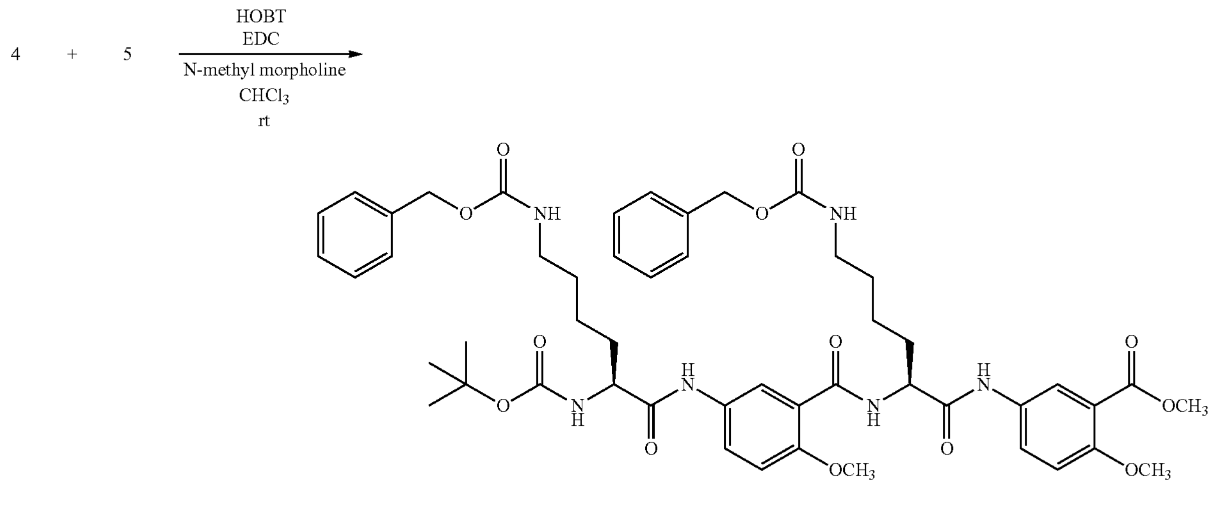

6

A mixture of 1.06 g (2.00 mmol) of 4 and 1.01 g (2.00 mmol) of 5 was dissolved in 60 mL of anhydrous $CHCl_3$. Added 0.54 g (4.0 mmol) of HOBT, 0.46 g (2.4 mmol) of EDC, and 0.33 mL (3.0 mmol) of N-methyl morpholine and stirred the resultant suspension at room temperature under Ar. The reaction became an orange solution and, after 24 hours, tlc and MS/HPLC showed it to be complete. The reaction mixture was diluted with $CH_2Cl_2$ and extracted twice with water, twice with saturated $NaHCO_3$ and once with brine. The $CH_2Cl_2$ fraction was dried over $Na_2SO_4$, filtered, and concentrated in vacuo to afford 1.98 g of brown crusty foam that was subjected to flash silica gel chromatography (1:1 hexane/EtOAc to 1:3 hexane/EtOAc). Obtained 1.71 g (89%) of 6.

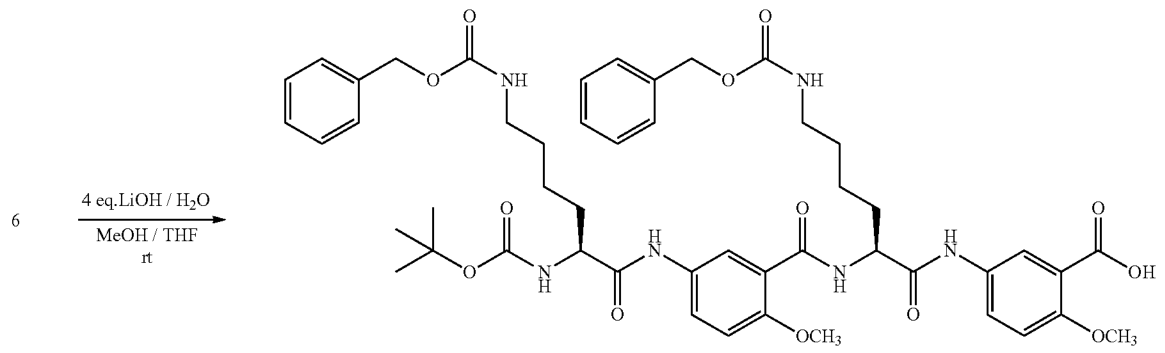

7

A solution of 0.33 g (0.346 mmol) of 6 in a mixture of 2.1 mL of THF and 1.4 mL of MeOH was treated with 0.70 mL of 2.0 M LiOH (aqueous) (1.4 mmol) and the resultant mixture was stirred at room temperature for 8 hours. The reaction mixture was cooled in an ice bath then treated with 1.4 mL of cold 1.0 M HCl (aqueous) to neutralize. The quenched reaction was partially concentrated in vacuo to an aqueous slurry that was extracted with EtOAc until tlc showed the extraction was complete. The EtOAc layer was dried over $Na_2SO_4$, filtered, and concentrated to afford 0.321 g (99%) of 7.

7

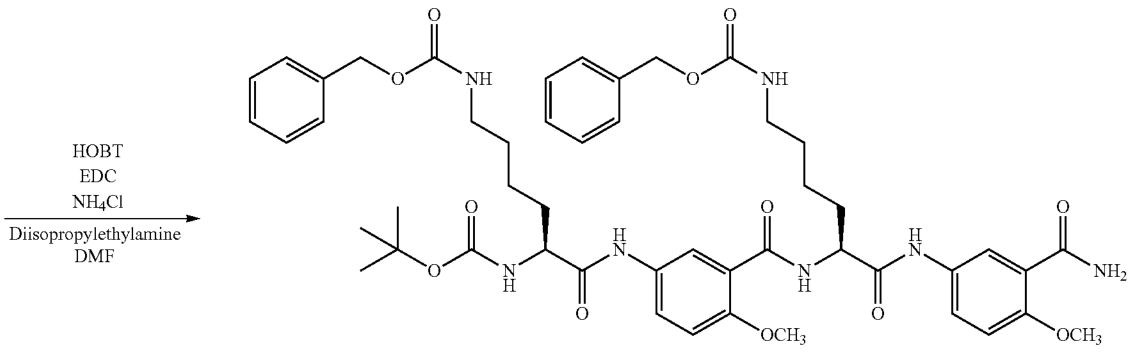

8

A mixture of 7 (0.798 g, 0.849 mmol), HOBT (0.224 g, 1.70 mmol), EDC (0.278 g, 1.70 mmol), and $NH_4Cl$ (0.099 g, 1.7 mmol) was dissolved in 8 mL of DMF under an Ar atmosphere. DIEA (0.59 mL, 3.4 mmol) was added and the reaction mixture stirred at room temperature for 8 hours. The mixture was poured into a mixture of 5 mL 1 N HCl and extracted with EtOAc. The organic phase was washed with $H_2O$ and brine, dried ($Na_2SO_4$) and the solvent evaporated to yield 0.729 g (91%) of 8 that was used without further purification in the subsequent reaction.

8

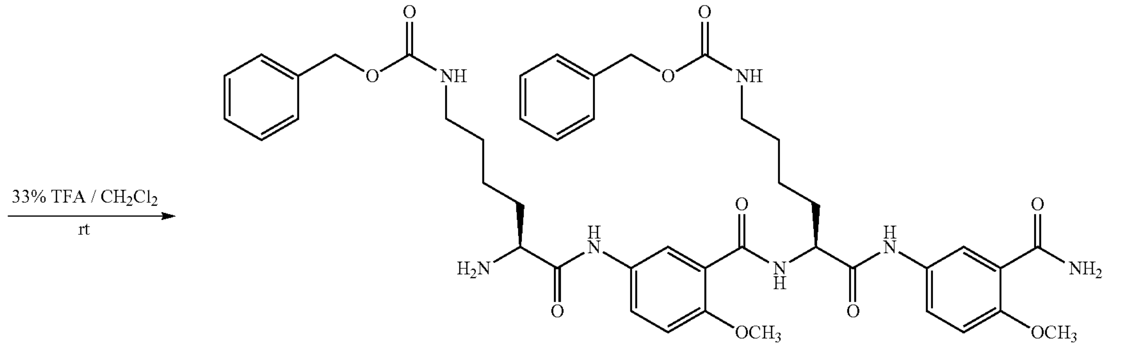

9

Compound 8 (0.900 g, 0.96 mmol) was stirred at room temperature in 4.5 mL of a 33% solution (v/v) of TFA/$CH_2Cl_2$ for 1.5 hours. $Et_2O$ was added, and the solid filtered or the mixture centrifuged and the solvent decanted. The resultant solid was triturated with $Et_2O$ and dried to yield 0.75 g (82%) of mono-TFA salt 9 as a white powder.

7 + 9

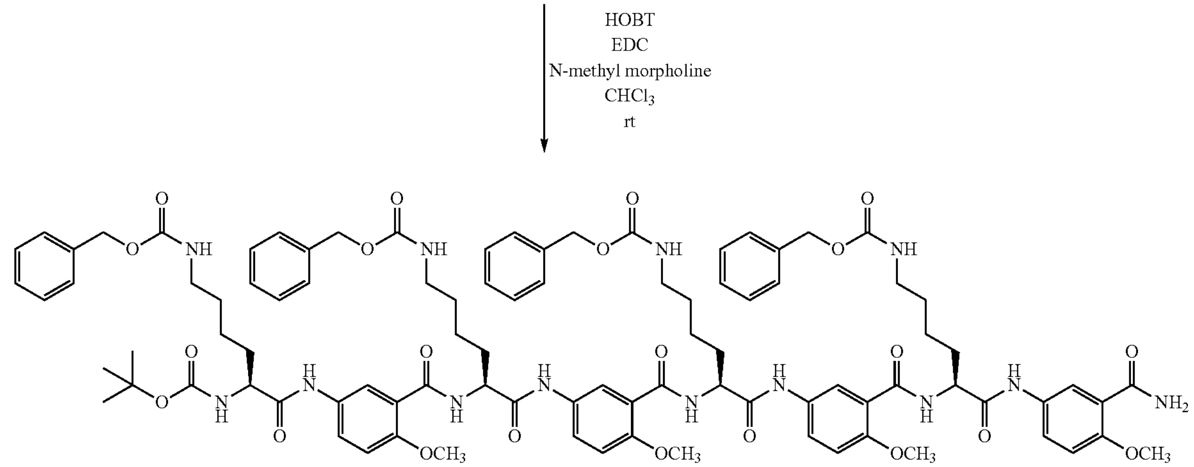

10

A mixture of 0.321 g (0.341 mmol) of 7 and 0.286 g (0.341 mmol) of 9 (free based from its TFA salt by extraction between saturated $NaHCO_3$ and EtOAc) was dissolved in 15 mL of anhydrous $CHCl_3$. Added 0.092 g (0.68 mmol) of HOBT, 0.079 g (0.41 mmol) of EDC, and 0.056 mL (0.51 mmol) of N-methyl morpholine and stirred the resultant suspension at room temperature under Ar. The reaction became a yellow solution and, after 40 hours, tlc and MS/HPLC showed it to be complete. The reaction mixture was diluted with $CH_2Cl_2$ and extracted twice with water, twice with saturated $NaHCO_3$, once with 10% citric acid (aqueous), and twice with brine. The $CH_2Cl_2$ fraction was dried over $Na_2SO_4$, filtered, and concentrated in vacuo to afford 0.607 g of beige wax that was subjected to flash silica gel chromatography ($CH_2Cl_2$ to 97:3 $CH_2Cl_2$/MeOH). Obtained 0.411 g (68%) of 10 as a beige solid.

Compound 10 (0.411 g, 0.233 mmol) was introduced to a 100 mL round bottom flask that was equipped with a ground glass stopper (secured by a Keck clamp) and treated with 5 mL of a cold 10% solution (v/v) of TFA in $CH_2Cl_2$. The resultant brick red solution was allowed to warm to room temperature. The reaction was followed by tlc and all of 10 was consumed after 24 hours. The reaction was diluted with $CH_3CN$ and concentrated in vacuo without heating to a brown syrup. This residue was dissolved in $CH_2Cl_2$ and extracted three times with saturated $NaHCO_3$. The aqueous fractions were combined and backwashed twice with $CH_2Cl_2$. The $CH_2Cl_2$ fractions were combined, dried over $Na_2SO_4$, filtered, and concentrated to afford 0.394 g (101% of theoretical) of a sample of crude 11 as a beige amorphous solid. This crude product was used without further purification in the subsequent reaction.

10

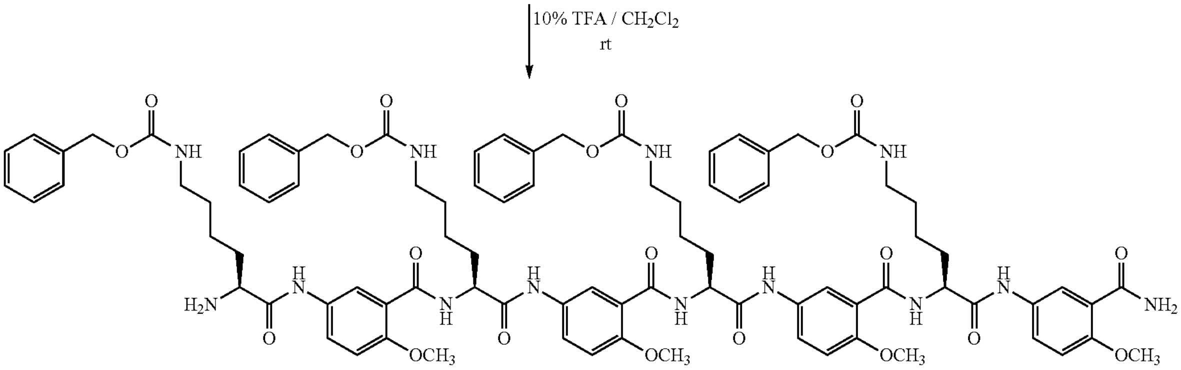

11

11

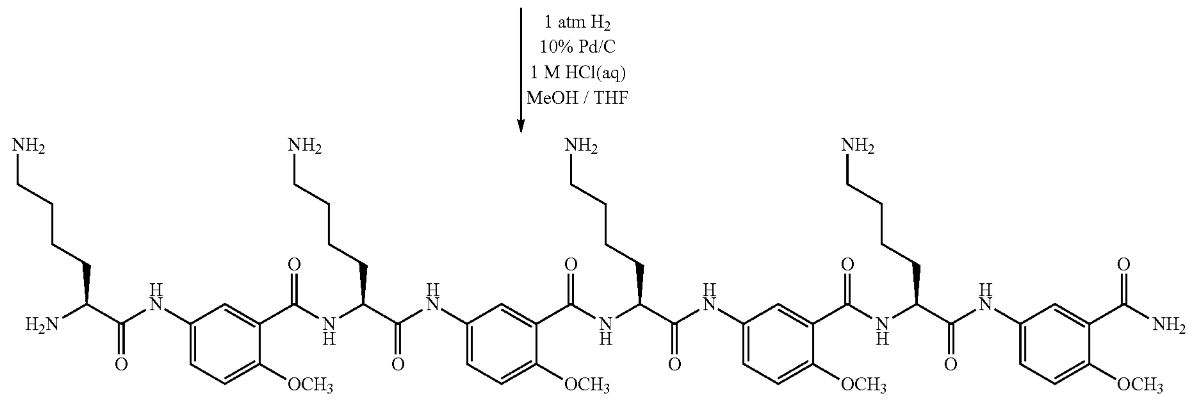

Introduced 0.197 g (assumed 0.118 mmol) of the crude sample of 11 to a 250 ml round bottom flask that was equipped with an adapter containing a three way stopcock to which a balloon was attached. Dissolved 11 in a mixture of 5 mL of THF and 5 mL of MeOH, added 0.59 ml of 1.0 M HCl (aqueous), and bubbled Ar through the reaction solution for 15 minutes. Carefully added a small scoop of 10% Pd/C and exposed the reaction to $H_2$ at 1 atm via the balloon. Stirred vigorously, followed the reaction by MS/HPLC, and recharged the balloon with $H_2$ as needed. After 60 hours, the completed reaction was suctioned filtered through Celite using MeOH to assist transfer and to wash the collected solids. The filtrate was concentrated to afford 0.150 g of beige waxy solid. The final product was purified by reverse phase column chromatography.

Synthesis of compound 12

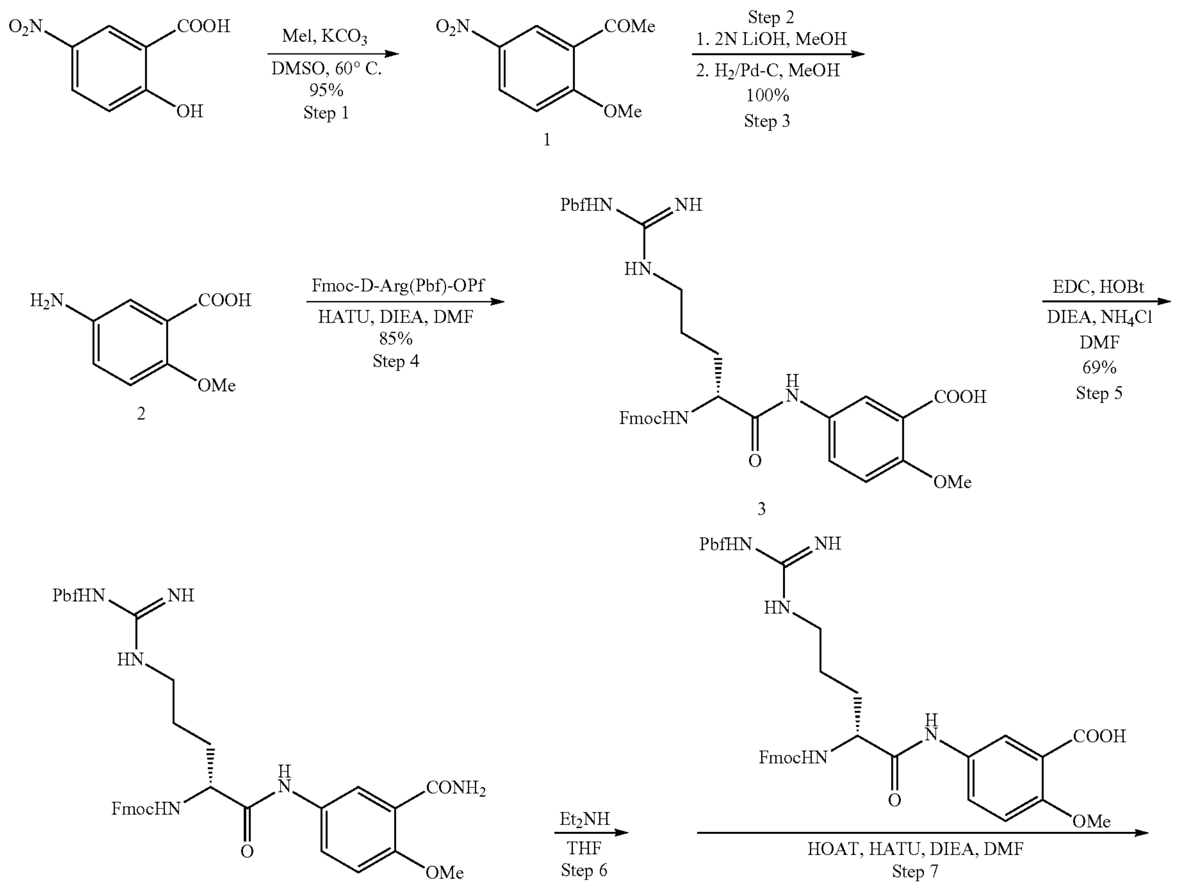

1

2

3

4

-continued

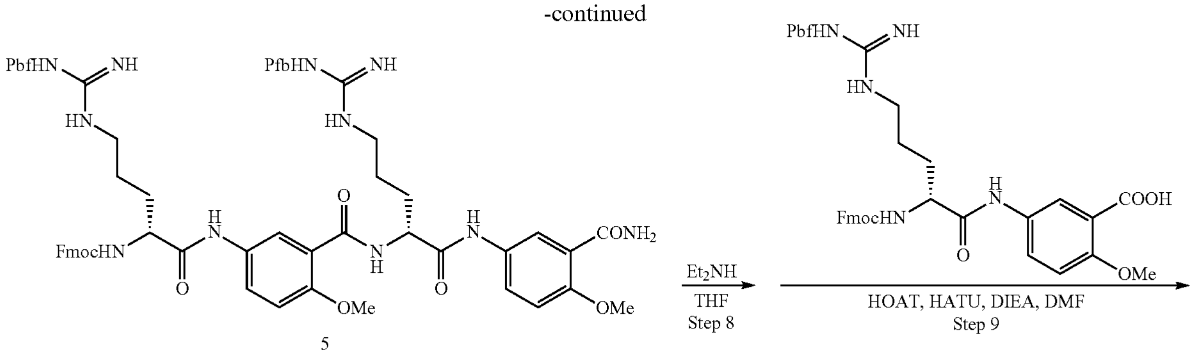

5

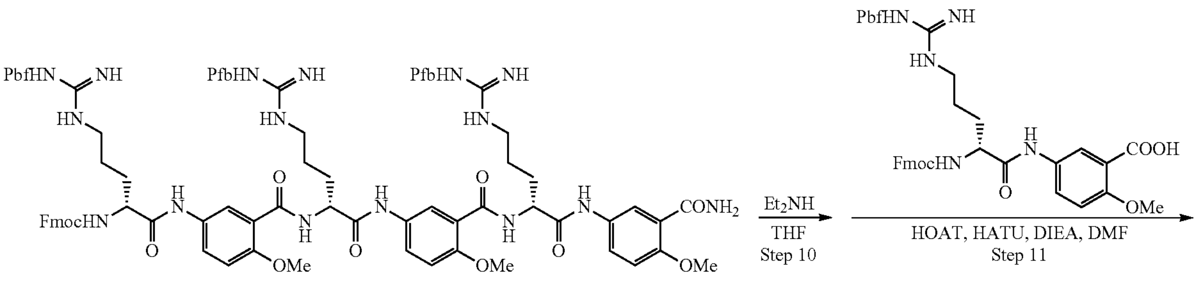

6

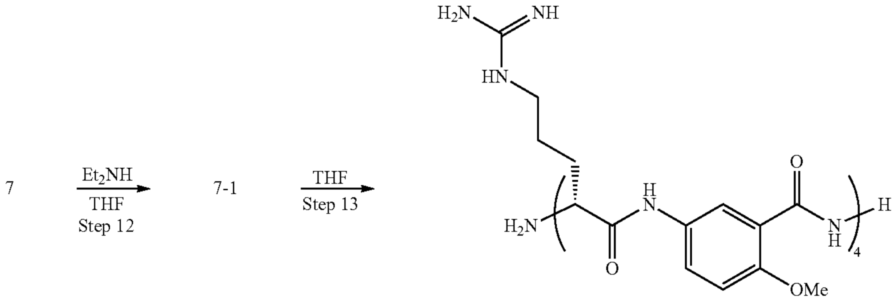

Step 1:

Starting material 5-nitro salicylic acid (40 g, 0.218 mol) was dissolved in 220 mL of DMSO followed by addition of $KCO_3$ (151 g, 1.09 mol). Methyl iodide (136 mL, 2.18 mol) was added to the solution. The reaction mixture was heated to 60° C. and stirred (mechanical stir) overnight. Ethyl acetate (6 L) was added to the reaction mixture in 4 portions to completely dissolve the desired product. The suspension was filtered to remove solid. The organic layer was washed with 1N HCl, saturate NaCl and water, dried over $Na_2SO_4$. The solvent was removed by rotovap. Yield: 45.7 g, 99%.

Steps 2 and 3:

To the solution of ester compound 1 (10 g, 47.36 mmol) in 4:1 methanol/acetonitrile (250 mL) there was added 2 N LiOH (47.4 mL, 94.7 mmol). The resulting solution was stirred at room temperature until no starting material remained (ca. 3 hours). The solution was then acidified to pH=4-5 with cold HCl, extracted with EtOAc-MeOH (10% MeOH) five times. The combined organic layers were washed with brine, dried over $Na_2SO_4$, filtered and concentrated to give 9.5 g of the acid.

The product from the hydrolysis was dissolved 120 mL of MeOH-THF (5:1), and Pd—C (10% wt. 1.7 g 94.7 mmol) was introduced. The resulting mixture was charged hydrogen by a balloon, and stirred at room temperature overnight. The catalyst was filtered with celite and solvent was removed under reduced pressure. The product was dried under vacuum overnight. Yield: 8.3 g, 100%.

Step 4:

Fmoc-D-Arg(Pbf)-Opf (25 g, 30.68 mmol), compound 2 (5.64 g, 33.75 mmol) were dissolved in anhydrous DMF (85 mL). HOAT (30.78 mmol in 61.4 mL of DMF) and DIEA (6.41 ml, 36.82 mmol) were added to the solution at 0° C. under Ar. The solution was warmed up to room temperature and stirred overnight. The solvent was removed on a rotovap. The product was purified by flash column using DCM: MeOH (25:1 to 15:1). Purification was done on a C18 reverse phase flash column as well using AcCN:water. Yield: 15.4 g, 57%.

Step 5:

The Fmoc protected compound 3 (6.74 g, 8.45 mmol), EDC (3.24 g, 16.9 mmol), HOBt (2.28 g, 16.9 mmol), DIEA (4.36 g, 33.8 mmol) and $NH_4Cl$ (0.904 g, 16.9 mmol) were mixed and dissolved in anhydrous DMF (35 mL), and stirred for 6 hours at 0° C. The solution was diluted with EtOAc and washed with 10% citric acid, sat. $NaHCO_3$ and NaCl. The final product was purified on a flash column with DCM: MeOH (35:1 to 20:1). Yield 3.77 g, 56%.

Steps 6 and 7:

Fmoc deprotection: The amide 4 (3.7 g, 4.6 mmol) was treated with $Et_2NH$ (7.76 ml) in 60 mL of THF at 0° C. for 6 hours. After the liquid is removed under vacuum, the solid was redissolved in AcCN:MeOH (1:1) and the solvent was remove on a rotovap. This process was repeated two times to remove any residual $Et_2NH$. The resulting off-white frothy material was triturated with diethyl ether (6×40 mL)

and the resulting thick liquid was dried on a vacuum pump overnight to afford the pure deprotected amine.

The deprotected amine was dissolved in 20 mL of anhydrous DMF. Compound 3 (3.69 g, 4.62 mmol), HATU (1.755 g, 4.62 mmol), HOAT (4.62 mmol) and DIEA (1.49 g, 11.57 mmol) were dissolved in 30 mL of anhydrous DMF and added to a solution of the deprotected amine in 10 mL of DMF. The reaction mixture was stirred at room temperature for 3 hours. The solution was diluted with 200 mL of DCM and washed with 10% citric acid, sat. $NaHCO_3$, brine and water. The organic layer was concentrated on a rotovap.

building units, they were made via solid phase synthesis which is described as following:

Solid phase synthesis procedure for salicylamides: The synthesis was carried at 0.2 mmol scale using Fmoc chemistry. PAL-PEG resin was used for amide oligomers, and Wang resin was used for acid oligomers. The coupling reagents are HATU/HOAT with DIEA, solvent was DMF. Piperidine (20% in DMF) was used for Fmoc removal. The cleavage and final deprotection were performed using 95% TFA with 5% TIS. The final products were purified on RP-HPLC.

Synthesis of Labeled Compound 121

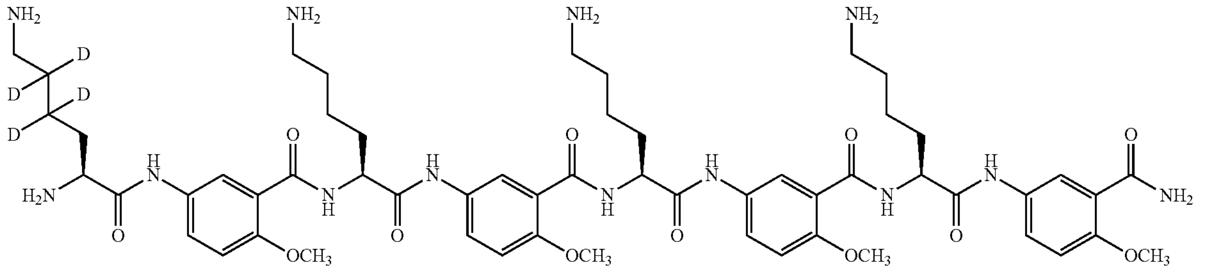

Final product was purified on a C18 reverse phase column using a gradient of AcCN/water. Yield: 4.72 g, 75%.

Steps 8 and 9:

Fmoc deprotection: The amide 5 (4.5 g, 3.32 mmol) was dissolved in 23 mL of DMF and cooled to 0° C. $Et_2NH$ (5.1 g) was added to the solution dropwise under Ar. The resulting solution was stirred at 0° C. for 3.5 hours. After the liquid is removed under vacuum, the deprotected amine was triturated and washed with EtOAc-Hexanes (3:1) three times to afford pure compound.

After the solid was dried under vacuum, it was coupled with compound 3 using HOAT, HATU, DIEA in DMF for 4 hours. (procedure and reactant are the same as the procedure for synthesize compound 5). The product was purified using a C18 reverse phase column with gradient of AcCN/water. Yield: 1.21 g, 20%

Steps 10 and 11:

Compound 7 was synthesized from 0.68 mmol of 6 using the same procedures (Fmoc deprotection and coupling) to synthesize compound 6. After work up, the crude compound 7 was used for next step without purification.

Steps 12 and 13:

The amide 7 (1.68 g, 70% purity) was treated with $Et_2NH$ (0.767 g) in 10 mL of DMF at 0° C. for 1.5 hours. The deprotected amine was worked up as usual. The Pbf group was removed by a treatment of 250 mL of TFA cocktail (95% TFA, 2.5% water and 2.5% triisopropylsilane) for 1 hour. The reaction mixture was concentrated on a rotovap to its half volume and cooled with ice water bath and triturated with 400 mL of cold MTBE. The solid was washed twice with cold MTBE and dried under vacuum. The final product was purified by prep HPLC on a C4 reverse phase column using a gradient of AcCN:water (with 0.1% TFA). Yield 0.379 g, 43%.

The Synthesis of Salicylamides: (Compounds 7-85, 89-102, 107-146)

For salicylamides with the same repeating unit, they are made using procedures that at similar to the synthesis of compound 12 and 89. For salicylamides with different The compound was made via solid phase synthesis. The last building block for the solid phase synthesis (3) was made by the following procedure:

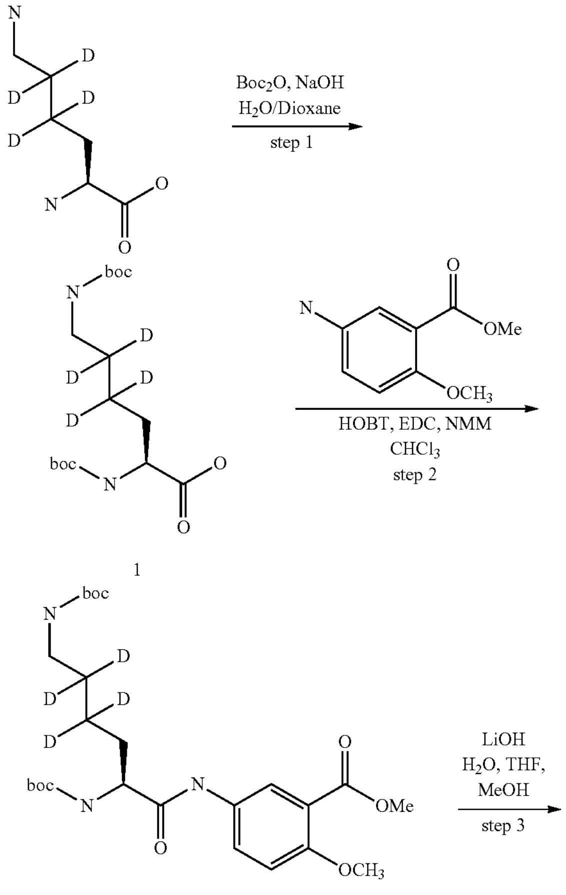

1

2

-continued

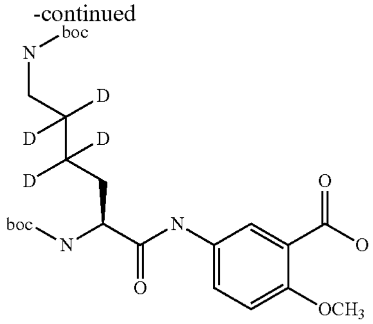

3

Step 1:

L-D4-Lysine (12.4 mmol) was dissolved in 36 mL of water/dioxane (1:1). $Boc_2O$ (31 mmol) was added to the solution, followed by 12.7 mL of 1N NaOH. The reaction mixture was stirred for 18 hours before more $Boc_2O$ (9.3 mmol), 1N NaOH (6.5 mL) and dioxane (6 mL) were added. The reaction was stirred for another 18 hours. The pH of the solution was adjusted to 2-3 with $KHSO_4$ while cooled with ice bath. The product was extracted by EtOAc for 4 times. The organic layer was dried and concentrated to a solid. The product was used for next step without purification.

Step 2:

Product from step 1 (1, 9 mmol) was dissolved in 130 mL of chloroform. To the solution were added 9 mmol of methyl 5-amino-2-methoxybenzoate, HOBT (18 mmol), EDC (10.8 mmol) and 1.5 mL of n-methyl morpholine. The reaction mixture was stirred overnight. The solution was diluted with DCM and washed with water. The aqueous layer was extracted twice with DCM. The combined organic layer was washed with sat. $NaHCO_3$ and brine, and dried and concentrated to a solid. The product was used for the next step without purification.

Step 3:

The product from step 2 (2, 8.37 mmol) was dissolved in 50 mL of THF/33 mL of MeOH. LiOH (2N, 16.75 mL) was added to the solution. The reaction mixture was stirred overnight. While cooled with ice bath, the solution was neutralized with 1N HCl to pH 6-7. The product was extracted by EtOAc. After the solvent was removed, the product was dried under vacuum.

Example 2

Irradiated Hamster Cheek Pouch Model of Oral Mucositis

In the irradiated hamster cheek pouch model of oral mucositis, the hamster cheek pouch is everted and irradiated to produce a localized mucositis. The progression and resolution of mucositis in the hamster model is very similar to that observed in the human condition and the model has been validated clinically with respect to dosing schedules of therapeutic agents (Murphy et al., Clin. Cancer Res., 2008, 14, 4292-4297; Alvarez et al., Clin. Cancer Res., 2003, 9, 3454-3461; and Schuster et al., J. Clin. Oncol., 2006, 24, 6537). Briefly, on day 0, all animals were given an acute radiation dose directed to their left buccal cheek pouch. Test articles were applied topically to the left pouch three times per day from day 0 to day 20 and mucositis was evaluated clinically starting on day 6, and continued on alternate days until day 20. Study endpoints were mucositis score, weight change and survival. Mucositis was scored visually by comparison to a validated photographic scale. The scale ranges from 0 for normal, to 5 for severe ulceration. The clinical mucositis score of 3 in hamsters indicates the presence of an ulcer. In terms of the syndrome, it is believed that the dose-limiting chemotherapeutic- or radiation-induced pain is associated with frank ulceration; therefore a compound that prevents ulceration in the model might have utility in the clinical setting.

To evaluate mucositis severity, animals were anesthetized with an inhalation anesthetic, and the left cheek pouch everted. Mucositis was scored visually by comparison to a validated photographic scale. The scale ranges from 0 for normal, to 5 for severe ulceration. In descriptive terms, this scale is defined as follows:

Mucositis Scoring

Score: Description:

0 Pouch completely healthy. No erythema or vasodilation.

1 Light to severe erythema and vasodilation. No erosion of mucosa.

2 Severe erythema and vasodilation. Erosion of superficial aspects of mucosa leaving denuded areas. Decreased stippling of mucosa.

3 Formation of off-white ulcers in one or more places. Ulcers may have a yellow/gray appearance due to pseudomembrane formation. Cumulative size of ulcers should equal about ¼ of the pouch. Severe erythema and vasodilation.

4 Cumulative size of ulcers should equal about ½ of the pouch. Loss of pliability. Severe erythema and vasodilation.

5 Virtually all of pouch is ulcerated. Loss of pliability (pouch can only partially be extracted from mouth.

A score of 1-2 is considered to represent a mild stage of injury, whereas a score of 3-5 is considered to indicate moderate to severe mucositis. In terms of the syndrome, it is believed that the dose-limiting chemotherapeutic- or radiation-induced pain is associated with frank ulceration; therefore a compound that prevents ulceration in the model might have utility in the clinical setting. In the hamster model, a clinical mucositis score of 3 indicates the presence of an ulcer and the duration of scores of 3 or greater is used as a primary measurement of efficacy in mucositis treatment. Ulceration is the point in the development of mucositis where the physical integrity of the oral mucosa is breached. In the clinic, a patient presenting with severe oral ulcerations may require hospitalization for analgesic, narcotic and/or antibiotic therapies or fluid support.

On day 0, all animals were given an acute radiation dose directed to their left buccal cheek pouch. This was accomplished by anesthetizing the animals and everting the left buccal pouch, while protecting the rest of the animals with a lead shield. Test agents were applied topically to the left buccal pouch three times per day from day 0 to day 20. Mucositis was evaluated clinically starting on day 6, and continued on alternate days until day 28. Study endpoints were mucositis score, weight change and survival. Mucositis was scored visually by comparison to a validated photographic scale. No treatment-related deaths were recorded throughout the study. The mean daily percent weight gains were similar in all groups and there were no apparent toxicities in any of the test agent treatment groups. Differences between the ulcerative severity in controls and the treated groups were assessed in two ways. First, mean daily mucositis scores for each group at each time-point were compared with the untreated control group using the Mann-Whitney Rank-sum analysis. For Compound X, robust efficacy was observed in the 1, 3 and 10 mg/ml groups by Day 12 through Day 28. At 0.3 mg/ml, efficacy was partial early in the treatment period. The presence of Kleptose in the vehicle or with 1 mg/kg Compound X did not significantly impact the response.

Alternately, ulcerative severity differences between control and treatment groups were assessed by the comparison of the number of days with an ulcer (i.e., a score of 3 or higher) using a chi-squared ($\chi 2$) test. There were statistically significant improvements ($p<0.001$) in the mucositis scores of the hamsters in the groups treated with Compound X at 1, 3 and 10 mg/ml/dose. In the vehicle control group, hamsters had a clinical score that was ≥3 for 42.7% of the treatment days. However, in hamsters treated with Compound X, maximum reductions to <5% of treatment days with a clinical score ≥3 were achieved at 1, 3 and 10 mg/ml/dose. These results far exceed the target reduction of 30% in mucositis severity that is suggested to be predictive for clinical efficacy.

Example 3

Evaluation of Compound X in a Fractionated Radiation-Induced Oral Mucositis Model in Hamsters Seventy (70) male Syrian Golden Hamsters were used in this example. Mucositis was induced using a combination of fractionated radiation and cisplatin. Cisplatin was administered on Days 0 and 6 at a dose of 5 mg/kg by i.p. injection. Each hamster was administered a total radiation dose of 60 Gy directed to their left buccal cheek pouch split into eight equal fractions of 7.5 Gy provided on Days 0, 1, 2, 3, 6, 7, 8 and 9. Radiation was generated with a 160 kilovolt potential (15-ma) source at a focal distance of 50 cm, hardened with a 0.35 mm Cu filtration system. Irradiation targeted the left buccal pouch mucosa at a rate of 2.0 Gy/minute. Prior to irradiation, animals were anesthetized with an i.p. injection of ketamine (160 mg/mL) and xylazine (8 mg/mL). The left buccal pouch was everted, fixed and isolated using a lead shield. Test materials were administered topically to the left cheek pouch three times daily, as detailed in Table 3 at a dose of 3 mg/mL in a volume of 0.5 mL per dose, either on the days of radiation (Days 0-3, 6-9), the days on which radiation was not administered (−1, 4, 5 and 10), Days 0-12 or Days 0-35. Mucositis in the left cheek pouch was evaluated clinically starting on Day 7, and continuing on alternate days until Day 35. On Day 35, all animals were euthanized by $CO_2$ inhalation and death was confirmed by monitoring heartbeat in accordance with USDA guidelines.

TABLE 3

| Group | Number of Animals | Treatment | Dose volume | Dose Schedule |
|---|---|---|---|---|
| 1 | 10 male | Saline | 0.5 mL | Days 0-35 |
| 2 | 10 male | Vehicle tid topical | 0.5 mL | Days 0, 1, 2, 3, 6, 7, 8 & 9 |
| 3 | 10 male | Vehicle tid topical | 0.5 mL | Days 0-35 |
| 4 | 10 male | Compound X, 3 mg/mL tid topical | 0.5 mL | Days 0, 1, 2, 3, 6, 7, 8 & 9 |
| 5 | 10 male | Compound X, 3 mg/mL tid topical | 0.5 mL | Days 0 through 12 |
| 6 | 10 male | Compound X, 3 mg/mL tid topical | 0.5 mL | Days 0-35 |
| 7 | 10 male | Compound X, 3 mg/mL tid topical | 0.5 mL | Days −1, 4, 5, 10 |

The mucositis score, weight change and survival were measured throughout the study. For the evaluation of mucositis, the animals were anesthetized with an inhalation anesthetic, and the left pouch everted. Mucositis was scored visually by comparison to a validated photographic scale, ranging from 0 for normal, to 5 for severe ulceration (as described above in Example 2). A score of 1-2 is considered to represent a mild stage of the disease, whereas a score of 3-5 is considered to indicate moderate to severe mucositis. Following visual scoring, a digital image was taken of each animal's mucosa using a standardized technique. At the conclusion of the experiment, images were randomly numbered and scored by two independent trained observers graded the photographs in blinded fashion using the above-described scale (blinded scoring).

The grade of mucositis was scored, beginning on day 7, and for every second day thereafter, through and including day 35. The effect on mucositis of each drug treatment compared to placebo was assessed according to the following parameters: the difference in the number of days hamsters in each group had ulcerative (score ≥3) mucositis and the rank sum differences in daily mucositis scores.

On each evaluation day, the number of animals with a blinded mucositis score of ≥3 in each drug treatment group was compared to the control group. Differences were compared on a cumulative basis and statistical significance was determined by chi-square analysis. Efficacy, in this analysis, is defined by a significant reduction in the number of days that a group of animals had ulcerations (scores ≥3) when compared to the control group.

For each evaluation day the scores of the control group were compared to those of the treated groups using non-parametric rank sum analysis. Treatment success was considered as a statistically significant lowering of scores in the treated group on 2 or more days from day 6 to day 28.

All animals were weighed daily and their survival recorded to assess possible differences in animal weight among treatment groups as an indication for mucositis severity and/or possible toxicity resulting from the treatments. No deaths were observed during this study.

The saline vehicle-treated control hamsters gained an average of 48.4% of their starting weight during the study. Hamsters in the group treated with Kleptose vehicle on Days 0-3 and Days 6-9 gained an average of 57.0% of their starting weights during the study. Hamsters in the groups treated with Kleptose vehicle on Days 0-3 and Days 6-9 gained an average of 49.5% of their starting weights respectively during the study. Hamsters in the groups treated with Compound X in Kleptose based vehicle on Days 0-3 and 6-9 or Days 0-12 gained 44.5% and 48.7% of their starting weights, respectively. Hamsters in the groups treated with Compound X in Kleptose based vehicle on Days 0-35 or Days −1, 4, 5, and 10 gained 47.6% and 46.9% of their starting weights, respectively.

The maximum mean mucositis observed in the saline vehicle control group was 3.2, which occurred on Days 17, 19 and 21. The group treated with Kleptose vehicle on Days 0-3 and 6-9 had a peak mucositis score of 3.2 on Day 19 and the group treated with Kleptose vehicle on Days 0-35 had a peak mucositis score of 3.1 on Day 21. The group treated with Compound X at 3 mg/mL (in Kleptose vehicle) on Days 0-3 and 6-9 had a peak mean mucositis score of 3.1 on Day 19. The group treated with Compound X on Days 0-12 had a maximum mean mucositis score of 3.1 on Days 19, 21 and 23. The group treated with Compound X on Days 0-35 had a maximum mean mucositis score of 2.1 on Days 19 and 21. The group treated with Compound X on Days −1, 4, 5, and 10 had a peak mean mucositis score of 3.1 on Day 19.

In the saline vehicle control group, the percentage of animal days with a score of 3 or higher was 54.7%. In the groups treated with the Kleptose vehicle on Days 0-3 and 6-9 or Days 0-35, the percentage of animal days with a score of 3 or higher was 46.7% and 56.0%, respectively. In the group treated with Compound X on Days 0-3 and 6-9, the percentage of animal days with a score of 3 or higher was 58.0%. In the group treated with Compound X on Days 0-12, the percentage of animal days with a score of 3 or higher was 58.0%. In the group treated with Compound X on Days −1, 4, 5, and 10, the percentage of animal days with a score of 3 or higher was 48.0%. In the group treated with Compound X on Days 0-35, however, the percentage of animal days with a score of 3 or higher was 3.3%, which was significantly lower than the saline control group and the Kleptose vehicle group dosed on the same days (p<0.001 for both comparisons).

An analysis of the severity of mucositis was performed using the Mann-Whitney rank sum analysis to compare the scores for each treatment group to the controls on each day of the analysis. In this analysis, 2 days of significant reduction in the mucositis score are generally required before it is regarded as meaningful.

The group treated with Compound X at 3 mg/mL tid from Day 0 until Day 35 had statistically significant reductions in mucositis scores on Days 11 (p=0.002), 13 (p=0.023) and 15-35 (p<0.001 for all 11 days) when compared to the saline control group. When compared to the Kleptose control group, statistically significant reductions in mucositis scores were observed on Days 17, 19, 21, 23, 25, 27, 29, 31, 33 and 35 (p<0.001 for all days).

When compared to the saline control group, the two Kleptose vehicle based groups had significant reductions in mucositis scores on Days 11, 13 and 15 (for the groups dosed on Days 0-3 and 6-9), or Days 11 and 15 (for the Group dosed on Days 0-35), and a significant increase in mucositis scores on Day 27. This pattern was also observed in the groups treated with Compound X on Days 0-3 and 6-9 or Days 0-12. The similarity of response in these four groups suggests that the Kleptose vehicle may slightly delay both the onset of severe mucositis and possibly also delay the resolution of oral mucositis.

The group treated with Compound X on Days −1, 4, 5 and 10 had statistically significant reductions in mucositis scores on Days 21 (p=0.018), 23 (p=0.040), 25 (p=0.040), 33 (p=0.036), and 35 (p=0.036). This pattern of improvement in mucositis scores differs markedly from the patterns observed in the groups treated on the days of radiation (0-3, 6-9), which Kleptose vehicle alone throughout the study (Days 0-35), or with Compound X on Days 0-12.

At least 90% of the saline control and the Kleptose vehicle treated animals developed ulcerative mucositis by Day 17, which persisted until Day 25 in the saline controls and Day 27 in the Kleptose vehicle groups. The groups treated with Compound X on Days 0-3 and 6-9 or Days 0-12 had a 100% ulceration rate on Day 17, which continued at until Day 27 in the group treated from Day 0 to Day 12, and until Day 29 in the group treated on Days 0-3 and 6-9. The group treated with Compound X on Days 0-35 had a 10% ulceration rate on Days 15-23. This represented a single hamster with an ulcer that persisted for 8 days. No other ulcers were observed in this group. The group treated with Compound X on Days −1, 4, 5, and 10 had a 100% ulceration rate on Day 19 only.

Several conclusions can be drawn from this study, including: 1) there was no evidence of any adverse reaction to treatment with Compound X, administered three times daily by topical application to the left buccal pouch for the duration of the study; 2) Compound X administered throughout the study reduced the incidence of ulcerative oral mucositis from 54.7% in the saline controls to 3.3% in the group treated with Compound X from Day 0 until Day 35; 3) the group treated with Compound X from Day 0 to Day 35 had statistically significant reductions in mucositis scores on Days 11 (p=0.002), 13 (p=0.023), and 15, 17, 19, 21, 23, 25, 37, 29 31, 33 and 35 (p<0.001 on all days); and 4) the percentage of hamsters in which an ulcer formed during the study was reduced from 100% in the saline and vehicle controls to 10% in the group treated with Compound X from Day 0 to Day 35.

Example 4

Evaluation of the Impact of Compound X on Tumor Growth and Response to Therapy in the FaDu Human Head and Neck Cancer Grown as a Xenograft Ninety (90) male nude mice (nu/nu) were divided into nine (9) groups of ten (10) mice per group. To ensure that a sufficient number of tumor-bearing animals were available for this study, a total of 100 mice were inoculated s.c. in the flank with $1\times10^6$ FaDu cells. FaDu (HTB-43) human head and neck cancer cells were obtained from ATCC. These cells were grown in EMEM medium supplemented with 10% Fetal Calf Serum (FCS), 1% penicillin and streptomycin, and 2 mM L-Glutamine. Cells were sub-cultured by removing the medium, rinsing twice with sterile calcium- and magnesium-free phosphate buffered saline (PBS) and adding 1 to 2 mL of 0.25% trypsin/0.03% EDTA solution. The flask was incubated at 37° C. until cells detached. Cells were then sub-cultured at a ratio of 1:3. When tumors reached an average volume of approximately 100 $mm^3$, animals were randomized by tumor volume and treated with radiation, chemotherapy, or Compound X, or combinations of Compound X and either radiation or chemotherapy, as shown in Table 4. Tumors were measured once every two days with micro-calipers, and tumor volume was calculated as (length× width× width)/2. Where animals were euthanized for tumor volume exceeding the maximum permissible by IACUC rules (1500 $mm^3$) or tumor ulceration, the last measurement was carried forward in calculations of mean tumor volume.

TABLE 4

| Group # | Number of Animals | Inoculum* | Treatment (IP) | Dosing Schedule (Days) |
|---|---|---|---|---|
| 1 | 10 Male | FaDu<br>$1 \times 10^6$ cells | Vehicle Control | QD, Days 0-28 |
| 2 | 10 Male | FaDu<br>$1 \times 10^6$ cells | Compound X 0.06 mg/kg | QD, Days 0-28 |
| 3 | 10 Male | FaDu<br>$1 \times 10^6$ cells | Compound X 0.3 mg/ kg | QD, Days 0-28 |
| 4 | 10 Male | FaDu<br>$1 \times 10^6$ cells | Radiation focal to tumor<br>8 fractions of 1.25Gy/10Gy total<br>Vehicle | Days 0-3, 6-9<br>Days 0-28 |
| 5 | 10 Male | FaDu<br>$1 \times 10^6$ cells | Radiation focal to tumor<br>8 fractions of 1.25Gy/10Gy total<br>Compound X 0.06 mg/ kg | Days 0-3, 6-9<br>QD, Days 0-28 |
| 6 | 10 Male | FaDu<br>$1 \times 10^6$ cells | Radiation focal to tumor<br>8 fractions of 1.25Gy/10Gy total<br>Compound X 0.3 mg/ kg | Days 0-3, 6-9<br>QD, Days 0-28 |
| 7 | 10 Male | FaDu<br>$1 \times 10^6$ cells | Cisplatin 5 mg/kg<br>Vehicle | Days 0, 14<br>QD, Days 0-28 |

TABLE 4-continued

| Group # | Number of Animals | Inoculum* | Treatment (IP) | Dosing Schedule (Days) |
|---|---|---|---|---|
| 8 | 10 Male | FaDu<br>1 × $10^6$ cells | Cisplatin 5 mg/kg<br>Compound X 0.06 mg/ kg | Days 0, 14<br>QD, Days 0-28 |
| 9 | 10 Male | FaDu<br>1 × $10^6$ cells | Cisplatin 5 mg/kg<br>Compound X 0.3 mg/ kg | Days 0, 14<br>QD, Days 0-28 |

All animals were weighed every day and their survival recorded, to assess possible differences in animal weight among treatment groups as an indication of possible toxicity resulting from the treatments. Any animals exhibiting a loss of >20% of starting weight during the course of the study were euthanized. Any animals whose tumor grew to over 1500 $mm^3$ were also euthanized.

No animal deaths occurred as a direct result of treatment during the course of this study. A total of 65 animals were euthanized during the course of the study, 39 of these were due to the tumor in these animals exceeding the maximum volume (1500 $mm^3$) allowed by IACUC and the remaining 26 were due to ulceration of the tumor and the resulting health risk posed by the wound. In the groups that did not receive either radiation or chemotherapy, 70% of the animals were euthanized for tumor size (range 6 of 10 to 8 of 10), 16.7% of the animals were euthanized for tumor ulceration (range 1 of 10 to 2 of 10), and 13.3% of the animals survived (range 0 to 2). In the groups receiving radiation therapy, 37.7% of the animals were euthanized for tumor size (range 3 of 10 to 4 of 10), 43.3% of the animals were euthanized for tumor ulceration (range 4 of 10 to 5 of 10), and 20% of the animals survived (range 1 to 3). In the groups receiving cisplatin chemotherapy, 23% of the animals were euthanized for tumor size (range 2 of 10 to 3 of 10), 26.7% of the animals were euthanized for tumor ulceration (range 2 of 10 to 4 of 10), and 50% of the animals survived (range 4 to 6). In the groups receiving vehicle 43.3% of the mice were euthanized for tumor volume in excess of 1500 $mm^3$, compared to 46.7% in groups treated with Compound X at 0.06 mg/kg, and 40% in groups treated with Compound X at 0.3 mg/kg. Similarly, 30% of the mice treated with vehicle were euthanized for tumor ulceration, compared to 33.3% in groups treated with Compound X at 0.06 mg/kg, and 23.3% in groups treated with Compound X at 0.3 mg/kg. Survival at Day 29 in the vehicle groups was 26.7%, compared to 20% in groups treated with Compound X at 0.06 mg/kg, and 36.7% in groups treated with Compound X at 0.3 mg/kg.

The mice receiving vehicle only had a mean weight gain of 5.9% by Day 15, when the first animal in the study was euthanized, and had gained an average of 15.2% of their starting weight by the end of the study. The mice receiving Compound X at 0.06 mg/kg had a mean weight gain of 9.1% by Day 15, and had gained an average of 16.1% of their starting weight by Day 27 when the last animal in this group was euthanized. Mice receiving Compound X at 0.3 mg/kg had a mean weight gain of 4.8% by Day 15, and had gained an average of 12.9% of their starting weight by the end of the study. The mice receiving vehicle in addition to radiation therapy had a mean weight gain of 10.3% by Day 15, and had gained an average of 0.6% of their starting weight by the end of the study. The mice receiving radiation therapy plus Compound X at 0.06 mg/kg had a mean weight gain of 4.2% by Day 15, and had gained an average of 13.4% of their starting weight by the end of the study. Mice receiving radiation therapy and Compound X at 0.3 mg/kg had a mean weight gain of 6.5% by Day 15, and had gained an average of 14.1% of their starting weight by the end of the study. The mice receiving vehicle in addition to cisplatin chemotherapy had a mean weight gain of 7.2% by Day 15, when and had gained an average of 13.0% of their starting weight by the end of the study. The mice receiving cisplatin chemotherapy plus Compound X at 0.06 mg/kg had a mean weight gain of 0.8% by Day 15, and had gained an average of 10.8% of their starting weight by the end of the study. Mice receiving cisplatin chemotherapy and Compound X at 0.3 mg/kg had a mean weight gain of 8.4% by Day 15, and had gained an average of 18.7% of their starting weight by the end of the study.

The mean tumor volume for the vehicle control group increased from 96 $mm^3$ on Day 1 to 928 $mm^3$ on Day 15, and to 1096 $mm^3$ at the end of the study. In the group treated with Compound X at 0.06 mg/kg, the mean tumor increased from 102 $mm^3$ on Day 1 to 904 $mm^3$ on Day 15, and to 2234 $mm^3$ on Day 27 when the final animal in this group was euthanized. In the group treated with Compound X at 0.3 mg/kg, the mean tumor increased from 96 $mm^3$ on Day 1 to 869 $mm^3$ on Day 15, and to 1002 $mm^3$ at the end of the study. The mean tumor volume for the group that received radiation plus vehicle increased from 102 $mm^3$ on Day 1 to 652 $mm^3$ on Day 15, and decreased by 11 $mm^3$ at the end of the study. In the group treated with radiation plus Compound X at 0.06 mg/kg, the mean tumor increased from 96 $mm^3$ on Day 1 to 596 $mm^3$ on Day 15, and to 1027 $mm^3$ at the end of the study. In the group treated with radiation plus Compound X at 0.3 mg/kg, the mean tumor increased from 108 $mm^3$ on Day 1 to 616 $mm^3$ on Day 15, and to 1376 $mm^3$ at the end of the study. The mean tumor volume for the group that received cisplatin plus vehicle increased from 100 $mm^3$ on Day 1 to 652 $mm^3$ on Day 15, and decreased to 302 $mm^3$ at the end of the study. In the group treated with cisplatin plus Compound X at 0.06 mg/kg, the mean tumor increased from 100 $mm^3$ on Day 1 to 518 $mm^3$ on Day 15, and decreased to 338 $mm^3$ at the end of the study. In the group treated with cisplatin plus Compound X at 0.3 mg/kg, the mean tumor increased from 104 $mm^3$ on Day 1 to 564 $mm^3$ on Day 15, and decreased to 510 $mm^3$ at the end of the study. The second dose of cisplatin, given to the final three groups on Day 21 had a noticeable impact on tumor volume in these groups, however while some of the tumors responded very well to the cisplatin, others did not show a noticeable response and a third subset ulcerated, causing the data to be relatively erratic from approximately Day 22 on.

Further analysis of the tumor volume data was performed by calculating the mean area under the curve (AUC) for the tumor volume for each animal and comparing the groups using an ANOVA on ranks test. Due to the impact of animals euthanized for tumor ulceration or volume in excess of 1500 $mm^3$, this analysis was performed on data to Day 15 as well as on the full data set to Day 29. The Day 15 analysis indicated that there were statistically significant differences between the vehicle control group and the groups treated with radiation plus Compound X at 0.3 mg/kg ($p=0.017$), cisplatin plus vehicle ($p=0.011$), cisplatin plus Compound X at 0.06 mg/kg ($p=0.001$), and cisplatin plus Compound X at 0.3 mg/kg ($p=0.002$).

Example 5

Efficacy of Compound X in Hamster Models of Ulcerative Oral Mucositis

Marked inhibitory effects were observed in the severity and course of radiation-induced mucosal injury in hamster models of ulcerative mucositis after topical administration of Compound X. In both acute and fractionated radiation hamster models, topical applications of Compound X as an oral rinse 3 times daily over 28 and 35 day treatment regimens significantly reduced the daily mean mucositis scores and the number of days animals exhibited ulceration. There were no adverse findings in weight gain, general behavior in the home cage, or clinical signs attributed to Compound X in any of the treatment groups. In the fractionated radiation model which better reflects the clinical situation for radiation therapy, Compound X significantly reduced the daily mucositis scores beginning prior to peak mucositis and significant reductions remained evident throughout the remaining course of treatment. Table 5 below shows the percent reduction of days the animals exhibited ulceration in the acute and fractionated radiation models with Compound X in comparison to published results for two other agents currently under clinical study, SCV-07 and AG013, that were tested in nearly identical models. Greater efficacy was achieved with Compound X in all comparisons.

TABLE 5

| | % reduction of animal days with OM scores ≥ 3 | | |
|---|---|---|---|
| Model/Compound | SCV-07 | AGO13 | Compound X |
| Acute Radiation | 68.3%-77.6% | 32.8%-40.0% | 90.6%-95.3% |
| Fractionated Radiation | 33.3% | Not reported | 92.6% |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is herein incorporated by reference in its entirety.

What is claimed is:

1. A method of treating mucositis in a mammal comprising administering to the mammal in need thereof a therapeutically effective amount of a compound having the formula

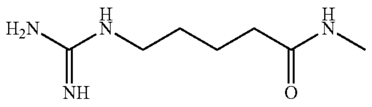

-continued

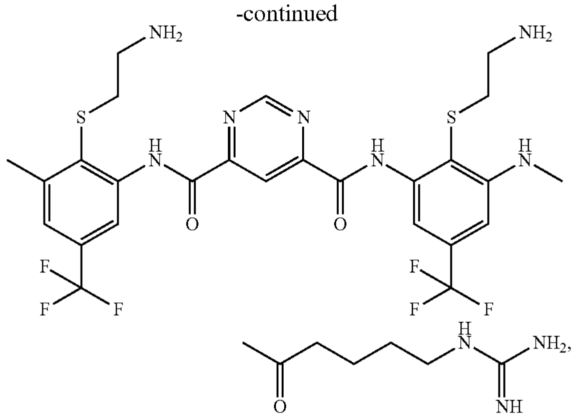

or a pharmaceutically acceptable salt thereof.

2. The method of claim 1 wherein the mammal is a human.

3. The method of claim 1 wherein the compound, or pharmaceutically acceptable salt thereof, administered to the mammal is present in a pharmaceutical composition.

4. The method of claim 3 wherein the pharmaceutical composition further comprises another therapeutic agent.

5. The method of claim 4 wherein the another therapeutic agent is palifermin.

6. The method of claim 1 wherein the mammal also receives chemotherapy, radiation therapy, or both.

7. The method of claim 1 wherein the compound is administered orally, bucally, or sublingually.

8. The method of claim 3 wherein the pharmaceutical composition is a liquid.

9. The method of claim 3 wherein the pharmaceutical composition is a rinse.

10. The method of claim 9 wherein the compound in the rinse is at 1 mg/ml, 3 mg/ml, or 10 mg/ml.

11. The method of claim 1 wherein the mammal also receives high-dose chemotherapy prior to hematopoietic cell transplantation, radiation therapy for tumors of the head and neck, induction therapy for leukemia, or conditioning regimens for bone marrow transplant.

12. A method of treating mucositis in a human comprising administering orally, bucally, or sublingually to the human in need thereof a liquid pharmaceutical composition in the form of a rinse comprising a compound having the formula

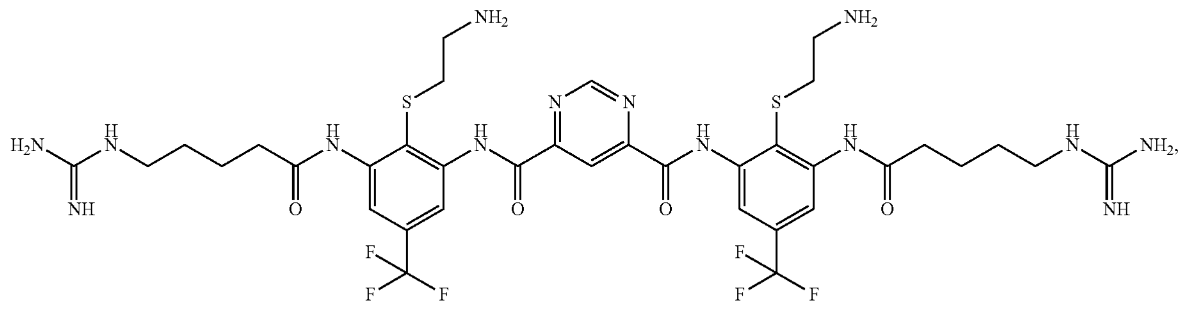 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3SCCN)ncn2)c1SCCN]

or a pharmaceutically acceptable salt thereof.

13. The method of claim 12 wherein the compound in the rinse is at 1 mg/ml, 3 mg/ml, or 10 mg/ml.

14. The method of claim 12 wherein the rinse further comprises palifermin.

15. A composition comprising
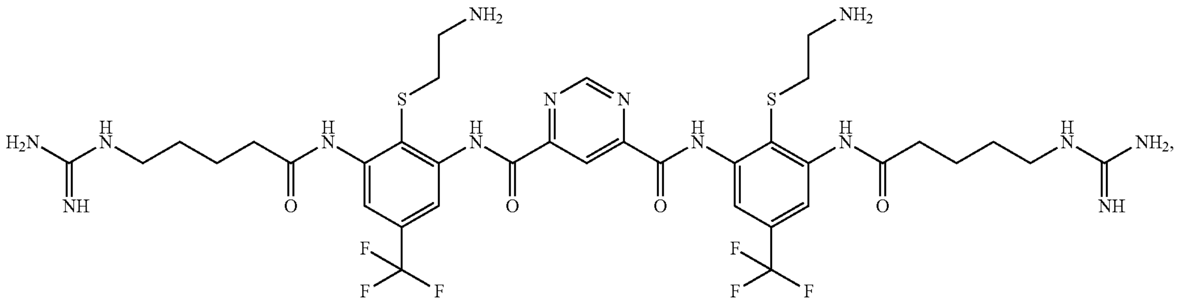 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3SCCN)ncn2)c1SCCN]
or a pharmaceutically acceptable salt thereof, and palifermin.
* * * * *